US00RE50320E

(19) United States
(12) Reissued Patent
Anantharamaiah et al.

(10) Patent Number: US RE50,320 E
(45) Date of Reissued Patent: Mar. 4, 2025

(54) APOE MIMETIC PEPTIDES AND HIGHER POTENCY TO CLEAR PLASMA CHOLESTEROL

(71) Applicants: UAB Research Foundation, Birmingham, AL (US); ANJI PHARMACEUTICALS INC., Cambridge, MA (US)

(72) Inventors: Gattadahalli M. Anantharamaiah, Birmingham, AL (US); Dennis Goldberg, Sudbury, MA (US)

(73) Assignees: UAB RESEARCH FOUNDATION, Birmingham, AL (US); ANJI Pharmaceuticals INC., Cambridge, MA (US)

(21) Appl. No.: 17/748,682

(22) Filed: May 19, 2022

Related U.S. Patent Documents

Reissue of:
(64) Patent No.: 10,653,747
Issued: May 19, 2020
Appl. No.: 15/329,735
PCT Filed: Jul. 20, 2015
PCT No.: PCT/US2015/041162
§ 371 (c)(1),
(2) Date: Jan. 27, 2017
PCT Pub. No.: WO2016/018665
PCT Pub. Date: Feb. 4, 2016

U.S. Applications:
(60) Provisional application No. 62/031,585, filed on Jul. 31, 2014.

(51) Int. Cl.

| | |
|---|---|
| ***A61K 38/17*** | (2006.01) |
| ***A61K 38/00*** | (2006.01) |
| ***A61P 3/06*** | (2006.01) |
| ***A61P 9/10*** | (2006.01) |
| ***C07K 14/775*** | (2006.01) |

(52) U.S. Cl.
CPC ..... *A61K 38/1709* (2013.01); *A61K 38/00* (2013.01); *A61P 3/06* (2018.01); *A61P 9/10* (2018.01); *C07K 14/775* (2013.01)

(58) Field of Classification Search
CPC ..... A61K 14/47; A61K 38/00; C07K 14/00
See application file for complete search history.

(56) References Cited

U.S. PATENT DOCUMENTS

| | | | |
|---|---|---|---|
| 3,687,808 | A | 8/1972 | Englisch et al. |
| 3,767,040 | A | 10/1973 | Tushaus |
| 4,155,913 | A | 5/1979 | Hellerbach et al. |
| 4,342,566 | A | 8/1982 | Theofilopoulos et al. |
| 4,428,938 | A | 1/1984 | Kisfaludy et al. |
| 4,469,863 | A | 9/1984 | Ts'o et al. |
| 4,476,301 | A | 10/1984 | Imbach et al. |
| 4,587,044 | A | 5/1986 | Miller et al. |
| 4,605,735 | A | 8/1986 | Miyoshi et al. |
| 4,643,988 | A | 2/1987 | Segrest et al. |
| 4,667,025 | A | 5/1987 | Miyoshi et al. |
| 4,684,520 | A | 8/1987 | Bertelli |
| 4,762,779 | A | 8/1988 | Snitman |
| 4,789,737 | A | 12/1988 | Miyoshi et al. |
| 4,816,567 | A | 3/1989 | Cabilly et al. |
| 4,824,941 | A | 4/1989 | Gordon et al. |
| 4,828,979 | A | 5/1989 | Kievan et al. |
| 4,835,263 | A | 5/1989 | Nguyen et al. |
| 4,845,205 | A | 7/1989 | Huynh Dinh et al. |
| 4,868,116 | A | 9/1989 | Morgan et al. |
| 4,876,335 | A | 10/1989 | Yamane et al. |
| 4,877,611 | A | 10/1989 | Cantrell |
| 4,897,355 | A | 1/1990 | Eppstein et al. |
| 4,904,582 | A | 2/1990 | Tullis |
| 4,946,778 | A | 8/1990 | Ladner et al. |
| 4,948,882 | A | 8/1990 | Ruth |
| 4,958,013 | A | 9/1990 | Letsinger |
| 4,980,286 | A | 12/1990 | Morgan et al. |
| 4,981,957 | A | 1/1991 | Lebleu et al. |
| 5,023,243 | A | 6/1991 | Tullis |
| 5,034,506 | A | 7/1991 | Summerton et al. |

(Continued)

FOREIGN PATENT DOCUMENTS

| | | |
|---|---|---|
| AU | 2003290825 | 6/2004 |
| AU | 200126732 | 10/2005 |

(Continued)

OTHER PUBLICATIONS

Arisaph Pharmaceuticals Reports on Promising Results Presented at American Heart Association: Novel Apo A-I-Mimetic Peptide Significantly Inhibits Atherosclerosis in Preclinical Animal Study, BioSpace News, (Nov. 14, 2005) (2 pages). http://www.biospace.com/News/arisaph-pharmaceuticals-reports-on-promising/2610.

Baumbach et al., Structure of Cerebral Arterioles in Cystathionine β-Synthase-Deficient Mice, Circ res, 91(10): 931-7 (2002).

Brown, B.G. et al. (2001) Simvastatin and Niacin, Antioxidant Vitamins, or the Combination for the Prevention of Coronary Disease. N Engl J Med. 345(22):1583-92.

Datta et al. (2001) Cationic domain 141-150 of apoE covalently linked to a class A amphipathic helix enhances atherogenic lipoprotein metabolism in vitro and in vivo. J Lipid Res. 42:959-66.

Garner et al. (1998) Oxidation of high density lipoproteins. I. Formation of methionine sulfoxide in apolipoproteins AI and AII is an early event that accompanies lipid peroxidation and can be enhanced by alpha-tocopherol. J Biol Chem. 273:6080-7.

(Continued)

*Primary Examiner* — Padmashri Ponnaluri
(74) *Attorney, Agent, or Firm* — BALLARD SPAHR LLP

(57) ABSTRACT

Disclosed are synthetic apolipoprotein E-mimicking peptides, derivatives thereof, and related peptides, which are useful as therapeutic agents for reducing plasma cholesterol; synthetic methods of making the peptides; pharmaceutical compositions comprising the peptides, and methods of treating lipid and metabolic disorders using the disclosed synthetic apolipoprotein E-mimicking peptides and compositions thereof. This abstract is intended as a scanning tool for purposes of searching in the particular art and is not intended to be limiting of the present invention.

18 Claims, 41 Drawing Sheets

Specification includes a Sequence Listing.

(56) References Cited

U.S. PATENT DOCUMENTS 5,082,830 A 1/1992 Brakel et al.
5,109,124 A 4/1992 Ramachandran et al.
5,112,963 A 5/1992 Pieles et al.
5,118,800 A 6/1992 Smith et al.
5,118,802 A 6/1992 Smith et al.
5,130,302 A 7/1992 Spielvogel et al.
5,134,066 A 7/1992 Rogers et al.
5,135,917 A 8/1992 Burch
5,138,045 A 8/1992 Cook et al.
5,166,315 A 11/1992 Summerton et al.
5,168,053 A 12/1992 Altman et al.
5,175,273 A 12/1992 Bischofberger et al.
5,176,996 A 1/1993 Hogan et al.
5,177,196 A 1/1993 Meyer, Jr. et al.
5,185,444 A 2/1993 Summerton et al.
5,188,897 A 2/1993 Suhadolnik et al.
5,214,134 A 5/1993 Weis et al.
5,214,136 A 5/1993 Lin et al.
5,216,141 A 6/1993 Benner
5,218,105 A 6/1993 Cook et al.
5,235,033 A 8/1993 Summerton et al.
5,245,022 A 9/1993 Weis et al.
5,254,469 A 10/1993 Warren, III et al.
5,258,506 A 11/1993 Urdea et al.
5,262,536 A 11/1993 Hobbs, Jr.
5,264,423 A 11/1993 Cohen et al.
5,264,562 A 11/1993 Matteucci
5,264,564 A 11/1993 Matteucci
5,272,250 A 12/1993 Spielvogel et al.
5,276,019 A 1/1994 Cohen et al.
5,278,302 A 1/1994 Caruthers et al.
5,286,717 A 2/1994 Cohen et al.
5,292,873 A 3/1994 Rokita et al.
5,294,533 A 3/1994 Lupski et al.
5,298,490 A 3/1994 Heavner et al.
5,317,098 A 5/1994 Shizuya et al.
5,319,080 A 6/1994 Leumann et al.
5,321,131 A 6/1994 Agrawal et al.
5,334,711 A 8/1994 Sproat et al.
5,344,822 A 9/1994 Levine et al.
5,358,934 A 10/1994 Schmickel
5,359,044 A 10/1994 Cook et al.
5,367,066 A 11/1994 Urdea et al.
5,371,241 A 12/1994 Brush
5,391,377 A 2/1995 Barnwell
5,391,723 A 2/1995 Priest
5,393,878 A 2/1995 Leumann
5,399,676 A 3/1995 Froehler
5,405,938 A 4/1995 Summerton et al.
5,405,939 A 4/1995 Suhadolnik et al.
5,414,077 A 5/1995 Lin et al.
5,416,203 A 5/1995 Letsinger
5,432,272 A 7/1995 Benner
5,434,257 A 7/1995 Matteucci et al.
5,436,330 A 7/1995 Taira et al.
5,446,137 A 8/1995 Maag et al.
5,451,463 A 9/1995 Nelson et al.
5,453,496 A 9/1995 Caruthers et al.
5,455,233 A 10/1995 Spielvogel et al.
5,457,135 A 10/1995 Baranowitz et al.
5,457,187 A 10/1995 Gmeiner et al.
5,459,255 A 10/1995 Cook et al.
5,466,677 A 11/1995 Baxter et al.
5,466,786 A 11/1995 Buhr et al.
5,470,967 A 11/1995 Huie et al.
5,473,039 A 12/1995 Dyer et al.
5,476,766 A 12/1995 Gold et al.
5,476,925 A 12/1995 Letsinger et al.
5,480,869 A 1/1996 Wei et al.
5,484,908 A 1/1996 Froehler et al.
5,486,603 A 1/1996 Buhr
5,489,677 A 2/1996 Sanghvi et al.
5,502,177 A 3/1996 Matteucci et al.
5,503,978 A 4/1996 Schneider et al.
5,508,060 A 4/1996 Perman et al.
5,510,475 A 4/1996 Agrawal et al.
5,512,439 A 4/1996 Hornes et al.
5,512,667 A 4/1996 Reed et al.
5,514,785 A 5/1996 Van Ness et al.
5,519,126 A 5/1996 Hecht
5,519,134 A 5/1996 Acevedo et al.
5,525,465 A 6/1996 Haralambidis et al.
5,525,711 A 6/1996 Hawkins et al.
5,536,821 A 7/1996 Agrawal et al.
5,539,082 A 7/1996 Nielsen et al.
5,541,306 A 7/1996 Agrawal et al.
5,541,307 A 7/1996 Cook et al.
5,541,313 A 7/1996 Ruth
5,543,293 A 8/1996 Gold et al.
5,545,730 A 8/1996 Urdea et al.
5,550,111 A 8/1996 Suhadolnik et al.
5,552,538 A 9/1996 Urdea et al.
5,552,540 A 9/1996 Haralambidis
5,561,225 A 10/1996 Maddry et al.
5,563,253 A 10/1996 Agrawal et al.
5,565,332 A 10/1996 Hoogenboom et al.
5,565,552 A 10/1996 Magda et al.
5,567,810 A 10/1996 Weis et al.
5,567,811 A 10/1996 Misiura et al.
5,571,799 A 11/1996 Tkachuk et al.
5,574,142 A 11/1996 Meyer, Jr. et al.
5,576,427 A 11/1996 Cook et al.
5,578,717 A 11/1996 Urdea et al.
5,578,718 A 11/1996 Cook et al.
5,579,250 A 11/1996 Balaji et al.
5,580,731 A 12/1996 Chang et al.
5,580,737 A 12/1996 Polisky et al.
5,580,967 A 12/1996 Joyce
5,585,481 A 12/1996 Arnold, Jr. et al.
5,587,361 A 12/1996 Cook et al.
5,587,371 A 12/1996 Sessler et al.
5,587,469 A 12/1996 Cook et al.
5,591,584 A 1/1997 Chang et al.
5,591,722 A 1/1997 Montgomery et al.
5,594,121 A 1/1997 Froehler et al.
5,595,726 A 1/1997 Magda et al.
5,595,873 A 1/1997 Joyce
5,595,973 A 1/1997 Bogden
5,596,086 A 1/1997 Matteucci et al.
5,596,091 A 1/1997 Switzer
5,597,696 A 1/1997 Linn et al.
5,597,909 A 1/1997 Urdea et al.
5,599,923 A 2/1997 Sessler et al.
5,599,928 A 2/1997 Hemmi et al.
5,602,240 A 2/1997 De Mesmaeker et al.
5,608,046 A 3/1997 Cook et al.
5,610,289 A 3/1997 Cook et al.
5,610,300 A 3/1997 Altmann et al.
5,612,895 A 3/1997 Balaji et al.
5,614,617 A 3/1997 Cook et al.
5,616,466 A 4/1997 Cantor et al.
5,618,704 A 4/1997 Sanghvi et al.
5,623,070 A 4/1997 Cook et al.
5,624,824 A 4/1997 Yuan et al.
5,625,050 A 4/1997 Beaton et al.
5,627,053 A 5/1997 Usman et al.
5,627,158 A 5/1997 Cho-Chung
5,631,115 A 5/1997 Ohtsuka et al.
5,631,146 A 5/1997 Szostak et al.
5,631,280 A 5/1997 Ciccarone et al.
5,633,133 A 5/1997 Long et al.
5,633,360 A 5/1997 Bischofberger et al.
5,639,873 A 6/1997 Barascut et al.
5,641,754 A 6/1997 Iversen
5,645,985 A 7/1997 Froehler et al.
5,646,020 A 7/1997 Swiggen et al.
5,646,031 A 7/1997 DeYoung et al.
5,646,042 A 7/1997 Stinchcomb et al.
5,646,265 A 7/1997 McGee
5,650,316 A 7/1997 Aggarwal et al.
5,652,094 A 7/1997 Usman et al.
5,652,107 A 7/1997 Lizardi et al.
5,658,873 A 8/1997 Bertsch-Frank et al.
5,663,312 A 9/1997 Chaturvedula

(56) References Cited

U.S. PATENT DOCUMENTS 5,670,633 A 9/1997 Cook et al.
5,677,437 A 10/1997 Teng et al.
5,677,439 A 10/1997 Weis et al.
5,681,941 A 10/1997 Cook et al.
5,683,873 A 11/1997 George et al.
5,683,874 A 11/1997 Kool
5,683,902 A 11/1997 Hampel et al.
5,688,670 A 11/1997 Szostak et al.
5,688,941 A 11/1997 Cook et al.
5,691,317 A 11/1997 Cho-Chung
5,693,535 A 12/1997 Draper et al.
5,693,773 A 12/1997 Kandimalla et al.
5,700,920 A 12/1997 Altmann et al.
5,700,922 A 12/1997 Cook
5,712,384 A 1/1998 Symonds et al.
5,714,331 A 2/1998 Buchardt et al.
5,719,262 A 2/1998 Buchardt et al.
5,721,138 A 2/1998 Lawn
5,721,367 A 2/1998 Kay et al.
5,728,521 A 3/1998 Yuan et al.
5,731,295 A 3/1998 Draper et al.
5,731,424 A 3/1998 Toothman et al.
5,733,549 A 3/1998 Yamada et al.
5,733,879 A 3/1998 Rosseneu et al.
5,770,576 A 6/1998 Morozov et al.
5,770,715 A 6/1998 Sugiyama et al.
5,780,228 A 7/1998 Parma et al.
5,780,607 A 7/1998 Goodnow, Jr. et al.
5,786,138 A 7/1998 Swenson
5,786,462 A 7/1998 Schneider et al.
5,792,613 A 8/1998 Schmidt et al.
5,795,721 A 8/1998 Rabin et al.
5,800,758 A 9/1998 Topolkaraev et al.
5,804,440 A 9/1998 Burton et al.
5,807,718 A 9/1998 Joyce et al.
5,811,300 A 9/1998 Sullivan et al.
5,814,467 A 9/1998 Curtiss et al.
5,834,185 A 11/1998 Ts'o et al.
5,837,243 A 11/1998 Deo et al.
5,837,855 A 11/1998 Chowrira et al.
5,843,708 A 12/1998 Hardman et al.
5,846,713 A 12/1998 Pagratis et al.
5,849,903 A 12/1998 Pietrzkowski et al.
5,854,238 A 12/1998 Kempen
5,856,103 A 1/1999 Gray et al.
5,856,188 A 1/1999 Hampel et al.
5,856,463 A 1/1999 Prydz et al.
5,858,660 A 1/1999 Eaton et al.
5,861,254 A 1/1999 Schneider et al.
5,861,288 A 1/1999 Usman et al.
5,864,026 A 1/1999 Jensen et al.
5,866,701 A 2/1999 Hampel et al.
5,869,246 A 2/1999 Matsuo et al.
5,869,248 A 2/1999 Yuan et al.
5,869,253 A 2/1999 Draper
5,869,339 A 2/1999 Hampel et al.
5,869,641 A 2/1999 Jayasena et al.
5,874,566 A 2/1999 Veerapanane et al.
5,877,021 A 3/1999 Stinchcomb et al.
5,877,022 A 3/1999 Stinchcomb et al.
5,877,153 A 3/1999 Harris et al.
5,877,162 A 3/1999 Werner et al.
5,891,683 A 4/1999 Usman et al.
5,891,684 A 4/1999 Usman et al.
5,910,408 A 6/1999 Szostak et al.
5,919,772 A 7/1999 Szyf et al.
5,939,598 A 8/1999 Kucherlapati et al.
5,955,590 A 9/1999 Levina et al.
5,958,691 A 9/1999 Pieken et al.
5,962,426 A 10/1999 Glazer
5,972,699 A 10/1999 Draper
5,972,704 A 10/1999 Draper et al.
5,985,621 A 11/1999 Usman et al.
5,989,906 A 11/1999 Thompson
5,989,908 A 11/1999 Scanlon
5,990,081 A 11/1999 Ageland et al.
5,990,088 A 11/1999 Ensoli et al.
5,994,320 A 11/1999 Low et al.
5,998,193 A 12/1999 Keese et al.
5,998,203 A 12/1999 Matulic-Adamic et al.
5,998,602 A 12/1999 Torrence et al.
6,001,988 A 12/1999 Parma et al.
6,004,925 A 12/1999 Dasseux et al.
6,005,013 A 12/1999 Suh et al.
6,005,095 A 12/1999 Capaccioli et al.
6,007,995 A 12/1999 Baker et al.
6,011,002 A 1/2000 Pastan et al.
6,011,020 A 1/2000 Gold et al.
6,013,443 A 1/2000 Heilig et al.
6,013,522 A 1/2000 Monia et al.
6,017,756 A 1/2000 Draper
6,017,898 A 1/2000 Pietrzkowski et al.
6,018,042 A 1/2000 Mett et al.
6,019,739 A 2/2000 Rhee et al.
6,020,130 A 2/2000 Gold et al.
6,022,962 A 2/2000 Chowrira et al.
6,025,198 A 2/2000 Bennett et al.
6,028,186 A 2/2000 Tasset et al.
6,030,776 A 2/2000 Eaton et al.
6,033,910 A 3/2000 Monia et al.
6,037,323 A 3/2000 Dasseux et al.
6,040,147 A 3/2000 Ridker et al.
6,040,296 A 3/2000 Nyce
6,046,004 A 4/2000 Wu et al.
6,046,166 A 4/2000 Dasseux et al.
6,046,319 A 4/2000 Power et al.
6,051,698 A 4/2000 Janjic et al.
6,057,437 A 5/2000 Kamiya et al.
6,086,918 A 7/2000 Stern et al.
6,090,921 A 7/2000 Winge et al.
6,107,457 A 8/2000 Arlinghaus et al.
6,113,898 A 9/2000 Anderson et al.
6,130,364 A 10/2000 Jakobovits et al.
6,156,727 A 12/2000 Anantharamaiah et al.
6,180,377 B1 1/2001 Morgan et al.
6,191,151 B1 2/2001 Zik
6,201,165 B1 3/2001 Grant et al.
6,228,989 B1 5/2001 Traugh et al.
6,265,377 B1 7/2001 Dasseux et al.
6,287,590 B1 9/2001 Dasseux et al.
6,303,619 B1 10/2001 Linden
6,329,341 B1 12/2001 Dasseux et al.
6,367,479 B1 4/2002 Williams et al.
6,376,464 B1 4/2002 Dasseux
6,383,808 B1 5/2002 Monia et al.
6,410,802 B1 6/2002 Dasseux et al.
6,423,511 B1 7/2002 Nakamura et al.
6,423,830 B1 7/2002 Winge et al.
6,444,111 B1 9/2002 Montgomery
6,444,230 B1 9/2002 Godin et al.
6,444,681 B1 9/2002 Flavahan et al.
6,455,088 B1 9/2002 Dasseux et al.
6,458,592 B1 10/2002 Jakobovits et al.
6,459,003 B1 10/2002 Dasseux et al.
6,464,975 B2 10/2002 Millis
6,472,184 B1 10/2002 Hegemann
6,498,038 B1 12/2002 Ghosh et al.
6,506,799 B1 1/2003 Dasseux et al.
6,506,879 B1 1/2003 Ageland et al.
6,506,880 B2 1/2003 Anantharamaiah
6,514,523 B1 2/2003 Sparks
6,518,412 B1 2/2003 Dasseux et al.
6,555,651 B2 4/2003 Stern et al.
6,559,284 B1 5/2003 Ageland et al.
6,573,239 B1 6/2003 Dasseux et al.
6,602,854 B1 8/2003 Dasseux et al.
6,617,134 B1 9/2003 Sirtori et al.
6,630,450 B1 10/2003 Dasseux
6,635,623 B1 10/2003 Hoogeveen et al.
6,646,170 B2 11/2003 Dasseux et al.
6,664,230 B1 12/2003 Fogelman et al.
6,673,780 B2 1/2004 Dasseux et al.
6,680,203 B2 1/2004 Dasseux et al.
6,696,545 B1 2/2004 Buelow et al.

(56) References Cited

U.S. PATENT DOCUMENTS

| | | | |
|---|---|---|---|
| 6,699,910 | B2 | 3/2004 | Dasseux et al. |
| 6,703,422 | B2 | 3/2004 | Dasseux et al. |
| 6,713,507 | B2 | 3/2004 | Dasseux et al. |
| 6,716,816 | B1 | 4/2004 | Dasseux et al. |
| 6,717,031 | B2 | 4/2004 | Games et al. |
| 6,727,063 | B1 | 4/2004 | Lander et al. |
| 6,734,169 | B2 | 5/2004 | Dasseux et al. |
| 6,753,313 | B1 | 6/2004 | Dasseux et al. |
| 6,773,719 | B2 | 8/2004 | Rodrigueza et al. |
| 6,790,953 | B2 | 9/2004 | Dasseux et al. |
| 6,831,105 | B2 | 12/2004 | Dasseux et al. |
| 6,846,636 | B1 | 1/2005 | Argraves et al. |
| 6,849,714 | B1 | 2/2005 | Bridon et al. |
| 6,869,568 | B2 | 3/2005 | Fogelman et al. |
| 6,887,470 | B1 | 5/2005 | Bridon et al. |
| 6,909,014 | B2 | 6/2005 | Dasseux et al. |
| 6,930,085 | B2 | 8/2005 | Fogelman et al. |
| 6,933,279 | B2 | 8/2005 | Fogelman et al. |
| 6,936,691 | B2 | 8/2005 | Fiscella et al. |
| 6,982,348 | B2 | 1/2006 | Kori et al. |
| 7,144,862 | B2 | 12/2006 | Fogelman et al. |
| 7,148,197 | B2 | 12/2006 | Fogelman et al. |
| 7,148,199 | B2 | 12/2006 | Neu et al. |
| 7,166,578 | B2 | 1/2007 | Fogelman et al. |
| 7,189,689 | B2 | 3/2007 | Dasseux et al. |
| 7,192,940 | B2 | 3/2007 | Dasseux et al. |
| 7,199,102 | B2 | 4/2007 | Fogelman et al. |
| 7,211,565 | B2 | 5/2007 | Dasseux et |
| 7,217,785 | B2 | 5/2007 | Bielicki |
| 7,291,590 | B2 | 11/2007 | Kisilevsky |
| 7,312,190 | B2 | 12/2007 | Dasseux et al. |
| 7,427,662 | B2 | 9/2008 | Hornick et al. |
| 7,470,660 | B2 | 12/2008 | Schwartz et al. |
| 7,531,514 | B2 | 5/2009 | Fogelman et al. |
| 7,563,771 | B2 | 7/2009 | Anantharamiah et al. |
| 7,579,319 | B2 | 8/2009 | Fogelman et al. |
| 7,638,494 | B2 | 12/2009 | Fogelman et al. |
| 7,723,303 | B2 | 5/2010 | Fogelman et al. |
| 7,807,640 | B2 | 10/2010 | Fogelman et al. |
| 7,820,784 | B2 | 10/2010 | Fogelman et al. |
| 7,994,132 | B2 | 8/2011 | Fogelman et al. |
| 8,048,851 | B2 | 11/2011 | Fogelman et al. |
| 8,084,423 | B2 | 12/2011 | Anantharamiah et al. |
| 8,148,328 | B2 | 4/2012 | Fogelman et al. |
| 8,236,754 | B2 | 8/2012 | Fogelman et al. |
| 8,288,335 | B2 | 10/2012 | Vitek et al. |
| 8,557,767 | B2 | 10/2013 | Anantharamaiah et al. |
| 8,568,766 | B2 | 10/2013 | Anantharamaiah et al. |
| 8,568,799 | B2 | 10/2013 | Anantharamaiah et al. |
| 2001/0005714 | A1 | 6/2001 | Boffelli et al. |
| 2002/0042441 | A1 | 4/2002 | Acton et al. |
| 2002/0071862 | A1 | 6/2002 | Williams et al. |
| 2002/0128175 | A1 | 9/2002 | Anantharamaiah |
| 2002/0142369 | A1 | 10/2002 | Fersht |
| 2003/0027769 | A1 | 2/2003 | Scialdone et al. |
| 2003/0040505 | A1 | 2/2003 | Fogelman et al. |
| 2003/0045460 | A1 | 3/2003 | Fogelman et al. |
| 2003/0077641 | A1 | 4/2003 | Laskowitz et al. |
| 2003/0087819 | A1 | 5/2003 | Bielicki |
| 2003/0109442 | A1 | 6/2003 | Bisgaier et al. |
| 2003/0125260 | A1 | 7/2003 | Haviv et al. |
| 2003/0203842 | A1 | 10/2003 | Dasseux et al. |
| 2003/0229015 | A1 | 12/2003 | Fogelman et al. |
| 2004/0059110 | A1 | 3/2004 | Nakano et al. |
| 2004/0122091 | A1 | 6/2004 | Dasseux et al. |
| 2004/0136989 | A1 | 7/2004 | Banerjee et al. |
| 2004/0152623 | A1 | 8/2004 | Varadhachary et al. |
| 2004/0186057 | A1 | 9/2004 | Anantharamiah et al. |
| 2004/0224011 | A1 | 11/2004 | Rodrigueza et al. |
| 2004/0266663 | A1 | 12/2004 | Schwartz et al. |
| 2004/0266671 | A1 | 12/2004 | Fogelman et al. |
| 2005/0070996 | A1 | 3/2005 | Dinh et al. |
| 2005/0154046 | A1 | 7/2005 | Wang et al. |
| 2005/0164950 | A1 | 7/2005 | Fogelman et al. |
| 2005/0197381 | A1 | 9/2005 | Wang et al. |
| 2005/0239136 | A1 | 10/2005 | Hazen et al. |
| 2006/0069030 | A1 | 3/2006 | Bachovchin |
| 2006/0172919 | A1 | 8/2006 | Hornick et al. |
| 2006/0173067 | A1 | 8/2006 | Fogelman et al. |
| 2006/0205634 | A1 | 9/2006 | Varadhachary et al. |
| 2006/0205669 | A1 | 9/2006 | Fogelman et al. |
| 2006/0217298 | A1 | 9/2006 | Srivastava |
| 2006/0217307 | A1 | 9/2006 | Takashi et al. |
| 2006/0234908 | A1 | 10/2006 | Fogelman |
| 2006/0292117 | A1 | 12/2006 | Loiler et al. |
| 2007/0032430 | A1 | 2/2007 | Fogelman et al. |
| 2007/0060527 | A1 | 3/2007 | Fogelman et al. |
| 2007/0071756 | A1 | 3/2007 | Peyman |
| 2007/0101448 | A1 | 5/2007 | Anantharamiah et al. |
| 2007/0254839 | A1 | 11/2007 | Fogelman et al. |
| 2008/0045459 | A1 | 2/2008 | Fogelman et al. |
| 2008/0095821 | A1 | 4/2008 | Fogelman et al. |
| 2008/0096814 | A1 | 4/2008 | Fogelman et al. |
| 2008/0096815 | A1 | 4/2008 | Fogelman et al. |
| 2008/0096816 | A1 | 4/2008 | Fogelman et al. |
| 2008/0293639 | A1 | 11/2008 | Fogelman et al. |
| 2009/0163408 | A1 | 6/2009 | Fogelman et al. |
| 2009/0286741 | A1 | 11/2009 | Fogelman |
| 2010/0286025 | A1 | 11/2010 | Anantharamaiah et al. |
| 2010/0298215 | A1 | 11/2010 | Anantharamaiah et al. |
| 2011/0182992 | A1 | 7/2011 | Anantharamaiah et al. |
| 2012/0245101 | A1 | 9/2012 | Anantharamaiah et al. |
| 2013/0005645 | A1 | 1/2013 | Vitek et al. |
| 2013/0295042 | A1 | 11/2013 | Anantharamaiah et al. |
| 2016/0002315 | A1 | 1/2016 | Anantharamaiah |

FOREIGN PATENT DOCUMENTS

| | | | |
|---|---|---|---|
| AU | 2001286732 | | 10/2005 |
| AU | 2005287004 | | 3/2006 |
| AU | 2008296487 | | 3/2009 |
| AU | 2008296478 | | 12/2014 |
| AU | 2015298263 | | 7/2015 |
| AU | 2017203911 | | 6/2017 |
| AU | 2014239186 | A1 | 8/2017 |
| BR | 112017001860 | | 7/2015 |
| CA | 2420222 | | 2/2002 |
| CA | 2580501 | | 3/2006 |
| CA | 2697957 | | 3/2009 |
| CA | 2704729 | | 3/2009 |
| CA | 2714082 | | 8/2009 |
| CA | 2514303 | | 5/2012 |
| CA | 2954475 | | 7/2015 |
| CN | 1469754 | | 1/2004 |
| CN | 1739787 | A | 3/2006 |
| CN | 1943781 | | 4/2007 |
| CN | 201580041913.0 | | 7/2015 |
| EP | 45665 | A1 | 2/1982 |
| EP | 0643965 | A1 | 3/1995 |
| EP | 1186299 | | 3/2002 |
| EP | 1318828 | | 6/2003 |
| EP | 1406656 | A2 | 4/2004 |
| EP | 1562624 | | 8/2005 |
| EP | 1599173 | | 11/2005 |
| EP | 1616572 | A1 | 1/2006 |
| EP | 1799242 | | 6/2007 |
| EP | 1974747 | A1 | 10/2008 |
| EP | 2195340 | | 6/2010 |
| EP | 2195331 | | 11/2013 |
| EP | 2682400 | | 1/2014 |
| EP | 2015826625 | | 7/2015 |
| EP | 2996706 | A1 | 3/2016 |
| IL | 250302 | | 7/2015 |
| IR | 139550140003013725 | | 7/2015 |
| JP | S61-126099 | | 6/1986 |
| JP | H07-507554 | | 8/1995 |
| JP | 2000-0136202 | | 6/2000 |
| JP | 2000-136202 | | 6/2000 |
| JP | 2006-312650 | | 11/2006 |
| JP | 2010-537638 | | 12/2010 |
| JP | 2010-538005 | | 12/2010 |
| JP | 2017505143 | | 7/2015 |
| JP | 2016-515137 | A | 5/2016 |
| MX | a/2017/001432 | | 7/2015 |

(56) References Cited

FOREIGN PATENT DOCUMENTS

| | | | |
|---|---|---|---|
| MX | MX/a/2017/001432 | | 7/2016 |
| NZ | 541504 | | 8/2009 |
| NZ | 729580 | | 7/2015 |
| SA | 517380803 | | 7/2015 |
| WO | WO 1993/025581 | | 12/1993 |
| WO | WO 1997/036927 | | 10/1997 |
| WO | WO 1998/009602 | | 3/1998 |
| WO | WO 1999/016408 | | 4/1999 |
| WO | WO 1999/016409 | | 4/1999 |
| WO | WO 1999/047566 | | 9/1999 |
| WO | WO 2001/075168 | | 10/2001 |
| WO | WO 2001/075170 | | 10/2001 |
| WO | WO 2001/0175170 | | 10/2001 |
| WO | WO-02/15923 | A1 | 2/2002 |
| WO | WO-2002/15923 | A1 | 2/2002 |
| WO | WO 2002/098446 | | 12/2002 |
| WO | WO 2003/086326 | | 10/2003 |
| WO | WO 2003/089612 | | 10/2003 |
| WO | WO 2004/027027 | | 4/2004 |
| WO | WO-2004/034977 | A2 | 4/2004 |
| WO | WO 2004/043396 | | 5/2004 |
| WO | WO 2004/043403 | | 5/2004 |
| WO | WO 2001/075067 | | 10/2004 |
| WO | WO 2005/016280 | | 2/2005 |
| WO | WO 2006/020652 | | 2/2006 |
| WO | WO 2006/034056 | | 3/2006 |
| WO | WO 2006/063132 | | 6/2006 |
| WO | WO 2006/118805 | | 11/2006 |
| WO | WO 2008/021088 | | 2/2008 |
| WO | WO 2008/143679 | | 11/2008 |
| WO | WO-2009/032693 | A2 | 3/2009 |
| WO | WO 2009/032702 | | 3/2009 |
| WO | WO 2009/073725 | | 6/2009 |
| WO | WO 2009/100348 | | 8/2009 |
| WO | WO-2014/152776 | A1 | 9/2014 |
| WO | PCT/US2015/041162 | | 7/2015 |
| WO | WO-2016/018665 | A1 | 2/2016 |
| WO | WO-2016/028665 | A1 | 2/2016 |

OTHER PUBLICATIONS

Garner et al. (1998) Oxidation of high density lipoproteins. II. Evidence for direct reduction of lipid hydroperoxides by methionine residures of apolipoproteins AI and AII. J Biol Chem. 273:6088-95.

Greenaway, P.J. et al. (1982) Human cytomegalovirus DNA: *Bam*HI, *Eco*RI and *Pst*I restriction endonuclease cleavage maps. Gene. 18:355-60.

Hoogenboom et al. (1992) By-passing immunisation: Human antibodies from synthetic repertoires of germline VH gene segments rearranged in vitro. J Mol Biol. 227:381-8.

Jones et al. (1992) Computer Programs to Identify and Classify Amphipathic a Helical Domains. J Lipid Res. 33:287-96.

Miller, A.D. and Buttimore, C. (1986) Redesign of Retrovirus Packaging Cell Lines To Avoid Recombination Leading to Helper Virus Production. Mol Cell Biol. 6: 2895.

Mishra et al. (2001) Solution NMR structure of a model class A (apolipoprotein) amphipathic a helical peptide. Peptides. 22:567-73.

Mishra et al. (2006) Association of a model class A (apolipoprotein) amphipathic a helical peptide with lipid: high resolution NMR studies of peptide lipid discoidal complexes. J Biol Chem. 281:6511-9.

Presta (1992) Antibody engineering. Curr Opin Struct Biol. 2:593-6.

Purdue News (2000) 'Microspheres' Offer Promise for Oral Drug Delivery (pp. 1-3).

Raha et al. (1988) KRDS a tetra peptide derived from lactotransferrin inhibits binding of monoclonal antibody against glycoprotein lib-llla on ADP-stimulated platelets and megakaryocytes. Blood. 72: 172-8.

Sabbatini et al. (2001) Microanatomical changes of intracerebral arteries in spontaneously hypertensive rats: a model of cerebrovascular disease of the elderly. Mech Aging Dev. 122:1257-68.

Sparrow, C.P. et al. (2002) A potent synthetic LXR agonist is more effective than cholesterol loading at inducing ABC A1-mRNA and stimulating cholesterol efflux. J Biol Chem. 277:10021-7.

Wool, G.D. et al. (2008) Apolipoprotein A-I mimetic peptide helix No. and helix linker influence potentially anti-atherogenic properties. J Lipid Res. 49(6): 1268-83.

Yamamoto et al. (1995) Overexpression of Apolipoprotein E Prevents Development of Diabetic Hyperlipidermia in Transgenic Mice. Diabetes. 44(5):580-5.

Restriction Requirement issued Sep. 12, 2002 for U.S. Appl. No. 09/645,454.

Non-Final Office Action issued Jan. 22, 2003 for U.S. Appl. No. 09/645,454.

Notice of Allowance issued Jun. 25, 2003 for U.S. Appl. No. 09/645,454.

Restriction Requirement issued Feb. 20, 2003 for U.S. Appl. No. 09/896,841 (4 pages).

Non-Final Office Action issued Oct. 21, 2003 for U.S. Appl. No. 09/896,841 (12 pages).

Final Office Action issued May 7, 2004 for U.S. Appl. No. 09/896,841 (9 pages).

Notice of Allowance issued Dec. 20, 2004 for U.S. Appl. No. 09/896,841 (5 pages).

International Search Report issued May 17, 2002 for PCT App. No. PCT/US01/26457 (3 pages).

International Preliminary Examination Report issued Mar. 4, 2003 for PCT App. No. PCT/US01/26457 (5 pages).

Restriction Requirement issued Jul. 15, 2003 for U.S. Appl. No. 10/187,215 (4 pages).

Non-Final Office Action issued Jan. 8, 2004 for U.S. Appl. No. 10/187,215 (15 pages).

Non-Final Office Action issued Aug. 26, 2004 for U.S. Appl. No. 10/187,215 (7 pages).

Final Office Action issued Apr. 11, 2005 for U.S. Appl. No. 10/187,215.

Non-Final Office Action issued Oct. 28, 2005 for U.S. Appl. No. 10/187,215.

Notice of Allowance issued May 1, 2006 for U.S. Appl. No. 10/187,215.

Restriction Requirement issued Feb. 19, 2004 for U.S. Appl. No. 10/273,386.

Non-Final Office Action issued Jun. 21, 2004 for U.S. Appl. No. 10/273,386.

Final Office Action issued Feb. 2, 2005 for U.S. Appl. No. 10/273,386.

Non-Final Office Action issued Sep. 7, 2005 for U.S. Appl. No. 10/273,386.

Final Office Action issued Mar. 31, 2006 for U.S. Appl. No. 10/273,386.

Notice of Allowance issued Aug. 20, 2006 for U.S. Appl. No. 10/273,386.

Restriction Requirement issued Nov. 9, 2004 for U.S. Appl. No. 10/423,830.

Non-Final Office Action issued Apr. 18, 2005 for U.S. Appl. No. 10/423,830.

Final Office Action issued Nov. 15, 05 for U.S. Appl. No. 10/423,830.

Notice of Allowance issued Nov. 21, 2006 for U.S. Appl. No. 10/423,830.

Restriction Requirement issued Aug. 21, 2007 for U.S. Appl. No. 11/407,390, which was filed on Apr. 18, 2006 and now U.S. Pat. No. 7,723,303 on May 25, 2010 (Inventor—Fogelman et al.;).

Response to Restriction Requirement filed Nov. 23, 2007 for U.S. Appl. No. 11/407,390, which was filed on Apr. 18, 2006 and now U.S. Pat. No. 7,723,303 on May 25, 2010 (Inventor—Fogelman et al.;).

Non-Final Office Action issued Jan. 17, 2008 for U.S. Appl. No. 11/407,390, which was filed on Apr. 18, 2006 and now U.S. Pat. No. 7,723,303 on May 25, 2010 (Inventor—Fogelman et al.;).

Response to Non-Final Office Action filed Jul. 17, 2008 for U.S. Appl. No. 11/407,390, which was filed on Apr. 18, 2006 and now U.S. Pat. No. 7,723,303 on May 25, 2010 (Inventor—Fogelman et al.;).

(56) References Cited

OTHER PUBLICATIONS

Final Office Action issued Sep. 11, 2008 for U.S. Appl. No. 11/407,390, which was filed on Apr. 18, 2006 and now U.S. Pat. No. 7,723,303 on May 25, 2010 (Inventor—Fogelman et al.;).
RCE/Response to Final Office Action filed Jul. 13, 2009 for U.S. Appl. No. 11/407,390, which was filed on Apr. 18, 2006 and now U.S. Pat. No. 7,723,303 on May 25, 2010 (Inventor—Fogelman et al.;).
Ex Parte Quayle Action issued Aug. 14, 2009 for U.S. Appl. No. 11/407,390, which was filed on Apr. 18, 2006 and now U.S. Pat. No. 7,723,303 on May 25, 2010 (Inventor—Fogelman et al.;).
Response to Ex Parte Quayle Action filed Oct. 14, 2009 for U.S. Appl. No. 11/407,390, which was filed on Apr. 18, 2006 and now U.S. Pat. No. 7,723,303 on May 25, 2010 (Inventor—Fogelman et al.;).
Notice of Allowance issued Dec. 2, 2009 for U.S. Appl. No. 11/407,390, which was filed on Apr. 18, 2006 and now U.S. Pat. No. 7,723,303 on May 25, 2010 (Inventor—Fogelman et al.;).
International Search Report and Written Opinion issued Sep. 1, 2009 for PCT App. No. PCT/US2009/033415.
International Preliminary Opinion on Patentability issued Aug. 19, 2010 for PCT App. No. PCT/US2009/033415.
Restriction Requirement issued Oct. 14, 2005 for U.S. Appl. No. 10/712,447 (9 pages).
Restriction Requirement issued Feb. 16, 2006 for U.S. Appl. No. 10/712,447 (9 pages).
Non-Final Office Action issued May 31, 2006 for U.S. Appl. No. 10/712,447 (11 pages).
Final Office Action issued Mar. 2, 2007 for U.S. Appl. No. 10/712,447 (7 pages).
Advisory Action issued Aug. 13, 2007 for U.S. Appl. No. 10/712,447 (3 pages).
Non-Final Office Action issued Nov. 19, 2007 for U.S. Appl. No. 10/712,447 (9 pages).
Non-Final Office Action issued Jun. 13, 2008 for U.S. Appl. No. 10/712,447 (8 pages).
Notice of Allowance with Interview Summary and Examiner's Amendment issued Feb. 24, 2009 for U.S. Appl. No. 10/712,447 (7 pages).
Issue Notification issued Jul. 1, 2009 for U.S. Appl. No. 10/712,447 (1 page).
Certificate of Correction issued Sep. 8, 2009 for U.S. Appl. No. 10/712,447 (1 page).
Restriction Requirement issued Jun. 26, 2008 for U.S. Appl. No. 11/405,601 (11 pages).
Miscellaneous Action issued Oct. 24, 2008 for U.S. Appl. No. 11/405,601 (2 pages).
Non-Final Office Action issued Jun. 10, 2009 for U.S. Appl. No. (14 pages).
Final Office Action issued Jan. 29, 2010 for U.S. Appl. No. 11/405,601 (10 pages).
Notice of Allowance issued Sep. 9, 2011 for U.S. Appl. No. 11/405,601 (5 pages).
Issue Notification issued on Dec. 27, 2011 by the U.S. Patent and Trademark Office for U.S. Appl. No. 11/405,601 (1 page).
International Search Report issued Nov. 17, 2005 for International Patent Application No. PCT/US2003/036268 (4 pages).
International Preliminary Report on Patentability issued on Jul. 25, 2011 for International Patent Application No. PCT/US2003/036268.
Examiner's First Report issued Apr. 30, 2008 for Australian Application No. 200390825 (2 pages).
Notice of Acceptance issued Oct. 14, 2008 for Australian Application No. 200390825 (3 pages).
Grant of Request for Leave to Amend issued Jul. 3, 2009 for Australian Application No. 200390825 (1 page).
First Examination Report issued Sep. 18, 2007 for New Zealand Application No. 541504 (2 pages).
Examination Report issued for Aug. 5, 2008 New Zealand Application No. 541504 (2 pages).
Examination Report issued Jan. 22, 2009 for New Zealand Application No. 541504 (2 pages).
Examination Report and Notice of Acceptance of Completed Specification issued Apr. 7, 2009 for New Zealand Application No. 541504 (2 pages).
Letters Patent issued Aug. 13, 2009 for New Zealand Application No. 541504 (1 page).
Office Action issued Aug. 10, 2009 for Canadian Application No. 2,514,303 (3 pages).
Office Action issued Oct. 6, 2010 for Canadian Application No. 2,514,303 (2 pages).
Notice of Allowance issued on Feb. 24, 2012 by the Canadian Intellectual Property Office for Canadian Patent Application No. 2,514,303, whichwas filed on Jul. 25, 2005 and granted on Sep. 18, 2012 (Inventor—Gattadahalli et al.; Applicant—UAB research Foundation) (1 page).
Letters of Patent issued on Sep. 18, 2012 by the Canadian Intellectual Property Office for Canadian Patent Application No. 2,514,303, whichwas filed on Jul. 25, 2005 and granted on Sep. 18, 2012 (Inventor—Gattadahalli et al.; Applicant—UAB research Foundation) (2 pages).
Supplementary European Search Report mailed on Nov. 29, 2011 by the European Patent Office for patent application No. 03783409.0, which was filed on Nov. 13, 2003 and published as 1599173 on Nov. 30, 2005 (Inventor—Gattadahalli et al.; Applicant—UAB research Foundation) (3 pages).
Extended European Search Report issued on Nov. 13, 2017 by the European Patent Office for patent application No. 17157243.1, which was filed on Feb. 21, 2017 and published as EP 3254673 on Dec. 13, 2017 (Inventor—Gattadahalli et al.; Applicant—UAB research Foundation) (7 pages).
Examination Report No. 1 issued on Dec. 3, 2012 by the Intellectual Property Office of Australia for Australian Patent Application No. 2008296487, which was filed on Mar. 11, 2010 (Inventor—Anantharamaiah et al.; Applicant—UAB Research Foundation) (3 pages).
Supplementary European Search Report issued on Apr. 8, 2011 by the European Patent Office for European Patent Application No. 08829135.6, which was filed on Mar. 26, 2010 and published as 2195340 on Jun. 16, 2010 (Inventor—Anantharamaiah et al.; Applicant—UAB Research Foundation) (6 pages).
Office Action mailed on Jul. 23, 2013 by the Patent Office of Japan for Japanese Patent Application No. 2010-523116, which was filed on Feb. 26, 2010 and published as 2010- 537638 on Dec. 9, 2010 (Inventor—Anantharamaiah et al.; Applicant—UAB Research Founadtion) (13 pages).
International Search Report and Written Opinion mailed on Jul. 28, 2009 by the International Searching Authority for International Patent Application No. PCT/US2008/074485, which was filed on Aug. 27, 2008 and published as WO 2009/032702 on Mar. 12, 2009 (Inventor—Anantharamaiah et al.; Applicant—UAB Research Foundation) (12 pages).
International Preliminary Report on Patentability issued on Mar. 2, 2010 by the International Searching Authority for International Patent Application No. PCT/US2008/074485, which was filed on Aug. 27, 2008 and published as WO 2009/032702 on Mar. 12, 2009 (Inventor—Anatharamaiah et al.; Applicant—UAB Research Foundation) (9 pages).
Preliminary Amendment filed on Mar. 16, 2010 with the U.S. Patent and Trademark Office for U.S. Appl. No. 12/675,073, which was filed on Mar. 22, 2010 and now U.S Pat. No. 8,557,767 on Oct. 15, 2013 (Inventor—Anantharamaiah et al.; Applicant—UAB research Foundation) (5 pages).
Preliminary Amendment filed on Jul. 6, 2010 with the U.S. Patent and Trademark Office for U.S. Appl. No. 12/675,073, which was filed on Mar. 22, 2010 and now U.S. Pat. No. 8,557,767 on Oct. 15, 2013 (Inventor—Anantharamaiah et al.; Applicant—UAB research Foundation) (3 pages).
Preliminary Amendment filed on Jul. 14, 2010 with the U.S. Patent and Trademark Office for U.S. Appl. No. 12/675,073, which was filed on Mar. 22, 2010 and now U.S. Pat. No. 8,557,767 on Oct. 15, 2013 (Inventor—Anantharamaiah et al.; Applicant—UAB research Foundation) (3 pages).

(56) References Cited

OTHER PUBLICATIONS

Restriction Requirement issued on Jul. 9, 2012 by the U.S. Patent and Trademark Office for U.S. Appl. No. 12/675,073, which was filed on Mar. 22, 2010 and now U.S. Pat. No. 8,557,767 on Oct. 15, 2013 (Inventor—Anantharamaiah et al.; Applicant—UAB research Foundation) (6 pages).
Response to Restriction Requirement filed on Sep. 12, 2012 with the U.S. Patent and Trademark Office for U.S. Appl. No. 12/675,073, which was filed on Mar. 22, 2010 and now U.S. Pat. No. 8,557,767 on Oct. 15, 2013 (Inventor—Anantharamaiah et al.; Applicant—UAB research Foundation) (8 pages).
Non-Final Office Action issued on Oct. 2, 2012 by the U.S. Patent and Trademark Office for U.S. Appl. No. 12/675,073, which was filed on Mar. 22, 2010 and now U.S. Pat. No. 8,557,767 on Oct. 15, 2013 (Inventor—Anantharamaiah et al.; Applicant—UAB research Foundation) (9 pages).
Response to Non-Final Office Action filed on Mar. 26, 2013 with the U.S. Patent and Trademark Office for U.S. Appl. No. 12/675,073, which was filed on Mar. 22, 2010 and now U.S. Pat. No. 8,557,767 on Oct. 15, 2013 (Inventor—Anantharamaiah et al.; Applicant—UAB research Foundation) (11 pages).
Notice of Allowance issued on Jul. 9, 2013 by the U.S. Patent and Trademark Office for U.S. Appl. No. 12/675,073, which was filed on Mar. 22, 2010 and granted as 8,557,767 on Oct. 15, 2013 (Inventor—Anantharamaiah et al.; Applicant—UAB research Foundation) (9 pages).
Notice of Allowability issued on Jul. 22, 2013 by the U.S. Patent and Trademark Office for U.S. Appl. No. 12/675,073, which was filed on Mar. 22, 2010 and now U.S. Pat. No. 8,557,767 on Oct. 15, 2013 (Inventor—Anantharamaiah et al.; Applicant—UAB research Foundation) (3 pages).
Issue Notification issued on Oct. 15, 2013 by the U.S. Patent and Trademark Office for U.S. Appl. No. 12/675,073, which was filed on Mar. 22, 2010 and now U.S. Pat. No. 8,557,767 on Oct. 15, 2013 (Inventor—Anantharamaiah et al.; Applicant—UAB research Foundation) (1 page).
Restriction Requirement issued on Feb. 7, 2013 by the U.S. Patent and Trademark Office for for U.S. Appl. No. 13/429,022, which was filed on Mar. 23, 2012 and published as US 2012/0245101 on Sep. 27, 2012 (Inventor—Anantharamaiah et al.; Applicant—UAB Research Foundation) (11 pages).
Response to Restriction Requirement filed on May 22, 2013 with the U.S. Patent and Trademark Office for for U.S. Appl. No. 13/429,022, which was filed on Mar. 23, 2012 and published as US 2012/0245101 on Sep. 27, 2012 (Inventor—Anantharamaiah et al.; Applicant—UAB Research Foundation) (11 pages).
Non-Final Office Action issued on Aug. 21, 2013 by the U.S. Patent and Trademark Office for for U.S. Appl. No. 13/429,022, which was filed on Mar. 23, 2012 and published as US 2012/0245101 on Sep. 27, 2012 (Inventor—Anantharamaiah et al.; Applicant—UAB Research Foundation) (23 pages).
Notice of Abandonment issued on Mar. 12, 2014 by the U.S. Patent and Trademark Office for for U.S. Appl. No. 13/429,022, which was filed on Mar. 23, 2012 and published as US 2012/0245101 on Sep. 27, 2012 (Inventor—Anantharamaiah et al.; Applicant—UAB Research Foundation) (2 pages).
Examination Report No. 1 issued on Nov. 9, 2012 by the Australian Patent Office for Australian Patent Application No. 2008295478, which was field on Aug. 27, 2008 and granted as 2008296478 on Dec. 11, 2014 (Inventor—Anantharamaiah et al.; Applicant—UAB Research Foundation) (3 pages).
Examination Report No. 2 issued on Jan. 6, 2014 by the Australian Patent Office for Australian Patent Application No. 2008295478, which was field on Aug. 27, 2008 and granted as 2008296478 on Dec. 11, 2014 (Inventor—Anantharamaiah et al.; Applicant—UAB Research Foundation) (4 pages).
Certificate of Grant issued on Dec. 11, 2014 by the Australian Patent Office for Australian Patent Application No. 2008295478, which was field on Aug. 27, 2008 and granted as 2008296478 on Dec. 11, 2014 (Inventor—Anantharamaiah et al.; Applicant—UAB Research Foundation) (97 pages).
Office Action issued on Feb. 3, 2015 by the Canadian Intellectual Property Office for Canadian Patent Application No. 2,704,729, which was filed on Aug. 27, 2008 (Inventor—Anantharamaiah et al.; Applicant—UAB Research Foundation) (4 pages).
Office Action issued on Apr. 25, 2016 by the Canadian Intellectual Property Office for Canadian Patent Application No. 2,704,729, which was filed on Aug. 27, 2008 (Inventor—Anantharamaiah et al.; Applicant—UAB Research Foundation) (4 pages).
Office Action issued on May 6, 2017 by the Canadian Intellectual Property Office for Canadian Patent Application No. 2,704,729, which was filed on Aug. 27, 2008 (Inventor—Anantharamaiah et al.; Applicant—UAB Research Foundation) (4 pages).
Supplementary European Search Report issued on Apr. 8, 2011 by the European Patent Office for European Patent Application No. 08798802.8, which was filed on Aug. 27, 2008 and granted as 2195331 on Nov. 20, 2013 (Inventor—Anantharamaiah et al.; Applicant—UAB research Foundation) (6 pages).
Extended European Search Report issued on Dec. 3, 2013 by the European Patent Office for European Patent Application No. 13187186.5, which was filed on Oct. 7, 2013 and published as 2682400 on Jan. 8, 2014 (Inventor—Anantharamaiah et al.; Applicant—UAB research Foundation) (10 pages).
Transmittal of the International Search Report and Written Opinion mailed on Mar. 9, 2009 by the International Searching Authority for International Patent Application No. PCT/US2008/074470, which was filed on Aug. 27, 2008 and published as WO 2009/032693 on Mar. 12, 2009 (Inventor—Anantharamaiah et al.; Applicant—UAB Research Foundation).
Internation Preliminary Report on Patentability issued on Mar. 2, 2010 by the International Searching Authority for International Patent Application No. PCT/US2008/074470, which was filed on Aug. 27, 2008 and published as WO 2009/032693 on Mar. 12, 2009 (Inventor—Anantharamaiah et al.; Applicant—UAB Research Foundation) (4 pages).
Restriction Requirement issued on Apr. 16, 2012 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (7 pages).
Non-Final Office Action issued on Jun. 29, 2012 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (13 pages).
Final Office Action issued on Jan. 10, 2013 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (21 pages).
Non-Final Office Action issued on Jul. 15, 2014 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (21 pages).
Final Office Action issued on Feb. 13, 2015 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (22 pages).
Notice of Allowance issued on Aug. 3, 2015 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (5 pages).
Notice of Allowance issued on Apr. 21, 2016 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (6 pages).

(56) References Cited

OTHER PUBLICATIONS

Issue Notification issued on Aug. 3, 2016 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (1 page).
Restriction Requirement issued on Mar. 6, 2017 by the U.S. Patent and Trademark Office for for U.S. Appl. No. 14/851,622, filed Sep. 11, 2015 and published as US 2016/0151455 on Jun. 2, 2016 (Inventor—Anantharamaiah et al.; Applicant—UAB Research Foundation) (7 pages).
Non-Final Office Action issued on Oct. 16, 2017 by the U.S. Patent and Trademark Office for for U.S. Appl. No. 14/851,622, filed Sep. 11, 2015 and published as US 2016/0151455 on Jun. 2, 2016 (Inventor—Anantharamaiah et al.; Applicant—UAB Research Foundation) (12 pages).
Office Action issued on Jan. 23, 2015 by the Canadian Intellectual Property Office for Canadian Patent Application No. 2,714,082, which was filed on Aug. 4, 2010 (Inventor—Anantharamaiah et al.; Applicant—UAB Research Foundation) (5 pages).
Restriction Requirement issued on Aug. 12, 2010 by the U.S. Patent and Trademark Office for U.S. Appl. No. 12/027,728, filed Feb. 7, 2008 and now U.S. Pat. No. 8,568,766 on Oct. 29, 2013 (Inventor—Anantharamaiah et al.; Applicant—UAB research Foundation) (7 pages).
Response to Restriction Requirement filed on Sep. 27, 2010 with the U.S. Patent and Trademark Office for U.S. Appl. No. 12/027,728, filed Feb. 7, 2008 and now U.S. Pat. No. 8,568,766 on Oct. 29, 2013 (Inventor—Anantharamaiah et al.; Applicant—UAB research Foundation).
Non-Final Office Action issued on May 27, 2011 by the U.S. Patent and Trademark Office for U.S. Appl. No. 12/027,728,filed Feb. 7, 2008 and now U.S. Pat. No. 8,568,766 on Oct. 29, 2013 (Inventor—Anantharamaiah et al.; Applicant—UAB research Foundation).
Response to Non-Final Office Action filed on Nov. 1, 2011 with the U.S. Patent and Trademark Office for U.S. Appl. No. 12/027,728, filed Feb. 7, 2008 and now U.S. Pat. No. 8,568,766 on Oct. 29, 2013 (Inventor—Anantharamaiah et al.; Applicant—UAB research Foundation).
Non-Final Office Action issued on Jan. 13, 2012 by the U.S. Patent and Trademark Office for U.S. Appl. No. 12/027,728, filed Feb. 7, 2008 and now U.S. Pat. No. 8,568,766 on Oct. 29, 2013 (Inventor—Anantharamaiah et al.; Applicant—UAB research Foundation) (15 pages).
Response to Non-Final Office Action filed on Apr. 10, 2012 with the U.S. Patent and Trademark Office for U.S. Appl. No. 12/027,728, filed Feb. 7, 2008 and now U.S. Pat. No. 8,568,766 on Oct. 29, 2013 (Inventor—Anantharamaiah et al.; Applicant—UAB research Foundation) (15 pages).
Non-Final Office Action issued on Jun. 14, 2012 by the U.S. Patent and Trademark Office for U.S. Appl. No. 12/027,728, filed Feb. 7, 2008 and now U.S. Pat. No. 8,568,766 on Oct. 29, 2013 (Inventor—Anantharamaiahet al .; Applicant—UAB research Foundation) (11 pages).
Response to Non-Final Office Action filed on Oct. 10, 2012 with the U.S. Patent and Trademark Office for U.S. Appl. No. 12/027,728, filed Feb. 7, 2008 and now U.S. Pat. No. 8,568,766 on Oct. 29, 2013 (Inventor—Anantharamaiah et al.; Applicant—UAB research Foundation) (10 pages).
Supplemental Response to Non-Final Office Action filed on Dec. 5, 2012 with the U.S. Patent and Trademark Office for U.S. Appl. No. 12/027,728, filed Feb. 7, 2008 and now U.S. Pat. No. 8,568,766 on Oct. 29, 2013 (Inventor—Anantharamaiah et al.; Applicant—UAB research Foundation) (8 pages).
Notice of Allowance issued on Dec. 17, 2012 by the U.S. Patent and Trademark Office for U.S. Appl. No. 12/027,728, filed Feb. 7, 2008 and now U.S. Pat. No. 8,568,766 on Oct. 29, 2013 (Inventor—Anantharamaiah et al.; Applicant—UAB research Foundation) (5 pages).
Notice of Allowance issued on Jan. 29, 2013 by the U.S. Patent and Trademark Office for U.S. Appl. No. 12/027,728, filed Feb. 7, 2008 and now U.S. Pat. No. 8,568,766 on Oct. 29, 2013 (Inventor—Anantharamaiah et al.; Applicant—UAB research Foundation) (2 pages).
Notice of Allowance issued on Feb. 12, 2013 by the U.S. Patent and Trademark Office for U.S. Appl. No. 12/027,728, filed Feb. 7, 2008 and now U.S. Pat. No. 8,568,766 on Oct. 29, 2013 (Inventor—Anantharamaiah et al.; Applicant—UAB research Foundation) (2 pages).
Issue Notification issued on Oct. 29, 2013 by the U.S. Patent and Trademark Office for U.S. Appl. No. 12/027,728, filed Feb. 7, 2008 and now U.S. Pat. No. 8,568,766 on Oct. 29, 2013 (Inventor—Anantharamaiah et al.; Applicant—UAB research Foundation) (1 page).
Restriction Requirement issued on Feb. 1, 2013 by the U.S. Patent and Trademark Office for U.S. Appl. No. 12/865,957, filed Oct. 15, 2010 and published as US 2011/0182992 on Jul. 28, 2011 (Inventor—Anantharamaiah et al.; Applicant—UAB research Foundation) (8 pages).
Non-Final Office Action issued on Nov. 1, 2013 by the U.S. Patent and Trademark Office for U.S. Appl. No. 12/865,957, filed Oct. 15, 2010 and published as US 2011/0182992 on Jul. 28, 2011 (Inventor—Anantharamaiah et al.; Applicant—UAB research Foundation) (6 pages).
Response to Non-Final Office Action filed on Mar. 25, 2014 with the U.S. Patent and Trademark Office for U.S. Appl. No. 12/865,957, filed Oct. 15, 2010 and published as US 2011/0182992 on Jul. 28, 2011 (Inventor—Anantharamaiah et al.; Applicant—UAB research Foundation) (14 pages).
Final Office Action issued on Jun. 9, 2014 by the U.S. Patent and Trademark Office for U.S. Appl. No. 12/865,957, filed Oct. 15, 2010 and published as US 2011/0182992 on Jul. 28, 2011 (Inventor—Anantharamaiah et al.; Applicant—UAB research Foundation) (5 pages).
Response After Final Office Action filed on Oct. 9, 2014 with the U.S. Patent and Trademark Office for U.S. Appl. No. 12/865,957, filed Oct. 15, 2010 and published as US 2011/0182992 on Jul. 28, 2011 (Inventor—Anantharamaiah et al.; Applicant—UAB research Foundation) (6 pages).
Notice of Allowance issued on Dec. 10, 2014 by the U.S. Patent and Trademark Office for U.S. Appl. No. 12/865,957, filed Oct. 15, 2010 and published as US 2011/0182992 on Jul. 28, 2011 (Inventor—Anantharamaiah et al.; Applicant—UAB research Foundation) (5 pages).
Notice of Abandonment issued on May 13, 2015 by the U.S. Patent and Trademark Office for U.S. Appl. No. 12/865,957, filed Oct. 15, 2010 and published as US 2011/0182992 on Jul. 28, 2011 (Inventor—Anantharamaiah et al.; Applicant—UAB research Foundation) (1 page).
Restriction Requirement issued on Nov. 27, 2013 by the U.S. Patent and Trademark Office for U.S. Appl. No. 13/804,161, filed Mar. 14, 2013 and published as US 2013/0295042 on Nov. 7, 2013 (Inventor—Anantharamaiah et al.; Applicant—UAB research Foundation) (7 pages).
Non-Final Office Action issued on Jul. 10, 2014 by the U.S. Patent and Trademark Office for U.S. Appl. No. 13/804,161, filed Mar. 14, 2013 and published as US 2013/0295042 on Nov. 7, 2013 (Inventor—Anantharamaiah et al.; Applicant—UAB research Foundation) (26 pages).
Notice of Allowance issued on Feb. 3, 2015 by the U.S. Patent and Trademark Office for U.S. Appl. No. 13/804,161, filed Mar. 14, 2013 and published as US 2013/0295042 on Nov. 7, 2013 (Inventor—Anantharamaiah et al.; Applicant—UAB Research Foundation) (10 pages).
Notice of Abandonment issued on May 21, 2015 by the U.S. Patent and Trademark Office for U.S. Appl. No. 13/804,161, filed Mar. 14, 2013 and published as US 2013/0295042 on Nov. 7, 2013 (Inventor—Anantharamaiah et al.; Applicant—UAB Research Foundation) (1 page).
Examination Report issued on Sep. 21, 2017 by the Canadian Intellectual Property Office for Patent Application No. 2903869,

(56) References Cited

OTHER PUBLICATIONS which was filed on Mar. 14, 2013 (Invento—G.M. Anantharamaiah, et al.; Applican—UAB Research Foundation) (6 pages).
Office Action issued on Feb. 1, 2018 by the European Patent Office for Patent Application No. 14769489.7, which was filed on Mar. 14, 2014 and published as EP 2996706 on Mar. 22, 2016 (Inventor—Anantharamaiah et al.; Applican—UAB Research Foundation) (5 pages).
Office Action issued on Dec. 11, 2017 by the Patent Office of Japan for Patent Application No. 2016-502527, which was filed on Mar. 14, 2014 and published as 2016-515137 on May 26, 2017 (Inventor—G.M. Anantharamaiah, et al.; Applican—UAB Research Foundation) (Origina—4 pages // Translation—6 pages).
Response to Final Office Action and Request for Continued Examination filed on Sep. 19, 2017 with the U.S. Patent and Trademark Office for U.S. Appl. No. 14/770,270, filed Aug. 25, 2015 and published as US 2016/0002315 on Jan. 17, 2016 (Inventor—G.M. Anantharamaiah, et al.; Applicant—UAB Research Foundation) (13 pages).
Non-Final Office Action issued on Mar. 12, 2018 by the U.S. Patent and Trademark Office for U.S. Appl. No. 14/770,270, which was filed on Aug. 25, 2015 and published as US 2016/0002315 on Jan. 17, 2016 (Inventor—G.M. Anantharamaiah, et al.; Applicant—UAB Research Foundation) (18 pages).
Applicant-Initiated Interview Summary issued on Jun. 26, 2018 by the U.S. Patent and Trademark Office for U.S. Appl. No. 14/770,270, filed Aug. 25, 2015 and published as US 2016/0002315 on Jan. 17, 2016 (Inventor—G.M. Anantharamaiah, et al.; Applicant—UAB Research Foundation) (3 pages).
Supplementary European Search Report issued on Feb. 2, 2018 by the European Patent Office for Patent Application No. 15826625.4, which was filed on Jul. 20, 2015 and published as EP 3189069 on Jul. 12, 2017 (Inventor—Anatharamaiah et al.; Applicant—UAB Reasearch Foundation et al.) (10 pages).
Office Action issued on Jul. 3, 2018 by the Canadian Intellectual Property Office for Patent Application No. 2,704,729, which was filed on Feb. 25, 2010 (Inventor Anatharamaiah et al.; Applicant—UAB Research Foundation) (3 pages).
Patent Examination Report No. 1 issued on Apr. 15, 2016 by the Intellectual Property Office of Australia for Patent Application No. AU 2014239186, which was filed on Mar. 14, 2014 (Inventor—Anatharamaiah et al.; Applicant—UAB Research Foundation) (3 pages).
Examination Report No. 2 issued on Dec. 22, 2016 by the Intellectual Property Office of Australia for Patent Application No. AU 2014239186, which was filed on Mar. 14, 2014 (Inventor—Anatharamaiah et al.; Applicant—UAB Research Foundation) (3 pages).
Notice of Acceptance issued on Apr. 11, 2017 by the Intellectual Property Office of Australia for Patent Application No. AU 2014239186, which was filed on Mar. 14, 2014 (Inventor—Anatharamaiah et al.; Applicant—UAB Research Foundation) (3 pages).
Certificate of Grant issued on Aug. 3, 2017 by the Intellectual Property Office of Australia for Patent Application No. AU 2014239186, which was filed on Mar. 14, 2014 (Inventor—Anatharamaiah et al.; Applicant—UAB Research Foundation) (1 page).
Examination Report issued on Sep. 8, 2016 by the Canadian Intellectual Property Office for Patent Application No. 2903869, which was filed on Mar. 14, 2013 (Inventor—G.M. Anantharamaiah, et al.; Applicant—UAB Research Foundation) (4 pages).
European Search Report was issued on Dec. 19, 2016 by the European Patent Office for Patent Application No. 14769489.7, which was filed on Mar. 14, 2014 and published as 2996706 on Mar. 23, 2016 (Applicant—UAB Research Foundation et al.) (8 pages).
First Examination Report issued on Apr. 8, 2016 by the New Zealand Intellectual Property Office for Patent No. 713291, which was filed on Mar. 14, 2014 (Inventor—Anatharamaiah et al.; Applicant—UAB Research Foundation) (5 pages).
Further Examination issued on Dec. 7, 2016 by the New Zealand Intellectual Property Office for Patent No. 713291, which was filed on Mar. 14, 2014 (Inventor—Anatharamaiah et al.; Applicant—UAB Research Foundation) (3 pages).
Notice of Acceptance issued on Apr. 10, 2017 by the New Zealand Intellectual Property Office for Patent No. 713291, which was filed on Mar. 14, 2014 (Inventor—Anatharamaiah et al.; Applicant—UAB Research Foundation) (1 page).
International Search Report and Written Opinion issued on Jul. 11, 2014 for application PCT/US14/27719, which was filed on Mar. 14, 2014 and published as WO 2014/0152776 on Sep. 25, 2014 (Inventor—Anantharamaiah; Applicant—UAB Research Foundation) (27 pages).
International Preliminary Report on Patentability issued on Sep. 24, for Patent Application No. PCT/US14/27719, which was filed on Mar. 14, 2014 and published as WO 2014/0152776 on Sep. 25, 2014 (Applicant—UAB Research Foundation// Inventor—Anantharamaiah) (8 pages).
Restriction Requirement issued on Dec. 18, 2015 by the U.S. Patent and Trademark Office for U.S. Appl. No. 14/770,270, filed Aug. 25, 2015 and published as US 2016/0002315 on Jan. 7, 2016 (Inventor—Anantharamaiah et al.; Applicant—UAB Research Foundation) (7 pages).
Non-Final Office Action issued on Jul. 6, 2016 by the U.S. Patent and Trademark Office for U.S. Appl. No. 14/770,270, filed Aug. 25, 2015 and published as US 2016/0002315 on Jan. 7, 2016 (Inventor—Anantharamaiah et al.; Applicant—UAB Research Foundation) (20 pages).
Final Office Action issued on Apr. 21, 2017 by the U.S. Patent and Trademark Office for U.S. Appl. No. 14/770,270, filed Aug. 25, 2015 and published as US 2016/0002315 on Jan. 7, 2016 (Inventor—Anantharamaiah et al.; Applicant—UAB Research Foundation) (19 pages).
International Search Report and Written Opinion mailed on Dec. 15, 2015 by the International Searching Authority for Patent Application No. PCT/US2015/041162, which was filed on Jul. 20, 2015 and published as WO 2016/018665 on Feb. 4, 2016 (Inventor—Anatharamaiah et al.; Applicant—UAB Research Foundation et al.) (11 pages).
International Preliminary Report on Patentability issued on Jan. 31, 2017 by the International Searching Authority for Patent Application No. PCT/US2015/041162, which was filed on Jul. 20, 2015 and published as WO 2016/018665 on Feb. 4, 2016 (Inventor—Anatharamaiah et al.; Applicant—UAB Research Foundation et al.) (6 pages).
Office Action was issued on Oct. 7, 2019 by the Canadian Patent Office for Candian Application No. 2903869, filed on Mar. 14, 2014 (Applicant—U.A.B. Research Foundation, et al.) (5 Pages).
Office Action was issued on Jun. 26, 2019 by the Canadian Patent Office for CA Application No. 2954475, which was filed on Jul. 20, 2015 and published as CA 2954475 A1 on Feb. 4, 2016 (Applicant—UAB Research Foundation, et al.) (4 pages).
Non Final Rejection was issued on Sep. 20, 2019 by the USPTO for U.S. Appl. No. 14/770,270, filed Aug. 25, 2015 and published as US 2016/0002315 A1 on Jan. 7, 2016 (Inventor—Gattadahalli M. Anantharamaiah, et al.) (6pages).
Office Action issued on Sep. 28, 2018 by the Intellectual Property Office of India for Patent Application No. 6250/CHENP/2015, which was filed on Oct. 9, 2015 and published on Jul. 1, 2016 (Inventor—Anantharamaiah et al.; Applicant—UAB Research Foundation) (6 pages).
U.S. Appl. No. 62/031,585, filed Jul. 31, 2014, Anantharamaiah.
U.S. Appl. No. 15/329,735, filed Jan. 27, 2017, Anantharamaiah.
Zhang et al, "Converting Peptides into Drug Leads by Lipidation," Current Medicinal Chemistry 19:1602-1618 (2012) .*
Abrahmsen, L. et al. (1991) Engineering Subtilisin and its Substrates for Efficient Ligation of Peptide Bonds in Aqueous Solution. Biochemistry. 30(17): 4151-9.
Acsadi, G. et al. (1991) Human Dystrophin Expression in MDX mice after Intramuscular Injection of DNA Constructs. Nature. 352(6338): 815-8.
Adachi, T. et al. (2003) Binding oh Human Xanthine Oxidase to Sulphated Glycosaminoglycans on the Endothelial-Cell Surface. Biochemistry. 289(2): 523-7.

(56) References Cited

OTHER PUBLICATIONS

Aikawa, M. et al. (2002) Lipid Loweing Reduces Oxidative Stress and Endothelial Cal Activation in Rabbit Atheroma. Circulation. 106(11): 1390-6.
Ajees, A.A. et al. (2006) Crystal Structure of Human Apolipoprotein A-1: Insights into its Protective Effect Against Cardiovascular Diseases. Proc Natl Acad Sci USA. 103(7): 2126-31.
Ali, K. et al. (2005) Apoliopoprotein E Suppresses the Type 1 Inflammatory Response in Vivo. Circ Res. 97(9): 922-7.
Anantharamaiah, G.M. et al. (1985) Studies of Synthetic Peptide Analogs of the Amphipathic Helix: Structure of Complexes with Dimyristoyl Phosphatidylcholine. J Biol Chem. 260(18): 10248-55.
Anantharamaiah, G.M. et al. (1988) Effect of Oxidation on the Properties of Apolipoproteins A-I and A-II. J Lipid Res. 29(3): 309-18.
Anantharamaiah, G.M. et al. (1990) Use of Synthetic Peptide Analogues to Localize Lecithin: Cholesterol Acyltransferase Activating Domain in Apolipoprotein A-I. Ateriosclerosis. 10(1): 95-105.
Anantharamaiah, G.M. et al. (2006) Synthetic Peptides: Managing Lipid Disorders. Curr Opin Lipidol. 17(3): 233-7.
Anantharamaiah, G.M. et al. (2007) Structural Requirements for Antioxidative and Anti-Inflammatory Properties of Apolipoprotein A-I Mimetic Peptides. J Lipid Res. 48(9): 1915-23.
Anantharamaiah, G.M. et al. (2001) Toward the Design of Peptide Mimics of Antiatherogenic Apolipoproteins A-I and E. Curr Sci. 81(1): 53-65.
Aoyagi, H. et al. (1988) Sytheses of Antibacterial Peptides, Gramicidin S Analogs and Designed Amphiphilic Oligopeptides. Tetrahedron. 44(3):877-86.
Aravinda, S. et al. (2003) Aromatic-Aromatic Interactions in Crystal Structures of Helical Peptide Scaffolds Containing Projecting Phenylalinine Residues. J Am Chem Soc. 125(18): 5308-15.
Arisaph Pharmaceuticals Reports on Promising Results Presented at American Heart Association: Novel Apo A-1-Mimetic Peptide Significantly Inhibits Atherosclerosis in Preclinical Animal Study, BioSpace News, (Nov. 14, 2005) (2 pages). http://www.biospace.com/News/arisaph-pharmaceuticals-reports-on-promising/2610.
Armitage, B. et al., Peptide Nucleic Acid-DNA Duplexes: Long Range Hole Migration from an Internally Linked Anthraquinone, Proc Natl Acad Sci USA, 94(23): 12320-5 (1997).
Ashby, D. et al., Lack of Effect of Serum Amyloid A (SAA) on the Ability of High-Density Lipoproteins to Inhibit Endothelial Cell Adhesion Molecule Expression, Atherosclerosis, 154(1): 113-21 (2001).
Ashby, D.T. et al., Factors influencing the Ability of HDL to Inhibit Expression of Vascular Cell Adhesion Molecule-1 in Endothelial Cells, Arterioscler Thromb Vasc Biol, 18(9): 1450-5 (1998).
Badimon, J.J. et al., Regression of Atherosclerosis Lesions by High Density Lipoprotein Plasma Fraction in the Cholesterol-Fed Rabbit, J Clin Invest, 85(4): 1234-41 (1990).
Baggiolini, M and I. Clark-Lewis, Interlukin-8, a Chemotactic and Inflammatory Cytokine, FEBS Lett, 307: 97-101 (1992).
Bailey, R.W. et al., Clusterin, a Binding Protein with a Molten Globule-Like Region, Biochemistry, 40(39): 11828-40 (2001).
Baker, P.W. et al., Ability of Reconstituted High Density Lipoproteins to Inhibit Cytokine-Induced Expression of Vascular Cell Adhesion Molecule-1 in Human Umbilical Vein Endothelial Cells, J Lipid Res, 40(2): 345-53 (1999).
Baker, P.W. et al., Phospholipid Composition of Reconstituted High Density Lipoproteins Influences Their Ability to Inhibit Endothelial Cell Adhesion Molecule Expression, J Lipid res, 41(8):1261-7 (2000).
Barengolts et al., Osteoporosis and Coronary Atherosclerosis in Asymptomatic Postmenopausal Woman, Calcif Tissue Int, 62(3):209-13 (1998).
Barter, P.J. and K.A. Rye, High Density Lipoproteins and Coronary Heart Disease, Atherosclerosis, 121(1): 1-12 (1996).
Baumbach et al., Structure of Cerebral Arterioles in Cystathionine β-Synthase-Deficient Deficient Mice, Circ res, 91(10): 931-7 (2002).
Baumbach et al., Cerebral Arteriolar Structure in Mice Overexpressing Human Renin and Angiotensinogen, Hypertension, 41(1): 50-5 (2003).
Beatty S, Koh H, Phil M, Henson D, Boulton M. (2000) The role of oxidative stress in the pathogenesis of age-related macular degeneration. Surv Ophthalmol. 45(2):115-134.
Bechinger B. (2000) Understanding peptide interactions with the lipid bilayer: a guide to membrane protein engineering. Curr Opin Chem Biol. 4(6):639-644.
Beisiegel, U. et al. The LDL-receptor-related protein, LRP, is an apolipoprotein E-binding protein. Nature 341: 162-164 (1989).
Bergt, C. et al., (2004) The myeloperoxidase product hypochlorous acid oxidizes HDL in the human artery wall and impairs ABCA1-dependent cholesterol transport. Natl Acad Sci USA. 101:13032-7.
Berkner et al. (1987) Abundant Expression of Polyomavirus Middle T Antigen and Dihydrofolate Reductase in an Adenovirus Recombinant. J. Virology 61:1213-1220.
Besiegel, U. et al. (1991) Lipoprotein lipase enhances the binding of chylomicrons to low density lipoprotein receptor-related protein Proc. Natl. Acad. Sci. U.S.A. 88:8342-8346.
Betteridge, D.J., Long-term risk reduction: Who needs treatment?, Diabetes Research and Clinical Practice. (2005) 68S2:S15-2.
Bisoendial et al. (2003) Restoration of Endothelial Function by Increasing High-Density Lipoprotein in Subjects With Isolated Low High-Density Lipoprotein Circulation 107: 2944-2948.
Blackburn WD Jr, et al. (1991) Apolipoprotein A-I decreases neutrophil degranulation and superoxide production. J Lipid Res. 32(12): 1911-1918.
Blankenberg et al. (2001) Circulating cell adhesion molecules and death in patients with coronary artery disease. Circulation 2001; 104:1336-1342.
Boerner et al. (1991) Production of Antigen-Specific Human Monoclonal Antibodies from in Vitro-Primed Human Splenocytes. J. Immunol., 147(1):86-95.
Boffa et al., Isolation of active genes containing CAG repeats by DNA strand invasion by a peptide nucleic acid. Proc Natl Acad Sci USA. Mar. 14, 1995; 92(6): 1901-5.
Boffelli et al. (1997) Reconstitution and Further Characterization of the Cholesterol Transport Activity of the Small-Intestinal Brush Border Membrane Biochemistry 36:10784-10792.
Boffelli et al., (1997) The uptake of cholesterol at the small-intestinal brush border membrane is inhibited by apolipoproteins. FEBS Letters, 411: 7-11.
Borhani et al. (1999) Crystal structure of truncated human apolipoprotein A-1 suggests a lipid bound conformation. Proc. Natl. Acad. Sci. USA. 94:12291-12296.
Bourdillon et al. (2000) ICAM 1 deficiency reduces atherosclerotic lesions in double-knockout mice (ApoE(-/ ) IICAM-1(-/-)) fed a fat or a chow diet. Arterioscler Thromb Vasc Biol 2000;20:2630-2635.
Bowry et al. (1992) High density lipoprotein is the major carrier of lipid hydroperoxides in human blood plasma from fasting donors. Proc Natl Acad Sci USA. 1992;89:10316-10320.
Braddock. D. T., et al., (1996) Conformationally Specific Enhancement of Receptor-ediated LDL Binding and Internalization by Peptide Models of a Conserved Anionic N-Termina Domain of Human Apolipoprotein E. Biochemistry 35, 13975-13984.
Bradley et al. (1982) Apolipoprotein E degradation in human very low density lipoproteins by protease(s): chemical and biological consequences. Biochim. Biophys. Res. Commun. 109:1360-1367.
Brigham et al. (1989) Expression of a prokaryotic gene in cultured lung endothelial cells after lipofection with a plasmid vector. Am. J. Resp. Cell. Mol. Biol. 1: 95-100.
Brousseau, M.E. (2005) Emerging role of high-density lipoprotein in the prevention of cardiovascular disease. Drug Discovery Today. 10:1095-1099.
Brousseau, M.E., and Hoeg, J.M. (1999) Transgenic rabbits as models for atherosclerosis research. J. lipid Res. 40:365-375.
Brown, D.T. and Burlingham, B.T., (1973) Penetration of Host Cell Membranes by Adenovirus 2 J. Virology 12:386-396.
Vitamins, or the Combination for the Prevention of Coronary Disease. N Engl J Med. 345(22):1583-92.

(56) References Cited

OTHER PUBLICATIONS

Brown M.L., et al. (2000) A Macrophage Receptor for Apolipoprotein B48: Clining, Expression, and Atherosclerosis. Proc. Natl. Acad. Sci. USA 97:7488-7493.
Burger et al. (2002) High-density lipoprotein-associated apolipoprotein A-I: the missing link between infection and chronic inflammation? Autoimmunity Reviews 2002;1:111-117.
Burnett, J.R. and Vasikaran, S.D. (2002) Cardiovascular disease and osteoporosis: is there a link between lipids and bone? Ann Clin Biochem. 39(Pt 3): 203-210.
Calabresi L, et al. (2002) Elevated cellular adhesion molecules in subjects with low ML-cholesterol. Arterioscler Thromb Vasc Biol.; 22:656-661.
Calabresi L, Franceschini G, Sirtoh CR, De Palma A, Saresella M, Ferrante P, Taramelli D. Inhibition of VCAM-1 expression in endothelial cells by reconstituted high density lipoproteins. Biochem Biophys Res Commun. (1997) 238:61-65.
Calabresi, L., et al., (2003) Entothelial Protection by High-Denisty Lipoproteins. Athero. Thromb. Vasc. Biol. 23:1724-1731.
Campbell, E.J. Human leukocyte elastase, cathepesin G and lactoferrin: family of neutrophil granule glycoproteins that bind to an alveolar macrophage receptor. Proc Natl Acad Sci USA (1982) 79:6941-6945.
Cardillo, C. et al., (1997) Xanthine Oxidase Inhibition With Oxypurinol Improves Endothelial Vasodilator Function in Hypercholesterolemic but Not in Hypertensive Patients. Hypertension 30:57-63.
Carlos TM, et al. (1990) Vascular cell adhesion molecule-1 mediates lymphocyte adherence to cytokine-activated cultured human endothelial cells. Blood;76:965-970.
Carr, A.C. et al. (2000) Oxidation of LDL by myeloperoxidase and reactive nitrogen species oxidation of LDL by myeloperoxidase and reactive nitrogen species. Arterioscler Thromb Vasc Biol; 20:1716-1723.
Carrara et al., Two helices plus a linker: A small model substrate for eukaryotic RNase P Proc. Natl. Acad. Sci. (USA) 92:2627-2631 (1995).
Casserly, I. and Topol, E. (2004) Convergence of atherosclerosis and Alzheimer's disease: inflammation, cholesterol, and misfolded proteins. Lancet. 363:1139-46.
Castelli, W.P. et al., Incidence of coronary heart disease and lipoprotein cholesterol levels. The Framingham study. JAMA. 1986. 256:2835-8. Abstract.
Catapano, A.L. et al. (1979) Suppression of 3-hydroxy-3-methylglutaryl-CoA reductase by low density lipoproteins produced in vitro by lipoprotein lipase action on nonsuppressive very low density lipoproteins. J Biol Chem. 254:1007-9.
Charles-Schoeman, C. et al. (2008) Treatment with an apolipoprotein A-1 mimetic peptide in combination with pravastatin inhibits collagen-induced arthritis. Clin Immunol. 127(2): 234-44.
Chiesa, G. et al. (2002) Recombinant apolipoprotein A-I(Milano) infusion into rabbit carotid artery rapidly removes lipid from fatty streaks. Circ Res. 90:974-80.
Chillon, J. and Baumbach, G.L. (1999) Effects of an Angiotensin-Converting Enzyme Inhibitor and a b-Blocker on Cerebral Arterioles in Rats. Hypertension. 33: 856-61.
Chorev, M. and Goodman, M. (1995) Recent developments in retro peptides and proteins-an ongoing topochemical exploration. Trends Biotechnol. 13(10): 438-45.
Christison J, (1996) Rapid reduction and removal of HDL- but not LDL-associated cholesteryl ester hydroperoxides by rat liver in situ. Biochem J. 314:739-42.
Chung, B.H. et al. (1994) Liposome-like Particles Isolated From Human Atherosclerotic Plaques are Structurally and Compositionally Similar to Surface Remnants of Triglyceride-Rich Lipoproteins. Arterioscler Thromb. 14:622-35.
Chung et al., (1985) Studies of Synthetic Peptide Analogs of the Amphipathic Helix. J Biol Chem. 60(18): 10256-62.
Chung, B.H., et al. (1996) Probing structure and function of VLDL by synthetic amphipathic helical peptides. J Lipid Res. 37:1099-112.
Clark-Lewis et al. (1991) Chemical Synthesis, Purification, and Characterization of Two Inflammatory Proteins, Neutrophil Activating Peptide 1 (Interleukin-8) and Neutrophil Activating Peptide 2. Biochemistry. 30: 3128-35.
Clark-Lewis I, et al. (1994) Structural requirements for interleukin-8 function identified by design of analogs and CXC chemokine hybrids. J Biol Chem. 269(23): 16075-81.
Clay, M.A. et al. (2001) Time sequence of the inhibition of endothelial adhesion molecule expression by reconstituted high density liproteins, Atherosclerosis 157: 23-9.
Clay, M.A. et al. (1995) Localization of a domain in apolipoprotein E with both cytostatic and cytotoxic activity. Biochemistry. 34:11142-51.
Clee, S.M. et al. (2000) Age and residual cholesterol efflux affect HDL cholesterol levels and coronary artery disease in ABCA1 hetrozygotes. J Clin Invest. 106:1263-70.
Clubb, F.J., et al. (2001) Development of atherosclerotic plaque with endothelial disruption in Watanabe heritable hyperlipidemic rabbit aortas. Cardiovasc. Pathol. 9:1-11.
Cockerill, G.W. et al. (2001) Elevation of plasma high-density lipoprotein concentration reduces interleukin-I induced expression of E-selectin in an in vivo model of acute inflammation. Rculation. 103:108-12.
Cockerill, G.W. et al. (1999) High-density lipoproteins differentially modulate cytokine induced expression of E-selectin and cyclooxygenase-2. Arterioscler Thromb Vasc Biol. 19:910-7.
Cockerill, G.W. et al. (1995) High-density lipoproteins inhibit crone-induced expression of endothelial cell adhesion molecules. Arterioscler Thromb Vasc Biol. 15:1987-94 (22 pages).
Collard, M.W. and Griswold, M.D. (1987) Biosynthesis and molecular cloning of sulfated glycoprotein 2 secreted by rat Sertoli cells. Biochemistry. 26(12):3297-303.
Colles, S.M. et al. (2001) Oxidized LDL-induced injury and apoptosis in atherosclerosis. Potential roles for oxysterols. Trends Cardiovasc Med. 11:131-8.
Corey, D.R. (1997) Peptide nucleic acids: expanding the scope of nucleic acid recognition. Trends Biotechnol. 15(6):224-9.
Coyne, E.F. et al. (2002) Methods for isolation and characterization of intracerebral arterioles in the C57/13L6 wild-type mouse. J Neurosci Meth. 120:145-53.
Curcio, C.A. et al. (2001) Accumulation of cholesterol with age in human Bruch's membrane. Invest Ophthalmol Vis Sci. 42(1):265-74.
Curcio CA, et al. (2005) Esterified and unesterified cholesterol in drusen and basal deposits of eyes with age-related maculopathy. Exp Eye Res. 81(6): 731-41.
Cybulsky MI, et al. (2001) a major role for VCAM-1, but not ICAM-I, in early atherosclerosis. J Clin Invest.107:1255-62.
Cyrus, et al., (2001) Absence of 12/15-lipoxygenase expression decreases lipid peroxidation and atherogenesis in apolipoprotein E-deficient mice. Circulation. 103:2277-82.
Dai et al. (2004) Implantation of Immature Neonatal Cardiac Cells Into the Wall of the Aorta in Rats: A Novel Model for Studying Morphological and Functional Development of Heart Cells in an Extracardiac Environment. Circulation. 110(3):324-9.
Dai et al. (2005) Allogeneic mesenchymal stem cell transplantation in postinfarcted rat myocardium: short- and long-term effects. Circulation 112(2):214-23.
Dansky HM, et al. (2001) Adhesion of monocytes to arterial endothelium and initiation of atherosclerosis are critically dependent on vascular cell adhesion molecule-1 gene dosage. Arterioscler Thromb Vasc Biol. 21:1662-7.
Dansky HM, et al. (1999) Apo A-I inhibits foam cell formation in Apo E-deficient mice after monocyte adherence to endothelium. J Clin Invest. 104:31-9.
Dashti et al. (2004) Model class A and class L peptides increase the production of apoA-I-containing lipoproteins in HepG2 cells. J Lipid Res. 45:1919-28.
Datta et al. (2001) Effects of Increasing Hydrophobicity on the Physical-Chemical and Biological Properties of a Class A Amphipathic Helical Peptide. J Lipid Res. 42(7):1096-104.

(56) References Cited

OTHER PUBLICATIONS

Datta et al. (2000) The Receptor Binding Domain of Apolipoprotein E, Linked to a Model Class A Amphipathic Helix, Enhances Internalization and Degradation of LDL by Fibroblasts. Biochemistry. 30:213-20.
Datta et al. (2001) Cationic domain 141-150 of apoE covalently linked to a class A amphipathic helix enhances atherogenic lipoprotcin metabolism in vitro and in vivo. J Lipid Res. 42:959-66.
Datta, G. et al. (2009) Anti-inflammatory and recycling properties of an apolipoprotein mimetic peptide, Ac-hE18A-NH(2). Atherosclerosis. 2008(1): 134 (24 pages).
Datta, G. et al. (2004) Aromatic Residue Position on the Nonpolar Face of Class A Amphipathic Helical Peptides Determines Biological Activity. J Biol Chem. 279:26509-17.
Davenport, P. and Tipping, P.G. (2003) The role of interleukin-4 and interleukin-12 in the progression of atherosclerosis in apolipoprotein E-deficient mice. Am J Pathol 163:1117-25.
Davidson, D. et al. (1987) Overproduction of Polyomavirus Middle T Antigen in Mammalian Cells through the Use of an Adenovirus Vector. J Virology. 61:1226-39.
Davidson, et al. (1994) The Influence of Apolipoprotein Structure on the Efflux of Celluar Free Cholesterol to High Density Lipoprotein. J Biol Chem. 269(37):22975-82.
Dawson, P.E. et al. (1994) Synthesis of Proteins by Native Chemical Ligations. Science. 266:776-9.
De Caterina, R. et al. (1998) Structural requirements for inhibition of cytokine-induced endothelial activation by unsaturated fatty acids. J Lipid Res. 39:1062-70.
Diederich et al. (2001) Apolipoprotein Al and HDL3 Inhibit Spreading of Primary Human Monocytes through a Mechanism that Involves Cholesterol Depletion and Regulation of CD42. Atherosclerosis. 159:313-24.
Dimayuga, P. et al. (1999) Reconstituted HDL containing human apolipoprotein A-1 reduces VCAM-1 expression and neointima formation following periadventitial cuffinduced carotid injury in apoE null mice. Biochem Biophys Res Commun. 264:465-8.
Dithmar, S. et al. (2000) Ultrastructural changes in Bruch's membrane of apolipoprotein E-deficient mice. Invest Ophthalmol Vis Sci. 41(8): 2035-42.
Dooley, C.T. et al. (1994) An All D-Amino Acid Opioid Peptide with Central Analgesic Activity from a Combinatorial Library. Science. 266:2019-22.
Dunlop, D.S. and Neidle, A. (1997) The Origin and Turnover of D-Serine in Brain. Biochem Biophys Res Commun. 235:26-30.
Duong, P. T. et al. (2006). Characterization of nascent HDL particles and macroparticles formed by ABC A1-mediated cholesterol efflux of cellular lipids to apo A-I. J Lipid Res. 47:832-43.
Dyer, C. A. et al. (1991) Only Multimers of a Synthetic Peptide of Human Apolipoprotein E are Biologically Active. J Biol Chem. 266(23):15009-15.
Dyer, C. A. et al., (1995) Structural features of synthetic peptides of apolipoprotein E that bind the LDL receptor. J Lipid Res. 36:80-8.
Ehara et al. (2001) Elevated Levels of Oxidized Low Density Lipoprotein Show a Positive Relationship With the Severity of Acute Coronary Syndromes. Circulation. 103:1955-60.
Eisenberg et al. (1992) Lipoprotein lipase enhances binding of lipoproteins to heparan sulfate on cell surfaces and extracellular matrix. J Clin Invest. 90:2013-21.
Epand et al. (1987) Studies Synthetic Peptide Analog of the Amphipathic Helix J. Biol. Chem. 262(19): 9389-96.
Epand, R.M. et al. (1994) HDL and apolipoprotein A-I protect erythrocytes against the generation of procoagulant activity. Arterioscler Thromb. 14(11): 1775-83.
Epand et al. (2004) An Apolipoprotein AI Mimetic Peptide: Membrane Interactions and the Role of Cholesterol. Biochemistry. 43:5073-83.
Epand et al. (2004) Two Homologous Apolipoprotein AI Mimetic Peptides: Relationship Between Membrane Interactions and Biological Activity. J Biol Chem. 279:51404-15.
Farkas, M.H. et al. (2004) The recycling of apolipoprotein E and its amino-terminal 22kDA fragment: evidence for multiple redundant pathways. J Lipid Res. 45:1546-54.
Felgner et al. (1987) Lipofection: a highly efficient, lipid-mediated DNA-transfection procedure. Proc Natl Acad Sci USA. 84:7413-7.
Field et al. (2001) Gene expression of sterol regulatory element-binding proteins in hamster small intestine. J Lipid Res. 42:1-9.
Fielding and Fielding (1995) Molecular physiology of reverse cholesterol transport. J Lipid Res. 36:211-28.
Fleisher et al. (1982) Stimulation of arterial endothelial cell prostacyclin synthesis by high density lipoproteins. J Biol Chem. 257:6653-5.
Fogelman et al. (1980) Malondialdehyde alteration of low density lipoproteins leads to cholesteryl ester accumulation in human monocyte-macrophages. Proc Natl Acad Sci USA. 77:2214-8.
Fogelman, A.M. (2004) When good cholesterol goes bad. Nat Med. 10:902-3.
Folch, J. et al. (1957) A simple method for isolation and purification of total lipides from animal tissues. J Biol Chem. 226:497-509.
Footer et al. (1996) Biochemical evidence that a D-Loop is part of a four-strandedPNA-DNA bundle. Nickel-mediated cleavage of duplex DNA by a Gly-Gly-His-Bis-PNA. Biochemistry. 35(33): 10673-9.
Forte et al. (2002) Altered activities of anti-atherogenic enzymes LCAT, paraoxonase, and platelet-activating factor acetylhydrolase in atherosclerosis susceptible mice. J Lipid Res. 43:477-85.
Fritz, I.B. (1992) What is clusterin? Clin Exp Immunol. 88(3): 375.
Fukuda, et al. (1990) Bilayer forming ion-pair amphi-philes from single chain surfactants. J Am Chem Soc. 112:1635-7.
Futterman, L.G and Lemberg, L. (2004) Statin pleiotropy: fact or fiction? Am J Crit Care. 13(3): 244-9.
Gabay C. and Kushner I. (1999) Acute-phase proteins and other systemic responses to inflammation, N Eng J Med. 340:448-54.
Gambacorti-Passerini et al. (1996) In Vitro Transcription and Translation Inhibition by Anti-PromyelocyticLeukemia (PML)/Retinoic Acid Receptor $\alpha$ and Anti-PML Peptide Nucleic Acid. Blood. 88(4):1411-7.
Garber, D.W. et al. (2003) Effect of an arginine-rich amphipathic helical peptide on plasma cholesterol in dyslipidemic mice. Atherosclerosis. 168(2):229-37.
Garber et al. (1992) Turnover of synthetic class a amphipathic peptide analogues of exchangeable apolipoproteins in rats. Correlation with physical properties. Arterioscler Thromb. 12(8): 886-94.
Garber et al. (2001) A new synthetic class A amphipathic peptide analogue protects from diet-induced atherosclerosis. J Lipid Res. 42:545-52.
Garber et al. (2001) An Arginine-rich amphipathic helical peptide mediates rapid clearance of plasma cholesterol is dyslipidemic mice. Arterioscler Thromb Vasc Biol. 21:650.
Garber, D.W. et al. (2000) A sensitive and convenient method for lipoprotein profile analysis of individual mouse plasma samples. J Lipid Res. 41:1020-6.
Garner et al. (1998) Oxidation of high density lipoproteins. I. Formation of methionine sulfoxide in apolipoproteins Al and All is an early event that accompanies lipid peroxidation and can be enhanced by alpha-tocopherol. J Biol Chem. 273 :6080-7.
Garner et al. (1998) Oxidation of high density lipoproteins. II. Evidence for direct reduction of lipid hydroperoxides by methionine residures of apolipoproteins Al and AII. J Biol Chem. 273:6088-95.
Gaut, et al. (2002) Myeloperoxidase produces nitrating oxidants in vivo. J Clin Invest. 109:1311-9.
Geetanjali, B. et al. (2002) Changes in heat shock protein 70 localization and its content in rabbit aorta at various stages of experimental atherosclerosis. Cardiovasc Pathol. 11:97-103.
Gehrs, K.M. et al. (2006) Age-related macular degeneration—emerging pathogenetic and therapeutic concepts. Ann Med. 38(7):450-71.
George et al. (2001) 12/15-lipoxygenase gene disruption attenuates atherogenesis in LDL, receptor-deficient mice. Circulation. 104:1646-50.
Geysen, H.M. et al. (1988) Cognitive features of continuous antigenic determinants. J Mol Recognit. 1(1): 32-41.

(56) References Cited

OTHER PUBLICATIONS

Ghersi-Egea et al. (1996) Fate of Cerebrospinal Bluid-Borne Amyloid B-Peptide: Rapid Clearance into Blood and Appreciable Accumulation by Cerebral Arteries, J Neurochem. 67: 880-3.
Gianturco, S. et al. (1982) Receptor-mediated uptake of hypertriglyceridemic very low density lipoproteins by normal human fibroblasts. J Lipid Res. 23: 984-93.
Gianturco, S.H. et al. (1983) Apolipoprotein E mediates uptake of Sf 100-400 hypertriglyceridemic very low density lipoproteins by the low density lipoprotein receptor pathway in normal human fibroblasts. J Biol Chem. 258:4526-33.
Gianturco, S.H. et al. (1978) Control of 3-hydroxy 3-methylglutaryl CoA reductase activity in cultured human fibroblasts by VLDL of subjects with hypertriglyceredemia. J Clin Invest. 61:320-8.
Gillote et al. (1999) Apolipoprotein-mediated plasma membrane microsolubilization. Role of lipid affinity and membrane penetration in the efflux of cellular cholesterol and phospholipid. J Biol Chem. 274(4):2021-8.
Glomset, J.A. (1968) The Plasma lecithin: cholesterol acytransferase reaction. J Lipid Res. 9:155-67.
Gomez-Foix, A.M. et al. (1992) Adenovirus-mediated Transfer of the Muscle Glycogen Phosphorylase Gene into Hepatocytes Confers Altered Regulation of Glycogen Metabolism. J Biol Chem. 267:25129-34.
Gong et al. (1994) Structural and functional properties of human and mouse apolipoprotein A-I. Biochim. Biophys. Acta. 1213:335-42; Abstract.
Graf, R. and Schachman, H.K. (1996) Random circular permutation of genes and expressed polypeptide chains: application of the method to the catalytic chains of aspartate transcarbamoylase. Proc Natl Acad Sci U S A. 93(21): 11591-6.
Greenaway, P.J. et al. (1982) Human cytomegalovirus DNA: BamHI, EcoRI and PstI restriction endonuclease cleavage maps. Gene. 18:355-60.
Greten, F.R. et al. (2004) IKKβ links inflammation and tumorigenesis in a mouse model of colitis-associated cancer. Cell. 118(3):285-96.
Griendling, K.K. et al. (2000) NAD(P)H Oxidase : Role in Cardiovascular Biology and Disease. Circulation Res. 86:494-501.
Grundy, S.M., (1998) Hypertriglyceridemia, Atherogenic Dyslipidemia, and the Metabolic Syndrome. Am J Cardiol. 81(4A): 18B-25B.
Grundy, S.M., (1999) Hypertriglyceridemia, Insulin Resistance, and the Metabolic Syndrome. Am J Cardiol. 83(9B): 25F-9F.
Grundy S.M., et al. (2004) Implications of Recent Clinical Trials for the National Cholesterol Education Program Adult Treatment Panel III Guidelines. Circulation. 110:227-39.
Gupta et al. (2004) Calculation of Creatinine Clearance Based on Unadjusted Body Weight Leads to Errors in Renal and Heart Failure Patients. Circulation. 110(7):e70 (2 pages).
Gupta, H. et al. (2005) Inhibition of lipopolysaccharide-induced inflammatory responses by an apolipoprotein AI mimetic peptide. Circ Res. 97(3): 236-43.
Gupta, H. et al. (2005) Apolipoprotein E mimetic Peptide dramatically lowers plasma cholesterol and restores endothelial function in watanabe heritable hyperlipidemic rabbits. Circulation. 111(23): 3112-8.
Gurfinkel et al. (2002) Influenza Vaccine Pilot Study in Acute Coronary Syndromes and Planned Percutaneous Coronary Interventions. The FLU Vaccination Acute Coronary Syndromes (FLUVACS) Study. Circulation. 105:2143-7.
Guzman, R.J. et al. (1993) Efficient Gene Transfer Into Myocardium by Direct Injection of Adenovirus Vectors. Circ Res. 73:1201-7.
Haimovici, R. et al. (2001) The lipid composition of drusen, Bruch's membrane, and sclera by hot stage polarizing light microscopy. Invest Ophthalmol Vis Sci. 42(7): 1592-9.
Haj-Ahmad et al. (1986) Development of a Helper-Independent Human Adenovirus Vectorand Its Use in the Transfer of the Herpes Simplex Virus Thymidine Kinase Gene. J Virology. 57:267-74.
Halcox, J.P. et al. (2002) Prognostic Value of Coronary Vascular Endothelial Dysfunction. Circulation. 106:653-8.
Hamase et al. (2001) Determination of Free D-Proline and D-Leucine in the Brains of Mutant Mice Lacking D-Amino Acid Oxidase Activity. Anal Biochem. 298:253-8.
Handattu et al. (2006) Physical, Chemical, and Structural Studies of Apolipoprotein A-I Mimetics Correlate Well with the Efficacy for Inhibiting Atherosclerosis. Atheroscler Thromb Vasc Biol. 26(5):e64.
Handattu, S.P. et al. (2007) ApoA-I Mimetic Peptides with Differing Ability to Inhibit Atherosclerosis Also Exhibit Differences in Their Interactions with Membrane Bilayers. J Biol Chem. 282:1980-8.
Handattu, S.P. et al. (2013) Two Apolipoprotein E Mimetic Peptides with Similar Cholesterol reducing Properties Exhibit Differential Atheroprotective Effects in LDL-R Null Mice. Atherosclerosis. 227(1):58-64.
Handwerger et al. (1999) Pre-β-HDL stimulates placental lactogen release from human trophoblast cells. Am J Physiol. 276:E384-9.
Hanvey et al. (1992) Antisense and Antigene properties of Peptide Nucleic Acids. Science. 258(5087): 1481-5.
Harats et al. (2000) Overexpression of 15-lipoxygenase in vascular endothelium accelerates early atherosclerosis in LDL receptor-deficient mice. Arterioscler Thromb Vasc Biol. 20:2100-5.
Hardy et al. (2001) An Automated High-Performance Liquid Chromatography Procedure for the Quantitation of L- and D-Amino Acids by Means of Stepwise Precolumn Derivatization. Anal Biochem. 291:297-9.
Harkin et al. (1997) The Effects of hyper-and hypocarbia on intraparenchymal arterioles in rat brian slices. Neuroreport. 8:1841-4.
Hashimoto (2000) Improvement of intestinal absorption of peptides: absorption of Bi-Phe monoglucosylated insulin to rat intestinal brush-border membrane vesicles. Eur J Pharm Biopharm. 50(2): 197-204.
Hasty, A.H. et al. (1999) Determination of lower threshold of apolipoprotein E resulting in lipoprotein remnant clearance. J Lipid Res. 40:1529-38.
Hauser et al. (1998) Identification of a Receptor Mediating Absorption of Dietary Cholesterol in the Intestine. Biochemistry. 37(51):17843-50.
Havel, R. J. (1985) George Lyman Duff memorial lecture. Role of the liver in atherosclerosis. Arteriosclerosis. 5: 569-80.
Hāyry et al. (1995) Stabile D peptide analog of insulin-like growth factor-1 inhibits smooth muscle cell proliferation after carotid balooning injury in the rat. FASEB J. 9(13): 1336-44.
Hein, T.W. et al. (2001) Integrin-binding peptides containing RGD produce coronary arteriolar dilation via cyclooxygenase activation. Am J Physiol Heart Circ Physiol. 281(6): H2378-84.
Henriksen et al. (1981) Enhanced macrophage degradation of low density lipoprotein prevously incubated with cultured endolelial cells; recognition by receptor for acetylated low density lipoproteins. Proc Natl Acad Sci USA. 78:6499-503.
Hermanowski-Vosatka, A. et al. (2005) 11beta-HSD1 inhibition ameliorates metabolic syndrome and prevents progression of atherosclerosis in mice. J Exp Med. 202(4):517-27.
Hessler et al. (1979) LDL-induced cytotoxicity and its inhibition by 1-DL in human vascular smooth muscle and endothelial cells in culture. Atherosclerosis. 32:213-29 (Abstract).
Hoffman et al. (1997) Isoprostanes: Free Radical-Generated Prostaglandins with constrictor Effects on cerebral Arterioles. Stroke. 28: 844-9.
Holvoet, P. et al. (1997) β-VLDL Hypercholesterolemia Relative to LDL Hypercholesterolemia is Associated With Higher Levels of Oxidized Lipoproteins and a More Rapid Progression of Coronary Atherosclerosis in Rabbits. Arterioscler Thromb Vasc Biol. 17:2376-82.
Hoogenboom et al. (1992) By-passing immunisation: Human antbodies from synthetic repertoires of germline VH gene segments rearranged in vitro. J Mol Biol. 227:381-8.
Houstis, N. et al. (2006) Reactive Oxygen Species Have a Causal Role in Multiple Forms of Insulin Resistance. Nature. 440: 944-8.
Hristova et al. (1999) An Amphipathic α-Helix at a Membrane Interface: A Structural Study using a Novel X-ray Diffraction Method. J Mol Biol. 290:99-117.

(56) References Cited

OTHER PUBLICATIONS

Huang and Mahley, Apolipoprotein E. Structure and Function in Lipid Metabolism, Neurobiology, and Alzheimer's Diseases. Neurobiol Dis. 2014; 72PA:3-12.
Huber, M.A. et al. (2004) NF-κB is essential for epithelial-mesenchymal transition and metastasis in a model of breast cancer progression. J Clin Invest. 114(4): 569-81.
Hussain et al. (2000) High affinity binding between lipoprotein lipase and lipoproteins involves multiple ionic and hydrophobic interactions, does not require enzyme activity, and is modulated by glycosaminoglycans. J Biol Chem. 275: 29324-30.
Hwang, S.J. et al. (1997) Circulating adhesion molecules VCAM-I, ICAM-1, and E-selectin in carotid therosclerosis and incident coronary heart disease cases. The atherosclerosis risk in communities (AMC) study. Circulation. 96:4219-4225.
Hyka et al. (2001) Apolipoprotein A-I Inhibits the Production of Interleukin-10 and Tumor Necrosis Factor-a by Blocking Contact-Mediated Activation of Monocytes by T Lymphocytes. Blood. 97:2381-9.
Hyrup, B. and Nielsen, P.E. (1996) Peptide Nucleic Acids (PNA):Synthesis, Properties and Potential Applications. Bioorg Med Chem. 4(1):5-23.
Ishigami, M., et al. (2000) Apolipoprotein E inhibition of vascular smooth muscle cell proliferation but not the inhibition of migration is mediated through activation of inducible nitric oxide synthase. Arteriosc Thromb Vasc Biol. 20:1020-6.
Jaeger et al. (1989) Improved predictions of secondary structures for RNA. Proc Natl Acad Sci USA. 86:7706-10.
Jakobovits et al. (1993) Germ-line transmission and expression of a human-derived yeast artificial chromosome. Nature. 362:255-8.
Jakobovits et al. (1993) Analysis of homozygous mutant chimeric mice: Deletion of the immunoglobulin heavy-chain joining region blocks B-cell development and antibody production. Proc Natl Acad Sci USA. 90:2551-5.
Jamaluddin et al. (1987) Aggregatory reactions of blood platelets in ustirred dilute suspensions and their monitoring by spectrophotometry. Curr Sci. 56:254-6.
Jamieson et al. (2001) Detection of Lipoprotein(a) in Intraparenchymal Cerebral Vessels: Correlation with Vascular Pathology and Clinical History. Exp Mol Pathol. 71: 99-105.
Jensen et al. (1997) Kinetics for Hybridization of Peptide Nucleic Acids (PNA) with DNA and RNA Studied with the BIAcore Technique Biochemistry. 36(16):5072-7.
Jin et al. (2003) Inhibition of endothelial lipase causes increased ML cholesterol levels in vivo. J Clin Invest. 111:357-62.
Johnson, J.H. (2006) Trends and Opportunities in the Metabolic Syndrome, Drug Dev Res. 67(7): 539-44.
Jones et al. (1992) Computer Programs to Identify and Classify Amphipathic α Helical Domains. J Lipid Res. 33:287-96.
Jong, M.C. et al. (1996) Both lipolysis and hepatic uptake of VLDL are impaired in transgenic mice coexpressing human apolipoprotein E*3Leiden human apolipoprotein C-I. Arterioscler Thromb Vasc Biol. 16:934-40.
Kabanov et al. (1990) A new class of antivirals: antisense oligonucleotides combined with a hydrophobic substituent effectively inhibit influenza virus reproduction and synthesis of virus-specific proteins in MDCK cells. FEBS Lett. 259: 327-30.
Kaler et al. (1989) Spontaneous vesicle formation in aqueous mixtures of single-tailed surfactants. Science. 245:1371-4.
Kandel ER, Schwartz JH, Jessell TM (Eds.) (1991) Principles of Neural Science, Third Edition. Elsevier: New York, pp. 188-189.
Karle et al. (2004) A combined extented and helical backbone for Boc-(Ala-Leu-Ac7C)2-OME. Peptides Res. 63:174-80.
Karle et al. (1998) Crystal structure of the channel-forming polypeptide antiamoebin in a membrane-mimetic environment. Proc Natl Acad Sci USA. 95:5501-4.
Karle et al. (2003) Crystal structure of hydrophobic 19-residue peptide helix containing three centrally located D amino acids. Proc Natl Acad Sci USA. 100(24): 13946-151.
Kaul, S. et al. (2004) Rapid Reversal of Endothelial Dysfunction in Hypercholesterolemic Apolipoprotein E-Null Mice by Recombinant Apolipoprotein A-$I_{Milano}$-Phospholipid Complex. J Am Coll Cardiol. 44:1311-9.
Keech, A. et al. (2005) Effects of long-term fenofibrate therapy on cardiovascular events in 9795 people with type 2 diabetes (the FIELD study): randomised controlled trial. Lancet. 366: 1849-61.
Kidson, W. et al. (1974) Treatment of Severe Diabetes Mellitus by Insulin Infusion. Br Med J. 2(5921): 691-4.
Kirshenbaum, L.A. et al. (1993) Highly Efficient Gene Transfer into Adult Ventricular Myocytes by Recombinant Adenovirus. J Clin Invest. 92:381-7.
Kissinger, C. et al. (1982) Analysis of Sertoli cell-secreted proteins by two-dimensional gel electrophoresis. Biol Reprod. 27(1): 233-40.
Kita, T. et al. (1981) Deficiency of low density lipoprotein receptors in liver and adrenal gland of the WHHL rabbit, an animal model of familial hypercholesterolemia. Proc Natl Acad Sci USA .78: 2268-72.
Klien, R. et al. (2002) The Association of Atherosclerosis, Vascular Risk Factors, and retinopathy in Adults with Diabetes: The Atherosclerosis Risk in Communities Study. Opthalmology. 109(7): 1225-34.
Knowler, W.C. et al. (2002) Reduction in the incidence of type 2 diabetes with lifestyle intervention or metformin. N Engl J Med. 346(6):393-403.
Ko et al. (1993) A. Highdensity lipoprotein reduces epidermal growth factor-induced DNA synthesis in vascular smooth muscle cells. Atherosclerosis, 99: 253-9 (Abstract).
Kockx, et al. (2004) Apolipoprotein A-I-stimulated Apolipoprotein E Secretion from Human Macrophages is Independent of Cholesterol Efflux. J Biol Chem. 279:25966-70.
Kolodgie, F.D. et al. (1996) Hypercholesterolemia in the Rabbit Induced by Feeding Graded Amounts of Low-Level Cholesterol: Methodological Considerations Regarding Individual Variability in Response to Dietary Cholesterol and Development of Lesion Type. Arterioscler Thromb Vasc Biol. 16:1454-64.
Kontos, H.A. and Wei, E.P. (1998) Cerebral arteriolar dilations by $K_{ATP}$ channel activators need L-lysine or L-arginine. Am J Physiol. 274 (3 Pt 2): H974-81.
Kowal, R.C. et al. (1989) Low density lipoprotein receptor related protein mediates uptake of cholesteryl ester derived from apolipoprotein E enriched lipoproteins. Proc Natl Acad Sci USA. 86:5810-4.
Kozbor, D. et al. (1982) Human hybridomas constructed with antigen-specific Epstein-Barr virus-transformed cell lines. Proc Natl Acad Sci USA. 79(21): 6651-5.
Kreiger (1999) Charting the Fate of the "Good Cholesterol": Identifcation and Characterization of the High-Density Lipoprotein Receptor Sr—Bi. Ann Rev Biochem. 68: 523-58.
Kullman et al. (1999) Evaluation of the Enantiomeric Composition of Amino Acids in Tobacco. Chirality. 11:669-673.
Kumar et al. (2002) A novel peptide derivative exhibits anti inflammatory and antioxidant activity in adjuvant induced arthritis in rats. Mol Cell Biochem. 229(1-2):9-17.
Kume et al. (1992) Lysophosphatidylcholine, a component of atherogenic lipoproteins, induces mononuclear leukocyte adhesion molecules in cultured human and rabbit arterial endothelial cells. J Clin Invest. 90:1138-44.
Kwiterovich, P.O. (1998) State-of-the-art update and review: clinical trials of lipid-lowering agents. Am J Cardiol. 82: 3U-7U.
Lawrence, M.B. and Springer, T.A. (1991) Leukocytes roll on a selectin at physiologic flow rates: distinction from and prerequisite for adhesion through integrins. Cell. 65:859-73.
Le Gal La Salle, G. et al. (1993) An adenovirus vector for gene transfer into neurons and glia in the brain. Science. 259:988-90.
Lee, S. et al. (2001) Vitamin C-induced decomposition of lipid hydroperoxides to endogenous genotoxins. Science. 292:2083-6.
Legrand et al. (1992) Molecular Interactions between Human Lactotransferrin and the Phytohemagglutinin-Activated Human Lymphocyte Lactotransferrin Receptor Lie in Two Loop-Containing Regions of the N-Terminal Domain I of Human Lactotransferrin. Biochemistry. 31: 9243-51.

(56) References Cited

OTHER PUBLICATIONS

Letsinger et al. (1989) Cholesteryl-conjugated oligonucleotides: Synthesis, properties, and activity as inhibitors of replication of human immunodeficiency virus in cell culture. Proc Natl Acad Sci USA. 86:6553-6.
Levine, et al.(1993) In vivo protection against endotoxin by plasma high density lipoprotein. Proc Natl Acad Sci USA. 90:12040-4.
Li et al. (1993) An atherogenic diet rapidly induces VCAM-1, a cytokine-regulatable mononuclear leukocyte adhesion molecule, in rabbit aortic endothelium. Arteriosc Thromb. 13:197-204.
Li, et al. (2004) Double Belt Structure of Discoidal High Density Lipoproteins: Molecular Basis for Size Heterogeneity. J Mol Biol. 343:1293-311.
Libby et al. (2002) Inflammation and atherosclerosis. Circulation. 105:1135-43.
Linsel-Nitschke, P. and Tall, A.R. (2005) HDL as a target in the treatment of atherosclerotic cardiovascular disease. Nat Rev Drug Discov. 4(3): 193-205.
Mach et al. (1998) Reduction of atherosclerosis in mice by inhibition of CD40 signalling. Nature. 394:200-3.
Mahley et al. (1999) Pathogenesis of type III hyperlipoproteinemia (dysbetalipoproteinemia): questions, quandaries, and paradoxes. J Lipid Res. 40: 1933-49.
Mahley, R.W. et al. (1989) Intravenous infusion of apolipoprotein E accelerates clearance of plasma lipoproteins in rabbits. J Clin Invest. 83: 2125-30.
Manchekar, M. et al. (2004) Apolipoprotein B-Containing Lipoprotein Particle Assembly: Lipid Capacity of the Nascent Lipoprotein Particle. J Biol Chem. 279(38): 39757-66.
Manikandan et al. (2002) Antioxidant potential of a novel tetrapeptide deri-vative in isoproterenol-induced myocardial. Pharmacology. 65:105-9.
Manoharan et al. (1994) Cholic acid-oligonucleotide conjugates for antisense applications. Bioorg Med Chem Lett. 4 1053-60.
Manoharan et al. (1995) Lipidic nucleic acids. Tetrahedron Lett. 36:3651-4.
Marks et al. (1991) By-passing immunization. Human antibodies from V-gene libraries displayed on phage. J Mol Biol. 222:581.
Massie et al. (1986) Construction of a Helper-Free Recombinant Adenovirus That Expresses Polyomavirus Large T Antigen. Mol Cell Biol. 6:2872-83.
Mato et al. (1996) Involvement of specific macrophage-lineage cells surrounding arterioles in barrier and scavenger function in brain cortex. Proc Natl Acad Sci USA. 93: 3269-74.
Mazoyer, E. et al. (1990) KRDS, a new peptide derived from human lactotransferrin, inhibits platelet aggregation and release reaction. Eur J Biochem. 194:43-9.
McGarry, J.D. (2002) Banting lecture 2001: dysregulation of fatty acid metabolism in the etiology of type 2 diabetes. Diabetes. 51(1):7-18.
Meera et al. (1999) Inhibition of neutrophil derived lysosomal enzymes and reactive oxygen species by a novel tetrapeptide. Inflamm Res. 48(9):479-84.
Mehrabian et al. (2002) Identification of 5-lipoxygenase as a major gene contributing to atherosclerosis susceptibility in mice. Circ Res. 91:120-6.
Mendez et al. (1994) Synthetic Amphipathic Helical Peptides that Mimic Apolipoprotein A-I in Clearing Cellular Cholesterol. J Clin Invest. 94: 1698-705.
Merrifield et al. (1995) Retro and Retroenantio Analogs of Cecropin-Melittin Hybrids. Proc Natl Acad Sci USA. 92: 3449-53.
Mertens, A. et al. (2003) Increased Low-Density Lipoprotein Oxidation and Impaired High-Density Lipoprotein Antioxidant Defense are Associated With Increased Macrophage Homing and Atherosclerosis in Dyslipidemic Obese Mice: LCAT Gene Transfer Decreases Atherosclerosis. Circulation. 107:1640-6.
Miller, A.D. and Buttimore, C. (1986) Redesign of Retrovirus Packaging Cell Lines to Avoid.
Mims, M. P. et al. (1994) A Nonexchangeable Apolipoprotein E Peptide That Mediates Binding to the Low Density Lipoprotein Receptor. J. Biol. Chem. 269: 20539-647.
Mishra et al. (1994) Interaction of Synthetic Peptide Analogs of the Class A Amphipathic Helix with Lipids: Evidence for the Snorkel Hypothesis. J Biol Chem. 269: 7185-91.
Mishra et al. (1995) Effect of the Arrangement of Tandem Repeating Units of Class A Amphipathic α-Helixes on Lipid Interaction. J Biol Chem. 270:1602-11.
Mishra et al. (1996) Interaction of Model Class A1, Class A2, and Class Y Amphipathic Helical Peptides with Membranes. Biochemistry. 35:11210-20.
Mishra et al. (1998) Studies of Synthetic Peptides of Human Apolipoprotein A-I Containing Tandem Amphipathic α-Helixes. Biochemistry. 37: 10313-24.
Mishra et al. (2001) Solution NMR structure of a model class A (apolipoprotein) amphipathic α helical peptide. Peptides. 22:567-73.
Mishra et al. (2006) Association of a model class A (apolipoprotein) amphipathic α helical peptide with lipid: high resolution NMR studies of peptide lipid discoidal complexes. J Biol Chem. 281:6511-9.
Miyazaki et al. (1995) Intravenous Injection of Rabbit Apolipoprotein A-I Inhibits the Progression of Atherosclerosis in Cholesterol-Fed Rabbits. Arterioscler Thromb Vasc Biol. 15:1882-8.
Moller, D.E. and K.D. Kaufman (2005) Metabolic Syndrome: A Clinical and Molecular Perspective. Ann Rev Med. 56: 25-62.
Moore, D.J. et al. (1995) Age-related variation in the hydraulic conductivity of Bruch's membrane. Invest Ophthalmol Vis Sci. 36(7): 1290-7.
Morrison et al. (1984) Chimeric human antibody molecules: Mouse antigen-binding domains with human constant region domains. Proc Natl Acad Sci USA. 81:6851-5.
Morsy et al. (1993) Efficient Adenoviral-mediated Ornithine Transcarbamylase Expression in Deficient Mouse and Human Hepatocytes. J Clin Invest. 92:1580-6.
Moullier et al. (1993) Correction of lysosomal storage in the liver and spleen of MPS VII mice by implantation of genetically madified skin fibroblast. NatGenet. 4:154-9.
Mulder et al. (2004) Low-density lipoprotein receptor-knockout mice display impaired spatial memory associated with a decreased synaptic density in the hippocampus. Neurobiol Disease. 16: 212-9.
Mulligan, R.C. (1993) The basic science of gene therapy. Science. 260:926-32.
Murugesan et al. (1994) High-density lipoprotein stimulates endothelial cell movement by a mechanism distinct from basic fibroblast growth factor. Circ Res. 74: 1149-56.
Nag et al. (1997) Cerebrovascular Changes in Chronic Hypertension Protective Effects of Enalapril in Rats. Stroke. 28: 1028-34.
Nagata et al. (1994) Distribution of free D-serine in vertebrate brains. Brain Res. 634: 291-5.
Nagata et al. (1995) Free D-serine concentration in normai and Alzheimer human brain. Brain Res Bull. 38(2): 181-3.
Nagata et al. (2002) Hemodynamic Aspects of Alzheimer's Disease. Ann N Acad Sci. 977: 391-402.
Naghavi, M. et al. (2003) Influenza infection exerts prominent inflammatory and thrombotic effects on the atherosclerotic plaques of apolipoprotein E-deficient mice. Circulation. 107(5): 762-8.
Nakamura et al. (1997) Deposition of amyloid β protein (Aβ)subtypes [Aβ40 and Aβ42(43)] in canine senile plaques and cerebral amyoloid angiopathy. Acta Neuropathol. 94: 323-8.
Nanjee et al. (1999) Acute effects of intravenous infusion of apoA-Uphosphos-phatidycholine discs on plasma lipoproteins in humans. Arterioscler Thromb Vase Biol. 19:979-89.
Nanjee et al. (2001) Intravenous apoA-1/lecithin discs increase pre-β-HDL concentration in tissue fluid and stimulate reverse cholesterol transport in humans. J Lipid Res. 42:1586-93.
Navab et al. (1991) Monocyte transmigration induced by modification of low density lipoprotein in cocultures of human aortic wall cells is due to induction of monocyte chemotactic protein 1 synthesis and is abolished by high density lipoprotein. J Clin Invest. 88:2039-46.

(56) References Cited

OTHER PUBLICATIONS

Navab et al. (1997) Mildly oxidized LDL induces an increased apolipoprotein J/paraoxonase ratio. J Clin Invest. 99:2005-19.
Navab et al. (2000) Normal high density lipoprotein inhibits three steps in the formation of midly oxidized low density lipoprotein: step 1. J Lipid Res. 41:1481-94.
Navab et al. (2000) Normal high density lipoprotein inhibits three steps in the formation of mildly oxidized low density lipoprotein: steps 2 and 3. J Lipid Res. 41:1495-508.
Navab et al. (2001) A cell-free assay for detecting HDL that is dysfunctional in preventing the formation of or inactivating oxidized phospholipids. J Lipid Res 2001; 42:1308-17.
Navab et al. (2001) HDL and the inflammatory response induced by LDL-derived oxidized phospholipids. Arterioscler Thromb Vasc Bio.21:481-8.
Navab et al. (2003) Oral synthetic phospholipids (DMPC) raises high-density lipoprotein cholesterol levels, improves high-density lipoprotein function, and markedly reduces atherosclerosis in apolipoprotein E-null mice. Circulation. 108:1735-9.
Navab et al. (2004) Oral D-4F causes formation of pre-β high-density lipoprotein and improves high-density lipoprotein-mediated cholesterol efflux and reverse cholesterol transport from macrophages in apo;ipoprotin E-null mice. Circulation. 109:3215-20.
Navab et al. (2004) The oxidation hypothesis of atherogenesis: the role of oxidized phospholipids and L. J Lipid Res. 45: 993-1007.
Navab et al. (2005) The double jeopardy of HDL. Ann Med 37(3):173-8.
Navab et al. (2005) Apolipoprotein A-I Mimetic Peptides. Arterioscler Thromb Vasc Biol. 25:1325-31.
Navab et al. (2005) D-4F and Statins Synergize to Render HDL Antiinflammatory in Mice and Monkeys and Cause Lesion Regression in Old Apolipoprotein E-Null Mice. Arterioscler Thromb Vasc Biol. 25:1426-32.
Navab et al. (2005) An oral ApoJ peptide renders HDL anti-inflammatory in Mice and Monkeys and dramatically reduces atherosclerosis in Apolipoprotein E-null mice. Arterioscler Thromb Vasc Biol. 25:1932-7.
Navab et al. (2005) The Role of High-Density Lipoprotein in Inflammation. Cardiovasc Med.15:158-61.
Navab et al. (2005) An Apolipoprotein A-I Mimetic Works Best in the Presence of Apolipoprotein A-I. Circ. Res. 97:1085-6.
Navab et al. (2005) Oral Small Peptides render HDL antiinflammatory in mice, and monkeys and reduce atherosclerosis in ApoE null mice. Circ Res. 97:524-32.
Navab M, et al. (2002) Oral administration of an Apo A-I mimetic Peptide synthesized from D-amino acids dramatically reduces atherosclerosis in mice independent of plasma cholesterol. Circulation. 105(3): 290-2.
Navab, M. et al. (2004) Apparent Paradox of Low-Fat "Healthy" Diets Increasing Plasma Levels of Oxidized Low-Density Lipoprotein and Lipoprotein(a). Arterioscler Thromb Vasc Biol. 24:392-3.
Nguyen et al. (2006) Apolipoprotein A-I-mimetic peptides with antioxidant actions. Arch Biochem Biophys. 451:34-42.
Nicholls, S.J. et al. (2006) Relationship Between Atheroma Regression and Change in Lumen Size After Infusion of Apolipoprotein A-I Milano. J Am Coll Cardiol. 47(5):992-7.
Nicholls, S.J. et al. (2005) Formation of Dysfunctional High-Density Lipoprotein by Myeloperoxidase. Trends Cardiovasc Med. 15(6): 212-9.
Nikoulin, I.R. et al. (1998) An Apolipoprotein E Synthetic Peptide Targets to Lipoproteins in Plasma and Mediates Both Cellular Lipoprotein Interactions in Vitro and Acute Clearance of Cholesterol-rich Lipoproteins in Vivo. J Clin Invest. 101(1): 223-34.
Nielsen et al. (1991) Sequence-Selective Recognition of DNA by Strand Displacement with a Thymine-Substituted Polyamide. Science. 254:1497-500.
Nievelstein et al. (1991) Lipid accumulation in rabbit aortic intima two hours after bolus infusion of low density lipoprotein: A deep-etch and immuno-localization study of ultra-rapidly frozen tissue. Arterioscler Thromb. 11: 1795-805.
Nirmala, C. and Puvanakrishnan, R. (1996) Effect of curcumin on certain lysosomal hydrolases in isoproterenol-induced myocardial infarction in rats. Biochem Pharmacol. 51(1):47-51.
Nirmala et al. (1999) Curcumin treatment modulates collagen metabolism in isoproterenol induced myocardial necrosis in rats. Mol Cell Bioche. 197(1-2):31-7.
Nofer, J.R. et al. (2004) HDL induces NO-dependent vasorelaxation via the lysophospholipid receptor $S1P_3$. J Clin Invest. 113:569-81.
Nomoto et al. (1998) Improvement of Intestinal Absorption of Peptide Drugs by Glycosylation: Transport of Tetrapeptide by the Sodium Ion-Dependent D-Glucose Transporter. J Phar Sci. 87(3):326-32.
Norton et al. (1995) Targeting Peptide Nucleic Acid-Protein Conjugates to Structural Features Within Duplex DNA. Bioorg Med Chem. 3(4):437-45.
Nuttall, M.E. an Gimble, J.M. (2000) Is there a therapeutic opportunity to either prevent or treat osteopenic disorders by inhibiting marrow adipogenesis? Bone. 27(2):177-84.
Oberhauser et al. (1992) Effective incorporation of 2'-O-methyl-oligoribonucleotides into liposomes and enhanced cell association through modification with thiocholesterol. Nucl Acids Res. 20(3):533-8.
O'Brien et al. (1996) Neovascular expression of E-selectin, intercellular adhesion molecule-1, and vascular cell adhesion molecule-1 in human atherosclerosis and their relation to intimal leukocyte content. Circulation. 93:672-82.
Obunike, J.C. et al. (2000) The heparin-binding proteins apolipoprotein E and lipoprotein lipase enhance cellular proteoglycan production. Arterioscler Thromb Vasc Biol. 20:111-8.
O'Connell, B.J. and Genest, J., Jr. (2001) High-density lipoproteins and endothelial function. Circulation. 104:1978-83.
Oguchi et al. (2000) Monoclonal antibody against vascular cell adhesion molecule-1 inhibits neointimal formation after periadventitial carotid artery injury in genetically hypercholesterolemic mice. Arterioscler Thromb Vasc Biol. 20:1729-36.
Oram and Yokoyama (1996) Apolipoprotein mediated removal of cellular cholesterol and phospholipids. J Lipid Res. 37: 2473-91.
Otvos, J.D. et al. (2006) Low-density lipoprotein and high-density lipoprotein particle subclasses predict coronary events and are favorably changed by gemfibrozil therapy in the Veterans Affairs High-Density Lipoprotein Intervention Trial. Circulation. 113(12):1556-63.
Ou et al. (2003) AP-4F, antennapedia peptide linked to an amphipathic a helical peptide, increases the efficiency of lipofectamine-mediated gene transfection in endothelial cells. Biochem Biophys Res Commun. 305:605-10.
Ou et al. (2003) L-4F, an apolipoprotein A-1 mimetic, dramatically improves vasodilation in hypercholesterolemic and sickle cell disease. Circulation. 107:2337-41.
Ou et al. (2005) Effects of D-4F on Vasodilation and Vessel Wall Thickness in Hyperholesterolemic LDL Receptor—Null and LDL Receptor/Apolipoprotein A-I Double-Knockout Mice on Western Diet. Circ Res. 97:1190-7.
Ou et al. (2003) L-4F, an apolipoprotein A-I mimetic, restores nitric oxide and superoxide anion balance in low-density lipoprotein-treated endothelial cells. Circulation. 107:1520-4.
Owens, B.J. et al. (1990) Apolipoprotein A-I and its amphipathic helix peptide analogues inhibit human immunodeficiency virus-induced syncytium formation. J Clin Invest. 86(4): 1142-50.
Paigen et al. (1990) Atherosclerosis Susceptibility Differences among Progenitors of Recombinant Inbred Strains of Mice. Arteriosclerosis. 10: 316-23.
Paka et al. (1999) Apolipoprotein E Containing High Density Lipoprotein Stimulates Endothelial Production of Heparan Sulfate Rich in Biologically Active Heparin-like Domains. J Biol Chem. 274:4816-23.
Palinski et al. (1994) ApoE-Deficient Mice are a Model of Lipoprotein Oxidation in Atherogenesis: Demonstration of Oxidation-Specific Epitopes in Lesions and High Titers of Autoantibodies to Malondialdehyde-Lysine in Serum. Arterioscler Thromb. 14(4):605-16.

(56) References Cited

OTHER PUBLICATIONS

Pan, T.C. et al. (1987) Rabbit apolipoprotein A-I mRNA and gene: Evidence that rabbit apolipoprotein A-I is synthesized in the intestine but not in the liver. Eur J Biochem. 30:99-104.
Panizzutti et al. (2001) A New Strategy to Decrease N-methyl-D-aspartate (NMDA) Receptor Coactivation: Inhibition of D-serine Synthesis by Converting Serine Racemase into an Eliminase. Proc Natl Acad Sci USA. 98:5294-9.
Papo et al. (2002) The consequence of sequence alteration of an amphipathic α-helical antimicrobial peptide and its diastereomers. J Biol Chem. 277(37):33913-21.
Pappenheimer et al. (1994) Intestinal Absorption and Excretion of Octapeptides Composed of D Amino Acids. Proc Nail Acad Sci USA. 91:1942-5.
Pappenheimer et al. (1997) Absorption and Excretion of Undegradable Peptides: Rols of Lipid Solubility and Net Charge. J Pharmacol Exp Ther. 280(1):292-300.
Pardridge et al. (1995) Vector-mediated delivery of a polyamide ("peptide") nucleic acid analogue through the blood-brain barrier in vivo. Proc Natl Acad Sci USA. 92(12):5592-6.
Parhami, F. et al. (1997) Lipid oxidation products have opposite effects on calcifying vascular cell and bone cell differentiation. A possible explanation for the paradox of arterial calcification in osteoporotic patients. Arterioscler Thromb Vasc Biol. 17(4): 680-7.
Pasceri et al. (2000) Direct proinflammatory effect of C-reactive protein on human endothelial cells. Circulation. 102:2165-8.
Pasceri et al. (2001) Modulation of Creactive protein-mediated monocyte chemoattractant protein-1 induction in human endothelial cells by anti-atherosclerosis drugs, Circulation. 103:2531-4.
Pasqui, A.L. et al. (2005) Structural and functional abnormality of systemic microvessels in cardiac syndrome X. Nutr Metab Cardiovasc Dis. 15(1): 56-64.
Pastan et al. (1988) A retrovirus carrying an MDR1 cDNA confers multidrug resistance and polarized expression of P-glycoprotein in MDCK cells. Proc Natl Acad Sci USA. 85: 4486.
Pászty et al. (1994) Apolipoprotein Al Transgene Corrects Apolipoprotein E Deficiency-induced Atherosclerosis in Mice. J Clin Invest. 94:899-903.
Pillot et al. (1997) The 118-135 peptide of the human prion protein forms amloid fibrils and induces liposome fusion. J Mol Biol. 274: 381-93.
Pilone (2000) D-amino acid oxidase: new findings. Cell Mol Life Sci. 57:1732-47.
Plump et al. (1994) Human apolipoprotein A-I gene expression increases high density lipoprotein and suppresses stherosclerosis in the apolipoprotein E-deficient mouse. Proc Natl Acad Sci USA. 91:9607-11.
Pohle, K. et al. (2001) Progression of aortic valve calcification: association with coronary atherosclerosis and cardiovascular risk factors. Circulation. 104(16): 1927-32.
Presta (1992) Antibody engineering. Curr Opin Struct Biol. 2:593-6.
Purdue News (2000) 'Microspheres' Offer Promise for Oral Drug Delivery (pp. 1-3).
Purdue News (2000) 'Migrosphergs' Offer Promise for Oral Drug Delivery (pp. 1-3).
Purdue News (1997) New Oral Insulin Delivery System Shows Promise (pp. 1-3).
Quyyumi, A.A. (1998) Endothelial Function in Health and Disease: New Insights into the Genesis of Cardiovascular Disease. Am J Med. 105:32S-9S.
Rader, D.J. (2003) Regulation of Reverse Cholesterol Transport and Clinical Implications. Am J Cardiol. 92:42J-9J.
Ragot, T. et al. (1993) Replication-defective recombinant adenovirus expressing the Epstein-Barr virus (EBV) envelope glycoprotein gp340]220 induces protective immunity against EBV-induced lymphomas in the cottontop tamarin. J Gen Virol. 74:501-7.
Raha et al. (1988) KRDS a tetra peptide derived from lactotransferrin inhibits binding of monoclonal antibody against glycoprotein Iib-IIIa on ADP-stimulated platelets and megakaryocytes. Blood. 72: 172-8.
Raj arathnam et al. (1994) $^{1}$H NMR studies of interleukin 8 analogs: characterization of the domains essential for function. Biochemistry. 33:6623-30.
Rajashree, S. and Puvanakrishnan, R. (1999) Dexamethasone induced alterations in the levels of proteases involved in blood pressure homeostasis and blood coagulation in rats. Mol Cell Biochem. 197(1-2):203-8.
Rajashree, S. and Puvanakrishnan, R. (1996) Alterations in certain lysosomal glycohydrolases and cathepsins in rats on dexamethasone administration. Mol Cell Biochem. 154(2):165-70.
Rajashree, S. and Puvanakrishnan, R. (1998) Dexamethasone induced alterations in enzymatic and nonenzymatic antioxidant status in heart and kidney of rats. Mol Cell Biochem. 181(1-2):77-85.
Ram et al. (1993) In Situ Retroviral-mediated Gene Transfer for the Treatment of Brain Tumors in Rats. Cancer Res. 53:83-8.
Ramesh et al. (1998) A novel surface-active peptide derivative exhibits in vitro inhibition of platelet aggregation. Peptides. 19:1695-702.
Ramesh et al. (1998) Effect of a novel tetrapeptide derivative in a model of isoproterenol induced myocardial necrosis. Mol Cell Biochem. 187(1-2):173-82.
Ramprasad et al. (2002) Sustained-delivery of an apolipoproteinE—peptidomimetic using multivesicular liposomes lowers serum cholesterol levels. J Controlled Release. 79:207-18.
Ranganathan, D. et al. (2000) Channel-Forming Self-Assembling, Bishelical Amphiphilic Peptides: Design, Synthesis and Crystal Structure of Py (Aibn)2, n=2, 3, 4. J Peptide Res. 56(6): 416-26.
Rapp, J.H. et al. (1994) Triglyceride rich lipoproteins isolated by selected affinity antiapolipoprotein B immunosorption from human atherosclerotic plaque. Atheroscler Thromb. 14:1767-74.
Raussens et al. (2002) NMR Structure and Dynamic of a Receptor-active Apolipoprotein E Peptide. J Biol Chem. 277: 29172-80.
Reape and Groot (1999) Chemokines and atherosclerosis. Atherosclerosis. 147:213-25.
Reddy et al. (2001) Human paraoxonase-3 is an HDLassociated enzyme with biological activity similar to paraoxonase-1 protein but is not regulated by oxidized lipids. Arterioscler Thromb Vasc Biol. 21:542-7.
Reddy et al. (2004) Potential role for mitogen-activated protein kinase phosphatase-1 in the development of atherosclerotic lesions in mouse models. Arterioscler Thromb Vasc Biol. 24:1676-81.
Remaley et al. (2003) Synthetic amphipathic helical peptides promote lipid efflux from cells by an ABCA1-dependent and an ABCA1-independent pathway. J Lipid Res. 44:828-36.
Rembold, C.M. (2004) Combination Therapy of Dyslipidemia in Non-Insulin-Dependent Diabetes Mellitus and the Metabolic Syndrome. Curr Diab Rep. 4(5): 330-4.
Rencurel, F. et al. (2006) Stimulation of AMP-activated protein kinase is essential for the induction of drug metabolizing enzymes by Phenobarbital in human and mouse liver. Mol Pharmacol. 70:1925-34.
Rensen, P.C., and van Berkel, T.J. (1996) Apolipoprotein E effectively inhibits lipoprotein lipase-mediated lipolysis of chylomicron-like triglyceride-rich lipid emulsions in vitro and in vivo. J Biol Chem. 271:14791-9.
Ridker, P. M. (2002) On evolutionary biology, inflammation, infection, and the causes of atherosclerosis. Circulation. 105:2-4.
Roessler, J. et al. (1993) Adenoviral-mediated gene transfer to rabbit synovium in vivo. J Clin Invest. 92:1085-92.
Rogers, et al. (1998) The lipid-free structure of apolipoprotein A-I: effects of aminoterminal deletions. Biochemistry. 37:11714-25.
Roher et al. (1993) β-Amyloid-(1-42) is a major component of cerebrovascular amyloid deposits: Implications for the pathology of Alzheimer disease. Proc Natl Acad Sci USA. 90:10836-40.
Rohlmann, A. et al. (1998) Inducible Inactivation of Hepatic LRP Gene by Cre-mediated Recombination Confirms Role of LRP in Clearance of Chylomicron Remnants. J Clin Invest. 101:689-95.
Romá n et al. (2002) Subcortical ischaemic vascular dementia. Lancet Neurol. 1:426-36.
Rong et al. (2001) Elevating high-density lipoprotein cholesterol in apolipoprotein E-deficient mice remodels advanced atherosclerotic lesions by decreasing macrophage and increasing smooth muscle cell content. Circulation. 104:2447-52.

(56) References Cited

OTHER PUBLICATIONS

Roscoe, H.G. and A.W. Vogel (1968) Lipid Changes in the Eye Concomitant with the Development of Atherosclerosis in the Aorta in the Rabbit. Circ Res. 23(5): 633-43.
Rose, D.J. (1993) Characterization of antisense binding properties of peptide nucleic acids by capillary gel electrophoresis. Anal Chem. 65(24):3545-9.
Rubin et al. (1991) Inhibition of early atherogenesis in transgenic mice by human apolipoprotein AI. Nature. 353:265-7.
Sabbatini et al. (2001) Microanatomical changes of intracerebral arteries in spontaneously hypertensive rats: a model of cerebrovasular disease of the elderly. Mech Aging Dev. 122:1257-68.
Saison-Behmoaras et al. (1991) Short modified antisense oligonucleotides directed against Ha-ras point mutation induce selective cleavage of the mRNA and inhibit T24 cells proliferation. EMBO J. 10:1111-8.
Sandana Mala, J.G. et al. (2001) Strain improvement of Aspergillus niger for enhanced lipase production. J Gen Appl Microbiol. 47 (4):181-6.
Sattler, W. and Stocker, R. (1993) Greater selective uptake by Hep G2 cells of highdensity lipoprotein cholesteryl ester hydroperoxides than of unoxidized cholesterylesters. Biochem J. 294:771-8.
Schmitz-Peiffer C. (2000) Signaling aspects of insulin resistance in skeletal muscle: mechanisms induced by lipid oversupply. Cell Signal. 12(9-10):583-94.
Schnölzer et al. (1992) Constructing proteins by dovetailing unprotected synthetic peptides: backbone-engineered HIV protease. Science. 256: 221.
Schönbeck, U. and Libby, P. (2004) Inflamation, Immunity, and HMG-COA Reductase Inhibitors, Statins as Anti inflammatory Agents? Circulation. 109(21 Suppl 1):II18-26.
Schonfeld et al. (1979) Lipolysis produces changes in the immunoreactivity and cell reactivity of very low density lipoproteins. J Clin Invest. 64:1288-97.
Segrest et al, (1974) A Molecular Theory of Lipid-Protein Interaction in the Plasma Lipoproteins. FEBS Left. 38: 247-253.
Segrest et al. (1990) Amphipathic Helix Motif: Classes and Properties. Proteins: Struct, Funct. Genet. 8:103-17.
Segrest et al. (1998) Apolipoprotein B-100: conservation of lipidassociating amphipathic secondary structural motifs in nine species of vertebrates. J Lipid Res. 39:85-102.
Segrest et al. (1994) ApoB-100 has a pentapartite structure composed of three amphipathic alpha-helical domains alternating with two amphipathic beta-strand domains. Detection by the computer program LOCATE. Arterioscler Thromb. 14:1674-85.
Senior (1999) New options developed for needle-free drug delivery. Lancet. 1998:354:1102.
Seth, et al. (1984) Role of a low-pH environment in adenovirus enhancement of the toxicity of a Pseudomonas exotoxin-epidermal growth factor conjugate. J Virol. 51:650-5.
Seth, et al. (1984) Evidence that the Penton Base of Adenovirus is Involved in Potentiation of Toxicity of Pseudomonas Exotoxin Conjugated to Epidermal Growth Factor. Mol Cell Biol. 4:1528-33.
Shah et al. (1998) Effects of recombinant apolipoprotein A-I(Milano) on aortic atherosclerosis in apolipoprotein E-deficient mice. Circulation. 97(8):780-5.
Shah et al. (2001) High-dose recombinant apolipoproteins A-Imilano mobilizes tissue cholesterol and rapidly reduces plaque lipid and macrophase content in apolipoprotein Edeficient mice: potential implications ofr acute plaque stabilization. Circulation. 103:3047-50.
Shah, P.K. et al. (2005) Apolipoprotein A-I mimetic peptides: potential role in atherosclerosis management. Trends Cardiovasc Med. 15:291-6.
Sharp, R.J. et al. (2004) Structural Features of Apolipoprotein B Synthetic Peptides that Inhibit Lipoprotein(a) Assembly. J Lipid Res. 45(12):2227-34.
Shea et al. (1990) Synthesis, hybridization properties and antiviral activity of lipid-oligodeoxynucleotide conjugates. Nucl Acids Res. 18:3777-83.
Shen, B.W. et al. (1977) Structure of human serum lipoproteins inferred from compositional analysis. Proc Natl Acad Sci USA. 74:837-41.
Shih et al. (1999) Minimally modified low-density lipoprotein induces monocyte adhesion to endothelial connecting segment-1 by activating beta integrin. J Clin Invest. 103:613-25.
Shih et al. (2000) Combined serum paraoxonase/apolipoprotein E knockout mice exhibit increased lipoprotein oxidation and atherosclerosis. J Biol Chem. 275:17527-35.
Shishehbor et al. (2003) Association of nitrotyrosine levels with cardiovascular disease and modulation by statin therapy. JAMA. 289(13):1675-80.
Silkensen et al. (1999) Identification of clusterin sequences mediating renal tubular cell interactions. J Peptide Res. 54:449-47.
Singh et al. (2000) Innate defences against viremia. Rev Med Virol. 10:395-403.
Sonntag et al. (1997) Decreases in Cerebral Microvasculature with Age are Associated with the Decline in Growth Hormone and Insulin-Like Growth Factor 1. Endocrinology. 138(8): 3515-20.
Sorescu et al. (2001) NAD(P)H oxidases and their relevance to atherosclerosis. Trends Cardiovasc Med. 11:124-31.
Sparrow, C.P. et al. (2002) A potent synthetic LXR agonist is more effective than cholesterol loading at inducing ABC Al-mRNA and stimulating cholesterol efflux. J Biol Chem. 277:10021-7.
Spieker et al. (2002) High-density lipoprotein restores endothelial function in hypercholesterolemic men. Circulation. 105:1399-402.
Sprecher et al. (1993) The Low HDL Cholesterol/High Triglyceride Trait. Arterioscler Thromb. 13: 495-504.
Springer, T.A. (1990) Adhesion receptors of the immune system. Nature. 346:425-34.
Srinivas et al. (1990) Antivrial Effects of Apolipoprotein A-I and Its Synthetic Amphipathic Peptide Analogs. Virology. 176:48-57.
Stannard et al. (2001) Inability of plasma high-density lipoproteins to inhibit cell adhesion molecule expression in human coronary artery endothelial cells. Atherosclerosis. 154:31-8.
Steplewski et al. (1985) Isolation and characterization of anti-monosialoganglioside monoclonal antibody 19-9 class-switch variants. Proc Natl Acad Sci USA. 82: 8653.
Sugatani et al. (1996) High-density lipoprotein inhibits the synthesis of platelet-activating factor in human vascular endothelial cells. J Lipid Mediators Cell Signal. 13:73-88.
Sumitra et al. (2001) Experimental myocardial necrosis in rats: role of arjunolic acid on platelet aggregation, coagulation and antioxidant status. Mol Cell Biochem. 224(1-2): 135-42.
Suresh, R. et al. (1992) Alterations in human gingival glycosaminoglycan pattern in inflammation and in phenytoin induced overgrowth. Mol Cell Biochem. 115(2):149-54.
Svensson, U. (1985) Role of vesicles during adenovirus 2 internalization into HeLa cells. J Virology. 55:442-9.
Swain, J. et al. (1995) Prooxidant iron and copper, with ferroxidase and xanthine oxidase activities in human atherosclerotic material. FEBS Lett. 368(3):513-5.
Swarnakar et al. (2001) The apolipoprotein E-dependent low density lipoprotein cholesteryl ester selective uptake pathway in murine adrenocortical cells involves chondroitin sulfate proteoglycans and an alpha 2-macroglobulin receptor. J Biol Chem. 276:21121-6.
Swift, L.L. et al. (2001) A recycling pathway for resecretion of internalized apolipoprotein E in liver cells. J Biol Chem. 276:22965-70.
Takahashi, S.Y. et al. (1992) Rabbit very low density lipoprotein receptor-a low density receptor like protein with distinct ligand specificity. Proc Natl Acad Sci USA. 89: 9252-6.
Tam et al. (1997) Interaction of a recombinant form of apolipoprotein[a] with human fibroblasts and with the human hepatoma cell line HepG2. J Lipid Res. 37(3): 518-33.
Tan et al. (1997) A Novel, highly Efficient Peptide-HLA Class TH:ca Binding Assay using unfolded heavy change molecules: Identification of HIV-1 Derived Peptides that Bind to FILA-A* 0201 and HLA-A* 0301. J Immunol Methods. 205:201-9.
Thomas, E.C. (1999) Brain macrophages: on the role of pericytes and perivascular cells. Brain Res Rev. 31: 42-57.

(56) References Cited

OTHER PUBLICATIONS

Throngate, F.E. et al. (2000) Low levels of extrahepatic nonmacrophage ApoE inhibit atherosclerosis without correcting hypercholesterolemia in ApoE-deficient mice. Arterioscler Thromb Vasc Biol. 20:1939-45.
Tian et al. (2002) Structure-affinity relationships in the gp41 ELDKWA epitope for the HIV-1 neutralizing monoclonal antibody 2F5: effects of side-chain and backbone modifications and conformational constraints. J Peptide Res. 59:264-76.
Toyoda, K. et al (1997) Effect of Aging on Regulation of Brain Stem Circulation During hypotension. J Cerebral Blood Flow Metab. 17(6): 680-5.
Triaggiai et al. (2004) An efficient method to make human monoclonal antibodies from memory B cells: potent neutralization of SARS coronavirus. Nat Med. 10(8):871-5.
Tsai et al. (1998) D-serine added to antipsychotics for the treatment of schizophrenia. Biol Psychiatry. 44: 1081-9.
Tsao et al. (2001) Hibernation-induction Peptide and Cell Death: [D-Ala2, D-Leulenkephalin Blocks Bax-related Apoptotic Processes. Eur J Pharmacol. 428:149-51.
Tsimikas et al. (2001) Measuring Circulating Oxidized Low-Density Lipoprotein to Evaluate Coronary Risk. Circulation 103:1930-2.
Tward et al. (2002) Decreased atherosclerotic lesion formation in human serum paraoxonase transgenic mice. Circulation. 106:484-90.
Tytler et al. (1993) Reciprocal effects of apolipoprotein and lytic peptide analogs on membranes. Cross-sectional molecular shapes of amphipathic alpha helixes control membrane stability. J Biol Chem. 268: 2212-8.
Valabhji, J. et al. (2001) High-density lipoprotein composition and paraoxonase activity in Type I diabetes. Clin Sci (Lond). 101(6):659-70.
Van Leeuwen, R. et al. (2003) Epidemiology of age-related maculopathy: a review. Eur J Epidemiol. (9):845-54.
Van Lenten et al. (2002) Influenza infection promotes macrophage traffic into arteries of mice that is prevented by D-4F, an apolipoprotein A-I mimetic peptide. Circulation. 106:1127-32.
Van Lenten, B.J. et al. (2001) High-density lipoprotein loses its anti-inflammatory properties during acute influenza A infection, Circulation. 103:2283-8.
Van Lenten et al. (1995) Anti-inflammatory HDL Becomes Pro-inflammatory during the Acute Phase Response. J Clin Invest. 96:2758-67.
Van Lenton et al. (2004) D-4F an ApoA-I mimetic peptide inhibits the inflammatory response induced by influenza A infection of human type II pneumocytes. Circulation. 110:3252-8.
Varga et al. (1991) Infectious entry pathway of adenovirus type 2. J Virol. 65:6061-70.
Venugopal et al. (2002) Demonstration that C-reactive protein decreases eNOS expression and bioactivity in human aortic endothelial cells. Circulation. 106:1439-41.
Verhoeyen et al. (1988) Reshaping human antibodies: grafting an antilysozyme activity. Science. 239:1534-6.
Vinters et al. (1998) Secondary microvascular degeneration in amyloid angiopathy of patients with hereditary cerebral hemorrhage with amyloidosis, Dutch type (HCHWA-D). Acta Neuropathol. 95:235-44.
Vovenko, E. (1999) Distribution of oxygen tension on the surface of arterioles, capillaries and venules of brain cortex and in tissue in normoxia; an experimental study on rats. Eur J Physiol. 437:617-23.
Wake, A.K. et al. (2008) Apolipoprotein A-1 mimetic peptide retains function after oxidant exposure. Proc ASME 2008 Summer Bioenginerring Conference (Marco Island, Florida), Jun. 25-29, 2008, SBC2008-189660.
Walpola et al. (1995) Expression of ICAM-1 and VCAM-1 and monocyte adherence in arteries exposed to altered shear stress. Arterioscler Thromb Vasc Biol. 15:2-10.
Watson et al. (1995) Effect of platelet activating factor-acetylhydrolase on the formation and action of minimally oxidized-low gensitylipoprotein. J Clin Invest. 95:774-82.
Watson et al. (1995) Protective effect of high density lipoprotein associated paraoxonase. Inhibition of the biological activity of minimally oxidized low density lipoprotein. J Clin Invest. 96:2882-91.
Watts et al. (1998) Dyslipoproteinaemia and hyperoxidative stress in the pathogenesis of endothelial dysfunction in non-insulin dependent diabetes mellitus: a hypothesis. Atherosclerosis. 141:17-30.
Weers, P.M. et al. (2001) Modulation of the lipid binding properties of the N-terminal domain of human apolipoprotein E3. Eur J Biochem. 268(13): 3728-35.
Wei et al. (1998) Antioxidants Inhibit ATP-Sensitive Potassium Channels in Cerebral Arterioles. Stroke. 29: 817-23.
White, C. R. et al. (1994) Superoxide and peroxynitrite in atherosclerosis. Proc Natl Acad Sci USA. 91:1044-8.
White, C.R. et al. (1996) Circulating plasma xanthine oxidase contributes to vascular dysfunction in hypercholesterolemic rabbits. Proc Natl Acad Sci USA. 93:8745-9.
Wickham et al. (1993) Integrins alpha v beta 3 and alpha v beta 5 promote adenovirus internalization but not virus attachment. Cell. 73:309-19.
Witztum, J.L. et al. (1991) Role of oxidized low density lipoprotein in atherogenesis. J Clin Invest. 88:1785-92.
Wolff, J.A. et al. (1990) Direct gene transfer into mouse muscle in vivo. Science. 247(4949 Pt 1): 1465-8.
Wool, G.D. et al. (2008) Apolipoprotein A-I mimetic peptide helix number and helix linker influence potentially anti-atherogenic properties. J Lipid Res. 49(6): 1268-83.
Wool, G.D. et al. (2009) An apoA-I mimetic peptide containing a proline residue has greater in vivo HDL binding and anti-inflammatory ability than the 4F peptide. J Lipid Res. 50(9): 1889-900.
Wu, G. et al. (1998) Effect of human apolipoprotein E isoforms on plasma lipids, lipoproteins and apolipoproteins in apolipoprotein E deficient mice. Atherosclerosis. 141:287-96.
Xia et al. (1999) High density lipoproteins (HDL) interrupt the sphingosine kinase signaling pathway. A possible mechanism for protection against atherosclerosis by HDL. J Biol Chem. 274:33143-7.
Yamamoto et al. (1995) Overexpression of Apolipoprotein E Prevents Development of Diabetic Hyperlipidemia in Transgenic Mice. Diabetes. 44(5):580-5.
Yamashita et al. (2000) Molecular mechanisms, lipoprotein abnormalities and atherogenicity of hyperalphalipoproteinemia. Atherosclerosis. 152:271-85.
Yan et al. (2004) PLTP deficiency improves the anti-inflammatory properties of HDL and reduces the ability of LDL to induce monocyte chemotactic activity. J Lipid Res. 45:1852-8.
Yancey et al. (1995) Efflux of Cellular Cholesterol and Phospholipid to Lipid-free Apolipoproteins and Class A Amphipathic Peptides. Biochemistry. 34:7955-65.
Yip, K.-P. and Marsh, D.J. (1997) An Arg-Gly-Asp peptide stimulates constriction in rat afferent arteriole. Am J Physiol. 273(5 Pt 2): F768-76.
Yla-Herttuala, S. et al. (1991) Macrophages and smooth muscle cells express lipoprotein lipase in human and rabbit atherosclerotic lesions. Proc Natl Acad Sci USA. 88:10143-7.
Yokoyama et al. (1980) The mechanism of activation of lecithin: cholesterol acyltransferase by apolipoprotein A-I and an amphiphilic peptide. J Biol Chem. 255:7333-9.
Yu et al. (2004) Tissue Doppler imaging is superior to strain rate imaging and postsystolic shortening on the prediction of reverse remodeling in both ischemic and nonischemic heart failure after cardiac resynchronization therapy. Circulation. 110:66-73.
Yuan and Altman (1995) Substrate recognition by human RNase P: identification of small, model substrates for the enzyme. EMBO J. 14:159-68.
Yuan et al. (1992) Targeted cleavage of mRNA by human RNase P. Proc Natl Acad Sci USA 89:8006-10.

(56) References Cited

OTHER PUBLICATIONS

Yui et al. (1988) Serum prostacyclin stabilizing factor is identical to apolipoprotein A-I (Apo A-I). A novel function of Apo A-1. J Clin Invest. 82: 803-7.
Zabner et al. (1993) Adenovirus-mediated gene transfer transiently corrects the chloride transport defect in nasal epithelia of patients with cystic fibrosis. Cell. 75:207-16.
Zabner et al. (1994) Safety and efficacy of repetitive adenovirus-mediated transfer of CFTR cDNA to airway epithelia of primates and cotton rats. Nat Genet. 6:75-83.
Zaiou et al. (2000) Apolipoprotein E-low density lipoprotein receptor interaction. Influences of basic residue and amphipathic α-helix organization in the ligand. J Lipid Res. 41:1087-95.
Zeiher, A.M. et al. (1994) Coronary Atherosclerotic Wall Thickening and Vascular Reactivity in Humans: Elevated High-Density Lipoprotein Levels Ameliorate Abnormal Vasoconstriction in Early Atherosclerosis. Circulation. 89(6):2525-32.
Zhang, Z. et al. (2007) D-4F, An Apolipoprotein A-I Mimetic Peptide, Prevents Endothelial Dysfunction Induced by Myeloperoxidase-Derived Hypochlorous Acid. FASEB J. 21:706-11 (Meeting Abstract).
Zhang, C. et al. (2001) L-arginine chlorination products inhibit endothelial nitric oxide production. J Biol Chem. 276: 27159-65.
Zhang, R. et al (2002) Myeloperoxidase functions as a major enzymatic catalyst for initiation of lipid peroxidation at sites of inflammation. J Biol Chem. 277:46116-22.
Zhang, W.-J. et al. (2002) Lack of inhibitory effect of HDL on TNF α-induced adhesion molecule expression in human aortic endothelial cells. Atherosclerosis. 165:241-9.
Zhao et al. (2002) Selective interleukin-12 synthesis defect in 12/15- lipoxygenase deficient macrophages associated with reduced atherosclerosis in a mouse model of familial hypercholesterolemia. J Biol Chem. 277: 35350-6.
Zhu, B. et al. (2000) Apolipoprotein E inhibits neointimal hyperplasia after arterial injury in mice. Am J Pathol. 157:1839-48.
Zhu, Y., and Hui, D.Y. (2003) Apolipoprotein E binding to low density lipoprotein receptor related protein-1 inhibits cell migration via activation of cAMP dependent protein kinase A. J. Biol. Chem. 278:36257-63.
Zilversmit, D.E. (1979) Atherogenesis: a postprandial phenomenon. Circulation. 60:473-85.
Zuker, M. (1989) On finding all suboptimal foldings of an RNA molecule. Science. 244:48-52.
Restriction Requirement dated Sep. 12, 2002 for U.S. Appl. No. 09/645,454.
Response to Restriction Requirement filed Dec. 12, 2002 for U.S. Appl. No. 09/645,454.
Non-Final Office Action dated Jan. 22, 2003 for U.S. Appl. No. 09/645,454.
Response to Non-Final Office Action filed May 27, 2003 for U.S. Appl. No. 09/645,454.
Notice of Allowance dated Jun. 25, 2003 for U.S. Appl. No. 09/645,454.
Restriction Requirement dated Feb. 20, 2003 for U.S. Appl. No. 09/896,841 (4 pages).
Response to Restriction Requirement filed Aug. 25, 2003 for U.S. Appl. No. 09/896,841 (16 pages).
Non-Final Office Action dated Oct. 21, 2003 for U.S. Appl. No. 09/896,841 (12 pages).
Response to Non-Final Office Action filed Apr. 23, 2004 for U.S. Appl. No. 09/896,841 (23 pages).
Final Office Action dated May 7, 2004 for U.S. Appl. No. 09/896,841 (9 pages).
RCE/Response to Final Office Action filed Nov. 15, 2004 for U.S. Appl. No. 09/896,841 (17 pages).
Notice of Allowance dated Dec. 20, 2004 for U.S. Appl. No. 09/896,841 (5 pages).
International Search Report dated May 17, 2002 for PCT App. No. PCT/US01/26457 (3 pages).
International Preliminary Examination Report dated Mar. 4, 2003 for PCT App. No. PCT/US01/26457 (5 pages).
Restriction Requirement dated Jul. 15, 2003 for U.S. Appl. No. 10/187,215 (4 pages).
Response to Restriction Reqirement filed Nov. 19, 2003 for U.S. Appl. No. 10/187,215 (17 pages).
Non-Final Office Action dated Jan. 8, 2004 for U.S. Appl. No. 10/187,215 (15 pages).
Response to Non-Final Office Action filed Jul. 12, 2004 for U.S. Appl. No. 10/187,215 (18 pages).
Non-Final Office Action dated Aug. 26, 2004 for U.S. Appl. No. 10/187,215 (7 pages).
Response to Non-Final Office Action filed Feb. 28, 2005 for U.S. Appl. No. 10/187,215.
Final Office Action dated Apr. 11, 2005 for U.S. Appl. No. 10/187,215.
RCE/Response to Final Office Action filed Oct. 7, 2005 for U.S. Appl. No. 10/187,215.
Non-Final Office Action dated Oct. 28, 2005 for U.S. Appl. No. 10/187,215.
Response to Non-Final Office Action filed Mar. 20, 2006 for U.S. Appl. No. 10/187,215.
Notice of Allowance dated May 1, 2006 for U.S. Appl. No. 10/187,215.
Restriction Requirement dated Feb. 19, 2004 for U.S. Appl. No. 10/273,386.
Response to Restriction Requirement filed May 3, 2004 for U.S. Appl. No. 10/273,386.
Non-Final Office Action dated Jun. 21, 2004 for U.S. App. No. 10/273,386.
Response to Non-Final Office Action filed Dec. 21, 2004 for U.S. Appl. No. 10/273,386.
Final Office Action dated Feb. 2, 2005 for U.S. Appl. No. 10/273,386.
RCE/Response to Final Office Action filed Aug. 15, 2005 for U.S. Appl. No. 10/273,386.
Non-Final Office Action dated Sep. 7, 2005 for U.S. Appl. No. 10/273,386.
Response to Non-Final Office Action filed Jan. 20, 2006 for U.S. Appl. No. 10/273,386.
Final Office Action dated Mar. 31, 2006 for U.S. Appl. No. 10/273,386.
Response to Final Office Action filed Jul. 3, 2006 for U.S. Appl. No. 10/273,386.
Notice of Allowance dated Aug. 20, 2006 for U.S. Appl. No. 10/273,386.
Restriction Requirement dated Nov. 9, 2004 for U.S. Appl. No. 10/423,830.
Response to Restriction Requirement filed Mar. 1, 2005 for U.S. Appl. No. 10/423,830.
Non-Final Office Action dated Apr. 18, 2005 for U.S. Appl. No. 10/423,830.
Response to Non-Final Office Action filed Oct. 19, 2005 for U.S. Appl. No. 10/423,830.
Final Office Action dated Nov. 15, 2005 for U.S. Appl. No. 10/423,830.
RCE/Response to Final Office Action filed Oct. 18, 2006 for U.S. Appl. No. 10/423,830.
Notice of Allowance dated Nov. 21, 2006 for U.S. Appl. No. 10/423,830.
Restriction Requirement dated Aug. 21, 2007 for U.S. Appl. No. 11/407,390, filed Apr. 18, 2006 and granted as U.S. Pat. No. 7,723,303 on May 25, 2010 (Inventor—Fogelman et al.).
Response to Restriction Requirement filed Nov. 23, 2007 for U.S. Appl. No. 11/407,390, filed Apr. 18, 2006 and granted as U.S. Pat. No. 7,723,303 on May 25, 2010 (Inventor—Fogelman et al.).
Non-Final Office Action dated Jan. 17, 2008 for U.S. Appl. No. 11/407,390, filed Apr. 18, 2006 and granted as U.S. Pat. No. 7,723,303 on May 25, 2010 (Inventor—Fogelman et al.).
Response to Non-Final Office Action filed Jul. 17, 2008 for U.S. Appl. No. 11/407,390, filed Apr. 18, 2006 and granted as U.S. Pat. No. 7,723,303 on May 25, 2010 (Inventor—Fogelman et al.).
Final Office Action dated Sep. 11, 2008 for U.S. Appl. No. 11/407,390, filed Apr. 18, 2006 and granted as U.S. Pat. No. 7,723,303 on May 25, 2010 (Inventor—Fogelman et al.).

(56) References Cited

OTHER PUBLICATIONS

RCE/Response to Final Office Action filed Jul. 13, 2009 for U.S. Appl. No. 11/407,390, filed Apr. 18, 2006 and granted as U.S. Pat. No. 7,723,303 on May 25, 2010 (Inventor—Fogelman et al.).
Ex Parte Quayle Action dated Aug. 14, 2009 for U.S. Appl. No. 11/407,390, filed Apr. 18, 2006 and granted as U.S. Pat. No. 7,723,303 on May 25, 2010 (Inventor—Fogelman et al.).
Response to Ex Parte Quayle Action filed Oct. 14, 2009 for U.S. Appl. No. 11/407,390, filed Apr. 18, 2006 and granted as U.S. Pat. No. 7,723,303 on May 25, 2010 (Inventor—Fogelman et al.).
Notice of Allowance dated Dec. 2, 2009 for U.S. Appl. No. 11/407,390, filed Apr. 18, 2006 and granted as U.S. Pat. No. 7,723,303 on May 25, 2010 (Inventor—Fogelman et al.).
International Search Report and Written Opinion dated Sep. 1, 2009 for PCT App. No. PCT/US2009/033415.
International Preliminary Opinion on Patentability dated Aug. 19, 2010 for PCT App. No. PCT/US2009/033415.
Preliminary Amendment filed Nov. 13, 2003 for U.S. Appl. No. 10/712,447 (6 pages).
Preliminary Amendment filed May 14, 2004 for U.S. Appl. No. 10/712,447 (7 pages).
Restriction Requirement dated Oct. 14, 2005 for U.S. Appl. No. 10/712,447 (9 pages).
Restriction Requirement dated Feb. 16, 2006 for U.S. Appl. No. 10/712,447 (9 pages).
Response to Restriction Requirement filed Mar. 16, 2006 for U.S. Appl. No. 10/712,447 (10 pages).
Non-Final Office Action dated May 31, 2006 for U.S. Appl. No. 10/712,447 (11 pages).
Response to Non-Final Office Action filed Nov. 29, 2006 for U.S. Appl. No. 10/712,447 (21 pages).
Final Office Action dated Mar. 2, 2007 for U.S. Appl. No. 10/712,447 (7 pages).
Response to Final Office Action filed Jul. 31, 2007 for U.S. Appl. No. 10/712,447(15 pages).
Advisory Action dated Aug. 13, 2007 for U.S. Appl. No. 10/712,447 (3 pages).
Response to Advisory Action and Final Office Action filed Sep. 4, 2007 for U.S. Appl. No. 10/712,447 (16 pages).
Non-Final Office Action dated Nov. 19, 2007 for U.S. Appl. No. 10/712,447 (9 pages).
Response after Non-Final Office Action filed Mar. 12, 2008 for U.S. Appl. No. 10/712,447 (14 pages).
Non-Final Office Action dated Jun. 13, 2008 for U.S. Appl. No. 10/712,447 (8 pages).
Response to Non-Final Office Action filed Sep. 3, 2008 for U.S. Appl. No. 10/712,447 (9 pages).
Terminal Disclaimer filed Sep. 3, 2008 for U.S. Appl. No. 10/712,447 (3 pages).
Terminal Disclaimer accepted Feb. 12, 2009 for U.S. Appl. No. 10/712,447 (1 page).
Notice of Allowance with Interview Summary and Examiner's Amendment dated Feb. 24, 2009 for U.S. Appl. No. 10/712,447 (7 pages).
Issue Notification dated Jul. 1, 2009 for U.S. Appl. No. 10/712,447 (1 page).
Request for Certificate of Correction filed Aug. 3, 2009 for U.S. Appl. No. 10/712,447 (4 pages).
Certificate of Correction dated Sep. 8, 2009 for U.S. Appl. No. 10/712,447 (1 page).
Restriction Requirement dated Jun. 26, 2008 for U.S. Appl. No. 11/405,601 (11 pages).
Response to Restriction Requirement filed Jul. 25, 2008 for U.S. Appl. No. 11/405,601 (8 pages).
Miscellaneous Action dated Oct. 24, 2008 for U.S. Appl. No. 11/405,601 (2 pages).
Response to Restriction Requirement filed Mar. 17, 2009 for U.S. Appl. No. 11/405,601 (5 pages).
Non-Final Office Action dated Jun. 10, 2009 for U.S. Appl. No. 11/405,601 (14 pages).
Response to Non-Final Rejection filed Oct. 9, 2009 for U.S. Appl. No. 11/405,601 (17 pages).
Final Office Action dated Jan. 29, 2010 for U.S. Appl. No. 11/405,601 (10 pages).
Response to Final Office Action filed Sep. 28, 2010 for U.S. Appl. No. 11/405,601 (20 pages).
Notice of Allowance dated Sep. 9, 2011 for U.S. Appl. No. 11/405,601 (5 pages).
Issue Notification dated Dec. 27, 2011 by the U.S. Patent and Trademark Office for U.S. Appl. No. 11/405,601 (1 page).
International Search Report dated Nov. 17, 2005 for International Patent Application No. PCT/US2003/036268 (4 pages).
International Preliminary Report on Patentability dated Jul. 25, 2011 for International Patent Application No. PCT/US2003/036268.
Examiner's First Report dated Apr. 30, 2008 for Australian Application No. 200390825 (2 pages).
First Statement of Proposed Amendments filed Sep. 18, 2008 for Australian Application No. 200390825 (13 pages).
Notice of Acceptance dated Oct. 14, 2008 for Australian Application No. 200390825 (3 pages).
Grant of Request for Leave to Amend dated Jul. 3, 2009 for Australian Application No. 200390825 (1 page).
First Examination Report dated Sep. 18, 2007 for New Zealand Application No. 541504 (2 pages).
Response to Examination Report filed Jul. 16, 2008 for New Zealand Application No. 541504 (18 pages).
Examination Report dated for Aug. 5, 2008 New Zealand Application No. 541504 (2 pages).
Response to Examination Report filed Dec. 23, 2008 for New Zealand Application No. 541504 (6 pages).
Examination Report dated Jan. 22, 2009 for New Zealand Application No. 541504 (2 pages).
Response to Examination Report filed Mar. 18, 2009 for New Zealand Application No. 541504 (3 pages).
Examination Report and Notice of Acceptance of Completed Specification dated Apr. 7, 2009 for New Zealand Application No. 541504 (2 pages).
Letters Patent dated Aug. 13, 2009 for New Zealand Application No. 541504 (1 page).
Office Action dated Aug. 10, 2009 for Canadian Application No. 2,514,303 (3 pages).
Response to Office Action filed Feb. 10, 2010 for Canadian Application No. 2,514,303 (19 pages).
Office Action dated Oct. 6, 2010 for Canadian Application No. 2,514,303 (2 pages).
Response to Office Action filed Mar. 29, 2011 for Canadian Application No. 2,514,303 (11 pages).
Notice of Allowance dated Feb. 24, 2012 by the Canadian Intellectual Property Office for Canadian Patent Application No. 2,514,303, whichwas filed on Jul. 25, 2005 and granted on Sep. 18, 2012 (Inventor—Gattadahalli et al.; Applicant—UAB research Foundation) (1 page).
Letters of Patent dated Sep. 18, 2012 by the Canadian Intellectual Property Office for Canadian Patent Application No. 2,514,303, whichwas filed on Jul. 25, 2005 and granted on Sep. 18, 2012 (Inventor Gattadahalli et al.; Applicant—UAB research Foundation) (2 pages).
Supplementary European Search Report dated Nov. 29, 2011 by the European Patent Office for patent application No. 03783409.0, which was filed on Nov. 13, 2003 and published as 1599173 on Nov. 30, 2005 (Inventor—Gattadahalli et al.; Applicant—UAB research Foundation) (3 pages).
Extended European Search Report dated Nov. 13, 2017 by the European Patent Office for patent application No. 17157243.1, which was filed on Feb. 21, 2017 and published as EP 3254673 on Dec. 13, 2017 (Inventor—Gattadahalli et al.; Applicant—UAB research Foundation) (7 pages).
Examination Report No. 1 dated Dec. 3, 2012 by the Intellectual Property Office of Australia for Australian Patent Application No. 2008296487, which was filed on Mar. 11, 2010 (Inventor—Anantharamaiah et al.; Applicant—UAB Research Foundation) (3 pages).

(56) References Cited

OTHER PUBLICATIONS

Supplementary European Search Report dated Apr. 8, 2011 by the European Patent Office for European Patent Application No. 08829135.6, which was filed on Mar. 26, 2010 and published as 2195340 on Jun. 16, 2010 (Inventor—Anantharamaiah et al.; Applicant—UAB Research Foundation) (6 pages).
Office Action dated Jul. 23, 2013 by the Patent Office of Japan for Japanese Patent Application No. 2010-523116, which was filed on Feb. 26, 2010 and published as 2010-537638 on Dec. 9, 2010 (Inventor—Anantharamaiah et al.; Applicant—UAB Research Foundation) (13 pages).
International Search Report and Written Opinion dated Jul. 28, 2009 by the International Searching Authority for International Patent Application No. PCT/US2008/074485, which was filed on Aug. 27, 2008 and published as WO 2009/032702 on Mar. 12, 2009 (Inventor—Anantharamaiah et al.; Applicant—UAB Research Foundation) (12 pages).
International Preliminary Report on Patentability dated Mar. 2, 2010 by the International Searching Authority for International Patent Application No. PCT/US2008/074485, which was filed on Aug. 27, 2008 and published as WO 2009/032702 on Mar. 12, 2009 (Inventor—Anatharamaiah et al.; Applicant—UAB Research Foundation) (9 pages).
Preliminary Amendment filed on Mar. 16, 2010 with the U.S. Patent and Trademark Office for U.S. Appl. No. 12/675,073, filed Mar. 22, 2010 and granted as U.S. Pat. No. 8,557,767 on Oct. 15, 2013 (Inventor—Anantharamaiah et al.; Applicant—UAB research Foundation) (5 pages).
Preliminary Amendment filed on Jul. 6, 2010 with the U.S. Patent and Trademark Office for U.S. Appl. No. 12/675,073, filed Mar. 22, 2010 and granted as U.S. Pat. No. 8,557,767 on Oct. 15, 2013 (Inventor—Anantharamaiah et al.; Applicant—UAB research Foundation) (3 pages).
Preliminary Amendment filed on Jul. 14, 2010 with the U.S. Patent and Trademark Office for U.S. Appl. No. 12/675,073, filed Mar. 22, 2010 and granted as U.S. Pat. No. 8,557,767 on Oct. 15, 2013 (Inventor—Anantharamaiah et al.; Applicant—UAB research Foundation) (3 pages).
Restriction Requirement dated Jul. 9, 2012 by the U.S. Patent and Trademark Office for U.S. Appl. No. 12/675,073, filed Mar. 22, 2010 and granted as U.S. Pat. No. 8,557,767 on Oct. 15, 2013 (Inventor—Anantharamaiah et al.; Applicant—UAB research Foundation) (6 pages).
Response to Restriction Requirement filed on Sep. 12, 2012 with the U.S. Patent and Trademark Office for U.S. Appl. No. 12/675,073, filed Mar. 22, 2010 and granted as U.S. Pat. No. 8,557,767 on Oct. 15, 2013 (Inventor—Anantharamaiah et al.; Applicant—UAB research Foundation) (8 pages).
Non-Final Office Action dated Oct. 2, 2012 by the U.S. Patent and Trademark Office for U.S. Appl. No. 12/675,073, filed Mar. 22, 2010 and granted as U.S. Pat. No. 8,557,767 on Oct. 15, 2013 (Inventor—Anantharamaiah et al.; Applicant—UAB research Foundation) (9 pages).
Response to Non-Final Office Action filed on Mar. 26, 2013 with the U.S. Patent and Trademark Office for U.S. Appl. No. 12/675,073, filed Mar. 22, 2010 and granted as U.S. Pat. No. 8,557,767 on Oct. 15, 2013 (Inventor—Anantharamaiah et al.; Applicant—UAB research Foundation) (11 pages).
Notice of Allowance issued on Jul. 9, 2013 by the U.S. Patent and Trademark Office for U.S. Appl. No. 12/675,073, filed Mar. 22, 2010 and granted as U.S. Pat. No. 8,557,767 on Oct. 15, 2013 (Inventor—Anantharamaiah et al.; Applicant—UAB research Foundation) (9 pages).
Notice of Allowability issued on Jul. 22, 2013 by the U.S. Patent and Trademark Office for U.S. Appl. No. 12/675,073, filed Mar. 22, 2010 and granted as U.S. Pat. No. 8,557,767 on Oct. 15, 2013 (Inventor—Anantharamaiah et al.; Applicant—UAB research Foundation) (3 pages).
Issue Notification dated Oct. 15, 2013 by the U.S. Patent and Trademark Office for U.S. Appl. No. 12/675,073, filed Mar. 22, 2010 and granted as U.S. Pat. No. 8,557,767 on Oct. 15, 2013 (Inventor—Anantharamaiah et al.; Applicant—UAB research Foundation) (1 page).
Restriction Requirement dated Feb. 7, 2013 by the U.S. Patent and Trademark Office for for U.S. Appl. No. 13/429,022, filed Mar. 23, 2012 and published as US 2012/0245101 on Sep. 27, 2012 (Inventor—Anantharamaiah et al.; Applican—UAB Research Foundation) (11 pages).
Response to Restriction Requirement filed on May 22, 2013 with the U.S. Patent and Trademark Office for for U.S. Appl. No. 13/429,022, filed Mar. 23, 2012 and published as US 2012/0245101 on Sep. 27, 2012 (Inventor—Anantharamaiah et al.; Applicant—UAB Research Foundation) (11 pages).
Non-Final Office Action dated Aug. 21, 2013 by the U.S. Patent and Trademark Office for for U.S. Appl. No. 13/429,022, filed Mar. 23, 2012 and published as US 2012/0245101 on Sep. 27, 2012 (Inventor—Anantharamaiah et al.; Applicant—UAB Research Foundation) (23 pages).
Notice of Abandonment dated Mar. 12, 2014 by the U.S. Patent and Trademark Office for for U.S. Appl. No. 13/429,022, filed Mar. 23, 2012 and published as US 2012/0245101 on Sep. 27, 2012 (Inventor—Anantharamaiah et al.; Applicant—UAB Research Foundation) (2 pages).
Examination Report No. 1 dated Nov. 9, 2012 by the Australian Patent Office for Australian Patent Application No. 2008295478, which was field on Aug. 27, 2008 and granted as 2008296478 on Dec. 11, 2014 (Inventor—Anantharamaiah et al.; Applicant—UAB Research Foundation) (3 pages).
Examination Report No. 2 dated Jan. 6, 2014 by the Australian Patent Office for Australian Patent Application No. 2008295478, which was field on Aug. 27, 2008 and granted as 2008296478 on Dec. 11, 2014 (Inventor—Anantharamaiah et al.; Applicant—UAB Research Foundation) (4 pages).
Certificate of Grant dated Dec. 11, 2014 by the Australian Patent Office for Australian Patent Application No. 2008295478, which was field on Aug. 27, 2008 and granted as 2008296478 on Dec. 11, 2014 (Inventor—Anantharamaiah et al.; Applicant—UAB Research Foundation) (97 pages).
Office Action dated Feb. 3, 2015 by the Canadian Intellectual Property Office for Canadian Patent Application No. 2,704,729, which was filed on Aug. 27, 2008 (Inventor—Anantharamaiah et al.; Applicant—UAB Research Foundation) (4 pages).
Office Action dated Apr. 25, 2016 by the Canadian Intellectual Poperty Office for Canadian Patent Application No. 2,704,729, which was filed on Aug. 27, 2008 (Inventor—Anantharamaiah et al.; Applicant—UAB Research Foundation) (4 pages).
Office Action dated May 6, 2017 by the Canadian Intellectual Property Office for Canadian Patent Application No. 2,704,729, which was filed on Aug. 27, 2008 (Inventor—Anantharamaiah et al.; Applicant—UAB Research Foundation) (4 pages).
Supplementary European Search Report dated Apr. 8, 2011 by the European Patent Office for European Patent Application No. 08798802.8, which was filed on Aug. 27, 2008 and granted as 2195331 on Nov. 20, 2013 (Inventor—Anantharamaiah et al.; Applicant—UAB research Foundation) (6 pages).
Extended European Search Report dated Dec. 3, 2013 by the European Patent Office for European Patent Application No. 13187186.5, which was filed on Oct. 7, 2013 and published as 2682400 on Jan. 8, 2014 (Inventor—Anantharamaiah et al.; Applicant—UAB research Foundation) (10 pages).
Transmittal of the International Search Report and Written Opinion dated Mar. 9, 2009 by the International Searching Authority for International Patent Application No. PCT/US2008/074470, which was filed on Aug. 27, 2008 and published as WO 2009/032693 on Mar. 12, 2009 (Inventor—Anantharamaiah et al.; Applicant—UAB Research Foundation).
Internation Preliminary Report on Patentability dated Mar. 2, 2010 by the International Searching Authority for International Patent Application No. PCT/US2008/074470, which was filed on Aug. 27, 2008 and published as WO 2009/032693 on Mar. 12, 2009 (Inventor—Anantharamaiah et al.; Applicant—UAB Research Foundation) (4 pages),

(56) References Cited

OTHER PUBLICATIONS

Preliminary Amendment filed Mar. 12, 2010 filed with the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (8 pages).
Preliminary Amendment filed on Jul. 6, 2010 with the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (3 pages).
Restriction Requirement dated Apr. 16, 2012 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applican—UAB Research Foundation) (7 pages).
Response to Restriction Requirement filed on May 16, 2012 with the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (9 pages).
Non-Final Office Action dated Jun. 29, 2012 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applican—UAB Research Foundation) (13 pages).
Response to Non-Final Office Action filed on Oct. 29, 2012 with the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (16 pages).
Final Office Action dated Jan. 10, 2013 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (21 pages).
Response to Final Office Action filed on May 9, 2013 with the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (18 pages).
Non-Final Office Action dated Jul. 15, 2014 by the U.S. Patent and Trademark Office for for U.S. Appl. No. 12/675,080, filed Apr. 21,2010 and published as US 2010/0298215 on Nov. 25, 2010 (Inventor—Anantharamaiah et al.; Applicant—UAB Research Foundation) (21 pages).
Response to Non-Final Office Action filed on Jan. 15, 2015 with the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (13 pages).
Final Office Action dated Feb. 13, 2015 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (22 pages).
Response After Final Office Action filed on Jul. 13, 2015 with the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (11 pages).
Notice of Allowance dated Aug. 3, 2015 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (5 pages).
Notice of Allowance dated Apr. 21, 2016 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (6 pages).
Issue Notification dated Aug. 3, 2016 by the U.S. Patent and Trademark Office for for U.S. Appl. No. 12/675,089, filed Apr. 21, 2010 and published as US 2010/0298215 on Nov. 25, 2010 (Inventor—Anantharamaiah et al.; Applicant—UAB Research Foundation) (1 page).
Preliminary Amendment filed on Sep. 11, 2015 with the U.S. Patent and Trademark Office for for U.S. Appl. No. 14/851,622, filed Sep. 11, 2015 and published as US 2016/0151455 on Jun. 2, 2016 (Inventor—Anantharamaiah et al; Applicant-UAB Research Foundation) (3 pages).
Restriction Requirement dated Mar. 6, 2017 by the U.S. Patent and Trademark Office for for U.S. Appl. No. 14/851,622, filed Sep. 11, 2015 and published as US 2016/0151455 on Jun. 2, 2016 (Inventor—Anantharamaiah et al.; Applicant—UAB Research Foundation) (7 pages).
Response to Restriction Requirement filed on Sep. 1, 2017 with the U.S. Patent and Trademark Office for for U.S. Appl. No. 14/851,622, filed Sep. 11, 2015 and published as US 2016/0151455 on Jun. 2, 2016 (Inventor—Anantharamaiah et al.; Applicant-UAB Research Foundation) (5 pages).
Non-Final Office Action dated Oct. 16, 2017 by the U.S. Patent and Trademark Office for for U.S. Appl. No. 14/851,622, filed Sep. 11, 2015 and published as US 2016/0151455 on Jun. 2, 2016 (Inventor—Anantharamaiah et al.; Applicant-UAB Research Foundation) (12 pages).
Office Action dated Jan. 23, 2015 by the Canadian Intellectual Property Office for Canadian Patent Application No. 2,714,082, which was filed Aug. 4, 2010 (Inventor—Anantharamaiah et al.; Applicant—UAB Research Foundation) (5 pages).
Restriction Requirement dated Aug. 12, 2010 by the U.S. Patent and Trademark Office for U.S. Appl. No. 12/027,728, filed Feb. 7, 2008 and granted as U.S. Pat. No. 8,568,766 on Oct. 29, 2013 (Inventor—Anantharamaiah et al.; Applicant—UAB research Foundation) (7 pages).
Response to Restriction Requirement filed on Sep. 27, 2010 with the U.S. Patent and Trademark Office for U.S. Appl. No. 12/027,728, filed Feb. 7, 2008 and granted as U.S. Pat. No. 8,568,766 on Oct. 29, 2013 (Invento—Anantharamaiah et al.; Applicant—UAB research Foundation).
Non-Final Office Action dated May 27, 2011 by the U.S. Patent and Trademark Office for U.S. Appl. No. 12/027,728, filed Feb. 7, 2008 and granted as U.S. Pat. No. 8,568,766 on Oct. 29, 2013 (Inventor—Anantharamaiah et al.; Applicant—UAB research Foundation).
Response to Non-Final Office Action filed on Nov. 1, 2011 with the U.S. Patent and Trademark Office for U.S. App. No. 12/027,728, filed Feb. 7, 2008 and granted as U.S. Pat. No. 8,568,766 on Oct. 29, 2013 (Inventor—Anantharamaiah et al.; Applicant—UAB research Foundation).
Non-Final Office Action dated Jan. 13, 2012 by the U.S. Patent and Trademark Office for U.S. Appl. No. 12/027,728, filed Feb. 7, 2008 and granted as U.S. Pat. No. 8,568,766 on Oct. 29, 2013 (Inventor—Anantharamaiah et al.; Applicant—UAB research Foundation) (15 pages).
Response to Non-Final Office Action filed on Apr. 10, 2012 with the U.S. Patent and Trademark Office for U.S. Appl. No. 12/027,728, filed Feb. 7, 2008 and granted as U.S. Pat. No. 8,568,766 on Oct. 29, 2013 (Inventor—Anantharamaiah et al.; Applicant—UAB research Foundation) (15 pages).
Non-Final Office Action dated Jun. 14, 2012 by the U.S. Patent and Trademark Office for U.S. Appl. No. 12/027,728, filed Feb. 7, 2008 and granted as U.S. Pat. No. 8,568,766 on Oct. 29, 2013 (Inventor—Anantharamaiahet al.; Applicant—UAB research Foundation) (11 pages).
Response to Non-Final Office Action filed on Oct. 10, 2012 with the U.S. Patent and Trademark Office for U.S. Appl. No. 12/027,728, filed Feb. 7, 2008 and granted as U.S. Pat. No. 8,568,766 on Oct. 29, 2013 (Inventor—Anantharamaiah et al.; Applicant—UAB research Foundation) (10 pages).
Supplemental Response to Non-Final Office Action filed on Dec. 5, 2012 with the U.S. Patent and Trademark Office for U.S. Appl. No.

(56) References Cited

OTHER PUBLICATIONS

12/027,728, filed Feb. 7, 2008 and granted as U.S. Pat. No. 8,568,766 on Oct. 29, 2013 (Inventor—Anantharamaiah et al.; Applicant—UAB research Foundation) (8 pages).
Notice of Allowance dated Dec. 17, 2012 by the U.S. Patent and Trademark Office for U.S. Appl. No. 12/027,728, filed Feb. 7, 2008 and granted U.S. Pat. No. 8,568,766 on Oct. 29, 2013 (Inventor—Anantharamaiah et al.; Applicant—UAB research Foundation) (5 pages).
Notice of Allowance dated Jan. 29, 2013 by the U.S. Patent and Trademark Office for U.S. Appl. No. 12/027,728, filed Feb. 7, 2008 and granted as U.S. Pat. No. 8,568,766 on Oct. 29, 2013 (Inventor—Anantharamaiah et al.; Applicant—UAB research Foundation) (2 pages).
Notice of Allowance dated Feb. 12, 2013 by the U.S. Patent and Trademark Office for U.S. Appl. No. 12/027,728, filed Feb. 7, 2008 and granted as U.S. Pat. No. 8,568,766 on Oct. 29, 2013 (Inventor—Anantharamaiah et al.; Applicant—UAB research Foundation) (2 pages).
Issue Notification dated Oct. 29, 2013 by the U.S. Patent and Trademark Office for U.S. Appl. No. 12/027,728, filed Feb. 7, 2008 and granted as U.S. Pat. No. 8,568,766 on Oct. 29, 2013 (Inventor—Anantharamaiah et al.; Applicant—UAB research Foundation) (1 page).
Restriction Requirement dated Feb. 1, 2013 by the U.S. Patent and Trademark Office for U.S. Appl. No. 12/865,957, filed Oct. 15, 2010 and published as US 2011/0182992 on Jul. 28, 2011 (Inventor—Anantharamaiah et al.; Applicant—UAB research Foundation) (8 pages).
Response to Restriction Requirement filed on Jul. 23, 2013 with the U.S. Patent and Trademark Office for U.S. Appl. No. 12/865,957, filed Oct. 15, 2010 and published as US 2011/0182992 on Jul. 28, 2011 (Inventor—Anantharamaiah et al.; Applicant—UAB research Foundation) (6 pages).
Non-Final Office Action dated Nov. 1, 2013 by the U.S. Patent and Trademark Office for U.S. Appl. No. 12/865,957, filed Oct. 15, 2010 and published as US 2011/0182992 on Jul. 28, 2011 (Inventor—Anantharamaiah et al.; Applicant—UAB research Foundation) (6 pages).
Response to Non-Final Office Action filed on Mar. 25, 2014 with the U.S. Patent and Trademark Office for U.S. Appl. No. 12/865,957, filed Oct. 15, 2010 and published as US 2011/0182992 on Jul. 28, 2011 (Inventor—Anantharamaiah et al.; Appliant—UAB research Foudation) (14 pages).
Final Office Action dated Jun. 9, 2014 by the U.S. Patent and Trademark Office for U.S. Appl. No. 12/865,957, filed Oct. 15, 2010 and published as US 2011/0182992 on Jul. 28, 2011 (Inventor—Anantharamaiah et al.; Applicant—UAB research Foundation) (5 pages).
Response After Final Office Action filed on Oct. 09, 2014 with the U.S. Patent and Trademark Office for U.S. Appl. No. 12/865,957, filed Oct. 15, 2010 and published as US 2011/0182992 on Jul. 28, 2011 (Inventor—Anantharamaiah et al.; Applicant—UAB research Foundation) (6 pages).
Notice of Allowance dated Dec. 10, 2014 by the U.S. Patent and Trademark Office for U.S. Appl. No. 12/865,957, filed Oct. 15, 2010 and published as US 2011/0182992 on Jul. 28, 2011 (Inventor—Anantharamaiah et al.; Applicant—UAB research Foundation) (5 pages).
Notice of Abandonment dated May 13, 2015 by the U.S. Patent and Trademark Office for U.S. Appl. No. 12/865,957, filed Oct. 15, 2010 and published as US 2011/0182992 on Jul. 28, 2011 (Inventor—Anantharamaiah et al.; Applicant—UAB research Foundation) (1 page).
Restriction Requirement dated Nov. 27, 2013 by the U.S. Patent and Trademark Office for U.S. Appl. No. 13/804,161, filed Mar. 14, 2013 and published as US 2013/0295042 on Nov. 7, 2013 (Inventor—Anantharamaiah et al.; Applicant—UAB research Foundation) (7 pages).
Response to Restriction Requirement filed on Apr. 25, 2014 with the U.S. Patent and Trademark Office for U.S. Appl. No. 13/804,161, filed Mar. 14, 2013 and published as US 2013/0295042 on Nov. 7, 2013 (Inventor—Anantharamaiah et al.; Applicant—UAB research Foundation) (9 pages).
Non-Final Office Action dated Jul. 10, 2014 by the U.S. Patent and Trademark Office for U.S. Appl. No. 13/804,161, filed Mar. 14, 2013 and published as US 2013/0295042 on Nov. 7, 2013 (Inventor—Anantharamaiah et al.; Applicant—UAB research Foundation) (26 pages).
Response to Non-Final Office Action filed on Jan. 12, 2015 with the U.S. Patent and Trademark Office for U.S. Appl. No. 13/804,161, filed Mar. 14, 2013 and published as US 2013/0295042 on Nov. 7, 2013 (Inventor—Anantharamaiah et al.; Applicant—UAB research Foundation) (17 pages).
Notice of Allowance dated Feb. 3, 2015 by the U.S. Patent and Trademark Office for U.S. Appl. No. 13/804,161, filed Mar. 14, 2013 and published as US 2013/0295042 on Nov. 7, 2013 (Inventor—Anantharamaiah et al.; Applicant—UAB Research Foundation) (10 pages).
Notice of Abandonment dated May 21, 2015 by the U.S. Patent and Trademark Office for U.S. Appl. No. 13/804,161, filed Mar. 14, 2013 and published as US 2013/0295042 on Nov. 7, 2013 (Inventor—Anantharamaiah et al.; Applicant—UAB Research Foundation) (1 page).
Examination Report dated Sep. 21, 2017 by the Canadian Intellectual Property Office for Patent Application No. 2903869, which was filed on Mar. 14, 2013 (Inventor—G.M. Anantharamaiah, et al.; Applicant—UAB Research Foundation) (6 pages).
Office Action dated Feb. 1, 2018 by the European Patent Office for Patent Application No. 14769489.7, which was filed on Mar. 14, 2014 and published as EP 2996706 on Mar. 22, 2016 (Inventor—Anantharamaiah et al.; Applicant—UAB Research Foundation) (5 pages).
Office Action dated Dec. 11, 2017 by the Patent Office of Japan for Patent Application No. 2016-502527, which was filed on Mar. 14, 2014 and published as 2016-515137 on May 26, 2017 (Inventor—G.M. Anantharamaiah, et al.; Applicant—UAB Research Foundation) (Original-4 pages // Translation—6 pages).
Response to Final Office Action and Request for Continued Examination filed on Sep. 19, 2017 with U.S. Patent and Trademark Office for U.S. Appl. No. 14/770,270, filed Aug. 25, 2015 and published as US 2016/0002315 on Jan. 17, 2016 (Inventor—G.M. Anantharamaiah et al.; Applicant—UAB Research Foundation) (13 pages).
Non-Final Office Action dated Mar. 12, 2018 by the U.S. Patent and Trademark Office for U.S. Appl. No. 14/770,270, filed Aug. 25, 2015 and published as US 2016/0002315 on Jan. 17, 2016 (Inventor—G.M. Anantharamaiah, et al.; Applicant-UAB Research Foundation) (18 pages).
Applicant-Initiated Interview Summary dated Jun. 26, 2018 by the U.S. Patent and Trademark Office for U.S. Appl. No. 14/770,270, filed Aug. 25, 2015 and published as US 2016/0002315 on Jan. 17, 2016 (Inventor—G.M. Anantharamaiah, et al.; Applicant—UAB Research Foundation) (3 pages).
Response to Non-Final Office Action filed on Aug. 14, 2018 with the U.S. Patent and Trademark Office for U.S. Appl. No. 14/770,270, filed Aug. 25, 2015 and published as US 2016/0002315 on Jan. 17, 2016 (Inventor—G.M. Anantharamaiah, et al.; Applicant—UAB Research Foundation) (12 pages).
Supplementary European Search Report dated Feb. 2, 2018 by the European Patent Office for Patent Application No. 15826625.4, which was filed on Jul. 20, 2015 and published as EP 3189069 on Jul. 12, 2017 (Inventor—Anatharamaiah et al.; Applicant—UAB Reasearch Foundation et al.) (10 pages).
Office Action dated Jul. 3, 2018 by the Canadian Intellectual Property Office for Patent Application No. 2,704,729, which was filed on Feb. 25, 2010 (Inventor Anatharamaiah et al.; Applicant—UAB Research Foundation) (3 pages).
Almquist et al., Synthesis and Biological Activity of a Ketomethylene Analogue of a Tripeptide Inhibitor of Angiotensin Converting Enzyme. J Med Chem. 1980; 23(12):1392-8.
Anantharamaiah, G.M., Synthetic Peptide Analogs of Apolipoproteins. Meth Enzymol. 1986; 128:627-47.

(56) References Cited

OTHER PUBLICATIONS

Bradley, W.A. and S.H. Gianturco, ApoE is Necessary and Sufficient for the Bidning of Large Triglyceride-Rice Lioproteins to the LDL Receptor; ApoB is Unnecessary. J Lipid Res. 1986; 27(1):40-8.
Cubeddu, L.X. et al., Statin Withdrawal: Clinical Implications and Molecular Mechanisms. Pharmacotherapy. 2006; 26(9):1288-96.
Cuchel, M. et al., Efficacy and safety of a microsomal triglyceride transfer protein inhibitor in patients with homozygous familial hypercholesterolaemia: a single-arm, open label, phase 3 study. Lancet. 2013; 381(9860):40-6.
Domanski, M.J., Primary Prevention of Coronary Artery Disease. N Engl J Med. 2007; 357(15): 1543-5.
Dyer, C.A. and L.K. Curtiss, A Synthetic Peptide Mimic of Plasma Apolipoprotein E that Binds the LDL Receptor. J Biol Chem. 1991; 266(34):22803-6.
Dyer, C.A. et al., Only Multimers of a Synthetic Peptide of Human Apolipoprotein E are Biologically Active. J Biol Chem. 1991; 266(23):15009-15.
Garber, D.W. et al., Atherosclerosis and Vascular Disease: Effects of Peptide Mimetics of Apolipoproteins. Curr Pharma Biothechnol. 2006; 7(4): 235-40.
Goldstein, J.L. et al., Receptor-Mediated Endocytosis: Concepts Emerging from the LDL Receptor System. Ann Rev Cell Biol. 1985; 1:1-39.
Goodman and Gilman, The Pharmacological Basis of Therapeutics, 11th ed., McGraw-Hill Publishing Co. (2005).
Greene et al. Protective Groups in Organic Synthesis, 2nd ed., John Wiley & Sons, Inc., Somerset, NJ (1991).
Hann, M.M., On the Double Bond Isotere of the Peptide Bond: Preparation of an Enkephalin Analogue. J ChemSoc Perkin Trans 1. 1982; 307-14.
Heeschen, C. et al., Withdrawal of Statins Increases Event Rates in Patients with Acute Coronary Syndromes. Circulation. 2002; 105(12):1446-52.
Herbert, P. et al., A Large-Scale Process to Produce Microencapsulated Proteins. Pharm Res. 1998; 15(2):357-61.
Holladay, M.W. and D.H. Rich, Synthesis of Hydroxyethylene and Ketomethylene Dipeptide Isoteres. Tetrahedron Lett. 1983; 24(41):4401-4.
Hruby, V.J., Conformational Restrictions of Biologically Active Peptides via Amino Acid Side Chain Groups. Life Sci. 1982; 31(3):189-99.
Hudson, D. et al., Methionine Enkephalin and Isoteric Analogues I. Synthesis on a Phenolic Resin Support. Int J Pept Prot Res. 1979; 14(3):177-85.
Ito, M.K. et al., Management of Familial Hypercholesterolemias in Adult Patients: Recommendations from the National Lipid Association Expert Panel on Familial Hypercholesterolemia. J Clin Lipidol. 2011; 5(3 Suppl):S38-45.
Jennings-White, C. and R.G. Almquist, Synthesis of Ketomethylene Analogs of Dipeptides. Tetra Lett. 1982; 23(25):2533-4.
Johnson, O.L. et al., A Month-Long Effect from a Single Injection of Microencapsulated Human Growth Hormone. Nature Med. 1996; 2(7):795-9.
Koh, K.K., Effects of Statins on Vascular Wall: Vasomotor Function, Inflammation, and Plaque Stability. Cardiovasc Res. 2000; 47(4):648-57.
Lalazar, A. et al., Site-Specific Mutagenesis of Human Apolipoprotein E. Receptor Binding Activity of Variants with Single Amino Acd Substitutions. J Biol Chem. 1988; 263(8):3542-5.
Li, J.J. et al., Rebound Phenomenon of Inflammatory Response May Be a Major Mechanism Responsible for Increased Cardiovascular Events After Abrupt Cessation of Statin Therapy. Med Hypotheses. 2006; 66(6):1199-204.
Mahley, R. W., Apolipoprotein E: Cholesterol Transport Protein with Expanding Role in Cell Biology. Science. 1988; 240(4852):622-30.
Mahley, R.W. and Z.S. Ji, Remnant Lipoprotein Metabolism: Key Pathways Involving Cell-Surface Heparan Sulfate Proteoglycans and Apolipoprotein E. J Lipid Res. 1999; 40(1):1-16.
Morley, J.S., Modulation of the Action of Regulatory Peptides by Structural Modification. Trends Pharm Sci. 1(2):463-8 (1980) (general review).
Navab et al., A Novel Method for Oral Delivery of Apolipoprotein Mimetic Peptides Synthesized from All L-Amino Acids. J Lipid Res. 2009; 50(8):1538-47.
Nissen, S.E. et al., Effect of Recombinant ApoA-1 Milano on Coronary Atherosclerosis in Patients with Acute Coronary Syndromes: a Randomized Controlled Trial. JAMA. 2003; 290(17):2292-300.
Oram, J.F. and J.W. Heinecke, ATP-Binding Cassette Transporter A1: A Cell Cholesterol Exporter that Protects Against cardiovascular Disease. Physiol Rev. 2005; 85(4): 1343-72.
Palgunachari, M.N. et al., Only the Two End Helixes of Eight Tandem Amphipathic Helical Domains of Human Apo A-I Have Significant Lipid Affinity. Implications for HDL Assembly. Arteriosclerosis, Thromb Vasc Biol. 1996; 16(2):328-38 (27 pages).
Posttranslational Covalent Modification of Proteins, B.C. Johnson, Ed., Academic Press, New York, pp. 1-12 (1983).
Rall, S. C., Jr. et al., Structural basis for Receptor Binding Heterogeneity of Apolipoprotein E from Type III Hyperlipoproteinemic Subjects. Proc Natl Acad Sci USA. 1982; 79(15):4696-700.
Recent Developments in the Synthesis of Fatty Acid Derivatives. Eds. Knothe, G. and Derksen, J.T.B., AOCS Press 1999; ISBN: 1-893997-00-6.
Remington: The Science and Practice of Pharmacy, 19th ed., A.R. Gennaro, Ed., Mack Publishing Company, Easton, PA (1995).
Segrest, J.P. et al., Structure of Apolipoproteins B-100 in Low Density Lipoproteins. J Lipid Res. 2001; 42(9):1346-67.
Segrest, J.P. et al., The Amphipathic Helix in the Exchangeable Apolipoproteins: A Review of Secondary Structure and Function. J Lipid Res. 1992; 33(2):141-66.
Shimano, H. et al., Plasma Lipoprotein Metabolism in Transgenic Mice Overexpressing Apolipoprotein E. Accelerated Clearance of Lipoproteins Containing Apolipoprotein B. J Clin Invest. 1992; 90(5):2084-91.
Spangenberg, J. and L.K. Curtiss, Influence of Macrophage-Derived Apolipoprotein E on Plasma Lipoprotein Distribution of Apolipoprotein A-I in Apoprotein E-Deficient Mice. Biochim Biophys Acta. 1997; 1349:109-21.
Sparrow, J.T. et al., Apolipoprotein E: Phospholipid Binding Studies with Synthetic Peptides from the Carboxyl Terminus. Biochemistry. 1992; 31(4):1065-8.
Spatola Vega Data 1(3) Peptide Backbone Modifications (1982) (general review).
Spatola, A.F., Structure-Activity Relationships of Enkephalins Containing Serially Replaced Thiomethylene Amide Bond Surrogates. Life Sci. 1986; 38(14):1243-9.
Spatola, Chemistry and Biochemistry of Amino Acids, Peptides, and Proteins. B. Weinstein, eds., Marcel Dekker, New York, p. 267 (1983).
Steinberg, D. and J.L. Witztum, Inhibition of PCSK9: A Powerful Weapon for Achieving Ideal LDL Cholesterol Levels. Proc Natl Acad Sci USA. 2009; 106(24):9546-7.
Steinberg, D. et al., Evidence Mandating Earlier and More Aggressive Treatment of Hypercholesterolemia. Circulation. 2008; 118(6):672-7.
Structure and Molecular Properties 2nd ed., T.E. Creighton, W.H. Freeman and Company, New York (1993).
Tam, S.P. et al., Interaction of a Recombinant Form of Apolipoprotein[a] with Human Fibroblasts and with Human Hepatoma Cell Ilne HepG2. J Lipid Res. 1997; 37(3):518-33.
Tracy, M.A., Development and Scale-up of a Microsphere Protein Delivery System. Biotechnol Prog. 1998; 14(1):108-15.
Van Velzen et al., Imagining of Atherosclerosis: Invasive and Noninvasive Techniques. Hellenic J Cardiol. 2009; 50:245-63.
Vaughan, C.J. et al., the Evolving Role of Statins in the Management of Atherosclrosis. J Am Coll Cardiol. 2000; 35(1):1-10.
Wilson, C. et al., Three-Dimensional Structure of the LDL receptor-Binding Domain of Human Apolipoprotein E. Science. 1991; 252(5014):1817-22.

(56) References Cited

OTHER PUBLICATIONS

Yamada, N. et al., Increased Clearance of Plasma Cholesterol After Injection of Apolipoprotein E into Wtanabe Heritable Hyperlipidemic Rabbits. Proc Natl Acad Sci USA. 1989; 86(2):665-9.
Zhang, S.H. et al., Spontaneous Hypercholesterolemia and Arterial Lesions in Mice Lacking Apolipoprotein E. Science. 1992; 258(5081):468-71.
Patent Examination Report No. 1 dated Apr. 15, 2016 by the Intellectual Property Office of Australia for Patent Application No. AU 2014239186, which was filed on Mar. 14, 2014 (Inventor—Anatharamaiah et al.; Applicant—UAB Research Foundation) (3 pages).
Examination Report No. 2 dated Dec. 22, 2016 by the Intellectual Property Office of Australia for Patent Application No. AU 2014239186, which was filed on Mar. 14, 2014 (Inventor—Anatharamaiah et al.; Applicant—Uab Research Foundation) (3 pages).
Notice of Acceptance dated Apr. 11, 2017 by the Intellectual Property Office of Australia for Patent Application No. AU 2014239186, which was filed on Mar. 14, 2014 (Inventor—Anatharamaiah et al.; Applicant—UAB Research Foundation) (3 pages).
Certificate of Grant dated Aug. 3, 2017 by the Intellectual Property Office of Australia for Patent Application No. AU 2014239186, which was filed on Mar. 14, 2014 (Inventor—Anatharamaiah et al.; Applicant—UAB Research Foundation) (1 page).
Examination Report dated Sep. 8, 2016 by the Canadian Intellectual Property Office for Patent Application No. 2903869, which was filed on Mar. 14, 2013 (Inventor—G.M. Anantharamaiah, et al.; Applicant—UAB Research Foundation) (4 pages).
European Search Report dated Dec. 19, 2016 by the European Patent Office for Patent Application No. 14769489.7, which was filed on Mar. 14, 2014 and published as 2996706 on Mar. 23, 2016 (Applicant—UAB Research Foundation et al.) (8 pages).
First Examination Report dated Apr. 8, 2016 by the New Zealand Intellectual Property Office for Patent No. 713291, which was filed on Mar. 14, 2014 (Inventor—Anatharamaiah et al.; Applicant—UAB Research Foundation) (5 pages).
Further Examination dated Dec. 7, 2016 by the New Zealand Intellectual Property Office for Patent No. 713291, which was filed on Mar. 14, 2014 (Inventor—Anatharamaiah et al.; Applicant—UAB Research Foundation) (3 pages).
Notice of Acceptance dated Apr. 10, 2017 by the New Zealand Intellectual Property Office for Patent No. 713291, which was filed on Mar. 14, 2014 (Inventor—Anatharamaiah et al.; Applicant—UAB Research Foundation) (1 page).
International Search Report and Written Opinion dated Jul. 11, 2014 for application PCT/US14/27719, which was filed on Mar. 14, 2014 and published as WO 2014/0152776 on Sep. 25, 2014 (Inventor—Anantharamaiah; Applicant—UAB Research Foundation) (27 pages).
International Preliminary Report on Patentability dated Sep. 24, for Patent Application No. PCT/US14/27719, which was filed on Mar. 14, 2014 and published as WO 2014/0152776 on Sep. 25, 2014 (Applicant—UAB Research Foundation//Inventor—Anantharamaiah) (8 pages).
Preliminary Amendment filed on Aug. 25, 2015 with the U.S. Patent and Trademark Office for U.S. Appl. No. 14/770,270, filed Aug. 25, 2015 and published as US 2016/0002315 on Jan. 7, 2016 (Inventor—Anantharamaiah et al.; Applicant—UAB Research Foundation) (5 pages).
Restriction Requirement dated Dec. 18, 2015 by the U.S. Patent and Trademark Office for U.S. Appl. No. 14/770,270, filed Aug. 25, 2015 and published as US 2016/0002315 on Jan. 7, 2016 (Inventor—Anantharamaiah et al.; Applicant—UAB Research Foundation) (7 pages).
Response to Restriction Requirement filed on Feb. 5, 2016 with the U.S. Patent and Trademark Office for U.S. Appl. No. 14/770,270, filed Aug. 25, 2015 and published as US 2016/0002315 on Jan. 7, 2016 (Inventor—Anantharamaiah et al.; Applicant—UAB Research Foundation) (4 pages).
Non-Final Office Action dated Jul. 6, 2016 by the U.S. Patent and Trademark Office for U.S. Appl. No. 14/770,270, filed Aug. 25, 2015 and published as US 2016/0002315 on Jan. 7, 2016 (Inventor—Anantharamaiah et al.; Applicant—UAB Research Foundation) (20 pages).
Response to Non-Final Office Action filed on Jan. 4, 2017 with the U.S. Patent and Trademark Office for U.S. Appl. No. 14/770,270, filed Aug. 25, 2015 and published as US 2016/0002315 on Jan. 7, 2016 (Inventor—Anantharamaiah et al.; Applicant—UAB Research Foundation) (10 pages).
Final Office Action dated Apr. 21, 2017 by the U.S. Patent and Trademark Office for U.S. Appl. No. 14/770,270, filed Aug. 25, 2015 and published as US 2016/0002315 on Jan. 7, 2016 (Inventor—Anantharamaiah et al.; Applicant—UAB Research Foundation) (19 pages).
International Search Report and Written Opinion dated Dec. 15, 2015 by the International Searching Authority for Patent Application No. PCT/US2015/041162, which was filed on Jul. 20, 2015 and published as WO 2016/018665 on Feb. 4, 2016 (Inventor—Anatharamaiah et al.; Applicant—UAB Research Foundation et al.) (11 pages).
International Preliminary Report on Patentability dated Jan. 31, 2017 by the International Searching Authority for Patent Application No. PCT/US2015/041162, which was filed on Jul. 20, 2015 and published as WO 2016/018665 on Feb. 4, 2016 (Inventor—Anatharamaiah et al.; Applicant—UAB Research Foundation et al.) (6 pages).
Office Action dated Sep. 28, 2018 by the Intellectual Property Office of India for Patent Application No. 6250/CHENP/2015, which was filed on Oct. 9, 2015 and published on Jul. 1, 2016 (Inventor—Anantharamaiah et al.; Applicant—UAB Research Foundation) (6 pages).
Office Action was dated Oct. 7, 2019 by the Canadian Patent Office for Canadian Application No. 2903869, filed on Mar. 14, 2014 (Applicant—U.A.B. Research Foundation, et al) (5 Pages).
Office Action was dated Jun. 26, 2019 by the Canadian Patent Office for CA Application No. 2954475, which was filed on Jul. 20, 2015 and published as CA 2954475 Al on Feb. 4, 2016 (Applicant—UAB Research Foundation, et al.) (4 pages).
Non Final Rejection dated Sep. 20, 2019 by the USPTO for U.S. Appl. No. 14/770,270, filed Aug. 25, 2015 and published as US 2016/0002315 A1 on Jan. 7, 2016 (Inventor—Gattadahalli M. Anantharamaiah, et al.) (6 pages).

* cited by examiner

| *Peptide* | *Sequence* | *Rationale* |
|---|---|---|
| Ac-hE18A-$NH_2$ | LRKLRLRLLR-DWLKAFYDKVAEKLKEAF | Original peptide sequence extensively studied |
| Ac-[R]hE18A-$NH_2$ | LRRLRRRLLR-DWLKAFYDKVAEKLKEAF | An Arg analog with K>R at 141-150 of apoE. More effective than Ac-hE18A-$NH_2$ in reducing plasma cholesterol. |
| Ac-hE-[GG]18A-$NH_2$<br>Ac-hE-[AA]18A-$NH_2$ | LRKLRLRLLR-GG-DWLKAFYDKVAEKLKEAF<br>LRKLRLRLLR-AA-DWLKAFYDKVAEKLKEAF | Original sequence with two G or A residures in between the 141-160 region and 18A. To determine the effect of space that breaks or maintains the helix. |
| Ac-hE-Aha*-18A-$NH_2$ | LRKLRLRLLR-Aha-DWLKAFYDKVAEKLKEAF | Original sequence with a spacer that is flexible to determine the effect of a flexible domain to bind to atherogenic lipoproteins and targeting to receptors. |
| Aha-hE18A-$NH_2$<br>Aha*-[R]hE18A-$NH_2$<br>Ac-Aha*-[R]hE18A-$NH_2$ | Aha-LRKLRLRLLR-DWLKAFYDKVAEKLKEAF<br>Aha-LRRLRRRLLR-DWLKAFYDKVAEKLKEAF<br>Ac-Aha- LRRLRRRLLR-DWLKAFYDKVAEKLKEAF | Aha at the N-terminus of 1) hE18A-$NH_2$, 2) [R]hE18A-$NH_2$, and 3) acetylation of hE18A-$NH_2$ to enhance lipoprotein anchoring. |
| Ac-[K]hE-18A-$NH_2$ | LKKLKLKLLK- DWLKAFYDKVAEKLKEAF | Original peptide in which R>K to vary the HSPG binding. |
| Ac-[R]hE-[$K^{4,15}$>R]18A-$NH_2$<br><br>Ac-[R]hE[F>L]18A-$NH_2$ | Ac-LRRLRRRLRR-DWLRAFYDKVAEKLREAF<br>Ac-LRRLRRRLLR-DWLRALYDKVAEKLREAL<br>Ac-LRRLRRRLLR-DLLRALYDKVAEKLREAW | In 18A, K4,15>R to enhance PON-1 bind to apoE-mimic containing HDL as published previously (see Nayyar, et al., J. Lipid Res. (2012) 53:849). |

FIG. 1

| Group | Number of Mice (Female) | Test Compound (Formulation) | Dosage Level, active basis | Dose Conc. (mg/mL) | Dosage Volume (mL/kg) | Dosing Regimen | Readout |
|---|---|---|---|---|---|---|---|
| **1 AEM-28 Saline** | 4 | AEM-28 (in Saline) | 100 µg/animal (4.0 mg/kg) | 0.4 | 10 | IV | Total Serum Cholesterol: t = pre, 1, 6 and 24 hours |
| **2 AEM-28(R) Saline** | 5 | AEM-28(R) (in Saline) | 100 µg/animal (4.0 mg/kg) | 0.4 | 10 | IV | Total Serum Cholesterol: t = pre, 1, 6 and 24 hours |
| **3 AES2-21 Saline** | 5 | AES2-21 (in Saline) | 100 µg/animal (4.0 mg/kg) | 0.4 | 10 | IV | Total Serum Cholesterol: t = pre, 1, 6 and 24 hours |

FIG. 7

| Total Serum Cholesterol (mg/dL) | Pre-Dose | | | 1 Hour Post Dose | | |
|---|---|---|---|---|---|---|
| | Group 1 | Group 2 | Group 3 | Group 1 | Group 2 | Group 3 |
| | AEM-28 in saline | AEM-28(R) in saline | AES-21 in saline | AEM-28 in saline | AEM-28(R) in saline | AES-21 in saline |
| | 100 ug/animal | 100 ug/animal | 100 ug/animal | 100 ug/animal | 100 ug/animal | 100 ug/animal |
| Animal 1 | 614.5 | 539.5 | 680.9 | 129.8 | 184.6 | 202.0 |
| Animal 2 | 620.3 | 568.4 | 545.3 | 167.3 | 124.1 | 326.0 |
| Animal 3 | | 556.8 | 666.4 | | 202.0 | 202.0 |
| Animal 4 | 643.4 | 709.7 | 718.4 | 308.7 | 357.7 | 268.3 |
| Animal 5 | 603.0 | 565.5 | 620.3 | 256.8 | 458.7 | 152.9 |
| **Mean** | **620.3** | **588.0** | **646.3** | **215.7** | **265.4** | **230.2** |
| *Rel. Std. Dev., %* | *2.7%* | *11.7%* | *10.3%* | *37.9%* | *52.1%* | *29.3%* |

| Total Serum Cholesterol (mg/dL) | 6 Hour Post Dose | | | 24 Hour Post Dose | | |
|---|---|---|---|---|---|---|
| | Group 1 | Group 2 | Group 3 | Group 1 | Group 2 | Group 3 |
| | AEM-28 in saline | AEM-28(R) in saline | AES-21 in saline | AEM-28 in saline | AEM-28(R) in saline | AES-21 in saline |
| | 100 ug/animal | 100 ug/animal | 100 ug/animal | 100 ug/animal | 100 ug/animal | 100 ug/animal |
| Animal 1 | 196.2 | 199.1 | 271.2 | 320.2 | 389.5 | 516.4 |
| Animal 2 | 181.8 | 147.1 | 331.8 | 438.5 | 389.5 | 571.2 |
| Animal 3 | | 239.5 | 230.8 | | 493.3 | 611.6 |
| Animal 4 | 297.2 | 337.6 | 262.5 | 571.2 | 623.2 | 591.4 |
| Animal 5 | 251.0 | 363.5 | 161.6 | 507.8 | 591.4 | 510.7 |
| **Mean** | **231.5** | **257.3** | **251.6** | **459.4** | **497.4** | **560.3** |
| *Rel. Std. Dev., %* | *22.9%* | *35.6%* | *24.7%* | *23.4%* | *22.0%* | *8.0%* |

FIG. 9

| Total Serum Chiolesterol (as % of Pre-Dose Level) | 1 Hour Post Dose | | | 6 Hour Post Dose | | | 24 Hour Post Dose | | |
|---|---|---|---|---|---|---|---|---|---|
| | Group 1 | Group 2 | Group 3 | Group 1 | Group 2 | Group 3 | Group 1 | Group 2 | Group 3 |
| | AEM-28 in saline | AEM-28(R) in saline | AES-21 in saline | AEM-28 in saline | AEM-28(R) in saline | AES-21 in saline | AEM-28 in saline | AEM-28(R) in saline | AES-21 in saline |
| | 100 ug/animal | 100 ug/animal | 100 ug/animal | 100 ug/animal | 100 ug/animal | 100 ug/animal | 100 ug/animal | 100 ug/animal | 100 ug/animal |
| Animal 1 | 21.1% | 34.2% | 29.7% | 31.9% | 36.9% | 39.8% | 52.1% | 72.2% | 75.8% |
| Animal 2 | 27.0% | 21.8% | 59.8% | 29.3% | 25.9% | 60.8% | 70.7% | 68.5% | 104.8% |
| Animal 3 | N/A died | 36.3% | 30.3% | N/A died | 43.0% | 34.6% | N/A died | 88.6% | 91.8% |
| Animal 4 | 48.0% | 50.4% | 37.3% | 46.2% | 47.6% | 36.5% | 88.8% | 87.8% | 82.3% |
| Animal 5 | 42.6% | 81.1% | 24.7% | 41.6% | 64.3% | 26.0% | 84.2% | 104.6% | 82.3% |
| **Mean** | **34.7%** | **44.8%** | **36.4%** | **37.3%** | **43.5%** | **39.6%** | **74.0%** | **84.3%** | **87.4%** |
| *Rel. Std. Dev., %* | *36.6%* | *50.7%* | *38.1%* | *21.4%* | *32.5%* | *32.7%* | *22.3%* | *17.2%* | *12.9%* |

FIG. 10

| Group | Number of Mice (Female) | Test Compound (Formulation) | Dosage Level, active basis | Dose Conc. (mg/mL) | Dosage Volume (mL/kg) | Dosing Regimen | Readout |
|---|---|---|---|---|---|---|---|
| **1 AEM-28 Saline** | 5 | AEM-28 (in Saline) | 50 µg/animal (2.0 mg/kg) | 0.2 | 10 | IV | Total Serum Cholesterol: t = pre, 1, 6 and 24 hours |
| **2 AEM-28(R) Saline** | 5 | AEM-28(R) (in Saline) | 50 µg/animal (2.0 mg/kg) | 0.2 | 10 | IV | Total Serum Cholesterol: t = pre, 1, 6 and 24 hours |
| **3 AES2-21 Saline** | 5 | AES2-21 (in Saline) | 50 µg/animal (2.0 mg/kg) | 0.2 | 10 | IV | Total Serum Cholesterol: t = pre, 1, 6 and 24 hours |

FIG. 11

| Total Serum Cholesterol (mg/dL) | Pre-Dose | | | 1 Hour Post Dose | | |
|---|---|---|---|---|---|---|
| | Group 1 | Group 2 | Group 3 | Group 1 | Group 2 | Group 3 |
| | AEM-28 in saline | AEM-28(R) in saline | AES-21 in saline | AEM-28 in saline | AEM-28(R) in saline | AES-21 in saline |
| | 50 ug/animal | 50 ug/animal | 50 ug/animal | 50 ug/animal | 50 ug/animal | 50 ug/animal |
| Animal 1 | 502.9 | 454.3 | 542.9 | 342.9 | 302.9 | 434.3 |
| Animal 2 | 511.4 | 397.1 | 448.6 | 291.4 | 202.9 | 394.3 |
| Animal 3 | 422.9 | 500.0 | 566.5 | 300.0 | 351.4 | 325.7 |
| Animal 4 | 457.1 | 517.1 | 520.0 | 348.6 | 420.0 | 362.9 |
| Animal 5 | 420.0 | 642.9 | 405.7 | 291.4 | 525.7 | 251.4 |
| **Mean** | **462.9** | **502.3** | **496.7** | **314.9** | **360.6** | **353.7** |
| *Rel. Std. Dev., %* | *9.3%* | *18.2%* | *13.6%* | *9.0%* | *33.7%* | *19.7%* |

| Total Serum Cholesterol (mg/dL) | 6 Hour Post Dose | | | 24 Hour Post Dose | | |
|---|---|---|---|---|---|---|
| | Group 1 | Group 2 | Group 3 | Group 1 | Group 2 | Group 3 |
| | AEM-28 in saline | AEM-28(R) in saline | AES-21 in saline | AEM-28 in saline | AEM-28(R) in saline | AES-21 in saline |
| | 50 ug/animal | 50 ug/animal | 50 ug/animal | 50 ug/animal | 50 ug/animal | 50 ug/animal |
| Animal 1 | 274.3 | 251.4 | 377.1 | 457.1 | 374.3 | 565.7 |
| Animal 2 | 237.1 | 134.3 | 308.6 | 500.0 | 340.0 | 480.0 |
| Animal 3 | 245.7 | 311.4 | 308.6 | 414.3 | 500.0 | 562.9 |
| Animal 4 | 362.9 | 360.0 | 328.6 | 434.3 | 474.3 | 465.7 |
| Animal 5 | 314.3 | 462.9 | 248.6 | 440.0 | 565.7 | 485.7 |
| **Mean** | **286.9** | **304.0** | **314.3** | **449.1** | **450.9** | **512.0** |
| *Rel. Std. Dev., %* | *18.2%* | *40.3%* | *14.7%* | *7.2%* | *20.5%* | *9.4%* |

FIG. 13

| Total Serum Chiolesterol (as % of Pre-Dose Level) | 1 Hour Post Dose | | | 6 Hour Post Dose | | | 24 Hour Post Dose | | |
|---|---|---|---|---|---|---|---|---|---|
| | Group 1 | Group 2 | Group 3 | Group 1 | Group 2 | Group 3 | Group 1 | Group 2 | Group 3 |
| | AEM-28 in saline | AEM-28(R) in saline | AE5-21 in saline | AEM-28 in saline | AEM-28(R) in saline | AE5-21 in saline | AEM-28 in saline | AEM-28(R) in saline | AE5-21 in saline |
| | 50 ug/animal | 50 ug/animal | 50 ug/animal | 50 ug/animal | 50 ug/animal | 50 ug/animal | 50 ug/animal | 50 ug/animal | 50 ug/animal |
| Animal 1 | 68.2% | 66.7% | 80.0% | 54.5% | 55.3% | 69.5% | 90.9% | 82.4% | 104.2% |
| Animal 2 | 57.0% | 51.1% | 87.9% | 46.4% | 33.8% | 68.8% | 97.8% | 85.6% | 107.0% |
| Animal 3 | 70.9% | 70.3% | 57.5% | 58.1% | 62.3% | 54.5% | 98.0% | 100.0% | 99.4% |
| Animal 4 | 76.3% | 81.2% | 69.8% | 79.4% | 69.6% | 63.2% | 95.0% | 91.7% | 89.6% |
| Animal 5 | 69.4% | 81.8% | 62.0% | 74.8% | 72.0% | 61.3% | 104.8% | 88.0% | 119.7% |
| **Mean** | **68.35%** | **70.20%** | **71.43%** | **62.65%** | **58.61%** | **63.44%** | **97.28%** | **89.54%** | **103.97%** |
| *Rel. Std. Dev, %* | *10.3%* | *17.9%* | *17.6%* | *22.3%* | *26.1%* | *9.7%* | *5.2%* | *7.6%* | *10.6%* |

FIG. 14

§Theoretical value for no change in levels from baseline to 24 h.

APOE MIMETIC PEPTIDES AND HIGHER POTENCY TO CLEAR PLASMA CHOLESTEROL

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application *is a reissue of U.S. Pat. No. 10,653,747, issued May 19, 2020, which* is a national phase filing of International Patent Application No. PCT/US2015/041162, filed Jul. 20, 2015, which claims priority to U.S. Application No. 62/031,585, filed Jul. 31, 2014, both of which are herein incorporated by reference in their entireties.

STATEMENT REGARDING FEDERALLY SPONSORED RESEARCH

This invention was made with government support under RO1 HL 090803 awarded by the National Institutes of Health. The government has certain rights in the invention.

REFERENCE TO A SEQUENCE LISTING SUBMITTED AS A TEXT FILE VIA EFS-WEB

The Sequence Listing submitted [Aug. 21, 2018 as a text file named "21085_0187U2_Updated_Sequence_Listing.txt," created on Aug. 14, 2018] *Aug. 6, 2024, as a text file named "21085.0187U3 Sequence Listing.txt" created on Aug. 6, 2024*, and having a size 311,540 *311,533* bytes is hereby incorporated by reference pursuant to 37 C.F.R. § 1.52(e)(5).

BACKGROUND

In the United States, heart disease is the leading cause of death in both men and women. Several causative factors are implicated in the development of cardiovascular disease including hereditary predisposition to the disease, gender, lifestyle factors such as smoking and diet, age, hypertension, and hyperlipidemia, including hypercholesterolemia. Several of these factors, particularly hyperlipidemia and hypercholesteremia (high blood cholesterol concentrations) provide a significant risk factor associated with atherosclerosis.

Atherosclerosis is associated with an inflammatory response caused by the accumulation of low-density lipoprotein (LDL) molecules in blood vessels. It can be asymptomatic for years. Atherosclerosis causes hardening and narrowing of blood vessels. There are several treatments for atherosclerosis, such as lifestyle change, medication and medical procedures. Statins are a well-known treatment for atherosclerosis. Statins have proven to reduce cardiac risk however the withdrawal of statin therapy abrogrates the protective effect (Heeschen et al. Circulation. 105:1446-1452, 2002).

The current approach to treating atherosclerosis is to provide earlier intervention and life-long treatment. This approach is problematic as it requires identifying asymptomatic patients early in their life cycle and, since risk increases with age, maintaining therapy for the duration of their life. Further, the most efficacious currently available therapies are unable to prevent major cardiac events in all patients whether as primary or secondary interventions. Therefore, there is a need for therapies that can provide rapid benefit in reducing atherosclerosis and have long-term effects that do not require constant administration. The compositions and methods disclosed herein provide an atherosclerosis therapy with sustained therapeutic effects even after the treatment is withdrawn.

BRIEF SUMMARY

Disclosed are synthetic apolipoprotein E (ApoE)-mimicking peptides comprising a receptor binding domain of ApoE and a lipid-associating peptide, wherein the synthetic ApoE-mimicking peptide comprises an acetylated amino hexanoic acid (Ac-Aha).

Also disclosed are synthetic ApoE-mimicking peptides comprising a receptor binding domain of ApoE and a lipid-associating peptide, wherein the synthetic ApoE-mimicking peptide comprises an Ac-Aha, wherein the Ac-Aha can be at the N-terminus of the peptide.

Also disclosed are synthetic ApoE-mimicking peptides comprising a receptor binding domain of ApoE and a lipid-associating peptide, wherein the synthetic ApoE-mimicking peptide comprises an Ac-Aha, wherein the lipid-associating peptide comprises a class A amphipathic-helical domain. For example, the class A amphipathic-helical domain can be DWLKAFYDKVAEKLKEAF (SEQ ID NO:5), DWLRAFYDKVAEKLREAF (SEQ ID NO:618), DWLRALYDKVAEKLREAL (SEQ ID NO:619), DLLRALYDKVAEKLREAW (SEQ ID NO:620), or FAEKLKEAVKDYFAKLWD (SEQ ID NO:616).

Also disclosed are synthetic ApoE-mimicking peptides comprising a receptor binding domain of ApoE and a lipid-associating peptide, wherein the synthetic ApoE-mimicking peptide comprises an Ac-Aha, wherein the receptor binding domain of ApoE can be covalently linked to the lipid-associating peptide.

Also disclosed are synthetic ApoE-mimicking peptides comprising a receptor binding domain of ApoE and a lipid-associating peptide, wherein the synthetic ApoE-mimicking peptide comprises an Ac-Aha, wherein said apolipoprotein E is from a species selected from the group consisting of human, mouse, rabbit, monkey, rat, bovine, pig and dog.

Also disclosed are synthetic ApoE-mimicking peptides comprising a receptor binding domain of ApoE and a lipid-associating peptide, wherein the synthetic ApoE-mimicking peptide comprises an Ac-Aha, wherein said synthetic peptide is protected using an amide group at the C-terminus.

Also disclosed are synthetic ApoE-mimicking peptides comprising a receptor binding domain of ApoE and a lipid-associating peptide, wherein the synthetic ApoE-mimicking peptide comprises an Ac-Aha, wherein the receptor binding domain of ApoE is LRKLRKRLLR (SEQ ID NO:4), LRRLRRRLLR (SEQ ID NO:11), LRKMRKRLMR (SEQ ID NO:7), or RLTRKRGLK (SEQ ID NO:13).

Also disclosed are synthetic ApoE-mimicking peptides comprising a receptor binding domain of ApoE and a lipid-associating peptide, wherein the synthetic ApoE-mimicking peptide comprises an Ac-Aha, wherein the receptor binding domain of ApoE is LRKLRKRLLR (SEQ ID NO:4), LRRLRRRLLR (SEQ ID NO:11), LRKMRKRLMR (SEQ ID NO:7), RLTRKRGLK (SEQ ID NO:13), LRRMRRRLMR (SEQ ID NO:621), or RLTRRRGK (SEQ ID NO:622).

Also disclosed are synthetic ApoE-mimicking peptides comprising a receptor binding domain of ApoE and a lipid-associating peptide, wherein the synthetic ApoE-mimicking peptide comprises an Ac-Aha, wherein the synthetic ApoE-mimicking peptide can be Ac-Aha-hE18A-$NH_2$ or Ac-Aha-[R]hE18A-$NH_2$.

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety.

Disclosed are synthetic ApoE-mimicking peptides comprising a receptor binding domain of ApoE and a lipid-associating peptide, wherein the synthetic ApoE-mimicking peptide comprises an acetylated ω-amino fatty acid moiety, wherein the acetylated ω-amino fatty acid moiety is at the N-terminus of the peptide. In some aspects the ω-amino fatty acid moiety can be inserted between the lipid-associating peptide and the receptor binding domain of apoE.

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein the lipid-associating peptide comprises a class A amphipathic-helical domain. For example, the class A amphipathic-helical domain is DWLKAFYDKVAEKLKEAF (SEQ ID NO:5), DWLRAFYDKVAEKLREAF (SEQ ID NO:618), DWLRALYDKVAEKLREAL (SEQ ID NO:619), DLLRALYDKVAEKLREAW (SEQ ID NO:620), or FAEKLKEAVKDYFAKLWD (SEQ ID NO:616).

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein the lipid-associating peptide comprises a class A amphipathic-helical domain, wherein the receptor binding domain of ApoE can be covalently linked to the lipid-associating peptide.

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein said apolipoprotein E can be from a species selected from the group consisting of human, mouse, rabbit, monkey, rat, bovine, pig and dog.

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein said synthetic peptide is protected using an amide group at the C-terminus.

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein the receptor binding domain of ApoE can be LRKLRKRLLR (SEQ ID NO:4), LRRLRRRLLR (SEQ ID NO:11), LRKMRKRLMR (SEQ ID NO:7), or RLTRKRGLK (SEQ ID NO:13). The receptor binding domain of ApoE can also be, but is not limited to, LRKLRKRFFR (SEQ ID NO:12), LRKLPKRLLR (SEQ ID NO:8), LRNVRKRLVR (SEQ ID NO:9), MRKLRKRVLR (SEQ ID NO:10), LRRLRRRLLR (SEQ ID NO:11), LRKLRKRFFR (SEQ ID NO:12), LRKLRKRLLR (SEQ ID NO:4), or LRKMRKRLMR (SEQ ID NO:7).

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein the receptor binding domain of ApoE can be LRKLRKRLLR (SEQ ID NO:4), LRRLRRRLLR (SEQ ID NO:11), LRKMRKRLMR (SEQ ID NO:7), RLTRKRGLK (SEQ ID NO:13), LRRMRRRLMR (SEQ ID NO:621), or RLTRRRGK (SEQ ID NO:22).

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein the synthetic ApoE-mimicking peptide can be: butanoyl-LRRLRRRLLR-DWLKAFYDKVAEKLKEAF-$NH_2$ (SEQ ID NO: 623); hexanoyl-LRRLRRRLLR-DWLKAFYDKVAEKLKEAF-$NH_2$ (SEQ ID NO: 624); octanoyl-LRRLRRRLLR-DWLKAFYDKVAEKLKEAF-$NH_2$ (SEQ ID NO: 625); decanoyl-LRRLRRRLLR-DWLKAFYDKVAEKLKEAF-$NH_2$ (SEQ ID NO: 626); lauroyl-LRRLRRRLLR-DWLKAFYDKVAEKLKEAF-$NH_2$ (SEQ ID NO: 627); myristoyl-LRRLRRRLLR-DWLKAFYDKVAEKLKEAF-$NH_2$ (SEQ ID NO: 628); palmitoyl-LRRLRRRLLR-DWLKAFYDKVAEKLKEAF-$NH_2$ (SEQ ID NO: 629); stearoyl-LRRLRRRLLR-DWLKAFYDKVAEKLKEAF-$NH_2$ (SEQ ID NO: 630); palmitoleoyl-LRRLRRRLLR-DWLKAFYDKVAEKLKEAF-$NH_2$ (SEQ ID NO: 631); arachidoyl-LRRLRRRLLR-DWLKAFYDKVAEKLKEAF-$NH_2$ (SEQ ID NO: 632); behenoyl-LRRLRRRLLR-DWLKAFYDKVAEKLKEAF-$NH_2$ (SEQ ID NO: 633); oleoyl-LRRLRRRLLR-DWLKAFYDKVAEKLKEAF-$NH_2$ (SEQ ID NO: 634); ricinoleoyl-LRRLRRRLLR-DWLKAFYDKVAEKLKEAF-$NH_2$ (SEQ ID NO: 635); linolenoyl-LRRLRRRLLR-DWLKAFYDKVAEKLKEAF-$NH_2$ (SEQ ID NO: 636); vacceoyl-LRRLRRRLLR-DWLKAFYDKVAEKLKEAF-$NH_2$ (SEQ ID NO: 637); gadoleoyl-LRRLRRRLLR-DWLKAFYDKVAEKLKEAF-$NH_2$ (SEQ ID NO: 638); erucoyl-LRRLRRRLLR-DWLKAFYDKVAEKLKEAF-$NH_2$ (SEQ ID NO: 639); cetoleoyl-LRRLRRRLLR-DWLKAFYDKVAEKLKEAF-$NH_2$ (SEQ ID NO: 640); nervonoyl-LRRLRRRLLR-DWLKAFYDKVAEKLKEAF-$NH_2$ (SEQ ID NO: 641); adrenoyl-LRRLRRRLLR-DWLKAFYDKVAEKLKEAF-$NH_2$ (SEQ ID NO: 642); α-linolenoyl-LRRLRRRLLR-DWLKAFYDKVAEKLKEAF-$NH_2$ (SEQ ID NO: 643); γ-linolenoyl-LRRLRRRLLR-DWLKAFYDKVAEKLKEAF-$NH_2$ (SEQ ID NO: 644); EPA-LRRLRRRLLR-DWLKAFYDKVAEKLKEAF-$NH_2$ (SEQ ID NO: 645); or DHA-LRRLRRRLLR-DWLKAFYDKVAEKLKEAF-$NH_2$ (SEQ ID NO: 646). In the foregoing, the fatty acid moiety is shown at the left side and is linked to the peptide LRRLRRRLLR (SEQ ID NO:11). "EPA" indicates a moiety derived from 5,8,11,14,17-eicosapentaenoic acid; and "DHA" indicates a moiety derived from 4,7,10,13,16,19-docosahexaenoic acid.

Disclosed are synthetic ApoE-mimicking peptides comprising a receptor binding domain of ApoE and a lipid-associating peptide, wherein the synthetic ApoE-mimicking peptide comprises a fatty acid moiety derived from a natural oil or fat, e.g. fish oil, wherein the synthetic ApoE-mimicking peptide can be: (fish oil)-LRRLRRRLLR-DWLKAFYDKVAEKLKEAF-$NH_2$ (SEQ ID NO: 647). In the foregoing "(fish oil)" indicates that the fatty acids in fish oil, including, but not limited to, fish oil components such as EPA and DHA, are linked to linked to the peptide LRRLRRRLLR (SEQ ID NO:11). Thus, the synthetic ApoE-mimicking peptide is a mixture of peptides comprising fatty acid groups derived from the fish oil used to prepare them.

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein the synthetic ApoE-mimicking peptide can be: 4-amino-butanoyl-LRRLRRRLLR-DWLKAFYDKVAEKLKEAF-$NH_2$ (SEQ ID NO: 648); 6-amino-hexanoyl-LRRLRRRLLR-DWLKAFYDKVAEKLKEAF-$NH_2$ (SEQ ID NO: 649); 8-amino-octanoyl-LRRLRRRLLR-DWLKAFYDKVAEKLKEAF-$NH_2$ (SEQ ID NO: 650); 10-amino-decanoyl-LRRLRRRLLR-DWLKAFYDK-VAEKLKEAF-$NH_2$ (SEQ ID NO: 651); 12-amino-lauroyl-LRRLRRRLLR-DWLKAFYDKVAEKLKEAF-$NH_2$ (SEQ ID NO: 652); 14-amino-myristoyl-LRRLRRRLLR-DWLKAFYDKVAEKLKEAF-$NH_2$ (SEQ ID NO: 653); 16-amino-palmitoyl-LRRLRRRLLR-DWLKAFYDK-VAEKLKEAF-$NH_2$ (SEQ ID NO: 654); 16-amino-palmitoleoyl-LRRLRRRLLR-DWLKAFYDKVAEKLKEAF-$NH_2$ (SEQ ID NO: 655); 18-amino-stearoyl-LRRLRRRLLR-DWLKAFYDKVAEKLKEAF-$NH_2$ (SEQ ID NO: 656); 18-amino-oleoyl-LRRLRRRLLR-DWLKAFYDK-VAEKLKEAF-$NH_2$ (SEQ ID NO: 657); 18-amino-linolenoyl-LRRLRRRLLR-DWLKAFYDKVAEKLKEAF-$NH_2$ (SEQ ID NO: 658); or 20-amino-arachidoyl-LRRLRRRLLR-DWLKAFYDKVAEKLKEAF-$NH_2$ (SEQ ID NO: 659). In the foregoing, the fatty acid moiety is shown at the left side and is linked to the peptide LRRLRRRLLR (SEQ ID NO:11).

Disclosed are pharmaceutical compositions comprising any one of the herein disclosed synthetic ApoE-mimicking peptides and a pharmaceutically acceptable carrier.

Disclosed are methods comprising administering any one of the disclosed synthetic ApoE-mimicking peptides to a subject, whereby plasma LDL, plasma VLDL, or both, are affected.

Disclosed are methods comprising administering any one of the disclosed synthetic ApoE-mimicking peptides to a subject, whereby plasma LDL, plasma VLDL, or both, are affected, wherein the synthetic apolipoprotein E-mimicking peptide is administered as a composition comprising the synthetic apolipoprotein E-mimicking peptide and a pharmaceutically acceptable carrier.

Disclosed are methods comprising administering any one of the disclosed synthetic ApoE-mimicking peptides to a subject, whereby plasma LDL, plasma VLDL, or both, are affected, wherein binding of LDL to a cell of the subject is enhanced.

Disclosed are methods comprising administering any one of the disclosed synthetic ApoE-mimicking peptides to a subject, whereby plasma LDL, plasma VLDL, or both, are affected, wherein degradation of LDL by a cell of the subject is increased.

Disclosed are methods comprising administering any one of the disclosed synthetic ApoE-mimicking peptides to a subject, whereby plasma LDL, plasma VLDL, or both, are affected, wherein LDL cholesterol in the subject is lowered.

Disclosed are methods comprising administering any one of the disclosed synthetic ApoE-mimicking peptides to a subject, whereby plasma LDL, plasma VLDL, or both, are affected, wherein binding of VLDL to a cell of the subject is enhanced.

Disclosed are methods comprising administering any one of the disclosed synthetic ApoE-mimicking peptides to a subject, whereby plasma LDL, plasma VLDL, or both, are affected, wherein degradation of VLDL by a cell of the subject is increased.

Disclosed are methods comprising administering any one of the disclosed synthetic ApoE-mimicking peptides to a subject, whereby plasma LDL, plasma VLDL, or both, are affected, wherein VLDL cholesterol in the subject is lowered.

Disclosed are methods comprising administering any one of the disclosed synthetic ApoE-mimicking peptides to a subject, whereby plasma LDL, plasma VLDL, or both, are affected, wherein total plasma concentration of cholesterol in the subject is lowered.

Disclosed are methods comprising administering any one of the disclosed synthetic ApoE-mimicking peptides to a subject, whereby plasma LDL, plasma VLDL, or both, are affected, wherein said synthetic apolipoprotein E-mimicking peptide is administered in an amount of about 0.01 mg/kg to about 12 mg/kg.

Disclosed are methods comprising administering any one of the disclosed synthetic ApoE-mimicking peptides to a subject, whereby plasma LDL, plasma VLDL, or both, are affected, wherein the subject has coronary artery disease, rheumatoid arthritis, diabetes, Alzheimer's disease, peripheral artery disease (PAD), cerebral vascular disease, diabetes-derived cardiovascular diseases, macular degeneration, congestive heart failure, and/or systemic lupus.

Also disclosed are methods of reducing plasma cholesterol comprising administering to a subject an effective amount of a composition comprising any one of the disclosed synthetic apolipoprotein E-mimicking peptides.

Disclosed are methods of reducing plasma cholesterol comprising administering to a subject an effective amount of a composition comprising any one of the disclosed synthetic apolipoprotein E-mimicking peptides, wherein the synthetic apolipoprotein E-mimicking peptide is administered as a composition comprising the synthetic apolipoprotein E-mimicking peptide and a pharmaceutically acceptable carrier.

Disclosed are methods of reducing plasma cholesterol comprising administering to a subject an effective amount of a composition comprising any one of the disclosed synthetic apolipoprotein E-mimicking peptides, wherein binding of LDL to a cell of the subject is enhanced.

Disclosed are methods of reducing plasma cholesterol comprising administering to a subject an effective amount of a composition comprising any one of the disclosed synthetic apolipoprotein E-mimicking peptides, wherein degradation of LDL by a cell of the subject is increased.

Disclosed are methods of reducing plasma cholesterol comprising administering to a subject an effective amount of a composition comprising any one of the disclosed synthetic apolipoprotein E-mimicking peptides, wherein LDL cholesterol in the subject is lowered.

Disclosed are methods of reducing plasma cholesterol comprising administering to a subject an effective amount of a composition comprising any one of the disclosed synthetic apolipoprotein E-mimicking peptides, wherein binding of VLDL to a cell of the subject is enhanced.

Disclosed are methods of reducing plasma cholesterol comprising administering to a subject an effective amount of a composition comprising any one of the disclosed synthetic apolipoprotein E-mimicking peptides, wherein degradation of VLDL by a cell of the subject is increased.

Disclosed are methods of reducing plasma cholesterol comprising administering to a subject an effective amount of a composition comprising any one of the disclosed synthetic apolipoprotein E-mimicking peptides, wherein VLDL cholesterol in the subject is lowered.

Disclosed are methods of reducing plasma cholesterol comprising administering to a subject an effective amount of a composition comprising any one of the disclosed synthetic apolipoprotein E-mimicking peptides, wherein total plasma concentration of cholesterol in the subject is lowered.

Disclosed are methods of reducing plasma cholesterol comprising administering to a subject an effective amount of a composition comprising any one of the disclosed synthetic apolipoprotein E-mimicking peptides, wherein said synthetic apolipoprotein E-mimicking peptide is administered in an amount of about 0.01 mg/kg to about 12 mg/kg.

Disclosed are methods of reducing plasma cholesterol comprising administering to a subject an effective amount of a composition comprising any one of the disclosed synthetic apolipoprotein E-mimicking peptides, wherein the subject has coronary artery disease, rheumatoid arthritis, diabetes, Alzheimer's disease, PAD, cerebral vascular disease, diabetes-derived cardiovascular diseases, macular degeneration, congestive heart failure, and/or systemic lupus.

Also disclosed are methods of treating atherosclerosis comprising administering to a subject an effective amount of a composition comprising any one of the disclosed synthetic apolipoprotein E-mimicking peptides.

Disclosed are methods of treating atherosclerosis comprising administering to a subject an effective amount of a composition comprising any one of the disclosed synthetic apolipoprotein E-mimicking peptides, wherein the synthetic apolipoprotein E-mimicking peptide is administered as a composition comprising the synthetic apolipoprotein E-mimicking peptide and a pharmaceutically acceptable carrier.

Disclosed are methods of treating atherosclerosis comprising administering to a subject an effective amount of a composition comprising any one of the disclosed synthetic apolipoprotein E-mimicking peptides, wherein binding of LDL to a cell of the subject is enhanced.

Disclosed are methods of treating atherosclerosis comprising administering to a subject an effective amount of a composition comprising any one of the disclosed synthetic apolipoprotein E-mimicking peptides, wherein degradation of LDL by a cell of the subject is increased.

Disclosed are methods of treating atherosclerosis comprising administering to a subject an effective amount of a composition comprising any one of the disclosed synthetic apolipoprotein E-mimicking peptides, wherein LDL cholesterol in the subject is lowered.

Disclosed are methods of treating atherosclerosis comprising administering to a subject an effective amount of a composition comprising any one of the disclosed synthetic apolipoprotein E-mimicking peptides, wherein binding of VLDL to a cell of the subject is enhanced.

Disclosed are methods of treating atherosclerosis comprising administering to a subject an effective amount of a composition comprising any one of the disclosed synthetic apolipoprotein E-mimicking peptides, wherein degradation of VLDL by a cell of the subject is increased.

Disclosed are methods of treating atherosclerosis comprising administering to a subject an effective amount of a composition comprising any one of the disclosed synthetic apolipoprotein E-mimicking peptides, wherein VLDL cholesterol in the subject is lowered.

Disclosed are methods of treating atherosclerosis comprising administering to a subject an effective amount of a composition comprising any one of the disclosed synthetic apolipoprotein E-mimicking peptides, wherein total plasma concentration of cholesterol in the subject is lowered.

Disclosed are methods of treating atherosclerosis comprising administering to a subject an effective amount of a composition comprising any one of the disclosed synthetic apolipoprotein E-mimicking peptides, wherein said synthetic apolipoprotein E-mimicking peptide is administered in an amount of about 0.01 mg/kg to about 12 mg/kg.

Disclosed are methods of treating atherosclerosis comprising administering to a subject an effective amount of a composition comprising any one of the disclosed synthetic apolipoprotein E-mimicking peptides, wherein the subject has coronary artery disease, rheumatoid arthritis, diabetes, Alzheimer's disease, PAD, cerebral vascular disease, diabetes-derived cardiovascular diseases, macular degeneration, congestive heart failure, and/or systemic lupus.

Also disclosed are methods for treating a subject with a Lipid Disorder, the method comprising administering to the subject an effective amount of any one of the disclosed synthetic apolipoprotein E-mimicking peptides, or a composition thereof.

Disclosed are methods for treating a subject with a Lipid Disorder, the method comprising administering to the subject an effective amount of any one of the disclosed synthetic apolipoprotein E-mimicking peptides, or a composition thereof, wherein the synthetic apolipoprotein E-mimicking peptide is administered as a composition comprising the synthetic apolipoprotein E-mimicking peptide and a pharmaceutically acceptable carrier.

Disclosed are methods for treating a subject with a Lipid Disorder, the method comprising administering to the subject an effective amount of any one of the disclosed synthetic apolipoprotein E-mimicking peptides, or a composition thereof, wherein binding of LDL to a cell of the subject is enhanced.

Disclosed are methods for treating a subject with a Lipid Disorder, the method comprising administering to the subject an effective amount of any one of the disclosed synthetic apolipoprotein E-mimicking peptides, or a composition thereof, wherein degradation of LDL by a cell of the subject is increased.

Disclosed are methods for treating a subject with a Lipid Disorder, the method comprising administering to the subject an effective amount of any one of the disclosed synthetic apolipoprotein E-mimicking peptides, or a composition thereof, wherein LDL cholesterol in the subject is lowered.

Disclosed are methods for treating a subject with a Lipid Disorder, the method comprising administering to the subject an effective amount of any one of the disclosed synthetic apolipoprotein E-mimicking peptides, or a composition thereof, wherein binding of VLDL to a cell of the subject is enhanced.

Disclosed are methods for treating a subject with a Lipid Disorder, the method comprising administering to the subject an effective amount of any one of the disclosed synthetic apolipoprotein E-mimicking peptides, or a composition thereof, wherein degradation of VLDL by a cell of the subject is increased.

Disclosed are methods for treating a subject with a Lipid Disorder, the method comprising administering to the subject an effective amount of any one of the disclosed synthetic apolipoprotein E-mimicking peptides, or a composition thereof, wherein VLDL cholesterol in the subject is lowered.

Disclosed are methods for treating a subject with a Lipid Disorder, the method comprising administering to the subject an effective amount of any one of the disclosed synthetic apolipoprotein E-mimicking peptides, or a composition thereof, wherein total plasma concentration of cholesterol in the subject is lowered.

Disclosed are methods for treating a subject with a Lipid Disorder, the method comprising administering to the subject an effective amount of any one of the disclosed synthetic apolipoprotein E-mimicking peptides, or a composition thereof, wherein said synthetic apolipoprotein E-mimicking peptide is administered in an amount of about 0.01 mg/kg to about 12 mg/kg.

Disclosed are methods for treating a subject with a Lipid Disorder, the method comprising administering to the subject an effective amount of any one of the disclosed synthetic apolipoprotein E-mimicking peptides, or a composition thereof, wherein the lipid disorder is coronary artery disease, rheumatoid arthritis, diabetes, Alzheimer's disease, PAD, cerebral vascular disease, diabetes-derived cardiovascular diseases, macular degeneration, congestive heart failure, and/or systemic lupus.

Also disclosed are dosing regimens comprising at least one treatment cycle followed by a rest phase, wherein the treatment cycle comprises administering an effective amount of any of the disclosed Apo E-mimicking peptides to allow for a sustained therapeutic effect after withdrawal of the Apo E-mimicking peptide, wherein the Apo E-mimicking peptide is not administered during the rest phase. In some instances, the treatment cycle comprises administration of an effective amount of the Apo E-mimicking peptide once a week for three months. In some instances, the treatment cycle comprises administration of an effective amount of the Apo E-mimicking peptide once every two weeks for up to 12 weeks.

Disclosed are dosing regimens comprising at least one treatment cycle followed by a rest phase, wherein the treatment cycle comprises administering an effective amount of any of the disclosed Apo E-mimicking peptides to allow for a sustained therapeutic effect after withdrawal of the Apo E-mimicking peptide, wherein the Apo E-mimicking peptide is not administered during the rest phase, wherein the dosing regimen further comprises a second treatment cycle after the rest phase.

Also disclosed are methods of treating acute coronary syndrome (ACS) comprising administering to a subject an effective amount of any of the disclosed Apo E-mimicking peptides for at least one treatment cycle, wherein the treatment cycle comprises administering an effective amount of an Apo E-mimicking peptide to allow for a sustained therapeutic effect after withdrawal of the Apo E-mimicking peptide, wherein the treatment cycle is followed by a rest phase, wherein Apo E-mimicking peptide is not administered during the rest phase.

Disclosed are methods of treating acute coronary syndrome (ACS) comprising administering to a subject an effective amount of any of the disclosed Apo E-mimicking peptides for at least one treatment cycle, wherein the treatment cycle comprises administering an effective amount of an Apo E-mimicking peptide to allow for a sustained therapeutic effect after withdrawal of the Apo E-mimicking peptide, wherein the treatment cycle is followed by a rest phase, wherein Apo E-mimicking peptide is not administered during the rest phase, wherein the rest phase is at least four weeks.

Disclosed are methods of treating acute coronary syndrome (ACS) comprising administering to a subject an effective amount of any of the disclosed Apo E-mimicking peptides for at least one treatment cycle, wherein the treatment cycle comprises administering an effective amount of an Apo E-mimicking peptide to allow for a sustained therapeutic effect after withdrawal of the Apo E-mimicking peptide, wherein the treatment cycle is followed by a rest phase, wherein Apo E-mimicking peptide is not administered during the rest phase, further comprising a second treatment cycle after the rest phase. In some instances, the second treatment cycle can be administered after a four week rest phase. In some instances, the second treatment cycle can be administered one year from the beginning of the initial treatment cycle.

Disclosed are methods of treating acute coronary syndrome (ACS) comprising administering to a subject an effective amount of any of the disclosed Apo E-mimicking peptides for at least one treatment cycle, wherein the treatment cycle comprises administering an effective amount of an Apo E-mimicking peptide to allow for a sustained therapeutic effect after withdrawal of the Apo E-mimicking peptide, wherein the treatment cycle is followed by a rest phase, wherein Apo E-mimicking peptide is not administered during the rest phase, further comprising a second treatment cycle after the rest phase, wherein an ACS therapeutic other than an Apo E-mimicking peptide is administered during the rest phase.

Disclosed are methods of treating acute coronary syndrome (ACS) comprising administering to a subject an effective amount of any of the disclosed Apo E-mimicking peptides for at least one treatment cycle, wherein the treatment cycle comprises administering an effective amount of an Apo E-mimicking peptide to allow for a sustained therapeutic effect after withdrawal of the Apo E-mimicking peptide, wherein the treatment cycle is followed by a rest phase, wherein Apo E-mimicking peptide is not administered during the rest phase, further comprising a second treatment cycle after the rest phase, wherein an ACS therapeutic other than an Apo E-mimicking peptide is administered during the rest phase, wherein the ACS therapeutic other than an Apo E-mimicking peptide is a conventional LDL lowering therapy or HDL elevating therapy. In some instances, the conventional LDL lowering therapy can be a statin. In some instances, the HDL elevating therapy can be an Apo A1 elevating drug, a CETP inhibitor, a phospholipase A2 inhibitor, an Apo A1 Milano, or an Apo A1 mimetic.

Disclosed are methods of treating acute coronary syndrome (ACS) comprising administering to a subject an effective amount of any of the disclosed Apo E-mimicking peptides for at least one treatment cycle, wherein the treatment cycle comprises administering an effective amount of an Apo E-mimicking peptide to allow for a sustained therapeutic effect after withdrawal of the Apo E-mimicking peptide, wherein the treatment cycle is followed by a rest phase, wherein Apo E-mimicking peptide is not administered during the rest phase, further comprising a second treatment cycle after the rest phase, wherein an ACS therapeutic other than an Apo E-mimicking peptide is administered during the rest phase, wherein the ACS therapeutic other than an Apo E-mimicking peptide is a conventional LDL lowering therapy or HDL elevating therapy, wherein the treatment cycle comprises administration of an effective amount of an Apo E-mimicking peptide once a week for three months.

Also disclosed are monoclonal antibodies that specifically bind to any one of the disclosed synthetic ApoE peptides.

Also disclosed are synthetic ApoE-mimicking peptides comprising a receptor binding domain of ApoE and a lipid-associating peptide, wherein the synthetic ApoE-mimicking peptide comprises an Ac-AHA, wherein the receptor binding domain of apolipoprotein E is scrambled.

Also disclosed are synthetic apolipoprotein E-mimicking peptides consisting of a receptor binding domain of apolipoprotein E and a lipid-associating peptide, wherein receptor binding domain is covalently linked to said lipid-associating peptide, wherein both the receptor binding domain of apolipoprotein E and the lipid-associating peptide are scrambled.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIG. 1 describes several strategies used to develop a highly effective peptide. From top to bottom in the "Sequence" column, the sequences are as follows: SEQ ID NO:664, 665, 666, 667, 668, 669, 670, 662, 671, 672, 673, 674.

FIG. 7 is a table showing experimental design. ApoE-null mice were dosed with the peptides Ac-he18A-$NH_2$ (AEM-28), Ac—[R]he18A-$NH_2$ (AEM-28(R)), or Ac-Aha-[R]he18A-$NH_2$ (AES-21), in saline via tail vein injection at a concentration of 100 ug/mouse. Blood was collected via a cheek bleed at pre-dose, and at 1, 6 and 24 hours post dose. Serum samples can be analyzed for total serum cholesterol (using Waco total cholesterol kit).

FIG. 9 is a table showing the results from the mouse injections described in FIG. 8.

FIG. 10 is a table showing the results of total serum cholesterol (as % of pre-dose level).

FIG. 11 shows an experimental design. ApoE-null mice were dosed with AC-hE18A-NH2 (AEM-28), AC-[R]hE18A-NH2 (AEM-28(R)), or AC-Aha-[R]he18A-NH2 (AES2-21), in saline via tail vein injection at a concentration of 50 μg/mouse. Blood was collected via a cheek bleed at pre-dose, and at 1, 6 and 24 hours post dose. Serum samples will be analyzed for total serum cholesterol (using a total cholesterol kit (Wako Chemicals USA, Inc., Richmond, Va.)).

FIG. 13 is a table showing raw cholesterol values.

FIG. 14 is a table showing % of pre-dose cholesterol.

DETAILED DESCRIPTION

Figure 2A:
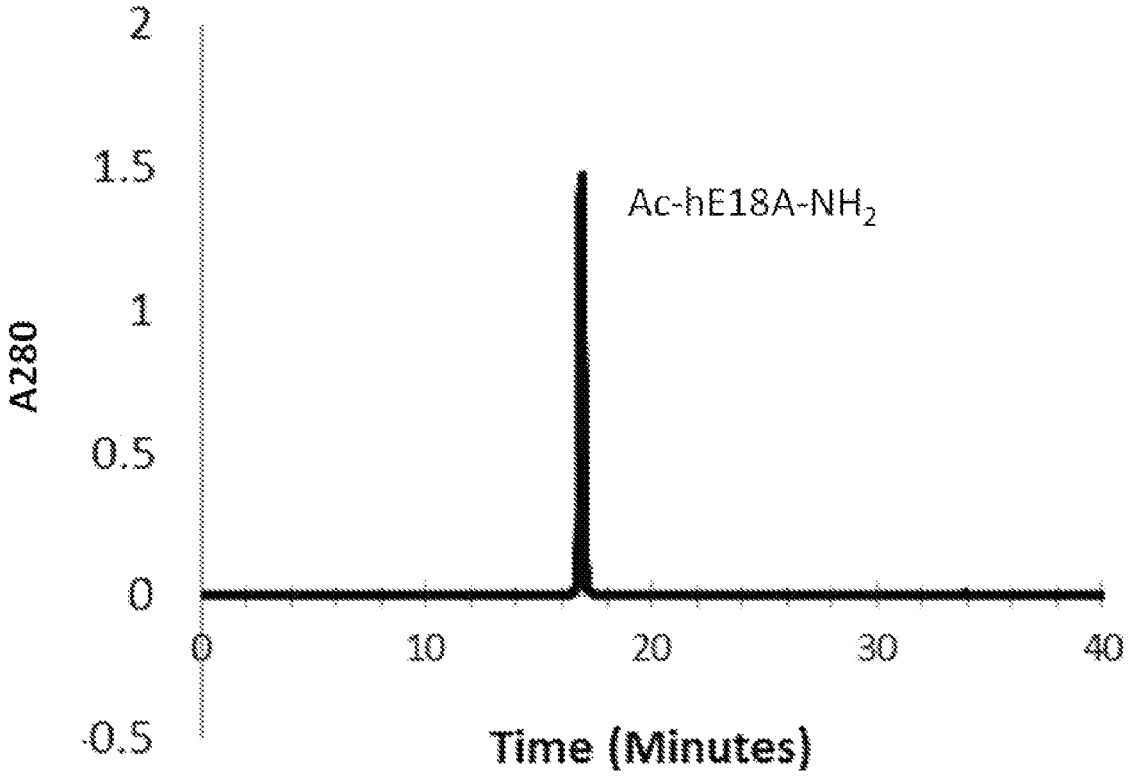
FIGS. 2A-2G shows the comparative analytical HPLC profiles of the indicated ApoE mimetic peptide analogs. Chromatography was carried out as follows: C-18 column-250×4.6 mm; mobile phase was a gradient of 30-70% acetonitrile in water over 35 minutes (with 0.1% TFA).
Figure 2B:
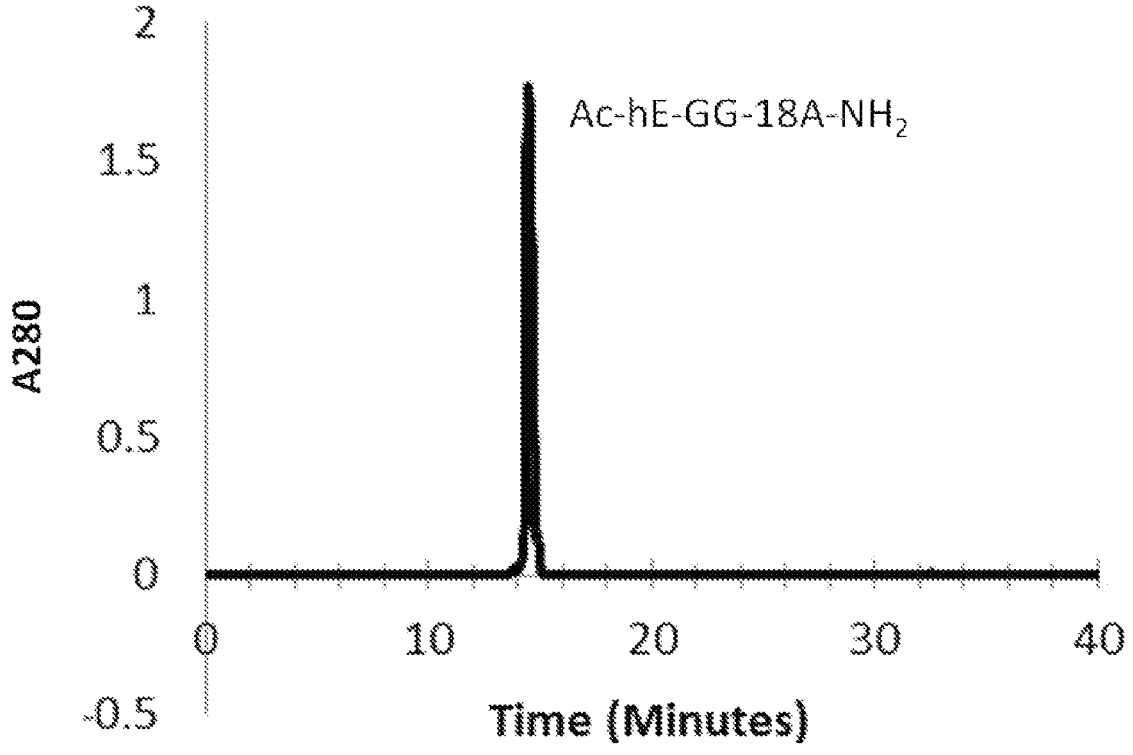
Figure 2C:
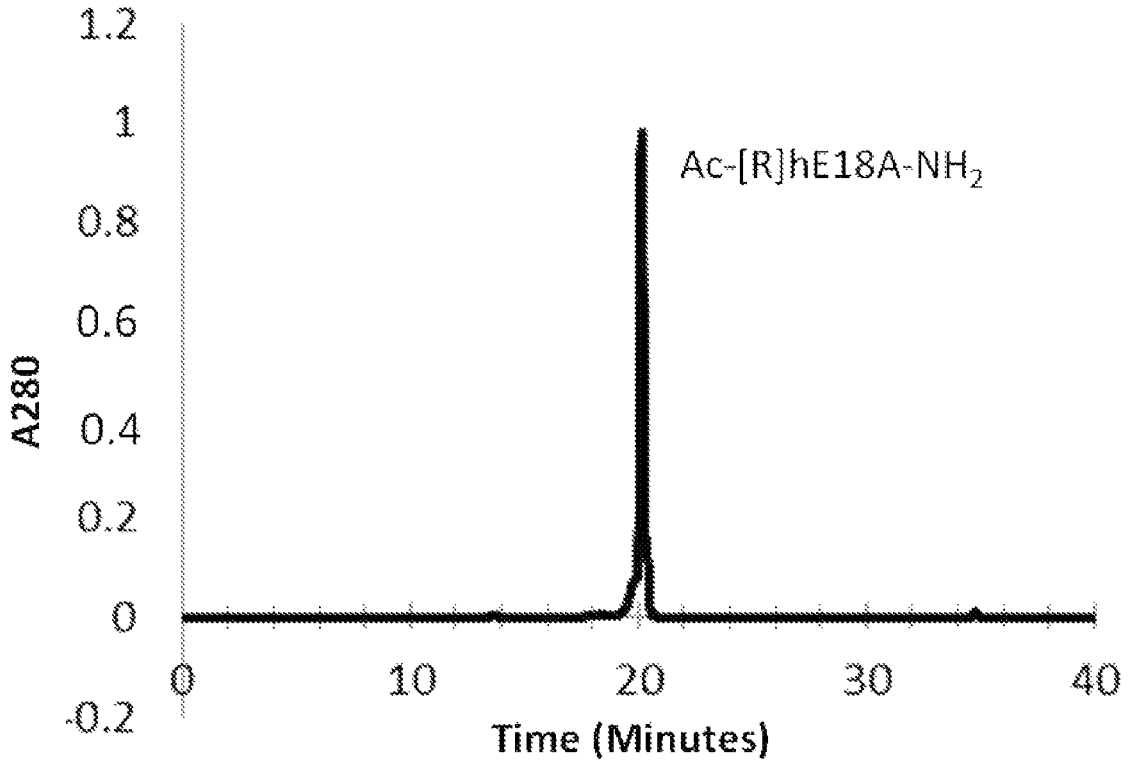
Figure 2D:
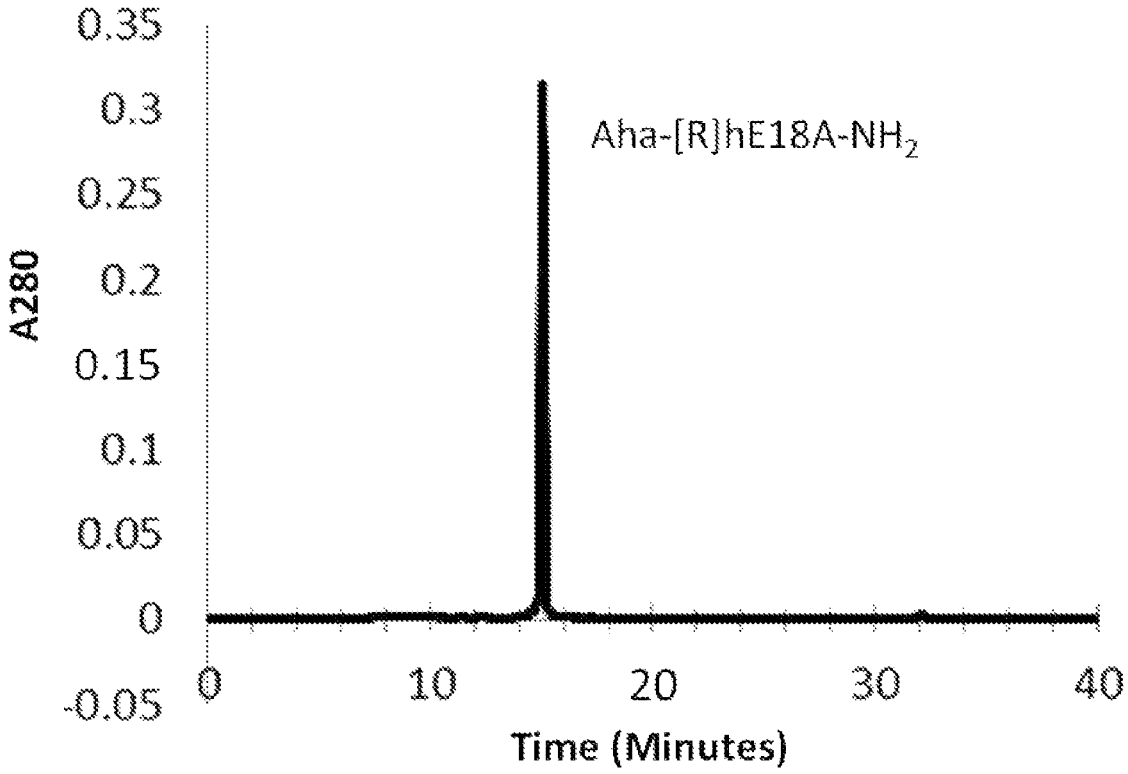
Figure 2E:
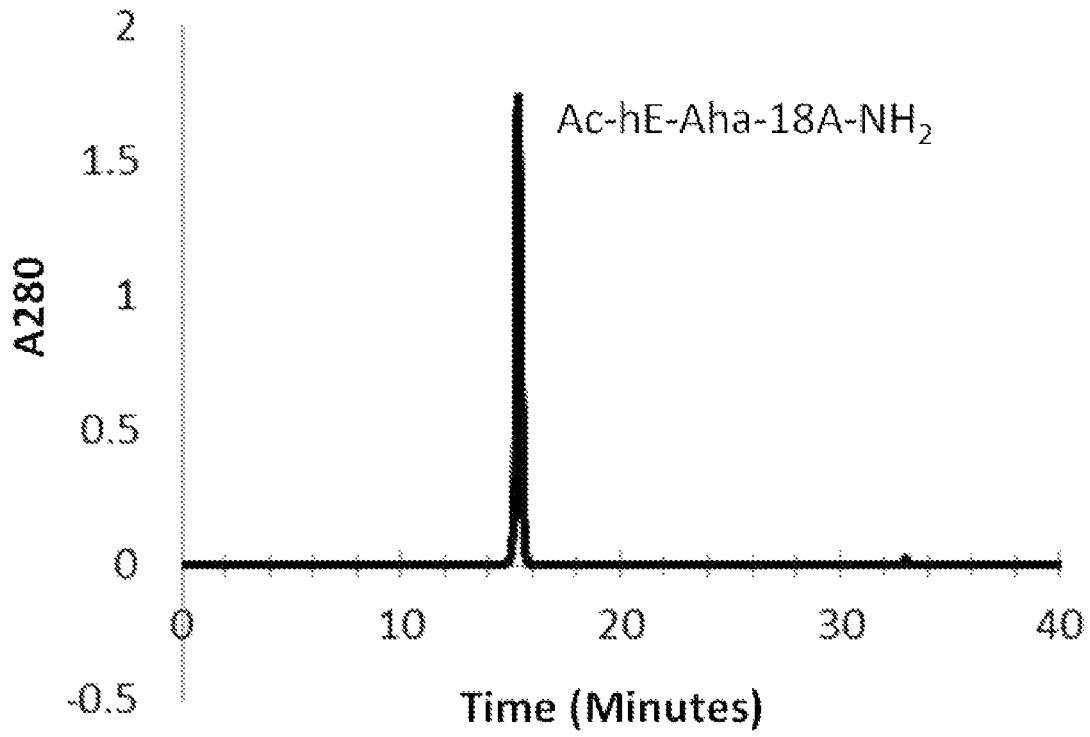
Figure 2F:
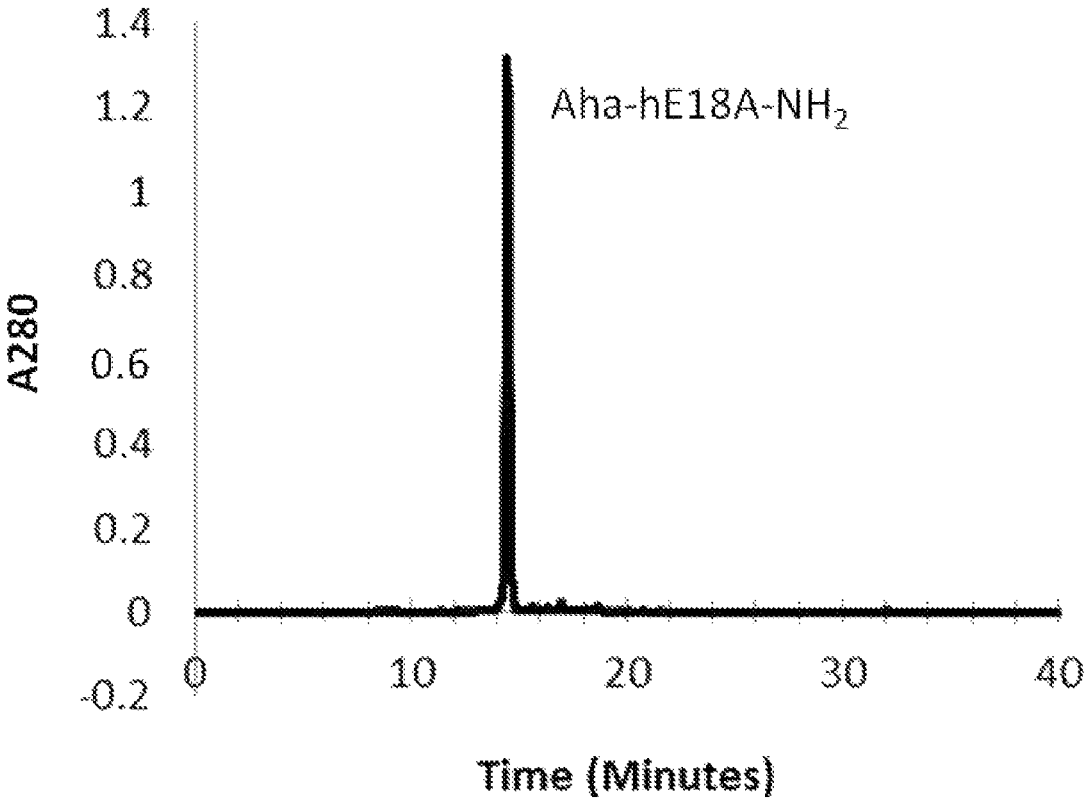
Figure 2G:
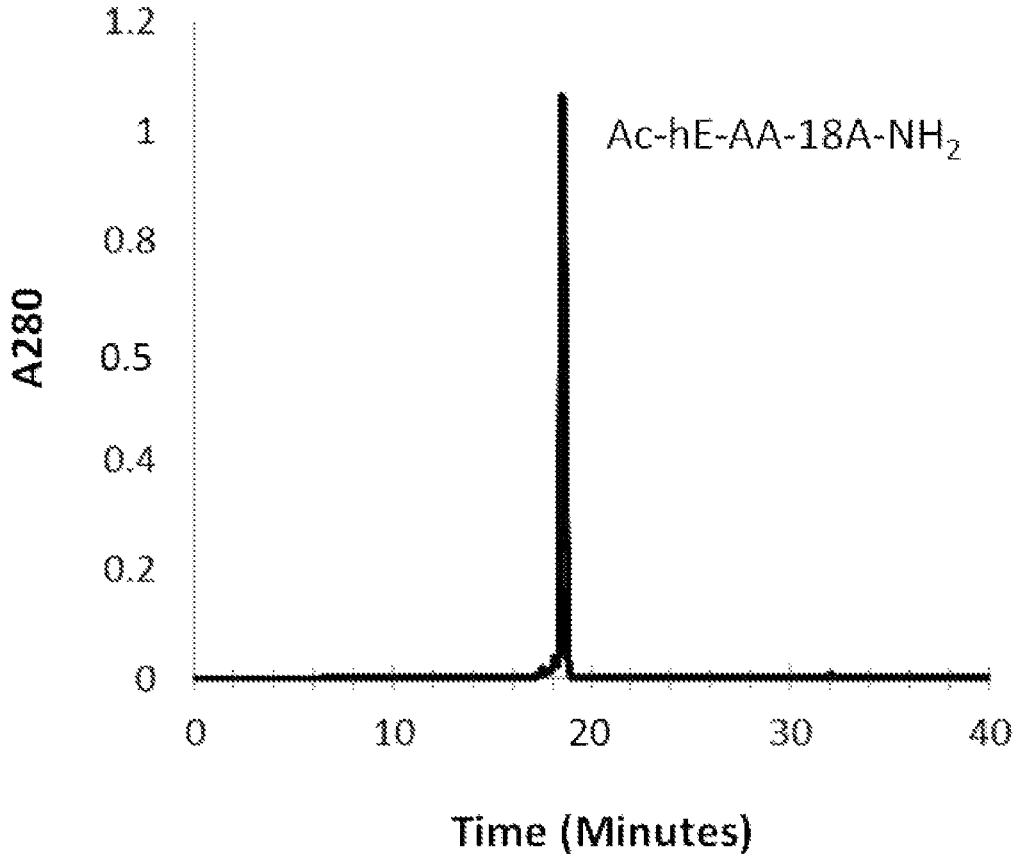
Figure 3:
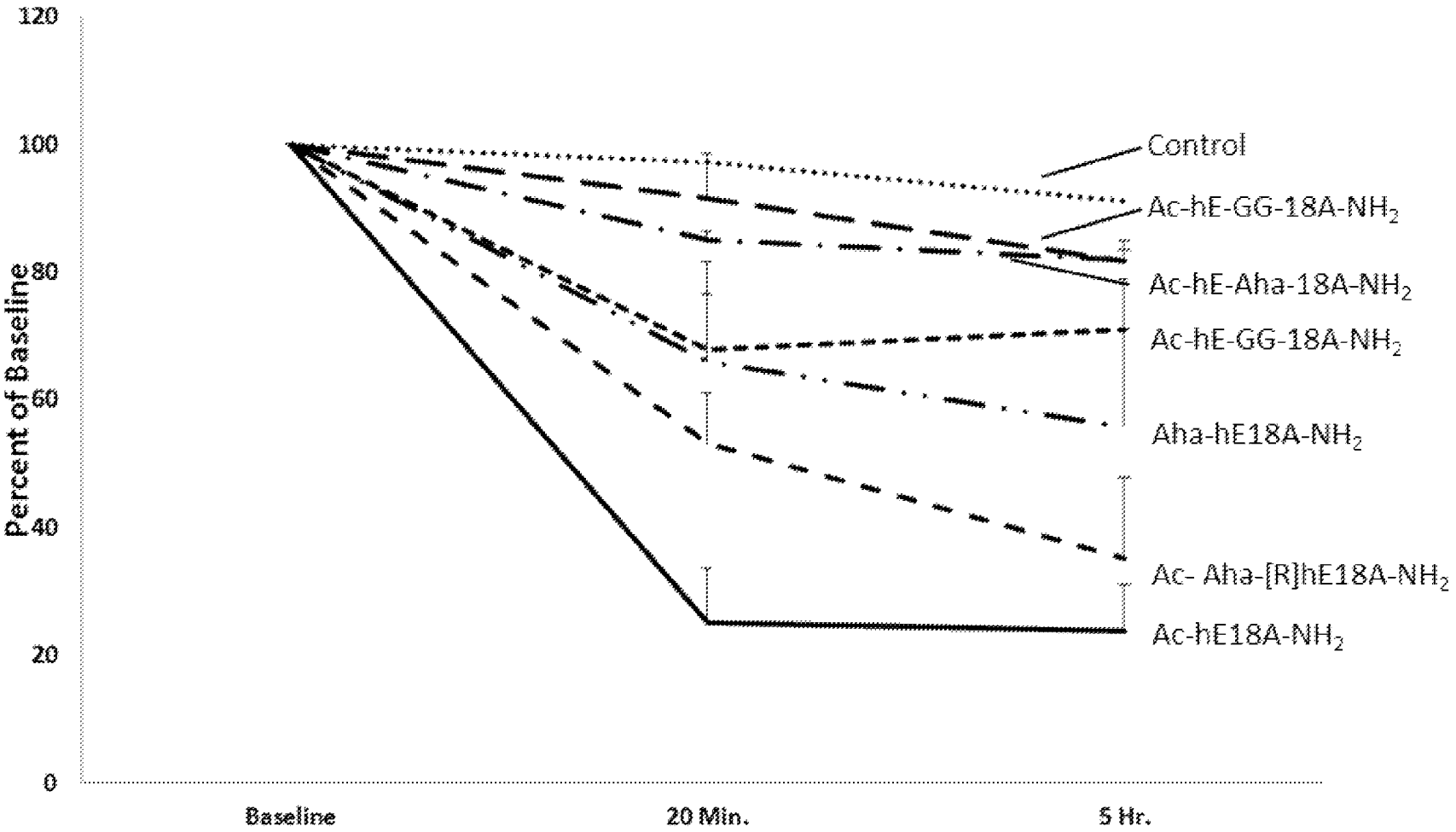
FIG. 3 shows cholesterol reduction (percent reduction in plasma cholesterol) by the indicated apoE mimetic peptide analogs in apoE null Mice (100 μg/mouse) following a single dose administration (n=4 animals/group). The baseline level is the relative plasma cholesterol level at the time of dose administration. The time points show the plasma cholesterol levels at the indicated times following a single dose administration. A single dose was administered using a saline vehicle.
Figure 4:
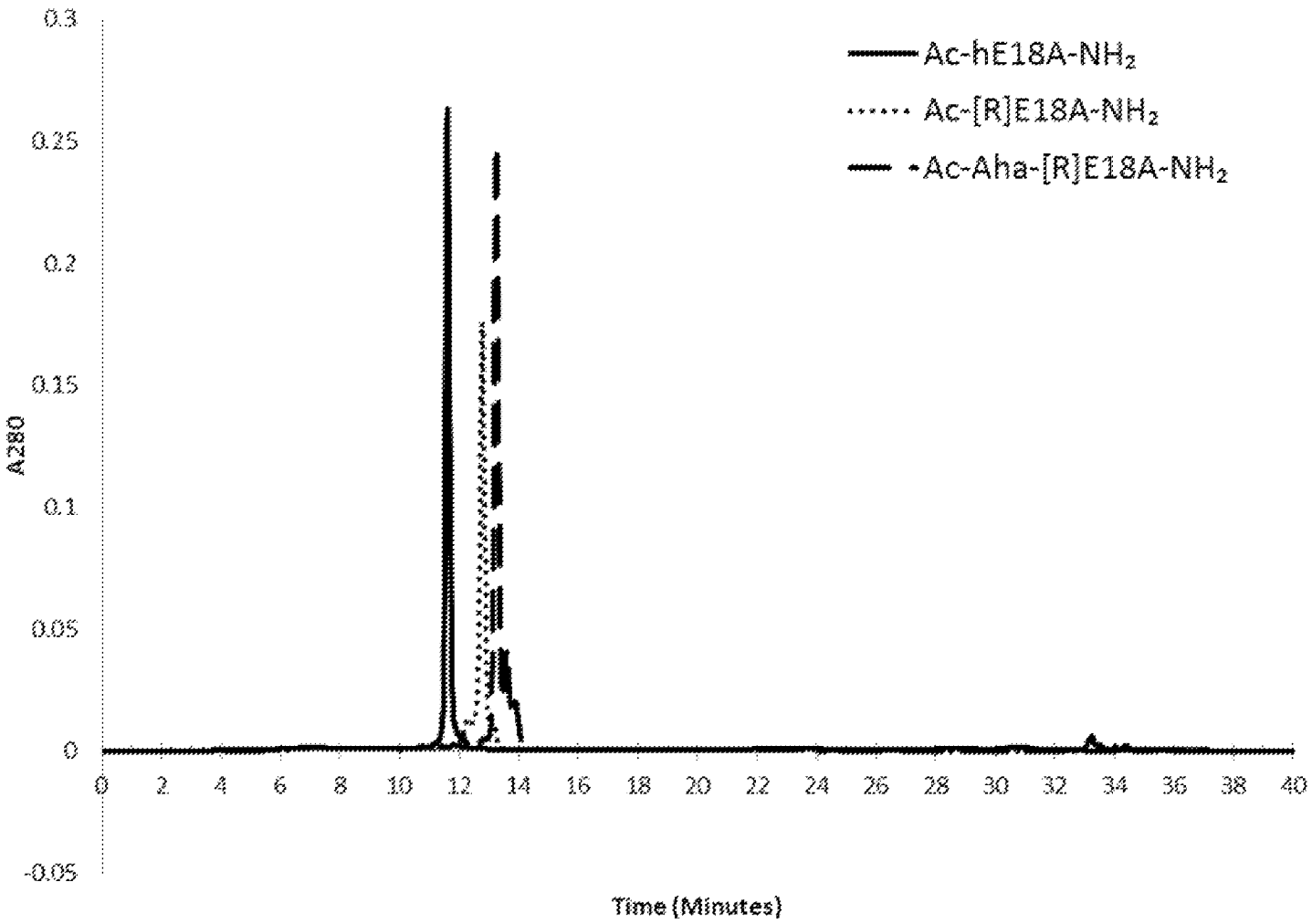
FIG. 4 shows the comparative analytical HPLC profiles of three active ApoE mimetic peptide analogs. Chromatography was carried out as follows: C-18 column-250×4.6 mm; mobile phase was a gradient of 30-70% acetonitrile in water over 12 minutes (with 0.1% TFA).
Figure 5A:
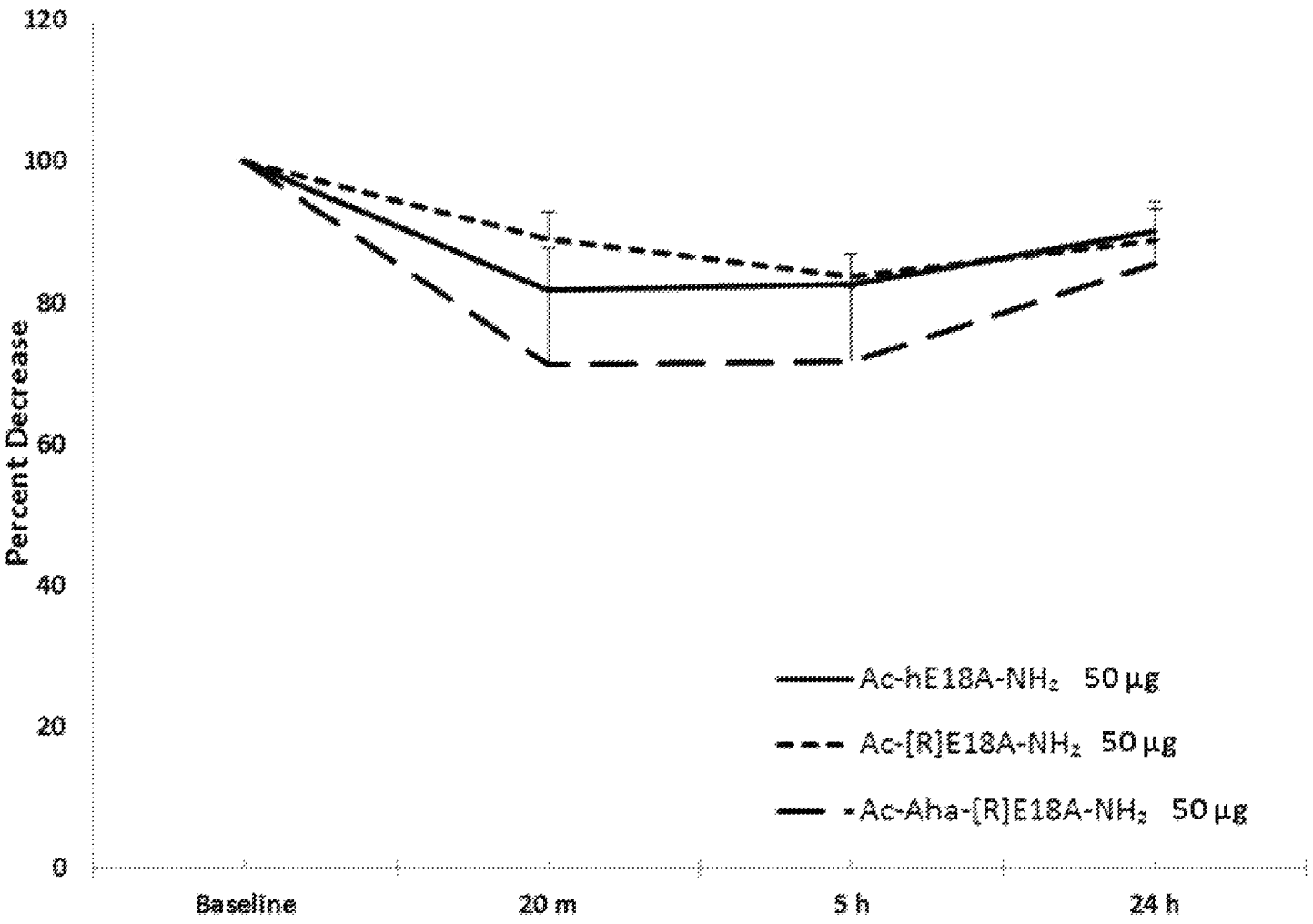
FIGS. 5A-5B shows representative data for the effect of three active ApoE mimetic peptide analogs in reducing plasma cholesterol (% reduction) at a dose level was either 50 μg (FIG. 5A) or a dose level was either 100 μg (FIG. 5B). The study was carried out in apoE null mice (n=4 animals/group). The time points show the plasma cholesterol levels at the indicated times following a single dose administration. A single dose was administered using a saline vehicle. The data show that AC-Aha-[R]hE18A-$NH_2$ is highly effective in reducing plasma cholesterol in ApoE-null mice at both 50 and 100 μg/mouse.
Figure 5B:
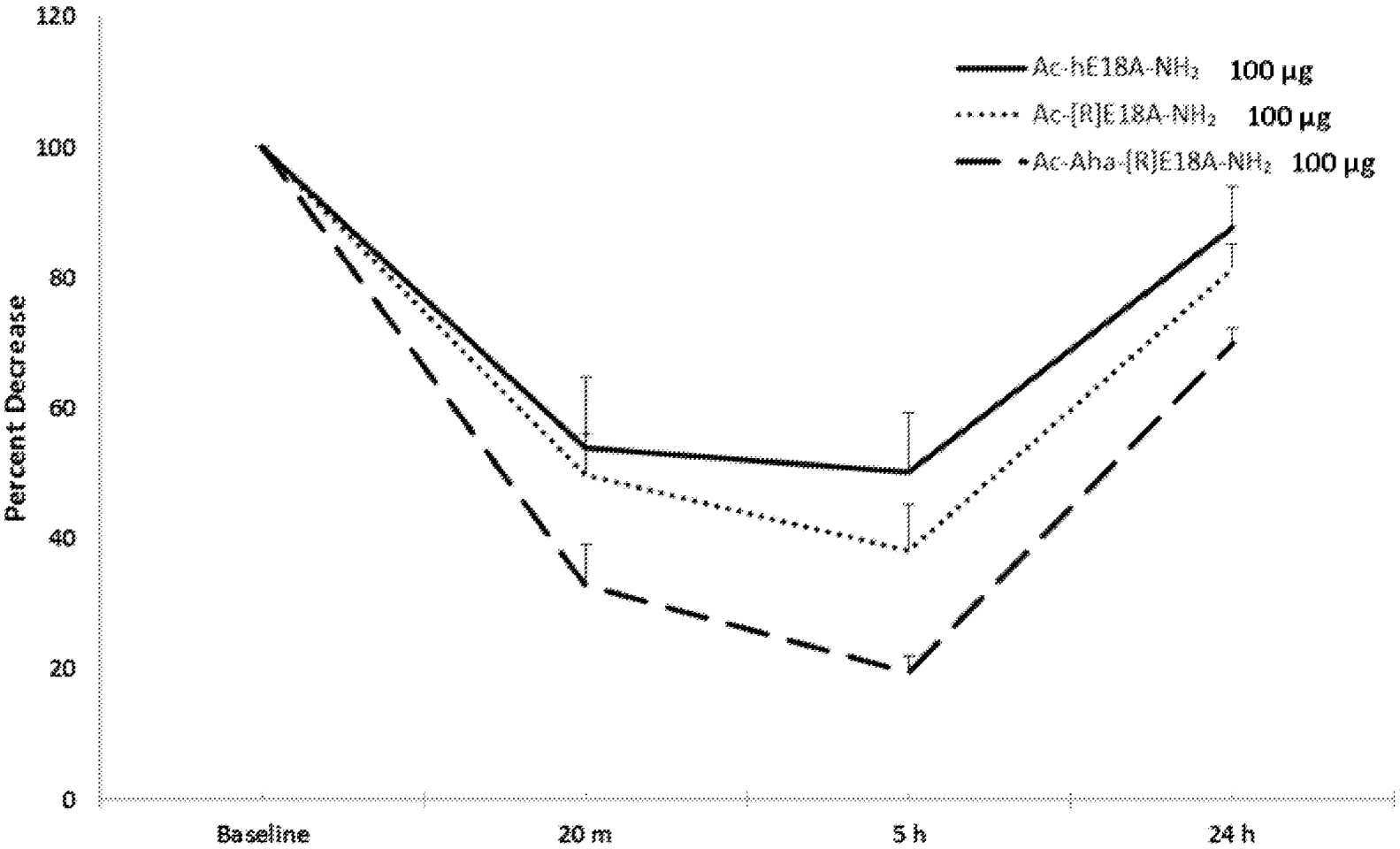
Figure 6:
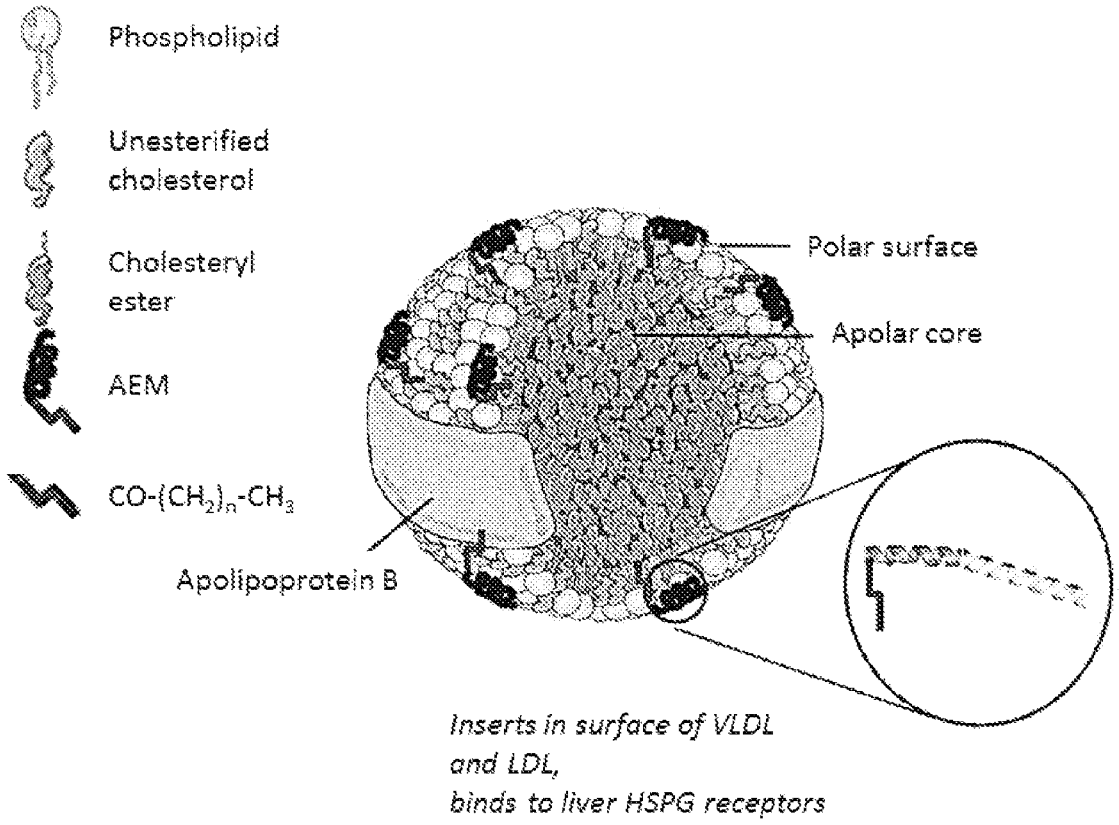
FIG. 6 shows a model for $CH_3$—$(CH_2)_n$—CO-(apoE mimetic peptide) molecules to more avidly attach to a lipid particle than an apoE mimetic peptide that does not comprise an alkyl carboxyl moiety, and thus provides a model for enhanced hepatic clearance.
Figure 8A:
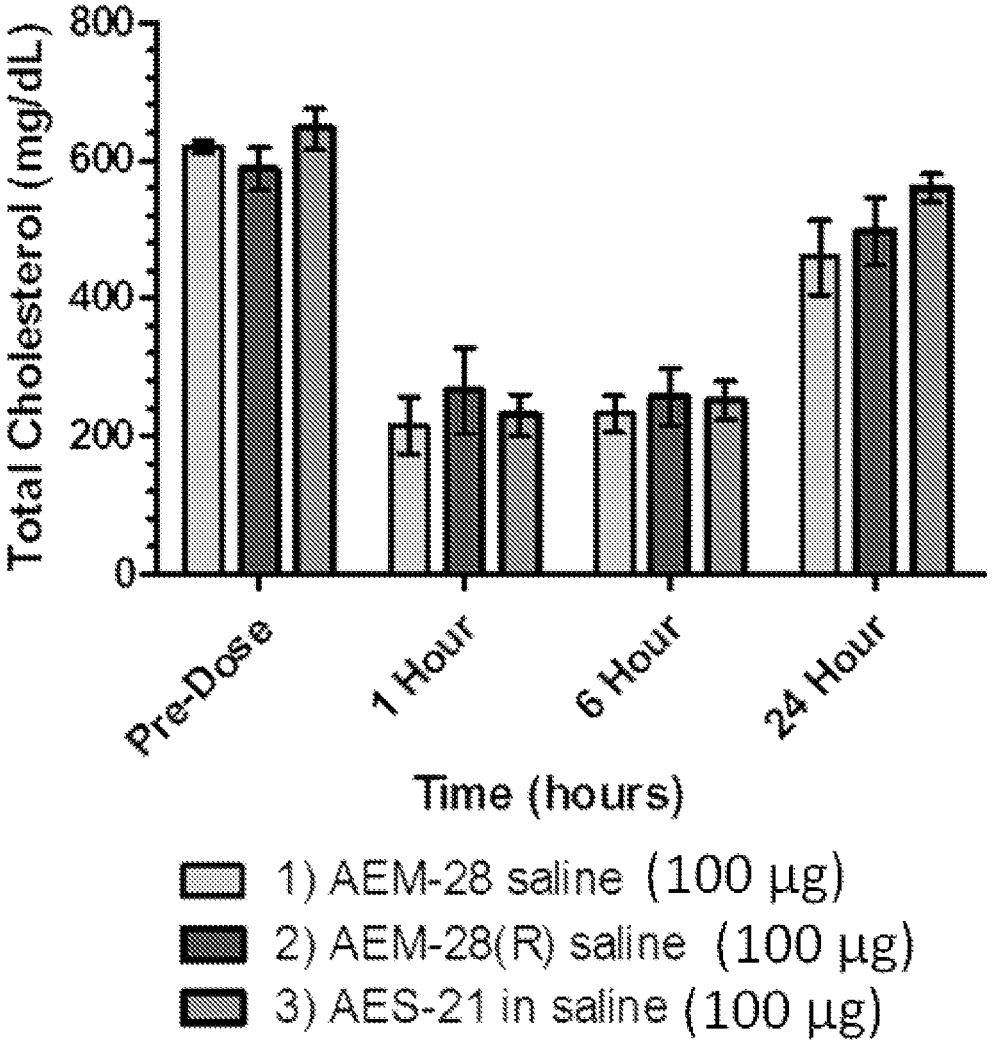
FIGS. 8A and 8B are graphs showing total cholesterol (mg/dL) versus time (FIG. 8A) and total cholesterol (% of pre-dose) versus time (FIG. 8B), respectively. Three different peptides were administered via tail vein injections into female apoE null mice, approximately 10 wks of age, using 100 ug of peptide in saline. Error bars shown are standard error of the mean (SEM). All results (n=5 animals) except Group 1 (n=4 animals all timepoints).
Figure 8B:
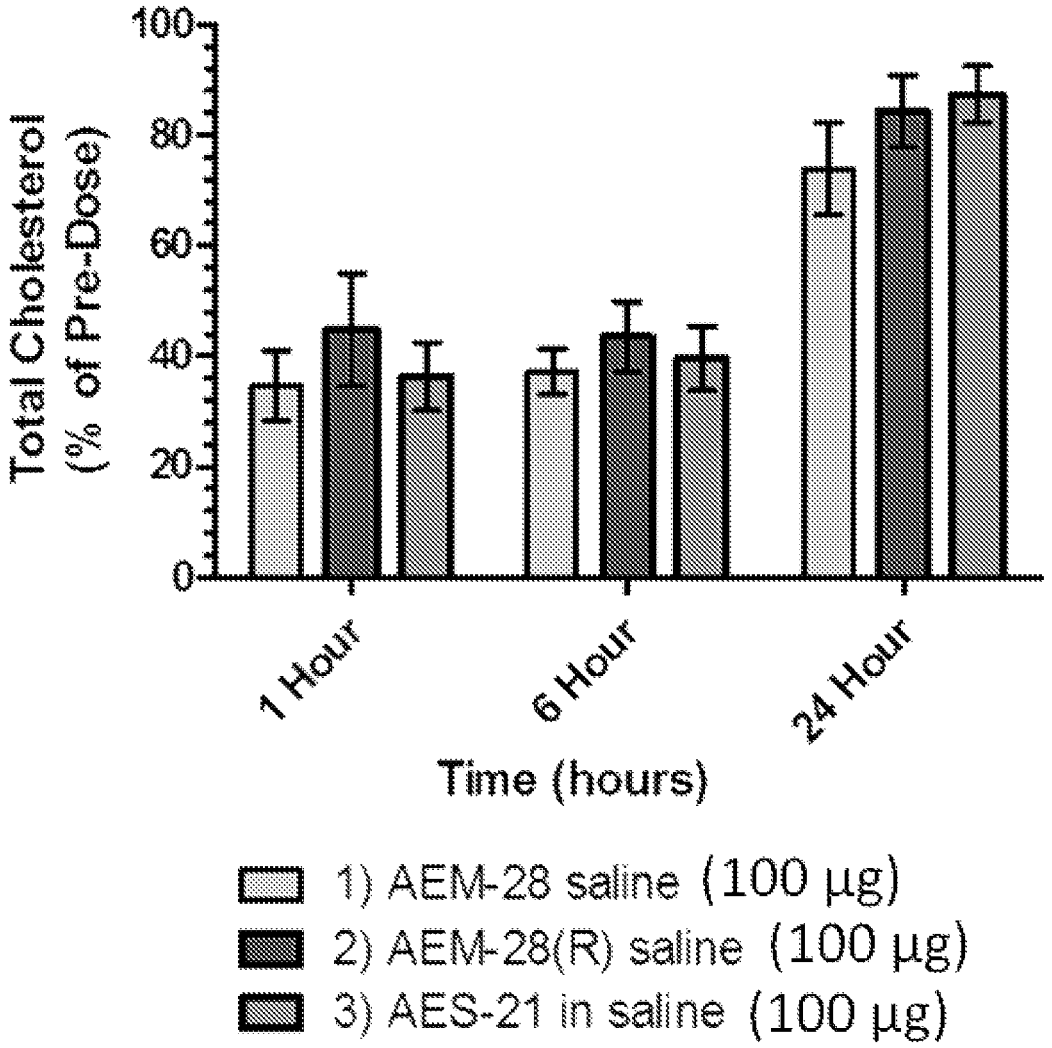
Figure 12A:
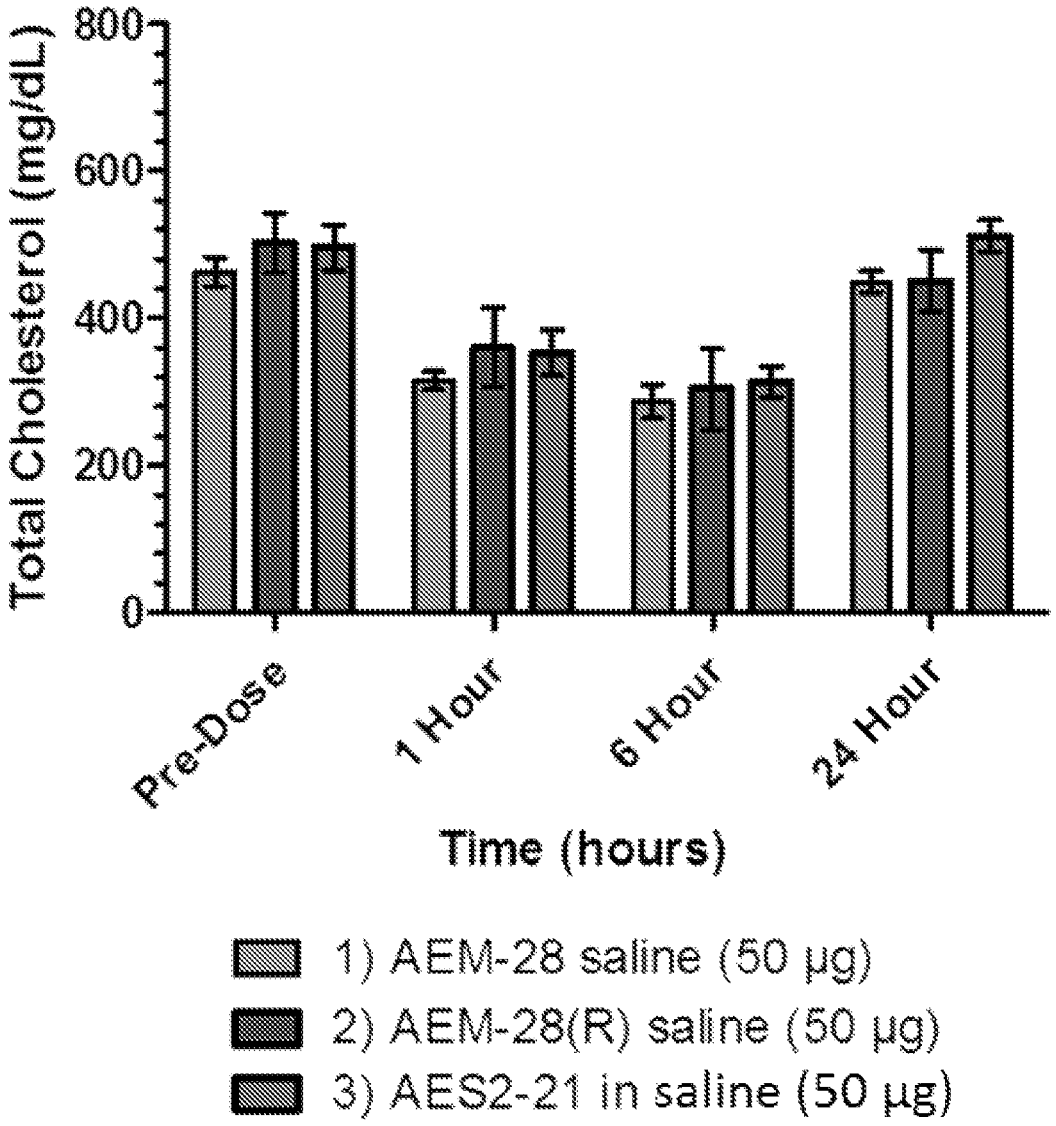
FIGS. 12A and 12B are graphs showing total cholesterol (mg/dL) vs time and total cholesterol (% of pre-dose) vs time, respectively. Three different peptides were administered via tail vein injections into female ApoE KO mice, approximately 10 wks of age, using 100 ug of peptide in saline. Animals were allowed to recover for 2 weeks prior to second dosing with 50 μg of peptide in saline. Error bars shown are standard error of the mean (SEM). All results (n=5 animals). "AEM-28 saline" indicates the peptide AC-hE18A-NH2; "AEM-28(R) saline" indicates the peptide AC-[R]hE18A-NH2; and "AES2-21" indicates the peptide AC-Aha-[R]he18A-NH2.
Figure 12B:
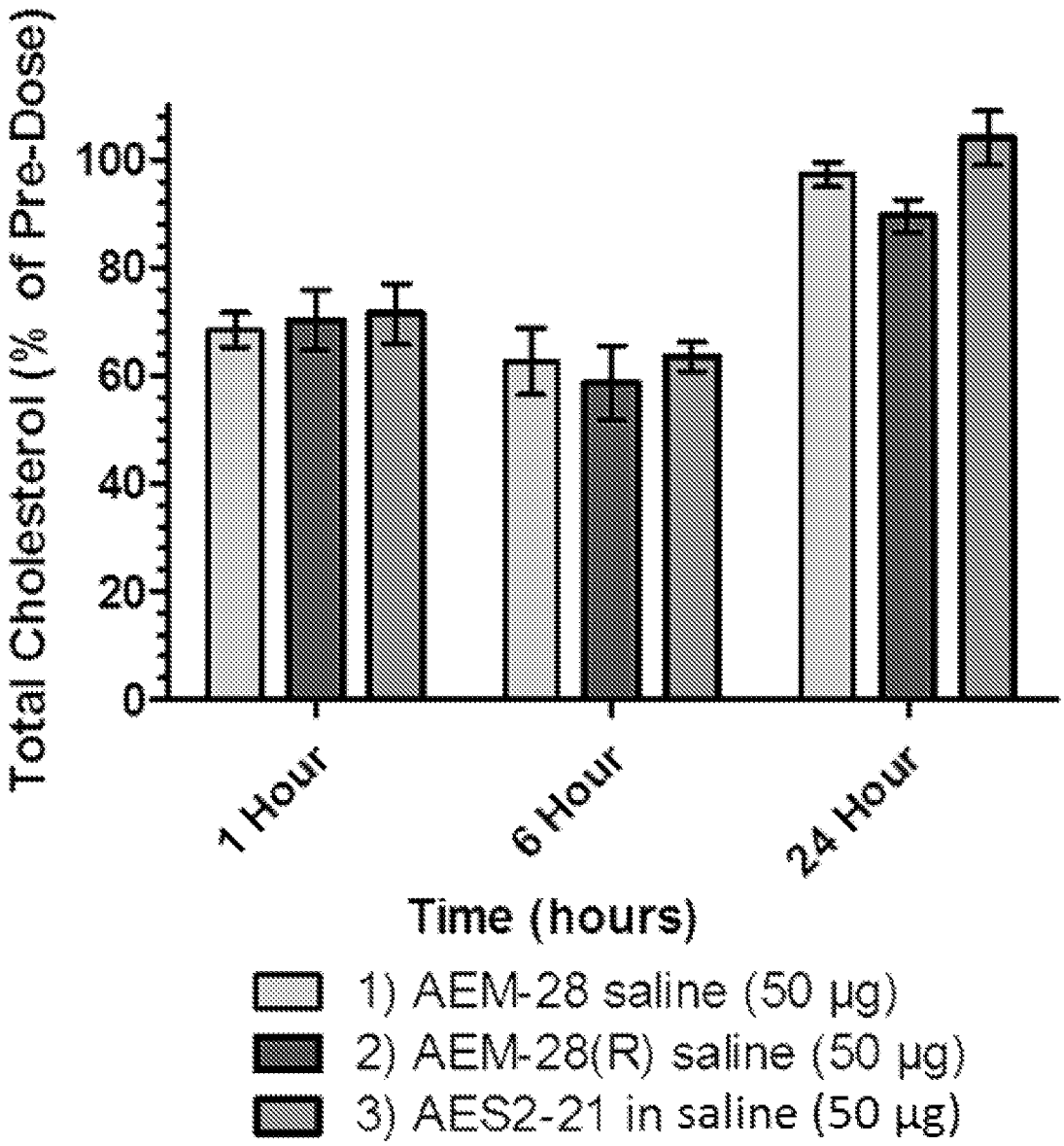

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

A. Definitions

The terminology used herein is for the purpose of describing particular embodiments only and is not intended to be limiting.

As used in the specification and the appended claims, the singular forms "a," "an" and "the" can include plural referents unless the context clearly dictates otherwise. Thus, for example, reference to "a compound" includes mixtures of compounds, reference to "a pharmaceutical carrier" includes mixtures of two or more such carriers, and the like.

The word "or" as used herein means any one member of a particular list and also includes any combination of members of that list.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the term "amino acid sequence" refers to a list of abbreviations, letters, characters or words representing amino acid residues. The amino acid abbreviations used herein are conventional one letter codes for the amino acids and are expressed as follows: A, alanine; C, cysteine; D aspartic acid; E, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; and Y, tyrosine.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

"Peptide" as used herein refers to any peptide, oligopeptide, polypeptide, gene product, expression product, or protein. A peptide is comprised of consecutive amino acids. The term "peptide" encompasses naturally occurring or synthetic molecules.

As used herein, the term "Apo E mimetic" is interchangeable with apolipoprotein-E mimicking peptide. Apo E mimetics are peptides that are related to, characteristic of, or mimic Apo E. Apo E mimetics include Apo E peptides (i.e. peptides derived from full length Apo E).

As used herein, "reverse oriented", "reversed orientation", "reverse analog" or "reverse sequence" refers to a peptide, or a portion of the peptide, has a reverse amino acid sequence as compared to a non-reverse oriented peptide (i.e., the original sequence is read (or written) from right to left). For example, if one peptide has the amino acid sequence ABCDE, its reverse analog or a peptide having its reverse sequence is as follows: EDCBA. In a dual domain peptide for example, Ac-hE-18A-NH2, either the hE sequence is read from right to left or the 18A sequence is read from right to left. For a reverse analog of, LRKLRKRLLR-DWLKAFYDKVAEKLKEAF (SEQ ID NO:1) can be RLLRKRLKRL-DWLKAFYDKVAEKLKEAF (SEQ ID NO:2) or LRKLRKRLLR-FAEKLKEAVKDYFAKLWD (SEQ ID NO:3).

As used herein a "dual-domain peptide", a "dual-domain synthetic peptide", or a "dual-domain Apo E mimicking peptide" is meant to mean a peptide comprising a lipid-associating peptide/domain and a receptor binding peptide/domain.

As used herein a "single-domain peptide", a "single-domain synthetic peptide", or a "single-domain Apo E mimicking peptide" is meant to mean a peptide comprising either a lipid-associating peptide/domain or a receptor binding peptide/domain, but not both.

As used herein "domain switched", "switched domain", or "switched" peptide is meant to mean that the lipid-associating peptide is covalently linked to the receptor binding domain of apolipoprotein E such that the lipid-associating peptide is at the N-terminus of the synthetic apolipoprotein E-mimicking peptide. For example, the peptide 18A-hE is exemplary of a domain switched peptide.

As used herein, "scrambled" "scrambled version", or "scrambled peptide" is meant to mean that the composition of the amino acid sequence is the same as the unscrambled peptide, however the sequence of the amino acids is altered thus rendering the peptide unable to form either an α-amphipathic helix or does not possess lipid associating (or HSPG associating) properties. However, in some cases, as described in this invention, the scrambled peptide remains able to form a different helical structure, such as a i-helix. For example, if one peptide has the amino acid sequence ABCDE, the scrambled version of the peptide could have the amino acid sequence DEABC. Scrambled peptides are often denoted as having a "Sc" prior to the portion of the peptide that is scrambled. For example, Sc-hE-18A denoted that the hE portion of the peptide is scrambled.

As used herein, "sample" is meant to mean an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, "subject" refers to the target of administration, e.g. an animal. Thus the subject of the disclosed methods can be a vertebrate, such as a mammal. For example, the subject can be a human. The term does not denote a particular age or sex. Subject can be used interchangeably with "individual" or "patient".

As used herein, "modulate" is meant to mean to alter, by increasing or decreasing.

As used herein "lipid binding domain E" and "lipid-associating peptide" are used interchangeably. As used herein, both terms can mean the lipid binding domain of Apolipoprotein E.

As used herein, "isolated polypeptide" or "purified polypeptide" is meant to mean a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length proteins and/or polypeptides.

As used herein, "18A" when used in the context of a peptide or peptide sequence refers to the peptide DWLKAFYDKVAEKLKEAF (SEQ ID NO:5). The peptide sequence can occur as an isolated peptide, or as a sequence within a larger peptide sequence.

As used herein, "hE" when used in the context of a peptide or peptide sequence refers to the peptide LRKLRKRLLR (SEQ ID NO:4). The peptide sequence can occur as an isolated peptide, or as a sequence within a larger peptide sequence.

As used herein, "[R]hE" when used in the context of a peptide or peptide sequence refers to the peptide LRRLRRRLLR (SEQ ID NO:11). The peptide sequence can occur as an isolated peptide, or as a sequence within a larger peptide sequence.

As used herein, the term "aliphatic" includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. In certain embodiments, as used herein, "lower alkyl" is used to indicate those alkyl groups (substituted, unsubstituted, branched or unbranched) having about 1-6 carbon atoms. "Substituted alkyl" refers to alkyl groups that are substituted with one or more functional groups. Substituents include, but are not limited to, any of the substituents mentioned below, i.e., the substituents recited below resulting in the formation of a stable compound.

As used herein, "alkenyl" denotes a monovalent group derived from a hydrocarbon moiety having at least one carbon-carbon double bond by the removal of a single hydrogen atom.

As defined herein, "$C_n$," where "n" is an integer, describes a hydrocarbon molecule or fragment (e.g., an alkyl group) wherein "n" denotes the number of carbon atoms in the fragment or molecule.

As used herein, "fatty acid moiety" refers to any molecular species and/or molecular fragment comprising the acyl component of a fatty (carboxylic) acid. That is, a fatty acid moiety is a group encompassing an acyl moiety derivable from a fatty acid, namely being generally of the form RC(═O)—, wherein R represents the aliphatic chain of the corresponding fatty acid.

As used herein the term "fatty acid" is meant to encompass a mono carboxylic acid having an aliphatic chain ("tail"), wherein said aliphatic chain may be either saturated, monounsaturated (having one unsaturated bond anywhere on the aliphatic chain) or poly unsaturated (having at least two unsaturated bonds anywhere on the aliphatic chain). An unsaturated bond on the aliphatic chain may be a double (in the cis and/or trans configuration) or a triple bond. The length of the aliphatic chain (being either saturated, monounsaturated or polyunsaturated) of a fatty acid may vary between 8 and 32 carbon atoms. Fatty acids may be derived from a natural source (either an animal or plant source), synthetic source or semi-synthetic source.

As used herein, the term "fatty acid" includes saturated fatty acids, which do not contain any double or triple bonds in the hydrocarbon chain. Saturated fatty acids include, but are not limited to propionic acid (C3) (by way of example, C3 indicates propionic acid has 3 carbon atoms in its hydrocarbon chain; the number of carbon atoms in the hydrocarbon chain of other example fatty acids is denoted in analogous fashion herein), butyric acid (C4), valeric acid (C5), caproic acid (C6), enanthic acid (C7), caprylic acid (C8), pelargonic acid (C9), capric acid (C10), undecylic acid (C11), lauric acid (C12), tridecylic acid (C13), myristic acid (C14), pentadecylic acid (C15), palmitic acid (C16), margaric acid (C17), stearic acid (C18), isostearic acid (C18), nonadecylic acid (C19), arachidic acid (C20), heneicosylic acid (C21), behenic acid (C22), tricosylic acid (C23), lignoceric acid (C24), pentacosylic acid (C25), cerotic acid (C26), heptacosylic acid (C27), montanic acid (C28), nonacocylic acid (C29), melissic acid (C30), henatriacontylic acid (C31), lacceroic acid (C32), psyllic acid (C33), geddic acid (C34), ceroplastic acid (C35) and hexatriacontylic acid (C36).

As used herein, the term "fatty acid" also includes monounsaturated fatty acids, which contain one double or triple bond in the hydrocarbon chain, and polyunsaturated fatty acids, which contain more than one double and/or triple bond in the hydrocarbon chain. Such acids include, but are not limited to the omega 3, omega 6, omega 9 fatty acids, other fatty acids such as myristoleic and palmitoleic acid and conjugated fatty acids. Examples of monounsaturated and polyunsaturated fatty acids include but are not limited to, (a) omega 3 fatty acids, such as hexadecatrienoic acid (C16:3); (by way of example, C16:3 indicates hexadecatrienoic acid has 16 carbon atoms in its hydrocarbon chain and 3 double bonds; the number of carbon atoms and double bonds in the hydrocarbon chain of other example unsaturated fatty acids is denoted in analogous fashion herein), alpha linolenic acid (C18:3) and eicosapentanoic acid (20:5), (b) omega 6 fatty acids, such as linoleic acid (18:2), docosadienoic acid (C22:2), arachidonic acid (C20:4) and tetracosatetraenoic acid (C24:5), (c) omega 9 fatty acids, such as oleic acid (C18:1), eicosenoic acid (C20:1) and nevronic acid (C24:1), and (d) conjugated fatty acids such as rumenic acid (C18:2), eleostatic acid (C18:3), and rumelenic acid (C18:3).

As used herein, the term "fatty acid" also includes branched fatty acids. Examples of branched fatty acids include, but are not limited to, monomethyl branched fatty acids, such as 14-methyl pentadecanoic acid, 6-methyl caprylic acid, 4-methyl-3-pentenoic acid, (pyroterebic acid), 2-methyl-2E-butenoic acid (tiglic acid), 2-methyl-2Z-butenoic acid (angelic acid), multimethyl branched acids, isoprenoid fatty acids (vittatalactone, all-trans-retinoic acid), branched methoxy fatty acids and hydroxy and other fatty acids such as 2-hydroxyoctanoic acid and 4-oxopentanoic acid (levulinic acid).

The term "fatty acid" also includes mixtures comprising fatty acids such as natural oils or fats which may comprise components that are not fatty acids. Natural oils or fats understood to comprise mixtures of fatty acids include, but are not limited to, animal fats, soya bean oil, coconut oil, palm oil, palm kernel oil, rapeseed oil, cottonseed oil, linseed oil, sunflower oil, fish oil, algae oil, and the like.

The term "ω-amino-fatty acid" refers to fatty acids which feature an amino group at the distal carbon of the hydrocarbon chain thereof. The ω-amino-fatty acid moieties that are used in the context of the present invention can be saturated or unsaturated hydrocarbon chains. These moieties have a carboxylic group at one end of the hydrocarbon chain and an amine group at the other. The hydrocarbon chain connecting the carboxylic and amine groups in such an ω-amino-fatty acid moiety typically has from 3 to 32 carbon atoms.

Exemplary ω-amino-fatty acids include, without limitation, 4-amino-butyric acid, 6-amino-caproic acid, 8-amino-caprylic acid, 10-amino-capric acid (10-amino-decanoic acid), 12-amino-lauric acid (12-amino-dodecanoic acid), 14-amino-myristic acid (14-amino-tetradecanoic acid), 14-amino-myristoleic acid, 16-amino-palmitic acid (16-amino-hexadecanoic acid), 18-amino-stearic acid, 18-amino-oleic acid, 16-amino-palmitoleic acid, 18-amino-linoleic acid, 18-amino-linolenic acid and 20-amino-arachidonic acid.

"Dosing regimen" as used herein refers to at least one treatment cycle followed by at least one rest phase. A dosing regimen can include more than one treatment cycle and more than one rest phase. For example, a dosing regimen can be a three month treatment cycle followed by a one year rest phase. Another example can be a six month treatment cycle followed by a six month rest phase and then a three month treatment cycle followed by a one year rest phase.

"Dose" or "dosage" as used herein refers to a specific quantity of a therapeutic agent, such as an Apo E mimetic, that is taken at specific times.

As used herein, "treat" is meant to mean administer one of the disclosed compositions to a subject, such as a human or other mammal (for example, an animal model), that has atherosclerosis, in order to prevent or delay a worsening of the effects of the disease or condition, or to partially or fully reverse the effects of the disease.

As used herein, "prevent" is meant to mean minimize the chance that a subject who has an increased susceptibility for developing atherosclerosis will develop atherosclerosis.

As used herein, the term "treatment cycle" refers to the administration of Apo E mimetics for an established period of time. A treatment cycle includes a wide range of dosages of Apo E mimetics as well as different lengths of time for administering the Apo E mimetics. For example, a treatment cycle can be a three month period wherein an Apo E mimetic is administered twice a week for the three month period.

As used herein, "effective amount" is meant to mean a sufficient amount of the composition or Apo E mimetic to provide the desired effect. For example, an effective amount of an Apo E mimetic can be an amount that provides a therapeutic affect and provides sustained therapeutic effects after withdrawal of the treatment. An effective amount of an Apo E mimetic is an amount that is able to cause a benefit illustrated by a decrease in atherosclerosis, a decrease in artery wall stiffness, a decrease in isolated systolic hypertension, a decrease in arterial inflammation, an increase in anti-oxidant capability of the HDL fraction and/or an improvement in myocardial function, as well as an amount that allows for a sustained therapeutic effect after withdrawal of the Apo E mimetic. The exact amount required will vary from subject to subject, depending on the species, age, and general condition of the subject, the severity of disease (or underlying genetic defect) that is being treated, the particular compound used, its mode of administration, and the like. Thus, it is not possible to specify an exact "effective amount." However, an appropriate "effective amount" may be determined by one of ordinary skill in the art using only routine experimentation.

As used herein, "sustained therapeutic effect" is a therapeutic effect that persists after the therapeutic has been withdrawn. For example, the sustained therapeutic effect is maintained even after the acute cholesterol lowering effect is gone.

"Rest phase" as used herein refers to a period of time wherein an Apo E mimetic is not administered.

"Atherosclerotic burden" as used herein is the amount of atherosclerosis in the arteries of a patient. This may include the coronary, carotid, peripheral and other arteries. The atheroma may be complex lesions with a smooth muscle and collagen containing fibrous cap, areas of calcification, cholesterol crystals and cholesterol laden macrophages (foam cells) and/or less complex and more unstable lesions with less calcification and a thinner fibrous cap, and more foam cells and cholesterol (unstable lesions). The unstable lesions may intrude into the lumen of the artery or expand away from the lumen of the artery.

The phrase "lipid disorder" is meant to mean when a subject has an excess of lipids or increased inflammatory lipids in their blood. Lipids include, but are not limited to lipids such as ox-LDL (i.e., oxidized PAPC (1-palmitoyl 2-arachidonyl phophyatidyl choline)). Oxidation of PAPC or PLPC, the lipid components of LDL, produce oxidized lipids. Having a lipid disorder can make one more likely to develop inflammatory disease such as atherosclerosis and heart disease. Lipid disorders can be caused by genetic predispositions or diet.

As used herein, "lipoprotein" or "lipoproteins" is meant to mean a biochemical assembly that contains both proteins and lipids. The lipids or their derivatives may be covalently or non-covalently bound to the proteins. Many enzymes, transporters, structural proteins, antigens, adhesins, and toxins are lipoproteins. Examples include the high density and low density lipoproteins of the blood, the transmembrane proteins of the mitochondrion and the chloroplast, and bacterial lipoproteins As used herein, "high-density lipoprotein" (HDL) is meant to mean a class of lipoproteins, varying somewhat in their size (8-11 nm in diameter), that can transport cholesterol. HDL cholesterol is cholesterol that is associated with HDLs. About one-fourth to one-third of blood cholesterol is carried by high-density lipoprotein (HDL). HDL cholesterol is known as "good" cholesterol, because high levels of HDL seem to protect against heart attack. Low levels of HDL (less than 40 mg/dL in men and less than 50 mg/dL in women) also increase the risk of heart disease. Medical experts think that HDL tends to carry cholesterol away from the arteries and back to the liver, where it is passed from the body. Some experts believe that that HDL removes excess cholesterol from arterial plaque, thus slowing its buildup As used herein, "very Low Density Lipoproteins" (VLDL) is meant to mean a lipoprotein subclass. It is assembled in the liver from cholesterol and apolipoproteins. It is converted in the bloodstream to low density lipoprotein (LDL). VLDL particles have a diameter of 30-80 nm. VLDL transports endogenous products where chylomicrons transport exogenous (dietary) products.

As used herein, "low-density lipoprotein" or "LDL" is meant to mean a lipoprotein that varies in size (approx. 22 nm) and can contain a changing number of triglycerides and cholesteryl esters they actually have a mass and size distribution. Each native LDL particle contains a single apolipoproteinB-100 molecule (Apo B-100, a protein with 4536 amino acid amino acid residues) and a phospholipid coat that circles the triglycerides and cholesteryl esters, keeping them soluble in the aqueous environment. LDL is commonly referred to as bad cholesterol. LDL cholesterol is cholesterol that is associated with LDLs. When too much LDL cholesterol circulates in the blood, it can slowly build up in the inner walls of the arteries that feed the heart and brain. Together with other substances, it can form plaque, a thick, hard deposit that can narrow the arteries and make them less flexible. This condition is known as atherosclerosis. If a clot forms and blocks a narrowed artery, then heart attack or stroke can result.

Cholesterol cannot dissolve in the blood. It has to be transported to and from the cells by carriers called lipoproteins. LDLs and HDLs along with triglyceride-rich lipoproteins (VLDL) and Lp(a) cholesterol, make up your total cholesterol count, which can be determined through a blood test.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

B. Apo E-mimicking Peptides

Disclosed are apolipoprotein E-mimicking peptides or Apo E mimetics. Non-limiting examples of the Apo E-mimicking peptides are provided herein. The Apo E-mimicking peptides can be single domain or dual domain peptides. Compositions containing the Apo E-mimicking peptides are also disclosed.

Disclosed are synthetic ApoE-mimicking peptides comprising a receptor binding domain of ApoE and a lipid-associating peptide, wherein the synthetic ApoE-mimicking peptide comprises an acetylated amino hexanoic acid (Ac-Aha).

Disclosed are synthetic ApoE-mimicking peptides comprising a receptor binding domain of ApoE and a lipid-associating peptide, wherein the synthetic ApoE-mimicking peptide comprises an Ac-Aha, wherein the Ac-Aha is at the N-terminus of the peptide. In some aspects the Aha can be inserted between the lipid-associating peptide comprises a class A amphipathic-helical domain.

Disclosed are synthetic ApoE-mimicking peptides comprising a receptor binding domain of ApoE and a lipid-associating peptide, wherein the synthetic ApoE-mimicking peptide comprises an Ac-Aha, wherein the lipid-associating peptide comprises a class A amphipathic-helical domain. For example, the class A amphipathic-helical domain is DWLKAFYDKVAEKLKEAF (SEQ ID NO:5), DWLRAFYDKVAEKLREAF (SEQ ID NO:618), DWLRALYDKVAEKLREAL (SEQ ID NO:619), DLLRALYDKVAEKLREAW (SEQ ID NO:620), or FAEKLKEAVKDYFAKLWD (SEQ ID NO:616).

Disclosed are synthetic ApoE-mimicking peptides comprising a receptor binding domain of ApoE and a lipid-associating peptide, wherein the synthetic ApoE-mimicking peptide comprises an Ac-Aha, wherein the lipid-associating peptide comprises a class A amphipathic-helical domain, wherein the receptor binding domain of ApoE can be covalently linked to the lipid-associating peptide.

Disclosed are synthetic ApoE-mimicking peptides comprising a receptor binding domain of ApoE and a lipid-associating peptide, wherein the synthetic ApoE-mimicking peptide comprises an Ac-Aha, wherein said apolipoprotein E can be from a species selected from the group consisting of human, mouse, rabbit, monkey, rat, bovine, pig and dog.

Disclosed are synthetic ApoE-mimicking peptides comprising a receptor binding domain of ApoE and a lipid-associating peptide, wherein the synthetic ApoE-mimicking peptide comprises an Ac-Aha, wherein said synthetic peptide is protected using an amide group at the C-terminus.

Disclosed are synthetic ApoE-mimicking peptides comprising a receptor binding domain of ApoE and a lipid-associating peptide, wherein the synthetic ApoE-mimicking peptide comprises an Ac-Aha, wherein the receptor binding domain of ApoE can be LRKLRKRLLR (SEQ ID NO:4), LRRLRRRLLR (SEQ ID NO:11), LRKMRKRLMR (SEQ ID NO:7), or RLTRKRGLK (SEQ ID NO:13). The receptor binding domain of ApoE can also be, but is not limited to, LRKLRKRFFR (SEQ ID NO:4), LRKLPKRLLR (SEQ ID NO:8), LRNVRKRLVR (SEQ ID NO:9), MRKLRKRVLR (SEQ ID NO:10), LRRLRRRLLR (SEQ ID NO:11), LRKLRKRFFR (SEQ ID NO:12), LRKLRKRLLR (SEQ ID NO:4), or LRKMRKRLMR (SEQ ID NO:7).

Disclosed are synthetic ApoE-mimicking peptides comprising a receptor binding domain of ApoE and a lipid-associating peptide, wherein the synthetic ApoE-mimicking peptide comprises an Ac-Aha, wherein the receptor binding domain of ApoE can be LRKLRKRLLR (SEQ ID NO:4), LRRLRRRLLR (SEQ ID NO:11), LRKMRKRLMR (SEQ ID NO:7), RLTRKRGLK (SEQ ID NO:13), LRRMRRRLMR (SEQ ID NO:621), or RLTRRRGK (SEQ ID NO:622).

Disclosed are synthetic ApoE-mimicking peptides comprising a receptor binding domain of ApoE and a lipid-associating peptide, wherein the synthetic ApoE-mimicking peptide comprises an Ac-Aha, wherein the synthetic ApoE-mimicking peptide can be Ac-Aha-hE18A-$NH_2$ or Ac-Aha-[R]hE18A-$NH_2$. The ApoE-mimicking peptide of Ac-Aha-hE18A-$NH_2$ is Ac-Aha-LRKLRKRLLR-DWLKAFYDKVAEKLKEAF-$NH_2$ (SEQ ID NO:1). The ApoE-mimicking peptide of Ac-Aha-[R]hE18A-$NH_2$ is Ac-Aha-LRRLRRRLLR-DWLKAFYDKVAEKLKEAF-$NH_2$. (SEQ ID NO:662)

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety.

Disclosed are synthetic ApoE-mimicking peptides comprising a receptor binding domain of ApoE and a lipid-associating peptide, wherein the synthetic ApoE-mimicking peptide comprises an acetylated ω-amino fatty acid moiety, wherein the acetylated ω-amino fatty acid moiety is at the N-terminus of the peptide. In some aspects the ω-amino fatty acid moiety can be inserted between the lipid-associating peptide comprises a class A amphipathic-helical domain.

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein the lipid-associating peptide comprises a class A amphipathic-helical domain. For example, the class A amphipathic-helical domain is DWLKAFYDKVAEKLKEAF (SEQ ID NO:5), DWLRAFYDKVAEKLREAF (SEQ ID NO:618), DWLRALYDKVAEKLREAL (SEQ ID NO:619), DLLRALYDKVAEKLREAW (SEQ ID NO:620), or FAEKLKEAVKDYFAKLWD (SEQ ID NO:616).

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein the lipid-associating peptide comprises a class A amphipathic-helical domain, wherein the receptor binding domain of ApoE can be covalently linked to the lipid-associating peptide.

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein said apolipoprotein E can be from a species selected from the group consisting of human, mouse, rabbit, monkey, rat, bovine, pig and dog.

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein said synthetic peptide is protected using an amide group at the C-terminus.

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein the receptor binding domain of ApoE can be LRKLRKRLLR (SEQ ID NO:4), LRRLRRRLLR (SEQ ID NO:11), LRKMRKRLMR (SEQ ID NO:7), or RLTRKRGLK (SEQ ID NO:13). The receptor binding domain of ApoE can also be, but is not limited to, LRKLRKRFFR (SEQ ID NO:4), LRKLPKRLLR (SEQ ID NO:8), LRNVRKRLVR (SEQ ID NO:9), MRKLRKRVLR (SEQ ID NO:10), LRRLRRRLLR (SEQ ID NO:11), LRKLRKRFFR (SEQ ID NO:12), LRKLRKRLLR (SEQ ID NO:4), or LRKMRKRLMR(SEQ ID NO:7).

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein the receptor binding domain of ApoE can be LRKLRKRLLR (SEQ ID NO:4), LRRLRRRLLR (SEQ ID NO:11), LRKMRKRLMR (SEQ ID NO:7), RLTRKRGLK (SEQ ID NO:13), LRRMRRRLMR (SEQ ID NO:621), or RLTRRRGK (SEQ ID NO:622).

Disclosed are synthetic ApoE-mimicking peptides comprising a receptor binding domain of ApoE and a lipid-associating peptide, wherein the synthetic ApoE-mimicking peptide comprises a fatty acid moiety, ω-amino fatty acid moiety, or an acetylated ω-amino fatty acid moiety, wherein the synthetic ApoE-mimicking peptide can be: butanoyl-LRRLRRRLLR-DWLKAFYDKVAEKLKEAF-$NH_2$ (SEQ ID NO: 623); hexanoyl-LRRLRRRLLR-DWLKAFYDKVAEKLKEAF-$NH_2$ (SEQ ID NO: 624); octanoyl-LRRLRRRLLR-DWLKAFYDKVAEKLKEAF-$NH_2$ (SEQ ID NO: 625); decanoyl-LRRLRRRLLR-DWLKAFYDKVAEKLKEAF-$NH_2$ (SEQ ID NO: 626); lauroyl-LRRLRRRLLR-DWLKAFYDKVAEKLKEAF-$NH_2$ (SEQ ID NO: 627); myristoyl-LRRLRRRLLR-DWLKAFYDKVAEKLKEAF-$NH_2$ (SEQ ID NO: 628); palmitoyl-LRRLRRRLLR-DWLKAFYDKVAEKLKEAF-$NH_2$ (SEQ ID NO: 629); stearoyl-LRRLRRRLLR-DWLKAFYDKVAEKLKEAF-$NH_2$ (SEQ ID NO: 630); palmitoleoyl-LRRLRRRLLR-DWLKAFYDKVAEKLKEAF-$NH_2$ (SEQ ID NO: 631); arachidoyl-LRRLRRRLLR-DWLKAFYDKVAEKLKEAF-$NH_2$ (SEQ ID NO: 632); behenoyl-LRRLRRRLLR-DWLKAFYDKVAEKLKEAF-$NH_2$ (SEQ ID NO: 633); oleoyl-LRRLRRRLLR-DWLKAFYDKVAEKLKEAF-$NH_2$ (SEQ ID NO: 634); ricinoleoyl-LRRLRRRLLR-DWLKAFYDKVAEKLKEAF-$NH_2$ (SEQ ID NO: 635); linolenoyl-LRRLRRRLLR-DWLKAFYDKVAEKLKEAF-$NH_2$ (SEQ ID NO: 636); vacceoyl-LRRLRRRLLR-DWLKAFYDKVAEKLKEAF-$NH_2$ (SEQ ID NO: 637); gadoleoyl-LRRLRRRLLR-DWLKAFYDKVAEKLKEAF-$NH_2$ (SEQ ID NO: 638); erucoyl-LRRLRRRLLR-DWLKAFYDKVAEKLKEAF-$NH_2$ (SEQ ID NO: 6239); cetoleoyl-LRRLRRRLLR-DWLKAFYDKVAEKLKEAF-$NH_2$ (SEQ ID NO: 640); nervonoyl-LRRLRRRLLR-DWLKAFYDKVAEKLKEAF-$NH_2$ (SEQ ID NO: 641); adrenoyl-LRRLRRRLLR-DWLKAFYDKVAEKLKEAF-$NH_2$ (SEQ ID NO: 642); α-linolenoyl-LRRLRRRLLR-DWLKAFYDKVAEKLKEAF-$NH_2$ (SEQ ID NO: 643); γ-linolenoyl-LRRLRRRLLR-DWLKAFYDKVAEKLKEAF-$NH_2$ (SEQ ID NO: 644); EPA-LRRLRRRLLR-DWLKAFYDKVAEKLKEAF-$NH_2$ (SEQ ID NO: 645); or DHA-LRRLRRRLLR-DWLKAFYDKVAEKLKEAF-$NH_2$ (SEQ ID NO: 646). In the foregoing, the fatty acid moiety is shown at the left side and is linked to the peptide LRRLRRRLLR (SEQ ID NO:11). "EPA" indicates a moiety derived from 5,8,11,14,17-eicosapentaenoic acid; and "DHA" indicates a moiety derived from 4,7,10,13,16,19-docosahexaenoic acid.

Disclosed are synthetic ApoE-mimicking peptides comprising a receptor binding domain of ApoE and a lipid-associating peptide, wherein the synthetic ApoE-mimicking peptide comprises a fatty acid moiety derived from a natural oil or fat, e.g. fish oil, wherein the synthetic ApoE-mimicking peptide can be: (fish oil)-LRRLRRRLLR-DWLKAFYDKVAEKLKEAF-$NH_2$ (SEQ ID NO:663). In the foregoing "(fish oil)" indicates that the fatty acids in fish oil, including, but not limited to, fish oil components such as EPA and DHA, are linked to linked to the peptide LRRLRRRLLR (SEQ ID NO:11). Thus, the synthetic ApoE-mimicking peptide is a mixture of peptides comprising fatty acid groups derived from the fish oil used to prepare them.

In some instances, the synthetic ApoE-mimicking peptide can be any of the disclosed peptides comprising a fatty acid.

In some instances, the synthetic ApoE-mimicking peptide can be any of the disclosed peptides comprising an acetylated fatty acid.

Also disclosed are synthetic ApoE-mimicking peptides comprising a receptor binding domain of ApoE and a lipid-associating peptide, wherein the synthetic ApoE-mimicking peptide comprises an Ac-Aha, wherein the receptor binding domain of apolipoprotein E is scrambled. Examples of scrambled receptor binding domains of ApoE are provided below.

Also disclosed are synthetic apolipoprotein E-mimicking peptide, consisting of: a receptor binding domain of apolipoprotein E and a lipid-associating peptide, wherein receptor binding domain is covalently linked to said lipid-associating peptide, wherein both the receptor binding domain of apolipoprotein E and the lipid-associating peptide are scrambled. Examples of scrambled receptor binding domains of ApoE and scrambled lipid-associating peptides are provided below.

Apolipoprotein E-mimicking peptides have both direct cholesterol lowering effects by providing an alternative ligand for receptors on the liver to clear atherogenic Apolipoprotein B containing lipoproteins (LDL, VLDL, and β-VLDL), and direct beneficial effects on the artery wall. New, more effective methods of imaging coronary atherosclerosis allow for direct measurement of benefits to the artery wall (Van Velzen, et al. Hellenic J Cardiol 50: 245-263, 2009). The Apo E-mimicking peptides can enhance the removal of cholesterol from the artery wall, working in conjunction with HDL, increasing the formation of lipid poor preβ-HDL that accept cholesterol from macrophages. The Apo E-mimicking peptides can stimulate macrophage-mediated clearance of dead and dying cells in the artery wall (efferocytosis), improve the quality of HDL by increasing PON-1 levels and bringing down plasma lipid hydroperoxide levels, decrease macrophage content in atherosclerotic lesions resulting in more stable lesions, and decrease inflammation in the artery wall. As a result, the Apo E-mimicking peptides reduce the size of atherosclerotic lesions more rapidly than apoA-I mimetic peptides and more rapidly than the statins (HMG-CoA reductase inhibitors). Atherosclerotic lesion regression persists in Apo E-mimicking peptides treated animals even when cholesterol levels are the same as in saline treated animals. Thus, the effects cannot be simply explained by cholesterol lowering.

1. Apolipoprotein E

Apolipoprotein E (Apo E) plays an important role in the metabolism of triglyceride-rich lipoproteins, such as very low density lipoprotein (VLDL) and chylomicrons. Apolipoprotein E mediates the high affinity binding of Apo E-containing lipoproteins to the low density lipoprotein (LDL) receptor (Apo B, E receptor) and the members of its gene family, including LDL receptor related protein (LRP), very low density lipoprotein receptor (VLDLR) and the Apo E2 receptor (Apo E2R) (Mahley, R. W., (1988) Science 240, 622-630). The putative and complex role of Apo E in atherosclerosis has been emphasized by several observations: (i) mice that over express human Apo E have lower levels of total plasma cholesterol levels (Shimono, H. N., et al., (1992) Eur. J. Clin. Invest. 90, 2084-2991), (ii) intravenous injection of human Apo E into cholesterol-fed rabbits protects these animals from atherosclerosis (Yamada, et al., (1989) Proc. Natl. Acad. Sci. U.S.A. 86, 665-669), and (iii) loss of the Apo E gene in mice produces spontaneous atherosclerosis (Zhang, S. H., et al., (1992) Science 258, 468-471) which is ameliorated when macrophage-specific apo E expression is initiated in Apo E-deficient mice (Spangenberg, J., et al., (1997) Biochem. Biophys. Acta 1349, 109-121).

Apo E is a protein that binds lipid and has two major domains (Mahley, R. W., et al. J. Lipid Res. 1999, 40:622-630). The 22 kDa amino terminal domain has been shown by X-ray crystallographic studies to be a 4-helix bundle (Wilson, C., et al. Science 1991; 252:1817-1822) and to contain a positively-charged receptor binding domain. For this region to mediate very low-density lipoprotein (VLDL) binding to its receptors, the apolipoprotein must associate with the lipoprotein surface; this is enabled by the C-terminal amphipathic helical region. If the 4-helix bundle that contains the positively charged receptor-binding domain does not open up on the lipoprotein surface, then the VLDL is defective in binding to receptors. Thus, the positively charged arginine (Arg)-rich cluster domain of the Apo E and the C-terminal amphipathic helical domain, are both required for the enhanced uptake of atherogenic Apo E-containing lipoproteins.

Apo E is secreted as a 299 amino acid residue protein with a molecular weight of 34,200. Based on thrombin cleavage of Apo E into two fragments, a two-domain hypothesis was initially suggested to explain the fact that the C-terminal region of Apo E (192-299) is essential for its binding to hypertriglyceridemic VLDL and the N-terminal 22 kDa domain (1-191), binds to the LDL-R (Bradley, W. A., et al., (1986) J. Lipid Res. 27, 40-48). Additional physical-chemical characterization of the protein and its mutants have extended this concept and have shown that the region 192-211 binds to phospholipid while the amino terminal domain (1-191) is a globular structure that contains the LDL receptor binding domain in the 4-helix bundle (Wilson, C., et al., (1991) Science 252, 1817-1822). Studies with synthetic peptides (Sparrow et al. Biochemistry 31(4):1065-8, 1992) and monoclonal antibodies pinpointed the LDL receptor binding domain of apo E between residues 129-169, a domain enriched in positively charged amino acids, Arg and Lys (Rall, S. C., Jr., et al., (1982) PNAS USA 79, 4696-4700; Lalazar, A., et al., (1988) J. Biol. Chem. 263, 3542-2545; Dyer, C. A., et al., (1991) J. Biol. Chem. 296, 22803-22806; and Dyer, C. A., et al., (1991) J. Biol. Chem. 266, 15009-15015).

To test the hypothesis that a minimal arginine-rich Apo E receptor binding domain (141-150) was sufficient to enhance low density lipoprotein (LDL) and very low density lipoprotein (VLDL) uptake and clearance when covalently linked to a class A amphipathic helix, a peptide was synthesized in which the receptor binding domain of human Apo E, LRKLRKRLLR (SEQ ID NO:4) (hApo E[141-150] also referred to as "hE"), was linked to 18A, a well characterized high affinity lipid-associating peptide (DWLKAFYDKVAEKLKEAF (SEQ ID NO:5), also referred to as "18A") to produce a peptide denoted as hApo E[141-150]-18A (also referred to as "hE-18A") (see U.S. Pat. No. 6,506,880, which is hereby incorporated by reference in its entirety for its teaching of specific Apo E mimetics and their uses). Also synthesized was an end protected analog of hE-18A, denoted Ac-hE18A-NH2. The importance of the lysine residues and the role of the hydrophobic residues in the receptor binding domain were also studied using two analogs, LRRLRRRLLR (SEQ ID NO:11)-18A (also referred to as "hE(R)-18A") and LRKMRKRLMR (SEQ ID NO:7)-18A (also referred to as "mE18A"), whereby the receptor binding domain of human Apo E was modified to substitute arginine (R) residues for lysine (K) residues at positions 143 and 146 (LRRLRRRLLR; SEQ ID NO:11) and whereby the receptor binding domain of mouse Apo E (LRKMRKRLMR; SEQ ID NO:7), were linked to 18A, respectively. The effect of the dual character peptides on the uptake and degradation of human LDL/VLDL by cells was then determined.

It was determined that in MEF 1 cells with induced LDL receptors, LDL internalization was enhanced three, five and seven times by Ac-mE-18A-$NH_2$, Ac-hE-18A-$NH_2$, and Ac-hE(R)-18A-$NH_2$ respectively. All three peptides increased degradation of LDL by 100 percent. Both Ac-hE-18A-$NH_2$ and the control peptide Ac-18A-$NH_2$ interacted with VLDL to cause a displacement of apo E from VLDL. However, only Ac-hE-18A-$NH_2$-associated VLDL enhanced the uptake of VLDL six fold and degradation three fold compared to VLDL alone in spite of the absence of apoE. The LDL binding to fibroblasts in the presence of these peptides was not saturable, however, over the LDL concentration range studied.

Furthermore, a similar enhancement of LDL internalization independent of the presence of the LDL receptor related protein (LRP) or LDL receptor or both was seen. Pretreatment of cells with heparinase and heparitinase however abolished greater than 80% of enhanced peptide-mediated LDL uptake and degradation by cells. The data indicated that the dual-domain peptides enhanced LDL uptake and degradation by binding to the LDL through the amphipathic lipid binding domain (18A). However, the minimal 141-150 Arg-rich domain did not decrease LDL levels but did so only in combination with 18A lipid associating domain, did not confer LDL-receptor binding but directed the LDL-peptide complex to the HSPG pathway for uptake and degradation by fibroblasts.

2. Fatty Acids

The disclosed peptides can be linked to a fatty acid moiety, an ω-amino fatty acid moiety, or an acetylated ω-amino fatty acid moiety. In various aspects, the fatty acid moiety, the ω-amino fatty acid moiety, or the acetylated ω-amino fatty acid moiety is linked to a disclosed peptide via the N-terminal amino group of the peptide.

In various aspects, the linkage between the fatty acid moiety, the ω-amino fatty acid moiety, or the acetylated ω-amino fatty acid moiety and the N-terminal amino group of the peptide has the a structure represented by the following formulas, respectively:

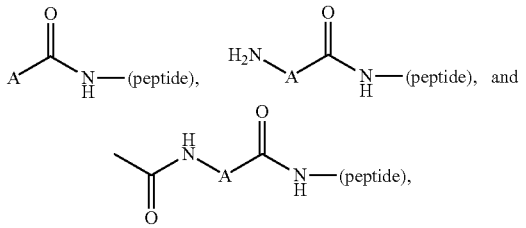

wherein A is an aliphatic group have 2-32 carbon atoms. In a further aspect, the aliphatic group is an alkyl group. In a still further aspect, the aliphatic group comprises 0-3 double bonds. In a yet further aspect, the aliphatic group is an alkenyl group.

In a further aspect, the fatty acid moiety linked to the disclosed peptide is derived from a purified fatty acid. In a still further aspect, the fatty acid moiety linked to the disclosed peptide is derived from a saturated fatty acid. In a yet further aspect, the fatty acid moiety linked to the disclosed peptide is derived from an unsaturated fatty acid. In an even further aspect, the unsaturated fatty acid is a polyunsaturated fatty acid with two or more double bonds.

In various aspects, the synthetic ApoE-mimicking peptide comprises a fatty acid moiety.

Exemplary fatty acids from which a fatty acid moiety is derived include, without limitation, butyric acid, caproic acid, caprylic acid, capric acid, decanoic acid, lauric acid, myristic acid, palmitic acid, pentadecanoic acid, stearic acid, arachidic acid, behenic acid, erucic acid, lignoceric acid, margaric acid, myristoleic acid, palmitoleic acid, oleic acid, gadoleic acid, ricinoleic acid, vaccenic acid, linoleic acid, linolenic acid, alpha-linolenic acid, gamma-linolenic acid, licanic acid, margaroleic acid, arachidic acid, gadoleic acid, nervonic acid, arachidonic acid, docosapentaenoic (DPA), eicosapentaenoic acid (EPA), docosahexaenoic acid (DHA), and the like.

Exemplary saturated fatty acids include, but are not limited to, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, henatriacontanoic acid, dotriacontanoic acid, tritriacontanoic acid, tetratriacontanoic acid, pentatriacontanoic acid, and hexatriacontanoic acid.

Exemplary unsaturated fatty acids include, but are not limited to, myristoleic acid, palmitoleic acid, sapienic acid, oleic acid, linoleic acid, α-linolenic acid, arachidonic acid, eicosapentaenoic acid (EPA), erucic acid, docosahexaenoic acid (DHA), and docosapentaenoic acid.

In various aspects, the fatty acid moiety linked to the disclosed peptide is derived from an unpurified fatty acid or mixture of fatty acids such as natural oil or fat. Typically, a natural oil or fat is a heterogeneous mixture of generally hydrophobic compounds comprising one or more fatty acids. The fatty acid source may comprise a natural oil or fat, such as (but not limited to) animal fats, biological oils, or vegetable oils such as soya bean oil, coconut oil, palm oil, palm kernel oil, rapeseed oil, cottonseed oil, linseed oil, sunflower oil, fish oil, algae oil, and the like.

In a further aspect, the natural oil or fat is one that contains or is enriched for one or more omega-3 fatty acids, for example, marine oil, for example, fish oil, krill oil and algae oil. Any oil containing DHA and/or EPA can be used. In a further aspect, the natural oil or fat contains at least 70% or about 70%, by weight, DHA, for example, at least 75% or about 75%, at least 80% or about 80%, at least 85% or about 85%, or at least 90% or about 90%, by weight, DHA. In a still further aspect, the natural oil or fat contains between 5% or about 5% and 15% or about 15% EPA, for example, 5, 6, 7, 8, 9, 10, 11, 12, 13, 14 or 15%, by weight, EPA. In a yet further aspect, the natural oil or fat contains not more than 10% or about 10% EPA or less than 10% or about 10%, EPA.

In a further aspect, the fatty acid moiety is derived from an omega-3 fatty acid. As used herein, the term "omega-3 polyunsaturated fatty acid(s)" or "omega-3 fatty acid" refers to a family of unsaturated fatty carboxylic acids that have in common a carbon-carbon bond in the n-3 position (i.e., the third bond from the methyl end of the molecule). Typically, they contain from about 16 to about 24 carbon atoms and from three to six carbon-carbon double bonds. Omega-3 polyunsaturated fatty acids can be found in nature, and these natural omega-3 polyunsaturated fatty acids frequently have all of their carbon-carbon double bonds in the cis-configuration.

Exemplary omega-3 fatty acids include, but are not limited to, 7,10,13-hexadecatrienoic acid (sometimes abbreviated as 16:3 (n-3)); 9,12,15-octadecatetrienoic acid (α-linolenic acid (ALA), 18:3 (n-3)); 6,9,12,15-octadecatetraenoic acid (stearidonic acid (STD), 18:4 (n-3)); 11,14,17-eicosatrienoic acid (eicosatrienoic acid (ETE), 20:3 (n-3)); 8,11,14,17-eicosatetraenoic acid (eicosatetraenoic acid (ETA), 20:4 (n-3)); 5,8,11,14,17-eicosapentaenoic acid (eicosapentaenoic acid (EPA), (20:5 (n-3)); 7,10,13,16,19-docosapentaenoic acid (docosapentaenoic acid (DPA), 22:5 (n-3)); 4,7,10,13,16,19-docosahexaenoic acid (docosahexaenoic acid (DHA), 22:6 (n-3)); 9,12,15,18,21-tetracosapentaenoic acid (tetracosapentaenoic acid, 24:5 (n-3)); and 6,9,12,15,18,21-tetracosahexaenoic acid (tetracosahexaenoic acid, 24:6 (n-3)). Eicosapentaenoic acid (EPA) and docosahexaenoic acid (DHA) are found in nature in fish oils, and have been used in a variety of dietary/therapeutic compositions.

Various lengths of fatty acids are contemplated. In one aspect, a fatty acid comprises a chain length between C6 and C24, C10 and C24, C10 and C28, or C10 and C32, including synthetic fatty acids with odd carbon numbers. In a further aspect, a fatty acid comprises a chain length selected from the group consisting of: C10, C12, C14, C16, C18, C20, C20, C22 and C24. In a still further aspect, the fatty acid has a chain length selected from the group consisting of C14, C16 and C18. In a yet further aspect, the fatty acid has a chain length selected from the group consisting of C13, C15 and C17. In a still further aspect, the fatty acid has between 4 and 28 carbons.

In various aspects of the present invention, the fatty acid aliphatic chain comprises 4, 6, 8, 10, 12, 14, 16, 18, 20, 22, 24, 26, 28, 30, or 32 carbon atoms.

In various aspects, the fatty acid is a naturally-occurring fatty acid. In a further aspect, the fatty acid is a short chain fatty acid (e.g., less than six carbons), a medium chain fatty acid (e.g., 6-12 carbons), long chain fatty acids (e.g., longer than 12 carbons), or a very long chain fatty acid (e.g., longer than 22 carbons). In a still further aspect, the fatty acid is an unsaturated fatty acid in the cis configuration. In still another embodiment, the fatty acid is an unsaturated fatty acid in the trans configuration.

In various aspects, the synthetic ApoE-mimicking peptide comprises a ω-amino fatty acid moiety.

Exemplary ω-amino-fatty acid moieties are derived from ω-amino-fatty acids including, without limitation, 4-amino-butyric acid, 6-amino-caproic acid, 8-amino-caprylic acid, 10-amino-capric acid (10-amino-decanoic acid), 12-amino-lauric acid (12-amino-dodecanoic acid), 14-amino-myristic acid (14-amino-tetradecanoic acid), 14-amino-myristoleic acid, 16-amino-palmitic acid (16-amino-hexadecanoic acid), 18-amino-stearic acid, 18-amino-oleic acid, 16-amino-palmitoleic acid, 18-amino-linoleic acid, 18-amino-linolenic acid and 20-amino-arachidonic acid. In a further aspect, the ω-amino-fatty acid moieties are derived from 6-amino-caproic acid.

In further aspects, the ω-amino fatty acid moiety is 4-amino-butanoyl, 6-amino-caproyl, 8-amino-octanoyl, 10-amino-decanoyl, 12-amino-lauroyl, 14-amino-myristoyl, 14-amino-myristoleoyl, 16-amino-palmiteoyl, 18-amino-stearoyl, 18-amino-oleoyl, 16-amino-palmitoleoyl, 18-amino-linoleoyl, 18-amino-linolenoyl, or 20-amino-arachidonoyl. In a still further aspect, ω-amino fatty acid moiety is 6-amino-caproyl (or alternatively referred to as 6-amino hexanoyl).

In various aspects, the ω-amino-fatty acid moiety is derived from a ω-amino-fatty acid having the structure:

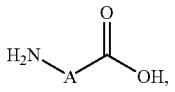

wherein A is an aliphatic group have 2-32 carbon atoms. In a further aspect, the aliphatic group is an alkyl group. In a still further aspect, the aliphatic group comprises 0-3 double bonds. In a yet further aspect, the aliphatic group is an alkenyl group. In various aspects, A is $—(CH_2)_5—$.

In a further aspect, the ω-amino-fatty acid moiety is linked to the peptide via the N-terminal amino group of the peptide, and following linking to the peptide, the ω-amino-fatty acid moiety has the structure:

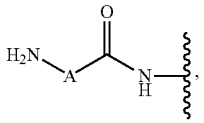

wherein A is an aliphatic group have 2-32 carbon atoms. In a further aspect, the aliphatic group is an alkyl group. In a still further aspect, the aliphatic group comprises 0-3 double bonds. In a yet further aspect, the aliphatic group is an alkenyl group. In various aspects, A is $—(CH_2)_5—$.

In various aspects, the synthetic ApoE-mimicking peptide comprises an acetylated ω-amino fatty acid moiety. In a further aspect, the disclosed peptides can be linked any of the disclosed ω-amino-fatty acids, and then further comprise an acetyl moiety on the ω-amino group.

In a further aspect, the ω-amino-fatty acid moiety is linked to the peptide via the N-terminal amino group of the peptide, and following linking to the peptide, the ω-amino group is acetylated, and the ω-amino-fatty acid moiety has the structure:

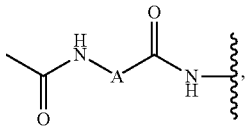

wherein A is an aliphatic group have 2-32 carbon atoms. In a further aspect, the aliphatic group is an alkyl group. In a still further aspect, the aliphatic group comprises 0-3 double bonds. In a yet further aspect, the aliphatic group is an alkenyl group. In various aspects, A is $—(CH_2)_5—$.

The fatty acids from which the fatty acid moiety is derived are commercially available and can be prepared by different chemical methods (Recent Developments in the Synthesis of Fatty Acid Derivatives, Editors: Knothe G and Derksen J T B, AOCS Press 1999, ISBN 1-893997-00-6.)

3. Single Domain Peptides

Disclosed are single-domain synthetic Apo E mimetics. The single-domain synthetic Apo E mimetics can consist of a receptor binding domain of Apo E or a lipid-associating peptide.

i. Receptor Binding Domain Peptides

The receptor binding domain peptide for the synthetic Apo E mimetics can be a human receptor binding domain peptide of Apo E. For example, receptor binding domain peptide of the disclosed synthetic Apo E mimetics can comprise the amino acid sequence of LRKLRKRLLR (SEQ ID NO:4), LRRLRRRLLR (SEQ ID NO:11), or LRKLRKRFFR (SEQ ID NO:12). The receptor binding domain peptide of such synthetic Apo E mimetics can also be from a species selected from the group consisting of mouse, rabbit, monkey, rat, bovine, pig and dog.

Examples of receptor binding domain peptides that can be used in the disclosed synthetic Apo E mimetics are provided in Table 1.

TABLE 1

Disclosed Synthetic Apo E mimetics

| Species | Starting Residue NO: | Sequence |
|---|---|---|
| Human | 141 | **L**RKLR**KRLLR** (SEQ ID NO: 4) |
| Rabbit | 134 | **L**RKLR**KRLLR** (SEQ ID NO: 4) |
| Monkey | 141 | **L**RKLR**KRLLR** (SEQ ID NO: 4) |
| Mouse | 133 | **L**RK*M*R**KR**L*M***R** (SEQ ID NO: 7) |
| Rat | 133 | **L**RK*M*R**KR**L*M***R** (SEQ ID NO: 7) |
| Bovine | 140 | **L**RKL***P***K**R**LLR (SEQ ID NO: 8) |
| Pig | 140 | **L**R*N*VR**KR**L*V***R** (SEQ ID NO: 9) |
| Dog | 133 | *M*RKLRKR*V*LR (SEQ ID NO: 10) |
| R Modified | 141 | **L**R*R*LR*R***R**LLR (SEQ ID NO: 11) |
| F Modified | 141 | **L**RKLR**KR*FF*R** (SEQ ID NO: 12) |
| ApoB | | ***RLTRKRGLK*** (SEQ ID NO: 13) |

The italicized residues in Table 1 indicate changes from the human sequence; however, the property of the amino acid is conserved. The bold-italicized residues in Table 1 indicate the difference from the human sequence at that position.

The receptor binding domain peptide for the synthetic Apo E mimetics can also be the LDL receptor (LDLR) binding domain of apolipoprotein B (ApoB). The LDL receptor (LDLR) binding domain of ApoB can have the sequence RLTRKRGLK (SEQ ID NO:13). ApoB-100 is a 550,000 Da glycoprotein with nine amino acids (3359-3367) serving as the binding domain for the LDL receptor (Segrest et al., J. Lipid. Res. 42, pp. 1346-1367 (2001)). Upon binding to LDLR in clathrin coated pits, LDL is internalized via endocytosis and moves into the endosome where a drop in pH causes the receptor to dissociate from the LDL. The receptor is recycled back to the surface of the cell while the LDL is moved into the lysosome where the particle is degraded (Goldstein et al., Ann. Rev. Cell Biol. 1, pp. 1-39 (1985)). The LDL receptor (LDLR) binding domain of ApoB when used with the disclosed peptides can also be altered and/or modified as described throughout this application for Apo E. For example, LDL receptor (LDLR) binding domain of ApoB can be used with the disclosed lipid-associating peptides, wherein the LDL receptor (LDLR) binding domain of ApoB is covalently linked to said lipid-associating peptide. In addition, the LDL receptor (LDLR) binding domain of ApoB can be scrambled, reverse-oriented, can be part of a domain switched peptide as described below.

ii. Lipid-Associating Peptides

Lipid-associating peptides can be used alone or in combination with the Apo E-mimicking peptides. The lipid associating peptide for these synthetic Apo E mimetics can be, but are not limited to, class A amphipathic helical peptides, class A amphipathic helical peptide mimetics of apoA-I having aromatic or aliphatic residues in the nonpolar face, small peptides including pentapeptides, tetrapeptides, tripeptides, dipeptides and pairs of amino acids, Apo-J (G* peptides), and peptide mimetics, e.g., as described below.

a. Class A Amphipathic Helical Peptides

In one aspect, the lipid-associating peptides for use in the disclosed methods include class A amphipathic helical peptides, e.g. as described in U.S. Pat. No. 6,664,230, and PCT Publications WO 02/15923 and WO 2004/034977. It was discovered that peptides comprising a class A amphipathic helix ("class A peptides"), are capable of mitigating one or more symptoms of atherosclerosis as well as treating other disorders.

Class A peptides are characterized by formation of an α-helix that produces a segregation of polar and non-polar residues thereby forming a polar and a nonpolar face with the positively charged residues residing at the polar-nonpolar interface and the negatively charged residues residing at the center of the polar face (see, e.g., Anantharamaiah (1986) Meth. Enzymol, 128: 626-668). It is noted that the fourth exon of apo A-I, when folded into 3.667 residues/turn produces a class A amphipathic helical structure.

One class A peptide, designated 18A (see, e.g., Anantharamaiah (1986) Meth. Enzymol, 128: 626-668) was modified as described herein to produce peptides orally administrable and highly effective at inhibiting or preventing one or more symptoms of atherosclerosis and/or other indications described herein. Without being bound by a particular theory, it is believed that the disclosed peptides can act in vivo by picking up seeding molecule(s) that mitigate oxidation of LDL.

Increasing the number of Phe residues on the hydrophobic face of 18A can increase lipid affinity as determined by the computation described by Palgunachari et al. (1996) Arteriosclerosis, Thrombosis, & Vascular Biol. 16: 328-338. Theoretically, a systematic substitution of residues in the nonpolar face of 18A with Phe could yield six peptides. Peptides with an additional 2, 3 and 4 Phe would have theoretical lipid affinity (2) values of 13, 14 and 15 units, respectively. However, the λ values jumped four units if the additional Phe were increased from 4 to 5 (to 19λ units). Increasing to 6 or 7 Phe would produce a less dramatic increase (to 20 and 21λ units, respectively).

A number of these class A peptides were made including, the peptide designated 4F, D4F, 5F, and D5F, and the like. Various class A peptides inhibited lesion development in atherosclerosis-susceptible mice and rabbits. In addition, the peptides show varying, but significant degrees of efficacy in mitigating one or more symptoms of the various pathologies described herein. A number of such peptides are illustrated in Table 2.

TABLE 2

Class A peptides.

| Peptide Name | Amino Acid Sequence |
|---|---|
| 18F | D-W-L-K-A-F-Y-D-K-V-A-E-K-L-K-E-A-F (SEQ ID NO: 5) |
| 2F | Ac-D-W-L-K-A-F-Y-D-K-V-A-E-K-L-K-E-A-F-$NH_2$ (SEQ ID NO: 5) |
| 3F | Ac-D-W-F-K-A-F-Y-D-K-V-A-E-K-L-K-E-A-F-$NH_2$ (SEQ ID NO: 14) |
| 3F14 | Ac-D-W-L-K-A-F-Y-D-K-V-A-E-K-F-K-E-A-F-$NH_2$ (SEQ ID NO: 15) |
| 4F | Ac-D-W-F-K-A-F-Y-D-K-V-A-E-K-F-K-E-A-F-$NH_2$ (SEQ ID NO: 16) |
| 5F | Ac-D-W-L-K-A-F-Y-D-K-V-F-E-K-F-K-E-F-F-$NH_2$ (SEQ ID NO: 17) |
| 6F | Ac-D-W-L-K-A-F-Y-D-K-F-F-E-K-F-K-E-F-F-$NH_2$ (SEQ ID NO: 18) |
| 7F | Ac-D-W-F-K-A-F-Y-D-K-F-F-E-K-F-K-E-F-F-$NH_2$ (SEQ ID NO: 19) |
| | Ac-D-W-L-K-A-F-Y-D-K-V-A-E-K-L-K-E-F-F-$NH_2$ (SEQ ID NO: 20) |
| | Ac-D-W-L-K-A-F-Y-D-K-V-F-E-K-F-K-E-A-F-$NH_2$ (SEQ ID NO: 21) |
| | Ac-D-W-L-K-A-F-Y-D-K-V-F-E-K-L-K-E-F-F-$NH_2$ (SEQ ID NO: 22) |
| | Ac-D-W-L-K-A-F-Y-D-K-V-A-E-K-F-K-E-F-F-$NH_2$ (SEQ ID NO: 23) |
| | Ac-D-W-L-K-A-F-Y-D-K-V-F-E-K-F-K-E-F-F-$NH_2$ (SEQ ID NO: 24) |
| | Ac-E-W-L-K-L-F-Y-E-K-V-L-E-K-F-K-E-A-F-$NH_2$ (SEQ ID NO: 25) |
| | Ac-E-W-L-K-A-F-Y-ID-K-V-A-E-K-F-K-E-A-F-$NH_2$ (SEQ ID NO: 26) |
| | Ac-E-W-L-K-A-F-Y-D-K-V-A-E-K-L-K-E-F-F-$NH_2$ (SEQ ID NO: 27) |
| | Ac-E-W-L-K-A-F-Y-D-K-V-F-E-K-F-K-E-A-F-$NH_2$ (SEQ ID NO: 28) |
| | Ac-E-W-L-K-A-F-Y-D-K-V-F-E-K-L-K-E-F-F-$NH_2$ (SEQ ID NO: 29) |
| | Ac-E-W-L-K-A-F-Y-D-K-V-A-E-K-F-K-E-F-F-$NH_2$ (SEQ ID NO: 30) |
| | Ac-E-W-L-K-A-F-Y-D-K-V-F-E-K-F-K-E-F-F-$NH_2$ (SEQ ID NO: 31) |
| | Ac-A-F-Y-D-K-V-A-E-K-L-K-E-A-F-$NH_2$ (SEQ ID NO: 32) |
| | Ac-A-F-Y-D-K-V-A-E-K-F-K-E-A-F-$NH_2$ (SEQ ID NO: 33) |
| | Ac-A-F-Y-D-K-V-A-E-K-F-K-E-A-F-$NH_2$ (SEQ ID NO: 34) |
| | Ac-A-F-Y-D-K-F-F-E-K-F-K-E-F-F-$NH_2$ (SEQ ID NO: 35) |
| | Ac-A-F-Y-D-K-F-F-E-K-F-K-E-F-F-$NH_2$ (SEQ ID NO: 36) |
| | Ac-A-F-Y-D-K-V-A-E-K-F-K-E-A-F-$NH_2$ (SEQ ID NO: 37) |
| | Ac-A-F-Y-D-K-V-A-E-K-L-K-E-F-F-$NH_2$ (SEQ ID NO: 38) |
| | Ac-A-F-Y-D-K-V-F-E-K-F-K-E-A-F-$NH_2$ (SEQ ID NO: 39) |
| | Ac-A-F-Y-D-K-V-F-E-K-L-K-E-F-F-$NH_2$ (SEQ ID NO: 40) |
| | Ac-A-F-Y-D-K-V-A-E-K-F-K-E-F-F-$NH_2$ (SEQ ID NO: 41) |
| | Ac-K-A-F-Y-D-K-V-F-E-K-F-K-E-F-$NH_2$ (SEQ ID NO: 42) |
| | Ac-L-F-Y-E-K-V-L-E-K-F-K-E-A-F-$NH_2$ (SEQ ID NO: 43) |
| | Ac-A-F-Y-D-K-V-A-E-K-F-K-E-A-F-$NH_2$ (SEQ ID NO: 44) |
| | Ac-A-F-Y-D-K-V-A-E-K-L-K-E-F-F-$NH_2$ (SEQ ID NO: 45) |
| | Ac-A-F-Y-D-K-V-F-E-K-F-K-E-A-F-$NH_2$ (SEQ ID NO: 46) |
| | Ac-A-F-Y-D-K-V-F-E-K-L-K-E-F-F-$NH_2$ (SEQ ID NO: 47) |
| | Ac-A-F-Y-D-K-V-A-E-K-F-K-E-F-F-$NH_2$ (SEQ ID NO: 48) |
| | Ac-A-F-Y-D-K-V-F-E-K-F-K-E-F-F-$NH_2$ (SEQ ID NO: 49) |
| | Ac-D-W-L-K-A-L-Y-D-K-V-A-E-K-L-K-E-A-L-$NH_2$ (SEQ ID NO: 50) |
| | Ac-D-W-F-K-A-F-Y-E-K-V-A-E-K-L-K-E-F-F-$NH_2$ (SEQ ID NO: 51) |
| | Ac-D-W-F-K-A-F-Y-E-K-F-F-E-K-F-K-E-F-F-$NH_2$ (SEQ ID NO: 52) |
| | Ac-E-W-L-K-A-L-Y-E-K-V-A-E-K-L-K-E-A-L-$NH_2$ (SEQ ID NO: 53) |
| | Ac-E-W-L-K-A-F-Y-E-K-V-A-E-K-L-K-E-A-F-$NH_2$ (SEQ ID NO: 54) |
| | Ac-E-W-F-K-A-F-Y-E-K-V-A-E-K-L-K-E-F-F-$NH_2$ (SEQ ID NO: 55) |
| | Ac-E-W-L-K-A-F-Y-E-K-V-F-E-K-F-K-E-F-F-$NH_2$ (SEQ ID NO: 56) |
| | Ac-E-W-L-K-A-F-Y-E-K-F-F-E-K-F-K-E-F-F-$NH_2$ (SEQ ID NO: 57) |
| | Ac-E-W-F-K-A-F-Y-E-K-F-F-E-K-F-K-E-F-F-$NH_2$ (SEQ ID NO: 58) |
| | Ac-D-F-L-K-A-W-Y-D-K-V-A-E-K-L-K-E-A-W-$NH_2$ (SEQ ID NO: 59) |
| | Ac-E-F-L-K-A-W-Y-E-K-V-A-E-K-L-K-E-A-W-$NH_2$ (SEQ ID NO: 60) |
| | Ac-D-F-W-K-A-W-Y-D-K-V-A-E-K-L-K-E-W-W-$NH_2$ (SEQ ID NO: 61) |
| | Ac-E-F-W-K-A-W-Y-E-K-V-A-E-K-L-K-E-W-W-$NH_2$ (SEQ ID NO: 62) |
| | Ac-D-K-L-K-A-F-Y-D-K-V-F-E-W-A-K-E-A-F-$NH_2$ (SEQ ID NO: 63) |
| | Ac-D-K-W-K-A-V-Y-D-K-F-A-E-A-F-K-E-F-L-$NH_2$ (SEQ ID NO: 64) |
| | Ac-E-K-L-K-A-F-Y-E-K-V-F-E-W-A-K-E-A-F-$NH_2$ (SEQ ID NO: 65) |
| | Ac-E-K-W-K-A-V-Y-E-K-F-A-E-A-F-K-E-F-L-$NH_2$ (SEQ ID NO: 66) |
| | Ac-D-W-L-K-A-F-V-D-K-F-A-E-K-F-K-E-A-Y-$NH_2$ (SEQ ID NO: 67) |
| | Ac-E-K-W-K-A-V-Y-E-K-F-A-E-A-F-K-E-F-L-$NH_2$ (SEQ ID NO: 68) |
| | Ac-D-W-L-K-A-F-V-Y-D-K-V-F-K-L-K-E-F-F-$NH_2$ (SEQ ID NO: 69) |
| | Ac-E-W-L-K-A-F-V-Y-E-K-V-F-K-L-K-E-F-F-$NH_2$ (SEQ ID NO: 70) |
| | Ac-D-W-L-R-A-F-Y-D-K-V-A-E-K-L-K-E-A-F-$NH_2$ (SEQ ID NO: 71) |
| | Ac-E-W-L-R-A-F-Y-E-K-V-A-E-K-L-K-E-A-F-$NH_2$ (SEQ ID NO: 72) |
| | Ac-D-W-L-K-A-F-Y-D-R-V-A-E-K-L-K-E-A-F-$NH_2$ (SEQ ID NO: 73) |
| | Ac-E-W-L-K-A-F-Y-E-R-V-A-E-K-L-K-E-A-F-$NH_2$ (SEQ ID NO: 74) |
| | Ac-D-W-L-K-A-F-Y-D-K-V-A-E-R-L-K-E-A-F-$NH_2$ (SEQ ID NO: 75) |
| | Ac-E-W-L-K-A-F-Y-E-K-V-A-E-R-L-K-E-A-F-$NH_2$ (SEQ ID NO: 76) |
| | Ac-D-W-L-K-A-F-Y-D-K-V-A-E-K-L-R-E-A-F-$NH_2$ (SEQ ID NO: 77) |
| | Ac-E-W-L-K-A-F-Y-E-K-V-A-E-K-L-R-E-A-F-$NH_2$ (SEQ ID NO: 78) |
| | Ac-D-W-L-K-A-F-Y-D-R-V-A-E-R-L-K-E-A-F-$NH_2$ (SEQ ID NO: 79) |

TABLE 2-continued

| Class A peptides. | |
|---|---|
| Peptide Name | Amino Acid Sequence |
| | Ac-E-W-L-K-A-F-Y-E-R-V-A-E-R-L-K-E-A-F-$NH_2$ (SEQ ID NO: 80) |
| | Ac-D-W-L-R-A-F-Y-D-K-V-A-E-K-L-R-E-A-F-$NH_2$ (SEQ ID NO: 81) |
| | Ac-E-W-L-R-A-F-Y-E-K-V-A-E-K-L-R-E-A-F-$NH_2$ (SEQ ID NO: 82) |
| | Ac-D-W-L-R-A-F-Y-D-R-V-A-E-K-L-K-E-A-F-$NH_2$ (SEQ ID NO: 83) |
| | Ac-E-W-L-R-A-F-Y-E-R-V-A-E-K-L-K-E-A-F-$NH_2$ (SEQ ID NO: 84) |
| | Ac-D-W-L-K-A-F-Y-D-K-V-A-E-R-L-R-E-A-F-$NH_2$ (SEQ ID NO: 85) |
| | Ac-E-W-L-K-A-F-Y-E-K-V-A-E-R-L-R-E-A-F-$NH_2$ (SEQ ID NO: 86) |
| | Ac-D-W-L-R-A-F-Y-D-K-V-A-E-R-L-K-E-A-F-$NH_2$ (SEQ ID NO: 87) |
| | Ac-E-W-L-R-A-F-Y-E-K-V-A-E-R-L-K-E-A-F-$NH_2$ (SEQ ID NO: 88) |
| | D-W-L-K-A-F-Y-D-K-V-A-E-K-L-K-E-A-F-P-D-W |
| | L-K-A-F-Y-D-K-V-A-E-K-L-K-E-A-F (SEQ ID NO: 89) |
| | D-W-L-K-A-F-Y-D-K-V-A-E-K-L-K-E-F-F-P-D-W |
| | L-K-A-F-Y-D-K-V-A-E-K-L-K-E-F-F (SEQ ID NO: 90) |
| | D-W-F-K-A-F-Y-D-K-V-A-E-K-L-K-E-A-F-P-D-W |
| | F-K-A-F-Y-D-K-V-A-E-K-L-K-E-A-F (SEQ ID NO: 91) |
| | D-K-L-K-A-F-Y-D-K-V-F-E-W-A-K-E-A-F-P-D-K |
| | L-K-A-F-Y-D-K-V-F-E-W-L-K-E-A-F (SEQ ID NO: 92) |
| | D-K-W-K-A-V-Y-D-K-F-A-E-A-F-K-E-F-L-P-D-K |
| | W-K-A-V-Y-D-K-F-A-E-A-F-K-E-F-L (SEQ ID NO: 93) |
| | D-W-F-K-A-F-Y-D-K-V-A-E-K-F-K-E-A-F-P-D-W |
| | F-K-A-F-Y-D-K-V-A-E-K-F-K-E-A-F (SEQ ID NO: 94) |
| | D-W-L-K-A-F-V-Y-D-K-V-F-K-L-K-E-F-F-P-D-W |
| | L-K-A-F-V-Y-D-K-V-F-K-L-K-E-F-F (SEQ ID NO: 95) |
| | D-W-L-K-A-F-Y-D-K-F-A-E-K-F-K-E-F-F-P-D-W |
| | L-K-A-F-Y-D-K-F-A-E-K-F-K-E-F-F (SEQ ID NO: 96) |
| | Ac-E-W-F-K-A-F-Y-E-K-V-A-E-K-F-K-E-A-F-$NH_2$ (SEQ ID NO: 97) |
| | Ac-D-W-F-K-A-F-Y-D-K-V-A-E-K-F-$NH_2$ (SEQ ID NO: 98) |
| | Ac-F-K-A-F-Y-D-K-V-A-E-K-F-K-E-$NH_2$ (SEQ ID NO: 99) |
| | Ac-F-K-A-F-Y-E-K-V-A-E-K-F-K-E-$NH_2$ (SEQ ID NO: 100) |
| | NMA-F-K-A-F-Y-D-K-V-A-E-K-F-K-E-$NH_2$ (SEQ ID NO: 101) |
| | NMA-F-K-A-F-Y-E-K-V-A-E-K-F-K-E-$NH_2$ (SEQ ID NO: 102) |
| | NMA-D-W-F-K-A-F-Y-D-K-V-A-E-K-F-K-E-A-F-$NH_2$ (SEQ ID NO: 103) |
| | NMA-E-W-F-K-A-F-Y-E-K-V-A-E-K-F-K-E-A-F-$NH_2$ (SEQ ID NO: 104) |
| | NMA-A-F-Y-D-K-V-A-E-K-F-K-E-A-F-$NH_2$ (SEQ ID NO: 105) |
| | NMA-D-W-F-K-A-F-Y-D-K-V-A-E-K-F-$NH_2$ (SEQ ID NO: 106) |
| | Ac-D-W-L-K-A-F-Y-D-K-V-F-E-K-F-K-E-F-F-$NH_2$ (SEQ ID NO: 107) |
| | NMA-D-W-L-K-A-F-Y-D-K-V-F-E-K-F-K-E-F-F-$NH_2$ (SEQ ID NO: 108) |
| | Ac-E-W-L-K-A-F-Y-E-K-V-F-E-K-F-K-E-F-F-$NH_2$ (SEQ ID NO: 109) |
| | NMA-E-W-L-K-A-F-Y-E-K-V-F-E-K-F-K-E-F-F-$NH_2$ (SEQ ID NO: 110) |
| | Ac-A-F-Y-D-K-V-F-E-K-F-K-E-F-F-$NH_2$ (SEQ ID NO: 111) |
| | NMA-A-F-Y-D-K-V-F-E-K-F-K-E-F-F-$NH_2$ (SEQ ID NO: 112) |
| | Ac-A-F-Y-E-K-V-F-E-K-F-K-E-F-F-$NH_2$ (SEQ ID NO: 113) |
| | NMA-A-F-Y-E-K-V-F-E-K-F-K-E-F-F-$NH_2$ (SEQ ID NO: 114) |
| | Ac-D-W-L-K-A-F-Y-D-K-V-F-E-K-F-$NH_2$ (SEQ ID NO: 115) |
| | NMA-D-W-L-K-A-F-Y-D-K-V-F-E-K-F-$NH_2$ (SEQ ID NO: 116) |
| | Ac-E-W-L-K-A-F-Y-E-K-V-F-E-K-F-$NH_2$ (SEQ ID NO: 117) |
| | NMA-E-W-L-K-A-F-Y-E-K-V-F-E-K-F-$NH_2$ (SEQ ID NO: 118) |
| | Ac-L-K-A-F-Y-D-K-V-F-E-K-F-K-E-$NH_2$ (SEQ ID NO: 119) |
| | NMA-L-K-A-F-Y-D-K-V-F-E-K-F-K-E-$NH_2$ (SEQ ID NO: 120) |
| | Ac-L-K-A-F-Y-E-K-V-F-E-K-F-K-E-$NH_2$ (SEQ ID NO: 121) |
| | NMA-L-K-A-F-Y-E-K-V-F-E-K-F-K-E-$NH_2$ (SEQ ID NO: 122) |

*Linkers are underlined; NMA is N-Methyl Anthranilyl

In certain aspects, the peptides include variations of 4F (D-W-F-K-A-F-Y-D-K-V-A-E-K-F-K-E-A-F (SEQ ID NO:16) in Table 2), also known as L-4F, where all residues are L form amino acids) or D-4F where one or more residues are D form amino acids). In any of the peptides described herein, the C-terminus, and/or N-terminus, and/or internal residues can be blocked with one or more blocking groups as described herein.

While various peptides of Table 2, are illustrated with an acetyl group or an N-methylanthranilyl group protecting the amino terminus and an amide group protecting the carboxyl terminus, any of these protecting groups may be eliminated and/or substituted with another protecting group as described herein. The peptides can comprise one or more D-form amino acids as described herein. In certain aspects, every amino acid (e.g., every enantiomeric amino acid) of the peptides of Table 2 is a D-form amino acid.

It is also noted that Table 2 is not fully inclusive. Using the teachings provided herein, other suitable class A amphipathic helical peptides can routinely be produced (e.g., by conservative or semi-conservative substitutions (e.g., D replaced by E), extensions, deletions, and the like). Thus, for example, one embodiment utilizes truncations of any one or more of peptides shown herein (e.g., peptides identified as 2F, 3F, $3F^{14}$, 4F, 5F, 6F, or 7F—in Table 2). Thus, for example, A-F-Y-D-K-V-A-E-K-L-K-E-A-F (amino acids 5-18 of SEQ ID NO:5) illustrates a peptide comprising 14 amino acids from the C-terminus of 18A comprising one or more D amino acids, while others illustrate other truncations.

Longer peptides are also suitable. Such longer peptides may entirely form a class A amphipathic helix, or the class A amphipathic helix (helices) can form one or more domains of the peptide. In addition, this invention contemplates multimeric versions of the peptides (e.g., concatamers). Thus, for example, the peptides illustrated herein can be coupled together (directly or through a linker (e.g., a carbon linker, or one or more amino acids) with one or more intervening amino acids). Illustrative polymeric peptides include 18A-Pro-18A and the peptides in the following table (Table 2B), in certain embodiments comprising one or more D amino acids, more preferably with every amino acid a D amino acid as described herein and/or having one or both termini protected.

TABLE 2B

| Multimeric peptides. Amino Acid Sequence |
|---|
| D-W-L-K-A-F-Y-D-K-V-A-E-K-L-K-E-A-F-P-D-W L-K-A-F-Y-D-K-V-A-E-K-L-K-E-A-F (SEQ ID NO: 90) |
| D-W-L-K-A-F-Y-D-K-V-A-E-K-L-K-E-F-F-P-D-W L-K-A-F-Y-D-K-V-A-E-K-L-K-E-F-F (SEQ ID NO: 91) |
| D-W-F-K-A-F-Y-D-K-V-A-E-K-L-K-E-A-F-P-D-W F-K-A-F-Y-D-K-V-A-E-K-L-K-E-A-F (SEQ ID NO: 92) |
| D-K-L-K-A-F-Y-D-K-V-F-E-W-A-K-E-A-F-P-D-K L-K-A-F-Y-D-K-V-F-E-W-L-K-E-A-F (SEQ ID NO: 93) |
| D-K-W-K-A-V-Y-D-K-F-A-E-A-F-K-E-F-L-P-D-K W-K-A-V-Y-D-K-F-A-E-A-F-K-E-F-L (SEQ ID NO: 94) |
| D-W-F-K-A-F-Y-D-K-V-A-E-K-F-K-E-A-F-P-D-W F-K-A-F-Y-D-K-V-A-E-K-F-K-E-A-F (SEQ ID NO: 95) |
| D-W-L-K-A-F-V-Y-D-K-V-F-K-L-K-E-F-F-P-D-W L-K-A-F-V-Y-D-K-V-F-K-L-K-E-F-F (SEQ ID NO: 96) |
| D-W-L-K-A-F-Y-D-K-F-A-E-K-F-K-E-F-F-P-D-W L-K-A-F-Y-D-K-F-A-E-K-F-K-E-F-F (SEQ ID NO: 97) |

b. Class A Amphipathic Helical Peptide Mimetics of apoA-I Having Aromatic or Aliphatic Residues in the Non-Polar Face.

Also disclosed are modified class A amphipathic helix peptides. Certain preferred peptides incorporate one or more aromatic residues at the center of the nonpolar face, e.g., $3F^{C\pi}$, (as present in 4F), or with one or more aliphatic residues at the center of the nonpolar face, e.g., $3F^{I\pi}$, see, e.g., Table 3. Without being bound to a particular theory, the central aromatic residues on the nonpolar face of the peptide $3F^{C\pi}$, due to the presence of π electrons at the center of the nonpolar face can allow water molecules to penetrate near the hydrophobic lipid alkyl chains of the peptide-lipid complex, which in turn would enable the entry of reactive oxygen species (such as lipid hydroperoxides) shielding them from the cell surface. The peptides with aliphatic residues at the center of the nonpolar face, e.g., $3F^{I\pi}$, can act similarly but not quite as effectively as $3F^{C\pi}$.

In one aspect, the peptides can convert pro-inflammatory HDL to anti-inflammatory HDL or make anti-inflammatory HDL more anti-inflammatory, and/or decrease LDL-induced monocyte chemotactic activity generated by artery wall cells equal to or greater than D4F or other peptides shown in Table 2.

TABLE 3

| Modified class A peptides. | |
|---|---|
| Name | Sequence |
| ($3F^{cn}$) | Ac-DKWKAVYDKFAEAFKEFL-$NH_2$ (SEQ ID NO: 123) |
| ($3F^{ln}$) | Ac-DKLKAFYDKVFEWAKEAF-$NH_2$ (SEQ ID NO: 124) |

c. Other Class A and Some Class Y Amphipathic Helical Peptides.

Class A amphipathic helical peptides that have an amino acid composition identical to one or more of the class A amphipathic helical peptides described above. Thus, for example, in certain embodiments this invention contemplates peptides having an amino acid composition identical to 4F. Thus, in certain embodiments, this invention includes active agents that comprise a peptide that consists of 18 amino acids, where the 18 amino acids consist of 3 alanines (A), 2 aspartates (D), 2 glutamates (E), 4 phenylalanines (F), 4 lysines (K), 1 valine (V), 1 tryptophan (W), and 1 tyrosine (Y); and where the peptide forms a class A amphipathic helix; and protects a phospholipid against oxidation by an oxidizing agent. In various embodiments, the peptides comprise least one "D" amino acid residue; and in certain embodiments, the peptides comprise all "D: form amino acid residues. A variety of such peptides are illustrated in Table 4. Reverse (retro-), inverse, retro-inverso-, and circularly permuted forms of these peptides are also contemplated. Table 4 provides the sequences and identifier names for representative 18 amino acid length class A amphipathic helical peptides with the amino acid composition comprising 3 alanines (A), 2 aspartates (D), 2 glutamates (E), 4 phenylalanines (F), 4 lysines (K), 1 valine (V), 1 tryptophan (W), and 1 tyrosine (Y).

TABLE 4

| 18 amino acid length class A amphipathic helical peptides. | |
|---|---|
| Name | Sequence |
| [Switch D-E]-4F analogs | |
| [Switch D-E]-1-4F | Ac-**E**WFKAFY**E**KVA**D**KFK**D**AF-$NH_2$ (SEQ ID NO: 125) |
| [Switch D-E]-2-4F | Ac-**E**WFKAFYDKVADKFK**E**AF-$NH_2$ (SEQ ID NO: 126) |
| [Switch D-E]-3-4F | Ac-DWFKAFY**E**KVA**D**KFKEAF-$NH_2$ (SEQ ID NO: 127) |
| [Switch D-E]-4-4F | Ac-DWFKAFY**E**KVAEKFK**D**AF-$NH_2$ (SEQ ID NO: 128) |
| [W-2, F-3 positions reversed] | |
| 4F-2 | Ac-D**FW**KAFYDKVAEKFKEAF-$NH_2$ (SEQ ID NO: 129) |
| [Switch D-E]-1-4F-2 | Ac-**E**FWKAFY**E**KVA**D**KFK**D**AF-$NH_2$ (SEQ ID NO: 130) |
| [Switch D-E]-2-4F-2 | Ac-**E**FWKAFYDKVADKFK**E**AF-$NH_2$ (SEQ ID NO: 131) |
| [Switch D-E]-3-4F-2 | Ac-DFWKAFY**E**KVA**D**KFKEAF-$NH_2$ (SEQ ID NO: 132) |
| [Switch D-E]-4-4F-2 | Ac-DFWKAFY**E**KVAEKFK**D**AF-$NH_2$ (SEQ ID NO: 133) |
| [F-6 and Y-7 positions switched] | |
| 4F-3 | Ac-DWFKA**YF**DKVAEKFKEAF-$NH_2$ (SEQ ID NO: 134) |
| [Switch D-E]-1-4F-5 | Ac-**E**WFKAYF**E**KVA**D**KFK**D**AF-$NH_2$ (SEQ ID NO: 135) |

TABLE 4-continued

| 18 amino acid length class A amphipathic helical peptides. | |
|---|---|
| Name | Sequence |
| [Switch D-E]-2-4F-5 | Ac-**E**WFKAYFDKVADKFK**E**AF-$NH_2$ (SEQ ID NO: 136) |
| [Switch D-E]-3-4F-5 | Ac-DWFKAYF**E**KVA**D**KFKEAF-$NH_2$ (SEQ ID NO: 137) |
| [Switch D-E]-4-4F-5 | Ac-DWFKAYFEKVA**E**KFK**D**AF-$NH_2$ (SEQ ID NO: 138) |
| [Y-1 and 10V positions switched] | |
| 4F-4 | Ac-DWFKAF**V**DK**Y**AEKFKEAF-$NH_2$ (SEQ ID NO: 139) |
| [Switch D-E]-1-4F-4 | Ac-**E**WFKAFV**E**KYA**D**KFK**D**AF-$NH_2$ (SEQ ID NO:140) |
| [Switch D-E]-2-4F-4 | Ac-**E**WFKAFVDKYADKFK**E**AF-$NH_2$ (SEQ ID NO: 141) |
| [Switch D-E]-3-4F-4 | Ac-DWFKAFV**E**KYA**D**KFKEAF-$NH_2$ (SEQ ID NO: 142) |
| [Switch D-E]-4-4F | Ac-DWFKAFV**E**KYAEKFK**D**AF-$NH_2$ (SEQ ID NO: 143) |
| [V-10 and A-11 switched] | |
| 4-F-5 | Ac-DWFKAFYDK**AV**EKFKEAF-$NH_2$ (SEQ ID NO: 144) |
| [Switch D-E]-1-4F-5 | Ac-**E**WFKAFY**E**KAV**D**KFK**D**AF-$NH_2$ (SEQ ID NO: 145) |
| [Switch D-E]-2-4F-5 | Ac-**E**WFKAFYDKAVDKFK**E**AF-$NH_2$ (SEQ ID NO: 146) |
| [Switch D-E]-3-4F-5 | Ac-DWFKAFY**E**KAV**D**KFKEAF-$NH_2$ (SEQ ID NO: 147) |
| [Switch D-E]-4-4F-5 | Ac-DWFKAFY**E**KAVEKFK**D**AF-$NH_2$ (SEQ ID NO: 148) |
| [A-11 and F-14 switched] | |
| 4F-6 | Ac-DWFKAFYDKV**F**EK**A**KEAF-$NH_2$ (SEQ ID NO: 149) |
| [Switch D-E]-1-4F-6 | Ac-**E**WFKAFY**E**KVF**D**KAK**D**AF-$NH_2$ (SEQ ID NO: 150) |
| [Switch D-E]-2-4F-6 | Ac-**E**WFKAFYDKVFDKAK**E**AF-$NH_2$ (SEQ ID NO: 151) |
| [Switch D-E]-3-4F-6 | Ac-DWFKAFY**E**KVF**D**KAKEAF-$NH_2$ (SEQ ID NO: 152) |
| [Switch D-E]-4-4F-6 | Ac-DWFKAFY**E**KVFEKAK**D**AF-$NH_2$ (SEQ ID NO: 153) |
| [F-14 and A-17 switched] | |
| 4F-7 | Ac-DWFKAFYDKVAEK**A**KE**F**F-$NH_2$ (SEQ ID NO: 154) |
| [Switch D-E]-1-4F-7 | Ac-**E**WFKAFY**E**KVA**D**KAK**D**FF-$NH_2$ (SEQ ID NO: 155) |
| [Switch D-E]-2-4F-7 | Ac-**E**WFKAFYDKVADKAK**E**FF-$NH_2$ (SEQ ID NO: 156) |
| [Switch D-E]-3-4F-7 | Ac-DWFKAFY**E**KVA**D**KAKEFF-$NH_2$ (SEQ ID NO: 157) |
| [Switch D-E]-4-4F-7 | Ac-DWFKAFY**E**KVAEKAK**D**FF-$NH_2$ (SEQ ID NO: 158) |
| [A-17 and F-18 switched] | |
| 4F-8 | Ac-DWFKAFYDKVAEKFKE**FA**-$NH_2$ (SEQ ID NO: 159) |
| [Switch D-E]-1-4F-8 | Ac-**E**WFKAFY**E**KVA**D**KFK**D**FA-$NH_2$ (SEQ ID NO: 160) |
| [Switch D-E]-2-4F-8 | Ac-**E**WFKAFYDKVADKFK**E**FA-$NH_2$ (SEQ ID NO: 161) |
| [Switch D-E]-3-4F-8 | Ac-DWFKAFY**E**KVA**D**KFKEFA-$NH_2$ (SEQ ID NO: 162) |
| [Switch D-E]-4-4F-8 | Ac-DWFKAFY**E**KVAEKFK**D**FA-$NH_2$ (SEQ ID NO: 163) |

TABLE 4-continued

| 18 amino acid length class A amphipathic helical peptides. | |
|---|---|
| Name | Sequence |
| [W-2 and A-17 switched] | |
| 4F-9 | Ac-D**A**FKAFYDKVAEKFKE**W**F-$NH_2$ (SEQ ID NO: 164) |
| [Switch D-E]-1-4F-9 | Ac-**E**AFKAFY**E**KVA**D**KFK**D**WF-$NH_2$ (SEQ ID NO: 165) |
| [Switch D-E]-2-4F-9 | Ac-**E**AFKAFYDKVADKFK**E**WF-$NH_2$ (SEQ ID NO: 166) |
| [Switch D-E]-3 4F-9 | Ac-DAFKAFY**E**KVA**D**KFKEWF-$NH_2$ (SEQ ID NO: 167) |
| [Switch D-E]-4-4F-9 | Ac-DAFKAFY**E**KVAEKFK**D**WF-$NH_2$ (SEQ ID NO: 168) |
| [W-2 and A-11 switched] | |
| 4F-10 | Ac-D**A**FKAFYDKV**W**EKFKEAF-$NH_2$ (SEQ ID NO: 169) |
| [Switch D-E]-1-4F-10 | Ac-**E**AFKAFY**E**KVW**D**KFK**D**AF-$NH_2$ (SEQ ID NO: 170) |
| [Switch D-E]-2-4F-10 | Ac-**E**AFKAFYDKVWDKFK**E**AF-$NH_2$ (SEQ ID NO: 171) |
| [Switch D-E]-3-4F-10 | Ac-DAFKAFY**E**KVW**D**KFKEAF-$NH_2$ (SEQ ID NO: 172) |
| [Switch D-E]-4-4F-10 | Ac-DAFKAFY**E**KVWEKFK**D**AF-$NH_2$ (SEQ ID NO: 173) |
| [W-2 and Y-7 switched] | |
| 4F-11 | Ac-D**Y**FKAF**W**DKVAEKFKEAF-$NH_2$ (SEQ ID NO: 174) |
| [Switch D-E]-1-4F-11 | Ac-**E**YFKAFW**E**KVA**D**KFK**D**AF-$NH_2$ (SEQ ID NO: 175) |
| [Switch D-E]-2-4F-11 | Ac-**E**YFKAFWDKVADKFK**E**AF-$NH_2$ (SEQ ID NO: 176) |
| [Switch D-E]-3-4F-11 | Ac-DYFKAFW**E**KVA**D**KFKEAF-$NH_2$ (SEQ ID NO: 177) |
| [Switch D-E]-4-4F-11 | Ac-DYFKAFW**E**KVAEKFK**D**AF-$NH_2$ (SEQ ID NO: 178) |
| [F-3 and A-17 switched] | |
| 4F-12 | Ac-DW**A**KAFYDKVAEKFKE**F**F-$NH_2$ (SEQ ID NO: 179) |
| [Switch D-E]-1-4F-12 | Ac-**E**WAKAFY**E**KVA**D**KFK**D**FF-$NH_2$ (SEQ ID NO: 180) |
| [Switch D-E]-2-4F-12 | Ac-**E**WAKAFYDKVADKFK**E**FF-$NH_2$ (SEQ ID NO: 181) |
| [Switch D-E]-3-4F-12 | Ac-DWAKAFY**E**KVA**D**KFKEFF-$NH_2$ (SEQ ID NO: 182) |
| [Switch D-E]-4-4F-12 | Ac-DWAKAFY**E**KVAEKFK**D**FF-$NH_2$ (SEQ ID NO: 183) |
| [F-6 and A-17 switched] | |
| 4F-13 | Ac-DWFKA**A**YDKVAEKFKE**F**F-$NH_2$ (SEQ ID NO: 184) |
| [Switch D-E]-1-4F-13 | Ac-**E**WFKAAY**E**KVA**D**KFK**D**FF-$NH_2$ (SEQ ID NO: 185) |
| [Switch D-E]-2-4F-13 | Ac-**E**WFKAAYDKVADKFK**E**FF-$NH_2$ (SEQ ID NO: 186) |
| [Switch D-E]-3-4F-13 | Ac-DWFKAAY**E**KVA**D**KFKEFF-$NH_2$ (SEQ ID NO: 187) |
| [Switch D-E]-4-4F-13 | Ac-DWFKAAY**E**KVAEKFK**D**FF-$NH_2$ (SEQ I DNO: 188) |
| [Y-7 and A-17 switched | |
| 4F-14 | Ac-DWFKAF**A**DKVAEKFKE**Y**F-$NH_2$ (SEQ ID NO: 189) |
| [Switch D-E]-1-4F-14 | Ac-**E**WFKAFA**E**KVA**D**KFK**D**YF-$NH_2$ (SEQ ID NO: 190) |
| [Switch D-E]-2-4F-14 | Ac-**E**WFKAFADKVADKFK**E**YF-$NH_2$ (SEQ ID NO: 191) |

TABLE 4-continued

| 18 amino acid length class A amphipathic helical peptides. | |
|---|---|
| Name | Sequence |
| [Switch D-E]-3-4F-14 | Ac-DWFKAFA**E**KVA**D**KFKEYF-$NH_2$ (SEQ ID NO: 192) |
| [Switch D-E]-4-4F | Ac-DWFKAFA**E**KVAEKFK**D**YF-$NH_2$ (SEQ ID NO: 193) |
| [V-10 and A-17 switched] | |
| 4F-15 | Ac-DWFKAFYDK**A**AEKFKE**V**F-$NH_2$ (SEQ ID NO: 194) |
| [Switch D-E]-1-4F-15 | Ac-**E**WFKAFY**E**KAA**D**KFK**D**VF-$NH_2$ (SEQ ID NO: 195) |
| [Switch D-E]-2-4F-15 | Ac-**E**WFKAFYDKAADKFK**E**VF-$NH_2$ (SEQ ID NO: 196) |
| [Switch D-E]-3-4F-15 | Ac-DWFKAFY**E**KAA**D**KFKEVF-$NH_2$ (SEQ ID NO: 197) |
| [Switch D-E]-4-4F-15 | Ac-DWFKAFY**E**KAAEKFK**D**VF-$NH_2$ (SEQ ID NO: 198) |
| [F3 and Y-7 switched] | |
| 4F-16 | Ac-DW**Y**KAF**F**DKVAEKFKEAF-$NH_2$ (SEQ ID NO: 199) |
| [Switch D-E]-1-4F-16 | Ac-**E**WYKAFF**E**KVA**D**KFK**D**AF-$NH_2$ (SEQ ID NO: 200) |
| [Switch D-E]-2-4F-16 | Ac-**E**WYKAFFDKVADKFK**E**AF-$NH_2$ (SEQ ID NO: 201) |
| [Switch D -E]-3-4F-16 | Ac-DWYKAFF**E**KVA**D**KFKEAF-$NH_2$ (SEQ ID NO: 202) |
| [Switch D-E]-4-4F-16 | Ac-DWYKAFF**E**KVAEKFK**D**AF-$NH_2$ (SEQ ID NO: 203) |
| [F-3 and V-10 switched] | |
| 4F-17 | Ac-DW**V**KAFYDK**F**AEKFKEAF-$NH_2$ (SEQ ID NO: 204) |
| [Switch D-E]-1-4F-17 | Ac-**E**WVKAFY**E**KFA**D**KFK**D**AF-$NH_2$ (SEQ ID NO: 205) |
| [Switch D-E]-2-4F-17 | Ac-**E**WVKAFYDKFADKFK**E**AF-$NH_2$ (SEQ ID NO: 206) |
| [Switch D-E]-3-4F-17 | Ac-DWVKAFY**E**KFA**D**KFKEAF-$NH_2$ (SEQ ID NO: 207) |
| [Switch D-E]-4-4F-17 | Ac-DWVKAFY**E**KFAEKFK**D**AF-$NH_2$ (SEQ ID NO: 208) |
| [Y-7 and F-14 switched] | |
| 4F-18 | Ac-DWFKA**F**FDKVAEK**Y**KEAF-$NH_2$ (SEQ ID NO: 209) |
| [Switch D-E]-1-4F-18 | Ac-**E**WFKAFF**E**KVA**D**KYK**D**AF-$NH_2$ (SEQ ID NO: 210) |
| [Switch D-E]-2-4F-18 | Ac-**E**WFKAFFDKVADKYK**E**AF-$NH_2$ (SEQ ID NO: 211) |
| [Switch D-E]-3-4F-18 | Ac-DWFKAFF**E**KVA**D**KYKEAF-$NH_2$ (SEQ ID NO: 212) |
| [Switch D-E]-3-4F-18 | Ac-DWFKAFF**E**KVA**D**KYKEAF-$NH_2$ (SEQ ID NO: 213) |
| [Y-7 and F-18 switched] | |
| 4F-19 | Ac-DWFKAF**F**DKVAEKFKEA**Y**-$NH_2$ (SEQ ID NO: 214) |
| [Switch D-E]-1-4F-19 | Ac-**E**WFKAFF**E**KVA**D**KFK**D**AY-$NH_2$ (SEQ ID NO: 215) |
| [Switch D-E]-2-4F-19 | Ac-**E**WFKAFFDKVADKFK**E**AY-$NH_2$ (SEQ ID NO: 216) |
| [Switch D-E]-3-4F-19 | Ac-DWFKAFF**E**KVA**D**KFKEAY-$NH_2$ (SEQ ID NO: 217) |
| [Switch D-E]-4-4F-19 | Ac-DWFKAFF**E**KVAEKFK**D**AY-$NH_2$ (SEQ ID NO: 218) |
| [V-10 and F-18 switched] | |
| 4F-20 | Ac-DWFKAFYDK**F**AEKFKEA**V**-$NH_2$ (SEQ ID NO: 219) |

TABLE 4-continued

| 18 amino acid length class A amphipathic helical peptides. | |
|---|---|
| Name | Sequence |
| [Switch D-E]-1-4F-20 | Ac-**E**WFKAFY**E**KFA**D**KFK**D**AV-$NH_2$ (SEQ ID NO: 220) |
| [Switch D-E]-2-4F-20 | Ac-**E**WFKAFYDKFADKFK**E**AV-$NH_2$ (SEQ ID NO: 221) |
| [Switch D-E]-3-4F-20 | Ac-DWFKAFY**E**KFA**D**KFKEAV-$NH_2$ (SEQ ID NO: 222) |
| [Switch D-E]-4-4F-20 | Ac-DWFKAFY**E**KFAEKFK**D**AV-$NH_2$ (SEQ ID NO: 223) |
| [W-2 and K13 switched] | |
| 4F-21 | Ac-D**K**FKAFYDKVAEKF**W**EAF-$NH_2$ (SEQ ID NO: 224) |
| [Switch D-E]-1-4F-21 | Ac-**E**KFKAFY**E**KVA**D**KFW**D**AF-$NH_2$ (SEQ ID NO: 225) |
| [Switch D-E]-2-4F-21 | Ac-**E**KFKAFYDKVADKFW**E**AF-$NH_2$ (SEQ ID NO: 226) |
| [Switch D-E]-3-4F-21 | Ac-DKFKAFY**E**KVA**D**KFWEAF-$NH_2$ (SEQ ID NO: 227) |
| [Switch D-E]-4-4F-21 | Ac-DKFKAFY**E**KVAEKFW**D**AF-$NH_2$ (SEQ ID NO: 228) |
| [W-3, F-13 and K-2 4F] | |
| 4F-22 | Ac-D**KW**KAFYDKVAEKF**F**EAF-$NH_2$ (SEQ ID NO :229) |
| [Switch D-E]-1-4F-22 | Ac-**E**KWKAFY**E**KVA**D**KFF**D**AF-$NH_2$ (SEQ ID NO: 230) |
| [Switch D-E]-2-4F-22 | Ac-**E**KWKAFYDKVADKFF**E**AF-$NH_2$ (SEQ ID NO: 231) |
| [Switch D-E]-3-4F-22 | Ac-DKWKAFY**E**KVA**D**KFFEAF-$NH_2$ (SEQ ID NO: 232) |
| [Switch D-E]-4-4F-22 | Ac-DKWKAFYEKVA**E**KFF**D**AF-$NH_2$ (SEQ ID NO: 233) |
| [K-2, W10, V-13] | |
| 4F-23 | Ac-DKF**K**AFYDK**W**AE**V**FKEAF-$NH_2$ (SEQ ID NO: 234) |
| [Switch D-E]-4F analogs | |
| [Switch D-E]-1-4F-23 | Ac-**E**KFKAFY**E**KWA**D**VFK**D**AF-$NH_2$ (SEQ ID NO: 235) |
| [Switch D-E]-2-4F-23 | Ac-**E**KFKAFYDKWADVFK**E**AF-$NH_2$ (SEQ ID NO: 236) |
| [Switch D-E]-3-4F-23 | Ac-DKFKAFY**E**KWA**D**VFKEAF-$NH_2$ (SEQ ID NO: 237) |
| [Switch D-E]-4-4F-23 | Ac-DKFKAFY**E**KWAEVFK**D**AF-$NH_2$ (SEQ ID NO: 238) |
| [K-2, F-13, W-14 4F] | |
| 4F-24 | Ac-D**K**FKAFYDKVAE**FW**KEAF-$NH_2$ (SEQ ID NO: 239) |
| [Switch D-E]-4F analogs | |
| [Switch D-E]-1-4F-24 | Ac-**E**KFKAFY**E**KVA**D**FWK**D**AF-$NH_2$ (SEQ ID NO :240) |
| [Switch D-E]-2-4F-24 | Ac-**E**KF1CAFYDKVADFWK**E**AF-$NH_2$ (SEQ ID NO: 241) |
| [Switch D-E]-3-4F-24 | Ac-DKFKAFY**E**KVA**D**FWKEAF-$NH_2$ (SEQ ID NO: 242) |
| [Switch D-E]-4-4F-24 | Ac-DKFKAFY**E**KVAEFWK**D**AF-$NH_2$ (SEQ ID NO: 243) |
| Reverse 4F analogs | |
| Rev-4F | Ac-FAEKFKEAVKDYFAKFWD-$NH_2$ (SEQ ID NO: 244) |
| [Switch D-E]-1-Rev-4F | Ac-FA**D**KFK**D**AVK**E**YFAKFW**E**-$NH_2$ (SEQ ID NO: 245) |
| [Switch D-E]-2-Rev-4F | Ac-FA**D**KFKEAVKDYFAKFW**E**-$NH_2$ (SEQ ID NO: 246) |

TABLE 4-continued

| 18 amino acid length class A amphipathic helical peptides. | |
|---|---|
| Name | Sequence |
| [Switch D-E]-3-Rev-4F | Ac-FAEKFK**D**AVKEYFAKFWD-$NH_2$ (SEQ ID NO: 247) |
| [Switch D-E]-4-Rev-4F | Ac-FAEKFK**D**AVKDYFAKFW**E**-$NH_2$ (SEQ ID NO: 248) |
| [A-2 and W-17 switched] | |
| Rev-4F -1 | Ac-F**W**EKFKEAVKDYFAKF**A**D-$NH_2$ (SEQ ID NO: 249) |
| [Switch D-E]-1-Rev-4F-1 | Ac-FW**D**KFK**D**AVK**E**YFAKFA**E**-$NH_2$ (SEQ ID NO: 250) |
| [Switch D-E]-2-Rev-4F-1 | Ac-FA**D**KFKEAVKDYFAKFW**E**-$NH_2$ (SEQ ID NO: 251) |
| [Switch D-E]-3-Rev-4F-1 | Ac-FAEKFK**D**AVK**E**YFAKFWD-$NH_2$ (SEQ ID NO: 252) |
| [Switch D-E]-4-Rev-4F-1 | Ac-FAEKFK**D**AVKDYFAKFW**E**-$NH_2$ (SEQ ID NO: 253) |
| [Switch A-2 and F-16] | |
| Rev-4F-2 | Ac-F**F**EKFKEAVKDYFAK**A**WD-$NH_2$ (SEQ ID NO :254) |
| [Switch D-E]-1-Rev-4F-2 | Ac-FF**D**KFK**D**AVK**E**YFAKAW**E**-$NH_2$ (SEQ ID NO: 255) |
| [Switch D-E]-2-Rev-4F-2 | Ac-FF**D**KFKEAVKDYFAKAW**E**-$NH_2$ (SEQ ID NO: 256) |
| [Switch D-E]-3-Rev-4F-2 | Ac-FFEKFK**D**AVK**E**YFAKAWD-$NH_2$ (SEQ ID NO: 257) |
| [Switch D-E]-4-Rev-4F-2 | Ac-FFEKFK**D**AVKDYFAKAW**E**-$NH_2$ (SEQ ID NO: 258) |
| [switch F-5 and A-8] | |
| Rev-4F-3 | Ac-FAEK**A**KE**F**VKDYFAKFWD-$NH_2$ (SEQ ID NO: 259) |
| [Switch D-E]-1-Rev-4F-3 | Ac-FA**D**KAK**D**FVK**E**YFAKFW**E**-$NH_2$ (SEQ ID NO: 260) |
| [Switch D-E]-2-Rev-4F-3 | Ac-FA**D**KAKEFVKDYFAKFW**E**-$NH_2$ (SEQ ID NO: 261) |
| [Switch D-E]-3-Rev-4F-3 | Ac-FAEKAK**D**FVK**E**YFAKFWD-$NH_2$ (SEQ ID NO: 262) |
| [Switch D-E]-4-Rev-4F-3 | Ac-FAEKAK**D**FVKDYFAKFW**E**-$NH_2$ (SE0 ID NO: 263) |
| [Switch A-8 and V9] | |
| Rev-4F-4 | Ac-FAEKFKE**VA**KDYFAKFWD-$NH_2$ (SEQ ID NO: 264) |
| [Switch D-E]-1-Rev-4F-4 | Ac-FA**D**KFK**D**VAK**E**YFAKFW**E**-$NH_2$ (SEQ ID NO: 265) |
| [Switch D-E]-2-Rev-4F-4 | Ac-FA**D**KFKEVAKDYFAKFW**E**-$NH_2$ (SEQ ID NO: 266) |
| [Switch D-E]-3-Rev-4F-4 | Ac-FAEKFK**D**VAK**E**YFAKFWD-$NH_2$ (SEQ ID NO: 267) |
| [Switch D-E]-4-Rev-4F-4 | Ac-FAEKFK**D**VAKDYFAKFW**E**-$NH_2$ (SEQ ID NO: 268) |
| [Switch V-9 to Y-12] | |
| Rev-4F-5 | Ac-FAEKFKEA**Y**KD**V**FAKFWD-$NH_2$ (SEQ ID NO: 267) |
| [Switch D-E]-1-Rev-4F-5 | Ac-FA**D**KFK**D**AYK**E**VFAKFW**E**-$NH_2$ (SEQ ID NO: 268) |
| [Switch D-E]-2-Rev-4F-5 | Ac-FA**D**KFKEAYKDVFAKFW**E**-$NH_2$ (SEQ ID NO: 269) |
| [Switch D-E]-3-Rev-4F-5 | Ac-FAEKFK**D**AYK**E**VFAKFWD-$NH_2$ (SEQ ID NO: 270) |
| [Switch D-E]-4-Rev-4F-5 | Ac-FAEKFK**D**AYKDVFAKFW**E**-$NH_2$ (SEQ ID NO: 271) |
| [Switch Y-12 and F-13] | |
| Rev-4F-6 | Ac-FAEKFKEAVKD**FY**AKFWD-$NH_2$ (SEQ ID NO: 272) |

TABLE 4-continued

| 18 amino acid length class A amphipathic helical peptides. | |
|---|---|
| Name | Sequence |
| [Switch D-E]-1-Rev-4F-6 | Ac-FA**D**KFK**D**AVK**E**FYAKFW**E**-$NH_2$ (SEQ ID NO: 273) |
| [Switch D-E]-2-Rev-4F-6 | Ac-FA**D**KFKEAVKDFYAKFW**E**-$NH_2$ (SEQ ID NO: 274) |
| [Switch D-E]-3-Rev-4F-6 | Ac-FAEKFK**D**AVK**E**FYAKFWD-$NH_2$ (SEQ ID NO: 275) |
| [Switch D-E]-4-Rev-4F-6 | Ac-FAEKFK**D**AVKDFYAKFW**E**-$NH_2$ (SEQ ID NO: 276) |
| [Switch K-6 and W-17] | |
| Rev-4F-7 | Ac-FAEKF**W**EAVKDYFAKF**K**D-$NH_2$ (SEQ ID NO: 277) |
| [Switch D-E]-1-Rev-4F-7 | Ac-FA**D**KFW**D**AVK**E**YFAKFK**E**-$NH_2$ (SEQ ID NO: 278) |
| [Switch D-E]-2-Rev-4F-7 | Ac-FA**D**KFWEAVKDYFAKFK**E**-$NH_2$ (SEQ ID NO: 279) |
| [Switch D-E]-3-Rev-4F-7 | Ac-FAEKFW**D**AVK**E**YFAKFKD-$NH_2$ (SEQ ID NO: 280) |
| [Switch D-E]-4-Rev-4F-7 | Ac-FAEKFW**D**AVKDYFAKFK**E**-$NH_2$ (SEQ ID NO: 281) |
| [Switch F-1 and A-2] | |
| Rev-4F-8 | Ac-**A F**EKFKEAVKDYFAKFWD-$NH_2$ (SEQ ID NO: 282) |
| [Switch D-E]-1-Rev-4F-8 | Ac-AF**D**KFK**D**AVK**E**YFAKFW**E**-$NH_2$ (SEQ ID NO: 283) |
| [Switch D-E]-2-Rev-4F-8 | Ac-AF**D**KFKEAVKDYFAKFW**E**-$NH_2$ (SEQ ID NO: 284) |
| [Switch D-E]-3-Rev-4F-8 | Ac-AFEKFK**D**AVK**E**YFAKFWD-$NH_2$ (SEQ ID NO: 285) |
| [Switch D-E]-4-Rev-4F-8 | Ac-AFEKFK**D**AVKDYFAKFW**E**-$NH_2$ (SEQ ID NO: 286) |
| [F-1 and V-9 are switched] | |
| Rev-F-9 | Ac-**V**AEKFKEA**F**KDYFAKFWD-$NH_2$ (SEQ ID NO: 287) |
| [Switch D-E]-1-Rev-4F-9 | Ac-VA**D**KFK**D**AFK**E**YFAKFW**E**-$NH_2$ (SEQ ID NO: 288) |
| [Switch D-E]-2-Rev-4F-9 | Ac-VA**D**KFKEAFKDYFAKFW**E**-$NH_2$ (SEQ ID NO: 289) |
| [Switch D-E]-3-Rev-4F-9 | Ac-VAEKFK**D**AFK**E**YFAKFWD-$NH_2$ (SEQ ID NO: 290) |
| [Switch D-E]-4-Rev-4F-9 | Ac-VAEKFK**D**AFKDYFAKFW**E**-$NH_2$ (SEQ ID NO: 291) |
| [F-1 and Y-12 are switched] | |
| Rev-4F -10 | Ac-**Y**AEKFKEAVKD**F**FAKFWD-$NH_2$ (SEQ ID NO: 292) |
| [Switch D-E]-1-Rev-4F-10 | Ac-YA**D**KFK**D**AVK**E**FFAKFW**E**-$NH_2$ (SEQ ID NO: 293) |
| [Switch D-E]-2-Rev-4F-10 | Ac-YA**D**KFKEAVKDFFAKFW**E**-$NH_2$ (SEQ ID NO: 294) |
| [Switch D-E]-3-Rev-4F-10 | Ac-YAEKFK**D**AVK**E**FFAKFWD-$NH_2$ (SEQ ID NO: 295) |
| [Switch D-E]-4-Rev-4F-10 | Ac-YAEKFK**D**AVKDFFAKFW**E**-$NH_2$ (SEQ ID NO: 296) |
| [F-1 and A-8 are switched] | |
| Rev-4F-11 | Ac-**A**AEKFKE**F**VKDYFAKFWD-$NH_2$ (SEQ ID NO: 297) |
| [Switch D-E]-1-Rev-4F-11 | Ac-AA**D**KFK**D**FVK**E**YFAKFW**E**-$NH_2$ (SEQ ID NO: 298) |
| [Switch D-E]-2-Rev-4F-11 | Ac-AA**D**KFKEFVKDYFAKFW**E**-$NH_2$ (SEQ ID NO :299) |
| [Switch D-E]-3-Rev-4F-11 | Ac-AAEKFK**D**FVK**E**YFAKFWD-$NH_2$ (SEQ ID NO: 300) |
| Switch D-E]-4-Rev-4F-11 | Ac-AAEKFKDFVK**D**YFAKFW**E**-$NH_2$ (SEQ ID NO: 301) |

TABLE 4-continued

| 18 amino acid length class A amphipathic helical peptides. | |
|---|---|
| Name | Sequence |
| [A-2 and F-5 are switched] | |
| Rev-4F -12 | Ac-F**F**EK**A**KEAVKDYFAKFWD-$NH_2$ (SEQ ID NO: 302) |
| [Switch D-E]-1-Rev-4F-12 | Ac-FF**D**KAK**D**AVK**E**YFAKFW**E**-$NH_2$ (SEQ ID NO: 303) |
| [Switch D-E]-2-Rev-4F-12 | Ac-FF**D**KAKEAVKDYFAKFW**E**-$NH_2$ (SEQ ID NO: 304) |
| [Switch D-E]-3-Rev-4F-12 | Ac-141-EKAK**D**AVK**E**YFAKFWD-$NH_2$ (SEQ ID NO: 305) |
| [Switch D-E]-4-Rev-4F-12 | Ac-1-1-EKAK**D**AVKDYFAKFW**E**-$NH_2$ (SEQ ID NO: 306) |
| [A-2 and Y12 are switched | |
| Rev-4F -13 | Ac-F**Y**EKFKEAVKD**A**FAKFWD-$NH_2$ (SEQ ID NO: 307) |
| [Switch D-E]-1-Rev-4F-13 | Ac-FY**D**KFK**D**AVK**E**AFAKFW**E**-$NH_2$ (SEQ ID NO: 308) |
| [Switch D-E]-2-Rev-4F-13 | Ac-FY**D**KFKEAVKDAFAKFW**E**-$NH_2$ (SEQ ID NO: 309) |
| [Switch D-E]-3-Rev-4F-13 | Ac-FYEKFK**D**AVK**E**AFAKFWD-$NH_2$ (SEQ ID NO: 310) |
| [Switch D-E]-4-Rev-4F-13 | Ac-FYEKFK**D**AVKDAFAKFW**E**-$NH_2$ (SEQ ID NO: 311) |
| [A-2 and V-9 are switched] | |
| Rev-4F -14 | Ac-F**V**EKFKEA**A**KDYFAKFWD-$NH_2$ (SEQ ID NO: 312) |
| [Switch D-E]-1-Rev-4F-14 | Ac-FV**D**KFK**D**AAK**E**YFAKFW**E**-$NH_2$ (SEQ ID NO: 313) |
| [Switch D-E]-2-Rev-4F-14 | Ac-FV**D**KFKEAAKDYFAKFW**E**-$NH_2$ (SEQ ID NO: 314) |
| [Switch D-E]-3-Rev-4F-14 | Ac-FVEKFK**D**AAK**E**YFAKFWD-$NH_2$ (SEQ ID NO: 315) |
| [Switch D-E]-4-Rev-4F-14 | Ac-FVEKFK**D**AAKDYFAKFW**E**-$NH_2$ (SEQ ID NO: 316) |
| [F-5 and Y-12 are switched] | |
| Rev-4F -15 | Ac-FAEK**Y**KEAVKD**F**FAKFWD-$NH_2$ (SEQ ID NO: 317) |
| [Switch D-E]-1-Rev-4F-15 | Ac-FA**D**KYK**D**AVK**E**FFAKFW**E**-$NH_2$ (SEQ ID NO: 318) |
| [Switch D-E]-2-Rev-4F-15 | Ac-FA**D**KYKEAVKDFFAKFW**E**-$NH_2$ (SEQ ID NO: 319) |
| [Switch D-E]-3-Rev-4F-15 | Ac-FAEKYK**D**AVK**E**FFAKFWD-$NH_2$ (SEQ ID NO: 320) |
| [Switch D-E]-4-Rev-4F-15 | Ac-FAEKYK**D**AVKDFFAKFW**E**-$NH_2$ (SE0 ID NO: 321) |
| [F-5 and V-9 are switched] | |
| Rev-4F -16 | Ac-FAEK**V**KEA**F**KDYFAKFWD-$NH_2$ (SEQ ID NO: 322) |
| [Switch D-E]-1-Rev-4F-16 | Ac-FA**D**KVK**D**AFK**E**YFAKFW**E**-$NH_2$ (SEQ ID NO: 323) |
| [Switch D-E]-2-Rev-4F-16 | Ac-FA**D**KVKEAFKDYFAKFW**E**-$NH_2$ (SEQ ID NO: 324) |
| [Switch D-E]-3-Rev-4F-16 | Ac-FAEKVK**D**AFK**E**YFAKFWD-$NH_2$ (SEQ ID NO: 325) |
| [Switch D-E]-4-Rev-4F-16 | Ac-FAEKVK**D**AFKDYFAKFW**E**-$NH_2$ (SEQ ID NO: 326) |
| [A-8 and Y-12 switched] | |
| Rev-4F -17 | Ac-FAEKFKE**Y**VKD**A**FAKFWD-$NH_2$ (SEQ ID NO: 327) |
| [Switch D-E]-1-Rev-4F-17 | Ac-FA**D**KFK**D**YVK**E**AFAKFW**E**-$NH_2$ (SEQ ID NO: 328) |
| [Switch D-E]-2-Rev-4F-17 | Ac-FA**D**KFKEYVKDAFAKFW**E**-$NH_2$ (SEQ ID NO: 329) |

TABLE 4-continued

| 18 amino acid length class A amphipathic helical peptides. | |
|---|---|
| Name | Sequence |
| [Switch D-E]-3-Rev-4F-17 | Ac-FAEKFK**D**YVK**E**AFAKFWD-$NH_2$ (SEQ ID NO: 330) |
| [Switch D-E]-4-Rev-4F-17 | Ac-FAEKFK**D**YVKDAFAKFW**E**-$NH_2$ (SEQ ID NO: 331) |
| [V-9 and F-13 are switched] | |
| Rev-4F -18 | Ac-FAEKFKEA**F**KDY**V**AKFWD-$NH_2$ (SEQ ID NO: 332) |
| [Switch D-E]-1-Rev-4F-18 | Ac-FA**D**KFK**D**AFK**E**YVAKFW**E**-$NH_2$ (SEQ ID NO: 333) |
| [Switch D-E]-2-Rev-4F-18 | Ac-FA**D**KFKEAFKDYVAKFW**E**-$NH_2$ (SEQ ID NO: 334) |
| [Switch D-E]-3-Rev-4F-18 | Ac-FAEKFK**D**AFK**E**YVAKFWD-$NH_2$ (SEQ ID NO: 335) |
| [Switch D-E]-4-Rev-4F-18 | Ac-FAEKFK**D**AFKDYVAKFW**E**-$NH_2$ (SEQ ID NO: 336) |
| [V-9 and F-16 switched] | |
| Rev-4F -19 | Ac-FAEKFKEA**F**KDYFAK**V**WD-$NH_2$ (SEQ ID NO: 337) |
| [Switch D-E]-1-Rev-4F-19 | Ac-FA**D**KFK**D**AFK**E**YFAKVW**E**-$NH_2$ (SEQ ID NO: 338) |
| [Switch D-E]-2-Rev-4F-19 | Ac-FA**D**KFKEAFKDYFAKVW**E**-$NH_2$ (SEQ ID NO: 339) |
| [Switch D-E]-3-Rev-4F-19 | Ac-FAEKFK**D**AFK**E**YFAKVWD-$NH_2$ (SEQ ID NO: 340) |
| Switch D-E]-4-Rev-4F-19 | Ac-FAEKFK**D**AFKDYFAKVW**E**-$NH_2$ (SEQ ID NO: 341) |
| [Y-12 and F-16 are switched | |
| Rev-4F-20 | Ac-FAEKFKEAVKD**F**FAK**Y**WD-$NH_2$ (SEQ ID NO: 342) |
| [Switch D-E]-1-Rev-4F-20 | Ac-FA**D**KFK**D**AVK**E**FFAKYW**E**-$NH_2$ (SEQ ID NO: 343) |
| [Switch D-E]-2-Rev-4F-20 | Ac-FA**D**KFKEAVKDFFAKYW**E**-$NH_2$ (SEQ ID NO: 344) |
| [Switch D-E]-3-Rev-4F-20 | Ac-FAEKFK**D**AVK**E**FFAKYWD-$NH_2$ (SEQ ID NO: 345) |
| [Switch D-E]-4-Rev-4F-20 | Ac-FAEKFK**D**AVKDFFAKYW**E**-$NH_2$ (SEQ ID NO: 346) |
| [W-1, F-6 and K-17 Rev 4F] | |
| Rev-4F -21 | Ac-**W**AEKFFEAVKDYFAKF**K**D-$NH_2$ (SEQ ID NO: 347) |
| [Switch D-E]-1-Rev-4F-7 | Ac-WA**D**KFF**D**AVKEYFAKF**K**E-$NH_2$ (SEQ ID NO: 348) |
| [Switch D-E]-2-Rev-4F-7 | Ac-WA**D**KFFEAVKDYFAKF**K**E-$NH_2$ (SEQ ID NO: 349) |
| [Switch D-E]-3-Rev-4F-7 | Ac-WAEKFF**D**AVK**E**YFAKFKD-$NH_2$ (SEQ ID NO: 350) |
| Switch D-E]-4-Rev-4F-7 | Ac-WAEKFF**D**AVKDYFAKF**K**E-$NH_2$ (SEQ ID NO: 351) |
| [W-5, F-6 and K-17 Rev-4F] | |
| Rev-4F-22 | Ac-FAEK**WF**EAVKDYFAKF**K**D-$NH_2$ (SEQ ID NO: 352) |
| [Switch D-E]-1-Rev-4F-22 | Ac-FA**D**KWF**D**AVK**E**YFAKF**K**E-$NH_2$ (SEQ ID NO: 353) |
| [Switch D-E]-2-Rev-4F-22 | Ac-FA**D**KWFEAVKDYFAKF**K**E-$NH_2$ (SEQ ID NO: 354) |
| [Switch D-E]-3-Rev-4F-22 | Ac-FAEKWF**D**AVK**E**YFAKFKD-$NH_2$ (SEQ ID NO: 355) |
| [Switch D-E]-4-Rev-4F-22 | Ac-FAEKWF**D**AVKDYFAKF**K**E-$NH_2$ (SEQ ID NO: 356) |
| [V-6, W-9, K-17 Rev-4F] | |
| Rev-4F-23 | Ac-FAEKF**V**EA**W**KDYFAKF**K**D-$NH_2$ (SEQ ID NO: 357) |
| [Switch D-E]-1-Rev-4F-23 | Ac-FA**D**KFV**D**AWK**E**YFAKFK**E**-$NH_2$ (SEQ ID NO: 358) |

TABLE 4-continued

| 18 amino acid length class A amphipathic helical peptides. | |
|---|---|
| Name | Sequence |
| [Switch D-E]-2-Rev-4F-23 | Ac-FADKFVEAWKDYFAKFKE-$NH_2$ (SEQ ID NO: 359) |
| [Switch D-E]-3-Rev-4F-23 | Ac-FAEKFVDAWKEYFAKFKD-$NH_2$ (SEQ ID NO: 360) |
| [Switch D-E]-4-Rev-4F-23 | Ac-FAEKFVDAWKDYFAKFKE-$NH_2$ (SEQ ID NO: 361) |
| [Y-2, A-4, W-12, K-17 Rev-4F] | |
| Rev-4F-24 | Ac-FYEKFAEAVKDWFAKFKD-$NH_2$ (SEQ ID NO: 362) |
| [Switch D-E]-1-Rev-4F-24 | Ac-FYDKFADAVKEWFAKFKE-$NH_2$ (SEQ ID NO: 363) |
| [Switch D-E]-2-Rev-4F-24 | Ac-FYDKFAEAVKDWFAKFKE-$NH_2$ (SEQ ID NO: 364) |
| [Switch D-E]-3-Rev-4F-24 | Ac-FYEKFADAVKEWFAKFKD-$NH_2$ (SEQ ID NO: 365) |
| [Switch D-E]-4-Rev-4F-24 | Ac-FYEKFADAVKDWFAKFKE-$NH_2$ (SEQ ID NO: 366) |

It is possible to readily identify biologically active and useful peptides. Thus, for example, the following peptides have been accurately identified as active: 3F1; 3F2; 4F the reverse (retro) forms thereof and the retro-inverso forms thereof. Lipid-associating peptides can comprise a peptide that is 18 amino acids in length and forms a class A amphipathic helix where the peptide has the amino acid composition 2 aspartates, 2 glutamates, 4 lysines, 1 tryptophan, 1 tyrosine, no more than one leucine, no more than 1 valine, no less than 1 and no more than 3 alanines, and with 3 to 6 amino acids from the group: phenylalanine, alpha-naphthalanine, beta-naphthalanine, histidine, and contains either 9 or 10 amino acids on the polar face in a helical wheel representation of the class A amphipathic helix including 4 amino acids with positive charge at neutral pH with two of the positively charged residues residing at the interface between the polar and non-polar faces and with two of the four positively charged residues on the polar face that are contiguous and on the non-polar face two of the amino acid residues from the group: phenylalanine, alpha-naphthalanine, beta-naphthalanine, histidine are also contiguous and if there are 4 or more amino acids from this group on the non-polar face there are also at least 2 residues from this group that are not contiguous. In some instances, all of the acidic amino acids are glutamic acid rather than having two aspartic acids and two glutamic acids. In some aspects, the lipid associating peptide can be 18A, wherein each of the acidic amino acids of 18A are Glu residues.

Certain class Y as well as class A amphipathic helical peptides are disclosed. Class Y amphipathic helical peptides are known to those of skill in the art (see, e.g., Segrest et al. (1992) J. Lipid Res. 33: 141-166; Oram and Heinecke (2005) Physiol Rev. 85: 1343-1372, and the like). These peptides include, but are not limited to, an 18 amino acid peptide that forms a class A amphipathic helix or a class Y amphipathic helix described by formula I:

(SEQ ID NO: 367)
D X X K Y X X D K X Y D K X K D Y X (I)

where the D's are independently Asp or Glu; the Ks are independently Lys or Arg; the Xs are independently Leu, nor Leu, Val, Ile, Trp, Phe, Tyr, β-Nal, or α-Nal and all X residues are on the non-polar face (e.g., when viewed in a helical wheel diagram) except for one that can be on the polar face between two K residues; the Y's are independently Ala, His, Ser, Gln, Asn, or Thr non-polar face (e.g., when viewed in a helical wheel diagram) and the Y's are independently one Ala on the polar face, one His, one Ser, one Gln one Asn, or one Thr on the polar face (e.g., when viewed in a helical wheel diagram), where no more than two K are be contiguous (e.g., when viewed in a helical wheel diagram); and where no more than 3 D's are contiguous (e.g., when viewed in a helical wheel diagram) and the fourth D is be separated from the other D's by a Y. Representative peptides of this kind which include peptides with histidine, and/or alpha- and/or beta-napthalanine are shown in Table 5. Reverse (retro-), inverse, retro-inverso-, and circularly permuted forms of these peptides are also contemplated.

TABLE 5

| Class Y Amphipathic Helical Peptides. | |
|---|---|
| Short Name | Peptide Sequence |
| [A-5 > H]4F | Ac-DWFKHFYDKVAEKFKEAF-$NH_2$ (SEQ ID NO: 368) |
| [A-5 > H, D-E switched] 4F | Ac-EWFKHFYEKVADKFKDAF-$NH_2$ (SEQ ID NO: 369) |
| [A-5 > H, D-1 > E]4F | Ac-EWFKHFYDKVAEKFKEAF-$NH_2$ (SEQ ID NO: 370) |
| [A-5 > H, D-8 > E]4-F | Ac-DWFKHFYEKVAEKFKEAF-$NH_2$ (SEQ ID NO: 371) |
| [A-5 > H, E-12 > D]4F | Ac-DWFKHFYDKVADKFKEAF-$NH_2$ (SEQ ID NO: 372) |
| [A-5 > H, E-16 > D]4F | Ac-DWFKHFYDKVAEKFKDAF-$NH_2$ (SEQ ID NO: 373) |
| [F-3 > H, A-5 > F]-4F | Ac-DWHKFFYDKVAEKFKEAF-$NH_2$ (SEQ ID NO: 374) |
| [F-3 > H, A-5 > F, D-E switched]-4F | Ac-EWHKFFYEKVADKFKDAF-$NH_2$ (SEQ ID NO: 375) |

TABLE 5-continued

| Class Y Amphipathic Helical Peptides. | |
|---|---|
| Short Name | Peptide Sequence |
| [F-3 > H, A-5 > F, D-1 > E]-4F | Ac-EWHKFFYDKVAEKFKEAF-$NH_2$ (SEQ ID NO: 376) |
| [F-3 > H, A-5 > F, D-8 > E]-4F | Ac-DWHKFFYEKVAEKFKEAF-$NH_2$ (SEQ ID NO: 377) |
| [F-3 > H, A-5 > F, E- 12 > D]-4F | Ac-DWHKFFYDKVADKFKEAF-$NH_2$ (SEQ ID NO: 378) |
| [F-3 > H, A-5 > F, E-16 > D]-4F | Ac-DWHKFFYDKVAEKFKDAF-$NH_2$ (SEQ ID NO: 379) |
| [A-5 > F, F-6 > H]4F | Ac-DWFKFHYDKVAEKFKEAF-$NH_2$ (SEQ ID NO: 380) |
| [A-5 > F, F-6 > H, D-E switched]4F | Ac-EWFKFHYEKVADKFKDAF-$NH_2$ (SEQ ID NO: 381) |
| [[A-5 > F, F-6 > H, D- 1 > E]4F | Ac-EWFKFHYDKVAEKFKEAF-$NH_2$ (SEQ ID NO: 382) |
| [A-5 > F, F-6 > H, D-8 > E]4F | Ac-DWFKFHYEKVAEKFKEAF-$NH_2$ (SEQ ID NO: 383) |
| [A-5 > F, F-6 > H, E-12 > D]4F | Ac-DWFKFHYDKVADKFKEAF-$NH_2$ (SEQ ID NO: 384) |
| [A-5 > F, F-6 > H, E- 16 > D]4F | Ac-DWFKFHYDKVAEKFKDAF-$NH_2$ (SEQ ID NO: 385) |
| [A-5 > V, V-10 > H]4F | Ac-DWFKVFYDKHAEKFKEAF-$NH_2$ (SEQ ID NO: 386) |
| [A-5 > V, V-10 > H, D-E switched]4F | Ac-EWFKVFYEKHADKFKDAF-$NH_2$ (SEQ ID NO: 387) |
| [A-5 > V, V-10 > H, D-1 > E]4F | Ac-EWFKVFYDKHAEKFKEAF-$NH_2$ (SEQ ID NO: 388) |
| [A-5 > V, V-10 > H, D-8 > E]4F | Ac-DWFKVFYEKHAEKFKEAF-$NH_2$ (SEQ ID NO: 389) |
| [A-5 > V, V-10 > H, E-12 > D]4F | Ac-DWFKVFYDKHADKFKEAF-$NH_2$ (SEQ ID NO: 390) |
| [A-5 > V, V-10 > H, E16 > D]4F | Ac-DWFKVFYDKHAEKFKDAF-$NH_2$ (SEQ ID NO: 391) |
| [[A-17 > H]4F | Ac-DWFKAFYDKVAEKFKEHF-NHA: (SEQ ID NO: 392) |
| [A-17 > H, D-E switched]4F | Ac-EWFKAFYEKVADKFKDHF-$NH_2$ (SEQ ID NO: 393) |
| [[A-17 > H, D-1 > E]4F | Ac-EWFKAFYDKVAEKFKEHF-$NH_2$ (SEQ ID NO: 394) |
| [[A-17 > H, D-8 > E]4F | Ac-DWFKAFYEKVAEKFKEHF-$NH_2$ (SEQ ID NO: 395) |
| [[A-17 > H, E-12 > D]4F | Ac-DWFKAFYDKVADKFKEHF-$NH_2$ (SEQ ID NO: 396) |
| [[A-17 > H, E16 > D]4F | Ac-DWFKAFYDKVAEKFKDHF-$NH_2$ (SEQ ID NO: 397) |
| [A-17 > F, F-18 > H]4F | Ac-DWFKAFYDKVAEKFKEFH-$NH_2$ (SEQ ID NO: 398) |
| [A-17 > F, F-18 > H, D-E switched]4F | Ac-EWFKAFYEKVADKFKDFH-$NH_2$ (SEQ ID NO: 399) |
| [A-17 > F, F-18 > H, D-1 > E]-4F | Ac-EWFKAFYDKVAEKFKEFH-$NH_2$ (SEQ ID NO: 400) |

TABLE 5-continued

| Class Y Amphipathic Helical Peptides. | |
|---|---|
| Short Name | Peptide Sequence |
| [A-17 > F, F-18 > H]4F | Ac-DWFKAFYDKVAEKFKEFH-$NH_2$ (SEQ ID NO: 401) |
| [A-17 > F, F-18 > H, D-8 > E]-4F | Ac-DWFKAFYEKVAEKFKEFH-$NH_2$ (SEQ ID NO: 402) |
| [A-17 > F, F-18 > H, E-12 > D]4F | Ac-DWFKAFYDKVAEKFKEFH-$NH_2$ (SEQ ID NO: 403) |
| [A-17 > F, F-1 8 > H], E-16 > D]-4F | Ac-DWFKAFYDKVAEKFKDFH-$NH_2$( (SEQ ID NO: 404) |
| Rev-4F | Ac-FAEKFKEAVKDYFAKFWD-$NH_2$ (SEQ ID NO: 405) |
| [A-2 > H]Rev4F | Ac-FHEKFKEAVKDYFAKFWD-$NH_2$ (SEQ ID NO: 406) |
| Rev-[A-2 > H, D > E]-4F | Ac-FHEKFKEAVKEYFAKFWE-$NH_2$ (SEQ ID NO: 407) |
| Rev-[A-2 > H, E > D]4F | Ac-FHDKFKDAVKDYFAKFWD-$NH_2$ (SEQ ID NO: 408) |
| [A-2 > H, D-E switched]Rev-4F | Ac-FHDKFKDAVKEYFAKFWE-$NH_2$ (SEQ ID NO: 409) |
| [A-2 > H, E-3 > D]Rev-4F | Ac-FHDKFKEAVKDYFAKFWD-$NH_2$ (SEQ ID NO: 410) |
| [A-2 > H, E-7 > D]Rev-4F | Ac-FHEKFKDAVKDYFAKFWD-$NH_2$ (SEQ ID NO: 411) |
| [A-2 > 2H, D-11 > E]Rev-4F | Ac-FHEKFKEAVKEYFAKFWD-$NH_2$ (SEQ ID NO: 412) |
| [A-2 > H, D-18 > E]Rev-4F | Ac-FHEKFKEAVKDYFAKFWE-$NH_2$ (SEQ ID NO: 413) |
| [F-1 > H, A-2 > F]Rev-4F | Ac-HFEKFKEAVKDYFAKFWD-$NH_2$ (SEQ ID NO: 414) |
| [F-1 > H, A-2 > F, D-E switched]Rev-4F | Ac-HFDKFKDAVKEYFAKFWE-$NH_2$ (SEQ ID NO: 415) |
| [F-1 > H, A-2 > F, D > E]Rev-4F | Ac-HFEKFKEAVKEYFAKFWE-$NH_2$ (SEQ ID NO: 416) |
| [F-1 > H, A-2 > F, E-3 > D]Rev-4F | Ac-HFDKFKEAVKDYFAKFWD-$NH_2$ (SEQ ID NO: 417) |
| [F-1 > H, A-2 > F, E-7 > D]Rev-4F | Ac-HFEKFKDAVKDYFAKFWD-$NH_2$ (SEQ ID NO: 418) |
| [F-1 > H, A-2 > F, D-11 > E]Rev-4F | Ac-HFEKFKEAVKEYFAKFWD-$NH_2$ (SEQ ID NO: 419) |
| [F-1 > H, A-2 > F, D-18 > E]Rev-4F | Ac-HFEKFKEAVKDYFAKFWE-$NH_2$ (SEQ ID NO: 420) |
| [A-2 > F, F-5 > H]Rev D-4F | Ac-FFEKHKEAVKDYFAKFWD-$NH_2$ (SEQ ID NO: 421) |
| [A-2 > F, F-5 > H, D-E switched] Rev D-4F | Ac-FFDKHKDAVKEYFAKFWE-$NH_2$ (SEQ ID NO: 422) |
| [A-2 > F, F-5 > H, D > E]Rev D-4F | Ac-FFEKHKEAVKEYFAKFWE-$NH_2$ (SEQ ID NO: 423) |
| [A-2 > F, F-5 > H, E > D]Rev D-4F [ | Ac-FFDKHKDAVKDYFAKFWD-$NH_2$ (SEQ ID NO: 424) |
| A-2 > F, F-5 > H, E-3 > D]Rev | Ac-FFDKHKEAVKDYFAKFWD-$NH_2$ (SEQ ID NO: 425) |

TABLE 5-continued

| Class Y Amphipathic Helical Peptides. | |
|---|---|
| Short Name | Peptide Sequence |
| D-4F [A-2 > F, F-5 > H, D-11 > E] Rev D-4F | Ac-FFEKHKEAVKEYFAKFWD-$NH_2$ (SEQ ID NO: 426) |
| [A-2 > F, F-5 > H, D-18 > E]Rev D-4F | Ac-FFEKHKEAVKDYFAKFWE-$NH_2$ (SEQ ID NO: 427) |
| [A-2 > V, V-9 > H]Rev D-4F | Ac-FVEKFKEAHKDYFAKFWD-$NH_2$ (SEQ ID NO: 428) |
| [A-2 > V, V-9 > H, D- E switched] Rev D-4 | Ac-FVDKFKDAHKEYFAKFWE-$NH_2$ (SEQ ID NO: 429) |
| [A-2 > V, V-9 > H, D > E]Rev D-4F | Ac-FVEKFKEAHKEYFAKFWE-$NH_2$ (SEQ ID NO: 430) |
| [A-2 > V, V-9 > H, E > D]Rev D-4F | Ac-FVDKFKDAHKDYFAKFWD-$NH_2$ (SEQ ID NO: 431) |
| [A-2 > V, V-9 > H, E-3 > D]Rev D-4F | Ac-FVDKFKEAHKDYFAKFWD-$NH_2$ (SEQ ID NO: 432) |
| [A-2 > V, V-9 > H, E-7 > D]Rev D-4F | Ac-FVEKFKDAHKDYFAKFWD-$NH_2$ (SEQ ID NO: 433) |
| [A-2 > V, V-9 > H, D-11 > E]Rev D-4F | Ac-FVEKFKEAHKEYFAKFWD-$NH_2$ (SEQ ID NO: 434) |
| [A-2 > V, V-9 > H, D-18 > E]Rev D-4F | Ac-FVEKFKEAHKDYFAKFWE-$NH_2$ (SEQ ID NO: 435) |
| [A-8 > H]Rev-4F | Ac-FAEKFKEHVKDYFAKFWD-$NH_2$ (SEQ ID NO: 436) |
| [A-8 > H, D-E switched]Rev-4F | Ac-FADKFKDHVKEYFAKFWE-$NH_2$ (SEQ ID NO: 437) |
| [A-8 > H, D > E]Rev-4F | Ac-FAEKFKEHVKEYFAKFWE-$NH_2$ (SEQ ID NO: 438) |
| [A-8 > H, E > D]Rev-4F | Ac-FADKFKDHVKDYFAKFWD-$NH_2$ (SEQ ID NO: 439) |
| [A-8 > H, E-3 > D]Rev-4F | Ac-FADKFKEHVKDYFAKFWD-$NH_2$( (SEQ ID NO: 440) |
| [A-8 > H, E-7 > D]Rev-4F | Ac-FAEKFKDHVKDYFAKFWD-$NH_2$ (SEQ ID NO: 441) |
| [A-8 > H, D-11 > E]Rev-4F | Ac-FAEKFKEHVKEYFAKFWD-$NH_2$ (SEQ ID NO: 442) |
| [A-8 > H, D-18 > E]Rev-4F | Ac-FAEKFKEHVKDYFAKFWE-$NH_2$ (SEQ ID NO: 443) |
| [A-8 > F, F-13 > H]Rev-4F | Ac-FAEKFKEFVKDYHAKFWD-$NH_2$ (SEQ ID NO: 444) |
| [A-8 > F, F-13 > H, D-E switched]Rev-4F | Ac-FADKFKDFVKEYHAKFWE-$NH_2$ (SEQ ID NO: 445) |
| [A-8 > F, F-13 > H, E-3 > D]Rev-4F | Ac-FADKFKEFVKDYHAKFWD-$NH_2$ (SEQ ID NO: 446) |
| [A-8 > F, F-13 > H, E-7 > D]Rev-4F | Ac-FAEKFKDFVKDYHAKFWD-$NH_2$ (SEQ ID NO: 447) |
| [A-8 > F, F-13 > H, E > D]Rev-4F | Ac-FADKFKDFVKDYHAKFWD-$NH_2$ (SEQ ID NO: 448) |
| [A-8 > F, F-13 > H, D > E]Rev-4F | Ac-FAEKFKEFVKEYHAKFWE-$NH_2$ (SEQ ID NO: 449) |
| [A-8 > F, F-13 > H, D-11 > E]Rev-4F | Ac-FAEKFKEFVKEYHAKFWD-$NH_2$ (SEQ ID NO: 450) |

TABLE 5-continued

| Class Y Amphipathic Helical Peptides. | |
|---|---|
| Short Name | Peptide Sequence |
| [A-8 > F, F-13 > H, D-18 > E]Rev-4F | Ac-FAEKFKEFVKDYHAKFWE-$NH_2$ (SEQ ID NO: 451) |
| [A-8 > F, F16 > H]Rev-4F | Ac-FAEKFKEFVKDYFAKHWD-$NH_2$ (SEQ ID NO: 452) |
| [A-8 > F, F16 > H, D-E switched]Rev-4F | Ac-FADKFKDFVKEYFAKHWE-$NH_2$ (SEQ ID NO: 453) |
| [A-8 > F, F16 > H, D > E]Rev-4F | Ac-FAEKFKEFVKEYFAKHWE-$NH_2$ (SEQ ID NO: 454) |
| [A-8 > F, F16 > H, E > D]Rev-4F | Ac-FADKFKDFVKDYFAKHWD-$NH_2$ (SEQ ID NO: 455) |
| [A-8 > F, F16 > H, E- 3 > D]Rev-4F | Ac-FADKFKEFVKDYFAKHWD-$NH_2$ (SEQ ID NO: 456) |
| [A-8 > F, F16 > H, E-7 > D]Rev-4F | Ac-FAEKFKDFVKDYFAKHWD-$NH_2$ (SEQ ID NO: 457) |
| [A-8 > F, F16 > H, D- 11 > E]Rev-4F | Ac-FAEKFKEFVKEYFAKHWD-$NH_2$ (SEQ ID NO: 458) |
| [A-8 > F, F16 > H, D-18 > E]Rev-4F | Ac-FAEKFKEFVKDYFAKHWE-$NH_2$ (SEQ ID NO: 459) |

Examples of class A 4F and Rev 4F analogs with beta-Nph. Similarly, alpha-Nph analogs can be designed. Similarly to the above analogs, His can be incorporated to Nph analogs. D>E analogs, E>D analogs and D–E switch analogs are additional possibilities similarly to the above described analogs.

4Nph
(SEQ ID NO: 460)
Ac-DWNphKANphYDKVAEKNphKEANph-NH2

[D-E switched] 4Nph
(SEQ ID NO: 461)
Ac-EWNphKANphYEKVADKNphKDANph-NH2

[D > E]4Nph
(SEQ ID NO: 462)
Ac-EWNphKANphYEKVAEKNphKEANph-NH2

[E > D]4Nph
(SEQ ID NO: 463)
Ac-DWNphKANphYDKVADKNphKDANph-NH2

[D-1 > E]4Nph
(SEQ ID NO: 464)
Ac-EWNphKANphYDKVAEKNphKEANph-NH2

[D-8 > E]4Nph
(SEQ ID NO: 465)
Ac-DWNphKANphYEKVAEKNphKEANph-NH2

[E-12 > D]4Nph
(SEQ ID NO: 466)
Ac-DWNphKANphYDKVADKNphKEANph-NH2

[E-16 > D]4Nph
(SEQ ID NO: 467
Ac-DWNphKANphYDKVAEKNphKDANph-NH2

As described above for 4 Nph, a minimum of 7 additional analogs for each of the analogs given below.

[F-3, 6, > Nph]4F
(SEQ ID NO: 468)
Ac-DWNphKANphYDKVAEKFKEAF-NH2

[F-14, 18 > Nph]4F
(SEQ ID NO: 469)
Ac-DWFKAFYDKVAEKNphKEANph-NH2

[[F-3 > Nph]4F
(SEQ ID NO: 470)
Ac-DWNphKAFYDKVAEKFKEAF-NH2

[F-6 > Nph]4F
(SEQ ID NO: 471)
Ac-DWFKANphYDKVAEKFKEAF-NH2

[F-14 > Nph]4F
(SEQ ID NO: 472)
Ac-DWFKAFYDKVAEKNphKEAF-NH2

[F-18 > Nph]4F
(SEQ ID NO: 473)
Ac-DWFKAFYDKVAEKFKEANph-NH2

For each of the analog described below, a minimum of 7 additional analogs are possible as described above by switching D–E, D>E and E>D and single D or E analogs.

Rev-4Nph
(SEQ ID NO: 474)
Ac-NphAEKNphKEAVKDYNphAKNphWD-NH2

[F-3, 6 > Nph]Rev
(SEQ ID NO: 475)
Ac-NphAEKNphKEAVKDYFAKFWD-NH2

4F [F-13, 16]Rev-4F
(SEQ ID NO: 476)
Ac-FAEKFKEAVKDYNphAKNphWD-NH2

-continued

[F-3 > Nph]Rev-4F
(SEQ ID NO: 477)
Ac-NphAEKFKEAVKDYFAKFWD-NH2

[F-6 > Nph]Rev-4F
(SEQ ID NO: 478)
Ac-FAEKNphKEAVKDYFAKFWD-NH2

[F-13 > Nph]Rev-4F
(SEQ ID NO: 479)
Ac-FAEKFKEAVKDYNphAKFWD-NH2

[F-16 > Nph]Rev-4F
(SEQ ID NO: 480)
Ac-FAEKEKEAVKDYFAKNphWD-NH2

For the analogs described below, additional analogs are possible by incorporating His or alpha-Nph and beta-Nph Rev-[D > E]-4F
(SEQ ID NO: 481)
Ac-FAEKFKEAVKEYFAKFWE-NH2

Rev-[E > D]4F
(SEQ ID NO: 482)
Ac-FADKFKDAVKDYFAKFWD-NH2

Rev-R4-4F
(SEQ ID NO: 483)
Ac-FAERFREAVKDYFAKFWD-NH2

Rev-R6-4F
(SEQ ID NO: 484)
Ac-FAEKFREAVKDYFAKFWD-NH2

Rev-R10-4F
(SEQ ID NO: 485)
Ac-FAEKFKEAVRDYFAKFWD-NH2

Rev-R14-4F
(SEQ ID NO: 486)
Ac-FAEKFKEAVKDYFARFWD-NH2

Rev-[D > E]-4F
(SEQ ID NO: 481)
Ac-FAEKFKEAVKEYFAKFWE-NH2

Rev-[E > D]4F
(SEQ ID NO: 482)
Ac-FADKFKDAVKDYFAKFWD-NH2

Rev-R4-4F
(SEQ ID NO: 483)
Ac-FAERFREAVKDYFAKFWD-NH2

Rev-R6-4F
(SEQ ID NO: 484)
Ac-FAEKFREAVKDYFAKFWD-NH2

Rev-R10-4F
(SEQ ID NO: 485)
Ac-FAEKFKEAVRDYFAKFWD-NH2

Rev-R14-4F
(SEQ ID NO: 486)
Ac-FAEKFKEAVKDYFARFWD-NH2

Rev-[D > E]-4F
(SEQ ID NO: 481)
Ac-FAEKFKEAVKEYFAKFWE-NH2

Rev-[E > D]4F
(SEQ ID NO: 482)
Ac-FADKFKDAVKDYFAKFWD-NH2

Rev-R4-4F
(SEQ ID NO: 483)
Ac-FAERFREAVKDYFAKFWD-NH2

Rev-R6-4F
(SEQ ID NO: 484)
Ac-FAEKFREAVKDYFAKFWD-NH2

Rev-R10-4F
(SEQ ID NO: 485)
Ac-FAEKFKEAVRDYFAKFWD-NH2

Rev-R14-4F
(SEQ ID NO: 486)
Ac-FAEKFKEAVKDYFARFWD-NH2

Rev-[D > E]-4F
(SEQ ID NO: 481)
Ac-FAEKFKEAVKEYFAKFWE-NH2

Rev-[E > D]4F
(SEQ ID NO: 482)
Ac-FADKFKDAVKDYFAKFWD-NH2

Rev-R4-4F
(SEQ ID NO: 483)
Ac-FAERFREAVKDYFAKFWD-NH2

Rev-R6-4F
(SEQ ID NO: 484)
Ac-FAEKFREAVKDYFAKFWD-NH2

Rev-R10-4F
(SEQ ID NO: 485)
Ac-FAEKFKEAVRDYFAKFWD-NH2

Rev-R14-4F
(SEQ ID NO: 486)
Ac-FAEKFKEAVKDYFARFWD-NH2

For each of the analogs below, additional H and Nph analogs are possible using the examples described above. Each analog can yield 7 analogs with the changes described in the examples given above.

Rev3F-2
(SEQ ID NO: 488)
Ac-LFEKFAEAFKDYVAKWKD-NH2

RevR4-3F-2
(SEQ ID NO: 489)
Ac-LFERFAEAFKDYVAKWKD-NH2

RevR10-3F2
(SEQ ID NO: 490)
Ac-LFEKFAEAFRDYVAKWKD-NH2

RevR15-3F-2
(SEQ ID NO: 491)
Ac-LFEKFAEAFKDYVARWKD-NH2

RevR17 3F-2
(SEQ ID NO: 492)
Ac-LFEKFAEAFKDYVAKWRD-NH2

-continued

Rev[D > E]3F2 (SEQ ID NO: 493)
Ac-LFEKFAEAFKEYVAKWKE-NH2

Rev[E > D]3F-2 (SEQ ID NO: 494)
Ac-LFDKFADAFKDYVAKWKD-NH2

Rev-[E3 > D]-3F-2 (SEQ ID NO: 495)
Ac-LFDKFAEAFKDYVAKWKD-NH2

Rev-[E7 > D]-3F-2 (SEQ ID NO: 496)
Ac-LFEKFADAFKDYVAKWKD-NH2

Rev[D11 > E]3F-2 (SEQ ID NO: 497)
Ac-LFEKFAEAFKEYVAKWKD-NH2

Rev-[D18 > E]3F-2 (SEQ ID NO: 498)
Ac-LFEKFAEAFKDYVAKWKE-NH2

Rev3F-1 (SEQ ID NO: 499)
Ac-FAEKAWEFVKDYFAKLKD-NH2

RevR4-3F-1 (SEQ ID NO: 500)
Ac-FAERAWEFVKDYFAKLKD-NH2

RevR10-3F-1 (SEQ ID NO: 501)
Ac-FAEKAWEFVKDYFAKLKD-NH2

RevR15-3F-1 (SEQ ID NO: 502)
Ac-FAEKAWEFVKDYFAKLKD-NH2

RevR17-3F-1 (SEQ ID NO: 503)
Ac-FAEKAWEFVKDYFAKLRD-NH2

Rev[D > E]3F-1 (SEQ ID NO: 504)
Ac-FAEKAWEFVKEYFAKLKE-NH2

Rev[E > D]3F-1 (SEQ ID NO: 505)
Ac-FADKAWDFVKDYFAKLKD-NH2

Rev[E3 > D}-3F-1 (SEQ ID NO: 506)
Ac-FADKAWEFVKDYFAKLKD-NH2

Rev[E7 > D]3F-1 (SEQ ID NO: 507)
Ac-FAEKAWDFVKDYFAKLKD-NH2

Rev-[D11 > E]3F-1 (SEQ ID NO: 508)
Ac-FAEKAWEFVKEYFAKLKD-NH2

Rev-[D18 > E]3F-1 (SEQ ID NO: 509)
Ac-FAEKAWEFVKDYFAKLKE-NH2

Rev-5F (SEQ ID NO: 510)
Ac-FFEKFKEFVKDYFAKLWD-NH2

Rev-[D > E]5F (SEQ ID NO: 511)
Ac-FFEKFKEFVKEYFAKLWE-NH2

Rev-[E > D]5F (SEQ ID NO: 512)
Ac-FFDKFKDFVKDYFAKLWD-NH2

-continued

Rev-R4-5F (SEQ ID NO: 513)
Ac-FFERFKEFVKDYFAKLWD-NH2

Rev-R6-5F (SEQ ID NO: 514)
Ac-FFEKFREFVKDYFAKLWD-NH2

Rev-R10-5F (SEQ ID NO: 515)
Ac-FFEKFKEFVRDYFAKLWD-NH2

Rev-R15-5F (SEQ ID NO: 516)
Ac-FFEKFKEFVKDYFARLWD-NH2

Rev-[E3 > D]-5F (SEQ ID NO: 517)
Ac-FFDKFKEFVKDYFAKLWD-NH2

Rev-[E7 > D]5F (SEQ ID NO: 518)
Ac-FFEKFKDFVKDYFAKLWD-NH2

Rev-[D11 > E]-5F (SEQ ID NO: 519)
Ac-FFEKFKEFVKEYFAKLWD-NH2

Rev-[D18 > E]-5F (SEQ ID NO: 520)
Ac-FFEKFKEFVKDYFAKLWE-NH2

Rev-5F-2 (SEQ ID NO: 521)
Ac-FLEKFKEFVKDYFAKFWD-NH2

Rev-[D > E]-5F-2 (SEQ ID NO: 522)
Ac-FLEKFKEFVKEYFAKFWE-NH2

Rev-[E > D]-5F-2 (SEQ ID NO: 523)
Ac-FLDKFKEFVKDYFAKFWD-NH2

Rev-[E3 > D]-5F-2 (SEQ ID NO: 524)
Ac-FLDKFKEFVKDYFAKFWD-NH2

Rev-[E7 > D]-5F-2 (SEQ ID NO: 525)
Ac-FLEKFKDFVKDYFAKFWD-NH2

Rev-[D11 > E]-5F-2 (SEQ ID NO: 526)
Ac-FLEKFKEFVKEYFAKFWD-NH2

Rev-[D18 > E]-5F-2 (SEQ ID NO: 527)
Ac-FLEKFKEFVKDYFAKFWE-NH2

Rev-R4-5F-2 (SEQ ID NO: 528)
Ac-FLERFKEFVKDYFAKFWD-NH2

Rev-R6-5F-2 (SEQ ID NO: 529)
Ac-FLEKFREFVKDYFAKFWD-NH2

RevR10-5F-2 (SEQ ID NO: 530)
Ac-FLEKFKEFVRDYFAKFWD-NH2

Rev-R16-5F-2 (SEQ ID NO: 531)
Ac-FLEKFKEFVKDYFARFWD-NH2

Rev-6F (SEQ ID NO: 532)
Ac-FFEKFKEFFKDYFAKLWD-NH2

-continued

Rev-[D > E]-6F
(SEQ ID NO: 533)
Ac-FFEKFKEFFKEYFAKLWE-NH2

Rev-[E > D]-6F
(SEQ ID NO: 534)
Ac-FFDKFKDFFKDYFAKLWD-NH2

Rev-R4-6F
(SEQ ID NO: 535)
Ac-FFERFKEFFKDYFAKLWD-NH2

Rev-R6-6F
(SEQ ID NO: 536)
Ac-FFEKFREFFKDYFAKLWD-NH2

Rev-R10-6F
(SEQ ID NO: 537)
Ac-FFEKFKEFFRDYFAKLWD-NH2

Rev-R14-6F
(SEQ ID NO: 538)
Ac-FFERFKEFFKDYFARLWD-NH2

Rev-[E3 > D]-6F
(SEQ ID NO: 539)
Ac-FFDKFKEFFKDYFAKLWD-NH2

Rev-[E7 > D]-6F
(SEQ ID NO: 540)
Ac-FFEKEKDFFKDYFAKLWD-NH2

Rev-[D11 > E]-6F
(SEQ ID NO: 541)
Ac-FFEKFKEFFKEYFAKLWD-NH2

Rev-[D18 > E]-6F
(SEQ ID NO: 542)
Ac-FFEKFKEFFKDYFAKLWE-NH2

Rev-4F
(SEQ ID NO: 543)
Ac-FAEKFKEAVKDYFAKFWD-NH2

Rev-[D > E]-4F
(SEQ ID NO: 481)
Ac-FAEKFKEAVKEYFAKFWE-NH2

Rev-[E > D]4F
(SEQ ID NO: 482)
Ac-FADKFKDAVKDYFAKFWD-NH2

Rev-R4-4F
(SEQ ID NO: 483)
Ac-FAERFREAVKDYFAKFWD-NH2

Rev-R6-4F
(SEQ ID NO: 484)
Ac-FAEKFREAVKDYFAKFWD-NH2

Rev-R10-4F
(SEQ ID NO: 485)
Ac-FAEKFKEAVRDYFAKFWD-NH2

Rev-R14-4F
(SEQ ID NO: 486)
Ac-FAEKFKEAVKDYFARFWD-NH2

4F-2
(SEQ ID NO: 544)
Ac-DKWKAVYDKFAEAFKEFF-NH2

[D > E]-4F-2
(SEQ ID NO: 545)
Ac-EKWKAVYEKFAEAFKEFF-NH2

[E > D]-4F-2
(SEQ ID NO: 546)
Ac-DKWKAVYDKFADAFKDFF-NH2

-continued

R2-4F-2
(SEQ ID NO: 547)
Ac-DRWKAVYDKFAEAFKEFF-NH2

R4-4F-2
(SEQ ID NO: 548)
Ac-DKWRAVYDKFAEAFKEFF-NH2

R9-4F-2
(SEQ ID NO: 549)
Ac-DKWKAVYDRFAEAFKEFF-NH2

R14-4F-2
(SEQ ID NO: 550)
Ac-DKWKAVYDKFAEAFREFF-NH2

Rev4F-2
(SEQ ID NO: 551)
Ac-FFEKFAEAFKDYVAKWKD-NH2

Rev-[D > E]-4F-2
(SEQ ID NO: 552)
Ac-FFEKFAEAFKEYVAKWKE-NH2

Rev-[E > D]-3F-2
(SEQ ID NO: 553)
Ac-FFDKFADAFKDYVAKWKD-NH2

Rev-R4-4F-2
(SEQ ID NO: 554)
Ac-FFERFAEAFKDYVAKWKD-NH2

Rev-R10-4F-2
(SEQ ID NO: 555)
Ac-EFERFAEAFRDYVAKWKD-NH2

Rev-R15-4F-2
(SEQ ID NO: 556)
Ac-FFEKFAEAFKDYVARWKD-NH2

Rev-R17-4F-2
(SEQ ID NO: 557)
Ac-FFERFAEAFKDYVAKWRD-NH2

Rev-[E3 > D]-4F-2
(SEQ ID NO: 558)
Ac-FFDKFAEAFKDYVAKWKD-NH2

Rev-[E7 > D]-4F-2
(SEQ ID NO: 559)
Ac-FFEKFADAFKDYVAKWKD-NH2

Rev-[D11 > E]-4F-2
(SEQ ID NO: 560)
Ac-FFERFAEAFKEYVAKWKD-NH2

Rev- [D18 > E]-4F-2
(SEQ ID NO: 561)
Ac-FFERFAEAFKDYVAKWKE-NH2

Rev-7F
(SEQ ID NO: 562)
Ac-FFEKFKEFFKDYFAKFWD-NH2

Rev-[E > D]-7F
(SEQ ID NO: 563)
Ac-FFDKFKDFFKDYFAKFWD-NH2

Rev-[D > E]-7F
(SEQ ID NO: 564)
Ac-FFEKFKEFFKEYFAKFWE-NH2

Rev-R4-7F
(SEQ ID NO: 565)
Ac-FFERFKEFFKDYFAKFWD-NH2

Rev-R6-7F
(SEQ ID NO: 566)
Ac-FFEKFREFFKDYFAKFWD-NH2

-continued

Rev-R10-7F
(SEQ ID NO: 567)
Ac-FFEKFKEFFRDYFAKFWD-NH2

Rev-R14-7F
(SEQ ID NO: 568)
Ac-FFEKFKEFFKDYFARFWD-NH2

Rev-[E3 > D]-7F
(SEQ ID NO: 569)
Ac-FFDKFKEFFKDYFAKFWD-NH2

Rev-[E7 > D]7F
(SEQ ID NO: 570)
Ac-FFEKFKDFFKDYFAKFWD-NH2

Rev-[D11 > E]-7F
(SEQ ID NO: 571)
Ac-FFEKFKEFFKEYFAKFWD-NH2

Rev-[D18 > E]-7F
(SEQ ID NO: 572)
Ac-FFEKFKEFFKDYFAKFWE-NH2

It is also noted that any of the peptides described herein can comprise non-natural amino acids in addition to or instead of the corresponding the natural amino acids identified herein. Such modifications include, but are not limited to acetylation, amidation, formylation, methylation, sulfation, and the like. Illustrative non-natural amino acids include, but are not limited to Ornithine, norleucine, norvaline, N-methylvaline, 6-N-methyllysine, N-methylisoleucine, N-methylglycine, sarcosine, inosine, allo-isoleucine, isodesmolysine, 4-hydroxyproline, 3-hydroxyproline, allo-hydroxylysine, hydoxylisine, N-ethylasparagine, N-ethylglycine, 2,3-diaminopropionic acid, 2,2'-diaminopropionic acid, desmosine, 2,4-diaminobutyric acid, 2-aminopimelic acid, 3-aminoisobutyric acid, 2-aminoisobutyric acid, 2-aminoheptanoic acid, 6-aminocaproic acid, 4-aminobutyric acid, 2-aminobutyric acid, beta-alanine, 3-aminoadipic acid, 2-aminoadipic acid, and the like. In certain embodiments and one or more of the "natural" amino acids of the peptides described herein, can be substituted with the corresponding non-natural amino acid (e.g. as describe above).

In certain embodiments, this invention contemplates particularly the use of modified lysines. Such modifications include, but are not limited to, biotin modification of epsilon lysines and/or methylation of the epsilon lysines. Illustrative peptide comprising epsilon methylated lysines include, but are not limited to: Ac-D-W-F-K($eCH_3$)$_2$-A-F-Y-D-K($eCH_3$)$_2$-V-A-E-K($eCH_3$)-$_2$-F-K($eCH_3$)$_2$-E-A-F-NH($CH_3$)$_2$ (SEQ ID NO:573) and: Ac-DWFK($eCH_3$)$_2$AFYDK($eCH_3$)$_2$VAEK($eCH_3$)$_2$FK($eCH_3$)$_2$EAF-NH($CH_3$) (SEQ ID NO:574). Other modified amino acids include but are not limited to ornithine analogs and homoaminoalanine analogs (instead of $(CH_2)_4$—$NH_2$ for Lys it can be —$(CH_2)_2$—$NH_2$ for Haa and —$(CH_2)_3$—$NH_2$ for Orn] and the like. It is noted that these modifications are illustrative and not intended to be limiting. Illustrative 4F analogues that possess modified amino acids are shown in Table 6.

TABLE 6

| Illustrative 4F analogs that comprise modified amino acids. |
|---|
| εN-Dimethyl-Lys derivative of 4F (εN-Dime) |
| Ac-D-W-F-K(εN-Dime)-A-F-Y-D-K(εN-Dime)-V-A-E-K(εN-Dime)-F-K(εN-Dime)-E-A-F-$NH_2$ (SEQ ID NO: 575)<br>Ac-D-W-F-K-(εN-Dime)-A-F-Y-D-K(εN-Dime)-V-A-E-K(εN-Dime)-F-K((εN- Dime)-E-A-F-NH-Me (SEQ ID NO: 576)<br>Ac-D-W-F-K-(εN-Dime)-A-F-Y-D-K(εN-Dime)-V-A-E-K(εN-Dime)-F-K(εN- Dime)-E-A-F-N-$(Me)_2$ (SEQ ID NO: 577) |
| εN-Diethyl-Lys derivatives of 4F (εN-Diet) |
| Ac-D-W-F-K(εN-Diet)-A-F-Y-D-K(εN-Diet)-V-A-E-K(εN-Diet)-F-K(εN-Diet)- E-A-F-$NH_2$ (SEQ ID NO: 578)<br>Ac-D-W-F-K(εN -Diet)-A-F-Y-D-K(εN -Diet)-V-A-E-K(εN -Diet)-F-K(εN -Diet)- E-A-F-NH-Et (SEQ ID NO: 579)<br>Ac-D-W-F-K(εN -Diet)-A-F-Y-D-K(εN -Diet)-V-A-E-K(εN -Diet)-F-K(εN -Diet)- E-A-F-NH-$(Et)_2$ (SEQ ID NO: 580) |
| εN-Monomethyl-Lys derivative of 4F (εN -Me) |
| Ac-D-W-F-K(EN Me)-A-F-Y-D-K(εN -Me)-V-A-E-K(εN -Me)-F-K(εN-Me)- E-A-F-$NH_2$ (SEQ ID NO: 581)<br>Ac-D-W-F-K(εN -Me)-A-F-Y-D-K(εN -Me)-V-A-E-K(εN -Me)-F-K(εN-Me)- E-A-F-NH-Me (SEQ ID NO: 582)<br>Ac-D-W-F-K(εN -Me)-A-F-Y-D-K(εN -Me)-V-A-E-K(εN -Me)-F-K(εN-Me)- E-A-F-N-$(Me)_2$ (SEQ ID NO: 583) |
| εN-ethylLys derivative of 4F (εN -Et) |
| Ac-D-W-F-K(εN -Et)-A-F-Y-D-K(εN -E0-V-A-E-K(εN -Et)-F-K(εN -Et)-E- A-F-$NH_2$ (SEQ ID NO: 584)<br>Ac-D-W-F-K(εN -Et)-A-F-Y-D-K(εN -E0-V-A-E-K(εN -Et)-F-K(εN -E0-E- A-F-NH-Et (SEQ ID NO: 585)<br>Ac-D-W-F-K(εN -Et)-A-F-Y-D-K(εN -Et)-V-A-E-K(εN -Et)-F-K(εN -Et)-E- A-F-NH-$(Et)_2$ (SEQ ID NO: 586) |
| HomoLys analogs of 4F (hK) $(--CH_2)_5$-$NH_2$ |
| Ac-D-W-F-hK-A-F-Y-D-hK-V-A-E-hK-F-hK-E-A-F-$NH_2$ (SEQ ID NO: 587)<br>Ac-D-W-F-hK(εN-Dime)-A-F-Y-D-hK(εN -Dime)-V-A-E-hK(εN -Dime)-F-hK(εN -Dime)-E-A-F-$NH_2$ (SEQ ID NO: 588) |

TABLE 6-continued

| Illustrative 4F analogs that comprise modified amino acids. |
|---|
| Ac-D-W-F-hK(εN -Dime)-A-F-Y-DhK(εN -Dime)-V-A-E-hK(εN -Dime)-F-hK(εN -Dime)-E-A-F-N-$(Me)_2$ (SEQ ID NO: 589) |
| Ac-D-W-F-hK(εN -Dime)-A -F -Y - D - hK(εN -Dime)-V-A-E-hK(εN -Dime)-F- hK(εN -Dime)-E-A-F-NH-Me (SEQ ID NO: 590) |
| Ac-D-W-F-hK(εN -Diet)-AF-Y-D-hK(εN -Diet)-V-A-E-hK(εN -Diet)-F-hK(εN -Diet)-E-A-F-NH-Et (SEQ ID NO: 591) |
| Ac-D-W-F-hK(εN -Me)-A-F-Y-D-hK(εN -Me)-V-A-E-hK(εN -Me)-F-hK(εN -Me)-E-A-F-$NH_2$ (SEQ ID NO: 592) |
| Ac-D-W-F-hK(εN -Me)-A-F-Y-D-hK(εN -Me)-V-A-E-hK(εN -Me)-F-hK(εN -Me)-E-A-F-NH-Me (SEQ ID NO: 593) |
| Ac-D-W-F-hK(εN -Me)-A-F-Y-D-hK(εN -Me)-V-A-E-hK(εN -Me)-F-hK(εN -Me)-E-A-F-N-$(Me)_2$ (SEQ ID NO: 594) |
| Ac-D-W-F-hK(εN -Et)-A-F-D-hK(εN -Et)-V-A-E-hK(εN -Et)-F-hK(εN -Et)-E-A-F-$NH_2$ (SEQ ID NO: 595) |
| Ac-D-W-F-hK(εN-Et-A-F-Y-D-hK(εN -Et)-V-A-E-hK(εN -Et)-F-hK(εN -Et)-E-A-F-NH-Et (SEQ ID NO: 596) |
| Ac-D-W-F-hK(εN -Et)-A-F-Y-D-hK(εN -Et)-V-A-E-hK(εN -Et)-F-hK(εN -Et)-E-A-F-NH-$(Et)_2$ (SEQ ID NO: 597) |
| 4F analogs in which K is replaced O (O = Ornithine, --$(CH_2)_3$-$NH_2$) |
| Ac-D-W-F-O-A-F-Y-D-O-V-A-E-O-F-O-E-A-F-$NH_2$(SEQ ID NO: 598) |
| Ac-D-W-F-O(δN-Dime)-A-F-Y-D-O(δN-Dime)-V-A-E-O(δN -Dime)-F-O(δN -Dime)-E-A-F-$NH_2$ (SEQ ID NO: 599) |
| Ac-D-W-F-O(δN -Dime)-A-F-Y-D-O(δN-Dime)-V-A-E-O(δN -Dime)-F-O(δN-Dime)-E-A-F-N-$(Me)_2$ (SEQ ID NO: 600) |
| Ac-D-W-F-O(δN -Dime)-A-F-Y-D-O(δN -Dime)-V-A-E-O(δN -Dime)-F-O(δN - Dime)-E-A-F-NH-Me (SEQ ID NO: 601) |
| Ac-D-W-F-O(δN -Diet)-A-F-Y-D-O(δN -Diet)-V-A-E-O(δN -Diet)-F-O(δN - Diet)-E-A-F-NH-Et (SEQ ID NO: 602) |
| Ac-D-W-F-O(δN-Me)-A-F-Y-D-O(δN-Me)-V-A-E-O(δN-Me)-F-O(δN-Me)- E-A-F-$NH_2$ (SEQ ID NO: 603) |
| Ac-D-W-F-O(δN-Me)-A-F-Y-D-O(δN-Me)-V-A-E-O(δN-Me)-F-O(δN-Me)- E-A-F-NH-Me (SEQ ID NO: 604) |
| Ac-D-W-F-O(δN-Me)-A-F-Y-D-O(δN-Me)-V-A-E-O(δN-Me)-F-O(δN-Me)- E-A-F-N-$(Me)_2$ (SEQ ID NO: 605) |
| Ac-D-W-F-O(δN -Et)-A-F-Y-D-O(δN -Et)-V-A-E-O(δN -Et)-F-O(δN -Et)-E- A-F-$NH_2$ (SEQ ID NO: 606) |
| Ac-D-W-F-O(δN -Et)-A-F-Y-D-O(δN -Et)-V-A-E-O(δN -Et)-F-O(δN -Et)-E- A-F-NH-Et (SEQ ID NO: 607) |
| Ac-D-W-F-O(δN -Et)-A-F-Y-D-O(δN-Et)-V-A-E-OdεN-Et)-F-O(δN-Et)-E-A-F-NH-$(Et)_2$ (SEQ ID NO: 608) |

4. Dual Domain Peptides

Dual domain peptides are also disclosed. Dual domain peptides can be synthetic Apo E-mimicking peptides, consisting of a combination of the disclosed receptor binding domains of apolipoprotein E and the disclosed lipid-associating peptides, wherein said receptor binding domain is covalently linked to said lipid-associating peptide.

Also disclosed are synthetic Apo E-mimicking peptides, consisting of a combination of the disclosed receptor binding domains of apolipoprotein B and the disclosed lipid-associating peptides, wherein said receptor binding domain is covalently linked to said lipid-associating peptide. Non-limiting examples of the disclosed synthetic Apo E-mimicking peptides are provided in Table 7. The disclosed synthetic Apo E-mimicking peptides can also be N-terminally protected using acetyl and amino groups. Table 7 provides non-limiting representative examples of the disclosed synthetic Apo E-mimicking peptides comprising a dual domain.

TABLE 7

Dual domain peptides.
Non-limiting Examples of the Disclosed Synthetic Apo E mimetics

| Receptor Binding Domains of Apo E | Lipid-Associating Peptides |
|---|---|
| **LR**KLR**KR**LL**R** (SEQ ID NO: 4) | DWLKAFYDKVAEKLKEAF (SEQ ID NO: 5) |
| **LR**KLR**KR**LL**R** (SEQ ID NO: 4) | DWLKAFYDKVAEKLKEAF (SEQ ID NO: 5) |
| **LR**KLR**KR**LL**R** (SEQ ID NO: 4) | DWLKAFYDKVAEKLKEAF (SEQ ID NO: 5) |
| **LR**K*M*R**KR**L*M***R** (SEQ ID NO: 7) | DWLKAFYDKVAEKLKEAF (SEQ ID NO: 5) |
| **LR**K*M*R**KR**L*M***R** (SEQ ID NO: 7) | DWLKAFYDKVAEKLKEAF (SEQ ID NO: 5) |
| **LR**KL***P***R**KR**LL**R** (SEQ ID NO: 8) | DWLKAFYDKVAEKLKEAF (SEQ ID NO: 5) |

TABLE 7-continued

| Dual domain peptides. Non-limiting Examples of the Disclosed Synthetic Apo E mimetics | |
|---|---|
| Receptor Binding Domains of Apo E | Lipid-Associating Peptides |
| **LR***N*VR**KR**L*V***R** (SEQ ID NO: 9) | DWLKAFYDKVAEKLKEAF (SEQ ID NO: 5) |
| *M*RKLRKR*V*LR (SEQ ID NO: 10) | DWLKAFYDKVAEKLKEAF (SEQ ID NO: 5) |
| **LR***R*LR***R***LL**R** (SEQ ID NO: 11) | DWLKAFYDKVAEKLKEAF (SEQ ID NO: 5) |
| **LR**KLR**KR*FF***FF**R** (SEQ ID NO: 12) | DWLKAFYDKVAEKLKEAF (SEQ ID NO: 5) |
| **LR**KLR**KR**LL**R** (SEQ ID NO: 4) | DWFKAFYDKVAEKFKEAF (SEQ ID NO: 16) |
| **LR**KLR**KR**LL**R** (SEQ ID NO: 4) | DWFKAFYDKVAEKFKEAF (SEQ ID NO: 16) |
| **LR**KLR**KR**LL**R** (SEQ ID NO: 4) | DWFKAFYDKVAEKFKEAF (SEQ ID NO: 16) |
| **LR***K*M**R**KR**L***M***R** (SEQ ID NO: 7) | DWFKAFYDKVAEKFKEAF (SEQ ID NO: 16) |
| **LR***K*M**R**KR**L***M***R** (SEQ ID NO: 7) | DWFKAFYDKVAEKFKEAF (SEQ ID NO: 16) |
| **LR**KL***P***KR**LL**R** (SEQ ID NO: 8) | DWFKAFYDKVAEKFKEAF (SEQ ID NO: 16) |
| **LR***N*VR**KR**L***V***R** (SEQ ID NO: 9) | DWFKAFYDKVAEKFKEAF (SEQ ID NO: 16) |
| *M*RKLRKR*V*LR (SEQ ID NO: 10) | DWFKAFYDKVAEKFKEAF (SEQ ID NO: 16) |
| **LR***R*LR***R***LL**R** (SEQ ID NO: 11) | DWFKAFYDKVAEKFKEAF (SEQ ID NO: 16) |
| **LR**KLR**KR*FF***FF**R** (SEQ ID NO: 12) | DWFKAFYDKVAEKFKEAF (SEQ ID NO: 16) |

i. Domain Switched Peptides

Also disclosed are synthetic Apo E mimetics, consisting of a combination of the disclosed receptor binding domains of apolipoprotein E and the disclosed lipid-associating peptides, wherein said receptor binding domain is covalently linked to said lipid-associating peptide in a domain switched orientation. Also disclosed are synthetic Apo E mimetics, consisting of a combination of the disclosed receptor binding domains of apolipoprotein B and the disclosed lipid-associating peptides, wherein said receptor binding domain is covalently linked to said lipid-associating peptide in a domain switched orientation. These peptides can be referred to as "domain switched" "switched domain", or "switched" peptides. For example, disclosed are synthetic Apo E mimetics, consisting of a combination of the disclosed receptor binding domains of apolipoprotein E and the disclosed lipid-associating peptides, wherein said receptor binding domain is covalently linked to said lipid-associating peptide in a domain switched orientation to those described above and in Table 7. Specifically, the lipid-associating peptide is covalently linked to the receptor binding domain of apolipoprotein E such that the lipid-associating peptide is at the N-terminus of the synthetic apolipoprotein E-mimicking peptide. Table 8 provides non-limiting examples of the disclosed synthetic Apo E mimetics comprising a combination of the disclosed receptor binding domains of apolipoprotein E and the disclosed lipid-associating peptides, wherein said receptor binding domain is covalently linked to said lipid-associating peptide in a domain switched orientation.

TABLE 8

| Domain Switched Peptides. Non-limiting Examples of Disclosed Synthetic Apo E mimetics | |
|---|---|
| Lipid-Associating Peptides | Receptor Binding Domains of ApoE |
| DWLKAFYDKVAEKLKEAF (SEQ ID NO: 5) | **LR**KLR**KR**LL**R** (SEQ ID NO: 6) |
| DWLKAFYDKVAEKLKEAF (SEQ ID NO: 5) | **LR**KLR**KR**LL**R** (SEQ ID NO: 6) |
| DWLKAFYDKVAEKLKEAF (SEQ ID NO: 5) | **LR**KLR**KR**LL**R** (SEQ ID NO: 6) |
| DWLKAFYDKVAEKLKEAF (SEQ ID NO: 5) | **LR***K*M**R**KR**L***M***R** (SEQ ID NO: 7) |
| DWLKAFYDKVAEKLKEAF (SEQ ID NO: 5) | **LR***K*M**R**KR**L***M***R** (SEQ ID NO: 7) |
| DWLKAFYDKVAEKLKEAF (SEQ ID NO: 5) | **LR**KL***P***KR**LL**R** (SEQ ID NO: 8) |
| DWLKAFYDKVAEKLKEAF (SEQ ID NO: 5) | **LR***N*VR**KR**L***V***R** (SEQ ID NO: 9) |
| DWLKAFYDKVAEKLKEAF (SEQ ID NO: 5) | *M*RKLRKR*V*LR (SEQ ID NO: 10) |
| DWLKAFYDKVAEKLKEAF (SEQ ID NO: 5) | **LR***R*LR***R***LL**R** (SEQ ID NO: 11) |
| DWLKAFYDKVAEKLKEAF (SEQ ID NO: 5) | **LR**KLR**KR*FF***FF**R** (SEQ ID NO: 12) |
| DWFKAFYDKVAEKFKEAF (SEQ ID NO: 16) | **LR**KLR**KR**LL**R** (SEQ ID NO: 6) |
| DWFKAFYDKVAEKFKEAF (SEQ ID NO: 16) | **LR**KLR**KR**LL**R** (SEQ ID NO: 6) |
| DWFKAFYDKVAEKFKEAF (SEQ ID NO: 16) | **LR**KLR**KR**LL**R** (SEQ ID NO: 6) |
| DWFKAFYDKVAEKFKEAF (SEQ ID NO: 16) | **LR***K*M**R**KR**L***M***R** (SEQ ID NO: 7) |
| DWFKAFYDKVAEKFKEAF (SEQ ID NO: 16) | **LR***K*M**R**KR**L***M***R** (SEQ ID NO: 7) |
| DWFKAFYDKVAEKFKEAF (SEQ ID NO: 16) | **LR**KL***P***KR**LL**R** (SEQ ID NO: 8) |
| DWFKAFYDKVAEKFKEAF (SEQ ID NO: 16) | **LR***N*VR**KR**L***V***R** (SEQ ID NO: 9) |
| DWFKAFYDKVAEKFKEAF (SEQ ID NO: 16) | *M*RKLRKR*V*LR (SEQ ID NO: 10) |
| DWFKAFYDKVAEKFKEAF (SEQ ID NO: 16) | **LR***R*LR***R***LL**R** (SEQ ID NO: 11) |
| DWFKAFYDKVAEKFKEAF (SEQ ID NO: 16) | **LR**KLR**KR*FF***FF**R** (SEQ ID NO: 12) |

The disclosed domain switched synthetic Apo E mimetics can also be N-terminally protected using acetyl and amino groups.

ii. Peptides with Reverse Orientation

Also disclosed are synthetic Apo E-mimicking peptides, consisting of a combination of the disclosed receptor binding domains of apolipoprotein E and the disclosed lipid-associating peptides, wherein said receptor binding domain is covalently linked to said lipid-associating peptide in a reversed orientation. For example, disclosed are synthetic Apo E-mimicking peptides, consisting of a combination of the disclosed receptor binding domains of apolipoprotein E and the disclosed lipid-associating peptides, wherein either the sequence of the receptor binding domain or the sequence of the lipid-associating peptide or both sequences are in the reversed orientation. Also disclosed are synthetic Apo E-mimicking peptides, consisting of a combination of the disclosed receptor binding domains of apolipoprotein B and the disclosed lipid-associating peptides, wherein said receptor binding domain is covalently linked to said lipid-associating peptide in a reversed orientation. Table 9 provides non-limiting examples of the disclosed synthetic Apo E-mimicking peptides comprising a combination of the disclosed receptor binding domains of apolipoprotein E and the disclosed lipid-associating peptides, wherein said receptor binding domain is covalently linked to said lipid-associating peptide in a reversed orientation.

TABLE 9

Reverse Orientation Peptides. Non-limiting Examples of Synthetic Apo E mimetics

| Receptor Binding Domains of Apo E | Lipid-Associating Peptides |
|---|---|
| RLLRKRLKRL (SEQ ID NO: 609) | DWLKAFYDKVAEKLKEAF (SEQ ID NO: 5) |
| RLLRKRLKRL (SEQ ID NO: 609) | DWLKAFYDKVAEKLKEAF (SEQ ID NO: 5) |
| RLLRKRLKRL (SEQ ID NO: 609) | DWLKAFYDKVAEKLKEAF (SEQ ID NO: 5) |
| RMLRKRMKRL (SEQ ID NO: 610) | DWLKAFYDKVAEKLKEAF (SEQ ID NO: 5) |
| RMLRKRMKRL (SEQ ID NO: 610) | DWLKAFYDKVAEKLKEAF (SEQ ID NO: 5) |
| RLLRKPLKRL (SEQ ID NO: 611) | DWLKAFYDKVAEKLKEAF (SEQ ID NO: 5) |
| RVLRKRVNRL (SEQ ID NO: 612) | DWLKAFYDKVAEKLKEAF (SEQ ID NO: 5) |
| RLVRKRLKRM (SEQ ID NO: 613) | DWLKAFYDKVAEKLKEAF (SEQ ID NO: 5) |
| RLLRRRLRRL (SEQ ID NO: 614) | DWLKAFYDKVAEKLKEAF (SEQ ID NO: 5) |
| RFFRKRLKRL (SEQ ID NO: 615) | DWLKAFYDKVAEKLKEAF (SEQ ID NO: 5) |
| RLLRKRLKRL (SEQ ID NO: 609) | DWFKAFYDKVAEKFKEAF (SEQ ID NO: 16) |
| RLLRKRLKRL (SEQ ID NO: 609) | DWFKAFYDKVAEKFKEAF (SEQ ID NO: 16) |
| RLLRKRLKRL (SEQ ID NO: 609) | DWFKAFYDKVAEKFKEAF (SEQ ID NO: 16) |
| RMLRKRMKRL (SEQ ID NO: 610) | DWFKAFYDKVAEKFKEAF (SEQ ID NO: 16) |
| RMLRKRMKRL (SEQ ID NO: 610) | DWFKAFYDKVAEKFKEAF (SEQ ID NO: 16) |
| RLLRKPLKRL (SEQ ID NO: 611) | DWFKAFYDKVAEKFKEAF (SEQ ID NO: 16) |
| RVLRKRVNRL (SEQ ID NO: 612) | DWFKAFYDKVAEKFKEAF (SEQ ID NO: 16) |
| RLVRKRLKRM (SEQ ID NO: 613) | DWFKAFYDKVAEKFKEAF (SEQ ID NO: 16) |
| RLLRRRLRRL (SEQ ID NO: 614) | DWFKAFYDKVAEKFKEAF (SEQ ID NO: 16) |
| RFFRKRLKRL (SEQ ID NO: 615) | DWFKAFYDKVAEKFKEAF (SEQ ID NO: 16) |
| LRKLRKRLLR (SEQ ID NO: 4) | FAEKLKEAVKDYFAKLWD (SEQ ID NO: 616) |
| LRKLRKRLLR (SEQ ID NO: 4) | FAEKLKEAVKDYFAKLWD (SEQ ID NO: 616) |
| LRKLRKRLLR (SEQ ID NO: 4) | FAEKLKEAVKDYFAKLWD (SEQ ID NO: 616) |
| LRK*M*RKRL*M*R (SEQ ID NO: 7) | FAEKLKEAVKDYFAKLWD (SEQ ID NO: 616) |
| LRK*M*RKRL*M*R (SEQ ID NO: 7) | FAEKLKEAVKDYFAKLWD (SEQ ID NO: 616) |
| LRKL*P*KRLLR (SEQ ID NO: 4) | FAEKLKEAVKDYFAKLWD (SEQ ID NO: 616) |
| LR*N*VRKRL*V*R (SEQ ID NO: 9) | FAEKLKEAVKDYFAKLWD (SEQ ID NO: 616) |
| *M*RKLRKR*V*LR (SEQ ID NO: 10) | FAEKLKEAVKDYFAKLWD (SEQ ID NO: 616) |
| LR*R*LR*R*RLLR (SEQ ID NO: 6) | FAEKLKEAVKDYFAKLWD (SEQ ID NO: 616) |
| LRKLRKR*FF*R (SEQ ID NO: 12) | FAEKLKEAVKDYFAKLWD (SEQ ID NO: 616) |
| LRKLRKRLLR (SEQ ID NO: 4) | FAEKFKEAVKDYFAKFWD (SEQ ID NO: 617) |
| LRKLRKRLLR (SEQ ID NO: 4) | FAEKFKEAVKDYFAKFWD (SEQ ID NO: 617) |
| LRKLRKRLLR (SEQ ID NO: 4) | FAEKFKEAVKDYFAKFWD (SEQ ID NO: 617) |
| LRK*M*RKRL*M*R (SEQ ID NO: 7) | FAEKFKEAVKDYFAKFWD (SEQ ID NO: 617) |
| LRK*M*RKRL*M*R (SEQ ID NO: 7) | FAEKFKEAVKDYFAKFWD (SEQ ID NO: 617) |
| LRKL*P*KRLLR (SEQ ID NO: 8) | FAEKFKEAVKDYFAKFWD (SEQ ID NO: 617) |
| LR*N*VRKRL*V*R (SEQ ID NO: 9) | FAEKFKEAVKDYFAKFWD (SEQ ID NO: 617) |
| *M*RKLRKR*V*LR (SEQ ID NO: 10) | FAEKFKEAVKDYFAKFWD (SEQ ID NO: 617) |

TABLE 9-continued

| Reverse Orientation Peptides. Non-limiting Examples of Synthetic Apo E mimetics | |
|---|---|
| Receptor Binding Domains of Apo E | Lipid-Associating Peptides |
| LRRLRRRLLR (SEQ ID NO: 4) | FAEKFKEAVKDYFAKFWD (SEQ ID NO: 617) |
| LRKLRKRFFR (SEQ ID NO: 12) | FAEKFKEAVKDYFAKFWD (SEQ ID NO: 617) |

iii. Scrambled Peptides

Also disclosed are synthetic Apo E-mimicking peptides, consisting of: a receptor binding domain of apolipoprotein E and a lipid-associating peptide, wherein said receptor binding domain is covalently linked to said lipid-associating peptide, wherein the receptor binding domain of apolipoprotein E is scrambled. For example, disclosed is a synthetic apolipoprotein E-mimicking peptide, consisting of: a receptor binding domain of apolipoprotein E comprising the amino acid sequence of D-W-L-K-A-F-V-Y-D-K-V-F-K-L-K-E-F-F (SEQ ID NO:69); and a lipid-associating peptide, wherein said receptor binding domain is covalently linked to said lipid-associating peptide. Also disclosed are synthetic Apo E-mimicking peptides, consisting of: a receptor binding domain of apolipoprotein B and a lipid-associating peptide, wherein said receptor binding domain is covalently linked to said lipid-associating peptide, wherein the receptor binding domain of apolipoprotein B is scrambled.

Also disclosed are synthetic Apo E-mimicking peptides, consisting of: a receptor binding domain of apolipoprotein E and a lipid-associating peptide, wherein said receptor binding domain is covalently linked to said lipid-associating peptide, wherein the lipid-associating peptide is scrambled. For example, disclosed herein is a synthetic Apo E-mimicking peptides, comprising: a lipid binding domain of apolipoprotein E comprising the amino acid sequence of E-W-L-K-A-F-V-Y-E-K-V-F-K-L-K-E-F-F (SEQ ID NO:70) and a receptor binding domain peptide, wherein said lipid binding domain is covalently linked to said receptor binding domain peptide.

Also disclosed are synthetic Apo E mimetics, consisting of: a receptor binding domain of apolipoprotein E and a lipid-associating peptide of apolipoprotein E, wherein receptor binding domain is covalently linked to said lipid-associating peptide, wherein both the receptor binding domain and the lipid-associating peptide are scrambled. Table 10 provides non-limiting examples of the disclosed scrambled synthetic Apo E mimetics comprising a receptor binding domain of apolipoprotein E and a lipid-associating peptide, wherein said receptor binding domain is covalently linked to said lipid-associating peptide, wherein the receptor binding domain of apolipoprotein E is scrambled.

TABLE 10

| Scrambled Domain Peptides. | | |
|---|---|---|
| Name | Receptor Binding Domains of Apo E | Lipid-Associating Peptides |
| hE-Sc18A (hE with Sc18A also referred toas Sc2F) | LRKLRKRLLR (SEQ ID NO: 4) | KAFEEVLAKKFYDKALWD (SEQ ID NO: 660) |
| SchE-18A | LRLLRKLKRR (SEQ ID NO: 661) | DWLKAFYDKVAEKLKEAF (SEQ ID NO: 5) |

The disclosed scrambled synthetic Apo E mimetics can also be N-terminally and C-terminally protected using acetyl and amide groups. The disclosed scrambled synthetic Apo E mimetics can also be reverse-oriented as described above.

iv. Linkages

Any suitable linker can be used in accordance with the present invention. The peptide linkages can be selected from the group consisting of: —$CH_2NH$—, —$CH_2S$—, —$CH_2$—$CH_2$—, —CH═CH—(cis and trans), —$COCH_2$—, —CH(OH)$CH_2$—, —$CH_2SO$—, etc. by methods known in the art and further described in the following references: Spatola (1983) p. 267 in Chemistry and Biochemistry of Amino Acids, Peptides, and Proteins, B. Weinstein, eds., Marcel Dekker, New York; Spatola (1983) Vega Data 1(3) Peptide Backbone Modifications. (general review); Morley (1980) Trends Pharm Sci pp. 463-468 (general review); Hudson et al. (1979) Int J PeptProt Res 14:177-185 (—$CH_2NH$—, $CH_2CH_2$—); Spatola et al. (1986) Life Sci 38:1243-1249 (—$CH_2$—S); Hann, (1982) J ChemSoc Perkin Trans I 307-314 (—CH—CH—, cis and trans); Almquist et al. (1980) J Med. Chem. 23:1392-1398 (—$COCH_2$—); Jennings-White et al. (1982) Tetrahedron Lett. 23:2533 (—$COCH_2$—); Szelke et al., European Appln. EP 45665 (1982) CA: 97:39405 (1982) (—CH(OH)CH2-); Holladay et al. (1983) Tetrahedron Lett 24:4401-4404 (—C(OH)$CH_2$—); and Hruby (1982) Life Sci., 31:189-199 (—$CH_2$—S—)).

One particularly preferred non-peptide linkage is —$CH_2NH$—. Such peptide mimetics may have significant advantages over polypeptide embodiments, including, for example: more economical production, greater chemical stability, enhanced pharmacological properties (half-life, absorption, potency, efficacy, etc.), reduced antigenicity, and others.

In one aspect, the linker is a cleavable linker. To give but a few examples, cleavable linkers include protease cleavable peptide linkers, nuclease sensitive nucleic acid linkers, lipase sensitive lipid linkers, glycosidase sensitive carbohydrate linkers, pH sensitive linkers, hypoxia sensitive linkers, photo-cleavable linkers, heat-labile linkers, enzyme cleavable linkers (e.g., esterase cleavable linker), ultrasound-sensitive linkers, x-ray cleavable linkers, etc.

5. Variants

The receptor binding domain or the lipid-associating peptide can be modified or altered as described above. For example, the receptor binding domain or the lipid-associating peptide can be mutated, scrambled, and/or reverse-oriented. Any other modifications or alterations disclosed herein for the dual-domain polypeptides can also be used for the single-domain peptides.

Numerous other variants or derivatives of the peptides disclosed herein are also contemplated. For example, scrambled peptides can also be reverse-oriented, or can be in a switched orientation. Additionally, reverse-oriented peptides can be in a switched orientation. All other combinations of the disclosed peptides are also contemplated. Non-limiting examples of the peptides have been described herein (see Tables 1-5, for example). As used herein, the term "analog" is used interchangeably with "variant" and "derivative." Variants and derivatives are well understood to those of skill in the art and can involve amino acid sequence modifications. Such, amino acid sequence modifications typically fall into one or more of three classes: substantial; insertional; or deletional variants. Insertions include amino and/or carboxyl terminal fusions as well as intrasequence insertions of single or multiple amino acid residues. Insertions ordinarily are smaller insertions than those of amino or carboxyl terminal fusions, for example, on the order of one to four residues. These variants ordinarily are prepared by site-specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once. Substitutions, deletions, insertions or any combination thereof may be combined to arrive at a final derivative or analog. Substitutional variants are those in which at least one residue has been removed and a different residue inserted in its place. Such substitutions generally are made in accordance with Tables 11 and 12 and are referred to as conservative substitutions.

Substantial changes in function or immunological identity are made by selecting substitutions that are less conservative than those in Table 11, i.e., selecting residues that differ more significantly in their effect on maintaining (a) the structure of the polypeptide backbone in the area of the substitution, for example as a sheet or helical conformation, (b) the charge or hydrophobicity of the molecule at the target site, or (c) the bulk of the side chain. The substitutions which in general are expected to produce the greatest changes in the protein properties are those in which: (a) the hydrophilic residue, e.g. seryl or threonyl, is substituted for (or by) a hydrophobic residue, e.g., leucyl, isoleucyl, phenylalanyl, valyl or alanyl; Tryptophan, Tyrosinyl (b) a cysteine or proline is substituted for (or by) any other residue; (c) a residue having an electropositive side chain, e.g., lysyl, arginyl, or hystidyl, is substituted for (or by) an electronegative residue, e.g. glutamyl or aspartyl; or (d) a residue having a bulky side chain, e.g., phenylalanine, is substituted for (or by) one not having a side chain, e.g., glycine, in this case, or (e) by increasing the number of sites for sulfation and/or glycosylation.

TABLE 11

Amino Acid Substitutions

| Original Residue | Non-limiting Exemplary Conservative Substitutions |
|---|---|
| Ala | Ser |
| Arg | Gly; Gln; Lys |
| Asn | Gln; His |
| Asp | Glu |
| Cys | Ser |
| Gln | Asn; Lys |
| Glu | Asp |
| Gly | Ala |
| His | Asn; Gln |

TABLE 11-continued

Amino Acid Substitutions

| Original Residue | Non-limiting Exemplary Conservative Substitutions |
|---|---|
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

TABLE 12

Amino Acid Abbreviations

| Amino Acid | Abbreviations |
|---|---|
| Alanine | Ala (A) |
| Allosoleucine | AIle |
| Arginine | Arg (R) |
| Asparagine | Asn (N) |
| Aspartic Acid | Asp (D) |
| Cysteine | Cys (C) |
| Glutamic Acid | Glu (E) |
| Glutamine | Gln (Q) |
| Glycine | Gly (G) |
| Histidine | His (H) |
| Isolelucine | Ile (I) |
| Leucine | Leu (L) |
| Lysine | Lys (K) |
| Phenylalanine | Phe (F) |
| Praline | Pro (P) |
| Pyroglutamic Acid | PGlu (U) |
| Serine | Ser (S) |
| Threonine | Thr (T) |
| Tyrosine | Tyr (Y) |
| Tryptophan | Trp (W) |
| Valine | Val (V) |

It is understood that one way to define the variants and derivatives of the disclosed proteins herein is to define them in terms of homology/identity to specific known sequences. Specifically disclosed are variants of synthetic Apo E mimetics and other proteins or peptides herein disclosed which have at least, 70% or at least 75% or at least 80% or at least 85% or at least 90% or at least 95% homology to the synthetic Apo E mimetics specifically recited herein. Those of skill in the art readily understand how to determine the homology of two proteins.

The polypeptides can be modified by either natural processes, such as posttranslational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pegylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

Variants can also include peptidomimetics. As used herein, "peptidomimetic" means a mimetic of a function of a protein which includes some alteration of the normal peptide chemistry. Peptidomimetics typically are short sequences of amino acids that in biological properties mimic one or more function(s) of a particular protein. Peptide analogs enhance some property of the original peptide, such as increases stability, increased efficacy, enhanced delivery, increased half-life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic Some non-limiting examples of unnatural amino acids which may be suitable amino acid mimics include β-alanine, L-α-amino butyric acid, L-γ-amino butyric acid, L-α-amino isobutyric acid, L-ϵ-amino caproic acid, 7-amino heptanoic acid, L-aspartic acid, L-glutamic acid, N-ϵ-Boc-N-α-CBZ-L-lysine, N-ϵ-Boc-N-α-Fmoc-L-lysine, L-methionine sulfone, L-norleucine, L-norvaline, N-α-Boc-N-δCBZ-L-omithine, N-δ-Boc-N-α-CBZ-L-ornithine, Boc-p-nitro-L-phenylalanine, Boc-hydroxyproline, and Boc-L-thioproline.

6. Nucleic Acids

As this specification discusses various peptide sequences it is understood that the nucleic acids that can encode those polypeptide sequences are also disclosed. This would include all degenerate sequences related to a specific polypeptide sequence, i.e. all nucleic acids having a sequence that encodes one particular polypeptide sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed polypeptide sequences.

7. Blocking/Protecting Groups and D Residues

The disclosed compositions can comprise an acetyl group followed by a protecting group. The protecting group can be, but is not limited to, a fatty acid. The fatty acids can be saturated, unsaturated or essential fatty acids. Fatty acids can include but are not limited to DHA, EPA, linoleic acid, or any other saturated amino acid such as myristic acid.

While the various compositions described herein may be shown with no protecting groups, in certain embodiments (e.g., particularly for oral administration), they can bear one, two, three, four, or more protecting groups. The protecting groups can be coupled to the C- and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g., an acetyl group protecting the amino terminus and/or an amide group protecting the carboxyl terminus. One example of such a "dual protected peptide" is Ac-LRKLRKRLLRDWLKAFYDKVAEKLKEAF-$NH_2$ (SEQ ID NO:1) with blocking groups), either or both of these protecting groups can be eliminated and/or substituted with another protecting group as described herein. Without being bound by a particular theory, it was a discovery of this invention that blockage, particularly of the amino and/or carboxyl termini of the subject peptides of this invention can improve oral delivery and can also increase serum half-life.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. For example, the protecting groups can include, but are not limited to alkyl chains as in fatty acids, propeonyl, formyl, and others. Carboxyl protecting groups include amides, esters, and ether-forming protecting groups can also be used. For example, an acetyl group can be used to protect the amino terminus and an amide group can be used to protect the carboxyl terminus. These blocking groups enhance the helix-forming tendencies of the peptides. Additional blocking groups include alkyl groups of various lengths, e.g., groups having the formula: $CH_3(CH_2)_nCO$ where n ranges from about 1 to about 20, preferably from about 1 to about 16 or 18, more preferably from about 3 to about 13, and most preferably from about 3 to about 10.

Additionally, the protecting groups include, but are not limited to alkyl chains as in fatty acids, propeonyl, formyl, and others. For example, carboxyl protecting groups can include amides, esters, and ether-forming protecting groups. These blocking groups can enhance the helix-forming tendencies of the peptides. Blocking groups can include alkyl groups of various lengths, e.g., groups having the formula: $CH_3(CH_2)_nCO$ where n ranges from about 3 to about 20, preferably from about 3 to about 16, more preferably from about 3 to about 13, and most preferably from about 3 to about 10.

Other protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxy-carbonyl (2-Br—Z), Benzyloxymethyl (Bom), cyclohexyloxy (cHxO), t-butoxymethyl (Bum), t-butoxy (tBuO), t-Butyl (tBu), Acetyl (Ac), and Trifluoroacetyl (TFA).

Protecting/blocking groups are well known to those of skill as are methods of coupling such groups to the appropriate residue(s) comprising the peptides of this invention (see, e.g., Greene et al., (1991) Protective Groups in Organic Synthesis, 2nd ed., John Wiley & Sons, Inc. Somerset, N.J.). For example, acetylation can be accomplished during the synthesis when the peptide is on the resin using acetic anhydride. Amide protection can be achieved by the selection of a proper resin for the synthesis.

The compositions disclosed herein can also comprise one or more D-form (dextro rather than levo) amino acids as described herein. For example, at least two enantiomeric amino acids, at least 4 enantiomeric amino acids or at least 8 or 10 enantiomeric amino acids can be in the "D" form amino acids. Additionally, every other, or even every amino acid (e.g., every enantiomeric amino acid) of the peptides described herein is a D-form amino acid.

Additionally, at least 50% of the enantiomeric amino acids can be "D" form, at least 80% of the enantiomeric amino acids are "D" form, at least 90%, or even all of the enantiomeric amino acids can be in the "D" form amino acids.

FMOC-Aha can be added to the growing chain as the last amino acid using the normal amino acid chain extension procedure (use of HOBt+DCC or HBTU as condensing agents). After the removal of the FMOC group using 20% piperidine in DMF, the NH2 can be acetylated using either excess of acetic anhydride under basic conditions or by condensing acetic acid using amino acid condensing agents used for peptide chain elongation.

C. Pharmaceutical Compositions

Disclosed are pharmaceutical compositions comprising any of the synthetic ApoE-mimicking peptides disclosed herein and a pharmaceutically acceptable carrier.

By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, Pa. 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

D. Methods for Affecting LDL and VLDL

Disclosed are methods comprising administering any one of the disclosed synthetic ApoE-mimicking peptides to a subject, whereby plasma LDL, plasma VLDL, or both, are affected. The ApoE-mimicking peptide can be a synthetic ApoE-mimicking peptide comprising a receptor binding domain of ApoE and a lipid-associating peptide, wherein the synthetic ApoE-mimicking peptide comprises an Ac-Aha. For example, the synthetic ApoE-mimicking peptide can be Ac-Aha-hE18A-$NH_2$ or Ac-Aha-[R]hE18A-$NH_2$.

Disclosed are methods comprising administering any one of the disclosed synthetic ApoE-mimicking peptides to a subject, whereby plasma LDL, plasma VLDL, or both, are affected, wherein the synthetic ApoE-mimicking peptide is administered as a composition comprising the synthetic ApoE-mimicking peptide and a pharmaceutically acceptable carrier.

Disclosed are methods comprising administering any one of the disclosed synthetic ApoE-mimicking peptides to a subject, whereby plasma LDL, plasma VLDL, or both, are affected, wherein binding of LDL to a cell of the subject is enhanced.

Disclosed are methods comprising administering any one of the disclosed synthetic ApoE-mimicking peptides to a subject, whereby plasma LDL, plasma VLDL, or both, are affected, wherein degradation of LDL by a cell of the subject is increased.

Disclosed are methods comprising administering any one of the disclosed synthetic ApoE-mimicking peptides to a subject, whereby plasma LDL, plasma VLDL, or both, are affected, wherein LDL cholesterol in the subject is lowered.

Disclosed are methods comprising administering any one of the disclosed synthetic ApoE-mimicking peptides to a subject, whereby plasma LDL, plasma VLDL, or both, are affected, wherein binding of VLDL to a cell of the subject is enhanced.

Disclosed are methods comprising administering any one of the disclosed synthetic ApoE-mimicking peptides to a subject, whereby plasma LDL, plasma VLDL, or both, are affected, wherein degradation of VLDL by a cell of the subject is increased.

Disclosed are methods comprising administering any one of the disclosed synthetic ApoE-mimicking peptides to a subject, whereby plasma LDL, plasma VLDL, or both, are affected, wherein VLDL cholesterol in the subject is lowered.

Disclosed are methods comprising administering any one of the disclosed synthetic ApoE-mimicking peptides to a subject, whereby plasma LDL, plasma VLDL, or both, are affected, wherein total plasma concentration of cholesterol in the subject is lowered.

Disclosed are methods comprising administering any one of the disclosed synthetic ApoE-mimicking peptides to a subject, whereby plasma LDL, plasma VLDL, or both, are affected, wherein said synthetic ApoE-mimicking peptide is administered in an amount of about 0.01 mg/kg to about 20 mg/kg. For example, the concentration of the ApoE-mimicking peptide can be 0.01, 0.1, 1, 2, 3, 4, 5, 6, 7, 8, 9, 10, 11, 12, 13, 14, 15, 16, 17, 18, 19, 20 mg/kg, or any range in between.

Disclosed are methods comprising administering any one of the disclosed synthetic ApoE-mimicking peptides to a subject, whereby plasma LDL, plasma VLDL, or both, are affected, wherein the subject has coronary artery disease, rheumatoid arthritis, systemic lupus, diabetes, Alzheimer's disease, PAD, cerebral vascular disease, diabetes-derived cardiovascular diseases, macular degeneration, and/or congestive heart failure, or bacterial infections.

E. Methods of Reducing Plasma Cholesterol

Disclosed are methods of reducing plasma cholesterol comprising administering to a subject an effective amount of a composition comprising any one of the disclosed synthetic ApoE-mimicking peptides. The ApoE-mimicking peptide can be a synthetic ApoE-mimicking peptide comprising a receptor binding domain of ApoE and a lipid-associating peptide, wherein the synthetic ApoE-mimicking peptide comprises an Ac-Aha. For example, the synthetic ApoE-mimicking peptide can be Ac-Aha-hE18A-$NH_2$ or Ac-Aha-[R]hE18A-$NH_2$.

Disclosed are methods of reducing plasma cholesterol comprising administering to a subject an effective amount of a composition comprising any one of the disclosed synthetic ApoE-mimicking peptides, wherein the synthetic ApoE-mimicking peptide is administered as a composition comprising the synthetic ApoE-mimicking peptide and a pharmaceutically acceptable carrier.

Disclosed are methods of reducing plasma cholesterol comprising administering to a subject an effective amount of a composition comprising any one of the disclosed synthetic ApoE-mimicking peptides, wherein binding of LDL to a cell of the subject is enhanced.

Disclosed are methods of reducing plasma cholesterol comprising administering to a subject an effective amount of a composition comprising any one of the disclosed synthetic ApoE-mimicking peptides, wherein degradation of LDL by a cell of the subject is increased.

Disclosed are methods of reducing plasma cholesterol comprising administering to a subject an effective amount of a composition comprising any one of the disclosed synthetic ApoE-mimicking peptides, wherein LDL cholesterol in the subject is lowered.

Disclosed are methods of reducing plasma cholesterol comprising administering to a subject an effective amount of a composition comprising any one of the disclosed synthetic ApoE-mimicking peptides, wherein binding of VLDL to a cell of the subject is enhanced.

Disclosed are methods of reducing plasma cholesterol comprising administering to a subject an effective amount of a composition comprising any one of the disclosed synthetic ApoE-mimicking peptides, wherein degradation of VLDL by a cell of the subject is increased.

Disclosed are methods of reducing plasma cholesterol comprising administering to a subject an effective amount of a composition comprising any one of the disclosed synthetic ApoE-mimicking peptides, wherein VLDL cholesterol in the subject is lowered.

Disclosed are methods of reducing plasma cholesterol comprising administering to a subject an effective amount of a composition comprising any one of the disclosed synthetic ApoE-mimicking peptides, wherein total plasma concentration of cholesterol in the subject is lowered.

Disclosed are methods of reducing plasma cholesterol comprising administering to a subject an effective amount of a composition comprising any one of the disclosed synthetic ApoE-mimicking peptides, wherein said synthetic ApoE-mimicking peptide is administered in an amount of about 0.01 mg/kg to about 20 mg/kg. For example, the concentration of the ApoE-mimicking peptide can be 0.01, 0.1, 1, 2, 3, 4, 5, 6, 7, 8, 9, 10, 11, 12, 13, 14, 15, 16, 17, 18, 19, 20 mg/kg, or any range in between.

Disclosed are methods of reducing plasma cholesterol comprising administering to a subject an effective amount of a composition comprising any one of the disclosed synthetic ApoE-mimicking peptides, wherein the subject has coronary artery disease, rheumatoid arthritis, systemic lupus, diabetes, Alzheimer's disease, PAD, cerebral vascular disease, diabetes-derived cardiovascular diseases, macular degeneration, and/or congestive heart failure.

F. Methods of Treating Atherosclerosis

Disclosed are methods of treating atherosclerosis comprising administering to a subject an effective amount of a composition comprising any one of the disclosed synthetic ApoE-mimicking peptides. The ApoE-mimicking peptide can be a synthetic ApoE-mimicking peptide comprising a receptor binding domain of ApoE and a lipid-associating peptide, wherein the synthetic ApoE-mimicking peptide comprises an Ac-Aha. For example, the synthetic ApoE-mimicking peptide can be Ac-Aha-hE18A-$NH_2$ or Ac-Aha-[R]hE18A-$NH_2$.

Disclosed are methods of treating atherosclerosis comprising administering to a subject an effective amount of a composition comprising any one of the disclosed synthetic ApoE-mimicking peptides, wherein the synthetic ApoE-mimicking peptide is administered as a composition comprising the synthetic ApoE-mimicking peptide and a pharmaceutically acceptable carrier.

Disclosed are methods of treating atherosclerosis comprising administering to a subject an effective amount of a composition comprising any one of the disclosed synthetic ApoE-mimicking peptides, wherein binding of LDL to a cell of the subject is enhanced.

Disclosed are methods of treating atherosclerosis comprising administering to a subject an effective amount of a composition comprising any one of the disclosed synthetic ApoE-mimicking peptides, wherein degradation of LDL by a cell of the subject is increased.

Disclosed are methods of treating atherosclerosis comprising administering to a subject an effective amount of a composition comprising any one of the disclosed synthetic ApoE-mimicking peptides, wherein LDL cholesterol in the subject is lowered.

Disclosed are methods of treating atherosclerosis comprising administering to a subject an effective amount of a composition comprising any one of the disclosed synthetic ApoE-mimicking peptides, wherein binding of VLDL to a cell of the subject is enhanced.

Disclosed are methods of treating atherosclerosis comprising administering to a subject an effective amount of a composition comprising any one of the disclosed synthetic ApoE-mimicking peptides, wherein degradation of VLDL by a cell of the subject is increased.

Disclosed are methods of treating atherosclerosis comprising administering to a subject an effective amount of a composition comprising any one of the disclosed synthetic ApoE-mimicking peptides, wherein VLDL cholesterol in the subject is lowered.

Disclosed are methods of treating atherosclerosis comprising administering to a subject an effective amount of a composition comprising any one of the disclosed synthetic ApoE-mimicking peptides, wherein total plasma concentration of cholesterol in the subject is lowered.

Disclosed are methods of treating atherosclerosis comprising administering to a subject an effective amount of a composition comprising any one of the disclosed synthetic ApoE-mimicking peptides, wherein said synthetic ApoE-mimicking peptide is administered in an amount of about 0.01 mg/kg to about 20 mg/kg. For example, the concentration of the ApoE-mimicking peptide can be 0.01, 0.1, 1, 2, 3, 4, 5, 6, 7, 8, 9, 10, 11, 12, 13, 14, 15, 16, 17, 18, 19, 20 mg/kg, or any range in between.

Disclosed are methods of treating atherosclerosis comprising administering to a subject an effective amount of a composition comprising any one of the disclosed synthetic ApoE-mimicking peptides, wherein the subject has coronary artery disease, rheumatoid arthritis, systemic lupus, diabetes, Alzheimer's disease, PAD, cerebral vascular disease, diabetes-derived cardiovascular diseases, macular degeneration, and/or congestive heart failure.

G. Methods for Treating Lipid Disorders

Disclosed are methods of treating a subject with a lipid disorder comprising administering to the subject an effective amount of any one of the disclosed ApoE-mimicking peptides or a composition thereof. The ApoE-mimicking peptide can be a synthetic ApoE-mimicking peptide comprising a receptor binding domain of ApoE and a lipid-associating peptide, wherein the synthetic ApoE-mimicking peptide comprises an Ac-Aha. For example, the synthetic ApoE-mimicking peptide can be Ac-Aha-hE18A-$NH_2$ or Ac-Aha-[R]hE18A-$NH_2$.

Disclosed are methods of treating a subject with a lipid disorder comprising administering to the subject an effective amount of any one of the disclosed ApoE-mimicking peptides or a composition thereof, wherein the synthetic ApoE-mimicking peptide is administered as a composition comprising the synthetic ApoE-mimicking peptide and a pharmaceutically acceptable carrier.

Disclosed are methods of treating a subject with a lipid disorder comprising administering to the subject an effective amount of any one of the disclosed ApoE-mimicking peptides or a composition thereof, wherein binding of LDL to a cell of the subject is enhanced.

Disclosed are methods of treating a subject with a lipid disorder comprising administering to the subject an effective amount of any one of the disclosed ApoE-mimicking peptides or a composition thereof, wherein degradation of LDL by a cell of the subject is increased.

Disclosed are methods of treating a subject with a lipid disorder comprising administering to the subject an effective amount of any one of the disclosed ApoE-mimicking peptides or a composition thereof, wherein LDL cholesterol in the subject is lowered.

Disclosed are methods of treating a subject with a lipid disorder comprising administering to the subject an effective amount of any one of the disclosed ApoE-mimicking peptides or a composition thereof, wherein binding of VLDL to a cell of the subject is enhanced.

Disclosed are methods of treating atherosclerosis comprising administering to a subject an effective amount of a composition comprising any one of the disclosed synthetic ApoE-mimicking peptides, wherein degradation of VLDL by a cell of the subject is increased.

Disclosed are methods of treating a subject with a lipid disorder comprising administering to the subject an effective amount of any one of the disclosed ApoE-mimicking peptides or a composition thereof, wherein VLDL cholesterol in the subject is lowered.

Disclosed are methods of treating a subject with a lipid disorder comprising administering to the subject an effective amount of any one of the disclosed ApoE-mimicking peptides or a composition thereof, wherein total plasma concentration of cholesterol in the subject is lowered.

Disclosed are methods of treating a subject with a lipid disorder comprising administering to the subject an effective amount of any one of the disclosed ApoE-mimicking peptides or a composition thereof, wherein said synthetic ApoE-mimicking peptide is administered in an amount of about 0.01 mg/kg to about 20 mg/kg. For example, the concentration of the ApoE-mimicking peptide can be 0.01, 0.1, 1, 2, 3, 4, 5, 6, 7, 8, 9, 10, 11, 12, 13, 14, 15, 16, 17, 18, 19, 20 mg/kg, or any range in between.

Disclosed are methods of treating a subject with a lipid disorder comprising administering to the subject an effective amount of any one of the disclosed ApoE-mimicking peptides or a composition thereof, wherein the lipid disorder can be coronary artery disease, rheumatoid arthritis, systemic lupus, diabetes, Alzheimer's disease, PAD, cerebral vascular disease, diabetes-derived cardiovascular diseases, macular degeneration, and/or congestive heart failure.

H. Monoclonal Antibodies

Disclosed are monoclonal antibodies that specifically bind to any one of the synthetic ApoE-mimicking peptides described herein.

I. Dosing Regimens

Disclosed are dosing regimens comprising at least one treatment cycle of an effective amount of any of the disclosed Apo E-mimicking peptides followed by a rest phase. The rest phase of the dosing regimen is a period of time where the Apo E-mimicking peptide is not administered. The ApoE-mimicking peptide can be, but is not limited to, Ac-Aha-hE18A-$NH_2$ or Ac-Aha-[R]hE18A-$NH_2$.

Disclosed are dosing regimens comprising at least one treatment cycle followed by a rest phase, wherein the treatment cycle comprises administering an effective amount of an Apo E-mimicking peptide to allow for a sustained therapeutic effect after withdrawal of the Apo E-mimicking peptide, wherein the Apo E-mimicking peptide is not administered during the rest phase. Not only does an effective amount of Apo E-mimicking peptide result in sustained therapeutic effects, but it is also an amount sufficient to cause an acute beneficial effect. Thus, the effects of the Apo E-mimicking peptide can be measured and seen during the treatment cycle, at the end of the treatment cycle and during the rest phase. The sustained therapeutic effects are the therapeutic effects seen even after an acute cholesterol lowering effect is gone.

Disclosed herein are dosing regimens comprising at least one treatment cycle followed by a rest phase, wherein the treatment cycle comprises administering an effective amount of an Apo E-mimicking peptide to allow for a sustained therapeutic effect after withdrawal of the Apo E mimetic, wherein the Apo E-mimicking peptide is not administered during the rest phase, wherein the treatment cycle comprises administration of an effective amount of the Apo E-mimicking peptide once a week for three months or wherein the treatment cycle comprises administration of an effective amount of the Apo E-mimicking peptide once every two weeks for up to 12 weeks.

Disclosed are dosing regimens comprising at least one treatment cycle followed by a rest phase, wherein the treatment cycle comprises administering an effective amount of an Apo E-mimicking peptide to allow for a sustained therapeutic effect after withdrawal of the Apo E-mimicking peptide, wherein the Apo E-mimicking peptide is not administered during the rest phase, wherein the dosing regimen further comprises a second treatment cycle after the rest phase.

In one aspect, dosing regimens can comprise at least one treatment cycle followed by a rest phase, wherein the treatment cycle comprises administering an effective amount of a synthetic ApoE-mimicking peptide comprising a receptor binding domain of ApoE and a lipid-associating peptide to allow for a sustained therapeutic effect after withdrawal of the Apo E-mimicking peptide, wherein the Apo E-mimicking peptide is not administered during the rest phase, wherein the synthetic ApoE-mimicking peptide comprises an Ac-Aha.

Dosing regimens can further include a second treatment cycle after the rest phase. A second rest phase can occur after the second treatment cycle. In some instances a third, fourth, fifth, sixth, seventh, eighth, ninth or tenth treatment cycle can be administered wherein each treatment cycle is followed by a rest phase. In one aspect, the dosing regimen includes infinite treatment cycles, each followed by a rest phase. For example, a subject may be prescribed a dosing regimen that involves consecutive treatment cycles followed by rest phases for the duration of their life.

In one aspect, a second dosing regimen can be prescribed based on the re-occurrence of atherosclerotic lesions or other atherosclerosis factors. The second dosing regimen can be administered 1, 2, 3, 4, 5 years or more than 5 years after the initial dosing regimen was administered. The second dosing regimen can be the same as the initial dosing regimen or can be different. For example, the initial dosing regimen can be a three month treatment cycle followed by a one year rest phase. After the one year rest phase the subject can be tested and if atherosclerotic lesions are building up again then a second dosing regimen consisting of another three month treatment cycle followed by a rest phase or a six month treatment cycle followed by a rest phase can be prescribed. The dose of Apo E mimetic can vary between the initial dosing regimen and any additionally prescribed dosing regimens.

In some instances, the second dosing can be administered based on vasoresponsiveness, presence of isolated systolic hypertension, or exercise-induced angina determined in the subject after the first treatment. In some instances, the second dose can be administered based on the amount of plasma cholesterol. The frequency of administration can be altered depending on the need for reducing plasma cholesterol to minimize or eliminate the risk for any of the disorders disclosed herein.

1. Treatment Cycle

Treatment cycles can include the administration of different dosages of ApoE-mimicking peptide as well as administration at different time points. The ApoE-mimicking peptide can be administered for varying amounts of time for up to 6 months. In some instances, the administration can occur for up to one, two, three, four, five or six months. For example, the ApoE-mimicking peptide can be administered once a week for 4, 6, 8, 10, 12, 14, 16, 18, 20, 22, or 24 weeks.

The length of time for each treatment cycle can vary depending on the amount of ApoE-mimicking peptide administered per dosage. A treatment cycle can include the administration of ApoE-mimicking peptide once, twice or three times a week. In some aspects, the ApoE-mimicking peptide can be administered daily. In some aspects, the ApoE-mimicking peptide can be administered once every two weeks or even once a month. In some instances, the Apo E mimetic can be administered every two weeks for 4, 6, 8, 10, 12, 14, 16, 18, 20, 22, or 24 weeks. For example, the treatment cycle can include administering an ApoE-mimicking peptide once a week for four weeks or once every two weeks for up to six months. Thus, each treatment cycle includes an established length of time for administration as well as an established dosing schedule during that time frame.

In one aspect, more than one ApoE-mimicking peptide can be administered during the treatment cycles. The more than one ApoE-mimicking peptide can be formulated together or in separate compositions. In some instances, one or more Apo E mimetic is administered in combination with one or more other therapeutic agents, such as cholesterol lowering drugs.

2. Rest Phase

The disclosed dosing regimens can include at least one treatment cycle followed by a rest phase. The rest phase is a period of time wherein ApoE-mimicking peptide is not administered and the length of the period of time can vary. The length of the rest phase is dependent on how long the sustained therapeutic effects of the Apo E mimetic administered during the treatment cycle last. In some instances the rest phase can be at least 1, 2, 3, 4, 5, 6, 7, 8, 9, 10, 11, or 12 months. In some instances the rest phase can be at least 1, 2, 3, 4, 5, 6, 7, 8, 9, or 10 years. For example, the rest phase can be at least four weeks (one month).

One way to determine how long the rest phase should last is to test the subject to determine the progression of the atherosclerosis burden in the subject's arteries. If the atherosclerosis burden has progressed to a level that increases the risk of cardiovascular disease, then the subject can be prescribed a second dosing regimen. If the atherosclerosis burden is stable then the rest phase can be prolonged. The length of the reset phase can also be based on VLDL reduction, LDL reduction, glucose reduction, inflammation reduction, vasoresponsiveness, presence of isolated systolic hypertension, or exercise-induced angina, or amount of plasma cholesterol. Subjects can be tested on a regular basis. For example, a subject can be tested every 3, 6, 9, 12, 18, 24, 30 or 36 months.

In one aspect, the rest phase can be decreased or extended depending on the dose of ApoE-mimicking peptide administered and the reduction in atherosclerosis achieved during the treatment cycle. For example, the rest phase can be extended if the dose of ApoE-mimicking peptide during the treatment cycle is increased and the atherosclerosis burden is substantially reduced. The length of the rest phase can also vary based on the length of the treatment cycle. For instance, if a subject receives a certain dose of ApoE-mimicking peptide once a week for three months then the rest phase may be shorter than a subject that receives the same dose of Apo E mimetic once a week for six months.

Although an Apo E mimetic is not administered during the rest phase, an atherosclerosis therapeutic other than an Apo E mimetic can be administered during the rest phase. The atherosclerosis therapeutic other than an Apo E mimetic can be a conventional lipid lowering therapy, such as a statin, a bile acid sequestrant or a fibrate, or a novel anti-atherosclerosis therapeutic like a CETP inhibitor, a VLDL synthesis inhibitor, a PCSK9 inhibitor, and/or an arterial inflammation inhibitor. In other words, the atherosclerosis therapeutic other than an Apo E mimetic can be a conventional LDL lowering therapeutic or a HDL elevating therapeutic.

In some instances, the beneficial effects of the Apo E mimetic can still be present in a subject even after the treatment cycle is complete. In one instance, the half-life of the Apo E mimetic is less than 1, 2, 3, 4, 5, 10, 15, 20, 25, or 30 days. In some instances the Apo E mimetic is no longer detectable in a subject after the treatment cycle is complete. Thus, the long-term therapeutic effects are not from residual Apo E mimetic.

3. Dose

The dose or dosage of ApoE-mimicking peptide can vary depending on many factors, such as but not limited to, age, condition, sex and extent of the disease in the patient, route of administration, length of treatment cycle, or whether other drugs are included in the regimen, and can be determined by one of skill in the art.

Effective dosages can be determined empirically, and making such determinations is within the skill in the art. The dosage ranges for the administration of the compositions are those large enough to produce the desired effect in which the disease is treated. For example, the dosage can be an amount effective to provide therapeutic effects and provide or allow for sustained therapeutic effects even after the treatment (i.e. ApoE-mimicking peptide) is withdrawn. The therapeutic effects can be, but are not limited to, a reduction in atherosclerotic lesions, decrease in arterial stiffness, decrease in isolated systolic hypertension, increase in vasoresponsiveness or improvement in cardiac function. The therapeutic effects can be measured by markers of arterial inflammation such as, but not limited to, C-reactive protein. The therapeutic effects can be measured by atherosclerosis imaging techniques, including MRI, intravascular ultrasound, ultrafast imaging CT scans, B-mode ultrasonography, virtual histology intravascular ultrasound, optical coherence tomography, or other known methods.

The dosage should not be so large as to cause adverse side effects, such as unwanted cross-reactions, anaphylactic reactions, and the like. The dosage can be adjusted by the individual physician in the event of any counter-indications. Dosage can vary, and can be administered in one or more dose administrations daily, for one or several days. Guidance can be found in the literature for appropriate dosages for given classes of pharmaceutical products.

Suitable dosages include, but are not limited to amounts between 0.01 mg/kg and 20 mg/kg. For example, disclosed herein are methods involving administering one or more of the disclosed ApoE-mimicking peptide to a subject, wherein the ApoE-mimicking peptide is administered in an amount of about 0.01 mg/kg to about 20 mg/kg. For example, the concentration of the ApoE-mimicking peptide can be 0.01, 0.1, 1, 2, 3, 4, 5, 6, 7, 8, 9, 10, 11, 12, 13, 14, 15, 16, 17, 18, 19, or 20 mg/kg.

The ApoE-mimicking peptide dose can be administered as a bolus injection or as an infusion over one or more hours.

J. Methods of Treating Using Dosing Regimens

Methods of treating acute coronary syndrome (ACS) or atherosclerosis comprising administering an effective amount of any one of the disclosed Apo E-mimicking peptides for at least one treatment cycle followed by a rest phase are provided. For example, the Apo E-mimicking peptide can be Ac-Aha-hE18A-$NH_2$ or Ac-Aha-[R]hE18A-$NH_2$. Thus, the disclosed methods involve administering an Apo E-mimicking peptide using one or more of the disclosed dosing regimens. Thus, any of the disclosed treatment cycles or rest phases can be used in the disclosed methods. The methods disclosed herein can allow for prolonged therapeutic effects even in the absence of the therapeutic. The disclosed methods can include the administration of an effective amount of Apo E mimetic. The effective amount of an Apo E mimetic can be an amount that allows for sustained therapeutic effects after the Apo E mimetic has been withdrawn.

Disclosed herein are methods of treating ACS comprising administering an effective amount of any one of the disclosed Apo E-mimicking peptides for at least one treatment cycle, wherein the treatment cycle comprises administering an effective amount of an Apo E-mimicking peptide to allow for a sustained therapeutic effect after withdrawal of the Apo E-mimicking peptide, wherein the treatment cycle is followed by a rest phase, wherein Apo-E mimicking peptide is not administered during the rest phase.

Disclosed herein are methods of treating ACS comprising administering an effective amount of any one of the disclosed Apo E-mimicking peptides for at least one treatment cycle, wherein the treatment cycle comprises administering an effective amount of an Apo E-mimicking peptide to allow for a sustained therapeutic effect after withdrawal of the Apo E-mimicking peptide, wherein the treatment cycle is followed by a rest phase, wherein Apo-E mimicking peptide is not administered during the rest phase, wherein the rest phase is at least four weeks.

Disclosed herein are methods of treating ACS comprising administering an effective amount of any one of the disclosed Apo E-mimicking peptides for at least one treatment cycle, wherein the treatment cycle comprises administering an effective amount of an Apo E-mimicking peptide to allow for a sustained therapeutic effect after withdrawal of the Apo E-mimicking peptide, wherein the treatment cycle is followed by a rest phase, wherein Apo-E mimicking peptide is not administered during the rest phase, further comprising a second treatment cycle after the rest phase. The second treatment cycle can be administered after a four week rest phase or one year from the beginning of the initial treatment cycle.

Disclosed herein are methods of treating ACS comprising administering an effective amount of any one of the disclosed Apo E-mimicking peptides for at least one treatment cycle, wherein the treatment cycle comprises administering an effective amount of an Apo E-mimicking peptide to allow for a sustained therapeutic effect after withdrawal of the Apo E-mimicking peptide, wherein the treatment cycle is followed by a rest phase, wherein Apo-E mimicking peptide is not administered during the rest phase, wherein an ACS therapeutic other than an Apo E-mimicking peptide is administered during the rest phase. The ACS therapeutic other than an Apo E-mimicking peptide can be a conventional LDL lowering therapy or HDL elevating therapy. A conventional LDL lowering therapy can be, but is not limited to, a statin. An HDL elevating therapy can be, but is not limited to, Apo A1 elevating drug, a CETP inhibitor, a phospholipase A2 inhibitor, an Apo A1 Milano, or an Apo A1 mimetic.

Disclosed herein are methods of treating atherosclerosis comprising administering to a subject an effective amount of an Apo E mimetic for at least one treatment cycle, wherein the treatment cycle comprises administering an effective amount of an Apo E mimetic to allow for a sustained therapeutic effect after withdrawal of the Apo E mimetic, wherein the Apo E mimetic consists of the Ac-Aha-hE18A-$NH_2$ or Ac-Aha-[R]hE18A-$NH_2$ peptide, wherein the treatment cycle is followed by a rest phase, wherein Apo E mimetic is not administered during the rest phase.

Disclosed herein are methods of treating ACS comprising administering an effective amount of any one of the disclosed Apo E-mimicking peptides for at least one treatment cycle, wherein the treatment cycle comprises administering an effective amount of an Apo E-mimicking peptide to allow for a sustained therapeutic effect after withdrawal of the Apo E-mimicking peptide, wherein the treatment cycle is followed by a rest phase, wherein Apo-E mimicking peptide is not administered during the rest phase, wherein the treatment cycle comprises administration of an effective amount of an Apo E-mimicking peptide once a week for three months.

The disclosed methods of treating can occur at different times depending on the subject. In particular, treatment can occur in a subject considered to be of high, or high residual risk of a cardio- or cerebrovascular event. In one instance, the treatment can be initiated after a subject is stabilized following an acute coronary event. In one instance, the treatment can be initiated immediately after the acute coronary event, or 3, 6, 9, or 12 months after the acute coronary event. The treatment can be initiated following acute interventional cardiology procedures such as coronary artery bypass surgery (CABG), percutaneous coronary intervention (angioplasty, PCI), or implant of a stent into a coronary artery. Subjects considered as high risk can be those individuals that have homozygous familial hypercholesterolemia (FH), severe refractory FH, diabetes or an individual following acute coronary syndrome (ACS). In high risk subjects, treatment can be extended.

1. Treatment Cycle

The treatment cycle, as previously described with respect to the dosing regimens, can vary in length of time. The treatment cycle can be at least four weeks but can last up to six months. In one instance, the disclosed methods have a treatment cycle that involves the administration of an effective amount of an ApoE-mimicking peptide once a week for one month (four weeks), three months (12 weeks) or six months (24 weeks). A treatment cycle can include the administration of ApoE-mimicking peptide once, twice or three times a week. In some aspects, the ApoE-mimicking peptide can be administered daily. In some aspects, the ApoE-mimicking peptide can be administered once every two weeks or even once a month. In some instances, the ApoE-mimicking peptide can be administered every two weeks for 4, 6, 8, 10, 12, 14, 16, 18, 20, 22, or 24 weeks. Each treatment cycle can include an established length of time for administration as well as an established dosing schedule during that time frame.

The methods can further include a second treatment cycle after the rest phase. In one aspect, the second treatment cycle can be administered after a four week rest phase. In another aspect, the second treatment cycle can be administered at least one year from the beginning of the initial treatment cycle.

2. Rest Phase

The rest phase, as previously described with regards to the dosing regimen, can be at least four weeks but can last for several years. The ApoE-mimicking peptide is not administered during the rest phase.

The length of the rest phase is dependent on how long the sustained therapeutic effects of the ApoE-mimicking peptide administered during the treatment cycle last. In some instances the rest phase can be at least 1, 2, 3, 4, 5, 6, 7, 8, 9, 10, 11, or 12 months. In some instances the rest phase can be at least 1, 2, 3, 4, 5, 6, 7, 8, 9, or 10 years. For example, the rest phase can be at least four weeks (one month).

In one aspect, the rest phase can be decreased or extended depending on the dose of ApoE-mimicking peptide administered during the treatment cycle. For example, the rest phase can be extended if the dose of ApoE-mimicking peptide during the treatment cycle is increased. The length of the rest phase can also vary based on the length of the treatment cycle. For instance, if a subject receives a certain dose of ApoE-mimicking peptide once a week for three months then the rest phase may be shorter than a subject that receives the same dose of ApoE-mimicking peptide once a week for six months.

Although an ApoE-mimicking peptide is not administered during the rest phase, an atherosclerosis therapeutic other than an ApoE-mimicking peptide can be administered during the rest phase. The atherosclerosis therapeutic other than an Apo E mimetic can be a conventional lipid lowering therapy, such as a statin, or bile acid sequestrant, and/or a therapeutic such as a PCSK9 inhibitor, a VLDL synthesis inhibitor and/or a CETP inhibitor.

3. Atherosclerosis

The combination of LDL accumulation in a vessel wall and an inflammatory response to the LDL's is responsible for initiating atherosclerosis. The LDL within the vessel wall becomes oxidized which damages the vessel wall and triggers an immune response. Immune cells, such as macrophages, are not able to process the oxidized-LDL and eventually rupture which leads to more oxidized cholesterol in the artery wall. This cycle continues which causes more and more damage to the vessel walls. The increase in cholesterol leads to plaques which ultimately results in hardening and narrowing of the vessel wall. The disclosed methods are useful for treating atherosclerosis and other lipid disorders.

K. Delivery

In the methods described herein, administration or delivery of the ApoE-mimicking peptides can be via a variety of mechanisms. As defined above, disclosed herein are methods of treating, dosing regimens and methods of using those dosing regimens to treat. The dosing regimens and methods include compositions containing any one or more of the polypeptides or nucleic acids described herein that can also include a carrier such as a pharmaceutically acceptable carrier. For example, disclosed are pharmaceutical compositions, comprising the ApoE-mimicking peptide disclosed herein, and a pharmaceutically acceptable carrier.

The disclosed ApoE-mimicking peptide can be in solution or in suspension (for example, incorporated into microparticles, liposomes, or cells). These compositions can be targeted to a particular cell type via antibodies, receptors, or receptor ligands. One of skill in the art knows how to make and use such targeting agents with the disclosed compositions. A targeting agent can be a vehicle such as an antibody conjugated liposomes; receptor mediated targeting of DNA through cell specific ligands, and highly specific retroviral targeting of cells in vivo. Any such vehicles can be part of the compositions herein. For example, targeting agents that direct the ApoE-mimicking peptide to the blood vessel walls can be included in the compositions.

Any suitable route of administration can be used for the disclosed compositions. Suitable routes of administration can, for example, include topical, enteral, local, systemic, or parenteral. For example, administration can be epicutaneous, inhalational, enema, conjunctival, eye drops, ear drops, alveolar, nasal, intranasal, enteral, oral, intraoral, transoral, intestinal, rectal, intrarectal, transrectal, injection, infusion, intravenous, intraarterial, intramuscular, intracerebral, intraventricular, intracerebroventricular, intracardiac, subcutaneous, intraosseous, intradermal, intrathecal, intraperitoneal, intravesical, intracavernosal, intramedullar, intraocular, intracranial, transdermal, transmucosal, transnasal, inhalational, intracisternal, epidural, peridural, intravitreal, etc. The disclosed compositions can be used in and with any other therapy.

Unlike typical peptide formulations, the peptides of this invention comprising D-form amino acids can be administered, even orally, without protection against proteolysis by stomach acid, etc. Nevertheless, in certain embodiments, peptide delivery can be enhanced by the use of protective excipients. This is typically accomplished either by complexing the polypeptide with a composition to render it resistant to acidic and enzymatic hydrolysis or by packaging the polypeptide in an appropriately resistant carrier such as a liposome. Means of protecting polypeptides for oral delivery are well known in the art (see, e.g., U.S. Pat. No. 5,391,377 describing lipid compositions for oral delivery of therapeutic agents).

Elevated serum half-life can be maintained by the use of sustained-release protein "packaging" systems. Such sustained release systems are well known to those of skill in the art. In one preferred embodiment, the ProLease biodegradable microsphere delivery system for proteins and peptides (Tracy (1998) Biotechnol. Prog., 14: 108; Johnson et al. (1996) Nature Med. 2: 795; Herbert et al. (1998), Pharmaceut. Res. 15, 357) a dry powder composed of biodegradable polymeric microspheres containing the active agent in a polymer matrix that can be compounded as a dry formulation with or without other agents.

The ProLease microsphere fabrication process was specifically designed to achieve a high encapsulation efficiency while maintaining integrity of the active agent. The process consists of (i) preparation of freeze-dried drug particles from bulk by spray freeze-drying the drug solution with stabilizing excipients, (ii) preparation of a drug-polymer suspension followed by sonication or homogenization to reduce the drug particle size, (iii) production of frozen drug-polymer microspheres by atomization into liquid nitrogen, (iv) extraction of the polymer solvent with ethanol, and (v) filtration and vacuum drying to produce the final dry-powder product. The resulting powder contains the solid form of the active agents, which is homogeneously and rigidly dispersed within porous polymer particles. The polymer most commonly used in the process, poly(lactide-co-glycolide) (PLG), is both biocompatible and biodegradable.

Encapsulation can be achieved at low temperatures (e.g., −40° C.). During encapsulation, the protein is maintained in the solid state in the absence of water, thus minimizing water-induced conformational mobility of the protein, preventing protein degradation reactions that include water as a reactant, and avoiding organic-aqueous interfaces where proteins may undergo denaturation. A preferred process uses solvents in which most proteins are insoluble, thus yielding high encapsulation efficiencies (e.g., greater than 95%).

In another embodiment, one or more components of the solution can be provided as a "concentrate", e.g., in a storage container (e.g., in a premeasured volume) ready for dilution, or in a soluble capsule ready for addition to a volume of water.

The foregoing formulations and administration methods are intended to be illustrative and not limiting. It will be appreciated that, using the teaching provided herein, other suitable formulations and modes of administration can be readily devised.

1. Combination Therapy

In one aspect of the disclosed methods, the Apo E mimetics can be administered alone or in combination with one or more additional therapeutic agents. The additional therapeutic agents are selected based on the disease or symptom to be treated. A description of the various classes of suitable pharmacological agents and drugs may be found in Goodman and Gilman, The Pharmacological Basis of Therapeutics, (11th Ed., McGraw-Hill Publishing Co.) (2005). For example, pharmaceutical compositions containing Apo E mimetics can be administered in combination with one or more known therapeutic agents for treating atherosclerosis. Therapeutic agents for treating atherosclerosis include, but are not limited to, cholesterol-lowering agents, HDL elevating agents, blood pressure-lowering agents, blood thinning agents (i.e. medicines that prevent blood clots), anti-inflammatory agents, and anti-atherogenic agents. Examples of cholesterol-lowering agents include, but are not limited to, a cholesterol absorption inhibitor, a bile acid sequestrant, a fibrate, a PCSK9 inhibitor, a microsomal triglyceride transfer protein inhibitor, an apolipoprotein B synthesis inhibitor, or a CETP inhibitor.

The Apo E mimetics can be administered in conjunction with or followed by any of the disclosed additional therapeutics. The treatments can be administered in conjunction with or followed by LDL apheresis.

The combination therapies can include administering the Apo E mimetic and an additional therapeutic agent during the treatment cycle of a dosing regimen. The combination therapies can also include administering the Apo E mimetic during the treatment cycle and an additional therapeutic agent during the rest phase.

EXAMPLES

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Those skilled in the art will recognize, or be able to ascertain using no more than routine experimentation, many equivalents to the specific embodiments of the method and compositions described herein. Such equivalents are intended to be encompassed by the following claims.

Example 1: Preparation and Analysis of Synthetic ApoE-mimicking Peptides Analogs The synthetic ApoE-mimicking peptides used in the studies described in FIGS. 3-14 were prepared were prepared by standard Fmoc solid-phase peptide synthesis techniques. Various peptides and the rationale for preparation are shown in FIG. 1. Representative analytical HPLC profiles of the synthesized peptides are shown in FIGS. 2A-2G.

Example 2: Effect of AEM Analogs in ApoE Null Mice

Studies showing the effects of various synthetic ApoE-mimicking peptides on plasma cholesterol levels are shown in FIGS. 3-14.

Example 3: Effect of AEM Analogs in High-Sucrose Fed Rats

Figure 15:
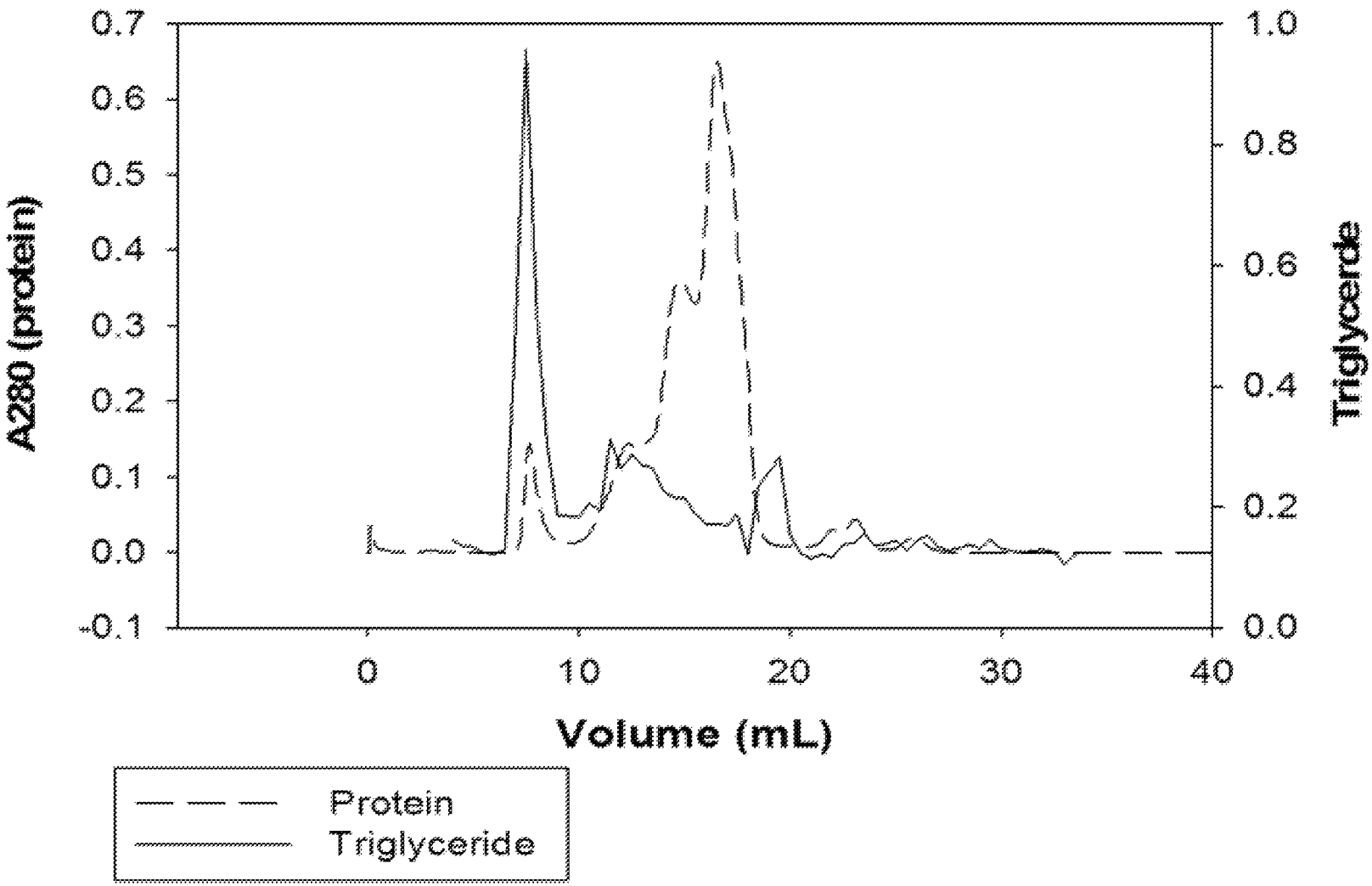
FIG. 15 shows representative data for the plasma triglyceride profile in a sucrose-fed rat model. The data show that following two weeks of a diet containing 65% (w/v) sucrose there was an increase in triglyceride levels. The study was carried out in male Sprague-Dawley rats.
Figure 16:
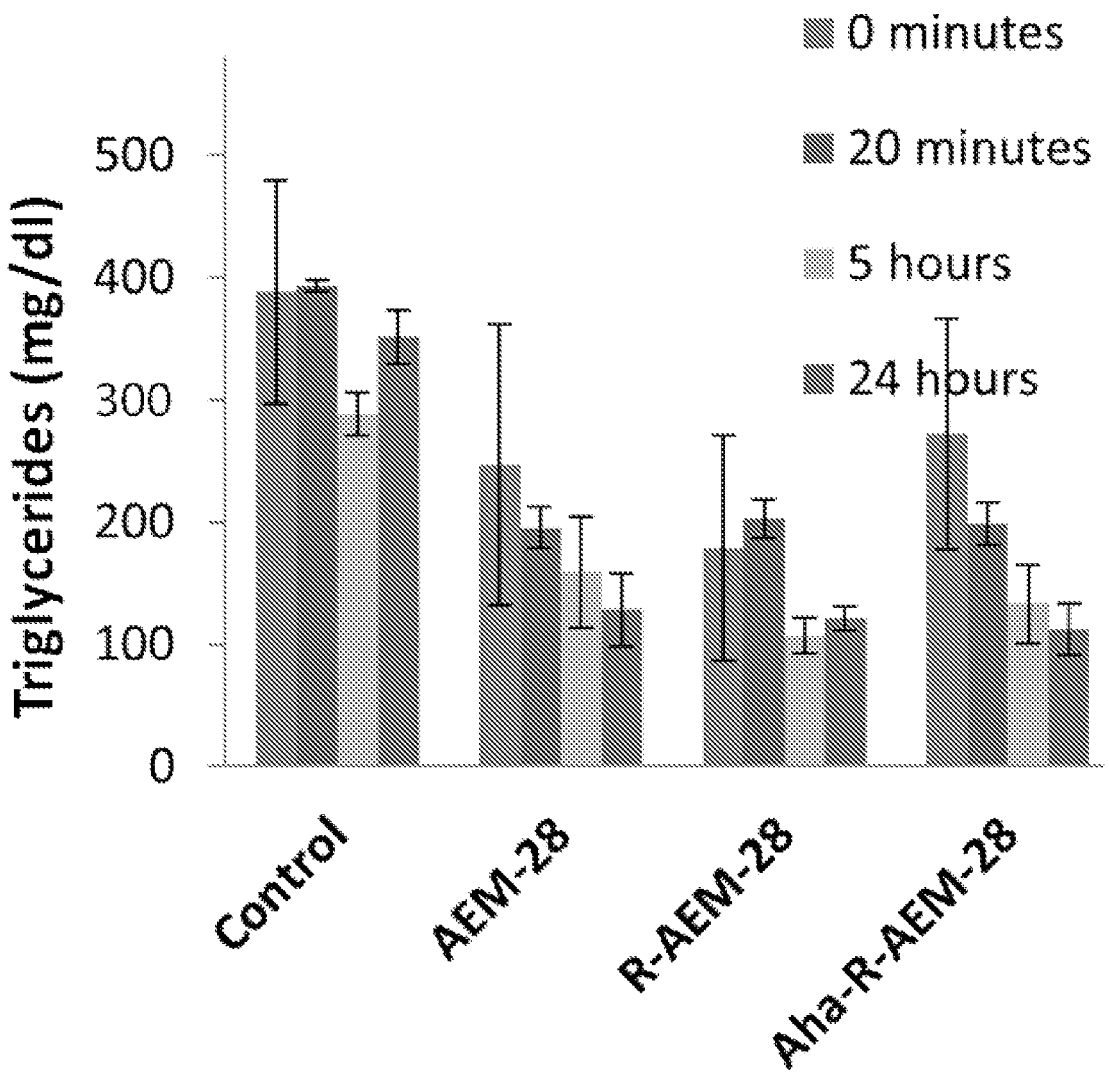
FIG. 16 show representative data for the effect of disclosed synthetic apolipoprotein E-mimicking peptides on triglyceride levels in rats fed a high sucrose (65% (w/v)) diet for two weeks at the indicated times post-administration of the indicated peptide (in saline vehicle) or control (saline) via a single dose (via intravenous tail vein injection). "Control" indicates rats administered administered saline; "AEM-28" indicates rats administered (i.v. via tail vein) 5 mg/kg of the peptide Ac-hE18A-$NH_2$; "R-AEM-28" indicates rats administered (i.v. via tail vein) 5 mg/kg of the peptide Ac—[R]hE18A-$NH_2$; and "Aha-R-AEM-28" indicates rats administered (i.v. via tail vein) 5 mg/kg of the peptide Aha-[R]hE18A-$NH_2$.
Figure 17:
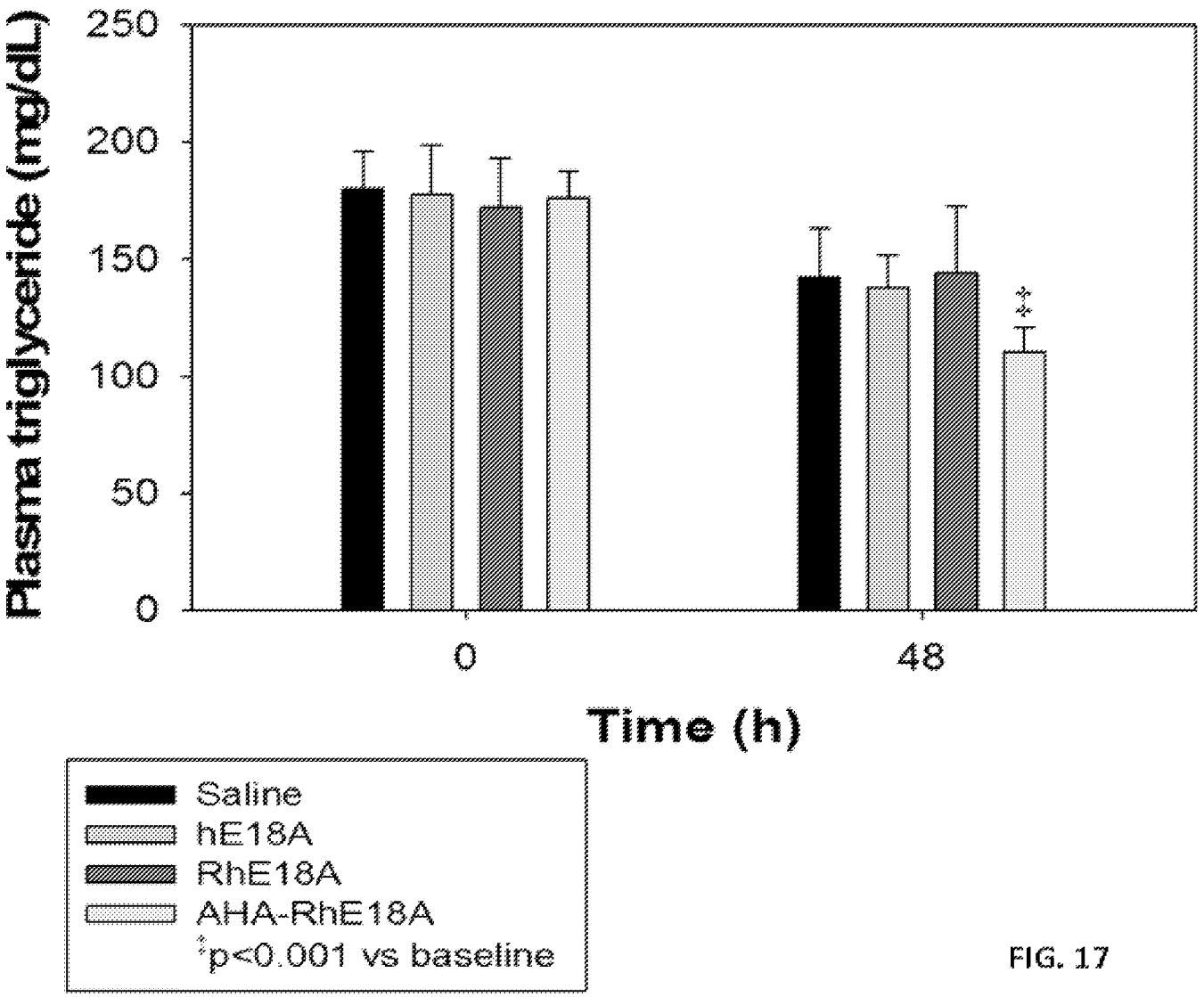
FIG. 17 show representative data for the effect of disclosed synthetic apolipoprotein E-mimicking peptides on triglyceride levels in rats fed a high sucrose (65% (w/v)) diet for two weeks at 48 h post-dosing with the indicated peptide or control (saline). "Saline" indicates rats administered administered (i.v. via tail vein) saline; "AEM-28" indicates rats administered (i.v. via tail vein) 5 mg/kg of the peptide Ac-hE18A-$NH_2$; "R-AEM-28" indicates rats administered (i.v. via tail vein) 5 mg/kg of the peptide Ac—[R]hE18A-$NH_2$; and "Aha-R-AEM-28" indicates rats administered (i.v. via tail vein) 5 mg/kg of the peptide Aha-[R]hE18A-$NH_2$.
Figure 18:
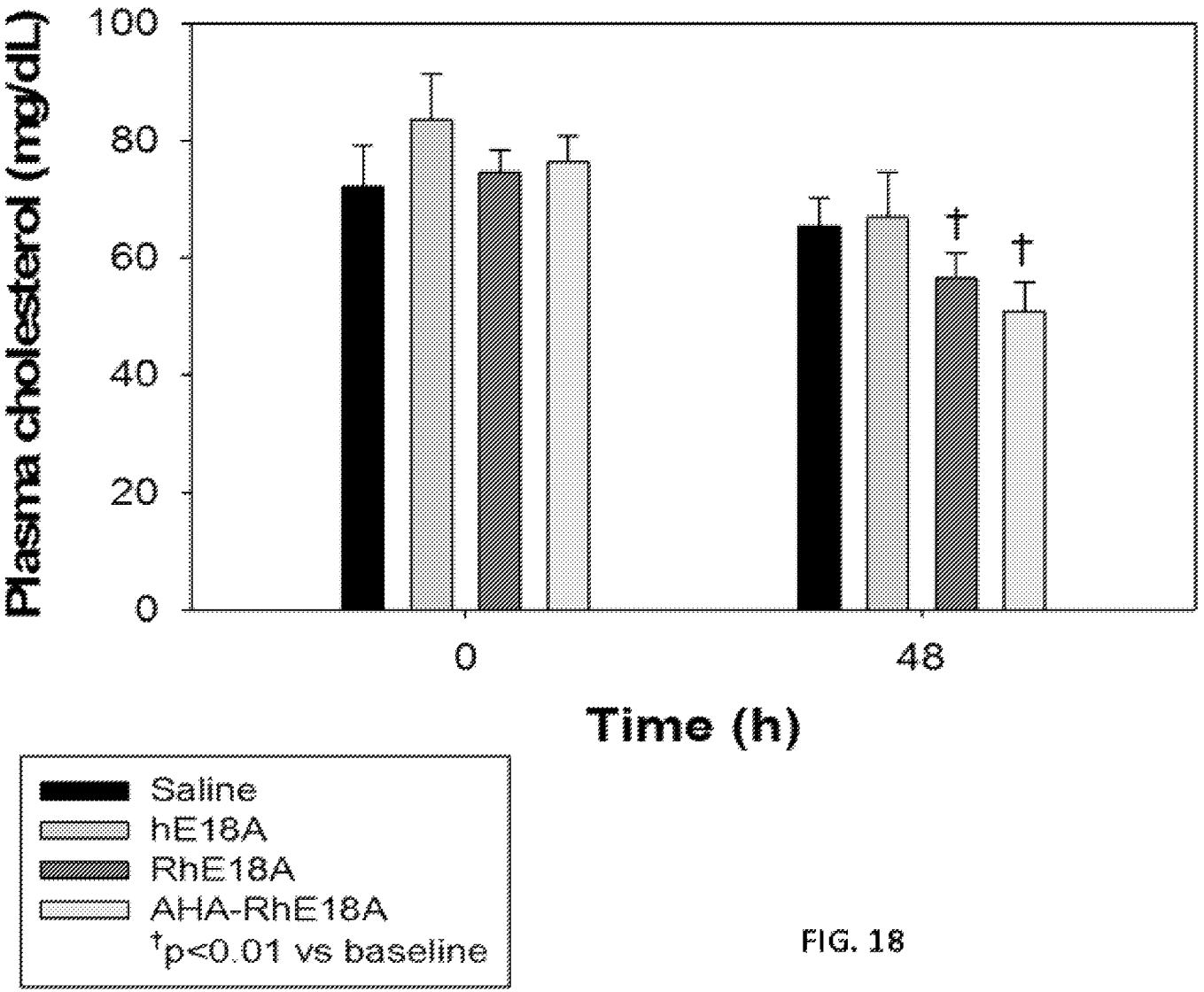
FIG. 18 show representative data for the effect of disclosed synthetic apolipoprotein E-mimicking peptides on plasm cholesterol levels in rats fed a high sucrose (65% (w/v)) diet for two weeks at 48 h post-dosing with the indicated peptide or control (saline). "Saline" indicates rats administered administered (i.v. via tail vein) saline; "AEM-28" indicates rats administered (i.v. via tail vein) 5 mg/kg of the peptide Ac-hE18A-$NH_2$; "R-AEM-28" indicates rats administered (i.v. via tail vein) 5 mg/kg of the peptide Ac—[R]hE18A-$NH_2$; and "Aha-R-AEM-28" indicates rats administered (i.v. via tail vein) 5 mg/kg of the peptide Aha-[R]hE18A-$NH_2$.
Figure 19:
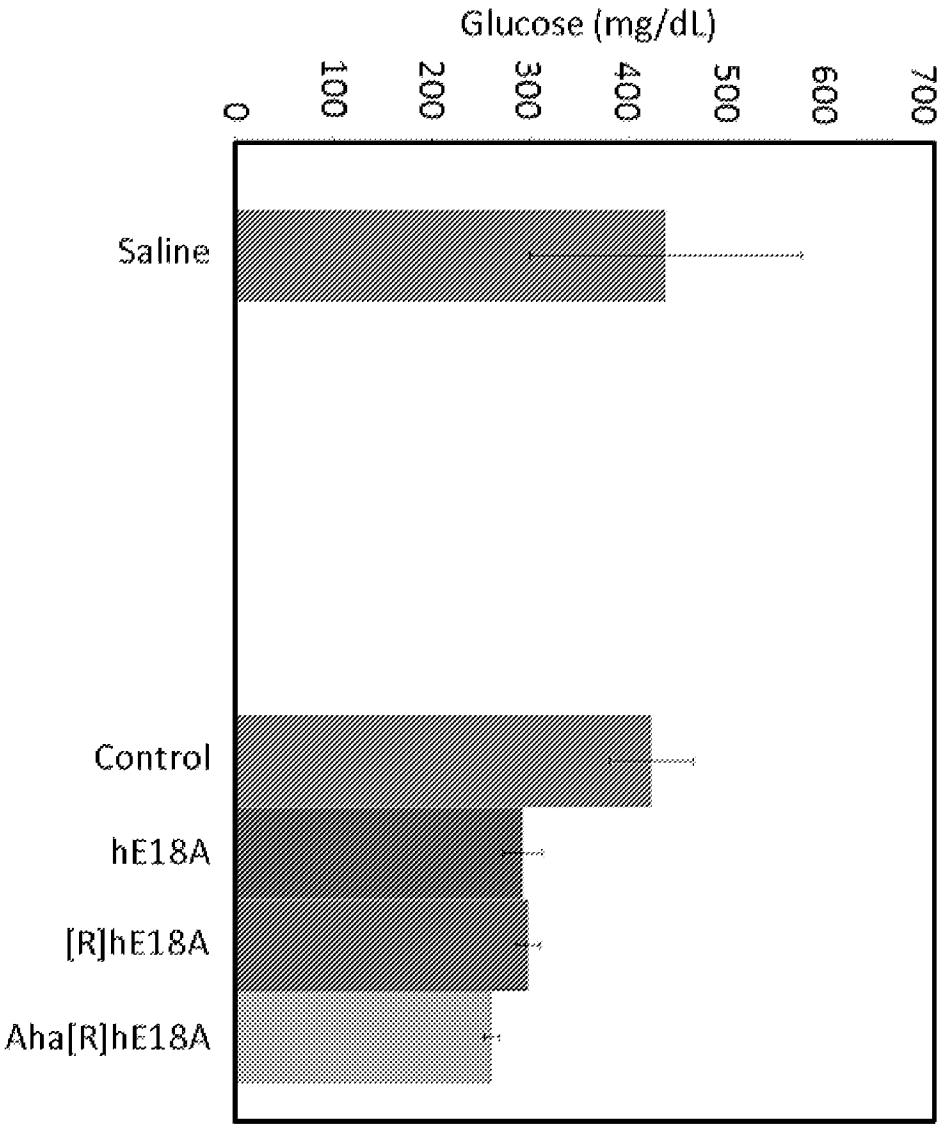
FIG. 19 show representative data for the effect of disclosed synthetic apolipoprotein E-mimicking peptides on plasma glucose levels in rats at 48 h post-dosing with the indicated peptide (in saline vehicle) or control (saline). The rats had been fed a high sucrose (65% (w/v)) diet for two weeks prior to peptide injection. "Saline" indicates rats administered administered (i.v. via tail vein) saline; "AEM-28" indicates rats administered (i.v. via tail vein) 5 mg/kg of the peptide Ac-hE18A-$NH_2$; "R-AEM-28" indicates rats administered (i.v. via tail vein) 5 mg/kg of the peptide Ac—[R]hE18A-$NH_2$; and "Aha-R-AEM-28" indicates rats administered (i.v. via tail vein) 5 mg/kg of the peptide Aha-[R]hE18A-$NH_2$.
Figure 20A:
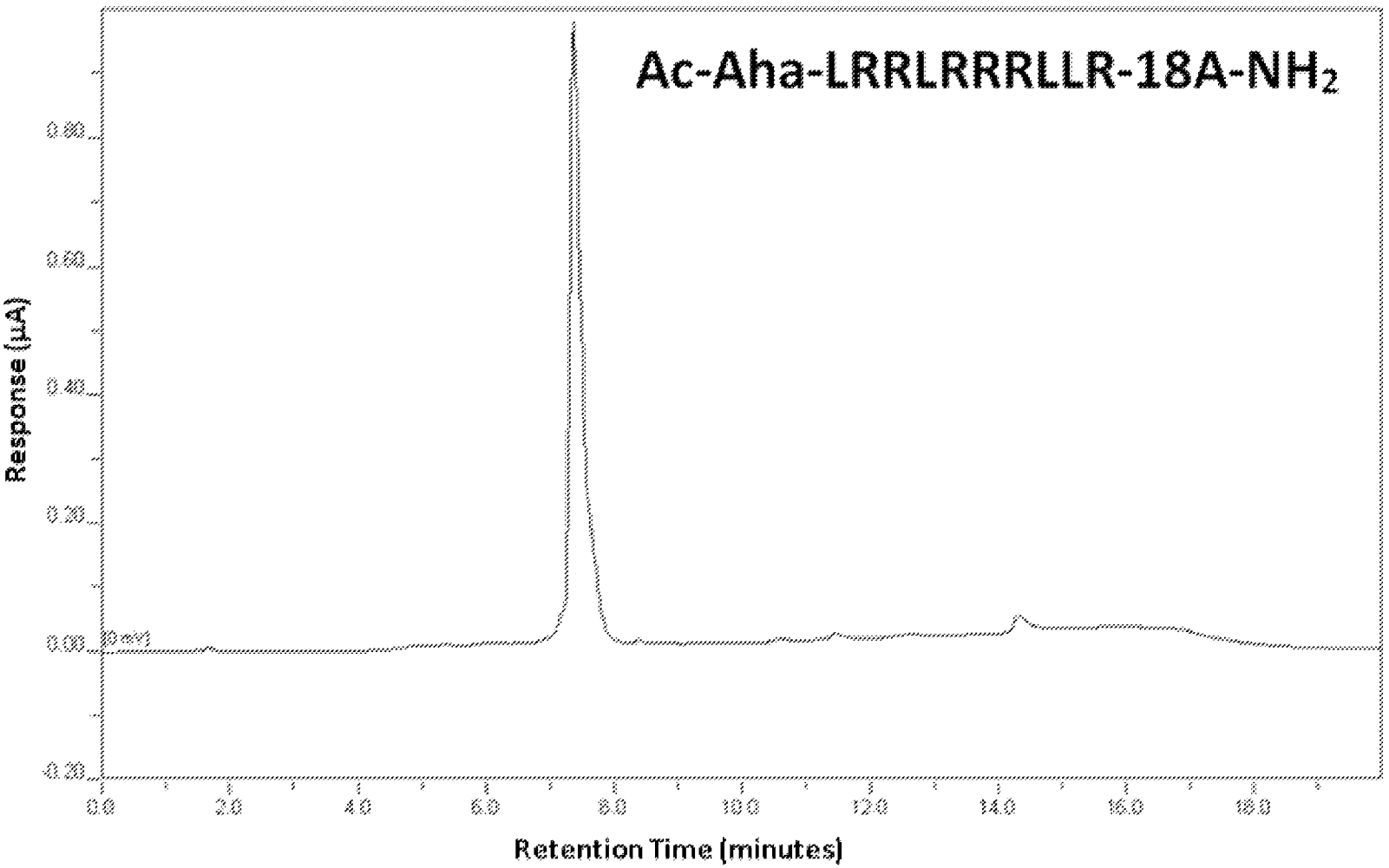
FIGS. 20A-20E shows representative analytical HPLC profiles for the indicated disclosed synthetic apolipoprotein E-mimicking peptides comprising a fatty acid moiety. Chromatography was carried out as follows: C-18 Vydac column-250×4.6 mm; mobile phase was a gradient of water/acetonitrile (0.1% TFA), 35-70% in 12 minutes.
Figure 20B:
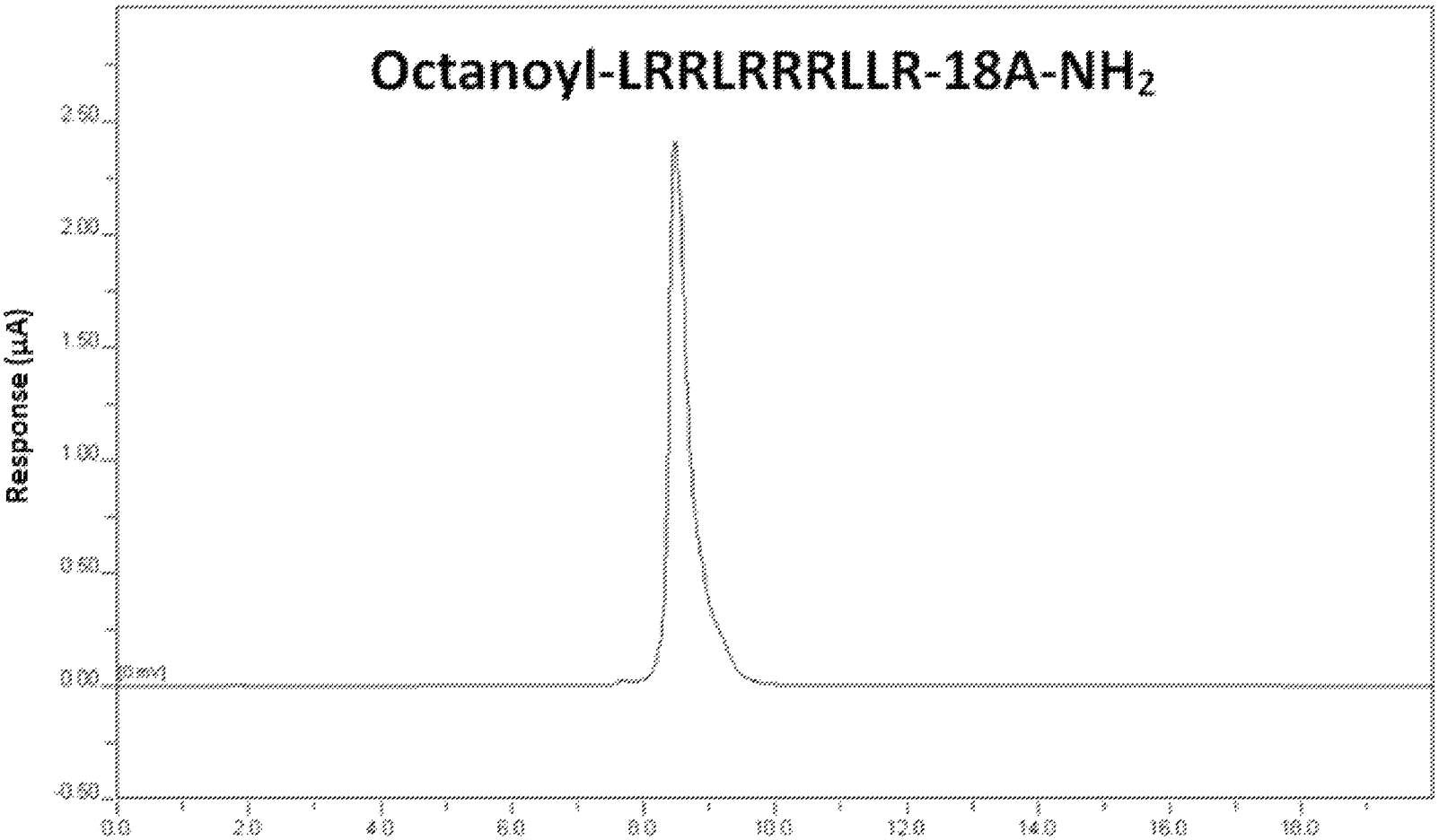
Figure 20C:
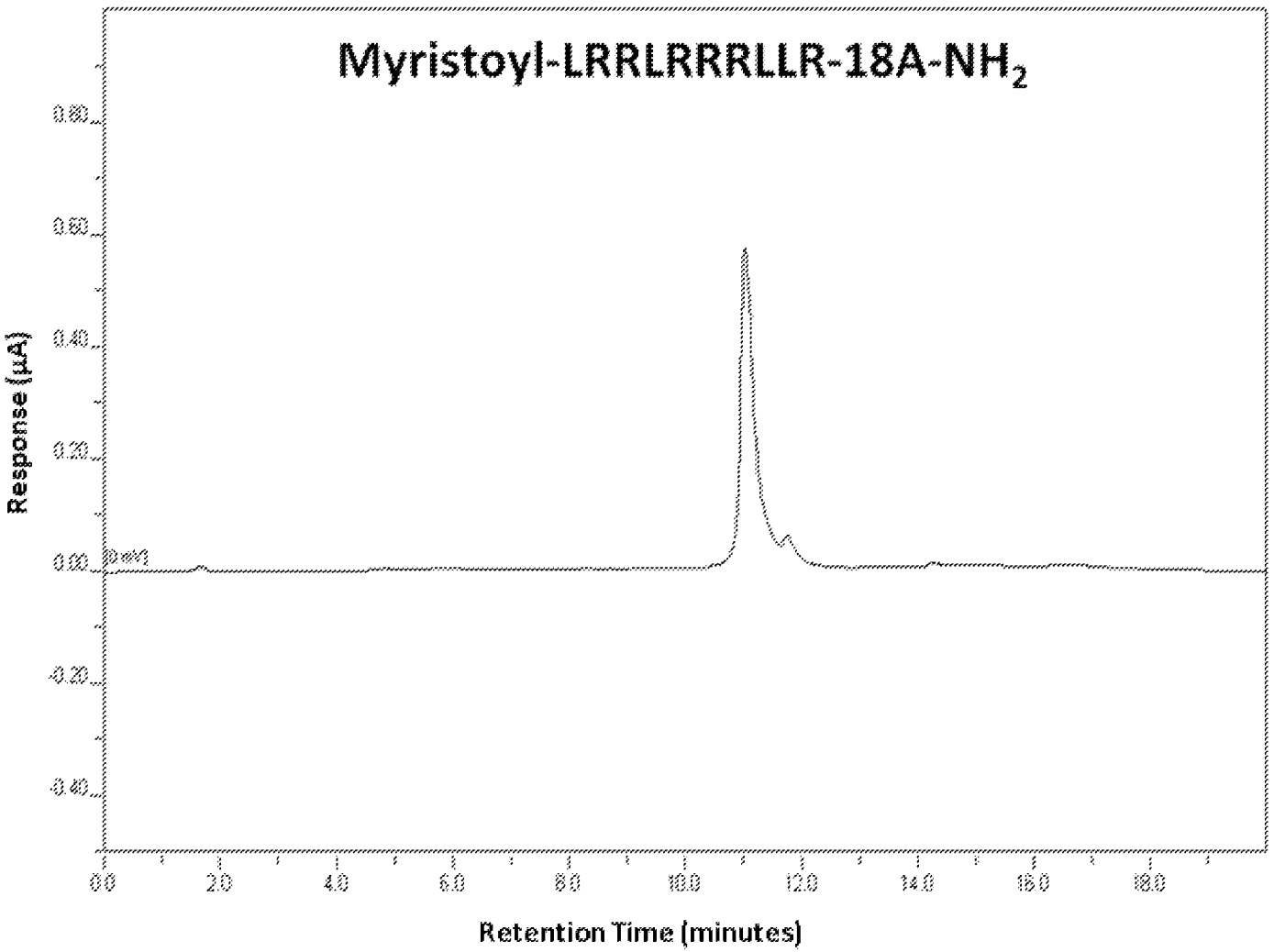
Figure 20D:
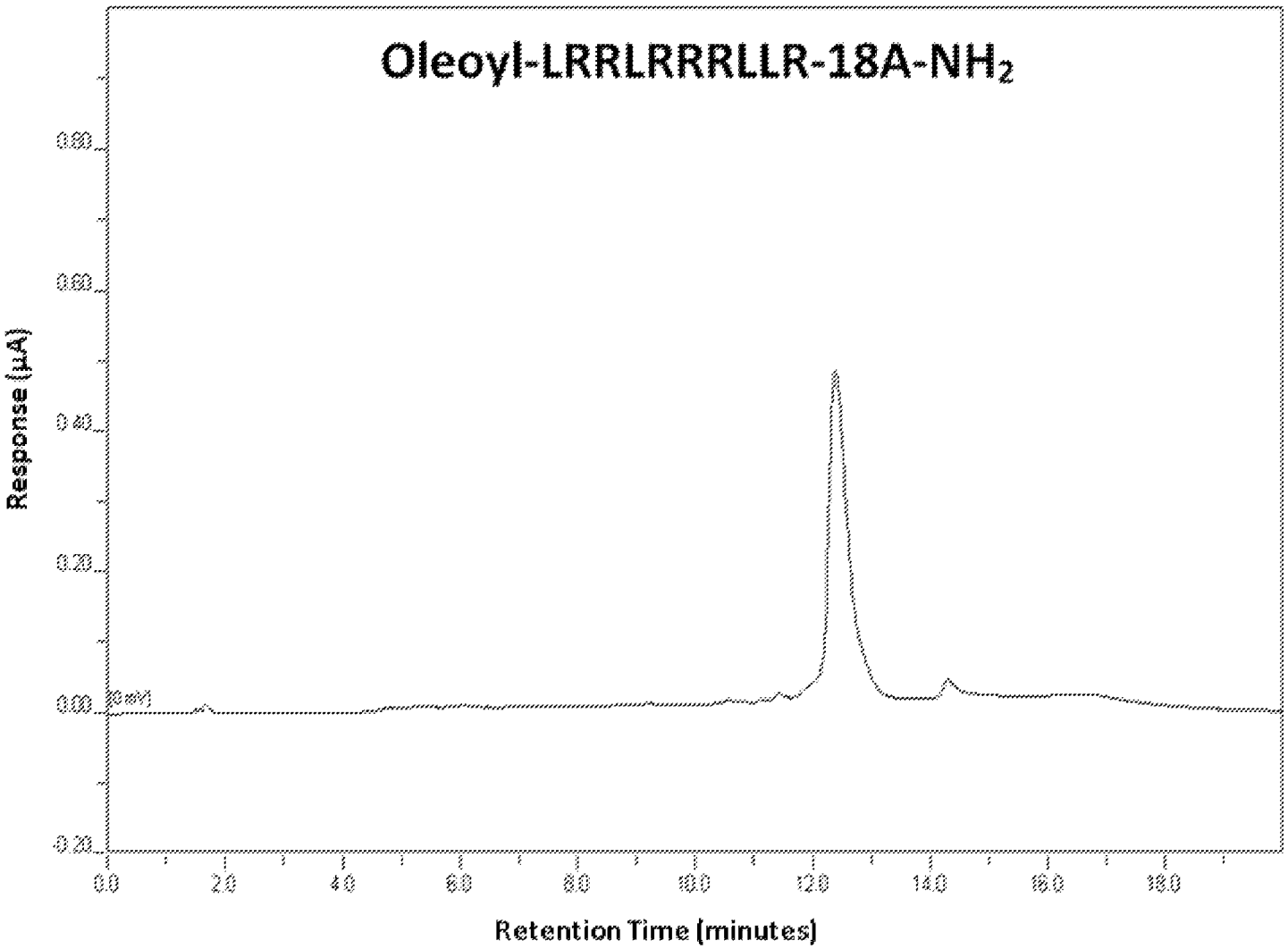
Figure 20E:
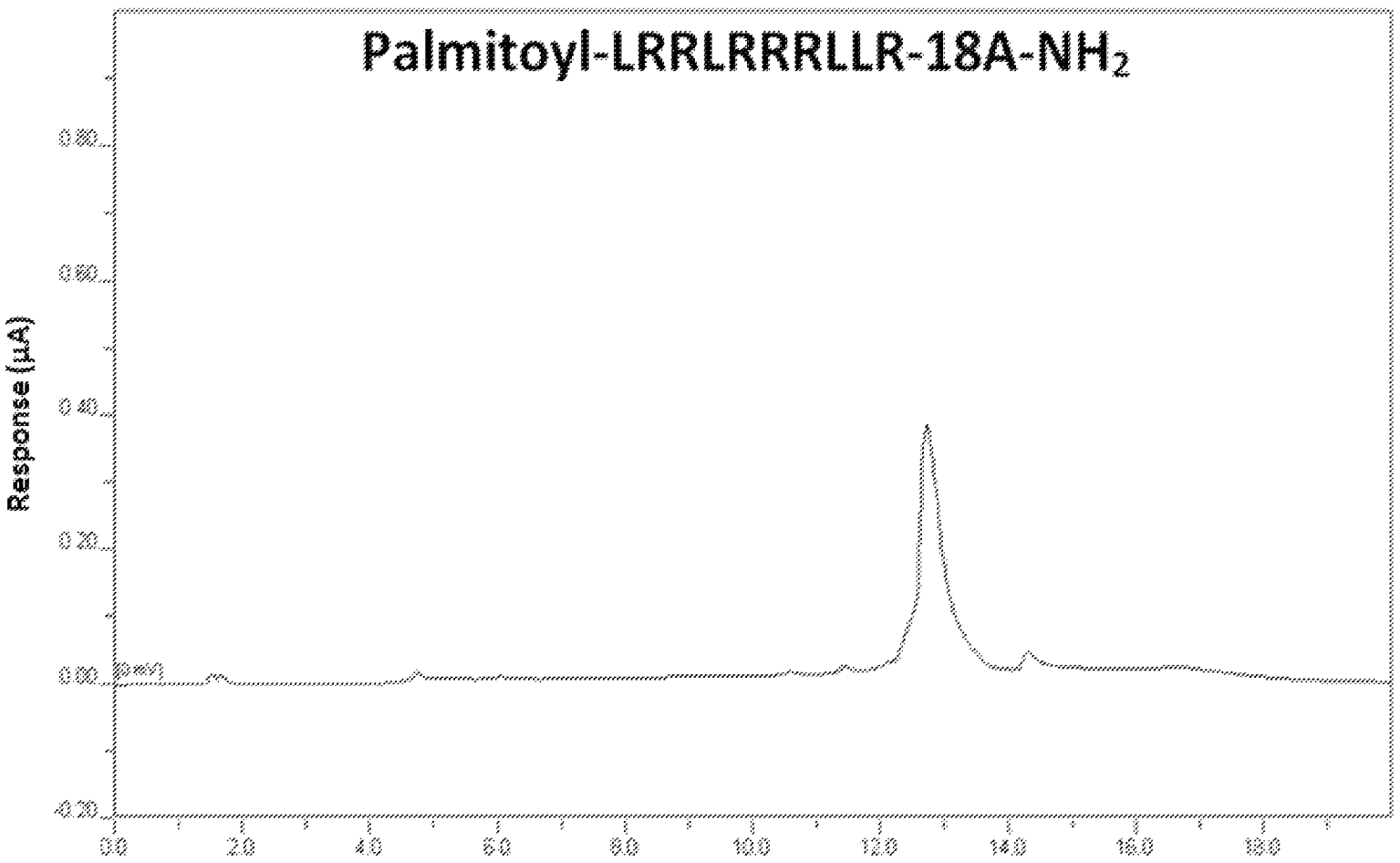
Figure 21:
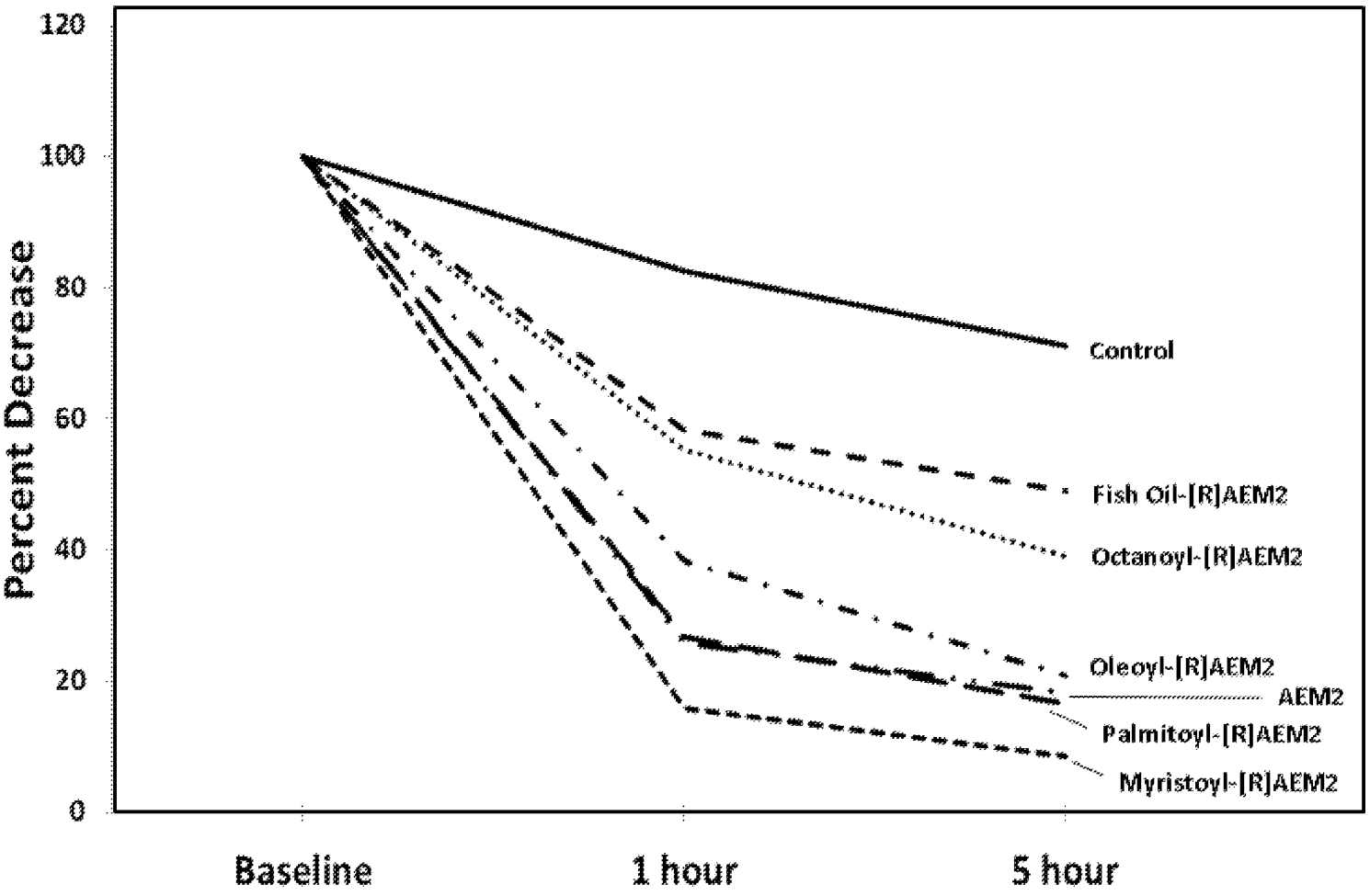
FIG. 21 shows representative data for the effect of for disclosed synthetic apolipoprotein E-mimicking peptides comprising a fatty acid moiety on plasma cholesterol levels (% reduction in plasma cholesterol). The data were obtained using apoE null mice (female; group=4) administered 100 μg of the indicated peptide (in saline vehicle) at the indicated times post-administration of the peptide. The peptides administered in this study were dialyzed following synthesis without further HPLC purification. Baseline levels are the plasma cholesterol levels at the time of peptide administration. All peptides were administered via intravenous tail vein injection.
Figure 22:
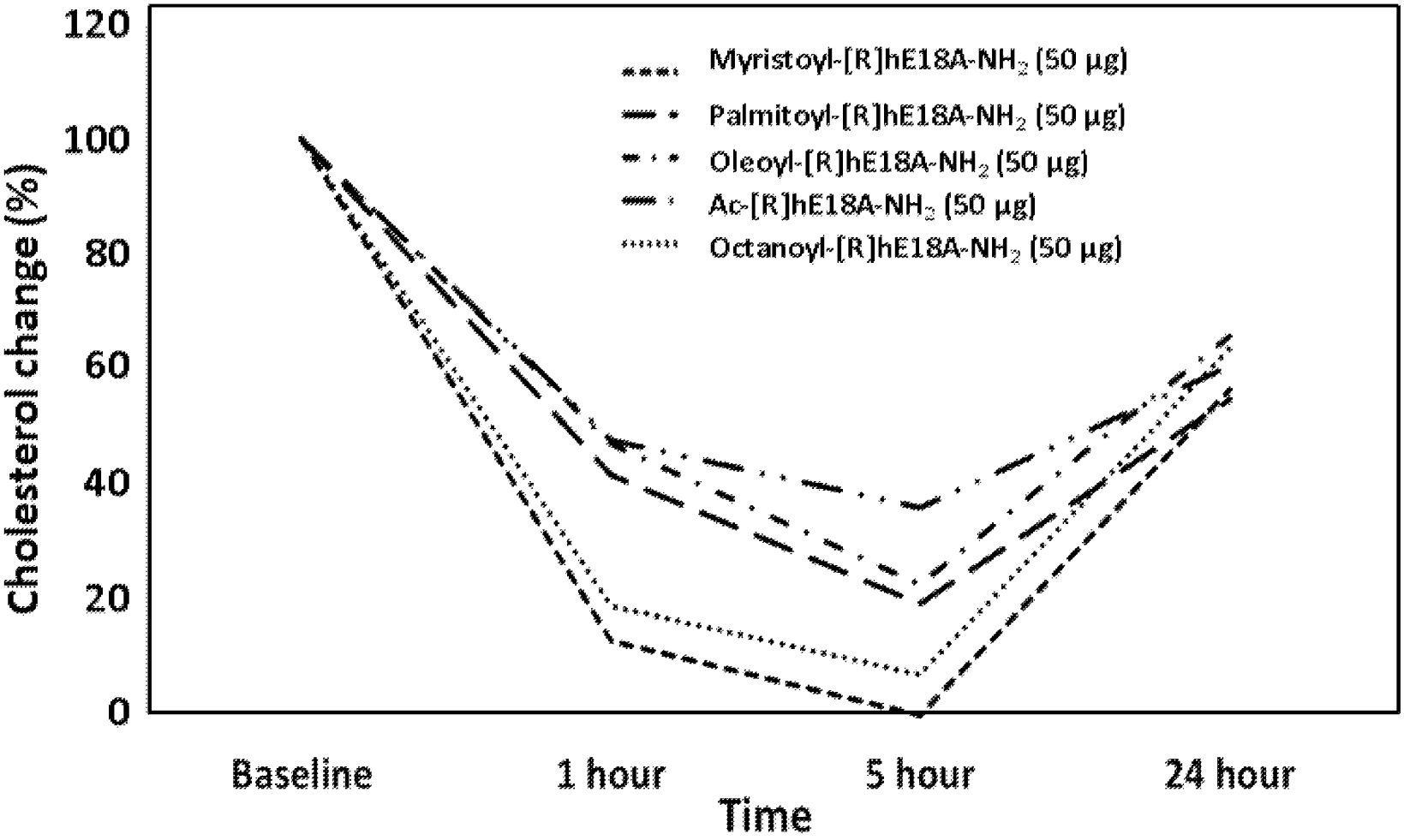
FIG. 22 shows representative data for the effect of for disclosed synthetic apolipoprotein E-mimicking peptides comprising a fatty acid moiety on plasma cholesterol levels. The data were obtained using apoE null mice (female; group=3) administered 50 μg of the indicated peptide. The study was otherwise carried out as described for FIG. 21. The indicated times are the times post-administration of a single 50 μg dose via intravenous tail vein injection.
Figure 23:
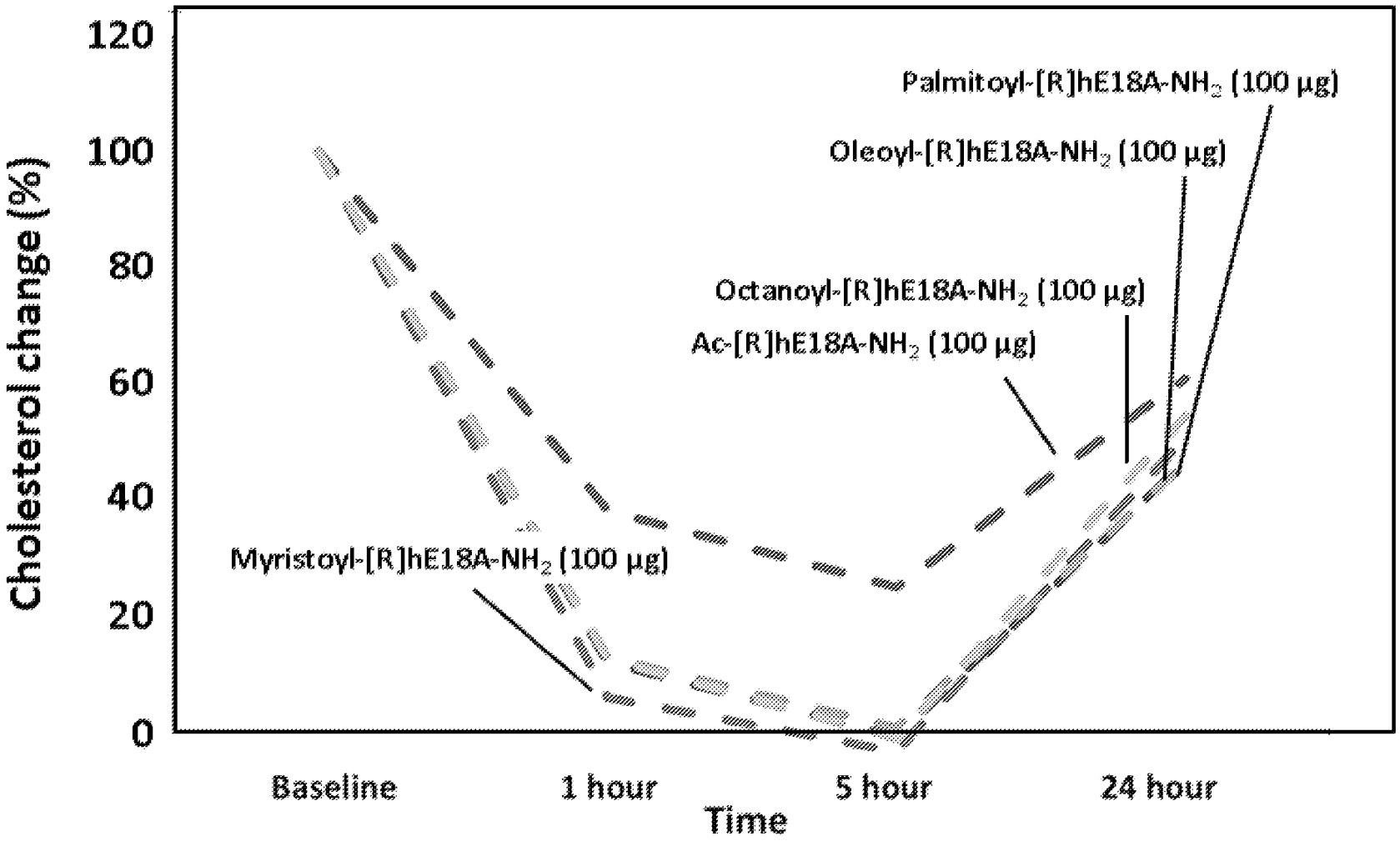
FIG. 23 shows representative data for the effect of for disclosed synthetic apolipoprotein E-mimicking peptides comprising a fatty acid moiety on plasma cholesterol levels. The data were obtained using apoE null mice (female; group=3) administered 100 μg of the indicated peptide. The study was otherwise carried out as described for FIG. 21. The indicated times are the times post-administration of a single 50 μg dose via intravenous tail vein injection.
Figure 24:
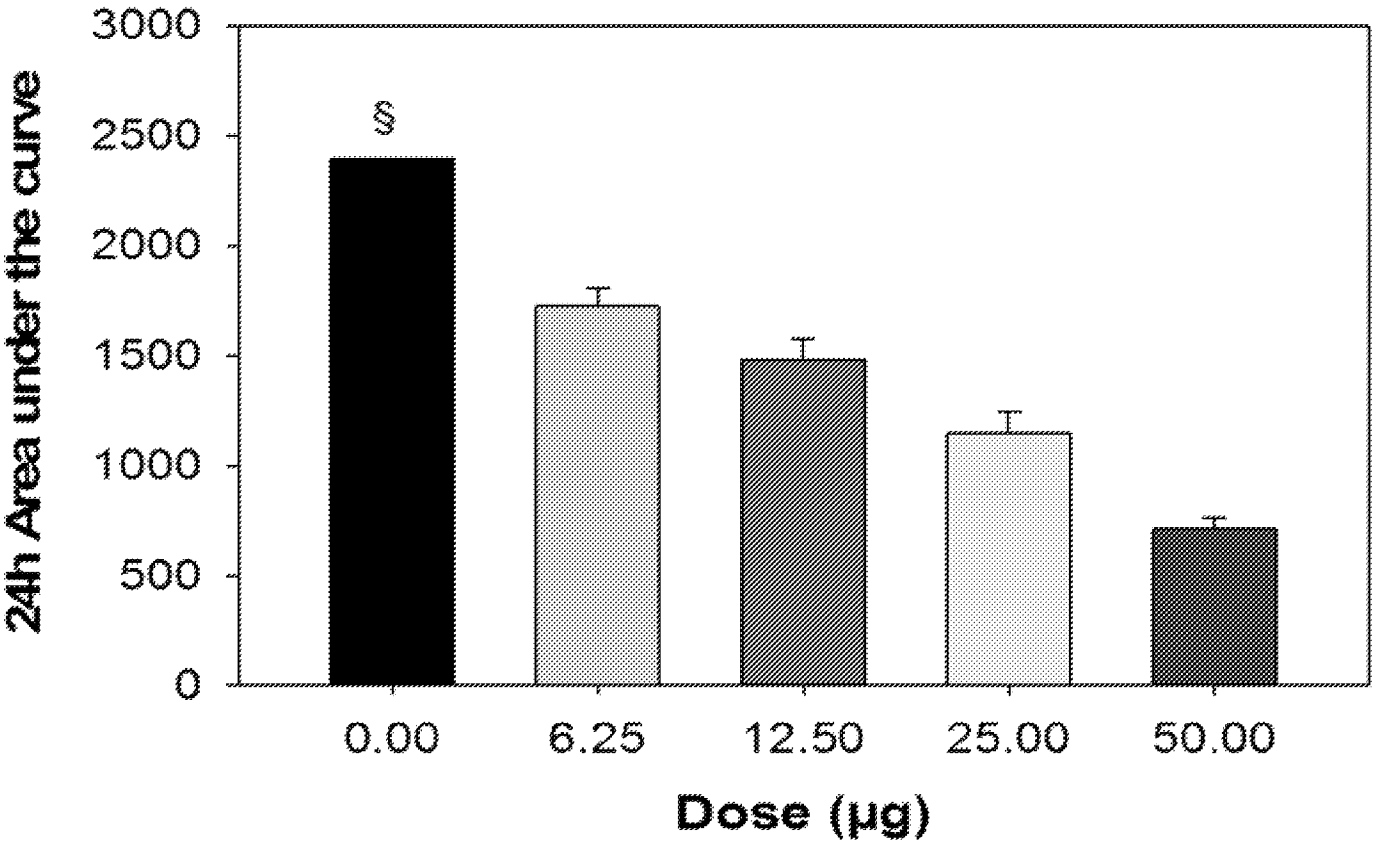
FIG. 24 show representative dose response data for the effect of myristoyl-LRRLRRRLLR-18A-NH2 (i.e., myristoyl-LRRLRRRLLR-DWLKAFYDKVAEKLKEAF-NH2 (SEQ ID NO: 628)) on plasma cholesterol levels. The data were obtained using apoE null mice (female; group=5) administered the indicated dose levels. Samples were collected at 24 hr post-administration of the peptide. The study was otherwise carried out as described for FIG. 21. The indicated doses were administered via intravenous tail vein injection.
Figure 25:
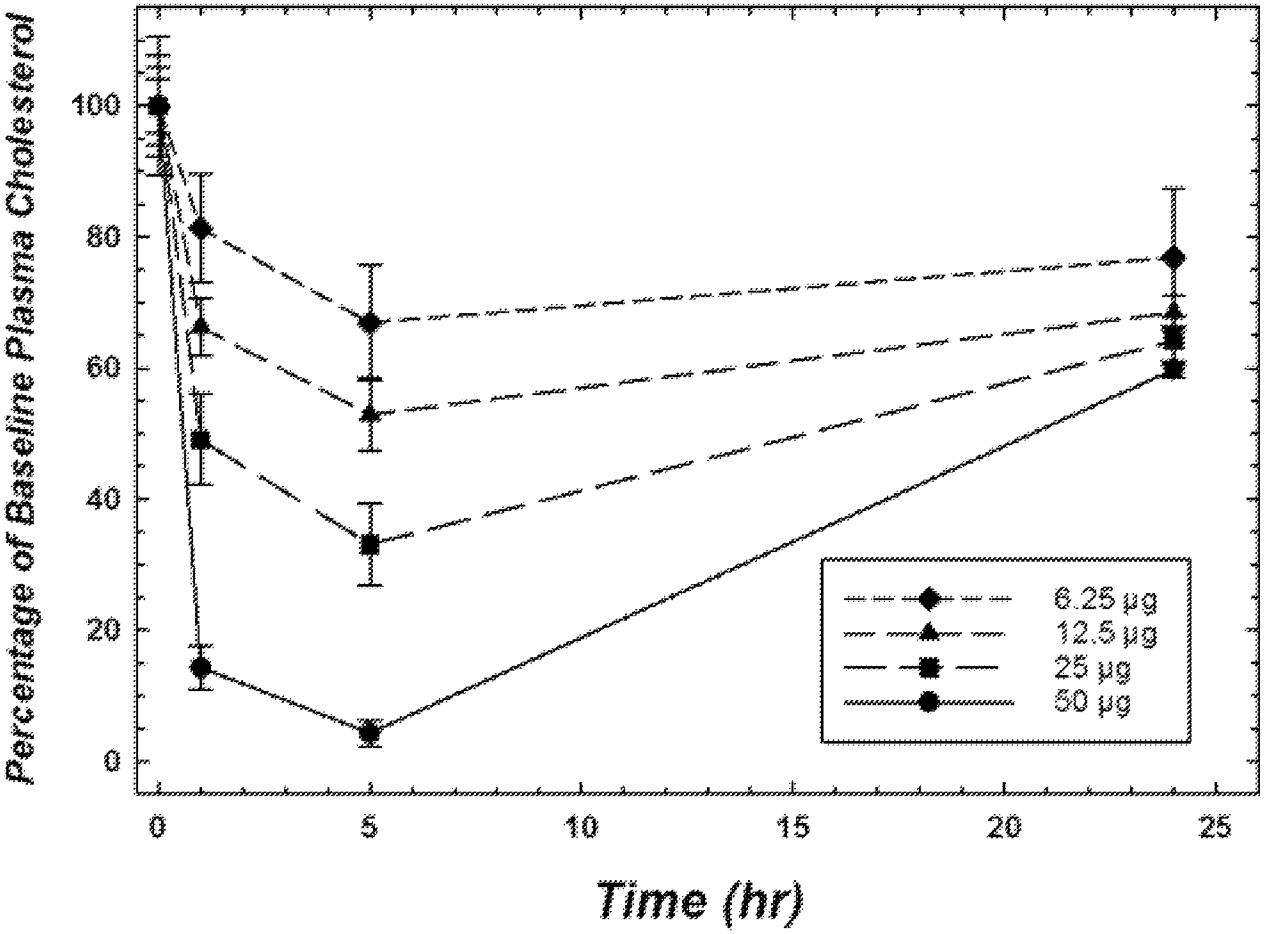
FIG. 25 show representative dose response data for the effect of myristoyl-LRRLRRRLLR-18A-NH2 (i.e., myristoyl-LRRLRRRLLR-DWLKAFYDKVAEKLKEAF-NH2 (SEQ ID NO: 628)) on plasma cholesterol levels. The data were obtained using apoE null mice (female; group=5) administered the indicated dose levels. Samples were collected at the indicated times post-administration of the peptide. The study was otherwise carried out as described for FIG. 21. The indicated doses were administered via intravenous tail vein injection.
Figure 26:
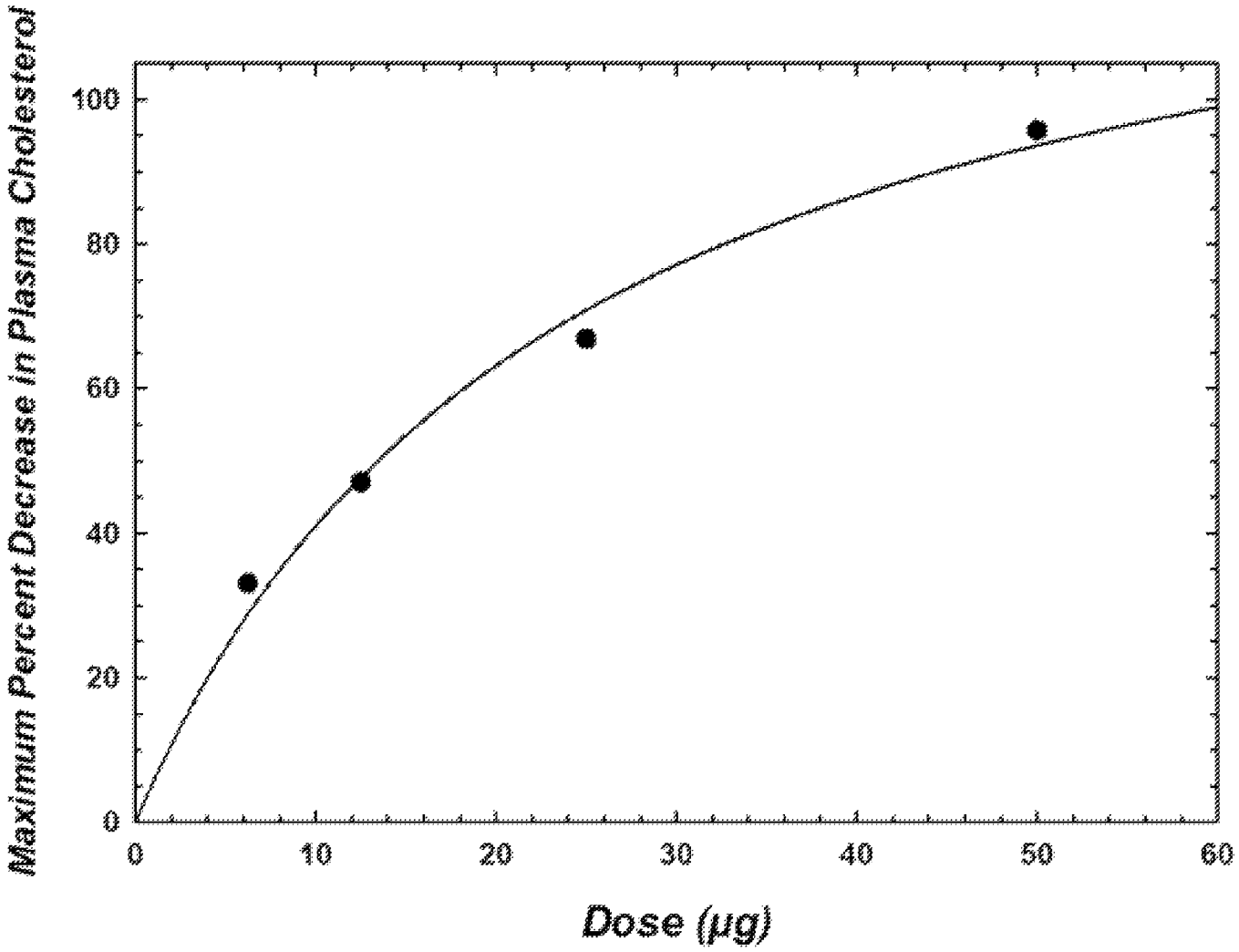
FIG. 26 shows data from the study described for FIG. 25 replotted in terms of maximum percent decrease in plasma cholesterol (at 5 hr) versus dose level (μg). The data are show as closed circles with the line the result of a hyperbolic curve fit to the data.
Figure 27:
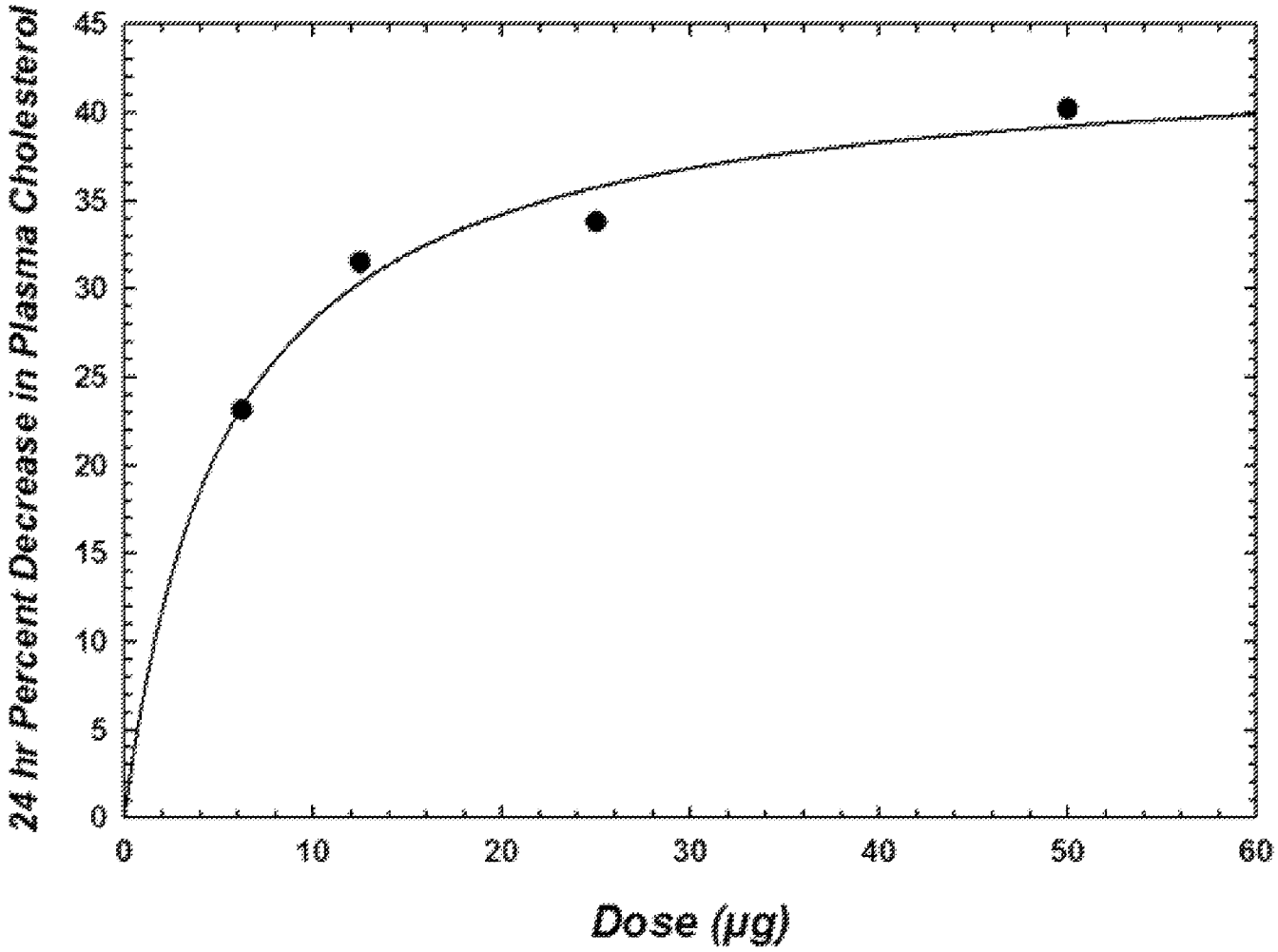
FIG. 27 shows data from the study described for FIG. 25 replotted in terms of the percent decrease in plasma cholesterol at 24 hr versus dose level (μg). The data are show as closed circles with the line the result of a hyperbolic curve fit to the data.
Figure 28:
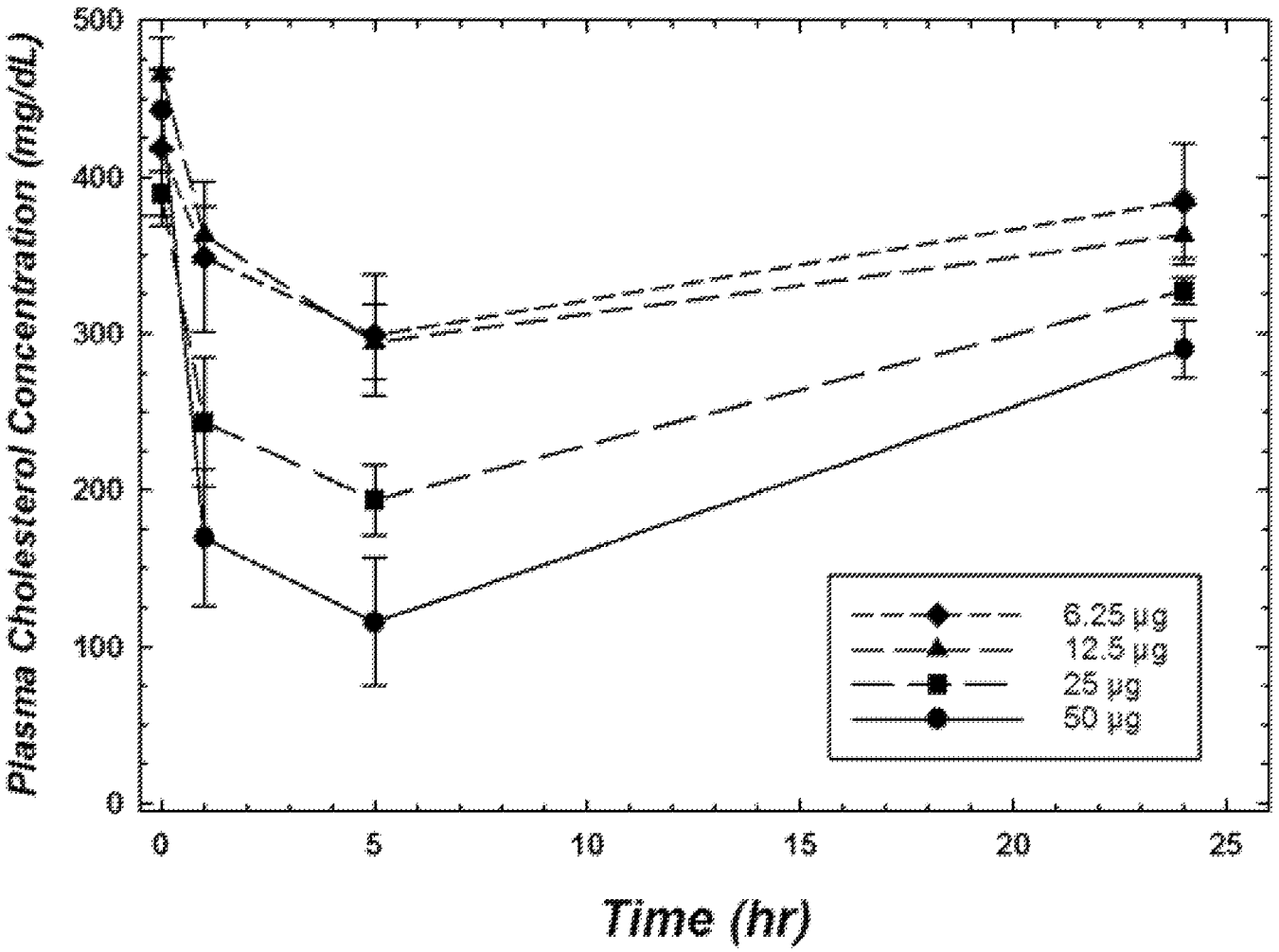
FIG. 28 show representative dose response data for the effect of octanoyl-LRRLRRRLLR-18A-NH2 (i.e., octanoyl-LRRLRRRLLR-DWLKAFYDKVAEKLKEAF-NH2 (SEQ ID NO: 625)) on plasma cholesterol levels (mg/dL). The data were obtained using apoE null mice (female; group=5) administered the indicated dose levels. Samples were collected at the indicated times post-administration of the peptide. The study was otherwise carried out as described for FIG. 21. The indicated doses were administered via intravenous tail vein injection.
Figure 29:
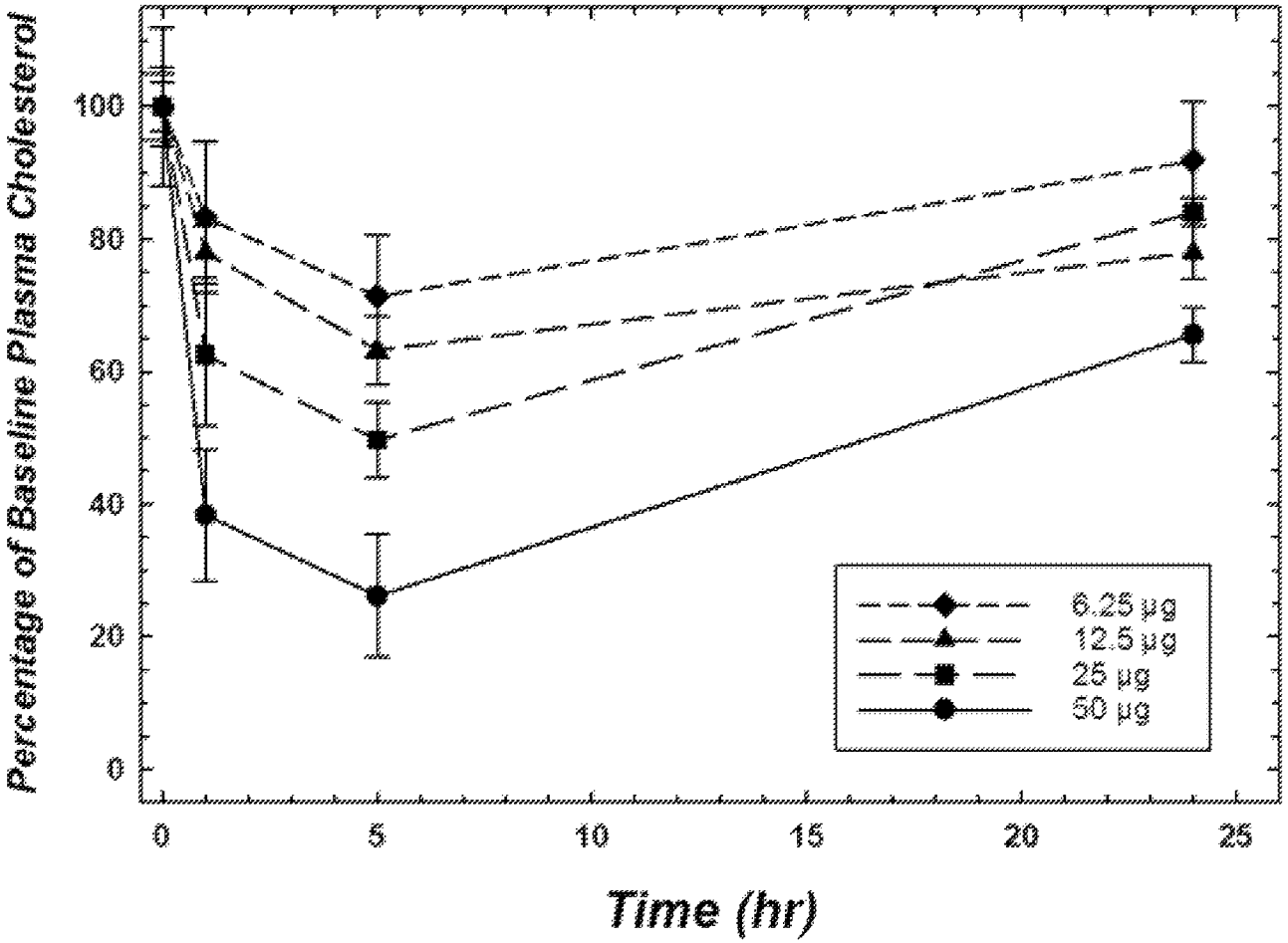
FIG. 29 show representative dose response data for the effect of octanoyl-LRRLRRRLLR-18A-NH2 (i.e., octanoyl-LRRLRRRLLR-DWLKAFYDKVAEKLKEAF-NH2 (SEQ ID NO: 625)) on plasma cholesterol levels (percent of baseline plasma cholesterol levels). The baseline level is the plasma cholesterol level at the time of the peptide administration. The data were obtained using apoE null mice (female; group=5) administered the indicated dose levels. Samples were collected at the indicated times post-administration of the peptide. The study was otherwise carried out as described for FIG. 21. The indicated doses were administered via intravenous tail vein injection.
Figure 30:
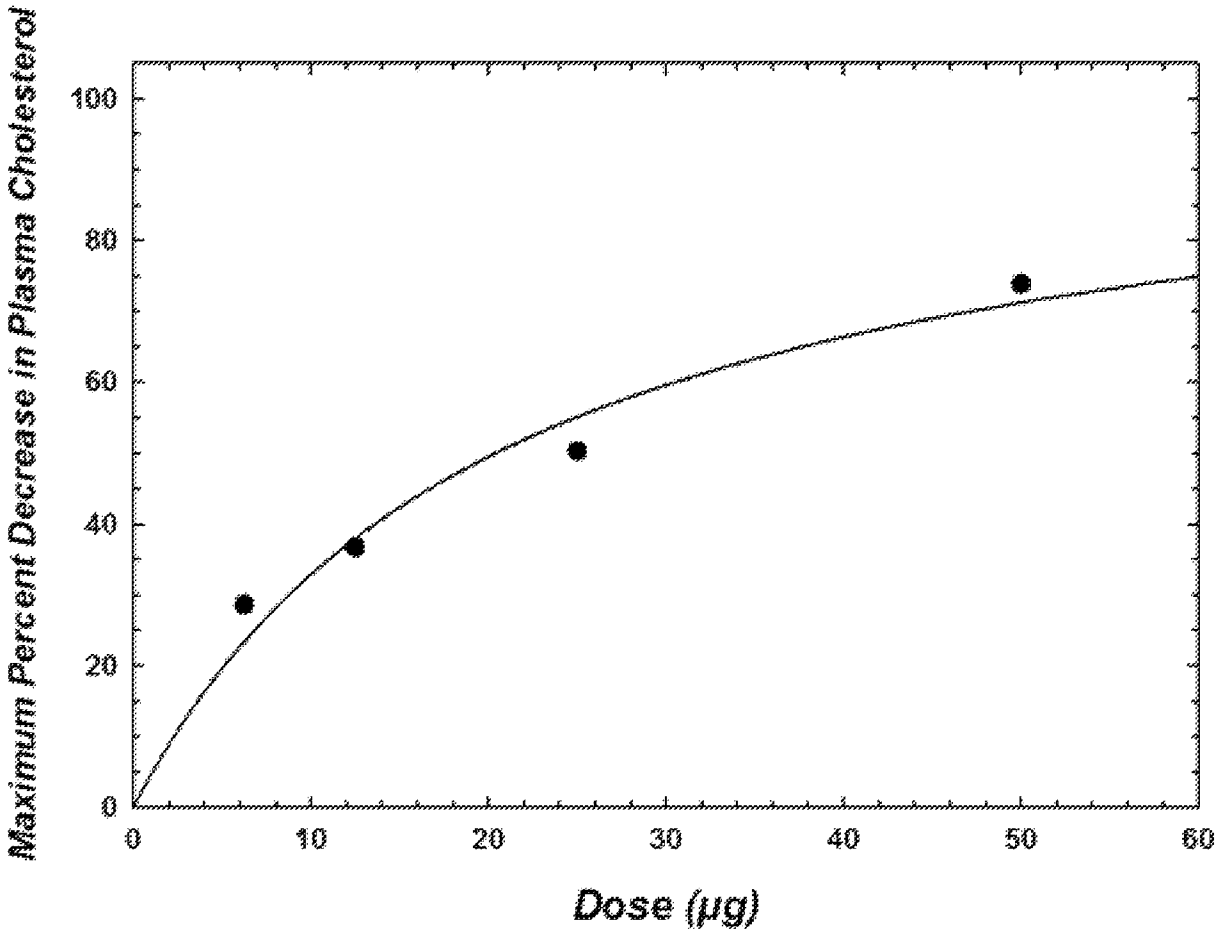
FIG. 30 shows data from the study described for FIGS. 28-29 replotted in terms of maximum percent decrease in plasma cholesterol (at 5 hr) versus dose level (μg). The data are show as closed circles with the line the result of a hyperbolic curve fit to the data.
Figure 31:
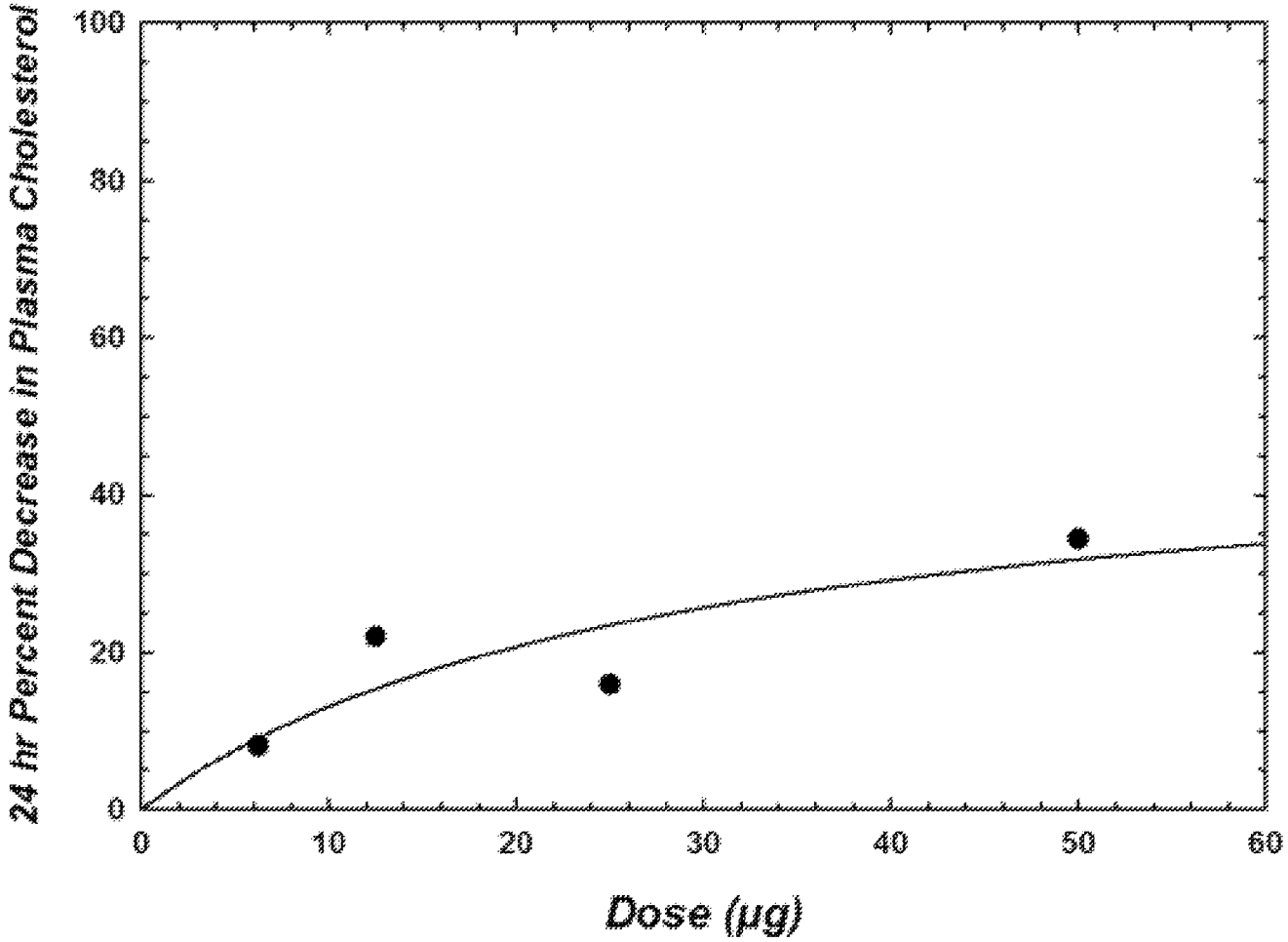
FIG. 31 shows data from the study described for FIGS. 28-29 replotted in terms of the percent decrease in plasma cholesterol at 24 hr versus dose level (μg). The data are show as closed circles with the line the result of a hyperbolic curve fit to the data.

Male Sprague-Dawley rats were purchased from Charles River and fed a diet containing 65% sucrose for two weeks. The lipoprotein profile (FIG. 15) showed an increase of triglycerides. The rats weighed 370+/−2 Og at the time of administration of peptides. The peptides administered (5 mg/kg tail vein) were as follows: Ac-hE18A-$NH_2$, Ac—[R]hE18A-$NH_2$ and Ac-Aha-[R]hE18A-$NH_2$ where hE refers to LRKLRKRLLR (SEQ ID NO:4) and [R]hE refers to LRRLRRRLLR (SEQ ID NO:6) and Aha refers to $H_2N$—$(CH_2)_5$—COOH. Blood was drawn at the times indicated in graphs and after separating cells, plasma was analyzed for cholesterol, triglycerides and glucose levels. Plasma triglycerid levels at different time points are shown in FIG. 16. Data were also obtained at 48 h post-administration of the peptide for plasma triglyceride (FIG. 17), cholesterol levels (FIG. 18), and plasma glucose levels (FIG. 19).

Example 4: Preparation and Analysis of Fatty Acid Containing Peptides

The following peptides were prepared: (1) octanoyl-LRRLRRRLLR-18A-$NH_2$ (SEQ ID NO:625); (2) myristoyl-LRRLRRRLLR-18A-$NH_2$ (SEQ ID NO:628); (3) oleoyl-LRRLRRRLLR-18A-$NH_2$ (SEQ ID NO:634); (4) palmitoyl-LRRLRRRLLR-18A-$NH_2$ (SEQ ID NO:629); and (5) Fish oil-LRRLRRRLLR-18A-$NH_2$ (SEQ ID NO:647), in which fish oil was principally a mixture of eicosapentaenoic acid (EPA) and docosahexaenoic acid (DHA), with other components in small amounts.

The peptides were synthesized on a Rink amide resin (5 mM of the functional group present on 10 g of the resin was used). Suitable FMOC-amino acid derivatives were added using HBTu method of condensation (three couplings for each amino acid at 5×, 3×, and 2× for three couplings). After the last amino acid leucine (L) was added, the resin weighed approximately 40 g, indicating quantitative yield for the coupling of amino acids. Resin (2 g) was taken for each fatty acid and each fatty acid was added two times with 10× and 5× couplings using HBTu in DMF. The peptide was released from the resin using TFA:water:anisole:ethylenedithiol (95:2:2:1 by volume, 10 ml/G of the reagent) for 3.5 hr at room temperature. After filtration of the resin, the peptide was precipitated by adding ether, washed by centrifugation with ether three times. Peptide was first dialyzed and then purified by HPLC. Since fish oil derivative is known to contain mixture that was very difficult to purify, this was not purified but the ability of this peptide to reduce plasma cholesterol in apoE null mice was compared with other dialyzed peptides. Purification of peptides was achieved using C18 silica gel column, and FIGS. 20A-20E shows representative analytical HPLC profiles of the peptides (C-18 Vydac column-250×4.6 mm; solvent system was a gradient of water/acetonitrile (0.1% TFA), 35-70% in 12 minutes).

Example 5: Effect of Fatty Acid Containing Peptides in ApoE Null Mice

The effects of synthetic ApoE-mimicking peptides comprising a fatty acid moiety at the N-terminus of the peptide on plasma cholesterol are shown in FIGS. 21-31.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

---

SEQUENCE LISTING

```
<160> NUMBER OF SEQ ID NOS: 674

<210> SEQ ID NO 1
<211> LENGTH: 28
<212> TYPE: PRT
<213> ORGANISM: Artificial Sequence
<220> FEATURE:
<223> OTHER INFORMATION: synthetic construct; ApoE mimetic

<400> SEQUENCE: 1

Leu Arg Lys Leu Arg Lys Arg Leu Leu Arg Asp Trp Leu Lys Ala Phe
1               5                   10                  15

Tyr Asp Lys Val Ala Glu Lys Leu Lys Glu Ala Phe
            20                  25


<210> SEQ ID NO 2
<211> LENGTH: 28
<212> TYPE: PRT
<213> ORGANISM: Artificial Sequence
<220> FEATURE:
<223> OTHER INFORMATION: synthetic construct; reverse analog of ApoE
      mimetic
```

<400> SEQUENCE: 2

Arg Leu Leu Arg Lys Arg Leu Lys Arg Leu Asp Trp Leu Lys Ala Phe
1 5 10 15

Tyr Asp Lys Val Ala Glu Lys Leu Lys Glu Ala Phe
20 25

<210> SEQ ID NO 3
<211> LENGTH: 28
<212> TYPE: PRT
<213> ORGANISM: Artificial Sequence
<220> FEATURE:
<223> OTHER INFORMATION: synthetic construct; reverse analog of ApoE
mimetic

<400> SEQUENCE: 3

Leu Arg Lys Leu Arg Lys Arg Leu Leu Arg Phe Ala Glu Lys Leu Lys
1 5 10 15

Glu Ala Val Lys Asp Tyr Phe Ala Lys Leu Trp Asp
20 25

<210> SEQ ID NO 4
<211> LENGTH: 10
<212> TYPE: PRT
<213> ORGANISM: Artificial Sequence
<220> FEATURE:
<223> OTHER INFORMATION: synthetic construct; receptor binding domain of
human Apo E

<400> SEQUENCE: 4

Leu Arg Lys Leu Arg Lys Arg Leu Leu Arg
1 5 10

<210> SEQ ID NO 5
<211> LENGTH: 18
<212> TYPE: PRT
<213> ORGANISM: Artificial Sequence
<220> FEATURE:
<223> OTHER INFORMATION: synthetic construct; lipid-associating peptide

<400> SEQUENCE: 5

Asp Trp Leu Lys Ala Phe Tyr Asp Lys Val Ala Glu Lys Leu Lys Glu
1 5 10 15

Ala Phe

<210> SEQ ID NO 6
<211> LENGTH: 18
<212> TYPE: PRT
<213> ORGANISM: Artificial Sequence
<220> FEATURE:
<223> OTHER INFORMATION: synthetic construct; lipid-associating peptide
<220> FEATURE:
<221> NAME/KEY: misc
<222> LOCATION: (1)..(1)
<223> OTHER INFORMATION: N-terminal end is acetylated
<220> FEATURE:
<221> NAME/KEY: misc
<222> LOCATION: (18)..(18)
<223> OTHER INFORMATION: C-terminal end contains an amide group

<400> SEQUENCE: 6

Asp Trp Leu Lys Ala Phe Tyr Asp Lys Val Ala Glu Lys Leu Lys Glu
1 5 10 15

Ala Phe

<210> SEQ ID NO 7
<211> LENGTH: 10
<212> TYPE: PRT
<213> ORGANISM: Artificial Sequence
<220> FEATURE:
<223> OTHER INFORMATION: synthetic construct; Rat ApoE mimetic

<400> SEQUENCE: 7

Leu Arg Lys Met Arg Lys Arg Leu Met Arg
1 5 10

<210> SEQ ID NO 8
<211> LENGTH: 10
<212> TYPE: PRT
<213> ORGANISM: Artificial Sequence
<220> FEATURE:
<223> OTHER INFORMATION: synthetic construct; Bovine Apo E mimetic

<400> SEQUENCE: 8

Leu Arg Lys Leu Pro Lys Arg Leu Leu Arg
1 5 10

<210> SEQ ID NO 9
<211> LENGTH: 10
<212> TYPE: PRT
<213> ORGANISM: Artificial Sequence
<220> FEATURE:
<223> OTHER INFORMATION: synthetic construct; Pig ApoE mimetic

<400> SEQUENCE: 9

Leu Arg Asn Val Arg Lys Arg Leu Val Arg
1 5 10

<210> SEQ ID NO 10
<211> LENGTH: 10
<212> TYPE: PRT
<213> ORGANISM: Artificial Sequence
<220> FEATURE:
<223> OTHER INFORMATION: synthetic construct; Dog ApoE mimetic

<400> SEQUENCE: 10

Met Arg Lys Leu Arg Lys Arg Val Leu Arg
1 5 10

<210> SEQ ID NO 11
<211> LENGTH: 10
<212> TYPE: PRT
<213> ORGANISM: Artificial Sequence
<220> FEATURE:
<223> OTHER INFORMATION: synthetic construct; R modified ApoE mimetic

<400> SEQUENCE: 11

Leu Arg Arg Leu Arg Arg Arg Leu Leu Arg
1 5 10

<210> SEQ ID NO 12
<211> LENGTH: 10
<212> TYPE: PRT
<213> ORGANISM: Artificial Sequence
<220> FEATURE:
<223> OTHER INFORMATION: synthetic construct; F modified ApoE mimetic

<400> SEQUENCE: 12

Leu Arg Lys Leu Arg Lys Arg Phe Phe Arg
1 5 10

<210> SEQ ID NO 13

<211> LENGTH: 9
<212> TYPE: PRT
<213> ORGANISM: Artificial Sequence
<220> FEATURE:
<223> OTHER INFORMATION: synthetic construct; ApoB mimetic

<400> SEQUENCE: 13

Arg Leu Thr Arg Lys Arg Gly Leu Lys
1 5

<210> SEQ ID NO 14
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 14

Asp Trp Phe Lys Ala Phe Tyr Asp Lys Val Ala Glu Lys Leu Lys Glu
1 5 10 15

Ala Phe

<210> SEQ ID NO 15
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 15

Asp Trp Leu Lys Ala Phe Tyr Asp Lys Val Ala Glu Lys Phe Lys Glu
1 5 10 15

Ala Phe

<210> SEQ ID NO 16
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 16

Asp Trp Phe Lys Ala Phe Tyr Asp Lys Val Ala Glu Lys Phe Lys Glu
1 5 10 15

Ala Phe

<210> SEQ ID NO 17
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 17

Asp Trp Leu Lys Ala Phe Tyr Asp Lys Val Phe Glu Lys Phe Lys Glu
1 5 10 15

Phe Phe

<210> SEQ ID NO 18
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 18

Asp Trp Leu Lys Ala Phe Tyr Asp Lys Phe Phe Glu Lys Phe Lys Glu
1 5 10 15

Phe Phe

<210> SEQ ID NO 19
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 19

Asp Trp Phe Lys Ala Phe Tyr Asp Lys Phe Phe Glu Lys Phe Lys Glu
1 5 10 15

Phe Phe

<210> SEQ ID NO 20
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC <222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 20

Asp Trp Leu Lys Ala Phe Tyr Asp Lys Val Ala Glu Lys Leu Lys Glu
1 5 10 15

Phe Phe

<210> SEQ ID NO 21
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 21

Asp Trp Leu Lys Ala Phe Tyr Asp Lys Val Phe Glu Lys Phe Lys Glu
1 5 10 15

Ala Phe

<210> SEQ ID NO 22
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 22

Asp Trp Leu Lys Ala Phe Tyr Asp Lys Val Phe Glu Lys Leu Lys Glu
1 5 10 15

Phe Phe

<210> SEQ ID NO 23
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 23

Asp Trp Leu Lys Ala Phe Tyr Asp Lys Val Ala Glu Lys Phe Lys Glu 1 5 10 15

Phe Phe

<210> SEQ ID NO 24
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 24

Asp Trp Leu Lys Ala Phe Tyr Asp Lys Val Phe Glu Lys Phe Lys Glu
1 5 10 15

Phe Phe

<210> SEQ ID NO 25
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 25

Glu Trp Leu Lys Leu Phe Tyr Glu Lys Val Leu Glu Lys Phe Lys Glu
1 5 10 15

Ala Phe

<210> SEQ ID NO 26
<211> LENGTH: 19
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (19)..(19)
<223> OTHER INFORMATION: C-terminal amidation

<400> SEQUENCE: 26

Glu Trp Leu Lys Ala Phe Tyr Ile Asp Lys Val Ala Glu Lys Phe Lys
1 5 10 15

Glu Ala Phe

<210> SEQ ID NO 27
<211> LENGTH: 19
<212> TYPE: PRT
<213> ORGANISM: Artificial Sequence
<220> FEATURE:

<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (19)..(19)
<223> OTHER INFORMATION: C-terminal amidation

<400> SEQUENCE: 27

Glu Glu Trp Leu Lys Ala Phe Tyr Asp Lys Val Ala Glu Lys Leu Lys
1 5 10 15

Glu Phe Phe

<210> SEQ ID NO 28
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 28

Glu Trp Leu Lys Ala Phe Tyr Asp Lys Val Phe Glu Lys Phe Lys Glu
1 5 10 15

Ala Phe

<210> SEQ ID NO 29
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 29

Glu Trp Leu Lys Ala Phe Tyr Asp Lys Val Phe Glu Lys Leu Lys Glu
1 5 10 15

Phe Phe

<210> SEQ ID NO 30
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 30

Glu Trp Leu Lys Ala Phe Tyr Asp Lys Val Ala Glu Lys Phe Lys Glu
1 5 10 15

Phe Phe

<210> SEQ ID NO 31
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 31

Glu Trp Leu Lys Ala Phe Tyr Asp Lys Val Phe Glu Lys Phe Lys Glu
1 5 10 15

Phe Phe

<210> SEQ ID NO 32
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 32

Ala Phe Tyr Asp Lys Val Ala Glu Lys Leu Lys Glu Ala Phe
1 5 10

<210> SEQ ID NO 33
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 33

Ala Phe Tyr Asp Lys Val Ala Glu Lys Phe Lys Glu Ala Phe
1 5 10

<210> SEQ ID NO 34
<211> LENGTH: 14
<212> TYPE: PRT
<213> ORGANISM: Artificial Sequence
<220> FEATURE:
<223> OTHER INFORMATION: synthetic construct; class A peptide <220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 34

Ala Phe Tyr Asp Lys Val Ala Glu Lys Phe Lys Glu Ala Phe
1 5 10

<210> SEQ ID NO 35
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 35

Ala Phe Tyr Asp Lys Phe Phe Glu Lys Phe Lys Glu Phe Phe
1 5 10

<210> SEQ ID NO 36
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 36

Ala Phe Tyr Asp Lys Phe Phe Glu Lys Phe Lys Glu Phe Phe
1 5 10

<210> SEQ ID NO 37
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 37

Ala Phe Tyr Asp Lys Val Ala Glu Lys Phe Lys Glu Ala Phe
1 5 10

<210> SEQ ID NO 38

<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 38

Ala Phe Tyr Asp Lys Val Ala Glu Lys Leu Lys Glu Phe Phe
1 5 10

<210> SEQ ID NO 39
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 39

Ala Phe Tyr Asp Lys Val Phe Glu Lys Phe Lys Glu Ala Phe
1 5 10

<210> SEQ ID NO 40
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 40

Ala Phe Tyr Asp Lys Val Phe Glu Lys Leu Lys Glu Phe Phe
1 5 10

<210> SEQ ID NO 41
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 41

Ala Phe Tyr Asp Lys Val Ala Glu Lys Phe Lys Glu Phe Phe
1 5 10

<210> SEQ ID NO 42
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 42

Lys Ala Phe Tyr Asp Lys Val Phe Glu Lys Phe Lys Glu Phe
1 5 10

<210> SEQ ID NO 43
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 43

Leu Phe Tyr Glu Lys Val Leu Glu Lys Phe Lys Glu Ala Phe
1 5 10

<210> SEQ ID NO 44
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 44

Ala Phe Tyr Asp Lys Val Ala Glu Lys Phe Lys Glu Ala Phe
1 5 10

<210> SEQ ID NO 45
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC <222> LOCATION: (14)..(14)
<223> OTHER INFORMATION: C-terminal amidation

<400> SEQUENCE: 45

Ala Phe Tyr Asp Lys Val Ala Glu Lys Leu Lys Glu Phe Phe
1 5 10

<210> SEQ ID NO 46
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 46

Ala Phe Tyr Asp Lys Val Phe Glu Lys Phe Lys Glu Ala Phe
1 5 10

<210> SEQ ID NO 47
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 47

Ala Phe Tyr Asp Lys Val Phe Glu Lys Leu Lys Glu Phe Phe
1 5 10

<210> SEQ ID NO 48
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 48

Ala Phe Tyr Asp Lys Val Ala Glu Lys Phe Lys Glu Phe Phe
1 5 10

<210> SEQ ID NO 49
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:

<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 49

Ala Phe Tyr Asp Lys Val Phe Glu Lys Phe Lys Glu Phe Phe
1 5 10

<210> SEQ ID NO 50
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 50

Asp Trp Leu Lys Ala Leu Tyr Asp Lys Val Ala Glu Lys Leu Lys Glu
1 5 10 15

Ala Leu

<210> SEQ ID NO 51
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 51

Asp Trp Phe Lys Ala Phe Tyr Glu Lys Val Ala Glu Lys Leu Lys Glu
1 5 10 15

Phe Phe

<210> SEQ ID NO 52
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 52

Asp Trp Phe Lys Ala Phe Tyr Glu Lys Phe Phe Glu Lys Phe Lys Glu
1 5 10 15

Phe Phe

<210> SEQ ID NO 53
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 53

Glu Trp Leu Lys Ala Leu Tyr Glu Lys Val Ala Glu Lys Leu Lys Glu
1 5 10 15

Ala Leu

<210> SEQ ID NO 54
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 54

Glu Trp Leu Lys Ala Phe Tyr Glu Lys Val Ala Glu Lys Leu Lys Glu
1 5 10 15

Ala Phe

<210> SEQ ID NO 55
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 55

Glu Trp Phe Lys Ala Phe Tyr Glu Lys Val Ala Glu Lys Leu Lys Glu
1 5 10 15

Phe Phe

<210> SEQ ID NO 56
<211> LENGTH: 18
<212> TYPE: PRT
<213> ORGANISM: Artificial Sequence
<220> FEATURE:
<223> OTHER INFORMATION: synthetic construct; class A peptide <220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 56

Glu Trp Leu Lys Ala Phe Tyr Glu Lys Val Phe Glu Lys Phe Lys Glu
1 5 10 15

Phe Phe

<210> SEQ ID NO 57
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 57

Glu Trp Leu Lys Ala Phe Tyr Glu Lys Phe Phe Glu Lys Phe Lys Glu
1 5 10 15

Phe Phe

<210> SEQ ID NO 58
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 58

Glu Trp Phe Lys Ala Phe Tyr Glu Lys Phe Phe Glu Lys Phe Lys Glu
1 5 10 15

Phe Phe

<210> SEQ ID NO 59
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 59

Asp Phe Leu Lys Ala Trp Tyr Asp Lys Val Ala Glu Lys Leu Lys Glu
1 5 10 15

Ala Trp

<210> SEQ ID NO 60
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 60

Glu Phe Leu Lys Ala Trp Tyr Glu Lys Val Ala Glu Lys Leu Lys Glu
1 5 10 15

Ala Trp

<210> SEQ ID NO 61
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 61

Asp Phe Trp Lys Ala Trp Tyr Asp Lys Val Ala Glu Lys Leu Lys Glu
1 5 10 15

Trp Trp

<210> SEQ ID NO 62
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 62

Glu Phe Trp Lys Ala Trp Tyr Glu Lys Val Ala Glu Lys Leu Lys Glu
1 5 10 15

Trp Trp

<210> SEQ ID NO 63
<211> LENGTH: 18
<212> TYPE: PRT

<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 63

Asp Lys Leu Lys Ala Phe Tyr Asp Lys Val Phe Glu Trp Ala Lys Glu
1 5 10 15

Ala Phe

<210> SEQ ID NO 64
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 64

Asp Lys Trp Lys Ala Val Tyr Asp Lys Phe Ala Glu Ala Phe Lys Glu
1 5 10 15

Phe Leu

<210> SEQ ID NO 65
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 65

Glu Lys Leu Lys Ala Phe Tyr Glu Lys Val Phe Glu Trp Ala Lys Glu
1 5 10 15

Ala Phe

<210> SEQ ID NO 66
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)

<223> OTHER INFORMATION: C-terminal amidation

<400> SEQUENCE: 66

Glu Lys Trp Lys Ala Val Tyr Glu Lys Phe Ala Glu Ala Phe Lys Glu
1 5 10 15

Phe Leu

<210> SEQ ID NO 67
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 67

Asp Trp Leu Lys Ala Phe Val Asp Lys Phe Ala Glu Lys Phe Lys Glu
1 5 10 15

Ala Tyr

<210> SEQ ID NO 68
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 68

Glu Lys Trp Lys Ala Val Tyr Glu Lys Phe Ala Glu Ala Phe Lys Glu
1 5 10 15

Phe Leu

<210> SEQ ID NO 69
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 69

Asp Trp Leu Lys Ala Phe Val Tyr Asp Lys Val Phe Lys Leu Lys Glu
1 5 10 15

Phe Phe

<210> SEQ ID NO 70
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 70

Glu Trp Leu Lys Ala Phe Val Tyr Glu Lys Val Phe Lys Leu Lys Glu
1 5 10 15

Phe Phe

<210> SEQ ID NO 71
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 71

Asp Trp Leu Arg Ala Phe Tyr Asp Lys Val Ala Glu Lys Leu Lys Glu
1 5 10 15

Ala Phe

<210> SEQ ID NO 72
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 72

Glu Trp Leu Arg Ala Phe Tyr Glu Lys Val Ala Glu Lys Leu Lys Glu
1 5 10 15

Ala Phe

<210> SEQ ID NO 73
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation <220> FEATURE:
<221> NAME/KEY: MISC
<222> LOCATION: (18)..(18)
<223> OTHER INFORMATION: C-terminal amidation

<400> SEQUENCE: 73

Asp Trp Leu Lys Ala Phe Tyr Asp Arg Val Ala Glu Lys Leu Lys Glu
1 5 10 15

Ala Phe

<210> SEQ ID NO 74
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 74

Glu Trp Leu Lys Ala Phe Tyr Glu Arg Val Ala Glu Lys Leu Lys Glu
1 5 10 15

Ala Phe

<210> SEQ ID NO 75
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 75

Asp Trp Leu Lys Ala Phe Tyr Asp Lys Val Ala Glu Arg Leu Lys Glu
1 5 10 15

Ala Phe

<210> SEQ ID NO 76
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)

<400> SEQUENCE: 76

Glu Trp Leu Lys Ala Phe Tyr Glu Lys Val Ala Glu Arg Leu Lys Glu
1 5 10 15

Ala Phe

<210> SEQ ID NO 77
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 77

Asp Trp Leu Lys Ala Phe Tyr Asp Lys Val Ala Glu Lys Leu Arg Glu
1 5 10 15

Ala Phe

<210> SEQ ID NO 78
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 78

Glu Trp Leu Lys Ala Phe Tyr Glu Lys Val Ala Glu Lys Leu Arg Glu
1 5 10 15

Ala Phe

<210> SEQ ID NO 79
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 79

Asp Trp Leu Lys Ala Phe Tyr Asp Arg Val Ala Glu Arg Leu Lys Glu
1 5 10 15

Ala Phe

<210> SEQ ID NO 80
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC <222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 80

Glu Trp Leu Lys Ala Phe Tyr Glu Arg Val Ala Glu Arg Leu Lys Glu
1 5 10 15

Ala Phe

<210> SEQ ID NO 81
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 81

Asp Trp Leu Arg Ala Phe Tyr Asp Lys Val Ala Glu Lys Leu Arg Glu
1 5 10 15

Ala Phe

<210> SEQ ID NO 82
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 82

Glu Trp Leu Arg Ala Phe Tyr Glu Lys Val Ala Glu Lys Leu Arg Glu
1 5 10 15

Ala Phe

<210> SEQ ID NO 83
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 83

Asp Trp Leu Arg Ala Phe Tyr Asp Arg Val Ala Glu Lys Leu Lys Glu 1 5 10 15

Ala Phe

<210> SEQ ID NO 84
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 84

Glu Trp Leu Arg Ala Phe Tyr Glu Arg Val Ala Glu Lys Leu Lys Glu
1 5 10 15

Ala Phe

<210> SEQ ID NO 85
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 85

Asp Trp Leu Lys Ala Phe Tyr Asp Lys Val Ala Glu Arg Leu Arg Glu
1 5 10 15

Ala Phe

<210> SEQ ID NO 86
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 86

Glu Trp Leu Lys Ala Phe Tyr Glu Lys Val Ala Glu Arg Leu Arg Glu
1 5 10 15

Ala Phe

<210> SEQ ID NO 87
<211> LENGTH: 18
<212> TYPE: PRT
<213> ORGANISM: Artificial Sequence
<220> FEATURE:

<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 87

Asp Trp Leu Arg Ala Phe Tyr Asp Lys Val Ala Glu Arg Leu Lys Glu
1 5 10 15

Ala Phe

<210> SEQ ID NO 88
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 88

Glu Trp Leu Arg Ala Phe Tyr Glu Lys Val Ala Glu Arg Leu Lys Glu
1 5 10 15

Ala Phe

<210> SEQ ID NO 89
<211> LENGTH: 37
<212> TYPE: PRT
<213> ORGANISM: Artificial Sequence
<220> FEATURE:
<223> OTHER INFORMATION: synthetic construct; class A peptide

<400> SEQUENCE: 89

Asp Trp Leu Lys Ala Phe Tyr Asp Lys Val Ala Glu Lys Leu Lys Glu
1 5 10 15

Ala Phe Pro Asp Trp Leu Lys Ala Phe Tyr Asp Lys Val Ala Glu Lys
20 25 30

Leu Lys Glu Ala Phe
35

<210> SEQ ID NO 90
<211> LENGTH: 37
<212> TYPE: PRT
<213> ORGANISM: Artificial Sequence
<220> FEATURE:
<223> OTHER INFORMATION: synthetic construct; class A peptide

<400> SEQUENCE: 90

Asp Trp Leu Lys Ala Phe Tyr Asp Lys Val Ala Glu Lys Leu Lys Glu
1 5 10 15

Phe Phe Pro Asp Trp Leu Lys Ala Phe Tyr Asp Lys Val Ala Glu Lys
20 25 30

Leu Lys Glu Phe Phe
35

<210> SEQ ID NO 91
<211> LENGTH: 37
<212> TYPE: PRT
<213> ORGANISM: Artificial Sequence
<220> FEATURE:
<223> OTHER INFORMATION: synthetic construct; class A peptide

<400> SEQUENCE: 91

Asp Trp Phe Lys Ala Phe Tyr Asp Lys Val Ala Glu Lys Leu Lys Glu
1 5 10 15

Ala Phe Pro Asp Trp Phe Lys Ala Phe Tyr Asp Lys Val Ala Glu Lys
20 25 30

Leu Lys Glu Ala Phe
35

<210> SEQ ID NO 92
<211> LENGTH: 37
<212> TYPE: PRT
<213> ORGANISM: Artificial Sequence
<220> FEATURE:
<223> OTHER INFORMATION: synthetic construct; class A peptide

<400> SEQUENCE: 92

Asp Lys Leu Lys Ala Phe Tyr Asp Lys Val Phe Glu Trp Ala Lys Glu
1 5 10 15

Ala Phe Pro Asp Lys Leu Lys Ala Phe Tyr Asp Lys Val Phe Glu Trp
20 25 30

Leu Lys Glu Ala Phe
35

<210> SEQ ID NO 93
<211> LENGTH: 37
<212> TYPE: PRT
<213> ORGANISM: Artificial Sequence
<220> FEATURE:
<223> OTHER INFORMATION: synthetic construct; class A peptide

<400> SEQUENCE: 93

Asp Lys Trp Lys Ala Val Tyr Asp Lys Phe Ala Glu Ala Phe Lys Glu
1 5 10 15

Phe Leu Pro Asp Lys Trp Lys Ala Val Tyr Asp Lys Phe Ala Glu Ala
20 25 30

Phe Lys Glu Phe Leu
35

<210> SEQ ID NO 94
<211> LENGTH: 37
<212> TYPE: PRT
<213> ORGANISM: Artificial Sequence
<220> FEATURE:
<223> OTHER INFORMATION: synthetic construct; class A peptide

<400> SEQUENCE: 94

Asp Trp Phe Lys Ala Phe Tyr Asp Lys Val Ala Glu Lys Phe Lys Glu
1 5 10 15

Ala Phe Pro Asp Trp Phe Lys Ala Phe Tyr Asp Lys Val Ala Glu Lys
20 25 30

Phe Lys Glu Ala Phe
35

<210> SEQ ID NO 95
<211> LENGTH: 37
<212> TYPE: PRT

<213> ORGANISM: Artificial Sequence
<220> FEATURE:
<223> OTHER INFORMATION: synthetic construct; class A peptide

<400> SEQUENCE: 95

Asp Trp Leu Lys Ala Phe Val Tyr Asp Lys Val Phe Lys Leu Lys Glu
1 5 10 15

Phe Phe Pro Asp Trp Leu Lys Ala Phe Val Tyr Asp Lys Val Phe Lys
20 25 30

Leu Lys Glu Phe Phe
35

<210> SEQ ID NO 96
<211> LENGTH: 37
<212> TYPE: PRT
<213> ORGANISM: Artificial Sequence
<220> FEATURE:
<223> OTHER INFORMATION: synthetic construct; class A peptide

<400> SEQUENCE: 96

Asp Trp Leu Lys Ala Phe Tyr Asp Lys Phe Ala Glu Lys Phe Lys Glu
1 5 10 15

Phe Phe Pro Asp Trp Leu Lys Ala Phe Tyr Asp Lys Phe Ala Glu Lys
20 25 30

Phe Lys Glu Phe Phe
35

<210> SEQ ID NO 97
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 97

Glu Trp Phe Lys Ala Phe Tyr Glu Lys Val Ala Glu Lys Phe Lys Glu
1 5 10 15

Ala Phe

<210> SEQ ID NO 98
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 98

Asp Trp Phe Lys Ala Phe Tyr Asp Lys Val Ala Glu Lys Phe
1 5 10

<210> SEQ ID NO 99
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 99

Phe Lys Ala Phe Tyr Asp Lys Val Ala Glu Lys Phe Lys Glu
1 5 10

<210> SEQ ID NO 100
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 100

Phe Lys Ala Phe Tyr Glu Lys Val Ala Glu Lys Phe Lys Glu
1 5 10

<210> SEQ ID NO 101
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: misc
<222> LOCATION: (1)..(1)
<223> OTHER INFORMATION: N-terminus contains an N-Methyl Anthranilyl
<220> FEATURE:
<221> NAME/KEY: misc
<222> LOCATION: (14)..(14)
<223> OTHER INFORMATION: C-terminus contains an amide group

<400> SEQUENCE: 101

Phe Lys Ala Phe Tyr Asp Lys Val Ala Glu Lys Phe Lys Glu
1 5 10

<210> SEQ ID NO 102
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: misc
<222> LOCATION: (1)..(1)
<223> OTHER INFORMATION: N-terminus contains an N-Methyl Anthranilyl
<220> FEATURE:
<221> NAME/KEY: misc
<222> LOCATION: (14)..(14)
<223> OTHER INFORMATION: C-terminus contains an amide group

<400> SEQUENCE: 102

Phe Lys Ala Phe Tyr Glu Lys Val Ala Glu Lys Phe Lys Glu
1 5 10

<210> SEQ ID NO 103
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: misc
<222> LOCATION: (1)..(1)
<223> OTHER INFORMATION: N-terminus contains an N-Methyl Anthranilyl
<220> FEATURE:
<221> NAME/KEY: misc
<222> LOCATION: (18)..(18)
<223> OTHER INFORMATION: C-terminus contains an amide group

<400> SEQUENCE: 103

Asp Trp Phe Lys Ala Phe Tyr Asp Lys Val Ala Glu Lys Phe Lys Glu
1 5 10 15

Ala Phe

<210> SEQ ID NO 104
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: misc
<222> LOCATION: (1)..(1)
<223> OTHER INFORMATION: N-terminus contains an N-Methyl Anthranilyl
<220> FEATURE:
<221> NAME/KEY: misc
<222> LOCATION: (18)..(18)
<223> OTHER INFORMATION: C-terminus contains an amide group

<400> SEQUENCE: 104

Glu Trp Phe Lys Ala Phe Tyr Glu Lys Val Ala Glu Lys Phe Lys Glu
1 5 10 15

Ala Phe

<210> SEQ ID NO 105
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: misc
<222> LOCATION: (1)..(1)
<223> OTHER INFORMATION: N-terminus contains an N-Methyl Anthranilyl
<220> FEATURE:
<221> NAME/KEY: misc
<222> LOCATION: (14)..(14)
<223> OTHER INFORMATION: C-terminus contains an amide group

<400> SEQUENCE: 105

Ala Phe Tyr Asp Lys Val Ala Glu Lys Phe Lys Glu Ala Phe
1 5 10

<210> SEQ ID NO 106
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:

<221> NAME/KEY: misc
<222> LOCATION: (1)..(1)
<223> OTHER INFORMATION: N-terminus contains an N-Methyl Anthranilyl
<220> FEATURE:
<221> NAME/KEY: misc
<222> LOCATION: (14)..(14)
<223> OTHER INFORMATION: C-terminus contains an amide group

<400> SEQUENCE: 106

Asp Trp Phe Lys Ala Phe Tyr Asp Lys Val Ala Glu Lys Phe
1 5 10

<210> SEQ ID NO 107
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 107

Asp Trp Leu Lys Ala Phe Tyr Asp Lys Val Phe Glu Lys Phe Lys Glu
1 5 10 15

Phe Phe

<210> SEQ ID NO 108
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: misc
<222> LOCATION: (1)..(1)
<223> OTHER INFORMATION: N-terminus contains an N-Methyl Anthranilyl
<220> FEATURE:
<221> NAME/KEY: misc
<222> LOCATION: (18)..(18)
<223> OTHER INFORMATION: C-terminus contains an amide group

<400> SEQUENCE: 108

Asp Trp Leu Lys Ala Phe Tyr Asp Lys Val Phe Glu Lys Phe Lys Glu
1 5 10 15

Phe Phe

<210> SEQ ID NO 109
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 109

Glu Trp Leu Lys Ala Phe Tyr Glu Lys Val Phe Glu Lys Phe Lys Glu
1 5 10 15

Phe Phe

<210> SEQ ID NO 110
<211> LENGTH: 18
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: misc
<222> LOCATION: (1)..(1)
<223> OTHER INFORMATION: N-terminus contains an N-Methyl Anthranilyl
<220> FEATURE:
<221> NAME/KEY: misc
<222> LOCATION: (18)..(18)
<223> OTHER INFORMATION: C-terminus contains an amide group

<400> SEQUENCE: 110

Glu Trp Leu Lys Ala Phe Tyr Glu Lys Val Phe Glu Lys Phe Lys Glu
1 5 10 15

Phe Phe

<210> SEQ ID NO 111
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 111

Ala Phe Tyr Asp Lys Val Phe Glu Lys Phe Lys Glu Phe Phe
1 5 10

<210> SEQ ID NO 112
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: misc
<222> LOCATION: (1)..(1)
<223> OTHER INFORMATION: N-terminus contains an N-Methyl Anthranilyl
<220> FEATURE:
<221> NAME/KEY: misc
<222> LOCATION: (14)..(14)
<223> OTHER INFORMATION: C-terminus contains an amide group

<400> SEQUENCE: 112

Ala Phe Tyr Asp Lys Val Phe Glu Lys Phe Lys Glu Phe Phe
1 5 10

<210> SEQ ID NO 113
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation <220> FEATURE:
<221> NAME/KEY: MISC
<222> LOCATION: (14)..(14)
<223> OTHER INFORMATION: C-terminal amidation

<400> SEQUENCE: 113

Ala Phe Tyr Glu Lys Val Phe Glu Lys Phe Lys Glu Phe Phe
1 5 10

<210> SEQ ID NO 114
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: misc
<222> LOCATION: (1)..(1)
<223> OTHER INFORMATION: N-terminus contains an N-Methyl Anthranilyl
<220> FEATURE:
<221> NAME/KEY: misc
<222> LOCATION: (14)..(14)
<223> OTHER INFORMATION: C-terminus contains an amide group

<400> SEQUENCE: 114

Ala Phe Tyr Glu Lys Val Phe Glu Lys Phe Lys Glu Phe Phe
1 5 10

<210> SEQ ID NO 115
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 115

Asp Trp Leu Lys Ala Phe Tyr Asp Lys Val Phe Glu Lys Phe
1 5 10

<210> SEQ ID NO 116
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: misc
<222> LOCATION: (1)..(1)
<223> OTHER INFORMATION: N-terminus contains an N-Methyl Anthranilyl
<220> FEATURE:
<221> NAME/KEY: misc
<222> LOCATION: (14)..(14)
<223> OTHER INFORMATION: C-terminus contains an amide group

<400> SEQUENCE: 116

Asp Trp Leu Lys Ala Phe Tyr Asp Lys Val Phe Glu Lys Phe
1 5 10

<210> SEQ ID NO 117
<211> LENGTH: 14
<212> TYPE: PRT
<213> ORGANISM: Artificial Sequence
<220> FEATURE:

<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 117

Glu Trp Leu Lys Ala Phe Tyr Glu Lys Val Phe Glu Lys Phe
1 5 10

<210> SEQ ID NO 118
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: misc
<222> LOCATION: (1)..(1)
<223> OTHER INFORMATION: N-terminus contains an N-Methyl Anthranilyl
<220> FEATURE:
<221> NAME/KEY: misc
<222> LOCATION: (14)..(14)
<223> OTHER INFORMATION: C-terminus contains an amide group

<400> SEQUENCE: 118

Glu Trp Leu Lys Ala Phe Tyr Glu Lys Val Phe Glu Lys Phe
1 5 10

<210> SEQ ID NO 119
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 119

Leu Lys Ala Phe Tyr Asp Lys Val Phe Glu Lys Phe Lys Glu
1 5 10

<210> SEQ ID NO 120
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: misc
<222> LOCATION: (1)..(1)
<223> OTHER INFORMATION: N-terminus contains an N-Methyl Anthranilyl
<220> FEATURE:
<221> NAME/KEY: misc
<222> LOCATION: (14)..(14)
<223> OTHER INFORMATION: C-terminus contains an amide group

<400> SEQUENCE: 120

Leu Lys Ala Phe Tyr Asp Lys Val Phe Glu Lys Phe Lys Glu
1 5 10

<210> SEQ ID NO 121
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (14)..(14)
<223> OTHER INFORMATION: C-terminal amidation

<400> SEQUENCE: 121

Leu Lys Ala Phe Tyr Glu Lys Val Phe Glu Lys Phe Lys Glu
1 5 10

<210> SEQ ID NO 122
<211> LENGTH: 14
<212> TYPE: PRT
<213> ORGANISM: Artificial Sequence
<220> FEATURE:
<223> OTHER INFORMATION: synthetic construct; class A peptide
<220> FEATURE:
<221> NAME/KEY: misc
<222> LOCATION: (1)..(1)
<223> OTHER INFORMATION: N-terminus contains an N-Methyl Anthranilyl
<220> FEATURE:
<221> NAME/KEY: misc
<222> LOCATION: (14)..(14)
<223> OTHER INFORMATION: C-terminus contains an amide group

<400> SEQUENCE: 122

Leu Lys Ala Phe Tyr Glu Lys Val Phe Glu Lys Phe Lys Glu
1 5 10

<210> SEQ ID NO 123
<211> LENGTH: 18
<212> TYPE: PRT
<213> ORGANISM: Artificial Sequence
<220> FEATURE:
<223> OTHER INFORMATION: synthetic construct; modified class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 123

Asp Lys Trp Lys Ala Val Tyr Asp Lys Phe Ala Glu Ala Phe Lys Glu
1 5 10 15

Phe Leu

<210> SEQ ID NO 124
<211> LENGTH: 18
<212> TYPE: PRT
<213> ORGANISM: Artificial Sequence
<220> FEATURE:
<223> OTHER INFORMATION: synthetic construct; modified class A peptide
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 124

Asp Lys Leu Lys Ala Phe Tyr Asp Lys Val Phe Glu Trp Ala Lys Glu
1 5 10 15

Ala Phe

<210> SEQ ID NO 125
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 125

Glu Trp Phe Lys Ala Phe Tyr Glu Lys Val Ala Asp Lys Phe Lys Asp
1 5 10 15

Ala Phe

<210> SEQ ID NO 126
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 126

Glu Trp Phe Lys Ala Phe Tyr Asp Lys Val Ala Asp Lys Phe Lys Glu
1 5 10 15

Ala Phe

<210> SEQ ID NO 127
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 127

Asp Trp Phe Lys Ala Phe Tyr Glu Lys Val Ala Asp Lys Phe Lys Glu
1 5 10 15

Ala Phe

<210> SEQ ID NO 128
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 128

Asp Trp Phe Lys Ala Phe Tyr Glu Lys Val Ala Glu Lys Phe Lys Asp
1 5 10 15

Ala Phe

<210> SEQ ID NO 129
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 129

Asp Phe Trp Lys Ala Phe Tyr Asp Lys Val Ala Glu Lys Phe Lys Glu
1 5 10 15

Ala Phe

<210> SEQ ID NO 130
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 130

Glu Phe Trp Lys Ala Phe Tyr Glu Lys Val Ala Asp Lys Phe Lys Asp
1 5 10 15

Ala Phe

<210> SEQ ID NO 131
<211> LENGTH: 18
<212> TYPE: PRT
<213> ORGANISM: Artificial Sequence
<220> FEATURE:

<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 131

Glu Phe Trp Lys Ala Phe Tyr Asp Lys Val Ala Asp Lys Phe Lys Glu
1 5 10 15

Ala Phe

<210> SEQ ID NO 132
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 132

Asp Phe Trp Lys Ala Phe Tyr Glu Lys Val Ala Asp Lys Phe Lys Glu
1 5 10 15

Ala Phe

<210> SEQ ID NO 133
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 133

Asp Phe Trp Lys Ala Phe Tyr Glu Lys Val Ala Glu Lys Phe Lys Asp
1 5 10 15

Ala Phe

<210> SEQ ID NO 134
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:

<221> NAME/KEY: MISC
<222> LOCATION: (18)..(18)
<223> OTHER INFORMATION: C-terminal amidation

<400> SEQUENCE: 134

Asp Trp Phe Lys Ala Tyr Phe Asp Lys Val Ala Glu Lys Phe Lys Glu
1 5 10 15

Ala Phe

<210> SEQ ID NO 135
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 135

Glu Trp Phe Lys Ala Tyr Phe Glu Lys Val Ala Asp Lys Phe Lys Asp
1 5 10 15

Ala Phe

<210> SEQ ID NO 136
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 136

Glu Trp Phe Lys Ala Tyr Phe Asp Lys Val Ala Asp Lys Phe Lys Glu
1 5 10 15

Ala Phe

<210> SEQ ID NO 137
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 137

Asp Trp Phe Lys Ala Tyr Phe Glu Lys Val Ala Asp Lys Phe Lys Glu 1 5 10 15

Ala Phe

<210> SEQ ID NO 138
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 138

Asp Trp Phe Lys Ala Tyr Phe Glu Lys Val Ala Glu Lys Phe Lys Asp
1 5 10 15

Ala Phe

<210> SEQ ID NO 139
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 139

Asp Trp Phe Lys Ala Phe Val Asp Lys Tyr Ala Glu Lys Phe Lys Glu
1 5 10 15

Ala Phe

<210> SEQ ID NO 140
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 140

Glu Trp Phe Lys Ala Phe Val Glu Lys Tyr Ala Asp Lys Phe Lys Asp
1 5 10 15

Ala Phe

<210> SEQ ID NO 141
<211> LENGTH: 18

<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 141

Glu Trp Phe Lys Ala Phe Val Asp Lys Tyr Ala Asp Lys Phe Lys Glu
1 5 10 15

Ala Phe

<210> SEQ ID NO 142
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 142

Asp Trp Phe Lys Ala Phe Val Glu Lys Tyr Ala Asp Lys Phe Lys Glu
1 5 10 15

Ala Phe

<210> SEQ ID NO 143
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 143

Asp Trp Phe Lys Ala Phe Val Glu Lys Tyr Ala Glu Lys Phe Lys Asp
1 5 10 15

Ala Phe

<210> SEQ ID NO 144
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC <222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 144

Asp Trp Phe Lys Ala Phe Tyr Asp Lys Ala Val Glu Lys Phe Lys Glu
1 5 10 15

Ala Phe

<210> SEQ ID NO 145
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 145

Glu Trp Phe Lys Ala Phe Tyr Glu Lys Ala Val Asp Lys Phe Lys Asp
1 5 10 15

Ala Phe

<210> SEQ ID NO 146
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 146

Glu Trp Phe Lys Ala Phe Tyr Asp Lys Ala Val Asp Lys Phe Lys Glu
1 5 10 15

Ala Phe

<210> SEQ ID NO 147
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 147

Asp Trp Phe Lys Ala Phe Tyr Glu Lys Ala Val Asp Lys Phe Lys Glu
1 5 10 15

Ala Phe

<210> SEQ ID NO 148
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 148

Asp Trp Phe Lys Ala Phe Tyr Glu Lys Ala Val Glu Lys Phe Lys Asp
1 5 10 15

Ala Phe

<210> SEQ ID NO 149
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 149

Asp Trp Phe Lys Ala Phe Tyr Asp Lys Val Phe Glu Lys Ala Lys Glu
1 5 10 15

Ala Phe

<210> SEQ ID NO 150
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 150

Glu Trp Phe Lys Ala Phe Tyr Glu Lys Val Phe Asp Lys Ala Lys Asp
1 5 10 15

Ala Phe

<210> SEQ ID NO 151
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 151

Glu Trp Phe Lys Ala Phe Tyr Asp Lys Val Phe Asp Lys Ala Lys Glu
1 5 10 15

Ala Phe

<210> SEQ ID NO 152
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 152

Asp Trp Phe Lys Ala Phe Tyr Glu Lys Val Phe Asp Lys Ala Lys Glu
1 5 10 15

Ala Phe

<210> SEQ ID NO 153
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 153

Asp Trp Phe Lys Ala Phe Tyr Glu Lys Val Phe Glu Lys Ala Lys Asp
1 5 10 15

Ala Phe

<210> SEQ ID NO 154
<211> LENGTH: 18
<212> TYPE: PRT
<213> ORGANISM: Artificial Sequence
<220> FEATURE:
<223> OTHER INFORMATION: synthetic construct; Class A amphipathic helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 154

Asp Trp Phe Lys Ala Phe Tyr Asp Lys Val Ala Glu Lys Ala Lys Glu
1 5 10 15

Phe Phe

<210> SEQ ID NO 155
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 155

Glu Trp Phe Lys Ala Phe Tyr Glu Lys Val Ala Asp Lys Ala Lys Asp
1 5 10 15

Phe Phe

<210> SEQ ID NO 156
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 156

Glu Trp Phe Lys Ala Phe Tyr Asp Lys Val Ala Asp Lys Ala Lys Glu
1 5 10 15

Phe Phe

<210> SEQ ID NO 157
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC <222> LOCATION: (18)..(18)
<223> OTHER INFORMATION: C-terminal amidation

<400> SEQUENCE: 157

Asp Trp Phe Lys Ala Phe Tyr Glu Lys Val Ala Asp Lys Ala Lys Glu
1 5 10 15

Phe Phe

<210> SEQ ID NO 158
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 158

Asp Trp Phe Lys Ala Phe Tyr Glu Lys Val Ala Glu Lys Ala Lys Asp
1 5 10 15

Phe Phe

<210> SEQ ID NO 159
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 159

Asp Trp Phe Lys Ala Phe Tyr Asp Lys Val Ala Glu Lys Phe Lys Glu
1 5 10 15

Phe Ala

<210> SEQ ID NO 160
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 160

Glu Trp Phe Lys Ala Phe Tyr Glu Lys Val Ala Asp Lys Phe Lys Asp
1 5 10 15

Phe Ala

<210> SEQ ID NO 161
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 161

Glu Trp Phe Lys Ala Phe Tyr Asp Lys Val Ala Asp Lys Phe Lys Glu
1 5 10 15

Phe Ala

<210> SEQ ID NO 162
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 162

Asp Trp Phe Lys Ala Phe Tyr Glu Lys Val Ala Asp Lys Phe Lys Glu
1 5 10 15

Phe Ala

<210> SEQ ID NO 163
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 163

Asp Trp Phe Lys Ala Phe Tyr Glu Lys Val Ala Glu Lys Phe Lys Asp
1 5 10 15

Phe Ala

<210> SEQ ID NO 164
<211> LENGTH: 18
<212> TYPE: PRT

<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 164

Asp Ala Phe Lys Ala Phe Tyr Asp Lys Val Ala Glu Lys Phe Lys Glu
1 5 10 15

Trp Phe

<210> SEQ ID NO 165
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 165

Glu Ala Phe Lys Ala Phe Tyr Glu Lys Val Ala Asp Lys Phe Lys Asp
1 5 10 15

Trp Phe

<210> SEQ ID NO 166
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 166

Glu Ala Phe Lys Ala Phe Tyr Asp Lys Val Ala Asp Lys Phe Lys Glu
1 5 10 15

Trp Phe

<210> SEQ ID NO 167
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)

<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 167

Asp Ala Phe Lys Ala Phe Tyr Glu Lys Val Ala Asp Lys Phe Lys Glu
1 5 10 15

Trp Phe

<210> SEQ ID NO 168
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 168

Asp Ala Phe Lys Ala Phe Tyr Glu Lys Val Ala Glu Lys Phe Lys Asp
1 5 10 15

Trp Phe

<210> SEQ ID NO 169
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 169

Asp Ala Phe Lys Ala Phe Tyr Asp Lys Val Trp Glu Lys Phe Lys Glu
1 5 10 15

Ala Phe

<210> SEQ ID NO 170
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 170

Glu Ala Phe Lys Ala Phe Tyr Glu Lys Val Trp Asp Lys Phe Lys Asp
1 5 10 15

Ala Phe

<210> SEQ ID NO 171
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 171

Glu Ala Phe Lys Ala Phe Tyr Asp Lys Val Trp Asp Lys Phe Lys Glu
1 5 10 15

Ala Phe

<210> SEQ ID NO 172
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 172

Asp Ala Phe Lys Ala Phe Tyr Glu Lys Val Trp Asp Lys Phe Lys Glu
1 5 10 15

Ala Phe

<210> SEQ ID NO 173
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 173

Asp Ala Phe Lys Ala Phe Tyr Glu Lys Val Trp Glu Lys Phe Lys Asp
1 5 10 15

Ala Phe

<210> SEQ ID NO 174
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 174

Asp Tyr Phe Lys Ala Phe Trp Asp Lys Val Ala Glu Lys Phe Lys Glu
1 5 10 15

Ala Phe

<210> SEQ ID NO 175
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 175

Glu Tyr Phe Lys Ala Phe Trp Glu Lys Val Ala Asp Lys Phe Lys Asp
1 5 10 15

Ala Phe

<210> SEQ ID NO 176
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 176

Glu Tyr Phe Lys Ala Phe Trp Asp Lys Val Ala Asp Lys Phe Lys Glu
1 5 10 15

Ala Phe

<210> SEQ ID NO 177
<211> LENGTH: 18
<212> TYPE: PRT
<213> ORGANISM: Artificial Sequence
<220> FEATURE:
<223> OTHER INFORMATION: synthetic construct; Class A amphipathic
helical peptides <220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 177

Asp Tyr Phe Lys Ala Phe Trp Glu Lys Val Ala Asp Lys Phe Lys Glu
1 5 10 15

Ala Phe

<210> SEQ ID NO 178
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 178

Asp Tyr Phe Lys Ala Phe Trp Glu Lys Val Ala Glu Lys Phe Lys Asp
1 5 10 15

Ala Phe

<210> SEQ ID NO 179
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 179

Asp Trp Ala Lys Ala Phe Tyr Asp Lys Val Ala Glu Lys Phe Lys Glu
1 5 10 15

Phe Phe

<210> SEQ ID NO 180
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)

<223> OTHER INFORMATION: C-terminal amidation

<400> SEQUENCE: 180

Glu Trp Ala Lys Ala Phe Tyr Glu Lys Val Ala Asp Lys Phe Lys Asp
1 5 10 15

Phe Phe

<210> SEQ ID NO 181
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 181

Glu Trp Ala Lys Ala Phe Tyr Asp Lys Val Ala Asp Lys Phe Lys Glu
1 5 10 15

Phe Phe

<210> SEQ ID NO 182
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 182

Asp Trp Ala Lys Ala Phe Tyr Glu Lys Val Ala Asp Lys Phe Lys Glu
1 5 10 15

Phe Phe

<210> SEQ ID NO 183
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 183

Asp Trp Ala Lys Ala Phe Tyr Glu Lys Val Ala Glu Lys Phe Lys Asp
1 5 10 15

Phe Phe

<210> SEQ ID NO 184
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 184

Asp Trp Phe Lys Ala Ala Tyr Asp Lys Val Ala Glu Lys Phe Lys Glu
1 5 10 15

Phe Phe

<210> SEQ ID NO 185
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 185

Glu Trp Phe Lys Ala Ala Tyr Glu Lys Val Ala Asp Lys Phe Lys Asp
1 5 10 15

Phe Phe

<210> SEQ ID NO 186
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 186

Glu Trp Phe Lys Ala Ala Tyr Asp Lys Val Ala Asp Lys Phe Lys Glu
1 5 10 15

Phe Phe

<210> SEQ ID NO 187
<211> LENGTH: 18
<212> TYPE: PRT
<213> ORGANISM: Artificial Sequence <220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 187

Asp Trp Phe Lys Ala Ala Tyr Glu Lys Val Ala Asp Lys Phe Lys Glu
1 5 10 15

Phe Phe

<210> SEQ ID NO 188
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 188

Asp Trp Phe Lys Ala Ala Tyr Glu Lys Val Ala Glu Lys Phe Lys Asp
1 5 10 15

Phe Phe

<210> SEQ ID NO 189
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 189

Asp Trp Phe Lys Ala Phe Ala Asp Lys Val Ala Glu Lys Phe Lys Glu
1 5 10 15

Tyr Phe

<210> SEQ ID NO 190
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation <220> FEATURE:
<221> NAME/KEY: MISC
<222> LOCATION: (18)..(18)
<223> OTHER INFORMATION: C-terminal amidation

<400> SEQUENCE: 190

Glu Trp Phe Lys Ala Phe Ala Glu Lys Val Ala Asp Lys Phe Lys Asp
1 5 10 15

Tyr Phe

<210> SEQ ID NO 191
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 191

Glu Trp Phe Lys Ala Phe Ala Asp Lys Val Ala Asp Lys Phe Lys Glu
1 5 10 15

Tyr Phe

<210> SEQ ID NO 192
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 192

Asp Trp Phe Lys Ala Phe Ala Glu Lys Val Ala Asp Lys Phe Lys Glu
1 5 10 15

Tyr Phe

<210> SEQ ID NO 193
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 193

Asp Trp Phe Lys Ala Phe Ala Glu Lys Val Ala Glu Lys Phe Lys Asp
1 5 10 15

Tyr Phe

<210> SEQ ID NO 194
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 194

Asp Trp Phe Lys Ala Phe Tyr Asp Lys Ala Ala Glu Lys Phe Lys Glu
1 5 10 15

Val Phe

<210> SEQ ID NO 195
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 195

Glu Trp Phe Lys Ala Phe Tyr Glu Lys Ala Ala Asp Lys Phe Lys Asp
1 5 10 15

Val Phe

<210> SEQ ID NO 196
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 196

Glu Trp Phe Lys Ala Phe Tyr Asp Lys Ala Ala Asp Lys Phe Lys Glu
1 5 10 15

Val Phe

<210> SEQ ID NO 197

<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 197

Asp Trp Phe Lys Ala Phe Tyr Glu Lys Ala Ala Asp Lys Phe Lys Glu
1 5 10 15

Val Phe

<210> SEQ ID NO 198
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 198

Asp Trp Phe Lys Ala Phe Tyr Glu Lys Ala Ala Glu Lys Phe Lys Asp
1 5 10 15

Val Phe

<210> SEQ ID NO 199
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 199

Asp Trp Tyr Lys Ala Phe Phe Asp Lys Val Ala Glu Lys Phe Lys Glu
1 5 10 15

Ala Phe

<210> SEQ ID NO 200
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:

<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 200

Glu Trp Tyr Lys Ala Phe Phe Glu Lys Val Ala Asp Lys Phe Lys Asp
1 5 10 15

Ala Phe

<210> SEQ ID NO 201
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 201

Glu Trp Tyr Lys Ala Phe Phe Asp Lys Val Ala Asp Lys Phe Lys Glu
1 5 10 15

Ala Phe

<210> SEQ ID NO 202
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 202

Asp Trp Tyr Lys Ala Phe Phe Glu Lys Val Ala Asp Lys Phe Lys Glu
1 5 10 15

Ala Phe

<210> SEQ ID NO 203
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 203

Asp Trp Tyr Lys Ala Phe Phe Glu Lys Val Ala Glu Lys Phe Lys Asp
1 5 10 15

Ala Phe

<210> SEQ ID NO 204
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 204

Asp Trp Val Lys Ala Phe Tyr Asp Lys Phe Ala Glu Lys Phe Lys Glu
1 5 10 15

Ala Phe

<210> SEQ ID NO 205
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 205

Glu Trp Val Lys Ala Phe Tyr Glu Lys Phe Ala Asp Lys Phe Lys Asp
1 5 10 15

Ala Phe

<210> SEQ ID NO 206
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 206

Glu Trp Val Lys Ala Phe Tyr Asp Lys Phe Ala Asp Lys Phe Lys Glu
1 5 10 15

Ala Phe

<210> SEQ ID NO 207
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 207

Asp Trp Val Lys Ala Phe Tyr Glu Lys Phe Ala Asp Lys Phe Lys Glu
1 5 10 15

Ala Phe

<210> SEQ ID NO 208
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 208

Asp Trp Val Lys Ala Phe Tyr Glu Lys Phe Ala Glu Lys Phe Lys Asp
1 5 10 15

Ala Phe

<210> SEQ ID NO 209
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 209

Asp Trp Phe Lys Ala Phe Phe Asp Lys Val Ala Glu Lys Tyr Lys Glu
1 5 10 15

Ala Phe

<210> SEQ ID NO 210
<211> LENGTH: 18
<212> TYPE: PRT
<213> ORGANISM: Artificial Sequence
<220> FEATURE:

<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 210

Glu Trp Phe Lys Ala Phe Phe Glu Lys Val Ala Asp Lys Tyr Lys Asp
1 5 10 15

Ala Phe

<210> SEQ ID NO 211
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 211

Glu Trp Phe Lys Ala Phe Phe Asp Lys Val Ala Asp Lys Tyr Lys Glu
1 5 10 15

Ala Phe

<210> SEQ ID NO 212
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 212

Asp Trp Phe Lys Ala Phe Phe Glu Lys Val Ala Asp Lys Tyr Lys Glu
1 5 10 15

Ala Phe

<210> SEQ ID NO 213
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:

<221> NAME/KEY: MISC
<222> LOCATION: (18)..(18)
<223> OTHER INFORMATION: C-terminal amidation

<400> SEQUENCE: 213

Asp Trp Phe Lys Ala Phe Phe Glu Lys Val Ala Asp Lys Tyr Lys Glu
1 5 10 15

Ala Phe

<210> SEQ ID NO 214
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 214

Asp Trp Phe Lys Ala Phe Phe Asp Lys Val Ala Glu Lys Phe Lys Glu
1 5 10 15

Ala Tyr

<210> SEQ ID NO 215
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 215

Glu Trp Phe Lys Ala Phe Phe Glu Lys Val Ala Asp Lys Phe Lys Asp
1 5 10 15

Ala Tyr

<210> SEQ ID NO 216
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 216

Glu Trp Phe Lys Ala Phe Phe Asp Lys Val Ala Asp Lys Phe Lys Glu 1 5 10 15

Ala Tyr

<210> SEQ ID NO 217
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 217

Asp Trp Phe Lys Ala Phe Phe Glu Lys Val Ala Asp Lys Phe Lys Glu
1 5 10 15

Ala Tyr

<210> SEQ ID NO 218
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 218

Asp Trp Phe Lys Ala Phe Phe Glu Lys Val Ala Glu Lys Phe Lys Asp
1 5 10 15

Ala Tyr

<210> SEQ ID NO 219
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 219

Asp Trp Phe Lys Ala Phe Tyr Asp Lys Phe Ala Glu Lys Phe Lys Glu
1 5 10 15

Ala Val

<210> SEQ ID NO 220
<211> LENGTH: 18

<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 220

Glu Trp Phe Lys Ala Phe Tyr Glu Lys Phe Ala Asp Lys Phe Lys Asp
1 5 10 15

Ala Val

<210> SEQ ID NO 221
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 221

Glu Trp Phe Lys Ala Phe Tyr Asp Lys Phe Ala Asp Lys Phe Lys Glu
1 5 10 15

Ala Val

<210> SEQ ID NO 222
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 222

Asp Trp Phe Lys Ala Phe Tyr Glu Lys Phe Ala Asp Lys Phe Lys Glu
1 5 10 15

Ala Val

<210> SEQ ID NO 223
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC <222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 223

Asp Trp Phe Lys Ala Phe Tyr Glu Lys Phe Ala Glu Lys Phe Lys Asp
1 5 10 15

Ala Val

<210> SEQ ID NO 224
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 224

Asp Lys Phe Lys Ala Phe Tyr Asp Lys Val Ala Glu Lys Phe Trp Glu
1 5 10 15

Ala Phe

<210> SEQ ID NO 225
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 225

Glu Lys Phe Lys Ala Phe Tyr Glu Lys Val Ala Asp Lys Phe Trp Asp
1 5 10 15

Ala Phe

<210> SEQ ID NO 226
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 226

Glu Lys Phe Lys Ala Phe Tyr Asp Lys Val Ala Asp Lys Phe Trp Glu
1 5 10 15

Ala Phe

<210> SEQ ID NO 227
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 227

Asp Lys Phe Lys Ala Phe Tyr Glu Lys Val Ala Asp Lys Phe Trp Glu
1 5 10 15

Ala Phe

<210> SEQ ID NO 228
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 228

Asp Lys Phe Lys Ala Phe Tyr Glu Lys Val Ala Glu Lys Phe Trp Asp
1 5 10 15

Ala Phe

<210> SEQ ID NO 229
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 229

Asp Lys Trp Lys Ala Phe Tyr Asp Lys Val Ala Glu Lys Phe Phe Glu
1 5 10 15

Ala Phe

<210> SEQ ID NO 230
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 230

Glu Lys Trp Lys Ala Phe Tyr Glu Lys Val Ala Asp Lys Phe Phe Asp
1 5 10 15

Ala Phe

<210> SEQ ID NO 231
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 231

Glu Lys Trp Lys Ala Phe Tyr Asp Lys Val Ala Asp Lys Phe Phe Glu
1 5 10 15

Ala Phe

<210> SEQ ID NO 232
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 232

Asp Lys Trp Lys Ala Phe Tyr Glu Lys Val Ala Asp Lys Phe Phe Glu
1 5 10 15

Ala Phe

<210> SEQ ID NO 233
<211> LENGTH: 18
<212> TYPE: PRT
<213> ORGANISM: Artificial Sequence
<220> FEATURE:
<223> OTHER INFORMATION: synthetic construct; Class A amphipathic helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 233

Asp Lys Trp Lys Ala Phe Tyr Glu Lys Val Ala Glu Lys Phe Phe Asp
1 5 10 15

Ala Phe

<210> SEQ ID NO 234
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 234

Asp Lys Phe Lys Ala Phe Tyr Asp Lys Trp Ala Glu Val Phe Lys Glu
1 5 10 15

Ala Phe

<210> SEQ ID NO 235
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 235

Glu Lys Phe Lys Ala Phe Tyr Glu Lys Trp Ala Asp Val Phe Lys Asp
1 5 10 15

Ala Phe

<210> SEQ ID NO 236
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC <222> LOCATION: (18)..(18)
<223> OTHER INFORMATION: C-terminal amidation

<400> SEQUENCE: 236

Glu Lys Phe Lys Ala Phe Tyr Asp Lys Trp Ala Asp Val Phe Lys Glu
1 5 10 15

Ala Phe

<210> SEQ ID NO 237
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 237

Asp Lys Phe Lys Ala Phe Tyr Glu Lys Trp Ala Asp Val Phe Lys Glu
1 5 10 15

Ala Phe

<210> SEQ ID NO 238
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 238

Asp Lys Phe Lys Ala Phe Tyr Glu Lys Trp Ala Glu Val Phe Lys Asp
1 5 10 15

Ala Phe

<210> SEQ ID NO 239
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 239

Asp Lys Phe Lys Ala Phe Tyr Asp Lys Val Ala Glu Phe Trp Lys Glu
1 5 10 15

Ala Phe

<210> SEQ ID NO 240
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 240

Glu Lys Phe Lys Ala Phe Tyr Glu Lys Val Ala Asp Phe Trp Lys Asp
1 5 10 15

Ala Phe

<210> SEQ ID NO 241
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 241

Glu Lys Phe Cys Ala Phe Tyr Asp Lys Val Ala Asp Phe Trp Lys Glu
1 5 10 15

Ala Phe

<210> SEQ ID NO 242
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 242

Asp Lys Phe Lys Ala Phe Tyr Glu Lys Val Ala Asp Phe Trp Lys Glu
1 5 10 15

Ala Phe

<210> SEQ ID NO 243
<211> LENGTH: 18
<212> TYPE: PRT

<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 243

Asp Lys Phe Lys Ala Phe Tyr Glu Lys Val Ala Glu Phe Trp Lys Asp
1 5 10 15

Ala Phe

<210> SEQ ID NO 244
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 244

Phe Ala Glu Lys Phe Lys Glu Ala Val Lys Asp Tyr Phe Ala Lys Phe
1 5 10 15

Trp Asp

<210> SEQ ID NO 245
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 245

Phe Ala Asp Lys Phe Lys Asp Ala Val Lys Glu Tyr Phe Ala Lys Phe
1 5 10 15

Trp Glu

<210> SEQ ID NO 246
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)

<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 246

Phe Ala Asp Lys Phe Lys Glu Ala Val Lys Asp Tyr Phe Ala Lys Phe
1 5 10 15

Trp Glu

<210> SEQ ID NO 247
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 247

Phe Ala Glu Lys Phe Lys Asp Ala Val Lys Glu Tyr Phe Ala Lys Phe
1 5 10 15

Trp Asp

<210> SEQ ID NO 248
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 248

Phe Ala Glu Lys Phe Lys Asp Ala Val Lys Asp Tyr Phe Ala Lys Phe
1 5 10 15

Trp Glu

<210> SEQ ID NO 249
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 249

Phe Trp Glu Lys Phe Lys Glu Ala Val Lys Asp Tyr Phe Ala Lys Phe
1 5 10 15

Ala Asp

<210> SEQ ID NO 250
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 250

Phe Trp Asp Lys Phe Lys Asp Ala Val Lys Glu Tyr Phe Ala Lys Phe
1 5 10 15

Ala Glu

<210> SEQ ID NO 251
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 251

Phe Ala Asp Lys Phe Lys Glu Ala Val Lys Asp Tyr Phe Ala Lys Phe
1 5 10 15

Trp Glu

<210> SEQ ID NO 252
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 252

Phe Ala Glu Lys Phe Lys Asp Ala Val Lys Glu Tyr Phe Ala Lys Phe
1 5 10 15

Trp Asp

<210> SEQ ID NO 253
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 253

Phe Ala Glu Lys Phe Lys Asp Ala Val Lys Asp Tyr Phe Ala Lys Phe
1 5 10 15

Trp Glu

<210> SEQ ID NO 254
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 254

Phe Phe Glu Lys Phe Lys Glu Ala Val Lys Asp Tyr Phe Ala Lys Ala
1 5 10 15

Trp Asp

<210> SEQ ID NO 255
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 255

Phe Phe Asp Lys Phe Lys Asp Ala Val Lys Glu Tyr Phe Ala Lys Ala
1 5 10 15

Trp Glu

<210> SEQ ID NO 256
<211> LENGTH: 18
<212> TYPE: PRT
<213> ORGANISM: Artificial Sequence
<220> FEATURE:
<223> OTHER INFORMATION: synthetic construct; Class A amphipathic
helical peptides <220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 256

Phe Phe Asp Lys Phe Lys Glu Ala Val Lys Asp Tyr Phe Ala Lys Ala
1 5 10 15

Trp Glu

<210> SEQ ID NO 257
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 257

Phe Phe Glu Lys Phe Lys Asp Ala Val Lys Glu Tyr Phe Ala Lys Ala
1 5 10 15

Trp Asp

<210> SEQ ID NO 258
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 258

Phe Phe Glu Lys Phe Lys Asp Ala Val Lys Asp Tyr Phe Ala Lys Ala
1 5 10 15

Trp Glu

<210> SEQ ID NO 259
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)

<223> OTHER INFORMATION: C-terminal amidation

<400> SEQUENCE: 259

Phe Ala Glu Lys Ala Lys Glu Phe Val Lys Asp Tyr Phe Ala Lys Phe
1 5 10 15

Trp Asp

<210> SEQ ID NO 260
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 260

Phe Ala Asp Lys Ala Lys Asp Phe Val Lys Glu Tyr Phe Ala Lys Phe
1 5 10 15

Trp Glu

<210> SEQ ID NO 261
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 261

Phe Ala Asp Lys Ala Lys Glu Phe Val Lys Asp Tyr Phe Ala Lys Phe
1 5 10 15

Trp Glu

<210> SEQ ID NO 262
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 262

Phe Ala Glu Lys Ala Lys Asp Phe Val Lys Glu Tyr Phe Ala Lys Phe
1 5 10 15

Trp Asp

<210> SEQ ID NO 263
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 263

Phe Ala Glu Lys Ala Lys Asp Phe Val Lys Asp Tyr Phe Ala Lys Phe
1 5 10 15

Trp Glu

<210> SEQ ID NO 264
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 264

Phe Ala Glu Lys Phe Lys Glu Val Ala Lys Asp Tyr Phe Ala Lys Phe
1 5 10 15

Trp Asp

<210> SEQ ID NO 265
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 265

Phe Ala Asp Lys Phe Lys Asp Val Ala Lys Glu Tyr Phe Ala Lys Phe
1 5 10 15

Trp Glu

<210> SEQ ID NO 266
<211> LENGTH: 18
<212> TYPE: PRT
<213> ORGANISM: Artificial Sequence <220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 266

Phe Ala Asp Lys Phe Lys Glu Val Ala Lys Asp Tyr Phe Ala Lys Phe
1 5 10 15

Trp Glu

<210> SEQ ID NO 267
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 267

Phe Ala Glu Lys Phe Lys Asp Val Ala Lys Glu Tyr Phe Ala Lys Phe
1 5 10 15

Trp Asp

<210> SEQ ID NO 268
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 268

Phe Ala Glu Lys Phe Lys Asp Val Ala Lys Asp Tyr Phe Ala Lys Phe
1 5 10 15

Trp Glu

<210> SEQ ID NO 269
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation <220> FEATURE:
<221> NAME/KEY: MISC
<222> LOCATION: (18)..(18)
<223> OTHER INFORMATION: C-terminal amidation

<400> SEQUENCE: 269

Phe Ala Asp Lys Phe Lys Glu Ala Tyr Lys Asp Val Phe Ala Lys Phe
1 5 10 15

Trp Glu

<210> SEQ ID NO 270
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 270

Phe Ala Glu Lys Phe Lys Asp Ala Tyr Lys Glu Val Phe Ala Lys Phe
1 5 10 15

Trp Asp

<210> SEQ ID NO 271
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 271

Phe Ala Glu Lys Phe Lys Asp Ala Tyr Lys Asp Val Phe Ala Lys Phe
1 5 10 15

Trp Glu

<210> SEQ ID NO 272
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 272

Phe Ala Glu Lys Phe Lys Glu Ala Val Lys Asp Phe Tyr Ala Lys Phe
1 5 10 15

Trp Asp

<210> SEQ ID NO 273
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 273

Phe Ala Asp Lys Phe Lys Asp Ala Val Lys Glu Phe Tyr Ala Lys Phe
1 5 10 15

Trp Glu

<210> SEQ ID NO 274
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 274

Phe Ala Asp Lys Phe Lys Glu Ala Val Lys Asp Phe Tyr Ala Lys Phe
1 5 10 15

Trp Glu

<210> SEQ ID NO 275
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 275

Phe Ala Glu Lys Phe Lys Asp Ala Val Lys Glu Phe Tyr Ala Lys Phe
1 5 10 15

Trp Asp

<210> SEQ ID NO 276

<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 276

Phe Ala Glu Lys Phe Lys Asp Ala Val Lys Asp Phe Tyr Ala Lys Phe
1 5 10 15

Trp Glu

<210> SEQ ID NO 277
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 277

Phe Ala Glu Lys Phe Trp Glu Ala Val Lys Asp Tyr Phe Ala Lys Phe
1 5 10 15

Lys Asp

<210> SEQ ID NO 278
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 278

Phe Ala Asp Lys Phe Trp Asp Ala Val Lys Glu Tyr Phe Ala Lys Phe
1 5 10 15

Lys Glu

<210> SEQ ID NO 279
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:

<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 279

Phe Ala Asp Lys Phe Trp Glu Ala Val Lys Asp Tyr Phe Ala Lys Phe
1 5 10 15

Lys Glu

<210> SEQ ID NO 280
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 280

Phe Ala Glu Lys Phe Trp Asp Ala Val Lys Glu Tyr Phe Ala Lys Phe
1 5 10 15

Lys Asp

<210> SEQ ID NO 281
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 281

Phe Ala Glu Lys Phe Trp Asp Ala Val Lys Asp Tyr Phe Ala Lys Phe
1 5 10 15

Lys Glu

<210> SEQ ID NO 282
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 282

Ala Phe Glu Lys Phe Lys Glu Ala Val Lys Asp Tyr Phe Ala Lys Phe
1 5 10 15

Trp Asp

<210> SEQ ID NO 283
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 283

Ala Phe Asp Lys Phe Lys Asp Ala Val Lys Glu Tyr Phe Ala Lys Phe
1 5 10 15

Trp Glu

<210> SEQ ID NO 284
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 284

Ala Phe Asp Lys Phe Lys Glu Ala Val Lys Asp Tyr Phe Ala Lys Phe
1 5 10 15

Trp Glu

<210> SEQ ID NO 285
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 285

Ala Phe Glu Lys Phe Lys Asp Ala Val Lys Glu Tyr Phe Ala Lys Phe
1 5 10 15

Trp Asp

<210> SEQ ID NO 286
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 286

Ala Phe Glu Lys Phe Lys Asp Ala Val Lys Asp Tyr Phe Ala Lys Phe
1 5 10 15

Trp Glu

<210> SEQ ID NO 287
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 287

Val Ala Glu Lys Phe Lys Glu Ala Phe Lys Asp Tyr Phe Ala Lys Phe
1 5 10 15

Trp Asp

<210> SEQ ID NO 288
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 288

Val Ala Asp Lys Phe Lys Asp Ala Phe Lys Glu Tyr Phe Ala Lys Phe
1 5 10 15

Trp Glu

<210> SEQ ID NO 289
<211> LENGTH: 18
<212> TYPE: PRT
<213> ORGANISM: Artificial Sequence
<220> FEATURE:

<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 289

Val Ala Asp Lys Phe Lys Glu Ala Phe Lys Asp Tyr Phe Ala Lys Phe
1 5 10 15

Trp Glu

<210> SEQ ID NO 290
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 290

Val Ala Glu Lys Phe Lys Asp Ala Phe Lys Glu Tyr Phe Ala Lys Phe
1 5 10 15

Trp Asp

<210> SEQ ID NO 291
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 291

Val Ala Glu Lys Phe Lys Asp Ala Phe Lys Asp Tyr Phe Ala Lys Phe
1 5 10 15

Trp Glu

<210> SEQ ID NO 292
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:

<221> NAME/KEY: MISC
<222> LOCATION: (18)..(18)
<223> OTHER INFORMATION: C-terminal amidation

<400> SEQUENCE: 292

Tyr Ala Glu Lys Phe Lys Glu Ala Val Lys Asp Phe Phe Ala Lys Phe
1 5 10 15

Trp Asp

<210> SEQ ID NO 293
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 293

Tyr Ala Asp Lys Phe Lys Asp Ala Val Lys Glu Phe Phe Ala Lys Phe
1 5 10 15

Trp Glu

<210> SEQ ID NO 294
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 294

Tyr Ala Asp Lys Phe Lys Glu Ala Val Lys Asp Phe Phe Ala Lys Phe
1 5 10 15

Trp Glu

<210> SEQ ID NO 295
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 295

Tyr Ala Glu Lys Phe Lys Asp Ala Val Lys Glu Phe Phe Ala Lys Phe 1 5 10 15

Trp Asp

<210> SEQ ID NO 296
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 296

Tyr Ala Glu Lys Phe Lys Asp Ala Val Lys Asp Phe Phe Ala Lys Phe
1 5 10 15

Trp Glu

<210> SEQ ID NO 297
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 297

Ala Ala Glu Lys Phe Lys Glu Phe Val Lys Asp Tyr Phe Ala Lys Phe
1 5 10 15

Trp Asp

<210> SEQ ID NO 298
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 298

Ala Ala Asp Lys Phe Lys Asp Phe Val Lys Glu Tyr Phe Ala Lys Phe
1 5 10 15

Trp Glu

<210> SEQ ID NO 299
<211> LENGTH: 18

<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 299

Ala Ala Asp Lys Phe Lys Glu Phe Val Lys Asp Tyr Phe Ala Lys Phe
1 5 10 15

Trp Glu

<210> SEQ ID NO 300
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 300

Ala Ala Glu Lys Phe Lys Asp Phe Val Lys Glu Tyr Phe Ala Lys Phe
1 5 10 15

Trp Asp

<210> SEQ ID NO 301
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 301

Ala Ala Glu Lys Phe Lys Asp Phe Val Lys Asp Tyr Phe Ala Lys Phe
1 5 10 15

Trp Glu

<210> SEQ ID NO 302
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC <222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 302

Phe Phe Glu Lys Ala Lys Glu Ala Val Lys Asp Tyr Phe Ala Lys Phe
1 5 10 15

Trp Asp

<210> SEQ ID NO 303
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 303

Phe Phe Asp Lys Ala Lys Asp Ala Val Lys Glu Tyr Phe Ala Lys Phe
1 5 10 15

Trp Glu

<210> SEQ ID NO 304
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 304

Phe Phe Asp Lys Ala Lys Glu Ala Val Lys Asp Tyr Phe Ala Lys Phe
1 5 10 15

Trp Glu

<210> SEQ ID NO 305
<211> LENGTH: 16
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (16)..(16)
<223> OTHER INFORMATION: C-terminal amidation

<400> SEQUENCE: 305

Glu Lys Ala Lys Asp Ala Val Lys Glu Tyr Phe Ala Lys Phe Trp Asp
1 5 10 15

<210> SEQ ID NO 306
<211> LENGTH: 16
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (16)..(16)
<223> OTHER INFORMATION: C-terminal amidation

<400> SEQUENCE: 306

Glu Lys Ala Lys Asp Ala Val Lys Asp Tyr Phe Ala Lys Phe Trp Glu
1 5 10 15

<210> SEQ ID NO 307
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 307

Phe Tyr Glu Lys Phe Lys Glu Ala Val Lys Asp Ala Phe Ala Lys Phe
1 5 10 15

Trp Asp

<210> SEQ ID NO 308
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 308

Phe Tyr Asp Lys Phe Lys Asp Ala Val Lys Glu Ala Phe Ala Lys Phe
1 5 10 15

Trp Glu

<210> SEQ ID NO 309
<211> LENGTH: 18
<212> TYPE: PRT

<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 309

Phe Tyr Asp Lys Phe Lys Glu Ala Val Lys Asp Ala Phe Ala Lys Phe
1 5 10 15

Trp Glu

<210> SEQ ID NO 310
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 310

Phe Tyr Glu Lys Phe Lys Asp Ala Val Lys Glu Ala Phe Ala Lys Phe
1 5 10 15

Trp Asp

<210> SEQ ID NO 311
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 311

Phe Tyr Glu Lys Phe Lys Asp Ala Val Lys Asp Ala Phe Ala Lys Phe
1 5 10 15

Trp Glu

<210> SEQ ID NO 312
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)

<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 312

Phe Val Glu Lys Phe Lys Glu Ala Ala Lys Asp Tyr Phe Ala Lys Phe
1 5 10 15

Trp Asp

<210> SEQ ID NO 313
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 313

Phe Val Asp Lys Phe Lys Asp Ala Ala Lys Glu Tyr Phe Ala Lys Phe
1 5 10 15

Trp Glu

<210> SEQ ID NO 314
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 314

Phe Val Asp Lys Phe Lys Glu Ala Ala Lys Asp Tyr Phe Ala Lys Phe
1 5 10 15

Trp Glu

<210> SEQ ID NO 315
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 315

Phe Val Glu Lys Phe Lys Asp Ala Ala Lys Glu Tyr Phe Ala Lys Phe
1 5 10 15

Trp Asp

<210> SEQ ID NO 316
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 316

Phe Val Glu Lys Phe Lys Asp Ala Ala Lys Asp Tyr Phe Ala Lys Phe
1 5 10 15

Trp Glu

<210> SEQ ID NO 317
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 317

Phe Ala Glu Lys Tyr Lys Glu Ala Val Lys Asp Phe Phe Ala Lys Phe
1 5 10 15

Trp Asp

<210> SEQ ID NO 318
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 318

Phe Ala Asp Lys Tyr Lys Asp Ala Val Lys Glu Phe Phe Ala Lys Phe
1 5 10 15

Trp Glu

<210> SEQ ID NO 319
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 319

Phe Ala Asp Lys Tyr Lys Glu Ala Val Lys Asp Phe Phe Ala Lys Phe
1 5 10 15

Trp Glu

<210> SEQ ID NO 320
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 320

Phe Ala Glu Lys Tyr Lys Asp Ala Val Lys Glu Phe Phe Ala Lys Phe
1 5 10 15

Trp Asp

<210> SEQ ID NO 321
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 321

Phe Ala Glu Lys Tyr Lys Asp Ala Val Lys Asp Phe Phe Ala Lys Phe
1 5 10 15

Trp Glu

<210> SEQ ID NO 322
<211> LENGTH: 18
<212> TYPE: PRT
<213> ORGANISM: Artificial Sequence
<220> FEATURE:
<223> OTHER INFORMATION: synthetic construct; Class A amphipathic
helical peptides <220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 322

Phe Ala Glu Lys Val Lys Glu Ala Phe Lys Asp Tyr Phe Ala Lys Phe
1 5 10 15

Trp Asp

<210> SEQ ID NO 323
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 323

Phe Ala Asp Lys Val Lys Asp Ala Phe Lys Glu Tyr Phe Ala Lys Phe
1 5 10 15

Trp Glu

<210> SEQ ID NO 324
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 324

Phe Ala Asp Lys Val Lys Glu Ala Phe Lys Asp Tyr Phe Ala Lys Phe
1 5 10 15

Trp Glu

<210> SEQ ID NO 325
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)

<223> OTHER INFORMATION: C-terminal amidation

<400> SEQUENCE: 325

Phe Ala Glu Lys Val Lys Asp Ala Phe Lys Glu Tyr Phe Ala Lys Phe
1 5 10 15

Trp Asp

<210> SEQ ID NO 326
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 326

Phe Ala Glu Lys Val Lys Asp Ala Phe Lys Asp Tyr Phe Ala Lys Phe
1 5 10 15

Trp Glu

<210> SEQ ID NO 327
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 327

Phe Ala Glu Lys Phe Lys Glu Tyr Val Lys Asp Ala Phe Ala Lys Phe
1 5 10 15

Trp Asp

<210> SEQ ID NO 328
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 328

Phe Ala Asp Lys Phe Lys Asp Tyr Val Lys Glu Ala Phe Ala Lys Phe
1 5 10 15

Trp Glu

<210> SEQ ID NO 329
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 329

Phe Ala Asp Lys Phe Lys Glu Tyr Val Lys Asp Ala Phe Ala Lys Phe
1 5 10 15

Trp Glu

<210> SEQ ID NO 330
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 330

Phe Ala Glu Lys Phe Lys Asp Tyr Val Lys Glu Ala Phe Ala Lys Phe
1 5 10 15

Trp Asp

<210> SEQ ID NO 331
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 331

Phe Ala Glu Lys Phe Lys Asp Tyr Val Lys Asp Ala Phe Ala Lys Phe
1 5 10 15

Trp Glu

<210> SEQ ID NO 332
<211> LENGTH: 18
<212> TYPE: PRT
<213> ORGANISM: Artificial Sequence <220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 332

Phe Ala Glu Lys Phe Lys Glu Ala Phe Lys Asp Tyr Val Ala Lys Phe
1 5 10 15

Trp Asp

<210> SEQ ID NO 333
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 333

Phe Ala Asp Lys Phe Lys Asp Ala Phe Lys Glu Tyr Val Ala Lys Phe
1 5 10 15

Trp Glu

<210> SEQ ID NO 334
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 334

Phe Ala Asp Lys Phe Lys Glu Ala Phe Lys Asp Tyr Val Ala Lys Phe
1 5 10 15

Trp Glu

<210> SEQ ID NO 335
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation <220> FEATURE:
<221> NAME/KEY: MISC
<222> LOCATION: (18)..(18)
<223> OTHER INFORMATION: C-terminal amidation

<400> SEQUENCE: 335

Phe Ala Glu Lys Phe Lys Asp Ala Phe Lys Glu Tyr Val Ala Lys Phe
1 5 10 15

Trp Asp

<210> SEQ ID NO 336
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 336

Phe Ala Glu Lys Phe Lys Asp Ala Phe Lys Asp Tyr Val Ala Lys Phe
1 5 10 15

Trp Glu

<210> SEQ ID NO 337
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 337

Phe Ala Glu Lys Phe Lys Glu Ala Phe Lys Asp Tyr Phe Ala Lys Val
1 5 10 15

Trp Asp

<210> SEQ ID NO 338
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 338

Phe Ala Asp Lys Phe Lys Asp Ala Phe Lys Glu Tyr Phe Ala Lys Val
1 5 10 15

Trp Glu

<210> SEQ ID NO 339
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 339

Phe Ala Asp Lys Phe Lys Glu Ala Phe Lys Asp Tyr Phe Ala Lys Val
1 5 10 15

Trp Glu

<210> SEQ ID NO 340
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 340

Phe Ala Glu Lys Phe Lys Asp Ala Phe Lys Glu Tyr Phe Ala Lys Val
1 5 10 15

Trp Asp

<210> SEQ ID NO 341
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 341

Phe Ala Glu Lys Phe Lys Asp Ala Phe Lys Asp Tyr Phe Ala Lys Val
1 5 10 15

Trp Glu

<210> SEQ ID NO 342

<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 342

Phe Ala Glu Lys Phe Lys Glu Ala Val Lys Asp Phe Phe Ala Lys Tyr
1 5 10 15

Trp Asp

<210> SEQ ID NO 343
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 343

Phe Ala Asp Lys Phe Lys Asp Ala Val Lys Glu Phe Phe Ala Lys Tyr
1 5 10 15

Trp Glu

<210> SEQ ID NO 344
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 344

Phe Ala Asp Lys Phe Lys Glu Ala Val Lys Asp Phe Phe Ala Lys Tyr
1 5 10 15

Trp Glu

<210> SEQ ID NO 345
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:

<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 345

Phe Ala Glu Lys Phe Lys Asp Ala Val Lys Glu Phe Phe Ala Lys Tyr
1 5 10 15

Trp Asp

<210> SEQ ID NO 346
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 346

Phe Ala Glu Lys Phe Lys Asp Ala Val Lys Asp Phe Phe Ala Lys Tyr
1 5 10 15

Trp Glu

<210> SEQ ID NO 347
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 347

Trp Ala Glu Lys Phe Phe Glu Ala Val Lys Asp Tyr Phe Ala Lys Phe
1 5 10 15

Lys Asp

<210> SEQ ID NO 348
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 348

Trp Ala Asp Lys Phe Phe Asp Ala Val Lys Glu Tyr Phe Ala Lys Phe
1 5 10 15

Lys Glu

<210> SEQ ID NO 349
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 349

Trp Ala Asp Lys Phe Phe Glu Ala Val Lys Asp Tyr Phe Ala Lys Phe
1 5 10 15

Lys Glu

<210> SEQ ID NO 350
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 350

Trp Ala Glu Lys Phe Phe Asp Ala Val Lys Glu Tyr Phe Ala Lys Phe
1 5 10 15

Lys Asp

<210> SEQ ID NO 351
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 351

Trp Ala Glu Lys Phe Phe Asp Ala Val Lys Asp Tyr Phe Ala Lys Phe
1 5 10 15

Lys Glu

<210> SEQ ID NO 352
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 352

Phe Ala Glu Lys Trp Phe Glu Ala Val Lys Asp Tyr Phe Ala Lys Phe
1 5 10 15

Lys Asp

<210> SEQ ID NO 353
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 353

Phe Ala Asp Lys Trp Phe Asp Ala Val Lys Glu Tyr Phe Ala Lys Phe
1 5 10 15

Lys Glu

<210> SEQ ID NO 354
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 354

Phe Ala Asp Lys Trp Phe Glu Ala Val Lys Asp Tyr Phe Ala Lys Phe
1 5 10 15

Lys Glu

<210> SEQ ID NO 355
<211> LENGTH: 18
<212> TYPE: PRT
<213> ORGANISM: Artificial Sequence
<220> FEATURE:

<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 355

Phe Ala Glu Lys Trp Phe Asp Ala Val Lys Glu Tyr Phe Ala Lys Phe
1 5 10 15

Lys Asp

<210> SEQ ID NO 356
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 356

Phe Ala Glu Lys Trp Phe Asp Ala Val Lys Asp Tyr Phe Ala Lys Phe
1 5 10 15

Lys Glu

<210> SEQ ID NO 357
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 357

Phe Ala Glu Lys Phe Val Glu Ala Trp Lys Asp Tyr Phe Ala Lys Phe
1 5 10 15

Lys Asp

<210> SEQ ID NO 358
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:

<221> NAME/KEY: MISC
<222> LOCATION: (18)..(18)
<223> OTHER INFORMATION: C-terminal amidation

<400> SEQUENCE: 358

Phe Ala Asp Lys Phe Val Asp Ala Trp Lys Glu Tyr Phe Ala Lys Phe
1 5 10 15

Lys Glu

<210> SEQ ID NO 359
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 359

Phe Ala Asp Lys Phe Val Glu Ala Trp Lys Asp Tyr Phe Ala Lys Phe
1 5 10 15

Lys Glu

<210> SEQ ID NO 360
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 360

Phe Ala Glu Lys Phe Val Asp Ala Trp Lys Glu Tyr Phe Ala Lys Phe
1 5 10 15

Lys Asp

<210> SEQ ID NO 361
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 361

Phe Ala Glu Lys Phe Val Asp Ala Trp Lys Asp Tyr Phe Ala Lys Phe 1 5 10 15

Lys Glu

<210> SEQ ID NO 362
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 362

Phe Tyr Glu Lys Phe Ala Glu Ala Val Lys Asp Trp Phe Ala Lys Phe
1 5 10 15

Lys Asp

<210> SEQ ID NO 363
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 363

Phe Tyr Asp Lys Phe Ala Asp Ala Val Lys Glu Trp Phe Ala Lys Phe
1 5 10 15

Lys Glu

<210> SEQ ID NO 364
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 364

Phe Tyr Asp Lys Phe Ala Glu Ala Val Lys Asp Trp Phe Ala Lys Phe
1 5 10 15

Lys Glu

<210> SEQ ID NO 365
<211> LENGTH: 18

<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 365

Phe Tyr Glu Lys Phe Ala Asp Ala Val Lys Glu Trp Phe Ala Lys Phe
1 5 10 15

Lys Asp

<210> SEQ ID NO 366
<211> LENGTH: 18
<212> TYPE: PRT
<213> ORGANISM: Artificial Sequence
<220> FEATURE:
<223> OTHER INFORMATION: synthetic construct; Class A amphipathic
helical peptides
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 366

Phe Tyr Glu Lys Phe Ala Asp Ala Val Lys Asp Trp Phe Ala Lys Phe
1 5 10 15

Lys Glu

<210> SEQ ID NO 367
<211> LENGTH: 18
<212> TYPE: PRT
<213> ORGANISM: Artificial Sequence
<220> FEATURE:
<223> OTHER INFORMATION: synthetic construct; class A or class Y
amphipathic helix peptide
<220> FEATURE:
<221> NAME/KEY: misc
<222> LOCATION: (1)..(1)
<223> OTHER INFORMATION: Xaa can be Asp or Glu
<220> FEATURE:
<221> NAME/KEY: misc
<222> LOCATION: (2)..(3)
<223> OTHER INFORMATION: Xaa can be Leu, norLeu, Val, Ile, Trp, Phe,
Tyr, beta-Nal, or alpha-Nal
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc
<222> LOCATION: (5)..(5)
<223> OTHER INFORMATION: Xaa can be Ala, His, Ser, Gln, Asn, or Thr
<220> FEATURE:
<221> NAME/KEY: misc
<222> LOCATION: (6)..(7)
<223> OTHER INFORMATION: Xaa can be Leu, norLeu, Val, Ile, Trp, Phe,
Tyr, beta-Nal, or alpha-Nal
<220> FEATURE:
<221> NAME/KEY: misc
<222> LOCATION: (8)..(8)
<223> OTHER INFORMATION: Xaa can be Asp or Glu <220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc
<222> LOCATION: (10)..(10)
<223> OTHER INFORMATION: Xaa can be Leu, norLeu, Val, Ile, Trp, Phe,
Tyr, beta-Nal, or alpha-Nal
<220> FEATURE:
<221> NAME/KEY: misc
<222> LOCATION: (11)..(11)
<223> OTHER INFORMATION: Xaa can be Ala, His, Ser, Gln, Asn, or Thr
<220> FEATURE:
<221> NAME/KEY: misc
<222> LOCATION: (12)..(12)
<223> OTHER INFORMATION: Xaa can be Asp or Glu
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc
<222> LOCATION: (14)..(14)
<223> OTHER INFORMATION: Xaa can be Leu, norLeu, Val, Ile, Trp, Phe,
Tyr, beta-Nal, or alpha-Nal
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc
<222> LOCATION: (16)..(16)
<223> OTHER INFORMATION: Xaa can be Asp or Glu
<220> FEATURE:
<221> NAME/KEY: misc
<222> LOCATION: (17)..(17)
<223> OTHER INFORMATION: Xaa can be Ala, His, Ser, Gln, Asn, or Thr
<220> FEATURE:
<221> NAME/KEY: misc
<222> LOCATION: (18)..(18)
<223> OTHER INFORMATION: Xaa can be Leu, norLeu, Val, Ile, Trp, Phe,
Tyr, beta-Nal, or alpha-Nal

<400> SEQUENCE: 367

Xaa Xaa Xaa Xaa Xaa Xaa Xaa Xaa Xaa Xaa Xaa Xaa Xaa Xaa Xaa Xaa
1 5 10 15

Xaa Xaa

<210> SEQ ID NO 368
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 368

Asp Trp Phe Lys His Phe Tyr Asp Lys Val Ala Glu Lys Phe Lys Glu
1 5 10 15

Ala Phe

<210> SEQ ID NO 369
<211> LENGTH: 18
<212> TYPE: PRT
<213> ORGANISM: Artificial Sequence <220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 369

Glu Trp Phe Lys His Phe Tyr Glu Lys Val Ala Asp Lys Phe Lys Asp
1 5 10 15

Ala Phe

<210> SEQ ID NO 370
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 370

Glu Trp Phe Lys His Phe Tyr Asp Lys Val Ala Glu Lys Phe Lys Glu
1 5 10 15

Ala Phe

<210> SEQ ID NO 371
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 371

Asp Trp Phe Lys His Phe Tyr Glu Lys Val Ala Glu Lys Phe Lys Glu
1 5 10 15

Ala Phe

<210> SEQ ID NO 372
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 372

Asp Trp Phe Lys His Phe Tyr Asp Lys Val Ala Asp Lys Phe Lys Glu
1 5 10 15

Ala Phe

<210> SEQ ID NO 373
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 373

Asp Trp Phe Lys His Phe Tyr Asp Lys Val Ala Glu Lys Phe Lys Asp
1 5 10 15

Ala Phe

<210> SEQ ID NO 374
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 374

Asp Trp His Lys Phe Phe Tyr Asp Lys Val Ala Glu Lys Phe Lys Glu
1 5 10 15

Ala Phe

<210> SEQ ID NO 375
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 375

Glu Trp His Lys Phe Phe Tyr Glu Lys Val Ala Asp Lys Phe Lys Asp
1 5 10 15

Ala Phe

<210> SEQ ID NO 376

<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 376

Glu Trp His Lys Phe Phe Tyr Asp Lys Val Ala Glu Lys Phe Lys Glu
1 5 10 15

Ala Phe

<210> SEQ ID NO 377
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 377

Asp Trp His Lys Phe Phe Tyr Glu Lys Val Ala Glu Lys Phe Lys Glu
1 5 10 15

Ala Phe

<210> SEQ ID NO 378
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 378

Asp Trp His Lys Phe Phe Tyr Asp Lys Val Ala Asp Lys Phe Lys Glu
1 5 10 15

Ala Phe

<210> SEQ ID NO 379
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:

<221> NAME/KEY: MISC
<222> LOCATION: (18)..(18)
<223> OTHER INFORMATION: C-terminal amidation

<400> SEQUENCE: 379

Asp Trp His Lys Phe Phe Tyr Asp Lys Val Ala Glu Lys Phe Lys Asp
1 5 10 15

Ala Phe

<210> SEQ ID NO 380
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 380

Asp Trp Phe Lys Phe His Tyr Asp Lys Val Ala Glu Lys Phe Lys Glu
1 5 10 15

Ala Phe

<210> SEQ ID NO 381
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 381

Glu Trp Phe Lys Phe His Tyr Glu Lys Val Ala Asp Lys Phe Lys Asp
1 5 10 15

Ala Phe

<210> SEQ ID NO 382
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 382

Glu Trp Phe Lys Phe His Tyr Asp Lys Val Ala Glu Lys Phe Lys Glu
1 5 10 15

Ala Phe

<210> SEQ ID NO 383
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 383

Asp Trp Phe Lys Phe His Tyr Glu Lys Val Ala Glu Lys Phe Lys Glu
1 5 10 15

Ala Phe

<210> SEQ ID NO 384
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 384

Asp Trp Phe Lys Phe His Tyr Asp Lys Val Ala Asp Lys Phe Lys Glu
1 5 10 15

Ala Phe

<210> SEQ ID NO 385
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 385

Asp Trp Phe Lys Phe His Tyr Asp Lys Val Ala Glu Lys Phe Lys Asp
1 5 10 15

Ala Phe

<210> SEQ ID NO 386
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC <222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 386

Asp Trp Phe Lys Val Phe Tyr Asp Lys His Ala Glu Lys Phe Lys Glu
1 5 10 15

Ala Phe

<210> SEQ ID NO 387
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 387

Glu Trp Phe Lys Val Phe Tyr Glu Lys His Ala Asp Lys Phe Lys Asp
1 5 10 15

Ala Phe

<210> SEQ ID NO 388
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 388

Glu Trp Phe Lys Val Phe Tyr Asp Lys His Ala Glu Lys Phe Lys Glu
1 5 10 15

Ala Phe

<210> SEQ ID NO 389
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 389

Asp Trp Phe Lys Val Phe Tyr Glu Lys His Ala Glu Lys Phe Lys Glu 1 5 10 15

Ala Phe

<210> SEQ ID NO 390
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 390

Asp Trp Phe Lys Val Phe Tyr Asp Lys His Ala Asp Lys Phe Lys Glu
1 5 10 15

Ala Phe

<210> SEQ ID NO 391
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 391

Asp Trp Phe Lys Val Phe Tyr Asp Lys His Ala Glu Lys Phe Lys Asp
1 5 10 15

Ala Phe

<210> SEQ ID NO 392
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 392

Asp Trp Phe Lys Ala Phe Tyr Asp Lys Val Ala Glu Lys Phe Lys Glu
1 5 10 15

His Phe

<210> SEQ ID NO 393
<211> LENGTH: 18
<212> TYPE: PRT
<213> ORGANISM: Artificial Sequence
<220> FEATURE:

<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 393

Glu Trp Phe Lys Ala Phe Tyr Glu Lys Val Ala Asp Lys Phe Lys Asp
1 5 10 15

His Phe

<210> SEQ ID NO 394
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 394

Glu Trp Phe Lys Ala Phe Tyr Asp Lys Val Ala Glu Lys Phe Lys Glu
1 5 10 15

His Phe

<210> SEQ ID NO 395
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 395

Asp Trp Phe Lys Ala Phe Tyr Glu Lys Val Ala Glu Lys Phe Lys Glu
1 5 10 15

His Phe

<210> SEQ ID NO 396
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 396

Asp Trp Phe Lys Ala Phe Tyr Asp Lys Val Ala Asp Lys Phe Lys Glu
1 5 10 15

His Phe

<210> SEQ ID NO 397
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 397

Asp Trp Phe Lys Ala Phe Tyr Asp Lys Val Ala Glu Lys Phe Lys Asp
1 5 10 15

His Phe

<210> SEQ ID NO 398
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 398

Asp Trp Phe Lys Ala Phe Tyr Asp Lys Val Ala Glu Lys Phe Lys Glu
1 5 10 15

Phe His

<210> SEQ ID NO 399
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 399

Glu Trp Phe Lys Ala Phe Tyr Glu Lys Val Ala Asp Lys Phe Lys Asp
1 5 10 15

Phe His

<210> SEQ ID NO 400
<211> LENGTH: 18

<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 400

Glu Trp Phe Lys Ala Phe Tyr Asp Lys Val Ala Glu Lys Phe Lys Glu
1 5 10 15

Phe His

<210> SEQ ID NO 401
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 401

Asp Trp Phe Lys Ala Phe Tyr Asp Lys Val Ala Glu Lys Phe Lys Glu
1 5 10 15

Phe His

<210> SEQ ID NO 402
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 402

Asp Trp Phe Lys Ala Phe Tyr Glu Lys Val Ala Glu Lys Phe Lys Glu
1 5 10 15

Phe His

<210> SEQ ID NO 403
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC <222> LOCATION: (18)..(18)
<223> OTHER INFORMATION: C-terminal amidation

<400> SEQUENCE: 403

Asp Trp Phe Lys Ala Phe Tyr Asp Lys Val Ala Glu Lys Phe Lys Glu
1 5 10 15

Phe His

<210> SEQ ID NO 404
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 404

Asp Trp Phe Lys Ala Phe Tyr Asp Lys Val Ala Glu Lys Phe Lys Asp
1 5 10 15

Phe His

<210> SEQ ID NO 405
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 405

Phe Ala Glu Lys Phe Lys Glu Ala Val Lys Asp Tyr Phe Ala Lys Phe
1 5 10 15

Trp Asp

<210> SEQ ID NO 406
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 406

Phe His Glu Lys Phe Lys Glu Ala Val Lys Asp Tyr Phe Ala Lys Phe
1 5 10 15

Trp Asp

<210> SEQ ID NO 407
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 407

Phe His Glu Lys Phe Lys Glu Ala Val Lys Glu Tyr Phe Ala Lys Phe
1 5 10 15

Trp Glu

<210> SEQ ID NO 408
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 408

Phe His Asp Lys Phe Lys Asp Ala Val Lys Asp Tyr Phe Ala Lys Phe
1 5 10 15

Trp Asp

<210> SEQ ID NO 409
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 409

Phe His Asp Lys Phe Lys Asp Ala Val Lys Glu Tyr Phe Ala Lys Phe
1 5 10 15

Trp Glu

<210> SEQ ID NO 410
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)

<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 410

Phe His Asp Lys Phe Lys Glu Ala Val Lys Asp Tyr Phe Ala Lys Phe
1 5 10 15

Trp Asp

<210> SEQ ID NO 411
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 411

Phe His Glu Lys Phe Lys Asp Ala Val Lys Asp Tyr Phe Ala Lys Phe
1 5 10 15

Trp Asp

<210> SEQ ID NO 412
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 412

Phe His Glu Lys Phe Lys Glu Ala Val Lys Glu Tyr Phe Ala Lys Phe
1 5 10 15

Trp Asp

<210> SEQ ID NO 413
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 413

Phe His Glu Lys Phe Lys Glu Ala Val Lys Asp Tyr Phe Ala Lys Phe
1 5 10 15

Trp Glu

<210> SEQ ID NO 414
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 414

His Phe Glu Lys Phe Lys Glu Ala Val Lys Asp Tyr Phe Ala Lys Phe
1 5 10 15

Trp Asp

<210> SEQ ID NO 415
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 415

His Phe Asp Lys Phe Lys Asp Ala Val Lys Glu Tyr Phe Ala Lys Phe
1 5 10 15

Trp Glu

<210> SEQ ID NO 416
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 416

His Phe Glu Lys Phe Lys Glu Ala Val Lys Glu Tyr Phe Ala Lys Phe
1 5 10 15

Trp Glu

<210> SEQ ID NO 417
<211> LENGTH: 18
<212> TYPE: PRT
<213> ORGANISM: Artificial Sequence
<220> FEATURE:
<223> OTHER INFORMATION: synthetic construct; peptide mimetic <220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 417

His Phe Asp Lys Phe Lys Glu Ala Val Lys Asp Tyr Phe Ala Lys Phe
1 5 10 15

Trp Asp

<210> SEQ ID NO 418
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 418

His Phe Glu Lys Phe Lys Asp Ala Val Lys Asp Tyr Phe Ala Lys Phe
1 5 10 15

Trp Asp

<210> SEQ ID NO 419
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 419

His Phe Glu Lys Phe Lys Glu Ala Val Lys Glu Tyr Phe Ala Lys Phe
1 5 10 15

Trp Asp

<210> SEQ ID NO 420
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 420

His Phe Glu Lys Phe Lys Glu Ala Val Lys Asp Tyr Phe Ala Lys Phe
1 5 10 15

Trp Glu

<210> SEQ ID NO 421
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 421

Phe Phe Glu Lys His Lys Glu Ala Val Lys Asp Tyr Phe Ala Lys Phe
1 5 10 15

Trp Asp

<210> SEQ ID NO 422
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 422

Phe Phe Asp Lys His Lys Asp Ala Val Lys Glu Tyr Phe Ala Lys Phe
1 5 10 15

Trp Glu

<210> SEQ ID NO 423
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 423

Phe Phe Glu Lys His Lys Glu Ala Val Lys Glu Tyr Phe Ala Lys Phe
1 5 10 15

Trp Glu

<210> SEQ ID NO 424
<211> LENGTH: 18
<212> TYPE: PRT

<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 424

Phe Phe Asp Lys His Lys Asp Ala Val Lys Asp Tyr Phe Ala Lys Phe
1 5 10 15

Trp Asp

<210> SEQ ID NO 425
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 425

Phe Phe Asp Lys His Lys Glu Ala Val Lys Asp Tyr Phe Ala Lys Phe
1 5 10 15

Trp Asp

<210> SEQ ID NO 426
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 426

Phe Phe Glu Lys His Lys Glu Ala Val Lys Glu Tyr Phe Ala Lys Phe
1 5 10 15

Trp Asp

<210> SEQ ID NO 427
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)

<223> OTHER INFORMATION: C-terminal amidation

<400> SEQUENCE: 427

Phe Phe Glu Lys His Lys Glu Ala Val Lys Asp Tyr Phe Ala Lys Phe
1 5 10 15

Trp Glu

<210> SEQ ID NO 428
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 428

Phe Val Glu Lys Phe Lys Glu Ala His Lys Asp Tyr Phe Ala Lys Phe
1 5 10 15

Trp Asp

<210> SEQ ID NO 429
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 429

Phe Val Asp Lys Phe Lys Asp Ala His Lys Glu Tyr Phe Ala Lys Phe
1 5 10 15

Trp Glu

<210> SEQ ID NO 430
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 430

Phe Val Glu Lys Phe Lys Glu Ala His Lys Glu Tyr Phe Ala Lys Phe
1 5 10 15

Trp Glu

<210> SEQ ID NO 431
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 431

Phe Val Asp Lys Phe Lys Asp Ala His Lys Asp Tyr Phe Ala Lys Phe
1 5 10 15

Trp Asp

<210> SEQ ID NO 432
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 432

Phe Val Asp Lys Phe Lys Glu Ala His Lys Asp Tyr Phe Ala Lys Phe
1 5 10 15

Trp Asp

<210> SEQ ID NO 433
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 433

Phe Val Glu Lys Phe Lys Asp Ala His Lys Asp Tyr Phe Ala Lys Phe
1 5 10 15

Trp Asp

<210> SEQ ID NO 434
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation <220> FEATURE:
<221> NAME/KEY: MISC
<222> LOCATION: (18)..(18)
<223> OTHER INFORMATION: C-terminal amidation

<400> SEQUENCE: 434

Phe Val Glu Lys Phe Lys Glu Ala His Lys Glu Tyr Phe Ala Lys Phe
1 5 10 15

Trp Asp

<210> SEQ ID NO 435
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 435

Phe Val Glu Lys Phe Lys Glu Ala His Lys Asp Tyr Phe Ala Lys Phe
1 5 10 15

Trp Glu

<210> SEQ ID NO 436
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 436

Phe Ala Glu Lys Phe Lys Glu His Val Lys Asp Tyr Phe Ala Lys Phe
1 5 10 15

Trp Asp

<210> SEQ ID NO 437
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 437

Phe Ala Asp Lys Phe Lys Asp His Val Lys Glu Tyr Phe Ala Lys Phe
1 5 10 15

Trp Glu

<210> SEQ ID NO 438
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 438

Phe Ala Glu Lys Phe Lys Glu His Val Lys Glu Tyr Phe Ala Lys Phe
1 5 10 15

Trp Glu

<210> SEQ ID NO 439
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 439

Phe Ala Asp Lys Phe Lys Asp His Val Lys Asp Tyr Phe Ala Lys Phe
1 5 10 15

Trp Asp

<210> SEQ ID NO 440
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 440

Phe Ala Asp Lys Phe Lys Glu His Val Lys Asp Tyr Phe Ala Lys Phe
1 5 10 15

Trp Asp

<210> SEQ ID NO 441
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:

<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 441

Phe Ala Glu Lys Phe Lys Asp His Val Lys Asp Tyr Phe Ala Lys Phe
1 5 10 15

Trp Asp

<210> SEQ ID NO 442
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 442

Phe Ala Glu Lys Phe Lys Glu His Val Lys Glu Tyr Phe Ala Lys Phe
1 5 10 15

Trp Asp

<210> SEQ ID NO 443
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 443

Phe Ala Glu Lys Phe Lys Glu His Val Lys Asp Tyr Phe Ala Lys Phe
1 5 10 15

Trp Glu

<210> SEQ ID NO 444
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 444

Phe Ala Glu Lys Phe Lys Glu Phe Val Lys Asp Tyr His Ala Lys Phe
1 5 10 15

Trp Asp

<210> SEQ ID NO 445
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 445

Phe Ala Asp Lys Phe Lys Asp Phe Val Lys Glu Tyr His Ala Lys Phe
1 5 10 15

Trp Glu

<210> SEQ ID NO 446
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 446

Phe Ala Asp Lys Phe Lys Glu Phe Val Lys Asp Tyr His Ala Lys Phe
1 5 10 15

Trp Asp

<210> SEQ ID NO 447
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 447

Phe Ala Glu Lys Phe Lys Asp Phe Val Lys Asp Tyr His Ala Lys Phe
1 5 10 15

Trp Asp

<210> SEQ ID NO 448
<211> LENGTH: 18
<212> TYPE: PRT
<213> ORGANISM: Artificial Sequence <220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 448

Phe Ala Asp Lys Phe Lys Asp Phe Val Lys Asp Tyr His Ala Lys Phe
1 5 10 15

Trp Asp

<210> SEQ ID NO 449
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 449

Phe Ala Glu Lys Phe Lys Glu Phe Val Lys Glu Tyr His Ala Lys Phe
1 5 10 15

Trp Glu

<210> SEQ ID NO 450
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 450

Phe Ala Glu Lys Phe Lys Glu Phe Val Lys Glu Tyr His Ala Lys Phe
1 5 10 15

Trp Asp

<210> SEQ ID NO 451
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 451

Phe Ala Glu Lys Phe Lys Glu Phe Val Lys Asp Tyr His Ala Lys Phe
1 5 10 15

Trp Glu

<210> SEQ ID NO 452
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 452

Phe Ala Glu Lys Phe Lys Glu Phe Val Lys Asp Tyr Phe Ala Lys His
1 5 10 15

Trp Asp

<210> SEQ ID NO 453
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 453

Phe Ala Asp Lys Phe Lys Asp Phe Val Lys Glu Tyr Phe Ala Lys His
1 5 10 15

Trp Glu

<210> SEQ ID NO 454
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 454

Phe Ala Glu Lys Phe Lys Glu Phe Val Lys Glu Tyr Phe Ala Lys His
1 5 10 15

Trp Glu

<210> SEQ ID NO 455

<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 455

Phe Ala Asp Lys Phe Lys Asp Phe Val Lys Asp Tyr Phe Ala Lys His
1 5 10 15

Trp Asp

<210> SEQ ID NO 456
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 456

Phe Ala Asp Lys Phe Lys Glu Phe Val Lys Asp Tyr Phe Ala Lys His
1 5 10 15

Trp Asp

<210> SEQ ID NO 457
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 457

Phe Ala Glu Lys Phe Lys Asp Phe Val Lys Asp Tyr Phe Ala Lys His
1 5 10 15

Trp Asp

<210> SEQ ID NO 458
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:

<221> NAME/KEY: MISC
<222> LOCATION: (18)..(18)
<223> OTHER INFORMATION: C-terminal amidation

<400> SEQUENCE: 458

Phe Ala Glu Lys Phe Lys Glu Phe Val Lys Glu Tyr Phe Ala Lys His
1 5 10 15

Trp Asp

<210> SEQ ID NO 459
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 459

Phe Ala Glu Lys Phe Lys Glu Phe Val Lys Asp Tyr Phe Ala Lys His
1 5 10 15

Trp Glu

<210> SEQ ID NO 460
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (3)..(3)
<223> OTHER INFORMATION: Xaa is beta-Nph
<220> FEATURE:
<221> NAME/KEY: misc
<222> LOCATION: (6)..(6)
<223> OTHER INFORMATION: Xaa is beta-Nph
<220> FEATURE:
<221> NAME/KEY: misc
<222> LOCATION: (14)..(14)
<223> OTHER INFORMATION: Xaa is beta-Nph
<220> FEATURE:
<221> NAME/KEY: misc
<222> LOCATION: (18)..(18)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 460

Asp Trp Xaa Lys Ala Xaa Tyr Asp Lys Val Ala Glu Lys Xaa Lys Glu
1 5 10 15

Ala Xaa

<210> SEQ ID NO 461
<211> LENGTH: 18
<212> TYPE: PRT
<213> ORGANISM: Artificial Sequence
<220> FEATURE:

<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (3)..(3)
<223> OTHER INFORMATION: Xaa is beta-Nph
<220> FEATURE:
<221> NAME/KEY: misc
<222> LOCATION: (6)..(6)
<223> OTHER INFORMATION: Xaa is beta-Nph
<220> FEATURE:
<221> NAME/KEY: misc
<222> LOCATION: (14)..(14)
<223> OTHER INFORMATION: Xaa is beta-Nph
<220> FEATURE:
<221> NAME/KEY: misc
<222> LOCATION: (18)..(18)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 461

Glu Trp Xaa Lys Ala Xaa Tyr Glu Lys Val Ala Asp Lys Xaa Lys Asp
1 5 10 15

Ala Xaa

<210> SEQ ID NO 462
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (3)..(3)
<223> OTHER INFORMATION: Xaa is beta-Nph
<220> FEATURE:
<221> NAME/KEY: misc
<222> LOCATION: (6)..(6)
<223> OTHER INFORMATION: Xaa is beta-Nph
<220> FEATURE:
<221> NAME/KEY: misc
<222> LOCATION: (14)..(14)
<223> OTHER INFORMATION: Xaa is beta-Nph
<220> FEATURE:
<221> NAME/KEY: misc
<222> LOCATION: (18)..(18)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 462

Glu Trp Xaa Lys Ala Xaa Tyr Glu Lys Val Ala Asp Lys Xaa Lys Glu
1 5 10 15

Ala Xaa

<210> SEQ ID NO 463
<211> LENGTH: 18
<212> TYPE: PRT
<213> ORGANISM: Artificial Sequence
<220> FEATURE:
<223> OTHER INFORMATION: synthetic construct, Nph peptide mimetic <220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (3)..(3)
<223> OTHER INFORMATION: Xaa is beta-Nph
<220> FEATURE:
<221> NAME/KEY: misc
<222> LOCATION: (6)..(6)
<223> OTHER INFORMATION: Xaa is beta-Nph
<220> FEATURE:
<221> NAME/KEY: misc
<222> LOCATION: (14)..(14)
<223> OTHER INFORMATION: Xaa is beta-Nph
<220> FEATURE:
<221> NAME/KEY: misc
<222> LOCATION: (18)..(18)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 463

Asp Trp Xaa Lys Ala Xaa Tyr Asp Lys Val Ala Asp Lys Xaa Lys Asp
1 5 10 15

Ala Xaa

<210> SEQ ID NO 464
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (3)..(3)
<223> OTHER INFORMATION: Xaa is beta-Nph
<220> FEATURE:
<221> NAME/KEY: misc
<222> LOCATION: (6)..(6)
<223> OTHER INFORMATION: Xaa is beta-Nph
<220> FEATURE:
<221> NAME/KEY: misc
<222> LOCATION: (14)..(14)
<223> OTHER INFORMATION: Xaa is beta-Nph
<220> FEATURE:
<221> NAME/KEY: misc
<222> LOCATION: (18)..(18)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 464

Glu Trp Xaa Lys Ala Xaa Tyr Asp Lys Val Ala Glu Lys Xaa Lys Glu
1 5 10 15

Ala Xaa

<210> SEQ ID NO 465
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:

<221> NAME/KEY: misc
<222> LOCATION: (1)..(1)
<223> OTHER INFORMATION: N-terminus acetylation
<220> FEATURE:
<221> NAME/KEY: misc
<222> LOCATION: (3)..(3)
<223> OTHER INFORMATION: Xaa is beta-Nph
<220> FEATURE:
<221> NAME/KEY: misc
<222> LOCATION: (6)..(6)
<223> OTHER INFORMATION: Xaa is beta-Nph
<220> FEATURE:
<221> NAME/KEY: misc
<222> LOCATION: (14)..(14)
<223> OTHER INFORMATION: Xaa is beta-Nph
<220> FEATURE:
<221> NAME/KEY: misc
<222> LOCATION: (18)..(18)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 465

Asp Trp Xaa Lys Ala Xaa Tyr Glu Lys Val Ala Glu Lys Xaa Lys Glu
1 5 10 15

Ala Xaa

<210> SEQ ID NO 466
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (3)..(3)
<223> OTHER INFORMATION: Xaa is beta-Nph
<220> FEATURE:
<221> NAME/KEY: misc
<222> LOCATION: (6)..(6)
<223> OTHER INFORMATION: Xaa is beta-Nph
<220> FEATURE:
<221> NAME/KEY: misc
<222> LOCATION: (14)..(14)
<223> OTHER INFORMATION: Xaa is beta-Nph
<220> FEATURE:
<221> NAME/KEY: misc
<222> LOCATION: (18)..(18)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 466

Asp Trp Xaa Lys Ala Xaa Tyr Asp Lys Val Ala Asp Lys Xaa Lys Glu
1 5 10 15

Ala Xaa

<210> SEQ ID NO 467
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc <222> LOCATION: (1)..(1)
<223> OTHER INFORMATION: N-terminus acetylation
<220> FEATURE:
<221> NAME/KEY: misc
<222> LOCATION: (3)..(3)
<223> OTHER INFORMATION: Xaa is beta-Nph
<220> FEATURE:
<221> NAME/KEY: misc
<222> LOCATION: (6)..(6)
<223> OTHER INFORMATION: Xaa is beta-Nph
<220> FEATURE:
<221> NAME/KEY: misc
<222> LOCATION: (14)..(14)
<223> OTHER INFORMATION: Xaa is beta-Nph
<220> FEATURE:
<221> NAME/KEY: misc
<222> LOCATION: (18)..(18)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 467

Asp Trp Xaa Lys Ala Xaa Tyr Asp Lys Val Ala Glu Lys Xaa Lys Asp
1 5 10 15

Ala Xaa

<210> SEQ ID NO 468
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (3)..(3)
<223> OTHER INFORMATION: Xaa is beta-Nph
<220> FEATURE:
<221> NAME/KEY: misc
<222> LOCATION: (6)..(6)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 468

Asp Trp Xaa Lys Ala Xaa Tyr Asp Lys Val Ala Glu Lys Phe Lys Glu
1 5 10 15

Ala Phe

<210> SEQ ID NO 469
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (14)..(14)
<223> OTHER INFORMATION: Xaa is beta-Nph
<220> FEATURE:
<221> NAME/KEY: misc
<222> LOCATION: (18)..(18)

<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 469

Asp Trp Phe Lys Ala Phe Tyr Asp Lys Val Ala Glu Lys Xaa Lys Glu
1 5 10 15

Ala Xaa

<210> SEQ ID NO 470
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (3)..(3)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 470

Asp Trp Xaa Lys Ala Phe Tyr Asp Lys Val Ala Glu Lys Phe Lys Glu
1 5 10 15

Ala Phe

<210> SEQ ID NO 471
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (6)..(6)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 471

Asp Trp Phe Lys Ala Xaa Tyr Asp Lys Val Ala Glu Lys Phe Lys Glu
1 5 10 15

Ala Phe

<210> SEQ ID NO 472
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminus acetylation
<220> FEATURE:

<221> NAME/KEY: misc
<222> LOCATION: (14)..(14)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 472

Asp Trp Phe Lys Ala Phe Tyr Asp Lys Val Ala Glu Lys Xaa Lys Glu
1 5 10 15

Ala Phe

<210> SEQ ID NO 473
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (18)..(18)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 473

Asp Trp Phe Lys Ala Phe Tyr Asp Lys Val Ala Glu Lys Phe Lys Glu
1 5 10 15

Ala Xaa

<210> SEQ ID NO 474
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: Xaa is beta-Nph
<220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (5)..(5)
<223> OTHER INFORMATION: Xaa is beta-Nph
<220> FEATURE:
<221> NAME/KEY: misc
<222> LOCATION: (13)..(13)
<223> OTHER INFORMATION: Xaa is beta-Nph
<220> FEATURE:
<221> NAME/KEY: misc
<222> LOCATION: (16)..(16)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 474

Xaa Ala Glu Lys Xaa Lys Glu Ala Val Lys Asp Tyr Xaa Ala Lys Xaa
1 5 10 15

Trp Asp

<210> SEQ ID NO 475
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: Xaa is beta-Nph
<220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (5)..(5)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 475

Xaa Ala Glu Lys Xaa Lys Glu Ala Val Lys Asp Tyr Phe Ala Lys Phe
1 5 10 15

Trp Asp

<210> SEQ ID NO 476
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (13)..(13)
<223> OTHER INFORMATION: Xaa is beta-Nph
<220> FEATURE:
<221> NAME/KEY: misc
<222> LOCATION: (16)..(16)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 476

Phe Ala Glu Lys Phe Lys Glu Ala Val Lys Asp Tyr Xaa Ala Lys Xaa
1 5 10 15

Trp Asp

<210> SEQ ID NO 477
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: Xaa is beta-Nph
<220> FEATURE:
<221> NAME/KEY: misc
<222> LOCATION: (1)..(1)
<223> OTHER INFORMATION: N-terminus acetylation <220> FEATURE:
<221> NAME/KEY: misc
<222> LOCATION: (18)..(18)
<223> OTHER INFORMATION: C-terminus is amidated

<400> SEQUENCE: 477

Xaa Ala Glu Lys Phe Lys Glu Ala Val Lys Asp Tyr Phe Ala Lys Phe
1 5 10 15

Trp Asp

<210> SEQ ID NO 478
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (5)..(5)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 478

Phe Ala Glu Lys Xaa Lys Glu Ala Val Lys Asp Tyr Phe Ala Lys Phe
1 5 10 15

Trp Asp

<210> SEQ ID NO 479
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminus acetylation
<220> FEATURE:
<221> NAME/KEY: misc
<222> LOCATION: (13)..(13)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 479

Phe Ala Glu Lys Phe Lys Glu Ala Val Lys Asp Tyr Xaa Ala Lys Phe
1 5 10 15

Trp Asp

<210> SEQ ID NO 480
<211> LENGTH: 18
<212> TYPE: PRT
<213> ORGANISM: Artificial Sequence
<220> FEATURE:
<223> OTHER INFORMATION: synthetic construct, Nph peptide mimetic
<220> FEATURE:
<221> NAME/KEY: misc
<222> LOCATION: (1)..(1)
<223> OTHER INFORMATION: N-terminus acetylation
<220> FEATURE:
<221> NAME/KEY: misc <222> LOCATION: (16)..(16)
<223> OTHER INFORMATION: Xaa is beta-Nph
<220> FEATURE:
<221> NAME/KEY: misc
<222> LOCATION: (18)..(18)
<223> OTHER INFORMATION: C-terminus is amidated

<400> SEQUENCE: 480

Phe Ala Glu Lys Glu Lys Glu Ala Val Lys Asp Tyr Phe Ala Lys Xaa
1 5 10 15

Trp Asp

<210> SEQ ID NO 481
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 481

Phe Ala Glu Lys Phe Lys Glu Ala Val Lys Glu Tyr Phe Ala Lys Phe
1 5 10 15

Trp Glu

<210> SEQ ID NO 482
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 482

Phe Ala Asp Lys Phe Lys Asp Ala Val Lys Asp Tyr Phe Ala Lys Phe
1 5 10 15

Trp Asp

<210> SEQ ID NO 483
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 483

Phe Ala Glu Arg Phe Arg Glu Ala Val Lys Asp Tyr Phe Ala Lys Phe 1 5 10 15

Trp Asp

<210> SEQ ID NO 484
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 484

Phe Ala Glu Lys Phe Arg Glu Ala Val Lys Asp Tyr Phe Ala Lys Phe
1 5 10 15

Trp Asp

<210> SEQ ID NO 485
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 485

Phe Ala Glu Lys Phe Lys Glu Ala Val Arg Asp Tyr Phe Ala Lys Phe
1 5 10 15

Trp Asp

<210> SEQ ID NO 486
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 486

Phe Ala Glu Lys Phe Lys Glu Ala Val Lys Asp Tyr Phe Ala Arg Phe
1 5 10 15

Trp Asp

<210> SEQ ID NO 487
<211> LENGTH: 18
<212> TYPE: PRT
<213> ORGANISM: Artificial Sequence
<220> FEATURE:

<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 487

Phe Ala Glu Lys Phe Arg Glu Ala Val Lys Asp Tyr Glu Ala Lys Phe
1 5 10 15

Trp Asp

<210> SEQ ID NO 488
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 488

Leu Phe Glu Lys Phe Ala Glu Ala Phe Lys Asp Tyr Val Ala Lys Trp
1 5 10 15

Lys Asp

<210> SEQ ID NO 489
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 489

Leu Phe Glu Arg Phe Ala Glu Ala Phe Lys Asp Tyr Val Ala Lys Trp
1 5 10 15

Lys Asp

<210> SEQ ID NO 490
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 490

Leu Phe Glu Lys Phe Ala Glu Ala Phe Arg Asp Tyr Val Ala Lys Trp
1 5 10 15

Lys Asp

<210> SEQ ID NO 491
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 491

Leu Phe Glu Lys Phe Ala Glu Ala Phe Lys Asp Tyr Val Ala Arg Trp
1 5 10 15

Lys Asp

<210> SEQ ID NO 492
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 492

Leu Phe Glu Lys Phe Ala Glu Ala Phe Lys Asp Tyr Val Ala Lys Trp
1 5 10 15

Arg Asp

<210> SEQ ID NO 493
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 493

Leu Phe Glu Lys Phe Ala Glu Ala Phe Lys Glu Tyr Val Ala Lys Trp
1 5 10 15

Lys Glu

<210> SEQ ID NO 494
<211> LENGTH: 18

<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 494

Leu Phe Asp Lys Phe Ala Asp Ala Phe Lys Asp Tyr Val Ala Lys Trp
1 5 10 15

Lys Asp

<210> SEQ ID NO 495
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 495

Leu Phe Asp Lys Phe Ala Glu Ala Phe Lys Asp Tyr Val Ala Lys Trp
1 5 10 15

Lys Asp

<210> SEQ ID NO 496
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 496

Leu Phe Glu Lys Phe Ala Asp Ala Phe Lys Asp Tyr Val Ala Lys Trp
1 5 10 15

Lys Asp

<210> SEQ ID NO 497
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC <222> LOCATION: (18)..(18)
<223> OTHER INFORMATION: C-terminal amidation

<400> SEQUENCE: 497

Leu Phe Glu Lys Phe Ala Glu Ala Phe Lys Glu Tyr Val Ala Lys Trp
1 5 10 15

Lys Asp

<210> SEQ ID NO 498
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 498

Leu Phe Glu Lys Phe Ala Glu Ala Phe Lys Asp Tyr Val Ala Lys Trp
1 5 10 15

Lys Glu

<210> SEQ ID NO 499
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 499

Phe Ala Glu Lys Ala Trp Glu Phe Val Lys Asp Tyr Phe Ala Lys Leu
1 5 10 15

Lys Asp

<210> SEQ ID NO 500
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 500

Phe Ala Glu Arg Ala Trp Glu Phe Val Lys Asp Tyr Phe Ala Lys Leu
1 5 10 15

Lys Asp

<210> SEQ ID NO 501
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 501

Phe Ala Glu Lys Ala Trp Glu Phe Val Lys Asp Tyr Phe Ala Lys Leu
1 5 10 15

Lys Asp

<210> SEQ ID NO 502
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 502

Phe Ala Glu Lys Ala Trp Glu Phe Val Lys Asp Tyr Phe Ala Lys Leu
1 5 10 15

Lys Asp

<210> SEQ ID NO 503
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 503

Phe Ala Glu Lys Ala Trp Glu Phe Val Lys Asp Tyr Phe Ala Lys Leu
1 5 10 15

Arg Asp

<210> SEQ ID NO 504
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)

<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 504

Phe Ala Glu Lys Ala Trp Glu Phe Val Lys Glu Tyr Phe Ala Lys Leu
1 5 10 15

Lys Glu

<210> SEQ ID NO 505
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 505

Phe Ala Asp Lys Ala Trp Asp Phe Val Lys Asp Tyr Phe Ala Lys Leu
1 5 10 15

Lys Asp

<210> SEQ ID NO 506
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 506

Phe Ala Asp Lys Ala Trp Glu Phe Val Lys Asp Tyr Phe Ala Lys Leu
1 5 10 15

Lys Asp

<210> SEQ ID NO 507
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 507

Phe Ala Glu Lys Ala Trp Asp Phe Val Lys Asp Tyr Phe Ala Lys Leu
1 5 10 15

Lys Asp

<210> SEQ ID NO 508
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 508

Phe Ala Glu Lys Ala Trp Glu Phe Val Lys Glu Tyr Phe Ala Lys Leu
1 5 10 15

Lys Asp

<210> SEQ ID NO 509
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 509

Phe Ala Glu Lys Ala Trp Glu Phe Val Lys Asp Tyr Phe Ala Lys Leu
1 5 10 15

Lys Glu

<210> SEQ ID NO 510
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 510

Phe Phe Glu Lys Phe Lys Glu Phe Val Lys Asp Tyr Phe Ala Lys Leu
1 5 10 15

Trp Asp

<210> SEQ ID NO 511
<211> LENGTH: 18
<212> TYPE: PRT
<213> ORGANISM: Artificial Sequence
<220> FEATURE:
<223> OTHER INFORMATION: synthetic construct; peptide mimetic <220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 511

Phe Phe Glu Lys Phe Lys Glu Phe Val Lys Glu Tyr Phe Ala Lys Leu
1 5 10 15

Trp Glu

<210> SEQ ID NO 512
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 512

Phe Phe Asp Lys Phe Lys Asp Phe Val Lys Asp Tyr Phe Ala Lys Leu
1 5 10 15

Trp Asp

<210> SEQ ID NO 513
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 513

Phe Phe Glu Arg Phe Lys Glu Phe Val Lys Asp Tyr Phe Ala Lys Leu
1 5 10 15

Trp Asp

<210> SEQ ID NO 514
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 514

Phe Phe Glu Lys Phe Arg Glu Phe Val Lys Asp Tyr Phe Ala Lys Leu
1 5 10 15

Trp Asp

<210> SEQ ID NO 515
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 515

Phe Phe Glu Lys Phe Lys Glu Phe Val Arg Asp Tyr Phe Ala Lys Leu
1 5 10 15

Trp Asp

<210> SEQ ID NO 516
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 516

Phe Phe Glu Lys Phe Lys Glu Phe Val Lys Asp Tyr Phe Ala Arg Leu
1 5 10 15

Trp Asp

<210> SEQ ID NO 517
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 517

Phe Phe Asp Lys Phe Lys Glu Phe Val Lys Asp Tyr Phe Ala Lys Leu
1 5 10 15

Trp Asp

<210> SEQ ID NO 518
<211> LENGTH: 18
<212> TYPE: PRT

<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 518

Phe Phe Glu Lys Phe Lys Asp Phe Val Lys Asp Tyr Phe Ala Lys Leu
1 5 10 15

Trp Asp

<210> SEQ ID NO 519
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 519

Phe Phe Glu Lys Phe Lys Glu Phe Val Lys Glu Tyr Phe Ala Lys Leu
1 5 10 15

Trp Asp

<210> SEQ ID NO 520
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 520

Phe Phe Glu Lys Phe Lys Glu Phe Val Lys Asp Tyr Phe Ala Lys Leu
1 5 10 15

Trp Glu

<210> SEQ ID NO 521
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)

<223> OTHER INFORMATION: C-terminal amidation

<400> SEQUENCE: 521

Phe Leu Glu Lys Phe Lys Glu Phe Val Lys Asp Tyr Phe Ala Lys Phe
1 5 10 15

Trp Asp

<210> SEQ ID NO 522
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 522

Phe Leu Glu Lys Phe Lys Glu Phe Val Lys Glu Tyr Phe Ala Lys Phe
1 5 10 15

Trp Glu

<210> SEQ ID NO 523
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 523

Phe Leu Asp Lys Phe Lys Glu Phe Val Lys Asp Tyr Phe Ala Lys Phe
1 5 10 15

Trp Asp

<210> SEQ ID NO 524
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 524

Phe Leu Asp Lys Phe Lys Glu Phe Val Lys Asp Tyr Phe Ala Lys Phe
1 5 10 15

Trp Asp

<210> SEQ ID NO 525
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 525

Phe Leu Glu Lys Phe Lys Asp Phe Val Lys Asp Tyr Phe Ala Lys Phe
1 5 10 15

Trp Asp

<210> SEQ ID NO 526
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 526

Phe Leu Glu Lys Phe Lys Glu Phe Val Lys Glu Tyr Phe Ala Lys Phe
1 5 10 15

Trp Asp

<210> SEQ ID NO 527
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 527

Phe Leu Glu Lys Phe Lys Glu Phe Val Lys Asp Tyr Phe Ala Lys Phe
1 5 10 15

Trp Glu

<210> SEQ ID NO 528
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation <220> FEATURE:
<221> NAME/KEY: MISC
<222> LOCATION: (18)..(18)
<223> OTHER INFORMATION: C-terminal amidation

<400> SEQUENCE: 528

Phe Leu Glu Arg Phe Lys Glu Phe Val Lys Asp Tyr Phe Ala Lys Phe
1 5 10 15

Trp Asp

<210> SEQ ID NO 529
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 529

Phe Leu Glu Lys Phe Arg Glu Phe Val Lys Asp Tyr Phe Ala Lys Phe
1 5 10 15

Trp Asp

<210> SEQ ID NO 530
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 530

Phe Leu Glu Lys Phe Lys Glu Phe Val Arg Asp Tyr Phe Ala Lys Phe
1 5 10 15

Trp Asp

<210> SEQ ID NO 531
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 531

Phe Leu Glu Lys Phe Lys Glu Phe Val Lys Asp Tyr Phe Ala Arg Phe
1 5 10 15

Trp Asp

<210> SEQ ID NO 532
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 532

Phe Phe Glu Lys Phe Lys Glu Phe Phe Lys Asp Tyr Phe Ala Lys Leu
1 5 10 15

Trp Asp

<210> SEQ ID NO 533
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 533

Phe Phe Glu Lys Phe Lys Glu Phe Phe Lys Glu Tyr Phe Ala Lys Leu
1 5 10 15

Trp Glu

<210> SEQ ID NO 534
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 534

Phe Phe Asp Lys Phe Lys Asp Phe Phe Lys Asp Tyr Phe Ala Lys Leu
1 5 10 15

Trp Asp

<210> SEQ ID NO 535
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:

<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 535

Phe Phe Glu Arg Phe Lys Glu Phe Phe Lys Asp Tyr Phe Ala Lys Leu
1 5 10 15

Trp Asp

<210> SEQ ID NO 536
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 536

Phe Phe Glu Lys Phe Arg Glu Phe Phe Lys Asp Tyr Phe Ala Lys Leu
1 5 10 15

Trp Asp

<210> SEQ ID NO 537
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 537

Phe Phe Glu Lys Phe Lys Glu Phe Phe Arg Asp Tyr Phe Ala Lys Leu
1 5 10 15

Trp Asp

<210> SEQ ID NO 538
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 538

Phe Phe Glu Arg Phe Lys Glu Phe Phe Lys Asp Tyr Phe Ala Arg Leu
1 5 10 15

Trp Asp

<210> SEQ ID NO 539
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 539

Phe Phe Asp Lys Phe Lys Glu Phe Phe Lys Asp Tyr Phe Ala Lys Leu
1 5 10 15

Trp Asp

<210> SEQ ID NO 540
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 540

Phe Phe Glu Lys Glu Lys Asp Phe Phe Lys Asp Tyr Phe Ala Lys Leu
1 5 10 15

Trp Asp

<210> SEQ ID NO 541
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 541

Phe Phe Glu Lys Phe Lys Glu Phe Phe Lys Glu Tyr Phe Ala Lys Leu
1 5 10 15

Trp Asp

<210> SEQ ID NO 542
<211> LENGTH: 18
<212> TYPE: PRT
<213> ORGANISM: Artificial Sequence <220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 542

Phe Phe Glu Lys Phe Lys Glu Phe Phe Lys Asp Tyr Phe Ala Lys Leu
1 5 10 15

Trp Glu

<210> SEQ ID NO 543
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 543

Phe Ala Glu Lys Phe Lys Glu Ala Val Lys Asp Tyr Phe Ala Lys Phe
1 5 10 15

Trp Asp

<210> SEQ ID NO 544
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 544

Asp Lys Trp Lys Ala Val Tyr Asp Lys Phe Ala Glu Ala Phe Lys Glu
1 5 10 15

Phe Phe

<210> SEQ ID NO 545
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 545

Glu Lys Trp Lys Ala Val Tyr Glu Lys Phe Ala Glu Ala Phe Lys Glu
1 5 10 15

Phe Phe

<210> SEQ ID NO 546
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 546

Asp Lys Trp Lys Ala Val Tyr Asp Lys Phe Ala Asp Ala Phe Lys Asp
1 5 10 15

Phe Phe

<210> SEQ ID NO 547
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 547

Asp Arg Trp Lys Ala Val Tyr Asp Lys Phe Ala Glu Ala Phe Lys Glu
1 5 10 15

Phe Phe

<210> SEQ ID NO 548
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 548

Asp Lys Trp Arg Ala Val Tyr Asp Lys Phe Ala Glu Ala Phe Lys Glu
1 5 10 15

Phe Phe

<210> SEQ ID NO 549

<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 549

Asp Lys Trp Lys Ala Val Tyr Asp Arg Phe Ala Glu Ala Phe Lys Glu
1 5 10 15

Phe Phe

<210> SEQ ID NO 550
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 550

Asp Lys Trp Lys Ala Val Tyr Asp Lys Phe Ala Glu Ala Phe Arg Glu
1 5 10 15

Phe Phe

<210> SEQ ID NO 551
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 551

Phe Phe Glu Lys Phe Ala Glu Ala Phe Lys Asp Tyr Val Ala Lys Trp
1 5 10 15

Lys Asp

<210> SEQ ID NO 552
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:

<221> NAME/KEY: MISC
<222> LOCATION: (18)..(18)
<223> OTHER INFORMATION: C-terminal amidation

<400> SEQUENCE: 552

Phe Phe Glu Lys Phe Ala Glu Ala Phe Lys Glu Tyr Val Ala Lys Trp
1 5 10 15

Lys Glu

<210> SEQ ID NO 553
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 553

Phe Phe Asp Lys Phe Ala Asp Ala Phe Lys Asp Tyr Val Ala Lys Trp
1 5 10 15

Lys Asp

<210> SEQ ID NO 554
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 554

Phe Phe Glu Arg Phe Ala Glu Ala Phe Lys Asp Tyr Val Ala Lys Trp
1 5 10 15

Lys Asp

<210> SEQ ID NO 555
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 555

Glu Phe Glu Arg Phe Ala Glu Ala Phe Arg Asp Tyr Val Ala Lys Trp
1 5 10 15

Lys Asp

<210> SEQ ID NO 556
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 556

Phe Phe Glu Lys Phe Ala Glu Ala Phe Lys Asp Tyr Val Ala Arg Trp
1 5 10 15

Lys Asp

<210> SEQ ID NO 557
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 557

Phe Phe Glu Arg Phe Ala Glu Ala Phe Lys Asp Tyr Val Ala Lys Trp
1 5 10 15

Arg Asp

<210> SEQ ID NO 558
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 558

Phe Phe Asp Lys Phe Ala Glu Ala Phe Lys Asp Tyr Val Ala Lys Trp
1 5 10 15

Lys Asp

<210> SEQ ID NO 559
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC <222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 559

Phe Phe Glu Lys Phe Ala Asp Ala Phe Lys Asp Tyr Val Ala Lys Trp
1 5 10 15

Lys Asp

<210> SEQ ID NO 560
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 560

Phe Phe Glu Arg Phe Ala Glu Ala Phe Lys Glu Tyr Val Ala Lys Trp
1 5 10 15

Lys Asp

<210> SEQ ID NO 561
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 561

Phe Phe Glu Arg Phe Ala Glu Ala Phe Lys Asp Tyr Val Ala Lys Trp
1 5 10 15

Lys Glu

<210> SEQ ID NO 562
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 562

Phe Phe Glu Lys Phe Lys Glu Phe Phe Lys Asp Tyr Phe Ala Lys Phe 1 5 10 15

Trp Asp

<210> SEQ ID NO 563
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 563

Phe Phe Asp Lys Phe Lys Asp Phe Phe Lys Asp Tyr Phe Ala Lys Phe
1 5 10 15

Trp Asp

<210> SEQ ID NO 564
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 564

Phe Phe Glu Lys Phe Lys Glu Phe Phe Lys Glu Tyr Phe Ala Lys Phe
1 5 10 15

Trp Glu

<210> SEQ ID NO 565
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 565

Phe Phe Glu Arg Phe Lys Glu Phe Phe Lys Asp Tyr Phe Ala Lys Phe
1 5 10 15

Trp Asp

<210> SEQ ID NO 566
<211> LENGTH: 18
<212> TYPE: PRT
<213> ORGANISM: Artificial Sequence
<220> FEATURE:

<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 566

Phe Phe Glu Lys Phe Arg Glu Phe Phe Lys Asp Tyr Phe Ala Lys Phe
1 5 10 15

Trp Asp

<210> SEQ ID NO 567
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 567

Phe Phe Glu Lys Phe Lys Glu Phe Phe Arg Asp Tyr Phe Ala Lys Phe
1 5 10 15

Trp Asp

<210> SEQ ID NO 568
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 568

Phe Phe Glu Lys Phe Lys Glu Phe Phe Lys Asp Tyr Phe Ala Arg Phe
1 5 10 15

Trp Asp

<210> SEQ ID NO 569
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 569

Phe Phe Asp Lys Phe Lys Glu Phe Phe Lys Asp Tyr Phe Ala Lys Phe
1 5 10 15

Trp Asp

<210> SEQ ID NO 570
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 570

Phe Phe Glu Lys Phe Lys Asp Phe Phe Lys Asp Tyr Phe Ala Lys Phe
1 5 10 15

Trp Asp

<210> SEQ ID NO 571
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 571

Phe Phe Glu Lys Phe Lys Glu Phe Phe Lys Glu Tyr Phe Ala Lys Phe
1 5 10 15

Trp Asp

<210> SEQ ID NO 572
<211> LENGTH: 18
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MISC
<222> LOCATION: (1)..(1)
<223> OTHER INFORMATION: N-terminal acetylation
<220> FEATURE:
<221> NAME/KEY: MISC
<222> LOCATION: (18)..(18)
<223> OTHER INFORMATION: C-terminal amidation

<400> SEQUENCE: 572

Phe Phe Glu Lys Phe Lys Glu Phe Phe Lys Asp Tyr Phe Ala Lys Phe
1 5 10 15

Trp Glu

<210> SEQ ID NO 573
<211> LENGTH: 18

<212> TYPE: PRT
<213> ORGANISM: Artificial Sequence
<220> FEATURE:
<223> OTHER INFORMATION: synthetic construct; epsilon-methylLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is epsilon methylated
<220> FEATURE:
<221> NAME/KEY: misc
<222> LOCATION: (9)..(9)
<223> OTHER INFORMATION: Lys at position 9 is epsilon methylated
<220> FEATURE:
<221> NAME/KEY: misc
<222> LOCATION: (13)..(13)
<223> OTHER INFORMATION: Lys at position 13 is epsilon methylated
<220> FEATURE:
<221> NAME/KEY: misc
<222> LOCATION: (15)..(15)
<223> OTHER INFORMATION: Lys at position 15 is epsilon methylated
<220> FEATURE:
<221> NAME/KEY: misc
<222> LOCATION: (18)..(18)
<223> OTHER INFORMATION: C-terminus contains NH(CH3)2

<400> SEQUENCE: 573

Asp Trp Phe Lys Ala Phe Tyr Asp Lys Val Ala Glu Lys Phe Lys Glu
1 5 10 15

Ala Phe

<210> SEQ ID NO 574
<211> LENGTH: 18
<212> TYPE: PRT
<213> ORGANISM: Artificial Sequence
<220> FEATURE:
<223> OTHER INFORMATION: synthetic construct; epsilon-methylLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is epsilon methylated
<220> FEATURE:
<221> NAME/KEY: misc
<222> LOCATION: (9)..(9)
<223> OTHER INFORMATION: Lys at position 9 is epsilon methylated
<220> FEATURE:
<221> NAME/KEY: misc
<222> LOCATION: (13)..(13)
<223> OTHER INFORMATION: Lys at position 13 is epsilon methylated
<220> FEATURE:
<221> NAME/KEY: misc
<222> LOCATION: (15)..(15)
<223> OTHER INFORMATION: Lys at position 15 is epsilon methylated
<220> FEATURE:
<221> NAME/KEY: misc
<222> LOCATION: (18)..(18)
<223> OTHER INFORMATION: C-terminus contains NH(CH3)

<400> SEQUENCE: 574

Asp Trp Phe Lys Ala Phe Tyr Asp Lys Val Ala Glu Lys Phe Lys Glu
1 5 10 15

Ala Phe

<210> SEQ ID NO 575
<211> LENGTH: 18
<212> TYPE: PRT

<213> ORGANISM: Artificial Sequence
<220> FEATURE:
<223> OTHER INFORMATION: synthetic construct; epsilon-N-dimethylLys
analog
<220> FEATURE:
<221> NAME/KEY: misc
<222> LOCATION: (1)..(1)
<223> OTHER INFORMATION: N-terminal aceytlation
<220> FEATURE:
<221> NAME/KEY: misc
<222> LOCATION: (4)..(4)
<223> OTHER INFORMATION: Lys at position 4 is and epsilon-N-Dimethyl-Lys
<220> FEATURE:
<221> NAME/KEY: misc
<222> LOCATION: (9)..(9)
<223> OTHER INFORMATION: Lys at position 9 is and epsilon-N-Dimethyl-Lys
<220> FEATURE:
<221> NAME/KEY: misc
<222> LOCATION: (13)..(13)
<223> OTHER INFORMATION: Lys at position 9 is and epsilon-N-Dimethyl-Lys
<220> FEATURE:
<221> NAME/KEY: misc
<222> LOCATION: (15)..(15)
<223> OTHER INFORMATION: Lys at position 9 is and epsilon-N-Dimethyl-Lys
<220> FEATURE:
<221> NAME/KEY: misc
<222> LOCATION: (18)..(18)
<223> OTHER INFORMATION: C-terminal amidation

<400> SEQUENCE: 575

Asp Trp Phe Lys Ala Phe Tyr Asp Lys Val Ala Glu Lys Phe Lys Glu
1 5 10 15

Ala Phe

<210> SEQ ID NO 576
<211> LENGTH: 18
<212> TYPE: PRT
<213> ORGANISM: Artificial Sequence
<220> FEATURE:
<223> OTHER INFORMATION: synthetic construct; epsilon-N-dimethylLys
analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is and epsilon-N-Dimethyl-Lys
<220> FEATURE:
<221> NAME/KEY: misc
<222> LOCATION: (9)..(9)
<223> OTHER INFORMATION: Lys at position 9 is and epsilon-N-Dimethyl-Lys
<220> FEATURE:
<221> NAME/KEY: misc
<222> LOCATION: (13)..(13)
<223> OTHER INFORMATION: Lys at position 13 is and epsilon-N-Dimethyl-
Lys
<220> FEATURE:
<221> NAME/KEY: misc
<222> LOCATION: (15)..(15)
<223> OTHER INFORMATION: Lys at position 15 is and epsilon-N-Dimethyl-
Lys
<220> FEATURE:
<221> NAME/KEY: misc
<222> LOCATION: (18)..(18)
<223> OTHER INFORMATION: C-terminus contains NH-Me

<400> SEQUENCE: 576

Asp Trp Phe Lys Ala Phe Tyr Asp Lys Val Ala Glu Lys Phe Lys Glu
1 5 10 15

Ala Phe

<210> SEQ ID NO 577
<211> LENGTH: 18
<212> TYPE: PRT
<213> ORGANISM: Artificial Sequence
<220> FEATURE:
<223> OTHER INFORMATION: synthetic construct; epsilon-N-dimethylLys
analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is and epsilon-N-Dimethyl-Lys
<220> FEATURE:
<221> NAME/KEY: misc
<222> LOCATION: (9)..(9)
<223> OTHER INFORMATION: Lys at position 9 is and epsilon-N-Dimethyl-Lys
<220> FEATURE:
<221> NAME/KEY: misc
<222> LOCATION: (18)..(18)
<223> OTHER INFORMATION: C-terminus contains N-(Me)2

<400> SEQUENCE: 577

Asp Trp Phe Lys Ala Phe Tyr Asp Lys Val Ala Glu Lys Phe Lys Glu
1 5 10 15

Ala Phe

<210> SEQ ID NO 578
<211> LENGTH: 18
<212> TYPE: PRT
<213> ORGANISM: Artificial Sequence
<220> FEATURE:
<223> OTHER INFORMATION: synthetic construct; epsilon-N-diethylLys
analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is and epsilon-N-Diethyl-Lys
<220> FEATURE:
<221> NAME/KEY: misc
<222> LOCATION: (9)..(9)
<223> OTHER INFORMATION: Lys at position 9 is and epsilon-N-Diethyl-Lys
<220> FEATURE:
<221> NAME/KEY: misc
<222> LOCATION: (13)..(13)
<223> OTHER INFORMATION: Lys at position 13 is and epsilon-N-Diethyl-Lys
<220> FEATURE:
<221> NAME/KEY: misc
<222> LOCATION: (15)..(15)
<223> OTHER INFORMATION: Lys at position 15 is and epsilon-N-Diethyl-Lys
<220> FEATURE:
<221> NAME/KEY: misc
<222> LOCATION: (18)..(18)
<223> OTHER INFORMATION: C-terminal amidation

<400> SEQUENCE: 578

Asp Trp Phe Lys Ala Phe Tyr Asp Lys Val Ala Glu Lys Phe Lys Glu
1 5 10 15

Ala Phe

<210> SEQ ID NO 579
<211> LENGTH: 18
<212> TYPE: PRT
<213> ORGANISM: Artificial Sequence
<220> FEATURE:
<223> OTHER INFORMATION: synthetic construct; epsilon-N-diethylLys
analog <220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is and epsilon-N-Diethyl-Lys
<220> FEATURE:
<221> NAME/KEY: misc
<222> LOCATION: (9)..(9)
<223> OTHER INFORMATION: Lys at position 9 is and epsilon-N-Diethyl-Lys
<220> FEATURE:
<221> NAME/KEY: misc
<222> LOCATION: (13)..(13)
<223> OTHER INFORMATION: Lys at position 13 is and epsilon-N-Diethyl-Lys
<220> FEATURE:
<221> NAME/KEY: misc
<222> LOCATION: (15)..(15)
<223> OTHER INFORMATION: Lys at position 15 is and epsilon-N-Diethyl-Lys
<220> FEATURE:
<221> NAME/KEY: misc
<222> LOCATION: (18)..(18)
<223> OTHER INFORMATION: C-terminus contains NH-Et

<400> SEQUENCE: 579

Asp Trp Phe Lys Ala Phe Tyr Asp Lys Val Ala Glu Lys Phe Lys Glu
1 5 10 15

Ala Phe

<210> SEQ ID NO 580
<211> LENGTH: 18
<212> TYPE: PRT
<213> ORGANISM: Artificial Sequence
<220> FEATURE:
<223> OTHER INFORMATION: synthetic construct; epsilon-N-diethylLys
analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is and epsilon-N-Diethyl-Lys
<220> FEATURE:
<221> NAME/KEY: misc
<222> LOCATION: (9)..(9)
<223> OTHER INFORMATION: Lys at position 9 is and epsilon-N-Diethyl-Lys
<220> FEATURE:
<221> NAME/KEY: misc
<222> LOCATION: (13)..(13)
<223> OTHER INFORMATION: Lys at position 13 is and epsilon-N-Diethyl-Lys
<220> FEATURE:
<221> NAME/KEY: misc
<222> LOCATION: (15)..(15)
<223> OTHER INFORMATION: Lys at position 15 is and epsilon-N-Diethyl-Lys
<220> FEATURE:
<221> NAME/KEY: misc
<222> LOCATION: (18)..(18)
<223> OTHER INFORMATION: C-terminus contains NH-(Et)2

<400> SEQUENCE: 580

Asp Trp Phe Lys Ala Phe Tyr Asp Lys Val Ala Glu Lys Phe Lys Glu
1 5 10 15

Ala Phe

<210> SEQ ID NO 581
<211> LENGTH: 18
<212> TYPE: PRT
<213> ORGANISM: Artificial Sequence
<220> FEATURE:
<223> OTHER INFORMATION: synthetic construct; epsilon-N-monomethylLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is and epsilon-N-monomethyl-
Lys
<220> FEATURE:
<221> NAME/KEY: misc
<222> LOCATION: (9)..(9)
<223> OTHER INFORMATION: Lys at position 9 is and epsilon-N-monomiethyl-
Lys
<220> FEATURE:
<221> NAME/KEY: misc
<222> LOCATION: (13)..(13)
<223> OTHER INFORMATION: Lys at position 13 is and epsilon-N-monomethyl-
Lys
<220> FEATURE:
<221> NAME/KEY: misc
<222> LOCATION: (15)..(15)
<223> OTHER INFORMATION: Lys at position 15 is and epsilon-N-monomethyl-
Lys
<220> FEATURE:
<221> NAME/KEY: misc
<222> LOCATION: (18)..(18)
<223> OTHER INFORMATION: C-terminal amidation

<400> SEQUENCE: 581

Asp Trp Phe Lys Ala Phe Tyr Asp Lys Val Ala Glu Lys Phe Lys Glu
1 5 10 15

Ala Phe

<210> SEQ ID NO 582
<211> LENGTH: 18
<212> TYPE: PRT
<213> ORGANISM: Artificial Sequence
<220> FEATURE:
<223> OTHER INFORMATION: synthetic construct; epsilon-N-monomethylLys
analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is and epsilon-N-monomethyl-
Lys
<220> FEATURE:
<221> NAME/KEY: misc
<222> LOCATION: (9)..(9)
<223> OTHER INFORMATION: Lys at position 9 is and epsilon-N-monomethyl-
Lys
<220> FEATURE:
<221> NAME/KEY: misc
<222> LOCATION: (13)..(13)
<223> OTHER INFORMATION: Lys at position 13 is and epsilon-N-monomethyl-
Lys
<220> FEATURE:
<221> NAME/KEY: misc
<222> LOCATION: (15)..(15)
<223> OTHER INFORMATION: Lys at position 15 is and epsilon-N-monomethyl-
Lys
<220> FEATURE:
<221> NAME/KEY: misc
<222> LOCATION: (18)..(18)
<223> OTHER INFORMATION: C-terminus contains NH-Me

<400> SEQUENCE: 582

Asp Trp Phe Lys Ala Phe Tyr Asp Lys Val Ala Glu Lys Phe Lys Glu
1 5 10 15

Ala Phe

<210> SEQ ID NO 583
<211> LENGTH: 18
<212> TYPE: PRT
<213> ORGANISM: Artificial Sequence
<220> FEATURE:
<223> OTHER INFORMATION: synthetic construct; epsilon-N-monomethylLys
analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is and epsilon-N-monomethyl-
Lys
<220> FEATURE:
<221> NAME/KEY: misc
<222> LOCATION: (9)..(9)
<223> OTHER INFORMATION: Lys at position 9 is and epsilon-N-monomethyl-
Lys
<220> FEATURE:
<221> NAME/KEY: misc
<222> LOCATION: (13)..(13)
<223> OTHER INFORMATION: Lys at position 13 is and epsilon-N-monomethyl-
Lys
<220> FEATURE:
<221> NAME/KEY: misc
<222> LOCATION: (15)..(15)
<223> OTHER INFORMATION: Lys at position 15 is and epsilon-N-monomethyl-
Lys
<220> FEATURE:
<221> NAME/KEY: misc
<222> LOCATION: (18)..(18)
<223> OTHER INFORMATION: C-terminus contains N-(Me)2

<400> SEQUENCE: 583

Asp Trp Phe Lys Ala Phe Tyr Asp Lys Val Ala Glu Lys Phe Lys Glu
1 5 10 15

Ala Phe

<210> SEQ ID NO 584
<211> LENGTH: 18
<212> TYPE: PRT
<213> ORGANISM: Artificial Sequence
<220> FEATURE:
<223> OTHER INFORMATION: synthetic construct; epsilon-N-ethylLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is and epsilon-N-ethyl-Lys
<220> FEATURE:
<221> NAME/KEY: misc
<222> LOCATION: (9)..(9)
<223> OTHER INFORMATION: Lys at position 9 is and epsilon-N-ethyl-Lys
<220> FEATURE:
<221> NAME/KEY: misc
<222> LOCATION: (13)..(13)
<223> OTHER INFORMATION: Lys at position 13 is and epsilon-N-ethyl-Lys
<220> FEATURE:
<221> NAME/KEY: misc
<222> LOCATION: (15)..(15)
<223> OTHER INFORMATION: Lys at position 15 is and epsilon-N-ethyl-Lys
<220> FEATURE:
<221> NAME/KEY: misc
<222> LOCATION: (18)..(18)
<223> OTHER INFORMATION: C-terminal amidation

<400> SEQUENCE: 584

Asp Trp Phe Lys Ala Phe Tyr Asp Lys Val Ala Glu Lys Phe Lys Glu
1 5 10 15

Ala Phe

<210> SEQ ID NO 585
<211> LENGTH: 18
<212> TYPE: PRT
<213> ORGANISM: Artificial Sequence
<220> FEATURE:
<223> OTHER INFORMATION: synthetic construct; epsilon-N-ethylLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is and epsilon-N-ethyl-Lys
<220> FEATURE:
<221> NAME/KEY: misc
<222> LOCATION: (9)..(9)
<223> OTHER INFORMATION: Lys at position 9 is and epsilon-N-ethyl-Lys
<220> FEATURE:
<221> NAME/KEY: misc
<222> LOCATION: (13)..(13)
<223> OTHER INFORMATION: Lys at position 13 is and epsilon-N-ethyl-Lys
<220> FEATURE:
<221> NAME/KEY: misc
<222> LOCATION: (15)..(15)
<223> OTHER INFORMATION: Lys at position 15 is and epsilon-N-ethyl-Lys
<220> FEATURE:
<221> NAME/KEY: misc
<222> LOCATION: (18)..(18)
<223> OTHER INFORMATION: C-terminus contains NH-Et

<400> SEQUENCE: 585

Asp Trp Phe Lys Ala Phe Tyr Asp Lys Val Ala Glu Lys Phe Lys Glu
1 5 10 15

Ala Phe

<210> SEQ ID NO 586
<211> LENGTH: 18
<212> TYPE: PRT
<213> ORGANISM: Artificial Sequence
<220> FEATURE:
<223> OTHER INFORMATION: synthetic construct; epsilon-N-ethylLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is and epsilon-N-ethyl-Lys
<220> FEATURE:
<221> NAME/KEY: misc
<222> LOCATION: (9)..(9)
<223> OTHER INFORMATION: Lys at position 9 is and epsilon-N-ethyl-Lys
<220> FEATURE:
<221> NAME/KEY: misc
<222> LOCATION: (13)..(13)
<223> OTHER INFORMATION: Lys at position 13 is and epsilon-N-ethyl-Lys
<220> FEATURE:
<221> NAME/KEY: misc
<222> LOCATION: (15)..(15)
<223> OTHER INFORMATION: Lys at position 15 is and epsilon-N-ethyl-Lys
<220> FEATURE:
<221> NAME/KEY: misc
<222> LOCATION: (18)..(18)
<223> OTHER INFORMATION: C-terminus contains NH-(Et)2

<400> SEQUENCE: 586

Asp Trp Phe Lys Ala Phe Tyr Asp Lys Val Ala Glu Lys Phe Lys Glu
1 5 10 15

Ala Phe

<210> SEQ ID NO 587
<211> LENGTH: 18
<212> TYPE: PRT
<213> ORGANISM: Artificial Sequence
<220> FEATURE:
<223> OTHER INFORMATION: synthetic construct; homoLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is a homoLys
<220> FEATURE:
<221> NAME/KEY: misc
<222> LOCATION: (9)..(9)
<223> OTHER INFORMATION: Lys at position 9 is a homoLys
<220> FEATURE:
<221> NAME/KEY: misc
<222> LOCATION: (13)..(13)
<223> OTHER INFORMATION: Lys at position 13 is a homoLys
<220> FEATURE:
<221> NAME/KEY: misc
<222> LOCATION: (15)..(15)
<223> OTHER INFORMATION: Lys at position 15 is a homoLys
<220> FEATURE:
<221> NAME/KEY: misc
<222> LOCATION: (18)..(18)
<223> OTHER INFORMATION: C-terminal amidation

<400> SEQUENCE: 587

Asp Trp Phe Lys Ala Phe Tyr Asp Lys Val Ala Glu Lys Phe Lys Glu
1 5 10 15

Ala Phe

<210> SEQ ID NO 588
<211> LENGTH: 18
<212> TYPE: PRT
<213> ORGANISM: Artificial Sequence
<220> FEATURE:
<223> OTHER INFORMATION: synthetic construct; homoLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is homoLys
<220> FEATURE:
<221> NAME/KEY: misc
<222> LOCATION: (9)..(9)
<223> OTHER INFORMATION: Lys at position 9 is homoLys
<220> FEATURE:
<221> NAME/KEY: misc
<222> LOCATION: (13)..(13)
<223> OTHER INFORMATION: Lys at position 13 is homoLys
<220> FEATURE:
<221> NAME/KEY: misc
<222> LOCATION: (15)..(15)
<223> OTHER INFORMATION: Lys at position 15 is homoLys
<220> FEATURE:
<221> NAME/KEY: misc
<222> LOCATION: (18)..(18)
<223> OTHER INFORMATION: C-terminal amidation

<400> SEQUENCE: 588

Asp Trp Phe Lys Ala Phe Tyr Asp Lys Val Ala Glu Lys Phe Lys Glu 1 5 10 15

Ala Phe

<210> SEQ ID NO 589
<211> LENGTH: 18
<212> TYPE: PRT
<213> ORGANISM: Artificial Sequence
<220> FEATURE:
<223> OTHER INFORMATION: synthetic construct; homoLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is homoLys
<220> FEATURE:
<221> NAME/KEY: misc
<222> LOCATION: (9)..(9)
<223> OTHER INFORMATION: Lys at position 9 is homoLys
<220> FEATURE:
<221> NAME/KEY: misc
<222> LOCATION: (13)..(13)
<223> OTHER INFORMATION: Lys at position 13 is homoLys
<220> FEATURE:
<221> NAME/KEY: misc
<222> LOCATION: (15)..(15)
<223> OTHER INFORMATION: Lys at position 13 is homoLys
<220> FEATURE:
<221> NAME/KEY: misc
<222> LOCATION: (18)..(18)
<223> OTHER INFORMATION: C-terminus contains N-(Me)2

<400> SEQUENCE: 589

Asp Trp Phe Lys Ala Phe Tyr Asp Lys Val Ala Glu Lys Phe Lys Glu
1 5 10 15

Ala Phe

<210> SEQ ID NO 590
<211> LENGTH: 18
<212> TYPE: PRT
<213> ORGANISM: Artificial Sequence
<220> FEATURE:
<223> OTHER INFORMATION: synthetic construct; homoLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is homoLys
<220> FEATURE:
<221> NAME/KEY: misc
<222> LOCATION: (9)..(9)
<223> OTHER INFORMATION: Lys at position 9 is homoLys
<220> FEATURE:
<221> NAME/KEY: misc
<222> LOCATION: (13)..(13)
<223> OTHER INFORMATION: Lys at position 13 is homoLys
<220> FEATURE:
<221> NAME/KEY: misc
<222> LOCATION: (15)..(15)
<223> OTHER INFORMATION: Lys at position 15 is homoLys
<220> FEATURE:
<221> NAME/KEY: misc
<222> LOCATION: (18)..(18)
<223> OTHER INFORMATION: C-terminus contains NH-Me

<400> SEQUENCE: 590

Asp Trp Phe Lys Ala Phe Tyr Asp Lys Val Ala Glu Lys Phe Lys Glu
1 5 10 15

Ala Phe

<210> SEQ ID NO 591
<211> LENGTH: 18
<212> TYPE: PRT
<213> ORGANISM: Artificial Sequence
<220> FEATURE:
<223> OTHER INFORMATION: synthetic construct; homoLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is homoLys
<220> FEATURE:
<221> NAME/KEY: misc
<222> LOCATION: (9)..(9)
<223> OTHER INFORMATION: Lys at position 9 is homoLys
<220> FEATURE:
<221> NAME/KEY: misc
<222> LOCATION: (13)..(13)
<223> OTHER INFORMATION: Lys at position 13 is homoLys
<220> FEATURE:
<221> NAME/KEY: misc
<222> LOCATION: (15)..(15)
<223> OTHER INFORMATION: Lys at position 15 is homoLys
<220> FEATURE:
<221> NAME/KEY: misc
<222> LOCATION: (18)..(18)
<223> OTHER INFORMATION: C-terminus contains NH-Et

<400> SEQUENCE: 591

Asp Trp Phe Lys Ala Phe Tyr Asp Lys Val Ala Glu Lys Phe Lys Glu
1 5 10 15

Ala Phe

<210> SEQ ID NO 592
<211> LENGTH: 18
<212> TYPE: PRT
<213> ORGANISM: Artificial Sequence
<220> FEATURE:
<223> OTHER INFORMATION: synthetic construct; homoLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is homoLys
<220> FEATURE:
<221> NAME/KEY: misc
<222> LOCATION: (9)..(9)
<223> OTHER INFORMATION: Lys at position 9 is homoLys
<220> FEATURE:
<221> NAME/KEY: misc
<222> LOCATION: (13)..(13)
<223> OTHER INFORMATION: Lys at position 13 is homoLys
<220> FEATURE:
<221> NAME/KEY: misc
<222> LOCATION: (15)..(15)
<223> OTHER INFORMATION: Lys at position 15 is homoLys
<220> FEATURE:
<221> NAME/KEY: misc
<222> LOCATION: (18)..(18)
<223> OTHER INFORMATION: C-terminal amidation

<400> SEQUENCE: 592

Asp Trp Phe Lys Ala Phe Tyr Asp Lys Val Ala Glu Lys Phe Lys Glu
1 5 10 15

Ala Phe

<210> SEQ ID NO 593
<211> LENGTH: 18
<212> TYPE: PRT
<213> ORGANISM: Artificial Sequence
<220> FEATURE:
<223> OTHER INFORMATION: synthetic construct; homoLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is homoLys
<220> FEATURE:
<221> NAME/KEY: misc
<222> LOCATION: (9)..(9)
<223> OTHER INFORMATION: Lys at position 9 is homoLys
<220> FEATURE:
<221> NAME/KEY: misc
<222> LOCATION: (13)..(13)
<223> OTHER INFORMATION: Lys at position 13 is homoLys
<220> FEATURE:
<221> NAME/KEY: misc
<222> LOCATION: (15)..(15)
<223> OTHER INFORMATION: Lys at position 15 is homoLys
<220> FEATURE:
<221> NAME/KEY: misc
<222> LOCATION: (18)..(18)
<223> OTHER INFORMATION: C-terminus contains NH-Me

<400> SEQUENCE: 593

Asp Trp Phe Lys Ala Phe Tyr Asp Lys Val Ala Glu Lys Phe Lys Glu
1 5 10 15

Ala Phe

<210> SEQ ID NO 594
<211> LENGTH: 18
<212> TYPE: PRT
<213> ORGANISM: Artificial Sequence
<220> FEATURE:
<223> OTHER INFORMATION: synthetic construct; homoLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is homoLys
<220> FEATURE:
<221> NAME/KEY: misc
<222> LOCATION: (9)..(9)
<223> OTHER INFORMATION: Lys at position 9 is homoLys
<220> FEATURE:
<221> NAME/KEY: misc
<222> LOCATION: (13)..(13)
<223> OTHER INFORMATION: Lys at position 13 is homoLys
<220> FEATURE:
<221> NAME/KEY: misc
<222> LOCATION: (15)..(15)
<223> OTHER INFORMATION: Lys at position 15 is homoLys
<220> FEATURE:
<221> NAME/KEY: misc
<222> LOCATION: (18)..(18)
<223> OTHER INFORMATION: C-terminus contains N-(Me)2

<400> SEQUENCE: 594

Asp Trp Phe Lys Ala Phe Tyr Asp Lys Val Ala Glu Lys Phe Lys Glu
1 5 10 15

Ala Phe

<210> SEQ ID NO 595
<211> LENGTH: 18
<212> TYPE: PRT
<213> ORGANISM: Artificial Sequence
<220> FEATURE:
<223> OTHER INFORMATION: synthetic construct; homoLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is homoLys
<220> FEATURE:
<221> NAME/KEY: misc
<222> LOCATION: (9)..(9)
<223> OTHER INFORMATION: Lys at position 9 is homoLys
<220> FEATURE:
<221> NAME/KEY: misc
<222> LOCATION: (13)..(13)
<223> OTHER INFORMATION: Lys at position 13 is homoLys
<220> FEATURE:
<221> NAME/KEY: misc
<222> LOCATION: (15)..(15)
<223> OTHER INFORMATION: Lys at position 15 is homoLys
<220> FEATURE:
<221> NAME/KEY: misc
<222> LOCATION: (18)..(18)
<223> OTHER INFORMATION: C-terminal amidation

<400> SEQUENCE: 595

Asp Trp Phe Lys Ala Phe Tyr Asp Lys Val Ala Glu Lys Phe Lys Glu
1 5 10 15

Ala Phe

<210> SEQ ID NO 596
<211> LENGTH: 18
<212> TYPE: PRT
<213> ORGANISM: Artificial Sequence
<220> FEATURE:
<223> OTHER INFORMATION: synthetic construct; homoLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is homoLys
<220> FEATURE:
<221> NAME/KEY: misc
<222> LOCATION: (9)..(9)
<223> OTHER INFORMATION: Lys at position 9 is homoLys
<220> FEATURE:
<221> NAME/KEY: misc
<222> LOCATION: (13)..(13)
<223> OTHER INFORMATION: Lys at position 13 is homoLys
<220> FEATURE:
<221> NAME/KEY: misc
<222> LOCATION: (15)..(15)
<223> OTHER INFORMATION: Lys at position 15 is homoLys
<220> FEATURE:
<221> NAME/KEY: misc
<222> LOCATION: (18)..(18)
<223> OTHER INFORMATION: C-terminus contains NH-Et

<400> SEQUENCE: 596

Asp Trp Phe Lys Ala Phe Tyr Asp Lys Val Ala Glu Lys Phe Lys Glu
1 5 10 15

Ala Phe

<210> SEQ ID NO 597
<211> LENGTH: 18
<212> TYPE: PRT
<213> ORGANISM: Artificial Sequence
<220> FEATURE:
<223> OTHER INFORMATION: synthetic construct; homoLys analog
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Lys at position 4 is homoLys
<220> FEATURE:
<221> NAME/KEY: misc
<222> LOCATION: (9)..(9)
<223> OTHER INFORMATION: Lys at position 9 is homoLys
<220> FEATURE:
<221> NAME/KEY: misc
<222> LOCATION: (13)..(13)
<223> OTHER INFORMATION: Lys at position 13 is homoLys
<220> FEATURE:
<221> NAME/KEY: misc
<222> LOCATION: (15)..(15)
<223> OTHER INFORMATION: Lys at position 15 is homoLys
<220> FEATURE:
<221> NAME/KEY: misc
<222> LOCATION: (18)..(18)
<223> OTHER INFORMATION: C-terminus contains NH-(Et)2

<400> SEQUENCE: 597

Asp Trp Phe Lys Ala Phe Tyr Asp Lys Val Ala Glu Lys Phe Lys Glu
1 5 10 15

Ala Phe

<210> SEQ ID NO 598
<211> LENGTH: 18
<212> TYPE: PRT
<213> ORGANISM: Artificial Sequence
<220> FEATURE:
<223> OTHER INFORMATION: synthetic construct; ornithine analogs
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Xaa at position 4 is a delta-N-dimethyl-
ornithine
<220> FEATURE:
<221> NAME/KEY: misc
<222> LOCATION: (9)..(9)
<223> OTHER INFORMATION: Xaa at position 9 is a delta-N-dimethyl-
ornithine
<220> FEATURE:
<221> NAME/KEY: misc
<222> LOCATION: (13)..(13)
<223> OTHER INFORMATION: Xaa at position 13 is a delta-N-dimethyl-
ornithine
<220> FEATURE:
<221> NAME/KEY: misc
<222> LOCATION: (15)..(15)
<223> OTHER INFORMATION: Xaa at position 15 is a delta-N-dimethyl-
ornithine
<220> FEATURE:
<221> NAME/KEY: misc
<222> LOCATION: (18)..(18)
<223> OTHER INFORMATION: C-terminal amidation

<400> SEQUENCE: 598

Asp Trp Phe Xaa Ala Phe Tyr Asp Xaa Val Ala Glu Xaa Phe Xaa Glu
1 5 10 15

Ala Phe

<210> SEQ ID NO 599
<211> LENGTH: 18
<212> TYPE: PRT
<213> ORGANISM: Artificial Sequence
<220> FEATURE:
<223> OTHER INFORMATION: synthetic construct; ornithine analogs
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Xaa at position 4 is a delta-N-dimethyl-
ornithine
<220> FEATURE:
<221> NAME/KEY: misc
<222> LOCATION: (9)..(9)
<223> OTHER INFORMATION: Xaa at position 9 is a delta-N-dimethyl-
ornithine
<220> FEATURE:
<221> NAME/KEY: misc
<222> LOCATION: (13)..(13)
<223> OTHER INFORMATION: Xaa at position 13 is a delta-N-dimethyl-
ornithine
<220> FEATURE:
<221> NAME/KEY: misc
<222> LOCATION: (15)..(15)
<223> OTHER INFORMATION: Xaa at position 15 is a delta-N-dimethyl-
ornithine
<220> FEATURE:
<221> NAME/KEY: misc
<222> LOCATION: (18)..(18)
<223> OTHER INFORMATION: C-terminal amidation

<400> SEQUENCE: 599

Asp Trp Phe Xaa Ala Phe Tyr Asp Xaa Val Ala Glu Xaa Phe Xaa Glu
1 5 10 15

Ala Phe

<210> SEQ ID NO 600
<211> LENGTH: 18
<212> TYPE: PRT
<213> ORGANISM: Artificial Sequence
<220> FEATURE:
<223> OTHER INFORMATION: synthetic construct; ornithine analogs
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Xaa at position 4 is a delta-N-dimethyl-
ornithine
<220> FEATURE:
<221> NAME/KEY: misc
<222> LOCATION: (9)..(9)
<223> OTHER INFORMATION: Xaa at position 9 is a delta-N-dimethyl-
ornithine
<220> FEATURE:
<221> NAME/KEY: misc
<222> LOCATION: (13)..(13)
<223> OTHER INFORMATION: Xaa at position 13 is a delta-N-dimethyl-
ornithine
<220> FEATURE:
<221> NAME/KEY: misc
<222> LOCATION: (15)..(15)
<223> OTHER INFORMATION: Xaa at position 15 is a delta-N-dimethyl-
ornithine
<220> FEATURE:
<221> NAME/KEY: misc <222> LOCATION: (18)..(18)
<223> OTHER INFORMATION: C-terminus contains N-(Me)2

<400> SEQUENCE: 600

Asp Trp Phe Xaa Ala Phe Tyr Asp Xaa Val Ala Glu Xaa Phe Xaa Glu
1 5 10 15

Ala Phe

<210> SEQ ID NO 601
<211> LENGTH: 18
<212> TYPE: PRT
<213> ORGANISM: Artificial Sequence
<220> FEATURE:
<223> OTHER INFORMATION: synthetic construct; ornithine analogs
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Xaa at position 4 is a delta-N-dimethyl-
ornithine
<220> FEATURE:
<221> NAME/KEY: misc
<222> LOCATION: (9)..(9)
<223> OTHER INFORMATION: Xaa at position 9 is a delta-N-dimethyl-
ornithine
<220> FEATURE:
<221> NAME/KEY: misc
<222> LOCATION: (13)..(13)
<223> OTHER INFORMATION: Xaa at position 13 is a delta-N-dimethyl-
ornithine
<220> FEATURE:
<221> NAME/KEY: misc
<222> LOCATION: (15)..(15)
<223> OTHER INFORMATION: Xaa at position 15 is a delta-N-dimethyl-
ornithine
<220> FEATURE:
<221> NAME/KEY: misc
<222> LOCATION: (18)..(18)
<223> OTHER INFORMATION: C-terminus contains NH-Me

<400> SEQUENCE: 601

Asp Trp Phe Xaa Ala Phe Tyr Asp Xaa Val Ala Glu Xaa Phe Xaa Glu
1 5 10 15

Ala Phe

<210> SEQ ID NO 602
<211> LENGTH: 18
<212> TYPE: PRT
<213> ORGANISM: Artificial Sequence
<220> FEATURE:
<223> OTHER INFORMATION: synthetic construct; ornithine analogs
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Xaa at position 4 is a delta-N-diethyl-
ornithine
<220> FEATURE:
<221> NAME/KEY: misc
<222> LOCATION: (9)..(9)
<223> OTHER INFORMATION: Xaa at position 9 is a delta-N-diethyl-
ornithine
<220> FEATURE:
<221> NAME/KEY: misc
<222> LOCATION: (13)..(13)
<223> OTHER INFORMATION: Xaa at position 13 is a delta-N-diethyl-
ornithine <220> FEATURE:
<221> NAME/KEY: misc
<222> LOCATION: (15)..(15)
<223> OTHER INFORMATION: Xaa at position 15 is a delta-N-diethyl-
ornithine
<220> FEATURE:
<221> NAME/KEY: misc
<222> LOCATION: (18)..(18)
<223> OTHER INFORMATION: C-terminus contains NH-Et

<400> SEQUENCE: 602

Asp Trp Phe Xaa Ala Phe Tyr Asp Xaa Val Ala Glu Xaa Phe Xaa Glu
1 5 10 15

Ala Phe

<210> SEQ ID NO 603
<211> LENGTH: 18
<212> TYPE: PRT
<213> ORGANISM: Artificial Sequence
<220> FEATURE:
<223> OTHER INFORMATION: synthetic construct; ornithine analogs
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Xaa at position 4 is a delta-N-methyl-ornithine
<220> FEATURE:
<221> NAME/KEY: misc
<222> LOCATION: (9)..(9)
<223> OTHER INFORMATION: Xaa at position 9 is a delta-N-methyl-ornithine
<220> FEATURE:
<221> NAME/KEY: misc
<222> LOCATION: (13)..(13)
<223> OTHER INFORMATION: Xaa at position 13 is a delta-N-methyl-
ornithine
<220> FEATURE:
<221> NAME/KEY: misc
<222> LOCATION: (15)..(15)
<223> OTHER INFORMATION: Xaa at position 15 is a delta-N-methyl-
ornithine
<220> FEATURE:
<221> NAME/KEY: misc
<222> LOCATION: (18)..(18)
<223> OTHER INFORMATION: C-terminal amidation

<400> SEQUENCE: 603

Asp Trp Phe Xaa Ala Phe Tyr Asp Xaa Val Ala Glu Xaa Phe Xaa Glu
1 5 10 15

Ala Phe

<210> SEQ ID NO 604
<211> LENGTH: 18
<212> TYPE: PRT
<213> ORGANISM: Artificial Sequence
<220> FEATURE:
<223> OTHER INFORMATION: synthetic construct; ornithine analogs
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Xaa at position 4 is a delta-N-methyl-ornithine
<220> FEATURE:
<221> NAME/KEY: misc
<222> LOCATION: (9)..(9)
<223> OTHER INFORMATION: Xaa at position 9 is a delta-N-methyl-ornithine
<220> FEATURE:
<221> NAME/KEY: misc <222> LOCATION: (13)..(13)
<223> OTHER INFORMATION: Xaa at position 13 is a delta-N-methyl-
ornithine
<220> FEATURE:
<221> NAME/KEY: misc
<222> LOCATION: (15)..(15)
<223> OTHER INFORMATION: Xaa at position 15 is a delta-N-methyl-
ornithine
<220> FEATURE:
<221> NAME/KEY: misc
<222> LOCATION: (18)..(18)
<223> OTHER INFORMATION: C-terminus contains NH-Me

<400> SEQUENCE: 604

Asp Trp Phe Xaa Ala Phe Tyr Asp Xaa Val Ala Glu Xaa Phe Xaa Glu
1 5 10 15

Ala Phe

<210> SEQ ID NO 605
<211> LENGTH: 18
<212> TYPE: PRT
<213> ORGANISM: Artificial Sequence
<220> FEATURE:
<223> OTHER INFORMATION: synthetic construct; ornithine analogs
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Xaa at position 4 is a delta-N-methyl-ornithine
<220> FEATURE:
<221> NAME/KEY: misc
<222> LOCATION: (9)..(9)
<223> OTHER INFORMATION: Xaa at position 9 is a delta-N-methyl-ornithine
<220> FEATURE:
<221> NAME/KEY: misc
<222> LOCATION: (13)..(13)
<223> OTHER INFORMATION: Xaa at position 13 is a delta-N-methyl-
ornithine
<220> FEATURE:
<221> NAME/KEY: misc
<222> LOCATION: (15)..(15)
<223> OTHER INFORMATION: Xaa at position 15 is a delta-N-methyl-
ornithine
<220> FEATURE:
<221> NAME/KEY: misc
<222> LOCATION: (18)..(18)
<223> OTHER INFORMATION: C-terminus contains N-(Me)2

<400> SEQUENCE: 605

Asp Trp Phe Xaa Ala Phe Tyr Asp Xaa Val Ala Glu Xaa Phe Xaa Glu
1 5 10 15

Ala Phe

<210> SEQ ID NO 606
<211> LENGTH: 18
<212> TYPE: PRT
<213> ORGANISM: Artificial Sequence
<220> FEATURE:
<223> OTHER INFORMATION: synthetic construct; ornithine analogs
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Xaa at position 4 is a delta-N-ethyl-ornithine
<220> FEATURE:
<221> NAME/KEY: misc
<222> LOCATION: (9)..(9)

<223> OTHER INFORMATION: Xaa at position 9 is a delta-N-ethyl-ornithine
<220> FEATURE:
<221> NAME/KEY: misc
<222> LOCATION: (13)..(13)
<223> OTHER INFORMATION: Xaa at position 13 is a delta-N-ethyl-ornithine
<220> FEATURE:
<221> NAME/KEY: misc
<222> LOCATION: (15)..(15)
<223> OTHER INFORMATION: Xaa at position 15 is a delta-N-ethyl-ornithine
<220> FEATURE:
<221> NAME/KEY: misc
<222> LOCATION: (18)..(18)
<223> OTHER INFORMATION: C-terminal amidation

<400> SEQUENCE: 606

Asp Trp Phe Xaa Ala Phe Tyr Asp Xaa Val Ala Glu Xaa Phe Xaa Glu
1 5 10 15

Ala Phe

<210> SEQ ID NO 607
<211> LENGTH: 18
<212> TYPE: PRT
<213> ORGANISM: Artificial Sequence
<220> FEATURE:
<223> OTHER INFORMATION: synthetic construct; ornithine analogs
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Xaa at position 4 is a delta-N-ethyl-ornithine
<220> FEATURE:
<221> NAME/KEY: misc
<222> LOCATION: (9)..(9)
<223> OTHER INFORMATION: Xaa at position 9 is a delta-N-ethyl-ornithine
<220> FEATURE:
<221> NAME/KEY: misc
<222> LOCATION: (13)..(13)
<223> OTHER INFORMATION: Xaa at position 13 is a delta-N-ethyl-ornithine
<220> FEATURE:
<221> NAME/KEY: misc
<222> LOCATION: (15)..(15)
<223> OTHER INFORMATION: Xaa at position 15 is a delta-N-ethyl-ornithine
<220> FEATURE:
<221> NAME/KEY: misc
<222> LOCATION: (18)..(18)
<223> OTHER INFORMATION: C-terminus contains NH-Et

<400> SEQUENCE: 607

Asp Trp Phe Xaa Ala Phe Tyr Asp Xaa Val Ala Glu Xaa Phe Xaa Glu
1 5 10 15

Ala Phe

<210> SEQ ID NO 608
<211> LENGTH: 18
<212> TYPE: PRT
<213> ORGANISM: Artificial Sequence
<220> FEATURE:
<223> OTHER INFORMATION: synthetic construct; ornithine analogs
<220> FEATURE:
<221> NAME/KEY: misc
<222> LOCATION: (1)..(1)
<223> OTHER INFORMATION: N-terminal acetylation
<220> FEATURE:
<221> NAME/KEY: misc
<222> LOCATION: (4)..(4)
<223> OTHER INFORMATION: Xaa at position 4 is a delta-N-ethyl-ornithine
<220> FEATURE:
<221> NAME/KEY: misc
<222> LOCATION: (9)..(9)
<223> OTHER INFORMATION: Xaa at position 9 is a delta-N-ethyl-ornithine <220> FEATURE:
<221> NAME/KEY: misc
<222> LOCATION: (13)..(13)
<223> OTHER INFORMATION: Xaa at position 13 is a delta-N-ethyl-ornithine
<220> FEATURE:
<221> NAME/KEY: misc
<222> LOCATION: (15)..(15)
<223> OTHER INFORMATION: Xaa at position 15 is a delta-N-ethyl-ornithine
<220> FEATURE:
<221> NAME/KEY: misc
<222> LOCATION: (18)..(18)
<223> OTHER INFORMATION: C-terminus contains NH-(Et)2

<400> SEQUENCE: 608

Asp Trp Phe Xaa Ala Phe Tyr Asp Xaa Val Ala Glu Xaa Phe Xaa Glu
1 5 10 15

Ala Phe

<210> SEQ ID NO 609
<211> LENGTH: 10
<212> TYPE: PRT
<213> ORGANISM: Artificial Sequence
<220> FEATURE:
<223> OTHER INFORMATION: synthetic construct; receptor binding domains
of ApoE

<400> SEQUENCE: 609

Arg Leu Leu Arg Lys Arg Leu Lys Arg Leu
1 5 10

<210> SEQ ID NO 610
<211> LENGTH: 10
<212> TYPE: PRT
<213> ORGANISM: Artificial Sequence
<220> FEATURE:
<223> OTHER INFORMATION: synthetic construct; receptor binding domain of
ApoE

<400> SEQUENCE: 610

Arg Met Leu Arg Lys Arg Met Lys Arg Leu
1 5 10

<210> SEQ ID NO 611
<211> LENGTH: 10
<212> TYPE: PRT
<213> ORGANISM: Artificial Sequence
<220> FEATURE:
<223> OTHER INFORMATION: synthetic construct; receptor binding domain of
ApoE

<400> SEQUENCE: 611

Arg Leu Leu Arg Lys Pro Leu Lys Arg Leu
1 5 10

<210> SEQ ID NO 612
<211> LENGTH: 10
<212> TYPE: PRT
<213> ORGANISM: Artificial Sequence
<220> FEATURE:
<223> OTHER INFORMATION: synthetic construct; receptor binding domain of
ApoE

<400> SEQUENCE: 612

Arg Val Leu Arg Lys Arg Val Asn Arg Leu
1 5 10

<210> SEQ ID NO 613
<211> LENGTH: 10

<212> TYPE: PRT
<213> ORGANISM: Artificial Sequence
<220> FEATURE:
<223> OTHER INFORMATION: synthetic construct; receptor binding domain of
ApoE

<400> SEQUENCE: 613

Arg Leu Val Arg Lys Arg Leu Lys Arg Met
1 5 10

<210> SEQ ID NO 614
<211> LENGTH: 10
<212> TYPE: PRT
<213> ORGANISM: Artificial Sequence
<220> FEATURE:
<223> OTHER INFORMATION: synthetic construct; receptor binding domain of
ApoE

<400> SEQUENCE: 614

Arg Leu Leu Arg Arg Arg Leu Arg Arg Leu
1 5 10

<210> SEQ ID NO 615
<211> LENGTH: 10
<212> TYPE: PRT
<213> ORGANISM: Artificial Sequence
<220> FEATURE:
<223> OTHER INFORMATION: synthetic construct; receptor binding domain of
ApoE

<400> SEQUENCE: 615

Arg Phe Phe Arg Lys Arg Leu Lys Arg Leu
1 5 10

<210> SEQ ID NO 616
<211> LENGTH: 18
<212> TYPE: PRT
<213> ORGANISM: Artificial Sequence
<220> FEATURE:
<223> OTHER INFORMATION: synthetic construct; Lipid-Associating Peptide

<400> SEQUENCE: 616

Phe Ala Glu Lys Leu Lys Glu Ala Val Lys Asp Tyr Phe Ala Lys Leu
1 5 10 15

Trp Asp

<210> SEQ ID NO 617
<211> LENGTH: 18
<212> TYPE: PRT
<213> ORGANISM: Artificial Sequence
<220> FEATURE:
<223> OTHER INFORMATION: synthetic construct; Lipid-Associating Peptide

<400> SEQUENCE: 617

Phe Ala Glu Lys Phe Lys Glu Ala Val Lys Asp Tyr Phe Ala Lys Phe
1 5 10 15

Trp Asp

<210> SEQ ID NO 618
<211> LENGTH: 18
<212> TYPE: PRT
<213> ORGANISM: Artificial Sequence
<220> FEATURE:
<223> OTHER INFORMATION: synthetic construct; lipid-associating peptide

<400> SEQUENCE: 618

Asp Trp Leu Arg Ala Phe Tyr Asp Lys Val Ala Glu Lys Leu Arg Glu
1 5 10 15

Ala Phe

<210> SEQ ID NO 619
<211> LENGTH: 18
<212> TYPE: PRT
<213> ORGANISM: Artificial Sequence
<220> FEATURE:
<223> OTHER INFORMATION: synthetic construct; lipid associating peptide

<400> SEQUENCE: 619

Asp Trp Leu Arg Ala Leu Tyr Asp Lys Val Ala Glu Lys Leu Arg Glu
1 5 10 15

Ala Leu

<210> SEQ ID NO 620
<211> LENGTH: 18
<212> TYPE: PRT
<213> ORGANISM: Artificial Sequence
<220> FEATURE:
<223> OTHER INFORMATION: synthetic construct; lipid associating peptide

<400> SEQUENCE: 620

Asp Leu Leu Arg Ala Leu Tyr Asp Lys Val Ala Glu Lys Leu Arg Glu
1 5 10 15

Ala Trp

<210> SEQ ID NO 621
<211> LENGTH: 10
<212> TYPE: PRT
<213> ORGANISM: Artificial Sequence
<220> FEATURE:
<223> OTHER INFORMATION: synthetic construct; Rat ApoE mimetic

<400> SEQUENCE: 621

Leu Arg Arg Met Arg Arg Arg Leu Met Arg
1 5 10

<210> SEQ ID NO 622
<211> LENGTH: 8
<212> TYPE: PRT
<213> ORGANISM: Artificial Sequence
<220> FEATURE:
<223> OTHER INFORMATION: synthetic construct; Rat ApoE mimetic

<400> SEQUENCE: 622

Arg Leu Thr Arg Arg Arg Gly Lys
1 5

<210> SEQ ID NO 623
<211> LENGTH: 28
<212> TYPE: PRT
<213> ORGANISM: Artificial Sequence
<220> FEATURE:
<223> OTHER INFORMATION: synthetic construct; ApoE-mimicking peptide
<220> FEATURE:
<221> NAME/KEY: MISC_FEATURE
<222> LOCATION: (1)..(1)
<223> OTHER INFORMATION: N-terminal butanoyl

<400> SEQUENCE: 623

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe 20 25

<210> SEQ ID NO 624
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal hexanoyl

<400> SEQUENCE: 624

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 625
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal octanoyl

<400> SEQUENCE: 625

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 626
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal decanoyl

<400> SEQUENCE: 626

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 627
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal lauroyl

<400> SEQUENCE: 627

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 628
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal myristoyl

<400> SEQUENCE: 628

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 629
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal palmitoyl

<400> SEQUENCE: 629

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 630
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal stearoyl

<400> SEQUENCE: 630

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 631
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal palmitoleoyl

<400> SEQUENCE: 631

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 632
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal arachidoyl

<400> SEQUENCE: 632

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 633
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal behenoyl

<400> SEQUENCE: 633

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 634
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal oleoyl

<400> SEQUENCE: 634

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 635
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal ricinoleoyl

<400> SEQUENCE: 635

Leu Arg Arg Leu Arg Arg Arg Leu Leu Arg Asp Trp Leu Lys Ala Phe 1 5 10 15

Tyr Asp Lys Val Ala Glu Lys Leu Lys Glu Ala Phe
20 25

<210> SEQ ID NO 636
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal linolenoyl

<400> SEQUENCE: 636

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 637
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal vacceoyl

<400> SEQUENCE: 637

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 638
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal gadoleoyl

<400> SEQUENCE: 638

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 639
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal erucoyl

<400> SEQUENCE: 639

```
Leu Arg Arg Leu Arg Arg Arg Leu Leu Arg Asp Trp Leu Lys Ala Phe
1               5                   10                  15

Tyr Asp Lys Val Ala Glu Lys Leu Lys Glu Ala Phe
            20                  25


<210> SEQ ID NO 640
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal cetoleoyl

<400> SEQUENCE: 640

Leu Arg Arg Leu Arg Arg Arg Leu Leu Arg Asp Trp Leu Lys Ala Phe
1               5                   10                  15

Tyr Asp Lys Val Ala Glu Lys Leu Lys Glu Ala Phe
            20                  25


<210> SEQ ID NO 641
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal nervonoyl

<400> SEQUENCE: 641

Leu Arg Arg Leu Arg Arg Arg Leu Leu Arg Asp Trp Leu Lys Ala Phe
1               5                   10                  15

Tyr Asp Lys Val Ala Glu Lys Leu Lys Glu Ala Phe
            20                  25


<210> SEQ ID NO 642
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal adrenoyl

<400> SEQUENCE: 642

Leu Arg Arg Leu Arg Arg Arg Leu Leu Arg Asp Trp Leu Lys Ala Phe
1               5                   10                  15

Tyr Asp Lys Val Ala Glu Lys Leu Lys Glu Ala Phe
            20                  25


<210> SEQ ID NO 643
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal alpha-linolenoyl

<400> SEQUENCE: 643
```

```
Leu Arg Arg Leu Arg Arg Arg Leu Leu Arg Asp Trp Leu Lys Ala Phe
1               5                   10                  15

Tyr Asp Lys Val Ala Glu Lys Leu Lys Glu Ala Phe
            20                  25


<210> SEQ ID NO 644
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal gamma-linolenoyl

<400> SEQUENCE: 644

Leu Arg Arg Leu Arg Arg Arg Leu Leu Arg Asp Trp Leu Lys Ala Phe
1               5                   10                  15

Tyr Asp Lys Val Ala Glu Lys Leu Lys Glu Ala Phe
            20                  25


<210> SEQ ID NO 645
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal EPA

<400> SEQUENCE: 645

Leu Arg Arg Leu Arg Arg Arg Leu Leu Arg Asp Trp Leu Lys Ala Phe
1               5                   10                  15

Tyr Asp Lys Val Ala Glu Lys Leu Lys Glu Ala Phe
            20                  25


<210> SEQ ID NO 646
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal DHA

<400> SEQUENCE: 646

Leu Arg Arg Leu Arg Arg Arg Leu Leu Arg Asp Trp Leu Lys Ala Phe
1               5                   10                  15

Tyr Asp Lys Val Ala Glu Lys Leu Lys Glu Ala Phe
            20                  25


<210> SEQ ID NO 647
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal fish oil
```

<400> SEQUENCE: 647

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 648
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal 4-amino-butanoyl

<400> SEQUENCE: 648

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 649
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal 6-amino-hexanoyl

<400> SEQUENCE: 649

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 650
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal 8-amino-octanoyl

<400> SEQUENCE: 650

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 651
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal 10-amino-decanoyl

<400> SEQUENCE: 651

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 652
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal 12-amino-lauroyl

<400> SEQUENCE: 652

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 653
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal 14-amino-myristoyl

<400> SEQUENCE: 653

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 654
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal 16-amino-palmitoyl

<400> SEQUENCE: 654

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 655
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)

<223> OTHER INFORMATION: N-terminal 16-amino-palmitoleoyl

<400> SEQUENCE: 655

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 656
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal 18-amino-stearoyl

<400> SEQUENCE: 656

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 657
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal 18-amino-oleoyl

<400> SEQUENCE: 657

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 658
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE
<222> LOCATION: (1)..(1)
<223> OTHER INFORMATION: N-terminal 18-amino-linolenoyl

<400> SEQUENCE: 658

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 659
<211> LENGTH: 28
<212> TYPE: PRT
<213> ORGANISM: Artificial Sequence
<220> FEATURE:
<223> OTHER INFORMATION: synthetic construct; ApoE mimicking peptide
<220> FEATURE:
<221> NAME/KEY: MISC_FEATURE <222> LOCATION: (1)..(1)
<223> OTHER INFORMATION: N-terminal 20-amino-arachidoyl

<400> SEQUENCE: 659

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 660
<211> LENGTH: 18
<212> TYPE: PRT
<213> ORGANISM: Artificial Sequence
<220> FEATURE:
<223> OTHER INFORMATION: synthetic construct; lipid associating peptide

<400> SEQUENCE: 660

Lys Ala Phe Glu Glu Val Leu Ala Lys Lys Phe Tyr Asp Lys Ala Leu
1 5 10 15

Trp Asp

<210> SEQ ID NO 661
<211> LENGTH: 10
<212> TYPE: PRT
<213> ORGANISM: Artificial Sequence
<220> FEATURE:
<223> OTHER INFORMATION: synthetic construct; receptor binding domain of
Apo E

<400> SEQUENCE: 661

Leu Arg Leu Leu Arg Lys Leu Lys Arg Arg
1 5 10

<210> SEQ ID NO 662
<211> LENGTH: 28
<212> TYPE: PRT
<213> ORGANISM: Artificial Sequence
<220> FEATURE:
<223> OTHER INFORMATION: synthetic construct; ApoE mimetic
<220> FEATURE:
<221> NAME/KEY: MOD_RES
<222> LOCATION: (1)..(1)
<223> OTHER INFORMATION: ACETYLATED amino-hexanoic acid (Aha)

<400> SEQUENCE: 662

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 663
<211> LENGTH: 28
<212> TYPE: PRT
<213> ORGANISM: Artificial Sequence
<220> FEATURE:
<223> OTHER INFORMATION: synthetic construct; peptide mimetic
<220> FEATURE:
<221> NAME/KEY: MOD_RES
<222> LOCATION: (1)..(1)
<223> OTHER INFORMATION: Fish oil conjugatied to amino terminus
<220> FEATURE:
<221> NAME/KEY: MOD_RES
<222> LOCATION: (28)..(28)
<223> OTHER INFORMATION: Amidated C-terminus

<400> SEQUENCE: 663

Leu Arg Arg Leu Arg Arg Arg Leu Leu Arg Asp Trp Leu Lys Ala Phe 1 5 10 15

Tyr Asp Lys Val Ala Glu Lys Leu Lys Glu Ala Phe
20 25

<210> SEQ ID NO 664
<211> LENGTH: 28
<212> TYPE: PRT
<213> ORGANISM: Artificial Sequence
<220> FEATURE:
<223> OTHER INFORMATION: synthetic construct; ApoE mimetic

<400> SEQUENCE: 664

Leu Arg Lys Leu Arg Leu Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 665
<211> LENGTH: 28
<212> TYPE: PRT
<213> ORGANISM: Artificial Sequence
<220> FEATURE:
<223> OTHER INFORMATION: synthetic construct; ApoE mimetic

<400> SEQUENCE: 665

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 666
<211> LENGTH: 30
<212> TYPE: PRT
<213> ORGANISM: Artificial Sequence
<220> FEATURE:
<223> OTHER INFORMATION: synthetic construct; ApoE mimetic

<400> SEQUENCE: 666

Leu Arg Lys Leu Arg Leu Arg Leu Leu Arg Gly Gly Asp Trp Leu Lys
1 5 10 15

Ala Phe Tyr Asp Lys Val Ala Glu Lys Leu Lys Glu Ala Phe
20 25 30

<210> SEQ ID NO 667
<211> LENGTH: 30
<212> TYPE: PRT
<213> ORGANISM: Artificial Sequence
<220> FEATURE:
<223> OTHER INFORMATION: synthetic construct; ApoE mimetic

<400> SEQUENCE: 667

Leu Arg Lys Leu Arg Leu Arg Leu Leu Arg Ala Ala Asp Trp Leu Lys
1 5 10 15

Ala Phe Tyr Asp Lys Val Ala Glu Lys Leu Lys Glu Ala Phe
20 25 30

<210> SEQ ID NO 668
<211> LENGTH: 28
<212> TYPE: PRT
<213> ORGANISM: Artificial Sequence
<220> FEATURE:
<223> OTHER INFORMATION: synthetic construct; ApoE mimetic
<220> FEATURE:
<221> NAME/KEY: MOD_RES
<222> LOCATION: (11)..(11)

<223> OTHER INFORMATION: ACETYLATED amino-hexanoic acid (Aha)

<400> SEQUENCE: 668

Leu Arg Lys Leu Arg Leu Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 669
<211> LENGTH: 28
<212> TYPE: PRT
<213> ORGANISM: Artificial Sequence
<220> FEATURE:
<223> OTHER INFORMATION: synthetic construct; ApoE mimetic
<220> FEATURE:
<221> NAME/KEY: MOD_RES
<222> LOCATION: (1)..(1)
<223> OTHER INFORMATION: ACETYLATED amino-hexanoic acid (Aha)

<400> SEQUENCE: 669

Leu Arg Lys Leu Arg Leu Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 670
<211> LENGTH: 28
<212> TYPE: PRT
<213> ORGANISM: Artificial Sequence
<220> FEATURE:
<223> OTHER INFORMATION: synthetic construct; ApoE mimetic
<220> FEATURE:
<221> NAME/KEY: MOD_RES
<222> LOCATION: (1)..(1)
<223> OTHER INFORMATION: ACETYLATED amino-hexanoic acid (Aha)

<400> SEQUENCE: 670

Leu Arg Arg Leu Arg Arg Arg Leu Leu Arg Asp Trp Leu Lys Ala Phe
1 5 10 15

Tyr Asp Lys Val Ala Glu Lys Leu Lys Glu Ala Phe
20 25

<210> SEQ ID NO 671
<211> LENGTH: 28
<212> TYPE: PRT
<213> ORGANISM: Artificial Sequence
<220> FEATURE:
<223> OTHER INFORMATION: synthetic construct; ApoE mimetic

<400> SEQUENCE: 671

Leu Lys Lys Leu Lys Leu Lys Leu Leu Lys Asp Trp Leu Lys Ala Phe
1 5 10 15

Tyr Asp Lys Val Ala Glu Lys Leu Lys Glu Ala Phe
20 25

<210> SEQ ID NO 672
<211> LENGTH: 28
<212> TYPE: PRT
<213> ORGANISM: Artificial Sequence
<220> FEATURE:
<223> OTHER INFORMATION: synthetic construct; ApoE mimetic

<400> SEQUENCE: 672

Leu Arg Arg Leu Arg Arg Arg Leu Arg Arg Asp Trp Leu Arg Ala Phe
1 5 10 15

-continued

```
Tyr Asp Lys Val Ala Glu Lys Leu Arg Glu Ala Phe
            20                  25


<210> SEQ ID NO 673
<211> LENGTH: 28
<212> TYPE: PRT
<213> ORGANISM: Artificial Sequence
<220> FEATURE:
<223> OTHER INFORMATION: synthetic construct; ApoE mimetic

<400> SEQUENCE: 673

Leu Arg Arg Leu Arg Arg Arg Leu Leu Arg Asp Trp Leu Arg Ala Leu
1               5                   10                  15

Tyr Asp Lys Val Ala Glu Lys Leu Arg Glu Ala Leu
            20                  25


<210> SEQ ID NO 674
<211> LENGTH: 28
<212> TYPE: PRT
<213> ORGANISM: Artificial Sequence
<220> FEATURE:
<223> OTHER INFORMATION: synthetic construct; ApoE mimetic

<400> SEQUENCE: 674

Leu Arg Arg Leu Arg Arg Arg Leu Leu Arg Asp Leu Leu Arg Ala Leu
1               5                   10                  15

Tyr Asp Lys Val Ala Glu Lys Leu Arg Glu Ala Trp
            20                  25
```

We claim:

1. A synthetic apolipoprotein E(ApoE)-mimicking peptide comprising a receptor binding domain of ApoE and a lipid-associating peptide, wherein the synthetic ApoE-mimicking peptide comprises a fatty acid moiety, a ω-amino fatty acid moiety, or an acetylated ω-amino fatty acid moiety, wherein the lipid-associating peptide comprises a class A amphipathic helical domain, wherein the fatty acid moiety is a saturated fatty acid moiety, wherein the receptor binding domain of ApoE is on the N-terminus of the synthetic ApoE-mimicking peptide, and wherein the saturated fatty acid moiety, *ω-amino fatty acid moiety, or acetylated ω-amino fatty acid moiety* is at the N-terminus of the receptor binding domain of ApoE.

2. The peptide of claim 1, wherein the synthetic ApoE-mimicking peptide comprises the acetylated ω-amino fatty acid moiety.

3. The peptide of claim 2, wherein the acetylated ω-amino fatty acid moiety is Ac-Aha.

4. The peptide of claim 2, wherein the Ac-Aha is at the N-terminus of the peptide.

5. The peptide of claim 1, wherein the synthetic ApoE-mimicking peptide comprises the ω-amino fatty acid moiety.

6. [The peptide of claim 5, wherein] *A synthetic apolipoprotein E(ApoE)-mimicking peptide comprising a lipid-associating peptide, a receptor-binding domain of ApoE at the N-terminus of the ApoE-mimicking peptide, and a w-amino fatty acid moiety at the N-terminus of the receptor-binding domain, wherein the lipid-associating peptide comprises a class A amphipathic helical domain, and* the ω-amino fatty acid moiety is 4-amino-butanoyl, 6-amino-caproyl, 8-amino-octanoyl, 10-amino-decanoyl, 12-amino-lauroyl, 14-amino-myristoyl, 14-amino-myristoleoyl, 16-amino-palmitoyl, 18-amino-stearoyl, 18-amino-oleoyl, 16-amino-palmitoleoyl, 18-amino-linoleoyl, [18-amino- linolenoyl] *18-amino-linolenoyl*, or 20-amino-arachidonoyl.

7. The peptide of claim 6, wherein the ω-amino group is acetylated.

8. The peptide of claim 1, wherein the fatty acid moiety, the ω-amino fatty acid moiety, or the acetylated ω-amino fatty acid moiety is at the N-terminus of the peptide.

9. The peptide of claim 1, wherein the class A amphipathic-helical domain is DWLKAFYDKVAEKLKEAF (SEQ ID NO:5), DWLRAFYDKVAEKLREAF (SEQ ID NO:618), DWLRALYDKVAEKLREAL (SEQ ID NO:619), DLLRALYDKVAEKLREAW (SEQ ID NO:620), or FAEKLKEAVKDYFAKLWD (SEQ ID NO:616).

10. The peptide of claim 1, wherein said synthetic ApoE-mimicking peptide is protected using an amide group at the C-terminus.

11. The peptide of claim 1, wherein the receptor binding domain of ApoE is LRKLRKRLLR (SEQ ID NO:4), LRRLRRRLLR (SEQ ID NO:11), LRKMRKRLMR (SEQ ID NO:7), RLTRKRGLK (SEQ ID NO:13), LRRMRRRLMR (SEQ ID NO:621), or RLTRRRGK (SEQ ID NO:622).

12. The peptide of claim 1, wherein the synthetic ApoE-mimicking peptide is Ac-Aha-hE18A-NH2 or Ac-Aha-[R]hE18A-NH2.

13. A pharmaceutical composition, comprising the synthetic apolipoprotein E-mimicking peptide of claim 1 and a pharmaceutically acceptable carrier.

14. [The peptide of claim 1, wherein the] *A* synthetic ApoE-mimicking peptide *that* is butanoyl-LRRLRRRLLRDWLKAFYDKVAEKLKEAF-$NH_2$ (SEQ ID NO: 623); hexanoyl-LRRLRRRLLRDWLKAFYDK-VAEKLKEAF-$NH_2$ (SEQ ID NO: 624); octanoyl-LRRLRRRLLRDWLKAFYDKVAEKLKEAF-$NH_2$ (SEQ ID NO: 625); decanoyl-LRRLRRRLLRDWLKAFYDK- VAEKLKEAF-$NH_2$ (SEQ ID NO: 626); lauroyl-LRRLRRRLLRDWLKAFYDKVAEKLKEAF-$NH_2$ (SEQ ID NO: 627); myristoyl-LRRLRRRLLRDWLKAFYDK-VAEKLKEAF-$NH_2$ (SEQ ID NO: 628); palmitoyl-LRRLRRRLLRDWLKAFYDKVAEKLKEAF-$NH_2$ (SEQ ID NO: 629); stearoyl-LRRLRRRLLRDWLKAFYDK-VAEKLKEAF-$NH_2$ (SEQ ID NO: 630); palmitoleoyl-LRRLRRRLLRDWLKAFYDKVAEKLKEAF-$NH_2$ (SEQ ID NO: 631); arachidoyl-LRRLRRRLLRDWLKAFYDK-VAEKLKEAF-$NH_2$ (SEQ ID NO: 632); behenoyl-LRRLRRRLLRDWLKAFYDKVAEKLKEAF-$NH_2$ (SEQ ID NO: 633); oleoyl-LRRLRRRLLRDWLKAFYDK-VAEKLKEAF-$NH_2$ (SEQ ID NO: 634); ricinoleoyl-LRRLRRRLLRDWLKAFYDKVAEKLKEAF-$NH_2$ (SEQ ID NO: 635); linolenoyl-LRRLRRRLLRDWLKAFYDK-VAEKLKEAF-$NH_2$ (SEQ ID NO: 636); vacceoyl-LRRLRRRLLRDWLKAFYDKVAEKLKEAF-$NH_2$ (SEQ ID NO: 637); gadoleoyl-LRRLRRRLLRDWLKAFYDK-VAEKLKEAF-$NH_2$ (SEQ ID NO: 638); erucoyl-LRRLRRRLLRDWLKAFYDKVAEKLKEAF-$NH_2$ (SEQ ID NO: 639); cetoleoyl-LRRLRRRLLRDWLKAFYDK-VAEKLKEAF-$NH_2$ (SEQ ID NO: 640); nervonoyl-LRRLRRRLLRDWLKAFYDKVAEKLKEAF-$NH_2$ (SEQ ID NO: 641); adrenoyl-LRRLRRRLLRDWLKAFYDK-VAEKLKEAF-$NH_2$ (SEQ ID NO: 642); α-linolenoyl-LRRLRRRLLRDWLKAFYDKVAEKLKEAF-$NH_2$ (SEQ ID NO: 643); γ-linolenoyl-LRRLRRRLLRDWLKAFYDK-VAEKLKEAF-$NH_2$ (SEQ ID NO: 644); EPA-LRRLRRRLLRDWLKAFYDKVAEKLKEAF-$NH_2$ (SEQ ID NO: 645); DHA-LRRLRRRLLRDWLKAFYDK-VAEKLKEAF-$NH_2$ (SEQ ID NO: 646), 4-amino-butanoyl-LRRLRRRLLRDWLKAFYDKVAEKLKEAF-$NH_2$ (SEQ ID NO: 648); 6-amino-hexanoyl-LRRLRRRLLRDWLKAFYDKVAEKLKEAF-$NH_2$ (SEQ ID NO: 649); 8-amino-octanoyl-LRRLRRRLLRDWLKAFYDKVAEKLKEAF-$NH_2$ (SEQ ID NO: 650); 10-amino-decanoyl-LRRLRRRLLRDWLKAFYDKVAEKLKEAF-$NH_2$ (SEQ ID NO: 651); 12-amino-lauroyl-LRRLRRRLLRDWLKAFYDKVAEKLKEAF-$NH_2$ (SEQ ID NO: 652); 14-amino-myristoyl-LRRLRRRLLRDWLKAFYDKVAEKLKEAF-$NH_2$ (SEQ ID NO: 653); 16-amino-palmitoyl-LRRLRRRLLRDWLKAFYDKVAEKLKEAF-$NH_2$ (SEQ ID NO: 654); 16-amino-palmitoleoyl-LRRLRRRLLRDWLKAFYDKVAEKLKEAF-$NH_2$ (SEQ ID NO: 655); 18-amino-stearoyl-LRRLRRRLLRDWLKAFYDKVAEKLKEAF-$NH_2$ (SEQ ID NO: 656); 18-amino-oleoyl-LRRLRRRLLRDWLKAFYDKVAEKLKEAF-$NH_2$ (SEQ ID NO: 657); 18-amino-linolenoyl-LRRLRRRLLRDWLKAFYDKVAEKLKEAF-$NH_2$ (SEQ ID NO: 658); or 20-amino-arachidoyl-LRRLRRRLLRDWLKAFYDKVAEKLKEAF-$NH_2$(SEQ ID NO: 659).

*15. The synthetic ApoE-mimicking peptide of claim 14, wherein the synthetic ApoE-mimicking peptide is oleovl-LRRLRRRLLRDWLKAFYDKVAEKLKEAF-NH2 (SEQ ID NO: 634).*

*16. The synthetic ApoE-mimicking peptide of claim 14, wherein the synthetic ApoE-mimicking peptide is octano 1-LRRLRRRLLRDWLKAFYDKVAEKLKEAF-NH2 (SE ID NO: 625).*

*17. The synthetic ApoE-mimicking peptide of claim 14, wherein the synthetic ApoE-mimicking peptide is myristoyl-LRRLRRRLLRDWLKAFYDKVAEKLKEAF-NH2 (SEQ ID NO: 628).*

*18. The synthetic ApoE-mimicking peptide of claim 14, wherein the synthetic ApoE-mimicking peptide is palmitoyl-LRRLRRRLLRDWLKAFYDKVAEKLKEAF-NH2 (SEQ ID NO: 629).*

* * * * *